United States Patent
Gao et al.

(10) Patent No.: US 10,308,958 B2
(45) Date of Patent: Jun. 4, 2019

(54) METHOD OF DETECTING AND/OR IDENTIFYING ADENO-ASSOCIATED VIRUS (AAV) SEQUENCES AND ISOLATING NOVEL SEQUENCES IDENTIFIED THEREBY

(71) Applicant: The Trustees of the University of Pennsylvania, Philadelphia, PA (US)

(72) Inventors: Guangping Gao, Westborough, MA (US); James M. Wilson, Philadelphia, PA (US); Mauricio R. Alvira, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/633,906

(22) Filed: Jun. 27, 2017

(65) Prior Publication Data
US 2017/0298388 A1    Oct. 19, 2017

Related U.S. Application Data

(60) Continuation of application No. 15/584,674, filed on May 2, 2017, which is a continuation of application No. 14/956,934, filed on Dec. 2, 2015, now Pat. No. 10,041,090, which is a continuation of application No. 13/633,971, filed on Oct. 3, 2012, now Pat. No. 9,790,472, which is a division of application No. 12/962,793, filed on Dec. 8, 2010, now Pat. No. 8,524,446, which is a continuation of application No. 10/291,583, filed on Nov. 12, 2002, now abandoned.

(60) Provisional application No. 60/386,675, filed on Jun. 5, 2002, provisional application No. 60/377,066, filed on May 1, 2002, provisional application No. 60/341,117, filed on Dec. 17, 2001, provisional application No. 60/350,607, filed on Nov. 13, 2001.

(51) Int. Cl.

| | |
|---|---|
| *C12N 7/00* | (2006.01) |
| *A61K 39/23* | (2006.01) |
| *C12N 15/86* | (2006.01) |
| *C07K 14/005* | (2006.01) |
| *C12Q 1/70* | (2006.01) |
| *A61K 38/17* | (2006.01) |
| *A61K 38/48* | (2006.01) |
| *A61K 48/00* | (2006.01) |

(52) U.S. Cl.
CPC .......... *C12N 15/86* (2013.01); *A61K 38/177* (2013.01); *A61K 38/4846* (2013.01); *C07K 14/005* (2013.01); *C12N 7/00* (2013.01); *C12Q 1/701* (2013.01); *C12Y 304/21022* (2013.01); *A61K 48/00* (2013.01); *C12N 2750/14121* (2013.01); *C12N 2750/14122* (2013.01); *C12N 2750/14143* (2013.01); *C12N 2750/14151* (2013.01); *C12N 2750/14152* (2013.01); *C12N 2750/14162* (2013.01); *C12N 2750/14171* (2013.01); *C12N 2830/008* (2013.01); *C12N 2830/48* (2013.01); *C12N 2830/85* (2013.01); *C12N 2830/90* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,412,073 A | 5/1995 | Kalsheker |
| 5,449,616 A | 9/1995 | Campbell |
| 5,871,982 A | 2/1999 | Wilson et al. |
| 5,866,552 A | 5/1999 | Chiorini et al. |
| 6,039,942 A | 3/2000 | Lassen |
| 6,156,303 A | 12/2000 | Russell et al. |
| 6,251,677 B1 | 6/2001 | Wilson et al. |
| 6,274,354 B1 | 8/2001 | Wilson et al. |
| 6,312,957 B1 | 11/2001 | Einerhand |
| 6,365,394 B1 | 4/2002 | Gao et al. |
| 6,376,237 B1 | 4/2002 | Colosi |
| 6,387,368 B1 | 5/2002 | Wilson et al. |
| 6,399,385 B1 | 6/2002 | Croyle et al. |
| 6,428,988 B1 | 8/2002 | Wilson et al. |
| 6,468,524 B1 | 10/2002 | Chiorini et al. |
| 6,475,769 B1 | 11/2002 | Wilson et al. |
| 6,482,634 B1 | 11/2002 | Wilson et al. |
| 6,485,966 B2 | 11/2002 | Gao et al. |
| 6,632,670 B1 | 10/2003 | Wadsworth et al. |
| 6,759,237 B1 | 7/2004 | Wilson et al. |
| 6,821,512 B1 | 11/2004 | Gao et al. |
| 6,943,019 B2 | 9/2005 | Wilson |
| 6,953,690 B1 | 10/2005 | Gao et al. |
| 7,022,519 B2 | 4/2006 | Gao |

(Continued)

FOREIGN PATENT DOCUMENTS

| | | |
|---|---|---|
| BR | PI0214119.1 | 6/2015 |
| BR | PI0214119.1 | 11/2015 |

(Continued)

OTHER PUBLICATIONS

Wang et al., "Adeno-associated virus vector carrying human minidystrophin genes effectively ameliorates muscular dystrophy in mdx mouse model," PNAS vol. 97, No. 25: 13714-13719 (Year: 2000).*

(Continued)

*Primary Examiner* — Janet L Andres
*Assistant Examiner* — M Franco G Salvoza
(74) *Attorney, Agent, or Firm* — Howson & Howson LLP

(57) ABSTRACT

Adeno-associated virus rh.10 sequences, vectors containing same, and methods of use are provided.

34 Claims, 112 Drawing Sheets
Specification includes a Sequence Listing.

(56) References Cited

U.S. PATENT DOCUMENTS

| | | |
|---|---|---|
| 7,056,502 B2 | 6/2006 | Hildinger |
| 7,235,393 B2 | 6/2007 | Gao |
| 7,238,526 B2 | 7/2007 | Wilson |
| 7,282,199 B2 | 10/2007 | Gao |
| 7,790,449 B2 | 9/2010 | Gao |
| 2001/0006955 A1 | 7/2001 | Wilson et al. |
| 2002/0037867 A1 | 3/2002 | Wilson et al. |
| 2002/0090717 A1 | 7/2002 | Gao et al. |
| 2003/0040101 A1 | 2/2003 | Wilson |
| 2003/0073232 A1 | 4/2003 | Wilson |
| 2003/0119191 A1 | 6/2003 | Gao |
| 2003/0138772 A1 | 7/2003 | Gao et al. |
| 2004/0052764 A1 | 3/2004 | Hildinger |
| 2007/0036760 A1 | 2/2007 | Wilson |
| 2008/0075737 A1 | 3/2008 | Gao et al. |
| 2008/0075740 A1 | 3/2008 | Gao |
| 2009/0054823 A1 | 2/2009 | Bridges |
| 2009/0197338 A1 | 8/2009 | Vandenberghe |
| 2009/0227030 A1 | 9/2009 | Gao |
| 2009/0275107 A1 | 11/2009 | Lock |
| 2009/0280103 A1 | 11/2009 | Flueck |
| 2011/0053221 A1 | 3/2011 | Chen |
| 2011/0070210 A1 | 3/2011 | Andrijauskas |
| 2011/0151434 A1 | 6/2011 | Gao |
| 2011/0301226 A1 | 12/2011 | Mendell |
| 2013/0195801 A1 | 8/2013 | Gao |
| 2015/0159173 A1 | 6/2015 | Vandenberghe et al. |

FOREIGN PATENT DOCUMENTS

| | | |
|---|---|---|
| BR | PI0214119.1 | 3/2016 |
| CA | 2046745 A1 | 1/2006 |
| CA | 2756866 | 5/2013 |
| CA | 2756866 | 3/2014 |
| CA | 2756866 | 5/2015 |
| CA | 2756866 | 1/2016 |
| CN | 201310326978.2 | 11/2014 |
| CN | 201310326978.2 | 8/2015 |
| CN | 201310326978.2 | 4/2016 |
| CN | 201310326978.2 | 1/2017 |
| EP | 1310571 A2 | 5/2003 |
| EP | 3085389 A1 | 10/2016 |
| JP | 2005-525086 | 8/2005 |
| JP | 2009-102988 | 10/2011 |
| JP | 2009-102988 | 6/2012 |
| MX | A/2011/08016 | 10/2014 |
| NO | 20150196 | 2/2015 |
| NO | 20150196 | 5/2015 |
| PH | 1-2014-501487 | 10/2016 |
| PH | 1-2014-501487 | 5/2017 |
| WO | WO-1996/000587 A1 | 1/1996 |
| WO | WO-1996/013598 A2 | 5/1996 |
| WO | WO-1998/009657 A2 | 3/1998 |
| WO | WO-1998/010086 A1 | 3/1998 |
| WO | WO-1998/010088 A1 | 3/1998 |
| WO | WO-1998/011244 | 3/1998 |
| WO | WO-1999/014354 A1 | 3/1999 |
| WO | WO-1999/015677 A1 | 4/1999 |
| WO | WO-1999/015685 A1 | 4/1999 |
| WO | WO-1999/047691 A1 | 9/1999 |
| WO | WO-1999/061601 | 12/1999 |
| WO | WO-1999/061601 A2 | 12/1999 |
| WO | WO-2000/028061 | 5/2000 |
| WO | WO-2000/028061 A2 | 5/2000 |
| WO | WO-2000/075353 A1 | 12/2000 |
| WO | WO-2001/014539 A2 | 3/2001 |
| WO | WO-2001/023001 A2 | 4/2001 |
| WO | WO-2001/023597 A3 | 4/2001 |
| WO | WO-2001/040455 A2 | 6/2001 |
| WO | WO-2001/068888 A2 | 9/2001 |
| WO | WO-2001/070276 A2 | 9/2001 |
| WO | WO-2001/083692 A2 | 11/2001 |
| WO | WO-2002/018659 A2 | 3/2002 |
| WO | WO-2003/042397 A2 | 5/2003 |
| WO | WO-2003/104392 A2 | 12/2003 |
| WO | WO-2004/112727 A2 | 12/2004 |
| WO | WO-2013/078316 A1 | 5/2013 |
| WO | WO-2013/123503 A1 | 8/2013 |

OTHER PUBLICATIONS

Gao et al., "Novel adeno-associated viruses from rhesus monkeys as vectors for human gene therapy", PNAS, vol. 99(18):11854-11859, Sep. 2002.

GenBank entry AF513851, Sep. 2002.

GenBank entry AF513852, Sep. 2002.

Gao et al., "Biology of Adenovirus vectors with E1 and E4 deletions for liver-directed gene therapy", Journal of Viroloy, vol. 70(12):8934-8943, Dec. 1996.

Rutledge et al., "Infectious clones and vectors derived from Adeno-Associated Virus (AAV) serotypes other than AAV Type 2", Journal of Virology, vol. 72(1):309-319, Jan. 1998.

Xiao et al., "Gene therapy vectors based on Adeno-Associated Virus Type 1", Journal of Virology, vol. 73(5):3994-4003, May 1999.

Durigon et al., "Multiple primer pairs for polymerase chain reaction (PCR) amplification of human parvovirus B19 DNA", Journal of Virological Methods, vol. 44:155-165, Feb. 1993.

Hernandez et al., "Latent Adeno-associated virus infection elicits humoral but no cell-mediated immune responses in a nonhuman primate model", Journal of Virology, vol. 73(10):8549-8558, Oct. 1999.

Afione et al., "In vivo model of adeno-associated virus vector persistence and rescue", Journal of Virology, vol. 70(5):3235-3241, May 1996.

Schnell et al., "Activation of innate immunity in nonhuman primates following intraportal administration of adenoviral vectors", Molecular Therapy, vol. 3(5):708-722, May 2001.

Molecular Therapy, "Information for Authors", pp. 1-13.

Green et al., "Rhesus and pig-tailed macaque parvoviruses: identification of two new members of the *Erythrovirus* genus in monkeys", Virology, vol. 269:105-112, Jan. 2000.

Brown et al., "Cloning and sequencing of the simial parvovirus genome", Virology, vol. 210:314-322, May 1995.

Zadori et al., "A viral phospholipase A2 is required for parvovirus infectivity", Developmental Cell, vol. 1:291-302, Aug. 2001.

Weitzman et al., "Adeno-associated virus (AAV) Rep proteins mediate complex formation between AAV DNA and its integration site in human DNA", PNAS, vol. 91:5808-5812, Jun. 1994.

Wang et al., "Enhancing Transgene Expression from Recombinant AAV8 Vectors in Different Tissues Using Woodchuck Hepatitis Virus Post-Transcriptional Regulatory Element", International Journal of Medical Sciences, vol. 13(4):286-291, Apr. 2016.

Charan et al., "Adeno-associated Virus Serotype 8 (AAV8) Delivery of Recombinant A20 to Skeletal Muscle Reduces Pathological Activation of Nuclear Factor (NF)-kB in Muscle of mdx Mice", Molecular Medicine, vol. 18:1527-1535, Nov. 2012.

Childers et al., "Gene Therapy Prolongs Survival and Restores Function in Murine and Canine Models of Myotubular Myopathy", Sci Transl Med, vol. 6(220):1-31, Jan. 2014.

Zhu et al., "Sustained Whole-Body Functional Rescue by Systemic Delivery of AAV8 Vectors in Heart Failure and Muscular Dystrophy Hamsters", Molecular Therapy, vol. 11(suppl 1):916, May 2005.

Lytle et al., "Effects of FVIII immunity on hepatocyte and hematopoietic stem cell-directed gene therapy of murine hemophilia A", Methods & Clinical Development, vol. 3:15056, Feb. 2016.

Gilkes et al., "Mucopolysaccharidosis IIIB confers enhanced neonatal intracranial transduction by AAV8 but not by 5, 9 or rh10", Gene Therapy, vol. 23:263-271, Jan. 2016.

Pignataro et al., "Adeno-Associated Viral Vectors Serotype 8 for Cell-Specific Delivery of Therapeutic Genes in the Central Nervous System", Frontiers in Neuroanatomy, vol. 11(2):1-13, Feb. 2017.

Black et al., "Adeno-associated virus 8-mediated gene therapy for choroideremia: preclinical studies in in vitro and in vivo models", The Journal of Gene Medicine, vol. 16:122-130, Jun. 2014.

Dai et al., "Long-term retinal cone rescue using a capsid mutant AAV8 vector in a mouse model of CNGA3-achromatopsia", PLOS One, vol. 12(11):e0188032, Nov. 2017.

(56) References Cited

OTHER PUBLICATIONS

Fischer et al., "Codon-Optimized RPGR Improves Stability and Efficacy of AAV8 Gene Therapy in Two Mouse Models of X-Linked Retinitis Pigmentosa", Molecular Therapy, vol. 25(8):1854-1865, May 2017.
ClinicalTrials.org, "AAV8 Vector Trials", Nov. 2017.
Mountz, "Monkey see, monkey do", vol. 10:194-196, Gene Therapy, vol. 10:194, Jan. 2003.
Statement of Opposition, dated Jun. 20, 2017, filed on related European Patent No. 1453547.
Proprietor's Response to the Opposition, dated Dec. 5, 2017, filed on related European Patent No. 1453547.
Gao, U.S. Appl. No. 15/584,674, filed May 2, 2017.
Gao, U.S. Appl. No. 11/985,096, filed Nov. 14, 2007, US 2011-0263027, Oct. 27, 2011, U.S. Pat. No. 8,906,675, Dec. 9, 2014.
Gao, U.S. Appl. No. 12/962,793, filed Dec. 8, 2010, US 2011-0151434, Jun. 23, 2011, U.S. Pat. No. 8,524,445, Sep. 3, 2013.
Gao, U.S. Appl. No. 13/633,971, filed Oct. 3, 2012, US 2013-0045186, Feb. 21, 2013.
Gao, U.S. Appl. No. 14/956,934, filed Dec. 2, 2014, US 2016-0079040, Apr. 7, 2016.
Jul. 28, 2003, PCT: International Search Report, PCT/US2002/033629.
Sep. 16, 2004, PCT: International Preliminary Examination Report, PCT/US2002/033629.
May 26, 2011, Extended European Search Report, EP 10178940.2
Gao, Journal of Virology, Novel Adeno-Associated Viruses from Rhesus Monkeys as Vectors for Human Gene Therapy, 99(18):11854-11859 Sep. 3, 2002.
Herzog, Proc. Natl. Acad. Sci., Stable Gene Transfer and Expression of Human Blood Coagulation Factor IX After Intramuscular Injection of Recombinant Adeno-Associated Virus, 94:5804-5809 May 1997.
Rutledge, Journal of Virology, Infectious clones and vectors derived from adeno-associated virus (AAV) serotypes other than AAV type 2, vol. 72(1):309-319, XP-002137089, (Jan. 1998).
Gao, Journal of Virology, Clades of Adeno-Associated Viruses are Widely Disseminated in human Tissues, vol. 78(12):6381-6388.
Gao, PNAS, Adeno-Associated Viruses Undergo Substantial Evolution in Primates During National Infections, vol. 100(10):6081-6086.
Tal, J Biomed Sci., Adeno-associated virus-based vectors in gene therapy, Jul.-Aug. 2000;7(4):279-91.
Xiao, Journal of Virology, Gene therapy vectors based on adeno-associated virus type 1, May 1999;73(5):3994-4003.
U.S. Appl. No. 13/633,971, filed Feb. 28, 2014.
U.S. Appl. No. 13/633,971, filed Nov. 6, 2014.
U.S. Appl. No. 13/633,971, filed Jul. 21, 2015.
U.S. Appl. No. 13/633,971, filed Jul. 28, 2016.
U.S. Appl. No. 13/633,971, filed Feb. 22, 2017.
U.S. Appl. No. 13/633,971, filed Aug. 23, 2017.
Allocca et al, Novel adeno-associated virus serotypes efficiently transduce murine photoreceptors, J Virol., Oct.;81(20):11372-80. (Epub Aug. 15, 2007).
Anissimov, M., "How many species of bacteria are there", accessed Sep. 23, 2011 from http://www.wisegeek.org/how-many-species-of-bacteria-are-there.htm (last modified Nov. 19, 2015).
Bantel-Schaal, Human adeno-associated virus type 5 is only distantly related to other know primate helper-dependent parviruses, Journal of Virology, vol. 73(2):939-947, (Feb. 1999).
Calcedo et al, Serologic Characterization of Human and Non-Human Primate AAVs, Abstract 102, Molecular Therapy, vol. 7(5): S41, (May 2003).
Cearley et al, A single injection of an adeno-associated virus vector into nuclei with divergent connections results in widespread vector distribution in the brain and global correction of a neurogenic disease, vol. 27((37):9928-40, (Sep. 12, 2007).
Cearley et al, Transduction characteristics of adeno-associated virus vectors expressing cap serotypes 7, 8, 9, and Rh10 in the mouse brain, vol. 13(3):528-37. (Epub Jan. 18, 2006).

Chicoine et al, Vascular Delivery of rAAVrh74lMCK.GALGT2 to the Gastrocnemius Muscle of the Rhesus Macaque Stimulates the Expression of Dystrophin and Laminin α2 Surrogates, Molecular Therapy, vol. 22(4):713-24, (Apr. 2014).
Chiorini et al, Cloning and characterization of AAV5, Journal of Virology, vol. 73(2):1309-1319, (Feb. 1999).
De et al, High levels of persistent expression of alpha1-antitrypsin mediated by the nonhuman primate serotype rh.10 adeno-associated virus despite preexisting immunity to common human adeno-associated viruses, Mol Ther., vol. 13(1):67-76, (Epub Nov. 2, 2005).
De et al, Therapeutic Levels for #945; 1-Antitrypsin Following Intrapleural Administration of a Non-Human Primate Serotype rh10 AAV Vector Expressing #945; 1-Antitrypsin, Abstract 338, $7^{th}$ Annual Meeting of The American Society of Gene Therapy [Jun. 2-6, 2004] Minneapolis, Minnesota, p. 1, (e-published May 2, 2004).
Forslund et al, A broad range of human papillomavirus types detected with a general PCR method suitable for analysis of cutaneous tumors and normal skin, Journal of General Virology, vol. 80(9):2437-2443, XP002229850, (Sep. 1999).
Gao et al, Adeno-Associated Viruses Undergo Substantial Evolution in Primates During Natural Infections, PNAS, vol. 100(10):6081-6086, (May 13, 2003).
Gao et al, Autoimmune Anemia in Macaques Following Erythropoietin Gene Therapy, Abstract 341, $7^{th}$ Annual Meeting of The American Society of Gene Therapy [Jun. 2-6, 2004] Minneapolis, Minnesota, p. 1, (e-published May 2, 2004).
Gao et al, Clades of Adeno-Associated Viruses are Widely Disseminated in human Tissues, Journal of Virology, vol. 78(12):6381-6388, (Jun. 2004).
Gao et al, Diversity of Latent AAV Genomes in Non-Human Primate and Human Tissues, Abstract 400, Molecular Therapy, vol. 7(5):S158, (May 2003).
Gao et al, Erythropoietin Gene Therapy leads to Autoimmune Anemia in Macaques, Blood, vol. 103(9):3300-3302, (May 2004).
Herzog et al, Stable gene transfer and expression of human blood coagulation factor IX after intramuscular injection of recombinant adeno-associated virus, Proc. Natl. Acad. Sci. USA, vol. 94:5804-5809, (May 1997).
Hicks et al, AAV-directed persistent expression of a gene encoding anti-nicotine antibody for smoking cessation, Science Translational Medicine, vol. 4(140):140ra87 (Jun. 27, 2012).
Hu et al, AAV-based neonatal gene therapy for hemophilia A: long-term correction and avoidance of immune responses in mice, vol. 19(12):1166-76. doi: 10.1038/gt.2011.200. (Epub Jan. 12, 2012).
Hu et al, RH10 provides superior transgene expression in mice when compared with natural AAV serotypes for neonatal gene therapy, vol. 12(9):766-78. doi: 10.1002/jgm.1496 (Sep. 2010).
Kelark et al, A common mechanism for cytoplasmic dynein-dependent microtubule binding shared among adeno-associated virus and adenovirus serotypes, vol. 80(15):7781-5. (Aug. 2006).
Kitajima et al, "Complete Prevention of Atherosclerosis in ApoE-Deficient Mice by Hepatic Human ApoE Gene Transfer with Adeno- Associated Virus Serotype 7 and 8" Arterioscler Thromb Vasc Biol, vol. 26:1852-1857, (Jun. 8, 2006).
Klein et al, AAV8, 9, Rh10, Rh43 vector gene transfer in the rat brain: effects of serotype, promoter and purification method, vol. 16(1):89-96. (Epub Oct. 23, 2007).
Kobinger et al, Pseudotyping HIV Vector with the Spike Envelope Protein of SARS-CoV for Studying Viral Tropism, Immunology and Gene Therapy Applications, Abstract 368, $7^{th}$ Annual Meeting of The American Society of Gene Therapy [Jun. 2-6, 2004] Minneapolis, Minnesota, p. 1 (e-published May 2, 2004).
Lawlor et al, Efficient gene delivery and selective transduction of glial cells in the mammalian brain by AAV serotypes isolated from nonhuman primates, Mol Ther., vol. 17(10):1692-702. doi: 10.1038/mt.2009.170. (Epub Jul. 28, 2009).
Lebherz et al, Gene Therapy with Novel Adeno-Associated Virus Vectors Substantially Diminishes Atherosclerosis in a Murine Model of Familial Hypercholesterolemia, The Journal of Gene Medicine, vol. 6(6):663-672, (Jun. 2004).

(56) References Cited

OTHER PUBLICATIONS

Lebherz, C., et al., Novel AAV serotypes for improved ocular gene transfer, J. Gene Med, vol. 10(4):375-382, (Apr. 2008).
Limberis et al., A Novel AAV Vector for the Treatment of Cystic Fibrosis Airway Disease, Abstract 692, 7th Annual Meeting of The American Society of Gene Therapy [Jun. 2-6, 2004] Minneapolis, Minnesota, p. 1, (e-published May 2, 2004).
Lin, et al, "Vaccines Based on Novel Adeno-Associated Virus Vectors Elicit Aberrant CD8+ T-Cell Responses in Mice", J Virol, vol. 81(21):11840-11849, (Nov. 2007).
Lu et al, Analysis of Homologous Recombination Between Different AAV Genomes in In Vitro co-Infections, Abstract 38, Molecular Therapy, vol. 7(5):S15, (May 2003).
Maguire Ca, et al, Directed evolution of adeno-associated virus for glioma cell transduction.J Neurooncol., vol. 96(3):337-47, (Epub Jul. 19, 2009).
Mao et al, Persistent suppression of ocular neovascularization with intravitreal administration of AAVrh.10 coding for bevacizumab, Human Gene Therapy, vol. 22(12):1525-35. doi: 10.1089/hum.2011.090. (Epub Oct. 27, 2011).
Monahan and Semulski, Adeno-Associated Virus Vectors for Gene Therapy: More Pros than Cons, Molecular Medicine Today, vol. 6(11):433-40, (Nov. 2000).
Mori et al, Two Novel Adeno-Associated Viruses from Cynomolgus Monkey: Pseudotyping Characterization of Capsid Protein, Virology, vol. 330(2):375-383, (Dec. 20, 2004).
Mountz et al, Monkey See, Monkey Do, Gene Therapy, vol. 10(3):194-196, (Feb. 2003).
Nathwani et al, Enhancing transduction of the liver by adeno-associated viral vectors, Gene Therapy, vol. 16(1):60-9. doi: 10.1038/gt.2008.137. (Epub Aug. 14, 2008.).
Pacak et al, Long-term skeletal muscle protection after gene transfer in a mouse model of LGMD-2D, Molecular Therapy, vol. 15(10):1775-81, (Jul. 2007).
Piguet et al, Correction of brain oligodendrocytes by AAVrh.10 intracerebral gene therapy in metachromatic leukodystrophy mice, Human Gene Therapy, vol. 23(8):903-14. doi: 10.1089/hum.2012.015. (Epub Jul. 23, 2012).
Price et al, Targeted Gene Transfer to Lung Airway Epithelium Using Plasmid or Adenoviral Vectors Formulated with an Anti-Inflammatory Dexamathasone-Spermine conjugate, Abstract 498, 7th Annual Meeting of The American Society of Gene Therapy [Jun. 2-6, 2004] Minneapolis, Minnesota, p. 1, (e-published May 2, 2004).
Quesada, O., et al., Production, purification and preliminary x-ray crystallographic studies of adeno-associated virus serotype 7, Acta Crystallographica, vol. F(63):1073-1076, (Dec. 2007).
Rafi et al, Extended normal life after AAVrh10-mediated gene therapy in the mouse model of krabbe disease, Molecular Therapy, vol. 20(11):2031-42. doi: 10.1038/mt.2012.153. (Epub Jul. 31, 2012).
Research Genetics, Designer PCR (advertisement), Nucleic Acids Research, vol. 22(15):2882, (Aug. 11, 1994).
Rick et al, ASH education Book—Congenital Bleeding Disorders, Hematology/American Society of Hematology Educational Program, vol. 2003(1):559-574, (Jan. 1, 2003).
Rosenberg et al, AAVrh.10-mediated expression of an anti-cocaine antibody mediates persistent passive immunization that suppresses cocaine-induced behavior, Human Gene Therapy, vol. 23(5):451-9. doi: 10.1089/hum.2011.178. (May 2012).
Ruffing, M., et al., Assembly of viruslike particles by recombinant structural proteins of adeno-associated virus type 2 in insect cells, J Virol, vol. 66(12):6922, (Dec. 1992).
Rutledge et al, Infectious clones and vectors derived from adeno-associated virus (AAV) serotypes other than AAV type 2, Journal of Virology, vol. 72(1):309-319, XP-002137089, (Jan. 1998).
Samaranch et al, "Strong Cortical and Spinal Cord Transduction after AAV7 and AAV9 Delivery into the Cerebrospinal Fluid of Nonhuman Primates", Hu Gene Therapy, vol. 24:526-53, (May 2013).

Sanmiguel et al, Real-time PCR as an Analytic Tool in Gene Therapy, Abstract 913, vol. 7(5):S352, (May 2003).
Skaricic et al, Genetic delivery of an anti-RSV antibody to protect against pulmonary infection with RSV, Jour. Virol., vol. 378(1):79-85. doi: 10.1016/j.virol.2008.04.016. (Epub Jun. 16, 2008).
Sommer and Tautz, Minimal homology requirement for PCR primers, Nucleic Acids Research, vol. 17(16):6749, (Aug. 25, 1989).
Sondhi et al, Enhanced survival of the LINCL mouse following CLN2 gene transfer using the rh.10 rhesus macaque-derived adeno-associated virus vector, Mol Ther., vol. 15(3):481-91. (Epub Dec. 19, 2006).
Sondhi et al, Long-term expression and safety of administration of AAVrh.10hCLN2 to the brain of rats and nonhuman primates for the treatment of late infantile neuronal ceroid lipofuscinosis, Human Gene Therapy, vol. 23(5):324-35. doi: 10.1089/hgtb.2012.120. (Epub Nov. 6, 2012).
Sondhi et al, Survival advantage of neonatal CNS gene transfer for late infantile neuronal ceroid lipofuscinosis, Jour Exp Neurol, vol. 213(1):18-27. doi: 10.1016/j.expneurol.2008.04.022. (Epub Apr. 30, 2008).
Tal, Adeno-associated virus-based vectors in gene therapy, Journal of Biomedical Science, vol. 7(4):279-291, (Jul. 2000).
Tobiasch, Discrimination between different types of human adeno-associated viruses clinical samples by PCR, Journal of Virology Methods, vol. 71(1):17-25, (Mar. 1998).
Vandenberghe et al, AAV Clades: Their Ability to Recombine and Cross Species-Barriers, Abstract 88, 7th Annual Meeting of The American Society of Gene Therapy [Jun. 2-6, 2004] Minneapolis, Minnesota, p. 1, (e-published May 2, 2004).
Vandenberghe et al, AAV9 Targets Cone Photoreceptors in the Nonhuman Primate Retina, PLoS One, vol. 8(1):e53463. doi: 10.1371/journal.pone.0053463. (Epub Jan. 30, 2013).
Vandenberghe et al, Structure-Function Relationship of the Novel Non-Human Primate Adeno-associated Viruses, Abstract 99, Molecular Therapy, vol. 7(5):S15, (May 2003).
Vandenberghe LH et al, Naturally occurring singleton residues in AAV capsid impact vector performance and illustrate structural constraints. Gene Ther., vol. 16(12):1416-28, (Dec. 2009).
Vincent M et al, Comparison of the efficacy of five adeno-associated virus vectors for transducing dorsal raphé nucleus cells in the mouse. J Neurosci Methods, vol. 30(235):189-92, (Epub Jul. 18, 2014.).
Wang et al, Persistent expression of biologically active anti-HER2 antibody by AAVrh.10-mediated gene transfer, Cancer Gene Therapy, vol. 17(8):559-70. doi: 10.1038/cgt.2010.11. (Epub May 7, 2010).
Wang et al, Production of AAV Vectors with Different Serotypes, Abstract 906, Molecular Therapy, vol. 7(5):S350, (May 2003).
Wang et al, Systematic evaluation of AAV vectors for liver directed gene transfer in murine models, Mol Ther., vol. 18(1):118-25. doi: 10.1038/mt.2009.246. (Epub Oct. 27, 2009).
Wang et al, The pleiotropic effects of natural AAV infections on liver-directed gene transfer in macaques, Molecular Therapy, vol. 18(1):126-34, doi: 10.1038/mt.2009.245. (Epub Nov. 3, 2009).
Watanabe et al, AAVrh.10-mediated genetic delivery of bevacizumab to the pleura to provide local anti-VEGF to suppress growth of metastatic lung tumors. Gene Ther., vol. 17(8):1042-51. doi: 10.1038/gt.2010.87. (Epub Jul. 1, 2010).
wikipedia.com, "Fungus", accessed Jun. 3, 2013 from https://en.wikipedia.org/wiki/Fungus (last modified Nov. 17, 2015).
wikipedia.com, "List of sequenced bacterial genomes", accessed Jan. 24, 2014 from https://en.wikipedia.org/wiki/List_of_sequenced_bacterial_genomes (last modified Oct. 19, 2015).
wikipedia.com, "Mammal", accessed Sep. 22, 2011 from https://en.wikipedia.org/wiki/Mammal (last modified Nov. 19, 2015).
wikipedia.com, "Murinae", accessed Mar. 18, 2013 from https://en.wikipedia.org/wiki/Murinae (last modified Nov. 7, 2015).
wikipedia.com, "Plant", accessed Mar. 8, 2013 from https:/en.wikipedia.org/wiki/Plant (last modified Oct. 5, 2015).
wikipedia.com, "Viruses", accessed Nov. 24, 2012 from https://en.wikipedia.org/wiki/Virus (last modified Nov. 1, 2015).
Xiao et al, Gene Therapy Vectors based on Adeno-Associated Virus Type 1, Journal of Virology, 73(5):3994-4003, (May 1999).

(56) References Cited

OTHER PUBLICATIONS

Xiao et al, Production of High-titer Recombinant Adeno-Associated Virus Vectors in the Absence of Helper Adenovirus, 72(3):2224-2232, (Mar. 1998).
Xie, Q., et al., Towards the atomic structure of the adeno-associated virus 2 capsid, Infectious Disease Review, from the VIIIth Parvbovirus Workshop, Mont Tremblant, Quebec, Canada, vol. 2(3):136, (Jun. 28-Jul. 20, 2000).
Xin et al, "Induction of Robust Immune Response Against Human Immunodeficiency Virus is Supported by the Inherent Tropism of Adeno-Associated Virus Type 5 for Dendritic Cells" J. Virol, vol. 80(24):11899-11910, (Dec. 2006).
Yang B, et al, Global CNS transduction of adult mice by intravenously delivered rAAVrh.8 and rAAVrh.10 and nonhuman primates by rAAVrh.10., Mol Ther., vol. 22(7):1299-309, (Epub Apr. 30, 2014).
Zhang, H., et al., Several rAAV vectors efficiently cross the blood-brain barrier and transduce neurons and astrocytes in the neonatal mouse central nervous system, Molecular Therapy, vol. 19(8):1440-1448, (Aug. 2011).
Zhou et al, Direct Rescue and Cloning of Infectious Novel AAV Genomes From Non-Human Primate Tissues, Abstract 907, Molecular Therapy, 7(5):S350, (May 2003).
Zhou et al, Evaluation of Novel Gene Transfer Vectors Derived from Infectious Molecular Clones of Primate AAVs, Abstract 90, $7^{th}$ Annual Meeting of The American Society of Gene Therapy [Jun. 2-6, 2004] Minneapolis, Minnesota, p. 1, (e-published May 2, 2004).
Davidson, Beverly L., et al., Recombinant adeno-associated virus type 2, 4, and 5 vectors: transduction of variant cell types and regions in the mammalian central nervous system, PNAS, vol. 97.7 (2000): 3428-3432, (Mar. 28, 2000).
Mori, et al. "Two novel adeno-associated viruses from cynomolgus monkey: pseudotyping characterization of capsid protein." Virology 330.2 (2004): 375-383. (Dec. 2004).
Yan et al. "Inverted terminal repeat sequences are important for intermolecular recombination and circularization of adeno-associated virus genomes" J Virol. Jan. 2005;79(1):364-79. (Jan. 2005).
Girod et al. "Genetic capsid modifications allow efficient re-targeting of adeno-associated virus type 2." Nat Med. Sep. 1999;5(9):1052-6. (Sep. 1999).
Wu et al. "Mutational analysis of the adeno-associated virus type 2 (AAV2) capsid gene and construction of AAV2 vectors with altered tropism." J Virol. Sep. 2000;74(18):8635-47. (Sep. 2000).
Xiao et al. "Gene therapy vectors based on adeno-associated virus type 1." J Virol. May 1999;73(5):3994-4003. (May 1999).
Zhang et al. Journal of Xi'an Medical University (Chinese), vol. 18, No. 3. pp. 312-316, 320. (Sep. 1997).
Wu et al. Science in China Series C, vol. 31, No. 5, pp. 423-430. (Oct. 2001).
Trempe et al. "Alternate mRNA splicing is required for synthesis of adeno-associated virus VP1 capsid protein." J Virol. Sep. 1988;62(9):3356-63. (Sep. 1988).
Kapturczak et al. "Adeno-Associated Virus (AAV) as a Vehicle for Therapeutic Gene Delivery Improvements in Vector Design and Viral Production Enhance Potential to Prolong Graft Survival in Pancreatic Islet Cell Transplantation for the Reversal of Type 1 Diabetes." Curr Mol Med. May 2001;1(2):245-58. (May 2001).
Requirement for Restriction/Election issued in related U.S. Appl. No. 13/633,971, dated Feb. 28, 2014.
Response to Requirement for Restriction/Election dated Feb. 28, 2014 in related U.S. Appl. No. 13/633,971, dated Aug. 26, 2014.
Requirement for Restriction/Election issued in related U.S. Appl. No. 13/633,971, dated Nov. 6, 2014.
Response to Requirement for Restriction/Election dated Nov. 6, 2014 in related U.S. Appl. No. 13/633,971, dated Mar. 6, 2015.
Notice of Allowance issued in related U.S. Appl. No. 13/633,971, dated Jul. 21, 2015.
Office Action issued in related U.S. Appl. No. 13/633,971, dated Jul. 28, 2016.
Response to Office Action dated Jul. 28, 2016 in related U.S. Appl. No. 13/633,971, dated Dec. 28, 2016.
Office Action issued in related U.S. Appl. No. 13/633,971, dated Feb. 22, 2017.
Response to Office Action dated Feb. 22, 2017 in related U.S. Appl. No. 13/633,971, dated Aug. 3, 2017.
Notice of Allowance issued in related U.S. Appl. No. 13/633,971, dated Aug. 23, 2017.
Office Action issued in corresponding Brazilian Patent Application No. PI0214119.1, dated Jun. 12, 2015.
Office Action issued in corresponding Brazilian Patent Application No. PI0214119.1, dated Nov. 3, 2015.
Office Action issued in corresponding Brazilian Patent Application No. PI0214119.1, dated Mar. 1, 2016.
Office Action issued in corresponding Canadian Patent Application No. 2,756,866, dated May 10, 2013.
Response to Office Action dated May 10, 2013 issued in corresponding Canadian Patent Application No. 2,756,866, dated Sep. 30, 2013.
Office Action issued in corresponding Canadian Patent Application No. 2,756,866, dated Mar. 18, 2014.
Response to Office Action dated Mar. 18, 2014 issued in corresponding Canadian Patent Application No. 2,756,866, dated Sep. 17, 2014.
Office Action issued in corresponding Canadian Patent Application No. 2,756,866, dated May 4, 2015.
Response to Office Action dated May 4, 2015 issued in corresponding Canadian Patent Application No. 2,756,866, dated Nov. 3, 2016.
Office Action issued in corresponding Canadian Patent Application No. 2,756,866, dated Jan. 4, 2016.
Response to Office Action dated Jan. 4, 2016 issued in corresponding Canadian Patent Application No. 2,756,866, dated Jul. 4, 2016.
Office Action issued in corresponding Chinese Patent Application No. 201310326978.2, dated Nov. 19, 2014.
Office Action issued in corresponding Chinese Patent Application No. 201310326978.2, dated Aug. 10, 2015.
Office Action issued in corresponding Chinese Patent Application No. 201310326978.2, dated Apr. 29, 2016.
Office Action issued in corresponding Chinese Patent Application No. 201310326978.2, dated Jan. 10, 2017.
Office Action issued in corresponding Japanese Patent Application No. 2009-102988, dated Oct. 4, 2011.
Office Action issued in corresponding Japanese Patent Application No. 2009-102988, dated Jun. 19, 2012.
Office Action issued in corresponding Norwegian Patent Application No. 20150196, dated May 13, 2015.
Office Action issued in corresponding Norwegian Patent Application No. 20150196, dated Feb. 13, 2015.
Office Action issued in corresponding Philippine Patent Application No. 1-2014-501487, dated Oct. 25, 2016.
Response to Office Action dated Oct. 25, 2016 issued in corresponding Philippine Patent Application No. 1-2014-501487, dated Dec. 21, 2016.
Office Action issued in corresponding Philippine Patent Application No. 1-2014-501487, dated May 31, 2017.
Office Action issued in corresponding Mexican Patent Application No. MX/A/2011/008016, dated Oct. 24, 2014.
Extended European search report issued in corresponding European Patent Application No. 10178940.2, dated May 26, 2011.
International Search Report issued in corresponding International Application No. PCT/US2002/033629, dated Jul. 28, 2003.
International Preliminary Examination Report issued in corresponding International Application No. PCT/US2002/033629, dated Sep. 16, 2004.
Written Opinion issued in corresponding International Application No. PCT/US2002/033629, dated Aug. 11, 2004.
Adverum Biotechnologies Press Release—"Adverum Biotechnologies Provides Program Updates," Nov. 1, 2018. Available online at << http://investors.adverum.com/news-releases/news-release-details/adverum-biotechnologies-provides-program-updates >>.

(56) References Cited

OTHER PUBLICATIONS

Nzilambi et al., The prevalence of infection with human immunodeficiency virus over a 10-year period in rural zaire, NE J Med, 318(5):276-279, Feb. 1988.
Kawamura et al., Hiv-2 in West Africa in 1966, The Lancet, Feb. 1989, 385.
Le Guenno, HIV1 and HIV2: two ancient viruses for a new disease? Transactions of the Royal Society of Tropical Medicine and Hygiene, 1989, 83, 847.
Faria et al., The early spread and epidemic ignition of HIV-1 in human populations, Science, Oct. 2014, 346(6205):56-61.
F. Gao et al., Origin of HIV-1 in the chimpanzee Pan troglodytes troglodytes, Nature, Feb. 1999, 397 :436-440.
G. Gao et al., Clades of Adeno Associated Viruses Are Widely Disseminated in Human Tissues, J. Virol, Jun. 2004, 78(12):6381-8.
Wu et al., Mutational Analysis of the Adeno-Associated Virus Type 2 (AAV2) Capsid Gene and Construction of AAV2 Vectors With Altered Tropism, J. Virol, Sep. 2000, 74(18) :8635-47.
Moskaleno et al., Epitope Mapping of Human Anti-Adeno-Associated Virus Type 2 Neutralizing Antibodies: Implications for Gene Therapy and Virus Structure, J Virol, Feb. 2000, 74(4):1761-6.
Wobus et al., Monoclonal Antibodies against the Adeno-Associated Virus Type 2 (AAV-2) Capsid: Epitope Mapping and identification of Capsid Domains Involved in AAV-2-Cell Interaction and Neutralization of AAV-2 Infection, J Virol, Oct. 2000, 74(19) :9281-93.
Nam et al., Structure of Adeno-Associated Virus Serotype 8, a Gene Therapy Vector, J Virol, 81(22) :12260-71, Nov. 2007.
Shen et al., Characterization of the Relationship of AAV Capsid Domain Swapping to Liver Transduction Efficiency, Mol Ther, Aug. 2007, 15(11):1955-62.
Wang et al., Comparative Study of Liver Gene Transfer With AAV Vectors Based on Natural and Engineered AAV Capsids, Molecular Therapy, Dec. 2015, 23(12):1877-87.
Hu et al., RH10 provides superior transgene expression in mice when compared with natural AAV serotypes for neonatal gene therapy, J. Gene Med, Sep. 2010, 12(9): 766-778.
Girod et al., The VP1 capsid protein of adeno-associated virus type 2 is carrying a phospholipase A2 domain required for virus infectivity, J. General Virol, 2002, 83:973-978.
Grieger et al, Surface-Exposed Adeno-Associated Virus Vpl-NLS Capsid Fusion Protein Rescues Infectivity of Noninfectious Wild-Type Vp2/Vp3 and , Vp3-Only Capsids but Not That of Fivefold Pore Mutant Virions, J. Virol, 81(15):7833-7483, Aug. 2007.
Warrington et al, Adeno-Associated Virus Type 2 VP2 Capsid Protein Is Nonessential and Can Tolerate Large Peptide Insertions at Its N Terminus, J Virol, 78(1):6595-6609, Jun. 2004.
Li et al, 2015, Site-Directed Mutagenesis of Surface-Exposed Lysine Residues Leads to Improved Transduction by AAV2,But Not AAV8, Vectors in Murine Hepatocytes In Vivo, Hum Gene Ther Methods. Oct. 2015;26(6):211-20.
Grosse et al, Relevance of Assembly-Activating Protein for Adeno-associated Virus Vector Production and Capsid Protein Stability in Mammalian and Insect Cells, J Virol 91:e01198-17, Aug. 2017.
Sonntag et al, A viral assembly factor promotes AAV2 capsid formation in the nucleolus, PNAS, 107(22):10220-5, Jun. 2010.
Liu et al, Neutralizing antibodies against AAV2, AAV5 and AAV8 in healthy and HIV-1-infected subjects in China: implications for gene therapy using AAV vectors, Gene Therapy, 21:732-738, May 2014.
Mimuro et al, The Prevalence of Neutralizing Antibodies Against Adeno-Associated Virus Capsids Is Reduced in Young Japanese Individuals, J. Med Virol, 86:1990-7 Oct. 2013.
Vercauteren, Superior In vivo Transduction of Human Hepatocytes Using Engineered AAV3 Capsid, Mol Therapy, 24(6):1042-1049, Jun. 2016.
Chirmule et al., Immune responses to adenovirus and adeno-associated virus in humans, Gene Therapy, 6:1574-1583, Sep. 1999.
Bevan et al, Systemic Gene Delivery in Large Species for Targeting Spinal Cord, Brain, and Peripheral Tissues for Pediatric Disorders, Mol Ther. Nov. 2011;19(11):1971-80. doi: 10.1038/mt.2011.157. Epub Aug. 2, 2011.
Messina et al., 2012, Repeat Transduction in the Mouse Lung by Using Adeno-Associated Virus Vectors with Different Serotypes.
Halbert et al., Repeat Transduction in the Mouse Lung by Using Adeno-Associated Virus Vectors with Different Serotypes, J. Virol, 74(3):1524-1532, Feb. 2000.
Wu, Asokan & Samulski, Adeno-associated Virus Serotypes: Vector Toolkit for Human Gene Therapy, Molecular Therapy, 14(3):316-327, Sep. 2006.
Mao, et al. Angiotensin 1-7 Overexpression Mediated by a Capsid-optimized AAV8 Vector Leads to Significant Growth Inhibition of Hepatocellular Carcinoma In vivo, Int. J. Biol. Sci, Jan. 14, 2018.
Ling et al., Human Hepatocyte Growth Factor Receptor is a Cellular Coreceptor for Adeno-Associated Virus Serotype 3, Human Gene Therapy, 21:1741-1747 (Dec. 2010).
Suhy et al. Safe, Long-term Hepatic Expression of Anti-HCV shRNA in a Nonhuman Primate Model, Mol Ther. Sep. 2012;20(9):1737-49. doi: 10.1038/mt.2012.119. Epub Jun. 26, 2012.
Ling et al, Selective In Vivo Targeting of Human Liver Tumors by Optimized AAV3 Vectors in a Murine Xenograft Model, Hum Gene Ther. Dec. 2014;25(12):1023-34.
Chen et al., Epidemiology of hepatitis B virus infection in the Asia-Pacific region, J Gastroenterol Hepatol. May 2000;15 Suppl:E3-6.
Looker et al., An estimate of the global prevalence and incidence of herpes simplex virus type 2, Bull World Health Organ. Oct. 2008;86(10):805-12, A.
Hamilton et al., Adenoviral-Mediated Gene Transfer to Murine Small Intestine Is More Efficient in Neonates Than Adults, J Pediatr Surg. Feb. 1997;32(2):373-7.
Ellis et al, Virology Journal, Mar. 2013, A survey of ex vivo/in vitro transduction efficiency of mammalian primary cells and cell lines with Nine natural adeno-associated virus (AAV1-9) and one engineered adeno-associated virus serotype, 10:74.
Giles et al, Deamidation of Amino Acids on the Surface of Adeno-Associated Virus Capsids Leads to Charge Heterogeneity and Altered Vector Function, Mol Ther, 26(12), Dec. 2018.
Declaration of Oliver Danos, Ph.D. dated Aug. 14, 2018 , submitted in Opposition of EP Patent No. 02795539.2.
Declaration of Prof Asokan, dated Aug. 23, 2018, submitted in Opposition of EP Patent No. 02795539.2.
Declaration of Roberto Calcedo, PhD dated Sep. 24, 2018, submitted in Opposition of EP Patent No. 02795539.2.
Second declaration of Olivier Danos, Ph.D. dated Sep. 25, 2018, submitted in Opposition of EP Patent No. 02795539.2.
Proprietor's Submission pursuant to Rule 116 prior to oral proceedings dated Aug. 24, 2018 submitted in Opposition of EP Patent No. 02795539.2.
Opposer's Submission pursuant to Rule 116 prior to oral proceedings dated Aug. 24, 2018 submitted in Opposition of EP Patent No. 02795539.2.
Proprietor's Further Submission prior to oral proceedings dated Sep. 26, 2018 submitted in Opposition of EP Patent No. 02795539.2.
Opposer's Further Submission prior to oral proceedings dated Oct. 23, 2018 submitted in Opposition of EP Patent 02795539.2.
Summons to attend oral proceedings and Communication dated Mar. 29, 2018, issued in related European Patent No. 1453547.
Interlocutory decision in Opposition proceedings issued in related European Patent No. 1453547 on Nov. 30, 2018.

\* cited by examiner

FIG. 1A

```
                1                                                                                    50
       42_2     ..........  ..........  ..........  ..........  ..........
       42_8     ..........  ..........  ..........  ..........  ..........
      42_15     ..........  ..........  ..........  ..........  ..........
      42_5b     ..........  ..........  ..........  ..........  ..........
      42_1b     ..........  ..........  ..........  ..........  ..........
      42_13     ..........  ..........  ..........  ..........  ..........
      42_3a     ..........  ..........  ..........  ..........  ..........
       42_4     ..........  ..........  ..........  ..........  ..........
      42_5a     ..........  ..........  ..........  ..........  ..........
      42_10     ..........  ..........  ..........  ..........  ..........
      42_3b     ..........  ..........  ..........  ..........  ..........
      42_11     ..........  ..........  ..........  ..........  ..........
      42_6b     ..........  ..........  ..........  ..........  ..........
       43_1     ..........  ..........  ..........  ..........  ..........
       43_5     ..........  ..........  ..........  ..........  ..........
      43_12     ..........  ..........  ..........  ..........  ..........
      43_20     ..........  ..........  ..........  ..........  ..........
      43_21     ..........  ..........  ..........  ..........  ..........
      43_23     ..........  ..........  ..........  ..........  ..........
      43_25     ..........  ..........  ..........  ..........  ..........
       44_1     ..........  ..........  ..........  ..........  ..........
       44_5     ..........  ..........  ..........  ..........  ..........
     223_10     ..........  ..........  ..........  ..........  ..........
      223_2     ..........  ..........  ..........  ..........  ..........
      223_4     ..........  ..........  ..........  ..........  ..........
      223_5     ..........  ..........  ..........  ..........  ..........
      223_6     ..........  ..........  ..........  ..........  ..........
      223_7     ..........  ..........  ..........  ..........  ..........
       A3_4     ..........  ..........  ..........  ..........  ..........
       A3_5     ..........  ..........  ..........  ..........  ..........
       A3_7     ..........  ..........  ..........  ..........  ..........
       A3_3     ..........  ..........  ..........  ..........  ..........
      42_12     ..........  ..........  ..........  ..........  ..........
       AAV1     TTGCCCACTC  CCTCTCTGCG  CGCTCGCTCG  CTCGGTGGGG  CCTGCGGACC
       AAV2     TTGGCCACTC  CCTCTCTGCG  CGCTCGCTCG  CTCACTGAGG  CCGGGCGACC
       AAV3     TTGGCCACTC  CCTCTATGCG  CACTCGCTCG  CTCGGTGGGG  CCTGGCGACC
       AAV8     ..........  ..........  ..........  ..........  ..........
       AAV9     ..........  ..........  ..........  ..........  ..........
       AAV7     TTGGCCACTC  CCTCTATGCG  CGCTCGCTCG  CTCGGTGGGG  CCTGCGGACC
       44_2     ..........  ..........  ..........  ..........  ..........
```

FIG. 1C

```
Rep binding site                                                      150
    ┌─────────────────────┐          TRS
    ◄                     │           │
    42_2      ..........  .│........  ..│.......  ..........  ..........
    42_8      ..........  .│........  ..│.......  ..........  ..........
    42_15     ..........  ..........  ..........  ..........  ..........
    42_5b     ..........  ..........  ..........  ..........  ..........
    42_1b     ..........  ..........  ..........  ..........  ..........
    42_13     ..........  ..........  ..........  ..........  ..........
    42_3a     ..........  ..........  ..........  ..........  ..........
    42_4      ..........  ..........  ..........  ..........  ..........
    42_5a     ..........  ..........  ..........  ..........  ..........
    42_10     ..........  ..........  ..........  ..........  ..........
    42_3b     ..........  ..........  ..........  ..........  ..........
    42_11     ..........  ..........  ..........  ..........  ..........
    42_6b     ..........  ..........  ..........  ..........  ..........
    43_1      ..........  ..........  ..........  ..........  ..........
    43_5      ..........  ..........  ..........  ..........  ..........
    43_12     ..........  ..........  ..........  ..........  ..........
    43_20     ..........  ..........  ..........  ..........  ..........
    43_21     ..........  ..........  ..........  ..........  ..........
    43_23     ..........  ..........  ..........  ..........  ..........
    43_25     ..........  ..........  ..........  ..........  ..........
    44_1      ..........  ..........  ..........  ..........  ..........
    44_5      ..........  ..........  ..........  ..........  ..........
    223_10    ..........  ..........  ..........  ..........  ..........
    223_2     ..........  ..........  ..........  ..........  ..........
    223_4     ..........  ..........  ..........  ..........  ..........
    223_5     ..........  ..........  ..........  ..........  ..........
    223_6     ..........  ..........  ..........  ..........  ..........
    223_7     ..........  ..........  ..........  ..........  ..........
    A3_4      ..........  ..........  ..........  ..........  ..........
    A3_5      ..........  ..........  ..........  ..........  ..........
    A3_7      ..........  ..........  ..........  ..........  ..........
    A3_3      ..........  ..........  ..........  ..........  ..........
    42_12     ..........  ..........  ..........  ..........  ..........
    AAV1      GAGCGCGCAG  AGAGGGAGTG  GGCAACTCCA  TCACTAGGGG  TAATCGCGAA
    AAV2      GAGCGCGCAG  AGAGGGAGTG  GCCAACTCCA  TCACTAGGGG  TTC.......
    AAV3      CAGTGCGCAT  AGAGGGAGTG  GCCAACTCCA  TCACTAGAGG  T.........
    AAV8      .......CAG  AGAGGGAGTG  GCCAACTCCA  TCACTAGGGG  TAG.CGCGAA
    AAV9      .......CAG  AGAGGGAGTG  GCCAACTCCA  TCACTAGGGG  TAATCGCGAA
    AAV7      GAGCGCGCAT  AGAGGGAGTG  GCCAACTCCA  TCACTAGGGG  TA.CCGCGAA
    44_2      ..........  .│........  ..│.......  ..........  ..........
    ◄─────────────────────┘           │
Rep binding site                     TRS
```

FIG. 1D

```
         151                                                              200
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     GCGCCTCCCA  CGCTGCCGCG  TCAGCGCTGA  CGTAAATTAC  GTCATAGGGG
AAV2     .......CTG  GAGGGGTGGA  GTCGTGACGT  GAATTACGTC  ATAGGGTTAG
AAV3     .......ATG  GCAGTGACGT  AACGCGAAGC  GCGCGAAGCG  AGACCACGCC
AAV8     GCGCCTCCCA  CGCTGCCGCG  TCAGCGCTGA  CGTAAATTAC  GTCATAGGGG
AAV9     GCGCCTCCCA  CGCTGCCGCG  TCAGCGCTGA  CGTAGATTAC  GTCATAGGGG
AAV7     GCGCCTCCCA  CGCTGCCGCG  TCAGCGCTGA  CGTAAATCAC  GTCATAGGGG
44_2     ..........  ..........  ..........  ..........  ..........
```

FIG. 1H

```
         351                                                          400
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
 223_10   ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   CGAGATCGTG  ATCAAGGTGC  CGAGCGACCT  GGACGAGCAC  CTGCCGGGCA
   AAV2   CGAGATTGTG  ATTAAGGTCC  CCAGCGACCT  TGACGGGCAT  CTGCCGGGCA
   AAV3   CGAGATTGTC  CTGAAGGTCC  CGAGTGACCT  GGACGAGCGC  CTGCCGGGCA
   AAV8   CGAGATCGTG  ATCAAGGTGC  CGAGCGACCT  GGACGAGCAC  CTGCCGGGCA
   AAV9   CGAGATTGTG  ATCAAGGTGC  CGAGCGACCT  GGACGAGCAC  CTGCCGGGCA
   AAV7   CGAGATCGTG  ATCAAGGTGC  CGAGCGACCT  GGACGAGCAC  CTGCCGGGCA
   44_2   ..........  ..........  ..........  ..........  ..........
```

FIG. 1I

```
         401                                                          450
  42_2   ..........  ..........  ..........  ..........  ..........
  42_8   ..........  ..........  ..........  ..........  ..........
  42_15  ..........  ..........  ..........  ..........  ..........
  42_5b  ..........  ..........  ..........  ..........  ..........
  42_1b  ..........  ..........  ..........  ..........  ..........
  42_13  ..........  ..........  ..........  ..........  ..........
  42_3a  ..........  ..........  ..........  ..........  ..........
  42_4   ..........  ..........  ..........  ..........  ..........
  42_5a  ..........  ..........  ..........  ..........  ..........
  42_10  ..........  ..........  ..........  ..........  ..........
  42_3b  ..........  ..........  ..........  ..........  ..........
  42_11  ..........  ..........  ..........  ..........  ..........
  42_6b  ..........  ..........  ..........  ..........  ..........
  43_1   ..........  ..........  ..........  ..........  ..........
  43_5   ..........  ..........  ..........  ..........  ..........
  43_12  ..........  ..........  ..........  ..........  ..........
  43_20  ..........  ..........  ..........  ..........  ..........
  43_21  ..........  ..........  ..........  ..........  ..........
  43_23  ..........  ..........  ..........  ..........  ..........
  43_25  ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
  42_12  ..........  ..........  ..........  ..........  ..........
  AAV1   TTTCTGACTC  GTTTGTGAGC  TGGGTGGCCG  AGAAGGAATG  GGAGCTGCCC
  AAV2   TTTCTGACAG  CTTTGTGAAC  TGGGTGGCCG  AGAAGGAATG  GGAGTTGCCG
  AAV3   TTTCTAACTC  GTTTGTTAAC  TGGGTGGCCG  AGAAGGAATG  GGACGTGCCG
  AAV8   TTTCTGACTC  GTTTGTGAAC  TGGGTGGCCG  AGAAGGAATG  GGAGCTGCCC
  AAV9   TTTCTGACTC  TTTTGTGAAC  TGGGTGGCCG  AGAAGGAATG  GGAGCTGCCC
  AAV7   TTTCTGACTC  GTTTGTGAAC  TGGGTGGCCG  AGAAGGAATG  GGAGCTGCCC
  44_2   ..........  ..........  ..........  ..........  ..........
```

FIG. 1J

```
          451                                                          500
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
 223_10   ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   CCGGATTCTG  ACATGGATCT  GAATCTGATT  GAGCAGGCAC  CCCTGACCGT
   AAV2   CCAGATTCTG  ACATGGATCT  GAATCTGATT  GAGCAGGCAC  CCCTGACCGT
   AAV3   CCGGATTCTG  ACATGGATCC  GAATCTGATT  GAGCAGGCAC  CCCTGACCGT
   AAV8   CCGGATTCTG  ACATGGATCG  GAATCTGATC  GAGCAGGCAC  CCCTGACCGT
   AAV9   CCGGATTCTG  ACATGGATCG  GAATCTGATC  GAGCAGGCAC  CCCTGACCGT
   AAV7   CCGGATTCTG  ACATGGATCT  GAATCTGATC  GAGCAGGCAC  CCCTGACCGT
   44_2   ..........  ..........  ..........  ..........  ..........
```

FIG. 1K

```
           501                                                          550
  42_2     ..........  ..........  ..........  ..........  ..........
  42_8     ..........  ..........  ..........  ..........  ..........
  42_15    ..........  ..........  ..........  ..........  ..........
  42_5b    ..........  ..........  ..........  ..........  ..........
  42_1b    ..........  ..........  ..........  ..........  ..........
  42_13    ..........  ..........  ..........  ..........  ..........
  42_3a    ..........  ..........  ..........  ..........  ..........
  42_4     ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    ..........  ..........  ..........  ..........  ..........
  43_1     ..........  ..........  ..........  ..........  ..........
  43_5     ..........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
  44_1     ..........  ..........  ..........  ..........  ..........
  44_5     ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
  A3_4     ..........  ..........  ..........  ..........  ..........
  A3_5     ..........  ..........  ..........  ..........  ..........
  A3_7     ..........  ..........  ..........  ..........  ..........
  A3_3     ..........  ..........  ..........  ..........  ..........
  42_12    ..........  ..........  ..........  ..........  ..........
  AAV1     GGCCGAGAAG  CTGCAGCGCG  ACTTCCTGGT  CCAATGGCGC  CGCGTGAGTA
  AAV2     GGCCGAGAAG  CTGCAGCGCG  ACTTTCTGAC  GGAATGGCGC  CGTGTGAGTA
  AAV3     GGCCGAAAAG  CTTCAGCGCG  AGTTCCTGGT  GGAGTGGCGC  CGCGTGAGTA
  AAV8     GGCCGAGAAG  CTGCAGCGCG  ACTTCCTGGT  CCAATGGCGC  CGCGTGAGTA
  AAV9     GGCCGAGAAG  CTGTAGCGCG  ACTTCCTGGT  CCAATGGCGC  CGCGTGAGTA
  AAV7     GGCCGAGAAG  CTGCAGCGCG  ACTTCCTGGT  CCAATGGCGC  CGCGTGAGTA
  44_2     ..........  ..........  ..........  ..........  ..........
```

FIG. 1L

```
          551                                                            600
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
 223_10   ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   AGGCCCCGGA  GGCCCTCTTC  TTTGTTCAGT  TCGAGAAGGG  CGAGTCCTAC
   AAV2   AGGCCCCGGA  GGCCCTTTTC  TTTGTGCAAT  TTGAGAAGGG  AGAGAGCTAC
   AAV3   AGGCCCCGGA  GGCCCTCTTT  TTTGTCCAGT  TCGAAAAGGG  GGAGACCTAC
   AAV8   AGGCCCCGGA  GGCCCTCTTC  TTTGTTCAGT  TCGAGAAGGG  CGAGAGCTAC
   AAV9   AGGCCCCGGA  GGCCCTCTTC  TTTGTTCAGT  TCGAGAAGGG  CGAGAGCTAC
   AAV7   AGGCCCCGGA  GGCCCTGTTC  TTTGTTCAGT  TCGAGAAGGG  CGAGAGCTAC
   44_2   ..........  ..........  ..........  ..........  ..........
```

FIG. 1M

```
           601                                                                      650
  42_2     ..........  ..........  ..........  ..........  ..........
  42_8     ..........  ..........  ..........  ..........  ..........
  42_15    ..........  ..........  ..........  ..........  ..........
  42_5b    ..........  ..........  ..........  ..........  ..........
  42_1b    ..........  ..........  ..........  ..........  ..........
  42_13    ..........  ..........  ..........  ..........  ..........
  42_3a    ..........  ..........  ..........  ..........  ..........
  42_4     ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    ..........  ..........  ..........  ..........  ..........
  43_1     ..........  ..........  ..........  ..........  ..........
  43_5     ..........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
  44_1     ..........  ..........  ..........  ..........  ..........
  44_5     ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
  A3_4     ..........  ..........  ..........  ..........  ..........
  A3_5     ..........  ..........  ..........  ..........  ..........
  A3_7     ..........  ..........  ..........  ..........  ..........
  A3_3     ..........  ..........  ..........  ..........  ..........
  42_12    ..........  ..........  ..........  ..........  ..........
  AAV1     TTCCACCTCC  ATATTCTGGT  GGAGACCACG  GGGGTCAAAT  CCATGGTGCT
  AAV2     TTCCACATGC  ACGTGCTCGT  GGAAACCACC  GGGGTGAAAT  CCATGGTTTT
  AAV3     TTCCACCTGC  ACGTGCTGAT  TGAGACCATC  GGGGTCAAAT  CCATGGTGGT
  AAV8     TTTCACCTGC  ACGTTCTGGT  CGAGACCACG  GGGGTCAAGT  CCATGGTGCT
  AAV9     TTTCACCTGC  ACGTTCTGGT  CGAGACCACG  GGGGTCAAGT  CCATGGTGCT
  AAV7     TTCCACCTTC  ACGTTCTGGT  GGAGACCACG  GGGGTCAAGT  CCATGGTGCT
  44_2     ..........  ..........  ..........  ..........  ..........
```

FIG. 1N

```
         651                                                              700
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     GGGCCGCTTC  CTGAGTCAGA  TTAGGGACAA  GCT.GGTGCA  GACCATCTAC
AAV2     GGGACGTTTC  CTGAGTCAGA  TTCGCGAAAA  ACT..GATTC  AGAGAATTTA
AAV3     CGGCCGCTAC  GTGAGCCAGA  TTAAAGAGAA  GCT..GGTGA  CCCGCATCTA
AAV8     AGGCCGCTTC  CTGAGTCAGA  TTCGGGAAAA  GCTTGGTCCA  GACCATCTAC
AAV9     AGGCCGCTTC  CTGAGTCAGA  TTCGGGAGAA  GCT.GGTCCA  GACCATCTAC
AAV7     AGGCCGCTTC  CTGAGTCAGA  TTCGGGAGAA  GCT.....G..  GTCCAGACCA
44_2     ..........  ..........  ..........  ..........  ..........
```

FIG. 10

```
          701                                                              750
 42_2     ..........  ..........  ..........  ..........  ..........
 42_8     ..........  ..........  ..........  ..........  ..........
 42_15    ..........  ..........  ..........  ..........  ..........
 42_5b    ..........  ..........  ..........  ..........  ..........
 42_1b    ..........  ..........  ..........  ..........  ..........
 42_13    ..........  ..........  ..........  ..........  ..........
 42_3a    ..........  ..........  ..........  ..........  ..........
 42_4     ..........  ..........  ..........  ..........  ..........
 42_5a    ..........  ..........  ..........  ..........  ..........
 42_10    ..........  ..........  ..........  ..........  ..........
 42_3b    ..........  ..........  ..........  ..........  ..........
 42_11    ..........  ..........  ..........  ..........  ..........
 42_6b    ..........  ..........  ..........  ..........  ..........
 43_1     ..........  ..........  ..........  ..........  ..........
 43_5     ..........  ..........  ..........  ..........  ..........
 43_12    ..........  ..........  ..........  ..........  ..........
 43_20    ..........  ..........  ..........  ..........  ..........
 43_21    ..........  ..........  ..........  ..........  ..........
 43_23    ..........  ..........  ..........  ..........  ..........
 43_25    ..........  ..........  ..........  ..........  ..........
 44_1     ..........  ..........  ..........  ..........  ..........
 44_5     ..........  ..........  ..........  ..........  ..........
223_10    ..........  ..........  ..........  ..........  ..........
223_2     ..........  ..........  ..........  ..........  ..........
223_4     ..........  ..........  ..........  ..........  ..........
223_5     ..........  ..........  ..........  ..........  ..........
223_6     ..........  ..........  ..........  ..........  ..........
223_7     ..........  ..........  ..........  ..........  ..........
 A3_4     ..........  ..........  ..........  ..........  ..........
 A3_5     ..........  ..........  ..........  ..........  ..........
 A3_7     ..........  ..........  ..........  ..........  ..........
 A3_3     ..........  ..........  ..........  ..........  ..........
 42_12    ..........  ..........  ..........  ..........  ..........
 AAV1     C.GCGGGATC  GAGCCG.ACC  CTGCCCAACT  GGTTCGCGGT  GACCAA.GAC
 AAV2     CCGCGGGATC  GAGCCG.ACT  TTGCCAAACT  GGTTCGCGGT  CACAAA...G
 AAV3     CCGCGGGGTC  GAGCCG.CAG  CTTCCGAACT  GGTTCGCGGT  GACCAA...A
 AAV8     CCGCGGGGTC  GAGCCCCACC  TTGCCCAACT  GGTTCGCGGT  GACCAAAGAC
 AAV9     C.GCGGGATC  GAGCCG.ACC  CTGCCCAACT  GGTTCGCGGT  GACCAA.GAC
 AAV7     TCTACCGCGG  GGTCGAGCCC  ACGCTGCCCA  ACTGGTTCGC  GGTGACCAAG
 44_2     ..........  ..........  ..........  ..........  ..........
```

FIG. 1P

```
         751                                                              800
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   GCG.TAATGG  CGCCGGAGGG  GCG.AACAAG  GTGGTGGACG  AGTGCTACAT
  AAV2   ACCAGAAATG  GCGCCGGAGG  CGGGAACAAG  GTGGTGGATG  AGTGCTACAT
  AAV3   ACGCGAAATG  GCGCCGGGGG  CGGGAACAAG  GTGGTCGACG  ACTGCTACAT
  AAV8   GCGGTAATGG  CGCCGGCGGG  GGGAACAAG   GTGGTGGACG  AGTGCTACAT
  AAV9   GCG.TAATGG  CGCCGGCGGG  GGG.AACAAG  GTGGTGGACG  AGTGCTACAT
  AAV7   ACGCGTAATG  GCGCCGGCGG  GGGGAACAAG  GTGGTGGACG  AGTGCTACAT
  44_2   ..........  ..........  ..........  ..........  ..........
```

FIG. 1Q

```
              801                                                      850
     42_2     ..........  ..........  ..........  ..........  ..........
     42_8     ..........  ..........  ..........  ..........  ..........
    42_15     ..........  ..........  ..........  ..........  ..........
    42_5b     ..........  ..........  ..........  ..........  ..........
    42_1b     ..........  ..........  ..........  ..........  ..........
    42_13     ..........  ..........  ..........  ..........  ..........
    42_3a     ..........  ..........  ..........  ..........  ..........
     42_4     ..........  ..........  ..........  ..........  ..........
    42_5a     ..........  ..........  ..........  ..........  ..........
    42_10     ..........  ..........  ..........  ..........  ..........
    42_3b     ..........  ..........  ..........  ..........  ..........
    42_11     ..........  ..........  ..........  ..........  ..........
    42_6b     ..........  ..........  ..........  ..........  ..........
     43_1     ..........  ..........  ..........  ..........  ..........
     43_5     ..........  ..........  ..........  ..........  ..........
    43_12     ..........  ..........  ..........  ..........  ..........
    43_20     ..........  ..........  ..........  ..........  ..........
    43_21     ..........  ..........  ..........  ..........  ..........
    43_23     ..........  ..........  ..........  ..........  ..........
    43_25     ..........  ..........  ..........  ..........  ..........
     44_1     ..........  ..........  ..........  ..........  ..........
     44_5     ..........  ..........  ..........  ..........  ..........
   223_30     ..........  ..........  ..........  ..........  ..........
    223_2     ..........  ..........  ..........  ..........  ..........
    223_4     ..........  ..........  ..........  ..........  ..........
    223_5     ..........  ..........  ..........  ..........  ..........
    223_6     ..........  ..........  ..........  ..........  ..........
    223_7     ..........  ..........  ..........  ..........  ..........
     A3_4     ..........  ..........  ..........  ..........  ..........
     A3_5     ..........  ..........  ..........  ..........  ..........
     A3_7     ..........  ..........  ..........  ..........  ..........
     A3_3     ..........  ..........  ..........  ..........  ..........
    42_12     ..........  ..........  ..........  ..........  ..........
     AAV1     CCCCAACTAC  CTCCTGCCCA  AGACTCAGCC  CGAGCTGCAG  TGGGCGTGGA
     AAV2     CCCCAATTAC  TTGCTCCCCA  AAACCCAGCC  TGAGCTCCAG  TGGGCGTGGA
     AAV3     CCCCAACTAC  CTGCTCCCCA  AGACCCAGCC  CGAGCTCCAG  TGGGCGTGGA
     AAV8     CCCCAACTAC  CTCCTGCCCA  AGACTCAGCC  CGAGCTGCAG  TGGGCGTGGA
     AAV9     CCCCAACTAC  CTCCTGCCCA  AGACTCAGCC  CGAGCTGCAG  TGGGCGTGGA
     AAV7     CCCCAACTAC  CTCCTGCCCA  AGACCCAGCC  CGAGCTGCAG  TGGGCGTGGA
     44_2     ..........  ..........  ..........  ..........  ..........
```

P19/TATA                        P19 RNA
   42_2      ..........   ..........   ..........   ..........   ..........
   42_8      ..........   ..........   ..........   ..........   ..........
   42_15     ..........   ..........   ..........   ..........   ..........
   42_5b     ..........   ..........   ..........   ..........   ..........
   42_1b     ..........   ..........   ..........   ..........   ..........
   42_13     ..........   ..........   ..........   ..........   ..........
   42_3a     ..........   ..........   ..........   ..........   ..........
   42_4      ..........   ..........   ..........   ..........   ..........
   42_5a     ..........   ..........   ..........   ..........   ..........
   42_10     ..........   ..........   ..........   ..........   ..........
   42_3b     ..........   ..........   ..........   ..........   ..........
   42_11     ..........   ..........   ..........   ..........   ..........
   42_6b     ..........   ..........   ..........   ..........   ..........
   43_1      ..........   ..........   ..........   ..........   ..........
   43_5      ..........   ..........   ..........   ..........   ..........
   43_12     ..........   ..........   ..........   ..........   ..........
   43_20     ..........   ..........   ..........   ..........   ..........
   43_21     ..........   ..........   ..........   ..........   ..........
   43_23     ..........   ..........   ..........   ..........   ..........
   43_25     ..........   ..........   ..........   ..........   ..........
   44_1      ..........   ..........   ..........   ..........   ..........
   44_5      ..........   ..........   ..........   ..........   ..........
   223_10    ..........   ..........   ..........   ..........   ..........
   223_2     ..........   ..........   ..........   ..........   ..........
   223_4     ..........   ..........   ..........   ..........   ..........
   223_5     ..........   ..........   ..........   ..........   ..........
   223_6     ..........   ..........   ..........   ..........   ..........
   223_7     ..........   ..........   ..........   ..........   ..........
   A3_4      ..........   ..........   ..........   ..........   ..........
   A3_5      ..........   ..........   ..........   ..........   ..........
   A3_7      ..........   ..........   ..........   ..........   ..........
   A3_3      ..........   ..........   ..........   ..........   ..........
   42_12     ..........   ..........   ..........   ..........   ..........
   AAV1      CTAACATGGA   GGAGTATATA   AGCGCCTGTT   TGAACCTGGC   CGAGCGCAAA
   AAV2      CTAATATGGA   ACAGTATTTA   AGCGCCTGTT   TGAATCTCAC   GGAGCGTAAA
   AAV3      CTAACATGGA   CCAGTATTTA   AGCGCCTGTT   TGAATCTCGC   GGAGCGTAAA
   AAV8      CTAACATGGA   GGAGTATATA   AGCGCGTGCT   TGAACCTGGC   CGAGCGCAAA
   AAV9      CTAACATGGA   GGAGTATATA   AGCGCGTGCT   TGAACCTGGC   CGAGCGCAAA
   AAV7      CTAACATGGA   GGAGTATATA   AGCGCGTGTT   TGAACCTGGC   CGAACGCAAA
   44_2      ..........   ..........   ..........   ..........   ..........
                                P19/TATA                        P19 RNA
```

FIG. 1S

|    | 901 | | | | 950 |
|---|---|---|---|---|---|
| 42_2 | .......... | .......... | .......... | .......... | .......... |
| 42_8 | .......... | .......... | .......... | .......... | .......... |
| 42_15 | .......... | .......... | .......... | .......... | .......... |
| 42_5b | .......... | .......... | .......... | .......... | .......... |
| 42_1b | .......... | .......... | .......... | .......... | .......... |
| 42_13 | .......... | .......... | .......... | .......... | .......... |
| 42_3a | .......... | .......... | .......... | .......... | .......... |
| 42_4 | .......... | .......... | .......... | .......... | .......... |
| 42_5a | .......... | .......... | .......... | .......... | .......... |
| 42_10 | .......... | .......... | .......... | .......... | .......... |
| 42_3b | .......... | .......... | .......... | .......... | .......... |
| 42_11 | .......... | .......... | .......... | .......... | .......... |
| 42_6b | .......... | .......... | .......... | .......... | .......... |
| 43_1 | .......... | .......... | .......... | .......... | .......... |
| 43_5 | .......... | .......... | .......... | .......... | .......... |
| 43_12 | .......... | .......... | .......... | .......... | .......... |
| 43_20 | .......... | .......... | .......... | .......... | .......... |
| 43_21 | .......... | .......... | .......... | .......... | .......... |
| 43_23 | .......... | .......... | .......... | .......... | .......... |
| 43_25 | .......... | .......... | .......... | .......... | .......... |
| 44_1 | .......... | .......... | .......... | .......... | .......... |
| 44_5 | .......... | .......... | .......... | .......... | .......... |
| 223_10 | .......... | .......... | .......... | .......... | .......... |
| 223_2 | .......... | .......... | .......... | .......... | .......... |
| 223_4 | .......... | .......... | .......... | .......... | .......... |
| 223_5 | .......... | .......... | .......... | .......... | .......... |
| 223_6 | .......... | .......... | .......... | .......... | .......... |
| 223_7 | .......... | .......... | .......... | .......... | .......... |
| A3_4 | .......... | .......... | .......... | .......... | .......... |
| A3_5 | .......... | .......... | .......... | .......... | .......... |
| A3_7 | .......... | .......... | .......... | .......... | .......... |
| A3_3 | .......... | .......... | .......... | .......... | .......... |
| 42_12 | .......... | .......... | .......... | .......... | .......... |
| AAV1 | CGGCTCGTGG | CGCAGCACCT | GACCCACGTC | AGCCAGACCC | AGGAGCAGAA |
| AAV2 | CGGTTGGTGG | CGCAGCATCT | GACGCACGTG | TCGCAGACGC | AGGAGCAGAA |
| AAV3 | CGGCTGGTGG | CGCAGCATCT | GACGCACGTG | TCGCAGACGC | AGGAGCAGAA |
| AAV8 | CGGCTCGTGG | CGCAGCACCT | GACCCACGTC | AGCCAGACGC | AGGAGCAGAA |
| AAV9 | CGGCTCGTGG | CGCAGCACCT | GACCCACGTC | AGCCAGACGC | AGGAGCAGAA |
| AAV7 | CGGCTCGTGG | CGCAGCACCT | GACCCACGTC | AGCCAGACGC | AGGAGCAGAA |
| 44_2 | .......... | .......... | .......... | .......... | .......... |

FIG. 1T

```
           951                                                          1000
  42_2     ..........  ..........  ..........  ..........  ..........
  42_8     ..........  ..........  ..........  ..........  ..........
  42_15    ..........  ..........  ..........  ..........  ..........
  42_5b    ..........  ..........  ..........  ..........  ..........
  42_1b    ..........  ..........  ..........  ..........  ..........
  42_13    ..........  ..........  ..........  ..........  ..........
  42_3a    ..........  ..........  ..........  ..........  ..........
  42_4     ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    ..........  ..........  ..........  ..........  ..........
  43_1     ..........  ..........  ..........  ..........  ..........
  43_5     ..........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
  44_1     ..........  ..........  ..........  ..........  ..........
  44_5     ..........  ..........  ..........  ..........  ..........
 223_10    ..........  ..........  ..........  ..........  ..........
 223_2     ..........  ..........  ..........  ..........  ..........
 223_4     ..........  ..........  ..........  ..........  ..........
 223_5     ..........  ..........  ..........  ..........  ..........
 223_6     ..........  ..........  ..........  ..........  ..........
 223_7     ..........  ..........  ..........  ..........  ..........
  A3_4     ..........  ..........  ..........  ..........  ..........
  A3_5     ..........  ..........  ..........  ..........  ..........
  A3_7     ..........  ..........  ..........  ..........  ..........
  A3_3     ..........  ..........  ..........  ..........  ..........
  42_12    ..........  ..........  ..........  ..........  ..........
  AAV1     CAAGGAGAAT  CTGAACCCCA  ATTCTGACGC  GCCTGTCATC  CGGTCAAAAA
  AAV2     CAAAGAGAAT  CAGAATCCCA  ATTCTGATGC  GCCGGTCATC  AGATCAAAAA
  AAV3     CAAAGAGAAT  CAGAACCCCA  ATTCTGACGC  GCCGGTCATC  AGGTCAAAAA
  AAV8     CAAGGAGAAT  CTGAACCCCA  ATTCTGACGC  GCCCGTGATC  AGGTCAAAAA
  AAV9     CAAGGAGAAT  CTGAACCCCA  ATTCTGACGC  GCCCGTGATC  AGGTCAAAAA
  AAV7     CAAGGAGAAT  CTGAACCCCA  ATTCTGACGC  GCCCGTGATC  AGGTCAAAAA
  44_2     ..........  ..........  ..........  ..........  ..........
```

FIG. 1U

```
                          1001                                                                    1050
                                Rep52/40 start codon
        42_2      ..........  ..........  ..........  ..........  ..........
        42_8      ..........  ..........  ..........  ..........  ..........
        42_15     ..........  ..........  ..........  ..........  ..........
        42_5b     ..........  ..........  ..........  ..........  ..........
        42_1b     ..........  ..........  ..........  ..........  ..........
        42_13     ..........  ..........  ..........  ..........  ..........
        42_3a     ..........  ..........  ..........  ..........  ..........
        42_4      ..........  ..........  ..........  ..........  ..........
        42_5a     ..........  ..........  ..........  ..........  ..........
        42_10     ..........  ..........  ..........  ..........  ..........
        42_3b     ..........  ..........  ..........  ..........  ..........
        42_11     ..........  ..........  ..........  ..........  ..........
        42_6b     ..........  ..........  ..........  ..........  ..........
        43_1      ..........  ..........  ..........  ..........  ..........
        43_5      ..........  ..........  ..........  ..........  ..........
        43_12     ..........  ..........  ..........  ..........  ..........
        43_20     ..........  ..........  ..........  ..........  ..........
        43_21     ..........  ..........  ..........  ..........  ..........
        43_23     ..........  ..........  ..........  ..........  ..........
        43_25     ..........  ..........  ..........  ..........  ..........
        44_1      ..........  ..........  ..........  ..........  ..........
        44_5      ..........  ..........  ..........  ..........  ..........
        223_10    ..........  ..........  ..........  ..........  ..........
        223_2     ..........  ..........  ..........  ..........  ..........
        223_4     ..........  ..........  ..........  ..........  ..........
        223_5     ..........  ..........  ..........  ..........  ..........
        223_6     ..........  ..........  ..........  ..........  ..........
        223_7     ..........  ..........  ..........  ..........  ..........
        A3_4      ..........  ..........  ..........  ..........  ..........
        A3_5      ..........  ..........  ..........  ..........  ..........
        A3_7      ..........  ..........  ..........  ..........  ..........
        A3_3      ..........  ..........  ..........  ..........  ..........
        42_12     ..........  ..........  ..........  ..........  ..........
        AAV1      CCTCCGCGCG  CTACATGGAG  CTGGTCGGGT  GGCTGGTGGA  CCGGGGCATC
        AAV2      CTTCAGCCAG  GTACATGGAG  CTGGTCGGGT  GGCTCGTGGA  CAAGGGGATT
        AAV3      CCTCAGCCAG  GTACATGGAG  CTGGTCGGGT  GGCTGGTGGA  CCGCGGGATC
        AAV6      CCTCCGCGCG  CTATATGGAG  CTGGTCGGGT  GGCTGGTGGA  CCGGGGCATC
        AAV9      CCTCCGCGCG  CTACATGGAG  CTGGTCGGGT  GGCTGGTGGA  CCGGGGCATC
        AAV7      CCTCCGCGCG  CTACATGGAG  CTGGTCGGGT  GGCTGGTGGA  CCGGGGCATC
        44_2      ..........  ..........  ..........  ..........  ..........
                                Rep 52/40 start
```

FIG. 1V

```
           1051                                                       1100
42_2       ..........  ..........  ..........  ..........  ..........
42_8       ..........  ..........  ..........  ..........  ..........
42_15      ..........  ..........  ..........  ..........  ..........
42_5b      ..........  ..........  ..........  ..........  ..........
42_1b      ..........  ..........  ..........  ..........  ..........
42_13      ..........  ..........  ..........  ..........  ..........
42_3a      ..........  ..........  ..........  ..........  ..........
42_4       ..........  ..........  ..........  ..........  ..........
42_5a      ..........  ..........  ..........  ..........  ..........
42_10      ..........  ..........  ..........  ..........  ..........
42_3b      ..........  ..........  ..........  ..........  ..........
42_11      ..........  ..........  ..........  ..........  ..........
42_6b      ..........  ..........  ..........  ..........  ..........
43_1       ..........  ..........  ..........  ..........  ..........
43_5       ..........  ..........  ..........  ..........  ..........
43_12      ..........  ..........  ..........  ..........  ..........
43_20      ..........  ..........  ..........  ..........  ..........
43_21      ..........  ..........  ..........  ..........  ..........
43_23      ..........  ..........  ..........  ..........  ..........
43_25      ..........  ..........  ..........  ..........  ..........
44_1       ..........  ..........  ..........  ..........  ..........
44_5       ..........  ..........  ..........  ..........  ..........
223_10     ..........  ..........  ..........  ..........  ..........
223_2      ..........  ..........  ..........  ..........  ..........
223_4      ..........  ..........  ..........  ..........  ..........
223_5      ..........  ..........  ..........  ..........  ..........
223_6      ..........  ..........  ..........  ..........  ..........
223_7      ..........  ..........  ..........  ..........  ..........
A3_4       ..........  ..........  ..........  ..........  ..........
A3_5       ..........  ..........  ..........  ..........  ..........
A3_7       ..........  ..........  ..........  ..........  ..........
A3_3       ..........  ..........  ..........  ..........  ..........
42_12      ..........  ..........  ..........  ..........  ..........
AAV1       ACCTCCGAGA  AGCAGTGGAT  CCAGGAGGAC  CAGGCCTCGT  ACATCTCCTT
AAV2       ACCTCGGAGA  AGCAGTGGAT  CCAGGAGGAC  CAGGCCTCAT  ACATCTCCTT
AAV3       ACGTCAGAAA  AGCAATGGAT  TCAGGAGGAC  CAGGCCTCGT  ACATCTCCTT
AAV8       ACCTCCGAGA  AGCAGTGGAT  CCAGGAGGAC  CAGGCCTCGT  ACATCTCCTT
AAV9       ACCTCCGAGA  AGCAGTGGAT  CCAGGAGGAC  CAGGCCTCGT  ACATCTCCTT
AAV7       ACCTCCGAGA  AGCAGTGGAT  CCAGGAGGAC  CAGGCCTCGT  ACATCTCCTT
44_2       ..........  ..........  ..........  ..........  ..........
```

FIG. 1W

```
         1101                                                          1150
  42_2    ..........  ..........  ..........  ..........  ..........
  42_8    ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
  42_4    ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
  43_1    ..........  ..........  ..........  ..........  ..........
  43_5    ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
  44_1    ..........  ..........  ..........  ..........  ..........
  44_9    ..........  ..........  ..........  ..........  ..........
  223_10  ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
  A3_4    ..........  ..........  ..........  ..........  ..........
  A3_5    ..........  ..........  ..........  ..........  ..........
  A3_7    ..........  ..........  ..........  ..........  ..........
  A3_3    ..........  ..........  ..........  ..........  ..........
  42_12   ..........  ..........  ..........  ..........  ..........
  AAV1    CAACGCCGCT  TCCAACTCGC  GGTCCCAGAT  CAAGGCCGCT  CTGGACAATG
  AAV2    CAATGCGGCC  TCCAACTCGC  GGTCCCAAAT  CAAGGCTGCC  TTGGACAATG
  AAV3    CAACGCCGCC  TCCAACTCGC  GGTCCCAGAT  CAAGGCCGCG  CTGGACAATG
  AAV8    CAACGCCGCC  TCCAACTCGC  GGTCCCAGAT  CAAGGCCGCG  CTGGACAATG
  AAV9    CAACGCCGCC  TCCAACTCGC  GGTCCCAGAT  CAAGGCCGCG  CTGGACAATG
  AAV7    CAACGCCGCC  TCCAACTCGC  GGTCCCAGAT  CAAGGCCGCG  CTGGACAATG
  44_2    ..........  ..........  ..........  ..........  ..........
```

FIG. 1X

```
        1151                                                    1200
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    CCGGCAAGAT  CATGGCGCTG  ACCAAATCCG  CGCCCGACTA  CCTGGTAGGC
AAV2    CGGGAAAGAT  TATGAGCCTG  ACTAAAACCG  CCCCCGACTA  CCTGGTGGGC
AAV3    CCTCCAAGAT  CATGAGCCTG  ACAAAGACGG  CTCCGGACTA  CCTGGTGGGC
AAV8    CCGGCAAGAT  CATGGCGCTG  ACCAAATCCG  CGCCCGACTA  CCTGGTGGGG
AAV9    CCGGCAAGAT  CATGGCGCTG  ACCAAATCCG  CGCCCGACTA  CCTGGTAGGC
AAV7    CCGGCAAGAT  CATGGCGCTG  ACCAAATCCG  CGCCCGACTA  CCTGGTGGGG
44_2    ..........  ..........  ..........  ..........  ..........
```

FIG 1Y

```
       1201                                                      1250
 42_2  ..........  ..........  ..........  ..........  ..........
 42_8  ..........  ..........  ..........  ..........  ..........
42_15  ..........  ..........  ..........  ..........  ..........
42_5b  ..........  ..........  ..........  ..........  ..........
42_1b  ..........  ..........  ..........  ..........  ..........
42_13  ..........  ..........  ..........  ..........  ..........
42_3a  ..........  ..........  ..........  ..........  ..........
 42_4  ..........  ..........  ..........  ..........  ..........
42_5a  ..........  ..........  ..........  ..........  ..........
42_10  ..........  ..........  ..........  ..........  ..........
42_3b  ..........  ..........  ..........  ..........  ..........
42_11  ..........  ..........  ..........  ..........  ..........
42_6b  ..........  ..........  ........GA  ATTCGCCCTT  TCTACGGCTG
 43_1  ..........  ..........  ..........  ..........  ..........
 43_5  ..........  ..........  ..........  ..........  ..........
43_12  ..........  ..........  ..........  ..........  ..........
43_20  ..........  ..........  ..........  ..........  ..........
43_21  ..........  ..........  ..........  ..........  ..........
43_23  ..........  ..........  ..........  ..........  ..........
43_25  ..........  ..........  ..........  ..........  ..........
 44_1  ..........  ..........  ..........  ..........  ..........
 44_5  ..........  ..........  ..........  ..........  ..........
223_10 ..........  ..........  ..........  ..........  ..........
223_2  ..........  ..........  ..........  ..........  ..........
223_4  ..........  ..........  ..........  ..........  ..........
223_5  ..........  ..........  ..........  ..........  ..........
223_6  ..........  ..........  ..........  ..........  ..........
223_7  ..........  ..........  ..........  ..........  ..........
 A3_4  ..........  ..........  ..........  ..........  ..........
 A3_5  ..........  ..........  ..........  ..........  ..........
 A3_7  ..........  ..........  ..........  ..........  ..........
 A3_3  ..........  ..........  ..........  ..........  ..........
42_12  ..........  ..........  ..........  ..........  ..........
 AAV1  CCCGCTCCGC  CCGCGGACAT  TAAAACCAAC  CGCATCTACC  GCATCCTGGA
 AAV2  CAGCAGCCCG  TGGAGGACAT  TTCCAGCAAT  CGGATTTATA  AAATTTTGGA
 AAV3  AGCAACCCGC  CGGAGGACAT  TACCAAAAAT  CGGATCTACC  AAATCCTGGA
 AAV8  CCCTCGCTGC  CCGCGGACAT  TACCCAGAAC  CGCATCTACC  GCATCCTCGC
 AAV9  CCTTCACTTC  CGGTGGACAT  TACGCAGAAC  CGCATCTACC  GCATCCTGCA
 AAV7  CCCTCGCTGC  CCGCGGACAT  TAAAACCAAC  CGCATCTACC  GCATCCTGGA
 44_2  ..........  ..........  ..........  ..........  ..........
```

FIG. 1Z

```
              1251                                                    1300
   42_2       ..........  ..........  ..........  ..........  ..........
   42_8       ..........  ..........  ..........  ..........  ..........
   42_15      ..........  ..........  ..........  ..........  ..........
   42_5b      ..........  ..........  ..........  ..........  ..........
   42_1b      ..........  ..........  ..........  ..........  ..........
   42_13      ..........  ..........  ..........  ..........  ..........
   42_3a      ..........  ..........  ..........  ..........  ..........
   42_4       ..........  ..........  ..........  ..........  ..........
   42_5a      ..........  ..........  ..........  ..........  ..........
   42_10      ..........  ..........  ..........  ..........  ..........
   42_3b      ..........  ..........  ..........  ..........  ..........
   42_11      ..........  ..........  ..........  ..........  ..........
   42_6b      CGTCAACTGG  ACCAATGAGA  ACTTTCCCTT  CAACGATTGC  GTCGACAAGA
   43_1       ..........  ..........  ..........  ..........  ..........
   43_5       ..........  ..........  ..........  ..........  ..........
   43_12      ..........  ..........  ..........  ..........  ..........
   43_20      ..........  ..........  ..........  ..........  ..........
   43_21      ..........  ..........  ..........  ..........  ..........
   43_23      ..........  ..........  ..........  ..........  ..........
   43_25      ..........  ..........  ..........  ..........  ..........
   44_1       ..........  ..........  ..........  ..........  ..........
   44_5       ..........  ..........  ..........  ..........  ..........
   223_10     ..........  ..........  ..........  ..........  ..........
   223_2      ..........  ..........  ..........  ..........  ..........
   223_4      ..........  ..........  ..........  ..........  ..........
   223_5      ..........  ..........  ..........  ..........  ..........
   223_6      ..........  ..........  ..........  ..........  ..........
   223_7      ..........  ..........  ..........  ..........  ..........
   A3_4       ..........  ..........  ..........  ..........  ..........
   A3_5       ..........  ..........  ..........  ..........  ..........
   A3_7       ..........  ..........  ..........  ..........  ..........
   A3_3       ..........  ..........  ..........  ..........  ..........
   42_12      ..........  ..........  ..........  ..........  ..........
   AAV1       GCTGAACGGC  TACGAACCTG  CCTACGCCGG  CTCCGTCTTT  CTCGGCTGGG
   AAV2       ACTAAACGGG  TACGATCCCC  AATATGCGGC  TTCCGTCTTT  CTGGGATGGG
   AAV3       GCTGAACGGG  TACGATCCGC  AGTACGCGGC  CTCCGTCTTC  CTGGGCTGGG
   AAV8       TCTCAACGGC  TACGACCCTG  CCTACGCCGG  CTCCGTCTTT  CTCGGCTGGG
   AAV9       GCTCAACGGC  TACGACCCTG  CCTACGCCGG  CTCCGTCTTT  CTCGGCTGGG
   AAV7       GCTGAACGGG  TACGATCCTG  CCTACGCCGG  CTCCGTCTTT  CTCGGCTGGG
   44_2       ..........  ..........  ..........  ..........  ..........
```

FIG. 1AA

```
        1301                                                                    1350
 42_2   ..........  ..........  ..........  ..........  ..........
 42_8   ..........  ..........  ..........  ..........  ..........
 42_15  ..........  ..........  ..........  ..........  ..........
 42_5b  ..........  ..........  ..........  ..........  ..........
 42_1b  ..........  ..........  ..........  ..........  ..........
 42_13  ..........  ..........  ..........  ..........  ..........
 42_3a  ..........  ..........  ..........  ..........  ..........
 42_4   ..........  ..........  ..........  ..........  ..........
 42_5a  ..........  ..........  ..........  ..........  ..........
 42_10  ..........  ..........  ..........  ..........  ..........
 42_3b  ..........  ..........  ..........  ..........  ..........
 42_11  ..........  ..........  ..........  ..........  ..........
 42_6b  TGGTGATCTG  GTGGGAGGAG  GGCAAGATGA  CGGCCAAGGT  CGTGGAGTCC
 43_1   ..........  ..........  ..........  ..........  ..........
 43_5   ..........  ..........  ..........  ..........  ..........
 43_12  ..........  ..........  ..........  ..........  ..........
 43_20  ..........  ..........  ..........  ..........  ..........
 43_21  ..........  ..........  ..........  ..........  ..........
 43_23  ..........  ..........  ..........  ..........  ..........
 43_25  ..........  ..........  ..........  ..........  ..........
 44_1   ..........  ..........  ..........  ..........  ..........
 44_5   ..........  ..........  ..........  ..........  ..........
 223_10 ..........  ..........  ..........  ..........  ..........
 223_2  ..........  ..........  ..........  ..........  ..........
 223_4  ..........  ..........  ..........  ..........  ..........
 223_5  ..........  ..........  ..........  ..........  ..........
 223_6  ..........  ..........  ..........  ..........  ..........
 223_7  ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
 42_12  ..........  ..........  ..........  ..........  ..........
 AAV1   CCCAGAAAAG  GTTCGGGAAG  CGCAACACCA  TCTGGCTGTT  TGGGCCGGCC
 AAV2   CCACGAAAAA  GTTCGGCAAG  AGGAACACCA  TCTGGCTGTT  TGGGCCTGCA
 AAV3   CGCAAAAGAA  GTTCGGGAAG  AGGAACACCA  TCTGGCTCTT  TGGGCCGGCC
 AAV8   CTCAGAAAAA  GTTCGGGAAA  CGCAACACCA  TCTGGCTGTT  TGGACCCGCC
 AAV9   CACAAAAGAA  GTTCGGGAAA  CGCAACACCA  TCTGGCTGTT  TGGGCCGGCC
 AAV7   CCCAGAAAAA  GTTCGGGAAG  CGCAACACCA  TCTGGCTGTT  TGGGCCCGCC
 44_2   ..........  ..........  ..........  ..........  ..........
```

42_2   ..........  ..........  ..........  .......GAA  TTCGCCCTTT
    42_8   ..........  ..........  ..........  .......GAA  TTCGCCCTTT
   42_15   ..........  ..........  ..........  .......GAA  TTCGCCCTTT
   42_5b   ..........  ..........  ..........  .......GAA  TTCGCCCTTT
   42_1b   ..........  ..........  ..........  ..........  ..........
   42_13   ..........  ..........  ..........  .......GAA  TTCGCCCTTT
   42_3a   ..........  ..........  ..........  .......GAA  TTCGCCCTTT
    42_4   ..........  ..........  ..........  ..........  ..........
   42_5a   ..........  ..........  ..........  ........GA  ATTCGCCCTT
   42_10   ..........  ..........  ..........  ..........  ..........
   42_3b   ..........  ..........  ..........  ..........  ..........
   42_11   ..........  ..........  ..........  .......GAA  TTCGCCCTTT
   42_6b   GCCAAGGCCA  TTCTCGGCGG  CAGCAAGGTG  CGCGTGGACC  AAAAGTGCAA
    43_1   ..........  ..........  ..........  .......GAA  TTCGCCCTTT
    43_5   ..........  ..........  ..........  .......GAA  TTCGCCCTTT
   43_12   ..........  ..........  ..........  .......GAA  TTCGCCCTT.
   43_20   ..........  ..........  ..........  .......GAA  TTCGCCCTTT
   43_21   ..........  ..........  ..........  .......GAA  TTCGCCCTT.
   43_23   ..........  ..........  ..........  .......GAA  TTCGCCCTT.
   43_25   ..........  ..........  ..........  .......GAA  TTCGCCCTTT
    44_1   ..........  ..........  ..........  .......GAA  TTCGCCCTTT
    44_5   ..........  ..........  ..........  .......GAA  TTCGCCCTTT
  223_10   ..........  ..........  ..........  ..........  ..........
   223_2   ..........  ..........  ..........  ..........  ..........
   223_4   ..........  ..........  ..........  ..........  ..........
   223_5   ..........  ..........  ..........  ..........  ..........
   223_6   ..........  ..........  ..........  ..........  ..........
   223_7   ..........  ..........  ..........  ..........  ..........
    A3_4   ..........  ..........  ..........  ........GA  ATTCGCCCTT
    A3_5   ..........  ..........  ..........  ........GA  ATTCGCCCTT
    A3_7   ..........  ..........  .........A  GCGGCCGCGA  ATTCGCCCTT
    A3_3   ..........  ..........  ..........  ........GA  ATTCGCCCTT
   42_12   ..........  ..........  ..........  .......GAA  TTCGCCCTTT
    AAV1   ACCACGGGCA  AGACCAACAT  CGCGGAAGCC  ATCGCCCACG  CCGTGCCCTT
    AAV2   ACTACCGGGA  AGACCAACAT  CGCGGAGGCC  ATAGCCCACA  CTGTGCCCTT
    AAV3   ACGACGGGTA  AAACCAACAT  CGCGGAAGCC  ATCGCCCACG  CCGTGCCCTT
    AAV8   ACCACCGGCA  AGACCAACAT  TGCGGAAGCC  ATCGCCCACG  CCGTGCCCTT
    AAV9   ACCACGGGAA  AGACCAACAT  CGCAGAAGCC  ATTGCCCACG  CCGTGCCCTT
    AAV7   ACCACCGGCA  AGACCAACAT  TGCGGAAGCC  ATCGCCCACG  CCGTGCCCTT
    44_2   ..........  ..........  ..........  ........GA  ATTCGCCCTT
```

FIG. 1AC

```
        1401                                                           1450
 42_2   .CTACGGCTG CGTCAACTGG ACCAATGAGA ACTTTCCCTT CAACGATTGC
 42_8   .CTACGGCTG CGTCAACTGG ACCAATGAGA ACTTTCCCTT CAACGATTGC
 42_15  .CTACGGCTG CGTCAACTGG ACCAATGAGA ACTTTCCCTT CAACGATTGC
 42_5b  .CTACGGCTG CGTCAACTGG ACCAATGAGA ACTTTCCCTT CAACGATTGC
 42_1b  .......... .......... .......... .......... ..........
 42_13  .CTACGGCTG CGTCAACTGG ACCAATGAGA ACTTTCCCTT CAACGATTGC
 42_3a  .CTACGGCTG CGTCAACTGG ACCAATGAGA ACTTTCCCTT CAACGATTGC
 42_4   .......... .......... .......... .......... ..........
 42_5a  .CTACGGCTG CGTCAACTGG ACCAATGAGA ACTTTCCCTT CAACGATTGC
 42_10  .......... .......... .......... .......... ..........
 42_3b  .......... .......... .......... .......... ..........
 42_11  .CTACGGCTG CGTCAACTGG ACCAATGAGA ACTTTCCCTT CAACGATTGC
 42_6b  .GTCTTCCGC CCAGATCGAT CCCACCCCCG TGATCGTCAC TTCCAACACC
 43_1   .CTACGGCTG CATCAACTGG ACCAATGAGA ACTTTCCCTT CAACGATTGC
 43_5   .CTACGGCTG CGTCAACTGG ACCAATGAGA ACTTTCCCTT CAACGATTGC
 43_12  .....GGCTG CGTCAACTGG ACCAATGAGA ACTTTCCCTT CAACGATTGC
 43_20  .CTACGGCTG CGTCAACTGG ACCAATGAGA ACTTTCCCTT CAACGATTGC
 43_21  .....GGCTG CGTCAACTGG ACCAATGAGA ACTTTCCCTT CAACGATTGC
 43_23  .CTACGGCTG CGTCAACTGG ACCAATGAGA ACTTTCCCTT CAACGATTGC
 43_25  .CTACGGCTG CGTCAACTGG ACCAATGAGA ACTTTCCCTT CAACGATTGC
 44_1   .CTACGGCTG CGTCAACTGG ACCAATGAGA ACTTTCCCTT CAACGATTGC
 44_5   .CTACGGCTG CGTCAACTGG ACCAATGAGA ACTTTCCCTT CAACGATTGC
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   TCTACGGCTG CGTCAACTGG ACCAATGAAA ACTTTCCCTT CAACGATTGC
 A3_5   TCTACGGCTG CGTCAACTGG ACCAATGAAA ACTTTCCCTT CAACGATTGC
 A3_7   TCTACGGCTG CGTCAACTGG ACCAATGAAA ACTTTCCCTT CAACGATTGC
 A3_3   TCTACGGCTG CGTCAACTGG ACCAATGAAA ACTTTCCCTT CAACGATTGC
 42_12  .CTACGGCTG CGTCAACTGG ACCAATGAGA ACTTTCCCTT CAACGATTGC
 AAV1   .CTACGGCTG CGTCAACTGG ACCAATGAGA ACTTTCCCTT CAATGATTGC
 AAV2   .CTACGGGTG CGTAAACTGG ACCAATGAGA ACTTCCCTT  CAACGACTGT
 AAV3   .CTACGGCTG CGTAAACTGG ACCAATGAGA ACTTCCCTT  CAACGATTGC
 AAV8   .CTACGGCTG CGTCAACTGG ACCAATGAGA ACTTTCCCTT CAATGATTGC
 AAV9   .CTACGGCTG CGTCAACTGG ACCAATGAGA ACTTTCCCTT CAACGATTGC
 AAV7   .CTACGGCTG CGTCAACTGG ACCAATGAGA ACTTTCCCTT CAACGATTGC
 44_2   TCTACGGCTG CGTCAACTGG ACCAATGAGA ACTTTCCCTT CAACGATTGC
```

FIG. 1AD

```
        1451                                                                    1500
42_2    GTCGACAAGA  TGGTGATCTG  GTGGGAGGAG  GGCAAGATGA  CGGCCAAGGT
42_8    GTCGACAAGA  TGGTGATCTG  GTGGGAGGAG  GGCAAGATGA  CGGCCAAGGT
42_15   GTCGACAAGA  TGGTGATCTG  GTGGGAGGAG  GGCAAGATGA  CGGCCAAGGT
42_5b   GTCGACAAGA  TGGTGATCTG  GTGGGAGGAG  GGCAAGATGA  CGGCCAAGGT
42_1b   ..........  ..........  ..........  ..........  ..........
42_13   GTCGACAAGA  TGGTGATCTG  GTGGGAGGAG  GGCAAGATGA  CGGCCAAGGT
42_3a   GTCGACAAGA  TGGTGATCTG  GTGGGAGGAG  GGCAAGATGA  CGGCCAAGGT
42_4    ..........  ..........  ..........  ..........  ..........
42_5a   GTCGACAAGA  TGGTGATCTG  GTGGGAGGAG  GGCAAGATGA  CGGCCAAGGT
42_10   ..........  ..........  ..........  ..........  ..........
42_3b   ..........  ..........  ..........  ..........  ..........
42_11   GTCGACAAGA  TGGTGATCTG  GTGGGAGGAG  GGCAAGATGA  CGGCCAAGGT
42_6b   AACATGTGCG  CCGTGATTGA  CGGGAACAGC  ACCACCTTCG  AGCACCAGCA
43_1    GTCGACAAGA  TGGTGATCTG  GTGGGAGGAG  GGCAAGATGA  CGGCCAAGGT
43_5    GTCGACAAGA  TGGTGATCTG  GTGGGAGGAG  GGCAAGATGA  CGGCCAAGGT
43_12   GTCGACAAGA  TGGTGATCTG  GTGGGAGGAG  GGCAAGATGA  CGGCCAAGGT
43_20   GTCGACAAGA  TGGTGATCTG  GTGGGAGGAG  GGCAAGATGA  CGGCCAAGGT
43_21   GTCGACAAGA  TGGTGATCTG  GTGGGAGGAG  GGCAAGATGA  CGGCCAAGGT
43_23   GTCGACAAGA  TGGTGATCTG  GTGGGAGGAG  GGCAAGATGA  CGGCCAAGGT
43_25   GTCGACAAGA  TGGTGATCTG  GTGGGAGGAG  GGCAAGATGA  CGGCCAAGGT
44_1    GTCGACAAGA  TGTTGATCTG  GTGGGAGGAG  GGCAAGATGA  CGGCCAAGGT
44_5    GTCGACAAGA  TGGTGATCTG  GTGGGAGGAG  GGCAAGATGA  CGGCCAAGGT
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    GTCGACAAGA  TGGTGATCTG  GTGGGAGGAG  GGAAAGATGA  CCGCCAAGGT
A3_5    GTCGACAAGA  TGGTGATCTG  GTGGGAGGAG  GGAAAGATGA  CCGCCAAGGT
A3_7    GTCGACAAGA  TGGTGATCTG  GTGGGAGGAG  GGAAAGATGA  CCGCCAAGGT
A3_3    GTCGACAAGA  TGGTGATCTG  GTGGGAGGAG  GGAAAGATGA  CCGCCAAGGT
42_12   GTCGACAAGA  TGGTGATCTG  GTGGGAGGAG  GGCAAGATGA  CGGCCAAGGT
AAV1    GTCGACAAGA  TGGTGATCTG  GTGGGAGGAG  GGCAAGATGA  CGGCCAAGGT
AAV2    GTCGACAAGA  TGGTGATCTG  GTGGGAGGAG  GGGAAGATGA  CCGCCAAGGT
AAV3    GTCGACAAGA  TGGTGATCTG  GTGGGAGGAG  GGCAAGATGA  CGGCCAAGGT
AAV8    GTCGACAAGA  TGGTGATCTG  GTGGGAGGAG  GGCAAGATGA  CGGCCAAGGT
AAV9    GTCGACAAGA  TGGTGATCTG  GTGGGAGGAG  GGCAAGATGA  CGGCCAAGGT
AAV7    GTCGACAAGA  TGGTGATCTG  GTGGGAGGAG  GGCAAGATGA  CGGCCAAGGT
44_2    GTCGACAAGA  TGGTGATCTG  GTGGGAGGAG  GGCAAGATGA  CGGCCAAGGT
```

FIG. 1AE

```
         1501                                                                      1550
  42_2   CGTGGAGTCC GCCAAGGCCA TTCTCGGCGG CAGCAAGGTG CGCGTGGACC
  42_8   CGTGGAGTCC GCCAAGGCCA TTCTCGGCGG CAGCAAGGTG CGCGTGGACC
 42_15   CGTGGAGTCC GCCAAGGCCA TTCTCGGCGG CAGCAAGGTG CGCGTGGACC
 42_5b   CGTGGAGTCC GCCAAGGCCA TTCTCGGCGG CAGCAAGGTG CGCGTGGACC
 42_1b   .......... .......... .......... .......... ..........
 42_13   CGTGGAGTCC GCCAAGGCCA TTCTCGGCGG CAGCAAGGTG CGCGTGGACC
 42_3a   CGTGCAGTCC GCCAAGGCCA TTCTCGGCGG CAGCAAGGTG CGCGTGGACC
  42_4   .......... .......... .......... .......... ..........
 42_5a   CGTGGAGTCC GCCAAGGCCA TTCTCGGCGG CAGCAAGGTG CGCGTGGACC
 42_10   .......... .......... .......... .......... ..........
 42_3b   .......... .......... .......... .......... ..........
 42_11   CGTGGAGTCC GCCAAGGCCA TTCTCGGCGG CAGCAAGGTG CGCGTGGACC
 42_6b   GCCGTTGCAG GACCGGATGT TCAAATTTGA ACTCACCCGC CGTCTGGAGC
  43_1   CGTGGAGTCC GCCAAGGCCA TTCTCGGCGG CAGCAAGGTG CGCGTGGACC
  43_5   CGTGGAGTCC GCCAAGGCCA TTCTCGGCGG CAGCAAGGTG CGCGTGGACC
 43_12   CGTGGAGTCC GCCAAGGCCA TTCTCGGCGG CAGCAAGGTG CGCGTGGACC
 43_20   CGTGGAGTCC GCCAAGGCCA TTCTCGGCGG CAGCAAGGTG CGTGTGGACC
 43_21   CGTGGAGTCC GCCAAGGCCA TTCTCGGCGG CAGCAAGGTG CGTGTGGACC
 43_23   CGTGGAGTCC GCCAAGGCCA TTCTCGGCGG CAGCAAGGTG CGTGTGGACC
 43_25   CGTGGAGTCC GCCAAGGCCA TTCTCGGCGG CAGCAAGGTG CGTGTGGACC
  44_1   CGTGGAGTCC GCCAAGGCCA TTCTCGGCGG CAGCAAAGTG CGCGTGGACC
  44_5   CGTGGAGTCC GCCAAGGCCA TTCTCGGCGG CAGCAAAGTG CGCGTGGACC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
   A3_4  CGTGGAATCT GCCAAAGCCA TTCTGGGTGG AAGCAAGGTT CGTGTGGACC
   A3_5  CGTGGAATCT GCCAAAGCCA TTCTGGGTGG AAGCAAGGTT CGTGTGGACC
   A3_7  CGTGGAATCT GCCAAAGCCA TTCTGGGTGG AAGCAAGGTT CGTGTGGACC
   A3_3  CGTGGAATCT GCCAAAGCCA TTCTGGGTGG AGGCAAGGTT CGTGTGGACC
  42_12  CGTGGAGTCC GCCAAGGCCA TTCTCGGCGG CAGCAAGGTG CGCGTGGACC
   AAV1  CGTGGAGTCC GCCAAGGCCA TTCTCGGCGG CAGCAAGGTG CGCGTGGACC
   AAV2  CGTGGAGTCG GCCAAAGCCA TTCTCGGAGG AAGCAAGGTG CGCGTGGACC
   AAV3  CGTGGAGAGC GCCAAGGCCA TTCTGGGCGG AAGCAAGGTG CGCGTGGACC
   AAV8  CGTGGAGTCC GCCAAGGCCA TTCTCGGCGG CAGCAAGGTG CGCGTGGACC
   AAV9  CGTGGAGTCC GCCAAGGCCA TTCTCGGCGG CAGCAAGGTG CGCGTGGACC
   AAV7  CGTGGAGTCC GCCAAGGCCA TTCTCGGCGG CAGCAAGGTG CGCGTGGACC
   44_2  CGTGGAGTCC GCCAAGGCCA TTCTCGGCGG CAGCAAAGTG CGCGTGGACC
```

FIG. 1AF

```
           1551                                                              1600
  42_2     AAAAGTGCAA  GTCTTCCGCC  CAGATCGATC  CCACCCCCGT  GATCGTCACT
  42_8     AAAAGTGCAA  GTCTTCCGCC  CAGATCGATC  CCACCCCCGT  GATCGTCACT
  42_15    AAAAGTGCAA  GTCGTCCGCC  CAGATCGACC  CCACCCCCGT  GATCGTCACC
  42_5b    AAAAGTGCAA  GTCGTCCGCC  CAGATCGACC  CCACCCCCGT  GATCGTCACC
  42_1b    ..........  ..........  ..........  ..........  ..........
  42_13    AAAAGTGCAA  GTCGTCCGCC  CAGATCGATC  CCACCCCCGT  GATCGTCACT
  42_3a    AAAAGTGCAA  GTCGTCCGCC  CAGATCGATC  CCACCCCCGT  GATCGTCACT
  42_4     ..........  ..........  ..........  ..........  ..........
  42_5a    AAAAGTGCAA  GTCGTCCGCC  CAGATCGACC  CCACCCCCGT  GATCGTCACC
  42_10    ..........  ..........  ..........  ..........  ..........
  42_3b    ..........  ..........  ..........  ..........  ..........
  42_11    AAAAGTGCAA  GTCTTCCGCC  CAGATCGATC  CCACCCCCGT  GATCGTCACT
  42_6b    ATGACTTTGG  CAAGGTGACA  AAGCAGGAAG  TCAAAGAGTT  CTTCCCTGG
  43_1     AAAAGTGCAA  GTCGTCCGCC  CAGATCGACC  CCACCCCCGT  GATCGTCACC
  43_5     AAAAGTGCAA  GTCGTCCGCC  CAGATCGACC  CCACCCCCGT  GATCGTCACC
  43_12    AAAAGTGCAA  GTCGTCCGCC  CAGATCGACC  CCACCCCCGT  GATCGTCACC
  43_20    AAAAGTGCAA  GTCTTCCGCC  CAGATCGATC  CCACCCCCGT  GATCGTCACC
  43_21    AAAAGTGCAA  GTCTTCCGCC  CAGATCGATC  CCACCCCCGT  GATCGTCACC
  43_23    AAAAGTGCAA  GTCTTCCGCC  CAGATCGATC  CCACCCCCGT  GATCGTCACC
  43_25    AAAAGTGCAA  GTCTTCCGCC  CAGATCGATC  CCACCCCCGT  GATCGTCACC
  44_1     AAAAGTGCAA  GCCGTCCGCC  CAGATCGACC  CCACCCCCGT  GATCGTCACC
  44_5     AAAAGTGCAA  GTCGTCCGCC  CAGATCGACC  CCACCCCCGT  GATCGTCACC
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
  A3_4     AGAAATGCAA  GTCTTCGGCC  CAGATCGACC  CGACTCCGGT  GATTGTCACC
  A3_5     AGAAATGCAA  GTCTTCGGCC  CAGATCGACC  CGACTCCGGT  GATTGTCACC
  A3_7     AGAAATGCAG  GTCTTCGGCC  CAGATCGACC  CGACTCCGGT  GATTGTCACC
  A3_3     AGAAATGCAA  GTCTTCGGCC  CAGATCGACC  CGACTCCGGT  GATTGTCACC
  42_12    AAAAGTGCAA  GTCGTCCGCC  CAGATCGACC  CCACCCCCGT  GATCGTCACC
  AAV1     AAAAGTGCAA  GTCGTCCGCC  CAGATCGACC  CCACCCCCGT  GATCGTCACC
  AAV2     AGAAATGCAA  GTCCTCGGCC  CAGATAGACC  CGACTCCCGT  GATCGTCACC
  AAV3     AAAAGTGCAA  GTCATCGGCC  CAGATCGAAC  CCACTCCCGT  GATCGTCACC
  AAV8     AAAAGTGCAA  GTCGTCCGCC  CAGATCGACC  CCACCCCCGT  GATCGTCACC
  AAV9     AAAAGTGCAA  GTCGTCCGCC  CAGATCGACC  CCACTCCCGT  GATCGTCACC
  AAV7     AAAAGTGCAA  GTCGTCCGCC  CAGATCGACC  CCACCCCCGT  GATCGTCACC
  44_2     AAAAGTGCAA  GTCGTCCGCC  CAGATCGACC  CCACCCCCGT  GATCGTCACC
```

FIG. 1AG

```
           1601                                                    1650
  42_2    TCCAACACCA ACATGTGCGC TGTGATTGAC GGGAACAGCA CCACCTTCGA
  42_8    TCCAACACCA ACATGTGCGC CGTGATTGAC GGGAACAGCA CCACCTTCGA
  42_15   TCCAACACCA ACATGTGCGC CGTGATTGAC GGGAACAGCA CCACCTTCGA
  42_5b   TCCAACACCA ACATGTGCGC CGTGATTGAC GGGAACAGCA CCACCTTCGA
  42_1b   .......... .......... .......... .......... ..........
  42_13   TCCAACACCA ACATGTGCGC CGTGATTGAC GGGAACAGCA CCACCTTCGA
  42_3a   TCCAACACCA ACATGTGCGC CGTGATTGAC GGGAACAGCA CCACCTTCGA
  42_4    .......... .......... .......... .......... ..........
  42_5a   TCCAACACCA ACATGTGCGC CGTGATTGAC GGGAACAGCA CCACCTTCGA
  42_10   .......... .......... .......... .......... ..........
  42_3b   .......... .......... .......... .......... ..........
  42_11   TCCAACACCA ACATGTGCGC CGTGATTGAC GGGAACAGCA CCACCTTCGA
  42_6b   GCGCAGGATC ACGTGACCGA GGTGGCGCAT GAGTTCTACG TCAGAAAGGG
  43_1    TCCAACACCA ACATGTGCGC CGTGATTGAC GGGAACAGCA CCACCTTCGA
  43_5    TCCAACACCA ACATGTGCGC CGTGATTGAC GGGAACAGCA CCACCTTCGA
  43_12   TCCAACACCA ACATGTGCGC CGTGATTGAC GGGAACAGCA CCACCTTCGA
  43_20   TCCAACACCA ACATGTGCGC CGTGATTGAC GGGAACAGCG CCACCTTCGA
  43_21   TCCAACACCA ACATGTGCGC CGTGATTGAC GGGAACAGCG CCACCTTCGA
  43_23   TCCAACACCA ACATGTGCGC CGTGATTGAC GGGAACAGCA CCACCTTCGA
  43_25   TCCAACACCA ACATGTGCGC CGTGATTGAC GGGAACAGCA CCACCTTCGA
  44_1    TCCAACACCA ACATGTGCGC CGTGATTGAC GGGAACAGCA CCACCTTCGA
  44_5    TCCAACACCA ACATGTGCGC CGTGATTGAC GGGAACAGCA CCACCTTCGA
  223_10  .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
  A3_4    TCTAACACCA ACATGTGCGC CGTGATTGAC GGAAACTCGA CCACCTTCGA
  A3_5    TCTAACACCA ACATGTGCGC CGTGATTGAC GGAAACTCGA CCACCTTCGA
  A3_7    TCTAACACCA ACATGTGCGC CGTGATTGAC GGAAACTCGA CCACCTTCGA
  A3_3    TCTAACACCA ACATGTGCGC CGTGATTGAC GGAAACTCGA CCACCTTCGA
  42_12   TCCAACACCA ACATGTGCGC CGTGATTGAC GGGAACAGCA CCACCTTCGA
  AAV1    TCCAACACCA ACATGTGCGC CGTGATTGAC GGGAACAGCA CCACCTTCGA
  AAV2    TCCAACACCA ACATGTGCGC CGTGATTGAC GGGAACTCAA CGACCTTCGA
  AAV3    TCCAACACCA ACATGTGCGC CGTGATTGAC GGGAACAGCA CCACCTTCGA
  AAV8    TCCAACACCA ACATGTGCGC CGTGATTGAC GGGAACAGCA CCACCTTCGA
  AAV9    TCCAACACCA ACATGTGCGC CGTGATTGAC GGGAACAGCA CCACCTTCGA
  AAV7    TCCAACACCA ACATGTGCGC CGTGATTGAC GGGAACAGCA CCACCTTCGA
  44_2    TCCAACACCA ACATGTGCGC CGTGATTGAC GGGAACAGCA CCACCTTCGA
```

FIG. 1AH

```
          1651                                                    1700
 42_2    GCACCAGCAG  CCGTTACAAG  ACCGGATGTT  CAAATTTGAA  CTCACCCGCC
 42_8    GCACCAGCAG  CCGTTACAAG  ACCGGATGTT  CAAATTTGAA  CTCACCCGCC
 42_15   GCACCAGCAG  CCGTTGCAGG  ACCGGATGTT  CAAATTTGAA  CTCACCCGCC
 42_5b   GCACCAGCAG  CCGTTACAAG  ACCGGATGTT  CAAATTTGAA  CTCACCCGCC
 42_1b   ..........  ..........  ..........  ..........  ..........
 42_13   GCACCAGCAG  CCGTTACAAG  ACCGGATGTT  CAAATTTGAA  CTCACCCGCC
 42_3a   GCACCAGCAG  CCGTTACAAG  ACCGGATGTT  CAAATTTGAA  CTCACCCGCC
 42_4    ..........  ..........  ..........  ..........  ..........
 42_5a   GCACCAGCAG  CCGTTGCAGG  ACCGGATGTT  CAAATTTGAA  CTCACCCGCC
 42_10   ..........  ..........  ..........  ..........  ..........
 42_3b   ..........  ..........  ..........  ..........  ..........
 42_11   GCACCAGCAG  CCGTTACAAG  ACCGGATGTT  CAAATTTGAA  CTCACCCGCC
 42_6b   TGGAGCCAAC  AAGAGACCCG  CCCCCGATGA  CGCGGATAAA  AGCGAGCCCA
 43_1    GCACCAGCAG  CCGTTGCAGG  ACCGGATGTT  CAAGTTCGAA  CTCACCCGCC
 43_5    GCACCAGCAG  CCGTTGCAGG  ACCGGATGTT  CAAGTTCGAA  CTCACCCGCC
 43_12   GCACCAGCAG  CCGTTGCAGG  ACCGGATGTT  CAAGTTCGAA  CTCACCCGCC
 43_20   GCACCAGCAG  CCGTTGCAGG  ACCGGATGTT  CAAATTTGAA  CTCACCCGCC
 43_21   GCACCAGCAG  CCGTTGCAGG  ACCGGATGTT  CAAATTTGAA  CTCACCCGCC
 43_23   GCACCAGCAG  CCGTTGCAGG  ACCGGATGTT  CAAATTTGAA  CTCACCCGCC
 43_25   GCACCAGCAG  CCGTTGCAGG  ACCGGATGTT  CAAATTTGAA  CTCACCCGCC
 44_1    GCACCAGCAG  CCGTTGCGGG  ACCGGATGTT  CAAGTTTGAA  CTCACCCGCC
 44_5    GCACCAGCAG  CCGTTGCAGG  ACCGGATGTT  CAAGTTTGAA  CTCACCCGCC
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
 A3_4    GCACCAGCAG  CCGTTGCAAG  ACCGGATGTT  CAAATTTGAA  CTTACCCGCC
 A3_5    GCACCAGCAG  CCGTTGCAAG  ACCGGATGTT  CAAATTTGAA  CTTACCCGCC
 A3_7    GCACCAGCAG  CCGTTGCAAG  ACCGGATGTT  CAAATTTGAA  CTTACCCGCC
 A3_3    GCACCAGCAG  CCGTTGCAAG  ACCGGATGTT  CAAATTTGAA  CTTACCCGCC
 42_12   GCACCAGCAG  CCGTTACAAG  ACCGGATGTT  CAAATTTGAA  CTCACCCGCC
 AAV1    GCACCAGCAG  CCGTTGCAGG  ACCGGATGTT  CAAATTTGAA  CTCACCCGCC
 AAV2    ACACCAGCAG  CCGTTGCAAG  ACCGGATGTT  CAAATTTGAA  CTCACCCGCC
 AAV3    GCATCAGCAG  CCGCTGCAGG  ACCGGATGTT  TGAATTTGAA  CTTACCCGCC
 AAV8    GCACCAGCAG  CCTCTCCAGG  ACCGGATGTT  TAAGTTCGAA  CTCACCCGCC
 AAV9    GCACCAGCAG  CCTCTCCAGG  ACCGGATGTT  TAAGTTCGAA  CTCACCCGCC
 AAV7    GCACCAGCAG  CCGTTGCAGG  ACCGGATGTT  CAAATTTGAA  CTCACCCGCC
 44_2    GCACCAGCAG  CCGTTGCAGG  ACCGGATGTT  CAAGTTTGAA  CTCACCCGCC
```

FIG. 1AI

```
          1701                                                              1750
  42_2    GTCTGGAGCA  CGACTTTGGC  AAGGTGACAA  AGCAGGAAGT  CAAAGAGTTC
  42_8    GTCTGGAGCA  CGACTTTGGC  AAGGTGACAA  AGCAGGAAGT  CAAAGAGTTC
  42_15   GTCTGGAGCA  TGACTTTGGC  AAGGTGACAA  AGCAGGAAGT  CAAAGAGTTC
  42_5b   GTCTGGAGCA  CGACTTTGGC  AAGGTGACAA  AGCAGGAAGT  CAAAGAGTTC
  42_1b   ..........  ..........  ..........  ..........  ..........
  42_13   GTCTGGAGCA  TGACTTTGGC  AAGGTGACAA  AGCAGGAAGT  CAAAGAGTTC
  42_3a   GTCTGGAGCA  TGACTTTGGC  AAGGTGACAA  AGCAGGAAGT  CAAAGAGTTC
  42_4    ..........  ..........  ..........  ..........  ..........
  42_5a   GTCTGGAGCA  TGACTTTGGC  AAGGCGACAA  AGCAGGAAGT  CAAAGAGTTC
  42_10   ..........  ..........  ..........  ..........  ..........
  42_3b   ..........  ..........  ..........  ..........  ..........
  42_11   GTCTGGAGCA  CGACTTTGGC  AAGGTGACAA  AGCAGGAAGT  CAAAGAGTTC
  42_6b   AGCGGGCCTG  CCCCTCAGTC  GCGGATCCAT  CGACGTCAGA  CGCGGAAGGA
  43_1    GTCTGGAGCA  CGACTTTGGC  AAGGTGACCA  AGCAGGAAGT  CAAAGAGTTC
  43_5    GTCTGGAGCA  CGACTTTGGC  AAGGTGACCA  AGCAGGAAGT  CAAAGAGTTC
  43_12   GTCTGGAGCA  CGACTTTGGC  AAGGTGACCA  AGCAGGAAGT  CAAAGAGTTC
  43_20   GTCTGGAGCA  TGACTTTGGC  AAGGTGACGA  AGCAGGAAGT  CAAAGAGTTC
  43_21   GTCTGGAGCA  TGACTTTGGC  AAGGTGACGA  AGCAGGAAGT  CAAAGAGTTC
  43_23   GTCTGGAGCA  TGACTTTGGC  AAGGTGACGA  AGCAGGAAGT  CAAAGAGTTC
  43_25   GTCTGGAGCA  TGACTTTGGC  AAGGTGACGA  AGCAGGAAGT  CAAAGGGTTC
  44_1    GTCTGGAGCA  CGACTTTGGC  AAGGTGACAA  AGCAGGAAGT  CAGAGAGTTC
  44_5    GTCTGGAGCA  CGACTTTGGC  AAGGTGACAA  AGCAGGAAGT  CAGAGAGTTC
  223_10  ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
  A3_4    GTTTGGATCA  TGACTTTGGG  AAGGTCACCA  AGCAGGAAGT  CAAAGACTTT
  A3_5    GTTTGGATCA  TGACTTTGGG  AAGGTCACCA  AGCAGGAAGT  CAAAGACTTT
  A3_7    GTTTGGATCA  TGACTTTGGG  AAGGTCACCA  AGCAGGAAGT  CAAAGACTTT
  A3_3    GTTTGGATCA  TGACTTTGGG  AAGGTCACCA  AGCAGGAAGT  CAAAGACTTT
  42_12   GTCTGGAGCA  CGACTTTGGC  AAGGTGACAA  AGCAGGAAGT  CAAAGAGTTC
  AAV1    GTCTGGAGCA  TGACTTTGGC  AAGGTGACAA  AGCAGGAAGT  CAAAGAGTTC
  AAV2    GTCTGGATCA  TGACTTTGGG  AAGGTCACCA  AGCAGGAAGT  CAAAGACTTT
  AAV3    GTTTGGACCA  TGACTTTGGG  AAGGTCACCA  AACAGGAAGT  AAAGGACTTT
  AAV8    GTCTGGAGCA  CGACTTTGGC  AAGGTGACAA  AGCAGGAAGT  CAAAGAGTTC
  AAV9    GTCTGGAGCA  CGACTTTGGC  AAGGTGACAA  AGCAGGAAGT  CAAAGAGTTC
  AAV7    GTCTGGAGCA  CGACTTTGGC  AAGGTGACGA  AGCAGGAAGT  CAAAGAGTTC
  44_2    GTCTGGAGCA  CGACTTTGGC  AAGGTGACAA  AGCAGGAAGT  CAGAGAGTTC
```

FIG. 1AJ

```
         1751                                                              1800
  42_2   TTCCGCTGGG CGCAGGATCA CGTGACCGAG GTGGCGCATG AGTTCTACGT
  42_8   TTCCGCTGGG CGCAGGATCA CGTGACCGAG GTGGCGCATG AGTTCTACGT
 42_15   TTCCGCTGGG CGCAGGATCA CGTGACCGAG GTGGCGCATG AGTTCTACGT
 42_5b   TTCCGCTGGG CGCAGGATCA CGTGACCGAG GTGGCGCATG AGTTCTACGT
 42_1b   .......... .......... .......... .......... ..........
 42_13   TTCCGCTGGG CGCAGGATCA CGTGACCGAG GTGGCGCATG AGTTCTACGT
 42_3a   TTCCGCTGGG CGCAGGATCA CGTGACCGAG GTGGCGCATG AGTTCTACGT
  42_4   .......... .......... .......... .......... ..........
 42_5a   TTCCGCTGGG CGCAGGATCA CGTGACCGAG GTGGCGCATG AGTTCTACGT
 42_10   .......... .......... .......... .......... ..........
 42_3b   .......... .......... .......... .......... ..........
 42_11   TTCCGCTGGG CGCAGGATCA CGTGACCGAG GTGGCGCATG AGTTCTACGT
 42_6b   GCTCCGGTGG ACTTTGCCGA CAGGTACCAA AACAAATGTT CTCGTCACGC
  43_1   TTCCGCTGGG CGCAGGATCA CGTGACCGAG GTGGCGCATG AGTTCTACGT
  43_5   TTCCGCTGGG CGCAGGATCA CGTGACCGAG GTGGCGCATG AGTTCTACGT
 43_12   TTCCGCTGGG CGCAGGATCA CGTGACCGAG GTGGCGCATG AGTTCTACGT
 43_20   TTCCGCTGGG CGCAGGATCA CGTGACCGAG GTGGCGCATG AGTTCCACGT
 43_21   TTCCGCTGGG CGCAGGATCA CGTGACCGAG GTGGCGCATG AGTTCCACGT
 43_23   TTCCGCTGGG CGCAGGATCA CGTGACCGAG GTGGCGCATG AGTTCCACGT
 43_25   TTCCGCTGGG CGCAGGATCA CGTGACCGAG GTGGCGCATG AGTTCCACGT
  44_1   TTCCGCTGGG CGCAGGATCA CGTGACCGAG GTGGCGCACG AGTTCTACGT
  44_5   TTCCGCTGGG CGCAGGATCA CGTGACCGAG GTGGCGCACG AGTTCTACGT
223_10   .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   TTCCGGTGGG CTCAAGATCA CGTGACTGAG GTGGAGCATG AGTTCTACGT
  A3_5   TTCCGGTGGG CTCAAGATCA CGTGACTGAG GTGGAGCATG AGTTCTACGT
  A3_7   TTCCGGTGGG CTCAAGATCA CGTGACTGAG GTGGAGCATG AGTTCTACGT
  A3_3   TTCCGGTGGG CTCAAGATCA CGTGACTGAG GTGGAGCATG AGTTCTACGT
 42_12   TTCCGCTGGG CGCAGGATCA CGTGACCGAG GTGGCGCATG AGTTCTACGT
  AAV1   TTCCGCTGGG CGCAGGATCA CGTGACCGAG GTGGCGCATG AGTTCTACGT
  AAV2   TTCCGGTGGG CAAAGGATCA CGTGGTTGAG GTGGAGCATG AATTCTACGT
  AAV3   TTCCGGTGGG CTTCCGATCA CGTGACTGAC GTGGCTCATG AGTTCTACGT
  AAV8   TTCCGCTGGG CCAGTGATCA CGTGACCGAG GTGGCGCATG AGTTTTACGT
  AAV9   TTCCGCTGGG CCAGTGATCA CGTGACCGAG GTGGCGCATG AGTTTTACGT
  AAV7   TTCCGCTGGG CCAGTGATCA CGTGACCGAG GTGGCGCATG AGTTCTACGT
  44_2   TTCCGCTGGG CGCAGGATCA CGTGACCGAG GTGGCGCACG AGTTCTACGT
```

FIG. 1AK

```
               1801                                                              1850
                                                                               P40/TATA
    42_2    CAGAAAGGGT  GGAGCCAACA  AGAGACCCGC  CCCCGATGAC  GCGGATAAAA
    42_8    CAGAAAGGGT  GGAGCCAACA  AGAGACCCGC  CCCCGATGAC  GCGGATAAAA
    42_15   CAGAAAGGGT  GGAGCCAACA  AGAGACCCGC  CCCCGATGAC  GCGGATAAAA
    42_5b   CAGAAAGGCT  GGAGCCAACA  AGAGACCCGC  CCCCGATGAC  GCGGATAAAA
    42_1b   ..........  ..........  ..........  ..........  ..........
    42_13   CAGAAAGGGT  GGAGCCAACA  AGAGACCCGC  CCCCGATGAC  GCGGATAAAA
    42_3a   CAGAAAGGGT  GGAGCCAACA  AGAGACCCGC  CCCCGATGAC  GCGGATAAAA
    42_4    ..........  ..........  ..........  ..........  ..........
    42_5a   CAGAAAGGGT  GGAGCCAACA  AGAGACCCGC  CCCCGATGAC  GCGGATAAAA
    42_10   ..........  ..........  ..........  ..........  ..........
    42_3b   ..........  ..........  ..........  ..........  ..........
    42_11   CAGAAAGGGT  GGAGCCAACA  AGAGACCCGC  CCCCGATGAC  GCGGATAAAA
    42_6b   GGGCATAGCG  CTGACGTAAA  TCACGTCATA  GGGGAGTGGT  CCTGTATTAG
    43_1    CAGAAAGGGC  GGAGCCAGCA  AAAGACCCGC  CCCCGATGAC  GCGGATATAA
    43_5    CAGAAAGGGC  GGAGCCAGCA  AAAGACCCGC  CCCCGATGAC  GCGGATATAA
    43_12   CAGAAAGGGC  GGAGCCAGCA  AAAGACCCGC  CCCCGATGAC  GCGGATATAA
    43_20   CAGAAAGGGT  GGAGCCAACA  AGAGACCCGC  CCCCGATGAC  GCGGATATAA
    43_21   CAGAAAGGGT  GGAGCCAACA  AGAGACCCGC  CCCCGATGAC  GCGGATATAA
    43_23   CAGAAAGGGT  GGCGCCAACA  AGAGACCCGC  CCCCGATGAC  GCGGATATAA
    43_25   CAGAAAGGGT  GGAGCCAACA  AGAGACCCGC  CCCCGATGAC  GCGGATATAA
    44_1    CAGAAAGGGT  GGAGCCAACA  AGAGACCCGC  CCCCGATGAC  GCGGATAAAA
    44_5    CAGAAAGGGT  GGAGCCAACA  AGAGACCCGC  CCCCGATGAC  GCGGATAAAA
    223_10  ..........  ..........  ..........  ..........  ..........
    223_2   ..........  ..........  ..........  ..........  ..........
    223_4   ..........  ..........  ..........  ..........  ..........
    223_5   ..........  ..........  ..........  ..........  ..........
    223_6   ..........  ..........  ..........  ..........  ..........
    223_7   ..........  ..........  ..........  ..........  ..........
    A3_4    CAAAAAGGGT  GGAGCCAAGA  AAAGGCCCGC  CCCCGATGAT  GTATATATAA
    A3_5    CAAAAAGGGT  GGAGCCAAGA  AAAGGCCCGC  CCCCGATGAT  GTATATATAA
    A3_7    CAAAAAGGGT  GGAGCCAAGA  AAAGGCCCGC  CCCCGATGAT  GTATATATAA
    A3_3    CAAAAAGGGT  GGAGCCAAGA  AAAGGCCCGC  CCCCGATGAT  GTATATATAA
    42_12   CAGAAAGGGT  GGAGCCAACA  AGAGACCCGC  CCCCGATGAC  GCGGATAAAA
    AAV1    CAGAAAGGGT  GGAGCCAACA  AAAGACCCGC  CCCCGATGAC  GCGGATAAAA
    AAV2    CAAAAAGGGT  GGAGCCAAGA  AAAGACCCGC  CCCCAGTGAC  GCAGATATAA
    AAV3    CAGAAAGGGT  GGAGCTAAGA  AACGCCCCGC  CTCCAATGAC  GCGGATGTAA
    AAV8    CAGAAAGGGC  GGAGCCAGCA  AAAGACCCGC  CCCCGATGAC  GCGGATAAAA
    AAV9    CAGAAAGGGC  GGAGCCAGCA  AAAGACCCGC  CCCCGATGAC  GCGGATAAAA
    AAV7    CAGAAAGGGC  GGAGCCAGCA  AAAGACCCGC  CCCCGATGAC  GCGGATATAA
    44_2    CAGAAAGGGT  GGAGCCAACA  AGAGACCCGC  CCCCGATGAC  GCGGATAAAA
                                                                               P40/TATA
```

FIG. 1AL

```
         1851                                                      1900
                                          P40 RNA
  42_2   GCGAGCCCAA GCGGGCCTGC CCCTCAGTCG CGGAT▼CATC GACGTCAGAC
  42_8   GCGAGCCCAA GCGGGCCTGC CCCTCAGTCG CGGATCCATC GACGTCAGAC
 42_15   GCGAGCCCAA GCGGGCCTGC CCCTCAGTCG CGGATCCATC GACGTCAGAC
 42_5b   GCGAGCCCAA GCGGGCCTGC CCCTCAGTCG CGGATCCATC GACGTCAGAC
 42_1b   .......... .......... .......... .......... ..........
 42_13   GCGAGCCCAA GCGGGCCTGC CCCTCAGTCG CGGATCCATC GACGTCAGAC
 42_3a   GCGAGCCCAA GCGGGCCTGC CCCTCAGTCG CGGATCCATC GACGTCAGAC
  42_4   .......... .......... .......... .......... ..........
 42_5a   GCGAGCCCAA GCGGGCCCGC CCCTCAGTCG CGGATCCATC GACGTCAGAC
 42_10   .......... .......... .......... .......... ..........
 42_3b   .......... .......... .......... .......... ..........
 42_11   GCGAGCCCAA GCGGGCCTGC CCCTCAGTCG CGGATCCATC GACGTCAGAC
 42_6b   CTGTCACGTG AGTGCTTTTG CGACATTTTG C..ATCCATC GACGTCAGAC
  43_1   GCGAGCCCAA GCGGGCCTGC CCCTCAGTCG CGGATCCATC GACGTCAGAC
  43_5   GCGAGCCCAA GCGGGCCTGC CCCTCAGTCG CGGATCCATC GACGTCAGAC
 43_12   GCGAGCCCAA GCGGGCCTGC CCCTCAGTCG CGGATCCATC GACGTCAGAC
 43_20   GCGAGCCCAA GCGGGCCTGC CCCTCAGTCG CGGATCCATC GACGTCAGAC
 43_21   GCGAGCCCAA GCGGGCCTGC CCCTCAGTCG CGGATCCATC GACGTCAGAC
 43_23   GCGAGCCCAA GCGGGCCTGC CCCTCAGTCG CGGATCCATC GACGTCAGAC
 43_25   GCGAGCCCAA GCGGGCCTGC CCCTCAGTCG CGGATCCATC GACGTCAGAC
  44_1   GCGAGCCCAA GCGGGCCTGC CCCTCAGTCG CGGATCCATC GACGTCAGAC
  44_5   GCGAGCCCAA GCGGGCCTGC CCCTCAGTCG CGGATCCATC GACGTCAGAC
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   ATGAGCCCAA GCGGGCGCGC GAGTCAGTTG CGCAGCCATC GACGTCAGAC
  A3_5   ATGAGCCCAA GCGGGCGCGC GAGTCAGTTG CGCAGCCATC GACGTCAGAC
  A3_7   ATGAGCCCAA GCGGGCGCGC GAGTCAGTTG CGCAGCCATC GACGTCAGAC
  A3_3   ATGAGCCCAA GCGGGCGCGC GAGTCAGTTG CGCAGCCATC GACGTCAGAC
 42_12   GCGAGCCCAA GCGGGCCTGC CCCTCAGTCG CGGATCCATC GACGTCAGAC
  AAV1   GCGAGCCCAA GCGGGCCTGC CCCTCAGTCG CGGATCCATC GACGTCAGAC
  AAV2   GTGAGCCCAA ACGGGTGCGC GAGTCAGTTG CGCAGCCATC GACGTCAGAC
  AAV3   GCGAGCCAAA ACGGAGTGC ACGTCACTTG CGCAGCCGAC AACGTCAGAC
  AAV8   GCGAGCCCAA GCGGGCCTGC CCCTCAGTCG CGGATCCATC GACGTCAGAC
  AAV9   GCGAGCCCAA GCGGGCCTGC CCCTCAGTCG CGGATCCATC GACGTCAGAC
  AAV7   GCGAGCCCAA GCGGGCCTGC CCCTCAGTCG CGGATCCATC GACGTCAGAC
  44_2   GCGAGCCCAA GCGGGCCTGC CCCTCAGTCG CGGAT▲CATC GACGTCAGAC
                                          P40 RNA
```

FIG. 1AM

```
           1901                                                        1950
   42_2    GCGGAAGGAG CTCCGGTGGA CTTTGCCGAC AGGTACCAAA ACAAATGTTC
   42_8    GCGGAAGGAG CTCCGGTGGA CTTTGCCGAC AGGTACCAAA ACAAATGTTC
  42_15    GCGGAAGGAG CTCCGGTGGA CTTTGCCGAC AGGTACCAAA ACAAATGTTC
  42_5b    GCGGAAGGAG CTCCGGTGGA CTTTGCCGAC AGGTACCAAA ACAAATGTTC
  42_1b    .......... .......... .......... .......... ..........
  42_13    GCGGAAGGAG CTCCGGTGGA CTTTGCCGAC AGGTACCAAA ACAAATGTTC
  42_3a    GCGGAAGGAG CTCCGGTGGA CTTTGCCGAC AGGTACCAAA ACAAATGTTC
   42_4    .......... .......... .......... .......... ..........
  42_5a    GCGGAAGGAG CTCCGGTGGA CTTTGCCGAC AGGTACCAAA ACAAATGTTC
  42_10    .......... .......... .......... .......... ..........
  42_3b    .......... .......... .......... .......... ..........
  42_11    GCGGAAGGAG CTCCGGTGGA CTTTGCCGAC AGGTACCAAA ACAAATGTTC
  42_6b    GCGGAAGGAG CTCCGGTGGA CTTTGCCGAC AGGTACCAAA ACAAGTGTTC
   43_1    GCGGAAGGAG CTCCGGTGGA CTTTGCCGAC AGGTACCAAA ACAAATGTTC
   43_5    GCGGAAGGAG CTCCGGTGGA CTTTGCCGAC AGGTACCAAA ACAAATGTTC
  43_12    GCGGAAGGAG CTCCGGTGGA CTTTGCCGAC AGGTACCAAA ACAAATGTTC
  43_20    GCGGAAGGAG CTCCGGTGGA CTTTGCCGAC AGGTACCAAA ACAAATGTTC
  43_21    GCGGAAGGAG CTCCGGTGGA CTTTGCCGAC AGGTACCAAA ACAAATGTTC
  43_23    GCGGAAGGAG CTCCGGTGGA CTTTGCCGAC AGGTACCAAA ACAAATGTTC
  43_25    GCGGAAGGAG CTCCGGTGGA CTTTGCCGAC AGGTACCAAA ACAAATGTTC
   44_1    GCGGAAGGAG CTCCGGTGGA CTTTGCCGAC AGGTACCAAA ACAAATGTTC
   44_5    GCGGAAGGAG CTCCGGTGGA CTTTGCCGAC AGGTACCAAA ACAAATGTTC
 223_10    .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    GCGGA...AG CTTCGATAAA CTACGCGGGC AGGTACCAAA ACAAATGTTC
   A3_5    GCGGA...AG CTTCGATAAA CTACGCGGAC AGGTACCAAA ACAAATGTTC
   A3_7    GCGGA...AG CTTCGATAAA CTACGCGGAC AGGTACCAAA ACAAATGTTC
   A3_3    GCGGA...AG CTTCGATAAA CTACGCGGAC AGGTACCAAA ACAAATGTTC
  42_12    GCGGAAGGAG CTCCGGTGGA CTTTGCCGAC AGGTACCAAA ACAAATGTTC
   AAV1    GCGGAAGGAG CTCCGGTGGA CTTTGCCGAC AGGTACCAAA ACAAATGTTC
   AAV2    GCGGA...AG CTTCGATCAA CTACGCAGAC AGGTACCAAA ACAAATGTTC
   AAV3    GCGGA...AG CACCGGCGGA CTACGCGGAC AGGTACCAAA ACAAATGTTC
   AAV8    GCGGAAGGAG CTCCGGTGGA CTTTGCCGAC AGGTACCAAA ACAAATGTTC
   AAV9    GCGGAAGGAG CTCCGGTGGA CTTTGCCGAC AGGTACCAAA ACAAATGTTC
   AAV7    GCGGAAGGAG CTCCGGTGGA CTTTGCCGAC AGGTACCAAA ACAAATGTTC
   44_2    GCGGAAGGAG CTCCGGTGGA CTTTGCCGAC AGGTACCAAA ACAAATGTTC
```

FIG. 1AN

```
          1951                                                    2000
 42_2   TCGTCACGCG GGCATGCTTC AGATGCTGTT TCCCTG.CAA GACATGCGAG
 42_8   TCGTCACGCG GGCATGCTTC AGATGCTGTT TCCCTG.CAA GACATGCGAG
 42_15  TCGTCACGCG GGCATGCTTC AGATGCTGTT TCCCTG.CAA GACATGCGAG
 42_5b  TCGTCACGCG GGCATGCTTC AGATGCTGTT TCCCTG.CAA GACATGCGAG
 42_1b  .......... .......... ....GAATTC GCCCTT.... .GGCTGCGTC
 42_13  TCGTCACGCG GGCATGCTTC AGATGCTGTT TCCCTG.CAA GACATGCGAG
 42_3a  TCGTCACGCG GGCATGCTTC AGATGCTGCT TCCCTG.CAA GACATGCGAG
 42_4   .......... .......... ....GAATTC GCCCTTCTA CGGCTGCGTC
 42_5a  TCGTCACGCG GGCATGCTTC AGATGCTGTT TCCCTG.CAA AACATGCGAG
 42_10  .......... .......... ....GAATTC GCCCTTCTA CGGCTGCGTC
 42_3b  .......... .......... ....GAATTC GCCCTTCTA CGGCTGCGTC
 42_11  TCGTCACGCG GGCATGCTTC AGATGCTGTT TCCCTG.CAA GACATGCGAG
 42_6b  TCGTCACGCG GGCATGCTTC AGATGCTGTT TCCCTG.CAA GACATGCGAG
 43_1   TCGTCACGCG GGCATGCTTC AGATGCTGTT TCCCTG.CAA AACGTGCGAG
 43_5   TCGTCACGCG GGCATGCTTC AGACGCTGTT TCCCTG.CAA AACGTGCGAG
 43_12  TCGTCACGCG GGCATGCTCC AGATGCTGTT TCCCTG.CAA AACGTGCGAG
 43_20  TCGTCACGCG GGCATGCTTC AGATGCTGTT TCCCTG.CAA GACATGCGAG
 43_21  TCGTCACGCG GGCATGCTTC AGATGCTGTT TCCCTG.CAA GACATGCGAG
 43_23  TCGTCACGCG GGCATGCTTC AGATGCTGTT TCCCTG.CAA GACATGCGAG
 43_25  TCGTCACGCG GGCATGCTTC AGATGCTGTT TCCCTG.CAA GACATGCGAG
 44_1   TCGTCACGCG GGCATGCTTC AGATGCTGTT TCCCTG.CAA AACATGCGAG
 44_5   TCGTCACGCG GGCATGCTTC AGATGCTGTT TCCCTG.CAA AACATGCGAG
223_10  .......... .......... .......... .......... ..........
223_2   .......... .......... .......... .......... ..........
223_4   .......... .......... .......... .......... ..........
223_5   .......... .......... .......... .......... ..........
223_6   .......... .......... .......... .......... ..........
223_7   .......... .......... .......... .......... ..........
 A3_4   TCGTCACGTG GGCATGAATC TGATGCTGTT TCCCTG.TCG ACAATGCGAA
 A3_5   TCGTCACGTG GGCATGAATC TGATGCTGTT TCCCTG.TCG ACAATGCGAA
 A3_7   TCGTCACGTG GGCATGAATC TGATGCTGTT TCCCTG.TCG ACAATGCGAA
 A3_3   TCGTCACGTG GGCATGAATC TGATGCTGTT TCCCTG.TCG ACAATGCGAA
 42_12  TCGTCACGCG GGCATGCTTC AGATGCTGTT TCCCTG.CAA GACATGCGAG
 AAV1   TCGTCACGCG GGCATGCTTC AGATGCTGTT TCCCTG.CAA GACATGCGAG
 AAV2   TCGTCACGTG GGCATGAATC TGATGCTGTT TCCCTG.CAG ACAATGCGAG
 AAV3   TCGTCACGTG GGCATGAATC TGATGCTTTT TCCCTG.TAA AACATGCGAG
 AAV8   TCGTCACGCG GGCATGCTTC AGATGCTGTT TCCCTG.CAA AACGTGCCAG
 AAV9   TCGTCACGCG GGCATGCTTC AGATGCTGCT TCCCTG.CAA AACGTGCGAG
 AAV7   TCGTCACGCG GGCATGATTC AGATGCTGTT TCCCTG.CAA AACGTGCGAG
 44_2   TCGTCACGCG GGCATGCTTC AGATGCTGTT TCCCTG.CAA AACATGCGAG
```

FIG. 1AO

```
           2001                                                              2050
  42_2     AGAATGAATC  AGAATTTCAA  CATTTGCTTC  ACGCACGGGA  CCAGAGACTG
  42_8     AGAATGAATC  AGAATTTCAA  CATTTGCTTC  ACGCACGGGA  CCAGAGACTG
  42_15    AGAATGAATC  AGAATTTCAA  CATTTGCTTC  ACGCGCGGGA  CCAGAGACTG
  42_5b    AGAATGAATC  AGAATTTCAA  CATTTGCTTC  ACGCACGGGA  CCAGAGACTG
  42_1b    A.ACTGGACC  A..ATGAGAA  CTTTCCCTTC  A........A  CGATTGCGTC
  42_13    AGAATGAATC  AGAATTTCAA  CATTTGCTTC  ACGCACGGGA  CCAGAGACTG
  42_3a    AGAATGAATC  AGAATTTCAG  CATTTGCTTC  ACGCACGGGA  CCAGAGACTG
  42_4     A.ACTGGACC  A..ATGAGAA  CTTTCCCTTC  A........A  CGATTGCGTC
  42_5a    AGAATGAATC  AGAATTTCAA  CATTTGCTTC  ACGCACGGGA  CCAGAGACTG
  42_10    A.ACTGGACC  A..ATGAGAA  CTTTCCCTTC  A........A  CGATTGCGTC
  42_3b    A.ACTAGACC  A..ATGAGAA  CTTTCCCTTC  A........A  CGATTGCGTC
  42_11    AGAATGAATC  AGAATTTCAA  CATTTGCTTC  ACGCACGGGA  CCGGAGACTG
  42_6b    AGAATGAATC  AGAATTTCAA  CATTTGCTTC  ACGCACGGGA  CCAGAGACTG
  43_1     AAAATGAATC  AGAATTTCAA  CATTTGCTTC  ACGCACGGGG  TCAGAGACTG
  43_5     AGAATGAATC  AGAATTTCAA  CATTTGCTTC  ACGCACGGGG  TCAGAGACTG
  43_12    AGAATGAATC  AGAATTTCAA  CATTTGCTTC  ACGCACGGGG  TCAGAGACTG
  43_20    AGAATGAATC  AGAATTTCAA  CATTTGCTTC  ACGCACGGGA  CCAGAGACTG
  43_21    AGAATGAATC  AGAATTTCAA  CATTTGCTTC  ACGCACGGGA  CCAGAGACTG
  43_23    AGAATGAATC  AGAATTTCAA  CATTTGCTTC  ACGCACGGGA  CCAGAGACTG
  43_25    AGAATGAATC  AGAATTTCAA  CATTTGCTTC  ACGCACGGGA  CCAGAGACTG
  44_1     AGAATGAATC  AGAATTTCAA  CATTTGCTTC  ACGCACGGGA  CCAGAGACTG
  44_5     AGAATGAATC  AGAATTTCAA  CATTTGCTTC  ACGCACGGGA  CCAGAGACTG
 223_10    ..........  ..........  ..........  ..........  ..........
 223_2     ..........  ..........  ..........  ..........  ..........
 223_4     ..........  ..........  ..........  ..........  ..........
 223_5     ..........  ..........  ..........  ..........  ..........
 223_6     ..........  ..........  ..........  ..........  ..........
 223_7     ..........  ..........  ..........  ..........  ..........
  A3_4     AGAATGAATC  AGAATTCAAA  TATCTGCTTC  ACACACGGGC  AAAAAGACTG
  A3_5     AGAATGAATC  AGAATTCAAA  TATCTGCTTC  ACACACGGGC  AAAAAGACTG
  A3_7     AGAATGAATC  AGAATTCAAA  TATCTGCTTC  ACACACGGGC  AAAAAGACTG
  A3_3     AGAATGAATC  AGAATTCAAA  TATCTGCTTC  ACACACGGGC  AAAAAGACTG
  42_12    AGAATGAATC  AGAATTTCAA  CATTTGCTTC  ACGCACGGGA  CCAGAGACTG
  AAV1     AGAATGAATC  AGAATTCAAA  CATTTGCTTC  ACGCACGGGA  CGAGAGACTG
  AAV2     AGAATGAATC  AGAATTCAAA  TATCTGCTTC  ACTCACGGAC  AGAAAGACTG
  AAV3     AGAATGAATC  AAATTTCCAA  TGTCTGTTTT  ACGCATGGTC  AAAGAGACTG
  AAV8     AGAATGAATC  AGAATTTCAA  CATTTGCTTC  ACACACGGGG  TCAGAGACTG
  AAV9     AGAATGAATC  AGAATTTCAA  CATTTGCTTC  ACACACGGGG  TCAGAGACTG
  AAV7     AGAATGAATC  AGAATTTCAA  CATTTGCTTC  ACACACGGGG  TCAGAGACTG
  44_2     AGAATGAATC  AGAATTTCAA  CATTTGCTTC  ACGCACGGGA  CCAGAGACTG
```

FIG. 1AP

```
              2051                                                       2100
    42_2     TTCAGAATGT TTCCCCGGCG TGTCAGAATC TCAACC.... ..GGTCGTCA

42_8     TTCAGAATGT TTCCCCGGCG TGTCAGAATC TCAACC.... ..GGTCGTCA
    42_15    TTCAGAATGT TTCCCCGGGCG TGTCAGAATC TCAACC.... ..GGTCGTCA
    42_5b    TTCAGAATGT TTCCCCGGCG TGTCAGAATC TCAACC.... ..GGTCGTCA
    42_1b    GACAAGATGG TGATCTGGTG GG..AGGAGG GCAAGA.... ..TGACGGCC
    42_13    TTCAGAATGT TTCCCCGGCG TGTCAGAATC TCAACC.... ..GGTCGTCA
    42_3a    TTCAGAATGT TTCCCCGGCG TGTCAGAATC TCAACC.... ..GGTCGTCA
    42_4     GACAAGATGG TGATCTGGTG GG..AGGAGG GCAAGA.... ..TGACGGCC
    42_5a    TTCAGAATGT TTCCCCGGCG TGTCAGAATC TCAACC.... ..GGTCGTCA
    42_10    GACAAGATGG TGATCTGGTG GG..AGGAGG GCAAGA.... ..TGACGGCC
    42_3b    GACAAGATGG TGATCTGGTG GG..AGGAGG GCAAGA.... ..TGACGGCC
    42_11    TTCAGAATGT TTCCCCGGCG TGTCAGAATC TCAACC.... ..GGTCGTCA
    42_6b    TTCAGAATGT TTCCCCGGCG TGTCAGAATC TCAACC.... ..GGTCGTCA
    43_1     CTCAGAATGT TTCCCCGGTG CATCAGAATC TCAACC.... ..GGTCGTCA
    43_5     CTCAGAATGT TTCCCCGGTG CATCAGAATC TCAACC.... ..GGTCGTCA
    43_12    CTCAGAATGT TTCCCCGGTG CATCAGAATC TCAACC.... ..GGTCGTCA
    43_20    TTCAGAATGT TTCCCCGGCG TGTCAGAATC TCAACC.... ..GGTCGTCA
    43_21    TTCAGAATGT TTCCCCGGCG TGTCAGAATC TCAACC.... ..GGTCGTCA
    43_23    TTCAGAATGT TTCCCCGGCG TGTCAGAATC TCAACC.... ..GGTCGTCA
    43_25    TTCAGAATGT TTCCCCGGCG TGTCAGAATC TCAACC.... ..GGTCGTCA
    44_1     TTCAGAATGT TTCCCCGGCG TGTCAGAATC TCAACC.... ..GGTCGTCA
    44_5     TTCAGAATGT TTCCCCGGCG TGTCAGAATC TCAACC.... ..GGTTGTCA
    223_10   .......... .......... .......... .......... ..........
    223_2    .......... .......... .......... .......... ..........
    223_4    .......... .......... .......... .......... ..........
    223_5    .......... .......... .......... .......... ..........
    223_6    .......... .......... .......... .......... ..........
    223_7    .......... .......... .......... .......... ..........
    A3_4     TTTGGAATGC TTTCCCG... TGTCAGAATC TCAACCCGTT TCTGTCGTCA
    A3_5     TTTGGAATGC TTTCCCG... TGTCAGAATC TCAACCCGTT CCTGTCGTCA
    A3_7     TTTGGAATGC TTTCCCG... TGTCAGAATC TCAACCCGTT TCTGTCGTCA
    A3_3     TTTGGAATGC TTTCCCG... TGTCAGAATC TCAACCCGTT TCTGTCGTCA
    42_12    TTCAGAATGT TTCCCCGGCG TGTCAGAATC TCAACC.... ..GGTCGTCA
    AAV1     TTCAGAGTGC TTCCCCGGCG TGTCAGAATC TCAACC.... ..GGTCGTCA
    AAV2     TTTAGAGTGC TTTCCCG... TGTCAGAATC TCAACCCGTT TCTGTCGTCA
    AAV3     TGGGGAATGC TTCCCTGGAA TGTCAGAATC TCAACCCGTT TCTGTCGTCA
    AAV8     CTCAGAGTGT TTCCCCGGCG TGTCAGAATC TCAACC.... ..GGTCGTCA
    AAV9     CTCAGAGTGT TTCCCCGGCG TGTCAGAATC TCAACC.... ..GGTCGTCA
    AAV7     TTTAGAGTGT TTCCCCGGCG TGTCAGAATC TCAACC.... ..GGTCGTCA
    44_2     TTCAGAATGT TTCCCCGGCG TGTCAGAATC TCAACC.... ..GGTCGTCA
```

FIG. 1AQ

```
           2101                                                      2150
  42_2    GAAAGAGGAC GTATCGGAAA CTCTGTGCCA TTCATCATCT GCTGGGG.CG

42_8    GAAAGAGGAC GTATCGGAAA CTCTGTGCCA TTCATCATCT GCTAGGG.CG
  42_15   GAAAGAGGAC GTATCGGAAA CTCTGTGCCA TTCATCATCT GCTGGGG.CG
  42_5b   GAAAGAGGAC GTATCGGAAA CTCTGTGCCA TTCATCATCT GCTGGGG.CG
  42_1b   .AAGGTCGTG GAGTCCGCCA AG....GCCA TTCATCATCT GCTGGGG.CG
  42_13   GAAAGAGGAC GTATCGGAAA CTCTGTGCCA TTCATCATCT GCTGGGG.CG
  42_3a   GAAAGAGGAC GTATCGGAAA CTCTGTGCCA TTCATCATCT GCTGGGG.CG
  42_4    .AAGGTCGTG GAGTCCGCCA AG....GCCA TTCATCATCT GCTGGGG.CG
  42_5a   GAAAGAGGAC GTATCGGAAA CTCTGTGCCA TTCATCATCT GCTGGGG.CG
  42_10   AA....GGTC GTGAAGTCCG CCAAG.GCCA TTCATCATCT GCTGGGG.CG
  42_3b   AA....GGTC GTGGAGTCCG CCAAG.GCCA TTCATCATCT GCTGGGG.CG
  42_11   GAAAGAGGAC GTATCGGAAA CTCTGTGCCA TTCATCATCT GCTGGGG.CG
  42_6b   GAAAGAGGAC GTATCGGAAA CTCTGTGCCA TTCATCATCT GCTGGGG.CG
  43_1    GAAAAAAAAC GTATCAGAAA CTGTGTGCCA TTCATCATCT GCTGGGG.CG
  43_5    GAAAAAAAAC GTATCAGAAA CTGTGTGCCA TTCATCATCT GCTGGGG.CG
  43_12   GAAAAAAAAC GTATCAGAAA CTGTGTGCCA TTCATCATCT GCTGGGG.CG
  43_20   GAAAGAGGAC GTATCGGAAA CTCTGTGCGA TTCATCATCT GCTGGGG.CG
  43_21   GAAAGAGGAC GTATCGGAAA CTCTGTGCGA TTCATCATCT GCTGGGG.CG
  43_23   GAAAGAGGAC GTATCGGAAA CTCTGTGCGA TTCATCATCT GCTGGGG.CG
  43_25   GAAAGAGGAC GTATCGGAAA CTCTGTGCGA TTCATCATCT GCTGGGG.CG
  44_1    GAAAAAAGAC GTATCGGAAA CTCTGTGCGA TTCATCATCT GCTGGGG.CG
  44_5    GAAAAAAGAC GTATCGGAAA CTCTGTGCGA TTCATCATCT GCTGGGG.CG
 223_10   .......... .......... .......... .......... ..........
 223_2    .......... .......... .......... .......... ..........
 223_4    .......... .......... .......... .......... ..........
 223_5    .......... .......... .......... .......... ..........
 223_6    .......... .......... .......... .......... ..........
 223_7    .......... .......... .......... .......... ..........
  A3_4    GAAAAACG.. .TATCAGAAA CTTTGTTACA TTCATCATAT CATGGGA.AA
  A3_5    GAAAAACG.. .TATCAGAAA CTTTGTTACA TTCATCATAT CATGGGA.AA
  A3_7    GAAAAACG.. .TATCAGAAA CTTTGTTACA TTCATCATAT CATGGGA.AA
  A3_3    GAAAAACG.. .TATCAGAAA CTTTGTTACA TTCATCATAT CATGGGA.AA
  42_12   GAAAGAGGAC GTATCGGAAA CTCTGTGCCA TTCATCATCT GCTGGGG.CG
  AAV1    GAAAGAGGAC GTATCGGAAA CTCTGTGCCA TTCATCATCT GCTGGGG.CG
  AAV2    AAAAGGCG.. .TATCAGAAA CTGTGCTACA TTCATCATAT CATGGGA.AA
  AAV3    AAAAGAAGAC TTATCAGAAA CTGTGTCCAA TTCATCATAT CCTGGGA.AG
  AAV8    GAAAGAGGAC GTATCGGAAA CTCTGTGCGA TTCATCATCT GCTGGGG.CG
  AAV9    GAAAGAGGAC GTATCGGAAA CTCTGTGCGA TTCATCATCT GCTGGGG.CG
  AAV7    GAAAAAAGAC GTATCGGAAA CTCTGCGCGA TTCATCATCT GCTGGGG.CG
  44_2    GAAAAAAGAC GTATCGGAAA CTCTGTGCGA TTCATCATCT GCTGGGGGCG
```

FIG. 1AR

```
         2151                                                              2200
 42_2    GGCTCCCGAG  ATTGCTTGCT  CGGCCTGCGA  TCTGGTCAAC  GTGGACCTGG
 42_8    GGCTCCCGAG  ATTGCTTGCT  CGGCCTGCGA  TCTGGTCAAC  GTGGACCTGG
 42_15   GGCTCCCGAG  ATTGCTTGCT  CGGCCTGCGA  TCTGGTCAAC  GTGGACCTGG
 42_5b   GGCTCCCGAG  ATTGCTTGCT  CGGCCTGCGA  TCTGGTCAAC  GTGGACCTGG
 42_1b   GGCTCCCGAG  ATTGCTTGCT  CGGCCTGCGA  TCTGGTCAAC  GTGGACCTGG
 42_13   GGCTCCCGAG  ATTGCTTGCT  CGGCCTGCGA  TCTGGTCAAC  GTGGACCTGG
 42_3a   GGCTCCCGAG  ATTGCTTGCT  CGGCCTGCGA  TCTGGTCAAC  GTGGACCTGG
 42_4    GGCTCCCGAG  ATTGCTTGCT  CGGCCTGCGA  TCTGGTCAAC  GTGGACCTGG
 42_5a   GGCTCCCGAG  ATTGCTTGCT  CGGCCTGCGA  TCTGGTCAAC  GTGGACCTGG
 42_10   GGCTCCCGAG  ATTGCTTGCT  CGGCCTGCGA  TCTGGTCAAC  GTGGACCTGG
 42_3b   GGCTCCCGAG  ATTGCTTGCT  CGGCCTGCGA  TCTGGTCAAC  GTGGACCTGG
 42_11   GGCTCCCGAG  ATTGCTTGCT  CGGCCTGCGA  TCTGGTCAAC  GTGGACCTGG
 42_6b   GGCTCCCGAG  ATTGCTTGCT  CGGCCTGCGA  TCTGGTCAAC  GTGGACCTGG
 43_1    GGCACCCGAG  ATTGCTTGCT  CGGCCTGCGA  TCTGGTCAAC  GTGGACCTGG
 43_5    GGCACCCGAG  ATTGCTTGCT  CGGCCTGCGA  TCTGGTCAAC  GTGGACCTGG
 43_12   GGCACCCGAG  ATTGCTTGCT  CGGCCTGCGA  TCTGGTCAAC  GTGGACCTGG
 43_20   GGCTCCCGAG  ATTGCTTGCT  CGGCCTGCGA  TCTGGTCAAC  GTGGACCTGG
 43_21   GGCTCCCGAG  ATTGCTTGCT  CGGCCTGCGA  TCTGGTCAAC  GTGGACCTGG
 43_23   GGCTCCCGAG  ATTGCTTGCT  CGGCCTGCGA  TCTGGTCAAC  GTGGACCTGG
 43_25   GGCTCCCGAG  ATTGCTTGCT  CGGCCTGCGA  TCTGGTCAAC  GTGGACCTGG
 44_1    GGCACCCGAG  ATTGCTTGCT  CGGCCTGCGA  TCTGGTCAAC  GTGGACCTAG
 44_5    GGCACCCGAG  ATTGCTTGCT  CGGCCTGCGA  TCTGGTCAAC  GTGGACCTAG
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
 A3_4    AGAACCAGAC  ...GCCTGCA  CTGCCTGCGA  CCTGGTAAAT  GTGGACTTGG
 A3_5    AGTACCAGAC  ...GCCTGCA  CTGCCTGCGA  CCTGGTAAAT  GTGGACTTGG
 A3_7    AGTACCAGAC  ...GCCTGCA  CTGCCTGCGA  CCTGGTAAAT  GTGGACTTGG
 A3_3    AGTACCAGAC  ...GCCTGCA  CTGCCTGCGA  CCTGGTAAAT  GTGGACTTGG
 42_12   GGCTCCCGAG  ATTGCTTGCT  CGGCCTGCGA  TCTGGTCAAC  GTGGACCTGG
 AAV1    GGCTCCCGAG  ATTGCTTGCT  CGGCCTGCGA  TCTGGTCAAC  GTGGACCTGG
 AAV2    GGTGCCAGAC  ...GCTTGCA  CTGCCTGCGA  TCTGGTCAAT  GTGGATTTGG
 AAV3    GGCACCCGAG  ATTGCCTGTT  CGGCCTGCGA  TTTGGCCAAT  GTGGACTTGG
 AAV8    GGCTCCCGAG  ATTGCTTGCT  CGGCCTGCGA  TCTGGTCAAC  GTGGACCTGG
 AAV9    GGCTCCCGAG  ATTGCTTGCT  CGGCCTGCGA  TCTGGTCAAC  GTGGACCTGG
 AAV7    GGCGCCCGAG  ATTGCTTGCT  CGGCCTGCGA  CCTGGTCAAC  GTGGACCTGG
 44_2    GGCACCCGAG  ATTGCTTGCT  CGGCCTGCGA  TCTGGTCAAC  GTGGACCTAG
```

FIG. 1AS

```
            2201                                                    2250
                              Rep 78 stop           vp1 start
    42_2    ATGACCGTGT  TTCTGAGCAA  TAAATGACTT  AAACCAGGTA  TGGCTGCCGA
    42_8    ATGACTGTGT  TTCTGAGCAA  TAAATGACTT  AAACCAGGTA  TGGCTGCCGA
   42_15    ATGACTGTGT  TTCTGAGCAA  TAAATGACTT  AAACCAGGTA  TGGCTGCCGA
   42_5b    ATGACTGTGT  TTCTGAGCAA  TAAATGACTT  AAACCAGGTA  TGGCTGCCGA
   42_1b    ATGACTGTGT  TTCTGAGCAA  TAAATGACTT  AAACCAGGTA  TGGCTGCCGA
   42_13    ATGACTGTGT  TTCTGAGCAA  TAAATGACTT  AAACCAGGTA  TGGCTGCCGA
   42_3a    ATGACTGTGT  TTCTGAGCAA  TAAATGACTT  AAACCAGGTA  TGGCTGCCGA
    42_4    ATGACTGTGT  TTCTGAGCAA  TAAATGACTT  AAACCAGGTA  TGGCTGCCGA
   42_5a    ATGACTGTGT  TTCTGAGCAA  TAAATGACTT  AAACCAGGTA  TGGCTGCCGA
   42_10    ATGACTGTGT  TTCTGAGCAA  TAAATGACTT  AAACCAGGTA  TGGCTGCCGA
   42_3b    ATGACTGTGT  TTCTGAGCAA  TAAATGACTT  AAACCAGGTA  TGGCTGCCGA
   42_11    ATGACTGTGT  TTCTGAGCAA  TAAATGACTT  AAACCAGGTA  TGGCTGCCGA
   42_6b    ATGACTGTGT  TTCTGAGCAA  TAAATGACTT  AAACCAGGTA  TGGCTGCCGA
    43_1    ACGACTGTGT  TTCTGAGCAA  TAAATGACTT  AAACCAGGTA  TGGCTGCCGA
    43_5    ACGACTGTGT  TTCTGAGCAA  TAAATGACTT  AAACCAGGTA  TGGCTGCCGA
   43_12    ACGACTGTGT  TTCTGAGCAA  TAAATGACTT  AAACCAGGTA  TGGCTGCCGA
   43_20    ATGACTGTGT  TTCTGAGCAA  TAAATGACTT  AAACCAGGTA  TGGCTGCCGA
   43_21    ATGACTGTGT  TTCTGAGCAA  TAAATGACTT  AAACCAGGTA  TGGCTGCCGA
   43_23    ATGACTGTGT  TTCTGAGCAA  TAAATGACTT  AAACCAGGTA  TGGCTGCCGA
   43_25    ATGACTGTGT  TTCTGAGCAA  TAAATGACTT  AAACCAGGTA  TGGCTGCCGA
    44_1    ATGACTGTGT  TTCTGAGCAA  TAAATGACTT  AAACCAGGTA  TGGCTGCCGA
    44_5    ATGACTGTGT  TTCTGAGCAA  TAAATGACTT  AAACCAGGTA  TGGCTGCCGA
  223_10    ..........  ..........  ..........  ..........  ..........
   223_2    ..........  ..........  ..........  ..........  ..........
   223_4    ..........  ..........  ..........  ..........  ..........
   223_5    ..........  ..........  ..........  ..........  ..........
   223_6    ..........  ..........  ..........  ..........  ..........
   223_7    ..........  ..........  ..........  ..........  ..........
    A3_4    ATGACTGTAT  TTCTGAGCAA  TAAATGACTT  AAATCAGGTA  TGGCTGCTGA
    A3_5    ATGACTGTAT  TTCTGAGCAA  TAAATGACTT  AAATCAGGTA  TGGCTGCTGA
    A3_7    ATGACTGTAT  TTCTGAGCAA  TAAATGACTT  AAATCAGGTA  TGGCTGCTGA
    A3_3    ATGACTGTAT  TTCTGAGCAA  TAAATGACTT  AAATCAGGTA  TGGCTGCTGA
   42_12    ATGACTGTGT  TTCTGAGCAA  TAAATGACTT  AAACCAGGTA  TGGCTGCCGA
    AAV1    ATGACTGTGT  TTCTGAGCAA  TAAATGACTT  AAACCAGGTA  TGGCTGCCGA
    AAV2    ATGACTGCAT  CTTTGAACAA  TAAATGATTT  AAATCAGGTA  TGGCTGCCGA
    AAV3    ATGACTGTGT  TTCTGAGCAA  TAAATGACTT  AAACCAGGTA  TGGCTGCTGA
    AAV8    ATGACTGTGT  TTCTGAGCAA  TAAATGACTT  AAACCAGGTA  TGGCTGCCGA
    AAV9    ATGACTGTGT  TTCTGAGCAA  TAAATGACTT  AAACCAGGTA  TGGCTGCCGA
    AAV7    ACGACTGCGT  TTCTGAGCAA  TAAATGACTT  AAACCAGGTA  TGGCTGCCGA
    44_2    ATGACTGTGT  TTCTGAGCAA  TAAATGACTT  AAACCAGGTA  TGGCTGCCGA
                              Rep78 stop           vp1 start
```

FIG. 1AT

```
        2251                                                          2300
                                                       Rep68 stop
  42_2   TGGTTATCTT  CCAGATTGGC  TCGAGGACAA  CCTCTCTGAG  GGCATTCGCG
  42_8   TGGTTATCTT  CCAGATTGGC  TCGAGGACAA  CCTCTCTGAG  GGCATTCGCG
  42_15  TGGTTATCTT  CCAGATTGGC  TCGAGGACAA  CCTCTCTGAG  GGCATTCGCG
  42_5b  TGGTTATCTT  CCAGATTGGC  TCGAGGACAA  CCTCTCTGAG  GGCATTCGCG
  42_1b  TGGTTATCTT  CCAGATTGGC  TCGAGGACAA  CCTCTCTGAG  GGCATTCGCG
  42_13  TGGTTATCTT  CCAGATTGGC  TCGAGGACAA  CCTCTCTGAG  GGCATTCGCG
  42_3a  TGGTCATCTT  CCAGATTGGC  TCGAGGACAA  CCTCTCTGAG  GGCATTCGCG
  42_4   TGGTTATCTT  CCAGATTGGC  TCGAGGACAA  CCTCTCTGAG  GGCATTCGCG
  42_5a  TGGTTATCTT  CCAGATTGGC  TCGAGGACAA  CCTCTCTGAG  GGCATTCGCG
  42_10  TGGTTATCTT  CCAGATTGGC  TCGAGGACAA  CCTCTCTGAG  GGCATTCGCG
  42_3b  TGGTTATCTT  CCAGATTGGC  TCGAGGACAA  CCTCTCTGAG  GGCATTCGCG
  42_11  TGGTTATCTT  CCAGATTGGC  TCGAGGACAA  CCTCTCTGAG  GGCATTCGCG
  42_6b  TGGTTATCTT  CCAGATTGGC  TCGAGGACAA  CCTCTCTGAG  GGCATTCGCG
  43_1   TGGTTATCTT  CCAGATTGGC  TTGAGGACAA  CCTCTCTGAG  GGCATTCGCG
  43_5   TGGTTATCTT  CCAGATTGGC  TTGAGGACAA  CCTCTCTGAG  GGCATTCGCG
  43_12  TGGTTATCTT  CCAGATTGGC  TTGAGGACAA  CCTCTCTGAG  GGCATTCGCG
  43_20  TGGTTATCTT  CCAGATTGGC  TCGAGGACAA  CCTCTCTGAG  GGCATTCGCG
  43_21  TGGTTATCTT  CCAGATTGGC  TCGAGGACAA  CCTCTCTGAG  GGCATTCGCG
  43_23  TGGTTATCTT  CCAGATTGGC  TCGAGGACAA  CCTCTCTGAG  GGCATTCGCG
  43_25  TGGTTATCTT  CCAGATTGGC  TCGAGGACAA  CCTCTCTGAG  GGCATTCGCG
  44_1   TGGTTATCTT  CCAGATTGGC  TCGAGGACAA  CCTCTCTGAG  GGCATTCGCG
  44_5   TGGTTATCTT  CCAGATTGGC  TCGAGGACAA  CCTCTCTGAG  GGCATTCGCG
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   CGGTTATCTT  CCAGATTGGC  TCGAGGACAC  TCTCTCTGAA  GGAATCAGAC
  A3_5   CGGTTATCTT  CCAGATTGGC  TCGAGGACAC  TCTCTCTGAA  GGAATCAGAC
  A3_7   CGGTTATCTT  CCAGATTGGC  TCGAGGACAC  TCTCTCTGAA  GGAATCAGAC
  A3_3   CGGTTATCTT  CCAGATTGGC  TCGAGGACAC  TCTCTCTGAA  GGAATCAGAC
  42_12  TGGTTATCTT  CCAGATTGGC  TCGAGGACAA  CCTCTCTGAG  GGCATCCGCG
  AAV1   TGGTTATCTT  CCAGATTGGC  TCGAGGACAA  CCTCTCTGAG  GGCATTCGCG
  AAV2   TGGTTATCTT  CCAGATTGGC  TCGAGGACAC  TCTCTCTGAA  GGAATAAGAC
  AAV3   CGGTTATCTT  CCAGATTGGC  TCGAGGACAA  CCTTTCTGAA  GGCATTCGTG
  AAV8   TGGTTATCTT  CCAGATTGGC  TCGAGGACAA  CCTCTCTGAG  GGCATTCGCG
  AAV9   TGGTTATCTT  CCAGATTGGC  TCGAGGACAA  CCTCTCTGAG  GGCATTCGCG
  AAV7   TGGTTATCTT  CCAGATTGGC  TCGAGGACAA  CCTCTCTGAG  GGCATTCGCG
  44_2   TGGTTATCTT  CCAGATTGGC  TCGAGGACAA  CCTCTCTGAG  GGCATTCGCG
                                                       Rep 68 stop
```

FIG. 1AU

```
         2301                                                              2350
 42_2    AGTGGTGGGA CTTGAAACCT GGAGCCCCGA AACCCAAAGC CAACCAGCAA

42_8    AGTGGTGGGA CTTGAAACCT GGAGCCCCGA AACCCAAAGC CAACCAGCAA
 42_15   AGTGGTGGGA CTTGAAACCT GGAGCCCCGA AACCCAAAGC CAACCAGCAA
 42_5b   AGTGGTGGGA CTTGAAACCT GGAGCCCCGA AACCCAAAGC CAACCAGCAA
 42_1b   AGTGGTGGGA CTTGAGACCT GGAGCCCCGA AACCCAAAGC CAACCAGCAA
 42_13   AGTGGTGGGA CTTGAAACCT GGAGCCCCGA AACCCAAAGC CAACCAGCAA
 42_3a   AGTGGTGGGA CTTGAAACCT GGAGCCCCGA AACCCAAAGC CAACCAGCAA
 42_4    AGTGGTGGGA CTTGAAACCT GGAGCCCCGA AACCCAAAGC CAACCAGCAA
 42_5a   AGTGGTGGGA CTTGAAACCT GGAGCCCCGA AACCCAAAGC CAACCAGCAA
 42_10   AGTGGTGGGA CTTGAAACCT GGAGCCCCGA AACCCAAAGC CAACCAGCAA
 42_3b   AGTGGTGGGA CTTGAAACCT GGAGCCCCGA AACCCAAAGC CAACCAGCAA
 42_11   AGTGGTGGGA CTTGAAACCT GGAGCCCCGA AACCCAAAGC CAACCAGCAA
 42_6b   AGTGGTGGGA CTTGAAACCT GGAGCCCCGA AACCCAAAGC CAACCAGCAA
 43_1    AGTGGTGGGA CCTGAAACCT GGAGCCCCGA AACCCAAAGC CAACCAGCAA
 43_5    AGTGGTGGGA CCTGAAACCT GGAGCCCCGA AACCCAAAGC CAACCAGCAA
 43_12   AGTGGTGGGA CCTGAAACCT GGAGCCCCGA AACCCAAAGC CAACCAGCAA
 43_20   AGTGGTGGGA CTTGAAACCT GGAGCCCCGA AACCCAAAGC CAACCAGCAA
 43_21   AGTGGTGGGA CTTGAAACCT GGAGCCCCGA AACCCAAAGC CAACCAGCAA
 43_23   AGTGGTGGGA CTTGAAACCT GGAGCCCCGA AACCCAAAGC CAACCAGCAA
 43_25   AGTGGTGGGA CTTGAAACCT GGAGCCCCGA AACCCAAAGC CAACCAGCAA
 44_1    AGTGGTGGGA CTTGAAACCT GGAGCCCCGA AACCCAAAGC CAACCAGCAA
 44_5    AGTGGTGGGA CTTGAAACCT GGAGCCCCGA AACCCAAAGC CAACCAGCAA
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    AGTGGTGGAA GCTCAAACCT GGCCCACCAC CGCCGAAACC TAACCAACAA
 A3_5    AGTGGTGGAA GCTCAAACCT GGCCCACCAC CGCCGAAACC TAACCAACAA
 A3_7    AGTGGTGGAA GCTCAAACCT GGCCCACCAC CGCCGAAACC TAACCAACAA
 A3_3    AGTGGTGGAA GCTCAAACCT GGCCCACCAC CGCCGAAACC TAACCAACAA
 42_12   AGTGGTGGGA CTTGAAACCT GGAGCCCCGA AACCCAAAGC CAACCAGCAA
 AAV1    AGTGGTGGGA CTTGAAACCT GGAGCCCCGA AGCCCAAAGC CAACCAGCAA
 AAV2    AGTGGTGGAA GCTCAAACCT GGCCCACCAC CACCAAAGCC CGCAGAGCGG
 AAV3    AGTGGTGGGC TCTGAAACCT GGAGTCCCTC AACCCAAAGC GAACCAACAA
 AAV8    AGTGGTGGGC GCTGAAACCT GGAGCCCCGA AGCCCAAAGC CAACCAGCAA
 AAV9    AGTGGTGGGC GCTGAAACCT GGAGCCCCGA AGCCCAAAGC CAACCAGCAA
 AAV7    AGTGGTGGGA CCTGAAACCT GGAGCCCCGA AACCCAAAGC CAACCAGCAA
 44_2    AGTGGTGGGA CTTGAAACCT GGAGCCCCGA AACCCAAAGC CAACCAGCAA
```

FIG. 1AV

```
       2351                                                        2400
42_2   AAGCAGGACG ACGGCCGGGG TCTGGTGCTT CCTGGCTACA AGTACCTCGG
42_8   AAGCAGGACG ACGGCCGGGG TCTGGTGCTT CCTGGCTACA AGTACCTCGG
42_15  AAGCAGGACG ACGGCCGGGG TCTGGTGCTT CCTGGCTACA AGTACCTCGG
42_5b  AAGCAGGACG ACGGCCGGGG TCTGGTGCTT CCTGGCTACA AGTACCTCGG
42_1b  AAGCAGGACG ACGGCCGGGG TCTGGTGCTT CCTGGCTACA AGTACCTCGG
42_13  AAGCAGGACG ACGGCCGGGG TCTGGTGCTT CCTGGCTACA AGTACCTCGG
42_3a  AAGCAGGACG ACGGCCGGGG TCTGGTGCTT CCTGGCTACA AGTACCTCGG
42_4   AAGCAGGACG ACGGCCGGGG TCTGGTGCTT CCTGGCTACA AGTACCTCGG
42_5a  AAGCAGGACG ACGGCCGGGG TCTGGTGCTT CCTGGCTACA AGTACCTCGG
42_10  AAGCAGGACG ACGGCCGGGG TCTGGTGCTT CCTGGCTACA AGTACCTCGG
42_3b  AAGCAGGACG ACGGCCGGGG TCTGGTGCTT CCTGGCTACA AGTACCTCGG
42_11  AAGCAGGACG ACGGCCGGGG TCTGGTGCTT CCTGGCTACA AGTACCTCGG
42_6b  AAGCAGGACG ACGGCCGGGG TCTGGTGCTT CCTGGCTACA AGTACCTCGG
43_1   AAGCAGGACG ACGGCCGGGG TCTGGTGCTT CCTGGCTACA AGTACCTCGG
43_5   AAGCAGGACG ACGGCCGGGG TCTGGTGCTT CCTGGCTACA AGTACCTCGG
43_12  AAGCAGGACG ACGGCCGGGG TCTGGTGCTT CCTGGCTACA AGTACCTCGG
43_20  AAGCAGGACG ACGGCCGGGG TCTGGTGCTT CCTGGCTACA AGTACCTCGG
43_21  AAGCAGGACG ACGGCCGGGG TCTGGTGCTT CCTGGCTACA AGTACCTCGG
43_23  AAGCAGGACG ACGGCCGGGG TCTGGTGCTT CCTGGCTACA AGTACCTCGG
43_25  AAGCAGGACG ACGGCCGGGG TCTGGTGCTT CCTGGCTACA AGTACCTCGG
44_1   AAGCAGGACG ACGGCCGGGG TCTGGTGCTT CCTGGCTACA AGTACCTCGG
44_5   AAGCAGGACG ACGGCCGGGG TCTGGTGCTT CCTGGCTACA AGTACCTCGG
223_10 .......... .......... .......... .......... ..........
223_2  .......... .......... .......... .......... ..........
223_4  .......... .......... .......... .......... ..........
223_5  .......... .......... .......... .......... ..........
223_6  .......... .......... .......... .......... ..........
223_7  .......... .......... .......... .......... ..........
A3_4   CACCGGGACG ACAGTAGGGG TCTTGTGCTT CCTGGGTACA AGTACCTCGG
A3_5   CACCGGGACG ACAGTAGGGG TCTTGTGCTT CCTGGGTACA AGTACCTCGG
A3_7   CACCGGGACG ACAGTAGGGG TCTTGTGCTT CCTGGGTACA AGTACCTCGG
A3_3   CACCGGGACG ACAGTAGGGG TCTTGTGCTT CCTGGGTACA AGTACCTCGG
42_12  AAGCAGGACG ACGGCCGGGG TCTGGTGCTT CCTGGCTACA AGTACCTCGG
AAV1   AAGCAGGACG ACGGCCGGGG TCTGGTGCTT CCTGGCTACA AGTACCTCGG
AAV2   CATAAGGACG ACAGCAGGGG TCTTGTGCTT CCTGGGTACA AGTACCTCGG
AAV3   CACCAGGACA ACCGTCGGGG TCTTGTGCTT CCGGGTTACA AATACCTCGG
AAV8   AAGCAGGACG ACGGCCGGGG TCTGGTGCTT CCTGGCTACA AGTACCTCGG
AAV9   AAGCAGGACG ACGGCCGGGG TCTGGTGCTT CCTGGCTACA AGTACCTCGG
AAV7   AAGCAGGACA ACGGCCGGGG TCTGGTGCTT CCTGGCTACA AGTACCTCGG
44_2   AAGCAGGACG ACGGCCGGGG TCTGGTGCTT CCTGGCTACA AGTACCTCGG
```

FIG. 1AW

```
           2401                                                            2450
  42_2     ACCCTTCAAC  GGACTCGACA  AGGGAGAGCC  GGTCAACGAG  GCAGACGCCG
  42_8     ACCCTTCAAC  GGACTCGACA  AGGGGGAGCC  CGTCAACGCG  GCGGACGCAG
  42_15    ACCCTTCAAC  GGACTCGACA  AGGGGGAGCC  CGTCAACGCG  GCGGACGCAG
  42_5b    ACCCTTCAAC  GGACTCGACA  AGGGAGAGCC  GGTCAACGAG  GCAGACGCCG
  42_1b    ACCCTTCAAC  GGACTCGACA  AGGGAGAGCC  GGTCAACGAG  GCAGACGCCG
  42_13    ACCCTTCAAC  GGACTCGACA  AGGGGGAGCC  CGTCAACGCG  GCGGACGCAG
  42_3a    ACCCTTCAAC  GGACTCGACA  AGGGGGAGCC  CGTCAACGCG  GCGGACGCAG
  42_4     ACCCTTCAAC  GGACTCGACA  AGGGAGAGCC  GGTCAACGAG  GCAGACGCCG
  42_5a    ACCCTTCAAC  GGACTCGACA  AGGGAGAGCC  GGTCAACGAG  GCAGACGCCG
  42_10    ACCCTTCAAC  GGACTCGACA  AGGGAGAGCC  GGTCAACGAG  GCAGACGCCG
  42_3b    ACCCTTCAAC  GGACTCGACA  AGGGAGAGCC  GGTCAACGAG  GCAGACGCCG
  42_11    ACCCTTCAAC  GGACTCGACA  AGGGAGAGCC  GGTCAACGCG  GCGGACGCAG
  42_6b    ACCCTTCAAC  GGACTCGACA  AGGGAGAGCC  GGTCAACGAG  GCAGACGCCG
  43_1     ACCCTTCAAC  GGACTCGACA  AGGGGGAGCC  CGTCAACGCG  GCGGACGCAG
  43_5     ACCCTTCAAC  GGACTCGACA  AGGGGGAGCC  CGTCAACGCG  GCGGACGCAG
  43_12    ACCCTTCAAC  GGACTCGACA  AGGGGGAGCC  CGTCAACGCG  GCGGACGCAG
  43_20    ACCCTTCAAC  GGACTCGACA  AGGGCGAGCC  CGTCAACGCG  GCGGACGCAG
  43_21    ACCCTTCAAC  GGACTCGACA  AGGGGGAGCC  CGTCAACGCG  GCGGACGCAG
  43_23    ACCCTTCAAC  GGACTCGACA  AGGGGGAGCC  CGTCAACGCG  GCGGACGCAG
  43_25    ACCCTTCAAC  GGACTCGACA  AGGGGGAGCC  CGTCAACGCG  GCGGACGCAG
  44_1     ACCCTTCAAC  GGACTCGACA  AGGGGGAGCC  CGTCAACGCG  GCGGACGCAG
  44_5     ACCCTTCAAC  GGACTCGACA  AGGGGGAGCC  CGTCAACGCG  GCGGACGCAG
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
  A3_4     ACCCTTCAAC  GGACTCGACA  AAGGAGAGCC  GGTCAACGAG  GCAGACGCCG
  A3_5     ACCCTTCAAC  GGACTCGACA  AAGGAGAGCC  GGTCAACGAG  GCAGACGCCG
  A3_7     ACCCTTCAAC  GGACTCGACA  AAGGAGAGCC  GGTCAACGAG  GCAGACGCCG
  A3_3     ACCCTTCAAC  GGACTCGACA  AAGGAGAGCC  GGTCAACGAG  GCAGACGCCG
  42_12    ACCCTTCAAC  GGACTCGACA  AGGGAGAGCC  GGTCAACGAG  GCAGACGCCG
  AAV1     ACCCTTCAAC  GGACTCGACA  AGGGGGAGCC  CGTCAACGCG  GCGGACGCAG
  AAV2     ACCCTTCAAC  GGACTCGACA  AGGGAGAGCC  GGTCAACGAG  GCAGACGCCG
  AAV3     ACCCGGTAAC  GGACTCGACA  AAGGAGAGCC  GGTCAACGAG  GCGGACGCGG
  AAV8     ACCCTTCAAC  GGACTCGACA  AGGGGGAGCC  CGTCAACGCG  GCGGACGCAG
  AAV9     ACCCTTCAAC  GGACTCGACA  AGGGGGAGCC  CGTCAACGCG  GCGGACGCAG
  AAV7     ACCCTTCAAC  GGACTCGACA  AGGGGGAGCC  CGTCAACGCG  GCGGACGCAG
  44_2     ACCCTTCAAC  GGACTCGACA  AGGGGGAGCC  CGTCAACGCG  GCGGACGCAG
```

FIG. 1AX

```
         2451                                                    2500
 42_2    CGGCCCTCGA GCACG.ACAA GGCCTACGAC AAGCAGCTCG AGCAGGGGGA
 42_8    CGGCCCTCGA GCACG.ACAA GGCCTACGAC CAGCAGCTCA AAGCGGGTGA
 42_15   CGGCCCTCGA GCACG.ACAA GGCCTACGAC CAGCAGCTCA AAGCGGGTGA
 42_5b   CGGCCCTCGA GCACG.ACAA GGCCTACGAC AAGCAGCTCG AGCAGGGGGA
 42_1b   CGGCCCTCGA GCACG.ACAA GGCCTACGAC AAGCAGCTCG AGCAGGGGGA
 42_13   CGGCCCTCGA GCACG.ACAA GGCCTACGAC CAGCAGCTCA AAGCGGGTGA
 42_3a   CGGCCCTCGA GCACG.ACAA GGCCTACGAC CAGCAGCTCA AAGCGGGTGA
 42_4    CGGCCCTCGA GCACG.ACAA GGCCTACGAC AAGCAGCTCG AGCAGGGGGA
 42_5a   CGGCCCTCGA GCACG.ACAA GGCCTACGAC AAGCAGCTCG AGCAGGGGGA
 42_10   CGGCCCTCGA GCACG.ACAA GGCCTACGAC AAGCAGCTCG AGCAGGGGGA
 42_3b   CGGCCCTCGA GCACG.ACAA GGCCTACGAC AAGCAGCTCG AGCAGGGGGA
 42_11   CGGCCCTCGA GCACG.ACAA GGCCTACGAC CAGCAGCTCA AAGCGGGTGA
 42_6b   CGGCCCTCGA GCACG.ACAA GGCCTACGAC AAGCAGCTCG AGCAGGGGGA
 43_1    CGGCCCTCGA GCACG.ACAA GGCCTACGAC CAGCAGCTCA AAGCGGGTGA
 43_5    CGGCCCTCGA GCACG.ACAA GGCCTACGAC CAGCAGCTCA AAGCGGGTGA
 43_12   CGGCCCTCGA GCACG.ACAA GGCCTACGAC CAGCAGCTCA AAGCGGGTGA
 43_20   CGGCCCTCGA GCACG.ACAA AGCCTACGAC CAGCAGCTCA AAGCGGGTGA
 43_21   CGGCCCTCGA GCACG.ACAA AGCCTACGAC CAGCAGCTCA AAGCGGGTGA
 43_23   CGGCCCTCGA GCACG.ACAA AGCCTACGAC CAGCAGCTCA AAGCGGGTGA
 43_25   CGGCCCTCGA GCACG.ACAA AGCCTACGAC CAGCAGCTCA AAGCGGGTGA
 44_1    CGGCCCTCGA GCACG.ACAA GGCCTACGAC CAGCAGCTCA AAGCGGGTGA
 44_5    CGGCCCTCGA GCACG.ACAA GGCCTACGAC CAGCAGCTCA AAGCGGGTGA
223_10   .......... .......CAA GGCCTACGAC CAGCAGCTCA AAGCGGGTGA
223_2    .......... .......CAA GGCCTACGAC CAGCAGCTCA AAGCGGGTGA
223_4    .......... .......CAA GGCCTACGAC CAGCAGCTCA AAGCGGGTGA
223_5    .......... .......CAA GGCCTACGAC CAGCAGCTCA AAGCGGGTGA
223_6    .......... .......CAA GGCCTACGAC CAGCAGCTCA AAGCGGGTGA
223_7    .......... .......CAA GGCCTACGAC CAGCAGCTCA AAGCGGGTGA
 A3_4    CGGCCCTCGA GCACG.ACAA AGCCTACGAC CACCAGCTCA AGCAAGGGGA
 A3_5    CGGCCCTCGA GCACG.ACAA AGCCTACGAC CACCAGCTCA AGCAAGGGGA
 A3_7    CGGCCCTCGA GCACG.ACAA AGCCTACGAC CACCAGCTCA AGCAAGGGGA
 A3_3    CGGCCCTCGA GCACG.ACAA AGCCTACGAC CACCAGCTCA AGCAAGGGGA
 42_12   CGGCCCTCGA GCACG.ACAA GGCCTACGAC AAGCAGCTCG AGCAGGGGGA
 AAV1    CGGCCCTCGA GCACG.ACAA GGCCTACGAC CAGCAGCTCA AAGCGGGTGA
 AAV2    CGGCCCTCGA GCACGTACAA AGCCTACGAC CGGCAGCTCG ACAGCGGAGA
 AAV3    CAGCCCTCGA ACACG.ACAA AGCTTACGAC CAGCAGCTCA AGGCCGGTGA
 AAV8    CGGCCCTCGA GCACG.ACAA GGCCTACGAC CAGCAGCTGC AGGCGGGTGA
 AAV9    CGGCCCTCGA GCACG.GCAA GGCCTACGAC CAGCAGCTGC AGGCGGGTGA
 AAV7    CGGCCCTCGA GCACG.ACAA GGCCTACGAC CAGCAGCTCA AAGCGGGTGA
 44_2    CGGCCCTCGA GCACG.ACAA GGCCTACGAC CAGCAGCTCA AAGCGGGTGA
```

FIG. 1AY

```
       2501                                                          2550
 42_2  CAACCCGTAC CTCAAGTACA ACCACGCCGA CGCCGAGTTT CAGGAGCGTC
 42_8  CAATCCGTAC CTGCGGTATA ACCACGCCGA CGCCGAGTTT CAGGAGCGTC
42_15  CAATCCGTAC CTGCGGTATA ACCACGCCGA CGCCGAGTTT CAGGAGCGTC
42_5b  CAACCCGTAC CTCAAGTACA ACCACGCCGA CGCCGAGTTT CAGGAGCGTC
42_1b  CAACCCGTAC CTCAAGTACA ACCACGCCGA CGCCGAGTTT CAGGAGCGTC
42_13  CAATCCGTAC CTGCGGTATA ACCACGCCGA CGCCGAGTTT CAGGAGCGTC
42_3a  CAATCCGTAC CTGCGGTATA ACCACGCCGA CGCCGAGTTT CAGGAGCGTC
 42_4  CAACCCGTAC CTCAAGTACA ACCACGCCGA CGCCGAGTTT CAGGAGCGTC
42_5a  CAACCCGTAC CTCAAGTACA ACCACGCCGA CGCCGAGTTT CAGGAGCGTC
42_10  CAACCCGTAC CTCAAGTACA ACCACGCCGA CGCCGAGTTT CAGGAGCGTC
42_3b  CAACCCGTAC CTCAAGTACA ACCACGCCGA CGCCGAGTTT CAGGAGCGTC
42_11  CAATCCGTAC CTGCGGTATA ACCACGCCGA CGCCGAGTTT CAGGAGCGTC
42_6b  CAACCCGTAC CTCAAGTACA ACCACGCCGA CGCCGAGTTT CAGGAGCGTC
 43_1  CAATCCGTAC CTGCGGTATA ACCACGCCGA CGCCGAGTTT CAGGAGCGTC
 43_5  CAATCCGTAC CTGCGGTATA ACCACGCCGA CGCCGAGTTT CAGGAGCGTC
43_12  CAATCCGTAC CTGCGGTATA ACCACGCCGA CGCCGAGTTT CAGGAGCGTC
43_20  CAATCCGTAC CTGCGGTATA ATCACGCCGA CGCCGAGTTT CAGGAGCGTC
43_21  CAATCCGTAC CTGCGGTATA ATCACGCCGA CGCCGAGTTT CAGGAGCGTC
43_23  CAATCCGTAC CTGCGGTATA ATCACGCCGA CGCCGAGTTT CAGGAGCGTC
43_25  CAATCCGTAC CTGCGGTATA ATCACGCCGA CGCCGAGTTT CAGGAGCGTC
 44_1  CAATCCGTAC CTGCGGTATA ACCACGCCGA CGCCGAGTTT CAGGAGCGTC
 44_5  CAATCCGTAC CTGCGGTATA ACCACGCCGA CGCCGAGTTT CAGGAGCGTC
223_10 CAATCCGTAC CTGCGGTATA ACCACGCCGA CGCCGAGTTT CAGGAGCGTC
223_2  CAATCCGTAC CTGCGGTATA ACCACGCCGA CGCCGAGTTT CAGGAGTGTC
223_4  CAATCCGTAC CTGCGGTATA ACCACGCCGA CGCCGAGTTT CAGGAGCGTC
223_5  CAATCCGTAC CTGCGGTATA ACCACGCCGA CGCCGAGTTT CAGGAGCGTC
223_6  CAATCCGTAC CTGCGGTATA ACCACGCCGA CGCCGAGTTT CAGGAGCGTC
223_7  CAATCCGTAC CTGCGGTATA ACCACGCCGA CGCCGAGTTT CAGGAGCGTC
 A3_4  CAACCCGTAC CTCAAATACA ACCACGCGGA CGCTGAATTT CAGGAGCGTC
 A3_5  CAACCCGTAC CTCAAATACA ACCACGCGGA CGCTGAATTT CAGGAGCGTC
 A3_7  CAACCCGTAC CTCAAATACA ACCACGCGGA CGCTGAATTT CAGGAGCGTC
 A3_3  CAACCCGTAC CTCAAATACA ACCACGCGGA CGCTGAATTT CAGGAGCGTC
42_12  CAACCCGTAC CTCAAGTACA ACCACGCCGA CGCCGAGTTT CAGGAGCGTC
 AAV1  CAATCCGTAC CTGCGGTATA ACCACGCCGA CGCCGAGTTT CAGGAGCGTC
 AAV2  CAACCCGTAC CTCAAGTACA ACCACGCCGA CGCGGAGTTT CAGGAGCGCC
 AAV3  CAACCCGTAC CTCAAGTACA ACCACGCCGA CGCCGAGTTT CAGGAGCGTC
 AAV8  CAATCCGTAC CTGCGGTATA ACCACGCCGA CGCCGAGTTT CAGGAGCGTC
 AAV9  CAATCCGTAC CTGCGGTATA ACCACGCCGA CGCCGAGTTT CAGGAGCGTC
 AAV7  CAATCCGTAC CTGCGGTATA ACCACGCCGA CGCCGAGTTT CAGGAGCGTC
 44_2  CAATCCGTAC CTGCGGTATA ACCACGCCGA CGCCGAGTTT CAGGAGCGTC
```

FIG. 1AZ

```
         2551                                                              2600
 42_2    TTCAAGAAGA TACGTCTTTT GGGGGCAACC TCGGGCGAGC AGTCTTCCAG
 42_8    TGCAAGAAGA TACGTCTTTT GGGGGCAACC TCGGGCGAGC AGTCTTCCAG
 42_15   TGCAAGAAGA TACGTCTTTT GGGGGCAACC TCGGGCGAGC AGTCTTCCAG
 42_5b   TTCAAGAAGA TACGTCTTTT GGGGGCAACC TCGGGCGAGC AGTCTTCCAG
 42_1b   TTCAAGAAGA TACGTCTTTT GGGGGCAACC TCGGGCGAGC AGTCTTCCAG
 42_13   TTCAAGAAGA TACGTCTTTT GGGGGCAACC TCGGGCGAGC AGTCTTCCAG
 42_3a   TTCAAGAAGA TACGTCTTTT GGGGGCAACC TCGGGCGAGC AGTCTTCCAG
 42_4    TTCAAGAAGA TACGTCTTTT GGGGGCAACC TCGGGCGAGC AGTCTTCCAG
 42_5a   TTCAAGAAGA TACGTCTTTT GGGGGCAACC TCGGGCGAGC AGTCTTCCGG
 42_10   TTCAAGAAGA TACGTCTTTT GGGGGCAACC TCGGGCGAGC AGTCTTCCAG
 42_3b   TTCAAGAAGA TACGTCTTTT GGGGGCAACC TCGGGCGAGC AGTCTTCCAG
 42_11   TTCAAGAAGA TACGTCTTTT GGGGGCAACC TCGGGCGAGC AGTCTTCCAG
 42_6b   TTCAAGAAGA TACGTCTTTT GGGGGCAACC TCGGGCGAGC AGTCTTCCAG
 43_1    TGCAAGAAGA TACGTCTTTT GGGGGCAACC TCGGGCGAGC AGTCTTCCAG
 43_5    TGCAAGAAGA TACGTCTTTT GGGGGCAACC TCGGGCGAGC AGTCTTCCAG
 43_12   TGCAAGAAGA TACGTCTTTT GGGGGCAACC TCGGGCGAGC AGTCTTCCAG
 43_20   TGCAAGAAGA TACGTCTTTT GGGGGCAACC TCGGGCGAGC AGTCTTCCAG
 43_21   TGCAAGAAGA TACGTCTTTT GGGGGCAACC TCGGGCGAGC AGTCTTCCAG
 43_23   TGCAAGAAGA TACGTCCTTT GGGGGCAACC TCGGGCGAGC AGTCTTCCAG
 43_25   TGCAAGAAGA TACGTCTTTT GGGGGCAACC TCGGGCGAGC AGTCTTCCAG
 44_1    TGCAAGAAGA TACGTCTTTT GGGGGCAACC TCGGGCGAGC AGTCTTCCAG
 44_5    TGCAAGAAGA TACGTCTTTT GGGGGCAACC TCGGGCGAGC AGTCTTCCAG
 223_10  TTCAAGAAGA TACGTCTTTT GGGGGCAACC TCGGGCGAGC AGTCTTCCAG
 223_2   TTCAAGAAGA TACGTCTTTT GGGGGCAACC TCGGGCGAGC AGTCTTCCAG
 223_4   TTCAAGAAGA TACGTCTTTT GGGGGCAACC TCGGGCGAGC AGTCTTCCAG
 223_5   TTCAAGAAGA TACGTCTTTT GGGGGCAACC TCGGGCGAGC AGTCTTCCAG
 223_6   TTCAAGAAGA TACGTCTTTT GGGGGCAACC TCGGGCGAGC AGTCTTCCAG
 223_7   TTCAAGAAGA TACGTCTTTT GGGGGCAACC TCGGGCGAGC AGTCTTCCAG
 A3_4    TTCAAGAAGA TACGTCTTTC GGGGGCAACC TCGGGCGAGC AGTCTTCCAG
 A3_5    TTCAAGAAGA TACGTCTTTC GGGGGCAACC TCGGGCGAGC AGTCTTCCAG
 A3_7    TTCAAGAAGA TACGTCTTTC GGGGGCAACC TCGGGCGAGC AGTCTTCCAG
 A3_3    TTCAAGAAGA TACGTCTTTC GGGGGCAACC TCGGGCGAGC AGTCTTCCAG
 42_12   TTCAAGAAGA TACGTCTTTT GGGGGCAACC TCGGGCGAGC AGTCTTCCAG
 AAV1    TGCAAGAAGA TACGTCTTTT GGGGGCAACC TCGGGCGAGC AGTCTTCCAG
 AAV2    TTAAGAAGA  TACGTCTTTT GGGGGCAACC TCGGACGAGC AGTCTTCCAG
 AAV3    TTCAAGAAGA TACGTCTTTT GGGGGCAACC TTGGCAGAGC AGTCTTCCAG
 AAV8    TGCAAGAAGA TACGTCTTTT GGGGGCAACC TCGGGCGAGC AGTCTTCCAG
 AAV9    TGCAAGAAGA TACGTCTTTT GGGGGCAACC TCGGGCGAGC AGTCTTCCAG
 AAV7    TGCAAGAAGA TACGTCATTT GGGGGCAACC TCGGGCGAGC AGTCTTCCAG
 44_2    TGCAAGAAGA TACGTCTTTT GGGGGCAACC TCGGGCGAGC AGTCTTCCAG
```

FIG. 1AAA

```
            2601                                                      2650
   42_2     GCCAAGAAGC  GGGTTCTCGA  ACCTCTCGGT  CTGGTTGAGG  AAGGCGCTAA
   42_8     GCCAAGAAGC  GGGTTCTCGA  ACCTCTCGGT  CTGGTTGAGG  AAGGCGCTAA
  42_15     GCCAAGAAGC  GGGTTCTCGA  ACCTCTCGGT  CTGGTTGAGG  AAGGCGCTAA
  42_5b     GCCAAGAAGC  GGGTTCTCGA  ACCTCTCGGT  CTGGTTGAGG  AAGGCGCTAA
  42_1b     GCCAAGAAGC  GGGTTCTCGA  ACCTCTCGGT  CTGGTTGAGG  AAGGCGCTAA
  42_13     GCCAAGAAGC  GGGTTCTCGA  ACCTCTCGGT  CTGGTTGAGG  AAGGCGCTAA
  42_3a     GCCAAGAAGC  GGGTTCTCGA  ACCTCTCGGT  CTGGTTGAGG  AAGGCGCTAA
   42_4     GCCAAGAAGC  GGGTTCTCGA  ACCTCTCGGT  CTGGTTGAGG  AAGGCGCTAA
  42_5a     GCCAAGAAGC  GGGTTCTCGA  ACCTCTCGGT  CTGGTTGAGG  AAGGCGCTAA
  42_10     GCCAAGAAGC  GGGTTCTCGA  ACCTCTCGGT  CTGGTTGAGG  AAGGCGCTAA
  42_3b     GCCAAGAAGC  GGGTTCTCGA  ACCTCTCGGT  CTGGTTGAGG  AAGGCGCTAA
  42_11     GCCAAGAAGC  GGGTTCTCGA  ACCTCTCGGT  CTGGTTGAGG  AAGGCGCTAA
  42_6b     GCCAAGAAGC  GGGTTCTCGA  ACCTCTCGGT  CTGGTTGAGG  AAGGCGCTAA
   43_1     GCCAAGAAGC  GGGTTCTCGA  ACCTCTCGGT  CTGGTTGAGG  AAGGCGCTAA
   43_5     GCCAAGAAGC  GGGTTCTCGA  ACCTCTCGGT  CTGGTTGAGG  AAGGCGCTAA
  43_12     GCCAAGAAGC  GGGTTCTCGA  ACCTCTCGGT  CTGGTTGAGG  AAGGCGCTAA
  43_20     GCCAAGAAGC  GGGTTCTCGA  ACCTCTCGGT  CTGGTTGAGG  AAGGCGCTAA
  43_21     GCCAAGAAGC  GGGTTCTCGA  ACCTCTCGGT  CTGGTTGAGG  AAGGCGCTAA
  43_23     GCCAAGAAGC  GGGTTCTCGA  ACCTCTCGGT  CTGGTTGAGG  AAGGCGCTAA
  43_25     GCCAAGAAGC  GGGTTCTCGA  ACCTCTCGGT  CTGGTTGAGG  AAGGCGCTAA
   44_1     GCCAAGAAGC  GGGTTCTCGA  ACCTCTCGGT  CTGGTTGAGG  AAGGCGCTAA
   44_5     GCCAAGAAGC  GGGTTCTCGA  ACCTCTCGGT  CTGGTTGAGG  AAGGCGCTAA
 223_10     GCCAAAAAGC  GGGTTCTCGA  ACCTCTTGGT  CTGGTTGAGA  CGCCAGCTAA
  223_2     GCCAAAAAGC  GGGTTCTCGA  ACCTCTTGGT  CTGGTTGAGA  CGCCAGCTAA
  223_4     GCCAAAAAGC  GGGTTCTCGA  ACCTCTTGGT  CTGGTTGAGA  CGCCAGCTAA
  223_5     GCCAAAAAGC  GGGTTCTCGA  ACCTCTTGGT  CTGGTTGAGA  CGCCAGCTAA
  223_6     GCCAAAAAGC  GGGTTCTCGA  ACCTCTTGGT  CTGGTTGAGA  CGCCAGCTAA
  223_7     GCCAAAAAGC  GGGTTCTCGA  ACCTCTTGGT  CTGGTTGAGA  CGCCAGCTAA
   A3_4     GCCAAAAAGA  GGGTACTCGA  GCCTCTTGGT  CTGGTTGAGG  AAGCTGTTAA
   A3_5     GCCAAAAAGA  GGGTACTCGA  GCCTCTTGGT  CTGGTTGAGG  AAGCTGTTAA
   A3_7     GCCAAAAAGA  GGGTACTCGA  GCCTCTTGGT  CTGGTTGAGG  AAGCTGTTAA
   A3_3     GCCAAAAAGA  GGGTACTCGA  GCCTCTTGGT  CTGGTTGAGG  AAGCTGTTAA
  42_12     GCCAAGAAGC  GGGTTCTCGA  ACCTCTCGGT  CTGGTTGAGG  AAGGCGCTAA
   AAV1     GCCAAGAAGC  GGGTTCTCGA  ACCTCTCGGT  CTGGTTGAGG  AAGGCGCTAA
   AAV2     GCGAAAAAGA  GGGTTCTTGA  ACCTCTGGGC  CTGGTTGAGG  AACCTGTTAA
   AAV3     GCCAAAAAGA  GGATCCTTGA  GCCTCTTGGT  CTGGTTGAGG  AAGCAGCTAA
   AAV8     GCCAAGAAGC  GGGTTCTCGA  ACCTCTCGGT  CTGGTTGAGG  AAGGCGCTAA
   AAV9     GCCAAGAAGC  GGGTTCTCGA  ACCTCTCGGT  CTGGTTGAGG  AAGGCGCTAA
   AAV7     GCCAAGAAGC  GGGTTCTCGA  ACCTCTCGGT  CTGGTTGAGG  AAGGCGCTAA
   44_2     GCCAAGAAGC  GGGTTCTCGA  ACCTCTCGGT  CTGGTTGAGG  AAGGCGCTAA
```

FIG. 1AAB

```
         2651                                                                    2700
            vp2 start
  42_2   GACGGCTCCT GGAAAGAAGA GACCCATAGA ...ATCCCCC ..........
  42_8   GACGGCTCCT GGAAAGAAGA GACCGGTAGA GCCATCACCC CAGCGTTCTC
  42_15  GACGGCTCCT GGAAAGAAGA GACCGGTAGA GCCATCACCC CAGCGTTCTC
  42_5b  GACGGCTCCT GGAAAGAAGA GACCGGTAGA GCCATCACCC CAGCGTTCTC
  42_1b  GACGGCTCCT GGAAAGAAGA GACCCATAGA ...ATCCCCC ..........
  42_13  GACGGCTCCT GGAAAGAAGA GACCCATAGA ...ATCCCCC ..........
  42_3a  GACGGCTCCT GGAAAGAAGA GACCCATAGA ...ATCCCCC ..........
  42_4   GACGGCTCCT GGAAAGAAGA GACCCATAGA ...ATCCCCC ..........
  42_5a  GACGGCTCCT GGAAAGAAGA GACCCATAGA ...ATCCCCC ..........
  42_10  GACGGCTCCT GGAAAGAAGA GACCCATAGA ...ATCCCCC ..........
  42_3b  GACGGCTCCT GGAAAGAAGA GACCCATAGA ...ATCCCCC ..........
  42_11  GACGGCTCCT GGAAAGAAGA GACCCATAGA ...ATCCCCC ..........
  42_6b  GACGGCTCCT GGAAAGAAGA GACCGGTAGA GCCATCACCC CAGCGTTCTC
  43_1   GACGGCTCCT GGAAAGAAGA GACCGGTAGA GCCATCACCT CAGCGTTCCC
  43_5   GACGGCTCCT GGAAAGAAGA GACCGGTAGA GCCATCACCT CAGCGTTCCC
  43_12  GACGGCTCCT GGAAAGAAGA GACCGGTAGA GCCATCACCT CAGCGTTCCC
  43_20  GACGGCTCCT GGAAAGAAGA GACTGGTAGA GCAGTCGCCA CAAGAG...C
  43_21  GACGGCTCCT GGAAAGAAGA GACCGGTAGA GCAGTCGCCA CAAGAG...C
  43_23  GACGGCTCCT GGAAAGAAGA GACCGGTAGA GCAGTCGCCA CAAGAG...C
  43_25  GACGGCTCCT GGAAAGAAGA GACCGGTAGA GCAGTCGCCA CAAGAG...C
  44_1   GACGGCTCCT GGAAAGAAGA GACCGGTAGA GCCATCACCC CAGCGTTCTC
  44_5   GACGGCTCCT GGAAAGAAGA GACCGGTAGA GCCATCACCC CAGCGTTCTC
  223_10 GACGGCACCT GGAAAGAAGC GACCGGTAGA CTCGCCA... ..........
  223_2  GACGGCACCT GGAAAGAAGC GACCGGTAGA CTCGCCA... ..........
  223_4  GACGGCACCT GGAAAGAAGC GACCGGTAGA CTCGCCA... ..........
  223_5  GACGGCACCT GGAAAGAAGC GACCGGTAGA CTCGCCA... ..........
  223_6  GACGGCACCT GGAAAGAAGC GACCGGTAGA CTCGCCA... ..........
  223_7  GACGGCACCT GGAAAGAAGC GACCGGTAGA CTCGCCA... ..........
  A3_4   GACGGCTCCT GGAAAAAAGA GACCTATAGA GCAGTCTCCT GCAGAA...C
  A3_5   GACGGCTCCT GGAAAAAAGA GACCTATAGA GCAGTCTCCT GCAGAA...C
  A3_7   GACGGCTCCT GGAAAAAAGA GACCTATAGA GCAGTCTCCT GCAGAA...C
  A3_3   GACGGCTCCT GGAAAAAAGA GACCTATAGA GCAGTCTCCT GCAGAA...C
  42_12  GACGGCTCCT GGAAAGAAGA GACCGGTAGA GCCATCACCC CAGCGTTCTC
  AAV1   GACGGCTCCT GGAAAGAAAC GTCCGGTAGA GCAGTCGCCA CAAGAG...C
  AAV2   GACGGCTCCG GGAAAAAAGA GGCCGGTAGA GCACTCTCCT GTGGAG...C
  AAV3   AACGGCTCCT GGAAAGAAGG GGGCTGTAGA TCAGTCTCCT CAGGAA...C
  AAV8   GACGGCTCCT GGAAAGAAGA GACCGGTAGA GCCATCACCC CAGCGTTCTC
  AAV9   GACGGCTCCT GGAAAGAAGA GACCGGTAGA GCCATCACCC CAGCGTTCTC
  AAV7   GACGGCTCCT GCAAAGAAGA GACCGGTAGA GCCGTCACCT CAGCGTTCCC
  44_2   GACGGCTCCT GGAAAGAAGA GACCGGTAGA GCCATCACCC CAGCGTTCTC
            vp2 start
```

FIG. 1AAC

```
        2701                                                        2750
 42_2    ..GACTCCTC CACGGGCATC GGCAAGAAAG GCCAGCAGCC CGCTAAAAAG
 42_8    CAGACTCCTC TACGGGCATC GGCAAGACAG GCCAGCAGCC CGCGAAAAAG
 42_15   CAGACTCCTC TACGGGCATC GGCAAGACAG GCCAGCAGCC CGCGAAAAAG
 42_5b   CAGACTCCTC TACGGGCATC GGCAAGACAG GCCAGCAGCC CGCGAAAAAG
 42_1b   ..GACTCCTC CACGGGCATC GGCAAGAAAG GCCAGCAGCC CGCTAAAAAG
 42_13   ..GACTCCTC CACGGGCATC GGCAAGAAAG GCCAGCAGCC CGCTAAAAAG
 42_3a   ..GACTCCTC CACGGGCATC GGCAAGAAAG GCCAGCAGCC CGCTAAAAAG
 42_4    ..GACTCCTC CACGGGCATC GGCAAGAAAG GCCAGCAGCC CGCTAAAAAG
 42_5a   ..GACTCCTC CACGGGCATC GGCAAGAAAG GCCAGCAGCC CGCTAAAAAG
 42_10   ..GACTCCTC CACGGGCATC GGCAGGAAAG GCCAGCAGCC CGCTAAAAAG
 42_3b   ..GACTCCTC CACGGGCATC GGCAAGAAAG GCCAGCAGCC CGCTAAAAAG
 42_11   ..GACTCCTC CACGGGCATC GGCAAGAAAG GCCAGCAGCC CGCTAAAAAG
 42_6b   CAGACTCCTC TACGGGCATC GGCAAGACAG GCCAGCAGCC CGCGAAAAAG
 43_1    CCGACTCCTC CACGGGCATC GGCAAGAAAG GCCACCAGCC CGCGAGAAAG
 43_5    CCGACTCCTC CACGGGCATC GGCAAGAAAG GCCACCAGCC CGCGAGAAAG
 43_12   CCGACTCCTC CACGGGCATC GGCAAGAAAG GCCACCAGCC CGCGAGAAAG
 43_20   CAGACTCCTC CTCGGGCATC GGCAAGACAG GCCAGCAGCC CGCTAAAAAG
 43_21   CAGACTCCTC CTCGGGCATC GGCAAGACAG GCCAGCAGCC CGCTAAAAAG
 43_23   CAGACTCCTC CTCGGGCATC GGCAAGACAG GCCAGCAGCC CGCTAAAAAG
 43_25   CAGACTCCTC CTCGGGCATC GGCAAGACAG GCCAGCAGCC CGCTAAAAAG
 44_1    CAGACTCCTC TACGGGCATC GGCAAGAAAG GCCAGCAGCC CGCGAAAAAG
 44_5    CAGACTCCTC TACGGGCATC GGCAAGAAAG GCCAGCAGCC CGCGAAAAAG
223_10   ..GACTCCAC CTCGGGCATC GGCAAGAAAG GCCAGCAGCC CGCGAAAAAG
223_2    ..GACTCCAC CTCGGGCATC GGCAAGAAAG GCCAGCAGCC CGCGAAAAAG
223_4    ..GACTCCAC CTCGGGCATC GGCAAGAAAG GCCAGCAGCC CGCGAAAAAG
223_5    ..GACTCCAC CTCGGGCATC GGCAAGAAAG GCCAGCAGCC CGCGAAAAAG
223_6    ..GACTCCAC CTCGGGCATC GGCAAGAAAG GCCAGCAGCC CGCGAAAAAG
223_7    ..GACTCCAC CTCGGGCATC GGCAAGAAAG GCCAGCAGCC CGCGAAAAAG
 A3_4    CGGACTCTTC CTCGGGCATC GGCGAATCAG GCCAGCAGCC CGCTAAGAAA
 A3_5    CGGACTCTTC CTCGGGCATC GGCAAATCAG GCCAGCAGCC CGCTAAGAAA
 A3_7    CGGACTCTTC CTCGGGCATC GGCAAATCAG GCCAGCAGCC CGCTAAGAAA
 A3_3    CGGACTCTTC CTCGGGCATC GGCAAATCAG GCCAGCAGCC CGCTAAGAAA
 42_12   CAGACTCCTC TACGGGCATC GGCAAGACAG GCCAGCAGCC CGCGAAAAAG
 AAV1    CAGACTCCTC CTCGGGCATC GGCAAGACAG GCCAGCAGCC CGCTAAAAAG
 AAV2    CAGACTCCTC CTCGGGAACC GGAAAGGCGG GCCAGCAGCC TGCAAGAAAA
 AAV3    CGGACTCATC ATCTGGTGTT GGCAAATCGG GCAAACAGCC TGCCAGAAAA
 AAV8    CAGACTCCTC TACGGGCATC GGCAAGAAAG GCCAACAGCC CGCCAGAAAA
 AAV9    CAGACTCCTC TACGGGCATC GGCAAGAAAG GCCAACAGCC CGCCAGAAAA
 AAV7    CCGACTCCTC CACGGGCATC GGCAAGAAAG GCCAGCAGCC CGCCAGAAAG
 44_2    CAGACTCCTC TACGGGCATC GGCAAGAAAG GCCAGCAGCC CGCGAAAAAG
```

FIG. 1AAD

```
         2751                                                    2800
  42_2   AAGCTCAACT TTGGGCAGAC TGGCGACTCA GAGTCAGTGC CCGACCCCCA
  42_8   AGACTCAACT TTGGGCAGAC TGGCGACTCA GAGTCAGTGC CCGACCCTCA
 42_15   AGACTCAACT TTGGGCAGAC TGGCGACTCA GAGTCAGTGC CCGACCCTCA
 42_5b   AGACTCAACT TTGGGCAGAC TGGCGACTCA GAGTCAGTGC CCGACCCTCA
 42_1b   AGACTCAACT TTGGGCAGAC TGGCGACTCA GAGTCAGTGC CCGACCCTCA
 42_13   AAGCTCAACT TTGGGCAGAC TGGCGACTCA GAGTCAGTGC CCGACCCTCA
 42_3a   AAGCTCAACT TTGGGCAGAC TGGCGACTCA GAGTCAGTGC CCGACCCTCA
  42_4   AAGCTCAACT TTGGGCAGAC TGGCGACTCA GAGTCAGTGC CCGACCCTCA
 42_5a   AAGCTCAACT TTGGGCAGAC TGGCGACTCA GAGTCAGTGC CCGACCCCCA
 42_10   AAGCTCAACT TTGGGCAGAC TGGCGACTCA GAGTCAGTGC CCGACCCTCA
 42_3b   AAGCTCAACT TTGGGCAGAC TGGCGACTCA GAGTCAGTGC CCGACCCTCA
 42_11   AAGCTCAACT TTGGGCAGAC TGGCGACTCA GAGTCAGTGC CCGACCCTCA
 42_6b   AGACTCAACT TTGGGCAGAC TGGCGACTCA GAGTCAGTGC CCGACCCTCA
  43_1   AGACTGAACT TTGGGCAGAC TGGCGACTCG GAGTCAGTCC CCGACCCTCA
  43_5   AGACTGAACT TTGGGCAGAC TGGCGACTCG GAGTCAGTCC CCGACCCTCA
 43_12   AGACTGAACT TTGGGCAGAC TGGCGACTCG GAGTCAGTCC CCGACCCTCA
 43_20   AGACTCAATT TTGGTCAGAC TGGCGACTCA GAGTCAGTCC CCGACCCACA
 43_21   AGACTCAATT TTGGTCAGAC TGGCGACTCA GAGTCAGTCC CCGACCCACA
 43_23   AGACTCAATT TTGGTCAGAC TGGCGACTCA GAGTCAGTCC CCGACCCACA
 43_25   AGACTCAATT TTGGTCAGAC TGGCGACTCA GAGTCAGTCC CCGACCCACA
  44_1   AGACTCAACT TTGGGCAGAC TGGCGACTCA GAGTCAGTGC CCGACCCTCA
  44_5   AGACTCAACT TTGGGCAGAC TGGCGACTCA GAGTCAGTGC CCGACCCTCA
 223_10  AGACTCAACT TTGGGCAGAC TGGCGACTCA GAGTCAGTCC CCGACCCTCA
 223_2   AGACTCAACT TTGGGCAGAC TGGCGACTCA GAGTCAGTCC CCGACCCTCA
 223_4   AGACTCAACT TTGGGCAGAC TGGCGACTCA GAGCCAGTCC CCGACCCTCA
 223_5   AGACTCAACT TTGGGCAGAC TGGCGACTCA GAGCCAGTCC CCGACCCTCA
 223_6   AGACTCAACT TTGGGCAGAC TGGCGACTCA GAGTCAGTCC CCGACCCTCA
 223_7   AGACTCAACT TTGGGCAGAC TGGCGACTCA GAGTCAGTCC CCGACCCTCA
  A3_4   AGACTCAATT TTGGTCAGAC TGGCGACACA GAGTCAGTCC CAGACCCTCA
  A3_5   AGACTCAATT TTGGTCAGAC TGGCGACACA GAGTCAGTCC CAGACCCTCA
  A3_7   AGACTCAATT TTGGTCAGAC TGGCGACACA GAGTCAGTCC CAGACCCTCA
  A3_3   AGACTCAATT TTGGTCAGAC TGGCGACACA GAGTCAGTCC CAGGCCCTCA
 42_12   AGACTCAACT TTGGGCAGAC TGGCGACTCA GAGTCAGTGC CCGACCCTCA
  AAV1   AGACTCAATT TTGGTCAGAC TGGCGACTCA GAGTCAGTCC CCGATCCACA
  AAV2   AGATTGAATT TTGGTCAGAC TGGAGACGCA GACTCAGTAC CTGACCCCCA
  AAV3   AGACTAAATT TCGGTCAGAC TGGAGACTCA GAGTCAGTCC CAGACCCTCA
  AAV8   AGACTCAATT TTGGTCAGAC TGGCGACTCA GAGTCAGTTC CAGACCCTCA
  AAV9   AGACTCAATT TTGGTCAGAC TGGCGACTCA GAGTCAGTTC CAGACCCTCA
  AAV7   AGACTCAATT TCGGTCAGAC TGGCGACTCA GAGTCAGTCC CCGACCCTCA
  44_2   AGACTCAACT TTGGGCAGAC TGGCGACTCA GAGTCAGTGC CCGACCCTCA
```

FIG. 1AAE

```
       2001                                                              2050
                                                                       vp3 start
 42_2   ACCTCTCGGA GAACCTCCCG CCGCGCCCTC AGGTCTGGGA TCTGGTACAA
 42_8   ACCAATCGGA GAACCCCCCG CAGGCCCCTC TGGTCTGGGA TCTGGTACAA
 42_15  ACCAATCGGA GAACCCCCCG CAGGCCCCTC TGGTCTGGGA TCTGGTACAA
 42_5b  ACCAATCGGA GAACCCCCCG CAGGCCCCTC TGGTCTGGGA TCTGGTACAA
 42_1b  ACCAATCGGA GAACCCCCCG CAGGCCCCTC TGGTCTGGGA TCTGGCACAA
 42_13  ACCAATCGGA GAACCCCCCG CACGCCCCTC TGGTCTGGGA TCTGGTACAA
 42_3a  ACCAATCGGA GAACCCCCCG CAGGCCCCTC TGGTCTGGGA TCTGGTACAA
 42_4   ACCAATCGGA GAACCCCCCG CAGGCCCCTC TGGTCTGGGA TCTGGTACAA
 42_5a  ACCTCTCGGA GAACCTCCCG CCGCGCCCTC AGGTCTGGGA TCTGGTACAA
 42_10  ACCAATCGGA GAACCCCCCG CAGGCCCCTC TGGTCTGGGA TCTGGTACAA
 42_3b  ACCAATCGGA GAACCCCCCG CAGGCCCCTC TGGTCTGGGA TCTGGTACAA
 42_11  ACCAATCGGA GAACCCCCCG CAGGCCCCTC TGGTCTGGGA TCTGGTACAA
 42_6b  ACCAATCGGA GAACCCCCCG CAGGCCCCTC TGGTCTGGGA TCTGGTACAA
 43_1   ACCAATCGGA GAACCACCAG CAGGCCCCTC TGGTCTGGGA TCTGGTACAA
 43_5   ACCAATCGGA GAACCACCAG CAGGCCCCTC TGGTCTGGGA TCTGGTACAA
 43_12  ACCAATCGGA GAACCACCAG CAGGCCCCTC TGGTCTGGGA TCTGGTACAA
 43_20  ACCTCTCGGA GAACCTCCAG CAGCCCCCTC AGGTCTGGGA CCTAATACAA
 43_21  ACCTCTCGGA GAACCTCCAG CAGCCCCCTC AGGTCTGGGA CCTAATACAA
 43_23  ACCTCTCGGA GAACCTCCAG CAGCCCCCTC AGGTCTGGGA CCTAATACAA
 43_25  ACCTCTCGGA GAACCTCCAG CAGCCCCCTC AGGTCTGGGA CCTAATACAA
 44_1   ACCAATCGGA GAACCCCCCG CAGGCCCCTC TGGTCTGGGA TCTGGTACAA
 44_5   ACCAATCGGA GAACCCCCCG CAGGCCCCTC TGGTCTGGGA TCTGGTACAA
223_10  ACCAATCGGA GAACCACCAG CAGGCCCCTC TGGTCTGGGA TCTGGTACAA
223_2   ACCAATCGGA GAACCACCAG CAGGCCCCTC TGGTCTGGGA TCTGGTACAA
223_4   ACCAATCGGA GAACCACCAG CAGGCCCCTC TGGTCTGGGA TCTGGTACAA
223_5   ACCAATCGGA GAACCACCAG CAGGCCCCTC TGGTCTGGGA TCTGGTACAA
223_6   ACCAATCGGA GAACCACCAG CAGGCCCCTC TGGTCTGGGA TCTGGTACAA
223_7   ACCAATCGGA GAACCACCAG CAGGCCCCTC TGGTCTGGGA TCTGGTACAA
 A3_4   ACCAATCGGA GAACCCCCCG CAGCCCCCTC TGGTGTGGGA TCTAATACAA
 A3_5   ACCAATCGGA GAACCCCCCG CAGCCCCCTC TGGTGTGGGA TCTAATACAA
 A3_7   ACCAATCGGA GAACCCCCCG CAGCCCCCTC TGGTGTGGGA TCTAATACAA
 A3_3   ACCAATCGGA GAACCCCCCG CAGCCCCCTC TGGTGTGGGA TCTAATACAA
 42_12  ACCAATCGGA GAACCCCCCG CAGGCCCCTC TGGTCTGGGA TCTGGTACAA
 AAV1   ACCTCTCGGA GAACCTCCAG CAACCCCCGC TGCTGTGGGA CCTACTACAA
 AAV2   GCCTCTCGGA CAGCCACCAG CAGCCCCCTC TGGTCTGGGA ACTAATACGA
 AAV3   ACCTCTCGGA GAACCACCAG CAGCCCCAC AAGTTTGGGA TCTAATACAA
 AAV8   ACCTCTCGGA GAACCTCCAG CAGCGCCCTC TGGTGTGGGA CCTAATACAA
 AAV9   ACCTCTCGGA GAACCTCCAG CAGCGCCCTC TGGTGTGGGA CCTAATACAA
 AAV7   ACCTCTCGGA GAACCTCCAG CAGCGCCCTC TAGTGTGGGA TCTGGTACAG
 44_2   ACCAATCGGA GAACCCCCCG CAGCCCCCTC TGGTCTGGGA TCTGGTACAA
                                                                       vp3 start
```

FIG. 1AAF

```
        2851                                                      2900
       vp3 start codon
  42_2    TGGCTGCAGG CGGTGGCGCA CCAATGGCAG ACAATAACGA AGGCGCCGAC
  42_8    TGGCTGCAGG CGGTGGCGCT CCAATGGCAG ACAATAACGA AGGCGCCGAC
  42_15   TGGCTGCAGG CGGTGGCGCT CCAATGGCAG ACAATAACGA AGGCGCCGAC
  42_5b   TGGCTGCAGG CGGTGGCGCT CCAATGGCAG ACAATAACGA AGGCGCCGAC
  42_1b   TGGCTGCAGG CGGTGGCGCT CCAATGGCAG ACAATAACGA AGGCGCCGAC
  42_13   TGGCTGCAGG CGGTGGCGCT CCAATGGCAG ACAATAACGA AGGCGCCGAC
  42_3a   TGGCTGCAGG CGGTGGCGCT CCAATGGCAG ACAATAACGA AGGCGCCGAC
  42_4    TGGCTGCAGG CGGTGGCGCT CCAATGGCAG ACAATAACGA AGGCGCCGAC
  42_5a   TGGCTGCAGG CGGTGGCGCA CCAATGGCAG ACAATAACGA AGGCGCCGAC
  42_10   TGGCTGCAGG CGGTGGCGCT CCAATGGCAG ACAATAACGA AGGCGCCGAC
  42_3b   TGGCTGCAGG CGGTGGCGCT CCAATGGCAG ACAATAACGA AGGCGCCGAC
  42_11   TGGCTGCAGG CGGTGGCGCT CCAATGGCAG ACAATAACGA AGGCGCCGAC
  42_6b   TGGCTGCAGG CGGTGGCGCT CCAATGGCAG ACAATAACGA AGGCGCCGAC
  43_1    TGGCTGCAGG CGGTGGCGCT CCAATGGCAG ACAATAACGA AGGCGCCGAC
  43_5    TGGCTGCAGG CGGTGGCGCT CCAATGGCAG ACAATAACGA AGGCGCCGAC
  43_12   TGGCTGCAGG CGGTGGCGCT CCAATGGCAG ACAATAACGA AGGCGCCGAC
  43_20   TGGCTTCAGG CGGTGGCGCT CCAATGGCAG ACAATAACGA AGGCGCCGAC
  43_21   TGGCTTCAGG CGGTGGCGCT CCAATGGCAG ACAATAACGA AGGCGCCGAC
  43_23   TGGCTTCAGG CGGTGGCGCT CCAATGGCAG ACAATAACGA AGGCGCCGAC
  43_25   TGGCTTCAGG CGGTGGCGCT CCAATGGCAG ACAATAACGA AGGCGCCGAC
  44_1    TGGCTGCAGG CGGTGGCGCT CCAATGGCAG ACAATAACGA AGGCGCCGAC
  44_5    TGGCTGCAGG CGGTGGCGCT CCAATGGCAG ACAATAACGA AGGCGCCGAC
  223_10  TGGCTGCAGG CGGTGGCGCA CCAATGGCTG ACAATAACGA GGGCGCCGAC
  223_2   TGGTTGCAGG CGGTGGCGCA CCAATGGCTG ACAATAACGA GGGCGCCGAC
  223_4   TGGCTGCAGG CGGTGGCGCA CCAATGGCTG ACAATAACGA GGGCGCCGAC
  223_5   TGGCTGCAGG CGGTGGCGCA CCAATGGCTG ACAATAACGA GGGCGCCGAC
  223_6   TGGCTGCAGG CGGTGGCGCA CCAATGGCTG ACAATAGCGA GGGCGCCGAC
  223_7   TGGCTGCAGG CGGTGGCGCA CCAATGGCTG ACAATAACGA GGGCGCCGAC
  A3_4    TGGCTTCAGG CGGTGGGGCA CCAATGGCAG ACGATAACGA AGGCGCCGAC
  A3_5    TGGCTTCAGG CGGTGGGGCA CCAATGGCAG ACAATAACGA AGGCGCCGAC
  A3_7    TGGCTTCAGG CGGTGGGGCA CCAATGGCAG ACAATAACGA AGGCGCCGAC
  A3_3    TGGCTTCAGG CGGTGGGGCA CCAATGGCAG ACAATAACGA AGGCGCCGAC
  42_12   TGGCTGCAGG CGGTGGCGCT CCAATGGCAG ACAATAACGA AGGCGCCGAC
  AAV1    TGGCTTCAGG CGGTGGCGCA CCAATGGCAG ACAATAACGA AGGCGCCGAC
  AAV2    TGGCTACAGG CAGTGGCGCA CCAATGGCAG ACAATAACGA GGGCGCCGAC
  AAV3    TGGCTTCAGG CGGTGGCGCA CCAATGGCAG ACAATAACGA GGGTGCCGAT
  AAV8    TGGCTGCAGG CGGTGGCGCA CCAATGGCAG ACAATAACGA AGGCGCCGAC
  AAV9    TGGCTGCAGG CGGTGGCGCA CCAATGGCAG ACAATAACGA AGGCGCCGAC
  AAV7    TGGCTGCAGG CGGTGGCGCA CCAATGGCAG ACAATAACGA AGGTGCCGAC
  44_2    TGGCTGCAGG CGGTGGCGCT CCAATGGCAG ACAATAACGA AGGCGCCGAC
       vp3 start codon (cont'd)
```

FIG. 1AAG

```
         2901                                                                        2950
  42_2   GGAGTGGGTA  ATGCCTCCGG  AAATTGGCAT  TGCGATTCCA  CATGGCTGGG
  42_8   GGAGTGGGTA  GTTCCTCAGG  AAATTGGCAT  TGCGATTCCA  CATGGCTGGG
 42_15   GGAGTGGGTA  GTTCCTCAGG  AAATTGGCAT  TGCGATTCCA  CATGGCTGGG
 42_5b   GGAGTGGGTA  GTTCCTCAGG  AAATTGGCAT  TGCGATTCCA  CATGGCTGGG
 42_1b   GGAGTGGGTA  GTTCCTCAGG  AAATTGGCAT  TGCGATTCCA  CATGGCTGGG
 42_13   GGAGTGGGTA  GTTCCTCAGG  AAATTGGCAT  TGCGATTCCA  CATGGCTGGG
 42_3a   GGAGTGGGTA  GTTCCTCAGG  AAATTGGCAT  TGCGATTCCA  CATAGCTGGG
  42_4   GGAGTGGGTA  ATGCCTCCGG  AAATTGGCAT  TGCGATTCCA  CATGGCTGGG
 42_5a   GGAGTGGGTA  ATGCCTCCGG  AAATTGGCAT  TGCGATTCCA  CATGGCTGGG
 42_10   GGAGTGGGTA  ATGCCTCCGG  AAATTGGCAT  TGCGATTCCA  CATGGCTGGG
 42_3b   GGAGTGGGTA  ATGCCTCCGG  AAATTGGCAT  TGCGATTCCA  CATGGCTGGG
 42_11   GGAGTGGGTA  ATGCCTCCGG  AAATTGGCAT  TGCGATTCCA  CATGGCTGGG
 42_6b   GGAGTGGGTA  GTTCCTCAGG  AAATTGGCAT  TGCGATTCCA  CATGGCTGGG
  43_1   GGAGTGGGTA  GTTCCTCAGG  AAATTGGCAT  TGCGATTCCA  CATGGCTGGG
  43_5   GGAGTGGGTA  GTTCCTCAGG  AAATTGGCAT  TGCGATTCCA  CATGGCTGGG
 43_12   GGAGTGGGTA  GTTCCTCAGG  AAATTGGCAT  TGCGATTCCA  CATGGCTGGG
 43_20   GGAGTGGGTA  ATTCCTCGGG  AAATTGGCAT  TGCGATTCCA  CATGGCTGGG
 43_21   GGAGTGGGTA  ATTCCTCGGG  AAATTGGCAT  TGCGATTCCA  CATGGCTGGG
 43_23   GGAGTGGGTA  ATTCCTCGGG  AAATTGGCAT  TGCGATTCCA  CATGGCTGGG
 43_25   GGAGTGGGTA  ATTCCTCGGG  AAATTGGCAT  TGCGATTCCA  CATGGCTGGG
  44_1   GGAGTGGGTA  GTTCCTCAGG  AAATTGGCAT  TGCGATTCCA  CATGGCTGGG
  44_5   GGAGTGGGTA  GTTCCTCAGG  AAATTGGCAT  TGCGATTCCA  CATGGCTGGG
 223_10  GGAGTGGGTA  ATGCCTCAGG  AAATTGGCAT  TGCGATTCCA  CATGGCTGGG
 223_2   GGAGTGGGTA  ATGCCTCAGG  AAATTGGCAT  TGCGATTCCA  CATGGCTGGG
 223_4   GGAGTGGGTA  ATGCCTCAGG  AAATTGGCAT  TGCGATTCCA  CACGGCTGGG
 223_5   GGAGTGGGTA  ATGCCTCAGG  AAATTGGCAT  TGCGATTCCA  CACGGCTGGG
 223_6   GGAGTGGGTA  ATGCCTCAGG  AAATTGGCAT  TGCGATTCCA  CATGGCTGGG
 223_7   GGAGTGGGTA  ATGCCTCAGG  AAATTGGCAT  TGCGATTCCA  CATGGCTGGG
  A3_4   GGAGTGGGTA  ATTCCTCGGG  AAATTGGCAT  TGCGATTCCA  CATGGATGGG
  A3_5   GGAGTGGGTA  ATTCCTCGGG  AAATTGGCAT  TGCGATTCCA  CATGGATGGG
  A3_7   GGAGTGGGTA  ATTCCTCGGG  AAATTGGCAT  TGCGATTCCA  CATGGATGGG
  A3_3   GGAGTGGGTA  ATTCCTCGGG  AAATTGGCAT  TGCGATTCCA  CATGGATGGG
 42_12   GGAGTGGGTA  GTTCCTCAGG  AAATTGGCAT  TGCGATTCCA  CATGGCTGGG
  AAV1   GGAGTGGGTA  ATGCCTCAGG  AAATTGGCAT  TGCGATTCCA  CATGGCTGGG
  AAV2   GGAGTGGGTA  ATTCCTCCGG  AAATTGGCAT  TGCGATTCCA  CATGGATGGG
  AAV3   GGAGTGGGTA  ATTCCTCAGG  AAATTGGCAT  TGCGATTCCC  AATGGCTGGG
  AAV8   GGAGTGGGTA  GTTCCTCGGG  AAATTGGCAT  TGCGATTCCA  CATGGCTGGG
  AAV9   GGAGTGGGTA  ATTCCTCGGG  AAATTGGCAT  TGCGATTCCA  CATGGCTGGG
  AAV7   GGAGTGGGTA  ATGCCTCAGG  AAATTGGCAT  TGCGATTCCA  CATGGCTGGG
 AAV10         GGTA  ATTCCTCCGG  AAATTGGCAT  TGCGATTCCA  CATGGCTGGG
 AAV11         GGTA  ATTCCTCCGG  AAATTGGCAT  TGCGATTCCA  CATGGCTGGG
 AAV12         GGTA  ATTCCTCCGG  AAATTGGCAT  TGCGATTCCA  CATGGCTGGG
  44_2   GGAGTGGGTA  GTTCCTCAGG  AAATTGGCAT  TGCGATTCCA  CATGGCTGGG
```

FIG. 1AAH

```
         2951                                                         3000
  42_2   CGACAGAGTC ATCACCACCA GCACCCGCAC CTGGGCCCTG CCCACCTACA
  42_8   CGACAGAGTC ATCACCACCA GCACCCGAAC CTGGGCCCTC CCCACCTACA
  42_15  CGACAGAGTC ATCACCACCA GCACCCGAAC CTGGGCCCTC CCCACCTACA
  42_5b  CGACAGAGTC ATCACCACCA GCACCCGAAC CTGGGCCCTC CCCACCTACA
  42_1b  CGACAGAGTC ATCACCACCA GCACCCGAAC CTGGGCCCTC CCCACCTACA
  42_13  CGACAGAGTC ATCACCACCA GCACCCGAAC CTGGGCCCTC CCCACCTACA
  42_3a  CGACAGAGTC ATCACCACCA GCACCCGAAC CTGGGCCCTC CCCACCTACA
  42_4   CGACAGAGTC ATCACCACCA GCACCCGCAC CTGGGCCCTG CCCACCTACA
  42_5a  CGACAGAGTC ATCACCACCA GCACCCGCAC CTGGGCCCTG CCCACCTACA
  42_10  CGACAGAGTC ATCACCACCA GCACCCGCAC CTGGGCCCTG CCCACCTACA
  42_3b  CGACAGAGTC ATCACCACCA GCACCCGCAC CTGGGCCCTG CCCACCTACA
  42_11  CGACAGAGTC ATCACCACCA GCACCCGCAC CTGGGCCCTG CCCACCTACA
  42_6b  CGACAGAGTC ATCACCACCA GCACCCGAAC CTGGGCCCTC CCCACCTACA
  43_1   CGACAGAGTC ATCACCACCA GCACCCGAAC CTGGGCCCTG CCCACCTACA
  43_5   CGACAGAGTC ATCACCACCA GCACCCGAAC CTGGGCCCTG CCCACCTACA
  43_12  CGACAGAGTC ATCACCACCA GCACCCGAAC CTGGGCCCTG CCCACCTACA
  43_20  GGACAGAGTC ATCACCACCA GCACCCGAAC CTGGGCCCTG CCCACCTACA
  43_21  GGACAGAGTC ATCACCACCA GCACCCGAAC CTGGGCCCTG CCCACCTACA
  43_23  GGACAGAGTC ATCACCACCA GCACCCGAAC CTGGGCCCTG CCCACCTACA
  43_25  GGACAGAGTC ATCACCACCA GCACCCGAAC CTGGGCCCTG CCCACCTACA
  44_1   CGACAGAGTC ATCACCACCA GCACCCGAAC CTGGGCCCTC CCCACCTACA
  44_5   CGACAGAGTC ATCACCACCA GCACCCGAAC CTGGGCCCTC CCCACCTACA
 223_10  CGACAGAGTC ATCACCACCA GCACCCGAAC CTGGGCCCTG CCCACCTACA
 223_2   CGACAGAGTC ATCACCACCA GCACCCGAAC CTGGGCCCTG CCCACCTACA
 223_4   CGACAGAGTC ATCACCACCA GCACCCGAAC CTGGGCCCTG CCCACCTACA
 223_5   CGACAGAGTC ATCACCACCA GCACCCGAAC CTGGGCCCTG CCCACCTACA
 223_6   CGACAGAGTC ATCACCACCA GCACCCGAAC CTGGGCCCTG CCCACCTACA
 223_7   CGACAGAGTC ATCACCACCA GCACCCGAAC CTGGGCCCTG CCCACCTACA
  A3_4   CGACAGAGTT ATCACCACCA GCACAAGAAC CTGGGCCCTC CCCACCTACA
  A3_5   CGACAGAGTT ATCACCACCA GCACAAGAAC CTGGGCCCTC CCCACCTACA
  A3_7   CGACAGAGTT ATCACCACCA GCACAAGAAC CTGGGCCCTC CCCACCTACA
  A3_3   CGACAGAGTT ATCACCACCA GCACAAGAAC CTGGGCCCTC CCCACCTACA
  42_12  CGACAGAGTC ATCACCACCA GCACCCGAAC CTGGGCCCTC CCCACCTACA
  AAV1   CGACAGAGTC ATCACCACCA GCACCCGCAC CTGGGCCTTG CCCACCTACA
  AAV2   CGACAGAGTC ATCACCACCA GCACCCGAAC CTGGGCCCTG CCCACCTACA
  AAV3   CGACAGAGTC ATCACCACCA GCACCAGAAC CTGGGCCCTG CCCACTTACA
  AAV8   CGACAGAGTC ATCACCACCA GCACCCGAAC CTGGGCCCTG CCCACCTACA
  AAV9   GGACAGAGTC ATCACCACCA GCACCCGAAC CTGGGCATTG CCCACCTACA
  AAV7   CGACAGAGTC ATTACCACCA GCACCCGAAC CTGGCCCCTG CCCACCTACA
  AAV10  CGACAGAGTC ATCACCACCA GCACCCGAAC CTGGGTCCTG CCCACCTACA
  AAV11  CGACAGAGTC ATCACCACCA GCACCCGAAC CTGGGCCCTG CCAACCTACA
  AAV12  CGACCGAGTC ATTACCACCA GCACCCGGAC TTGGGCCCTG CCCACCTACA
  44_2   CGACAGAGTC ATCACCACCA GCACCCGAAC CTGGGCCCTC CCCACCTACA
```

FIG. 1AAl

```
         3001                                                       3050
   42_2   ACAACCACCT CTACAAGCAG ATATCAA..G TCAGAGCGGG GCT....ACC
   42_8   ACAACCACCT CTACAAGCAA ATCTCCAACG GGACATCGGG AGGAAGCACC
  42_15   ACAACCACCT CTACAAGCAA ATCTCCAACG GGACATCGGG AGGAAGCACC
  42_5b   ACAACCACCT CTACAAGCAA ATCTCCAACG GGACATCGGG AGGAAGCACC
  42_1b   ACAACCACCT CTACAAGCAA ATCTCCAACG GGACATCGGG AGGAAGCACC
  42_13   ACAACCACCT CTACAAGCAA ATCTCCAACG GGACATCGGG AGGAAGCACC
  42_3a   ACAACCACCT CTACAAGCAA ATCTCCAACG GGACATCGGG AGGAAGCACC
   42_4   ACAACCACCT CTACAAGCAG ATATCAA... .GTCAGAGCG GGGC..TACC
  42_5a   ACAACCACCT CTACAAGCAG ATATCAA... .GTCAGAGCG GGGC..TACC
  42_10   ACAACCACCT CTACAAGCAG ATATCAA..G TCAGAGCGGG GCTA....CC
  42_3b   ACAACCACCT CTACAAGCAG ATATCAA..G TCAGAGCGGG GCTA....CC
  42_11   ACAACCACCT CTACAAGCAG ATATCAA..G TCAGAGCGGG GCTA....CC
  42_6b   ACAACCACCT CTACAAGCAA ATCTCCAACG GGACATCGGG AGGAAGCACC
   43_1   ACAACCATCT CTACAAGCAA ATCTCCAACG GGACATCGGG AGGAAGCACT
   43_5   ACAACCATCT CTACAAGCAA ATCTCCAACG GGACATCGGG AGGAAGCACT
  43_12   ACAACCATCT CTACAAGCAA ATCTCCAACG GGACATCGGG AGGAAGCACT
  43_20   ACAACCACCT CTACAAGCAA ATCTCCAACG GCACCTCGGG AGGAAGCACC
  43_21   ACAACCACCT CTACAAGCAA ATCTCCAACG GCACCTCGGG AGGAAGCACC
  43_23   ACAACCACCT CTACAAGCAA ATCTCCAACG GCACCTCGGG AGGAAGCACC
  43_25   ACAACCACCT CTACAAGCAA ATCTCCAACG GCACCTCGGG AGGAAGCACC
   44_1   ACAACCACCT CTACAAGCAA ATCTCCAACG GGACTTCGGG AGGAAGCACC
   44_5   ACAACCACCT CTACAAGCAA ATCTCCAACG GGACTTCGGG AGGAAGCACC
  223_10  ACAACCACCT CTACAAGCAA ATCTCCAGTC AGTCAGCAGG GAG...CACC
  223_2   ACAACCACCT CTACAAGCAA ATCTCCAGTC AGTCAGCAGG GAG...CACC
  223_4   ACAACCACCT CTACAAGCAA ATCTCCAGTC AGTCAGCAGG GAG...CACC
  223_5   ACAACCACCT CTACAAGCAA ATCTCCAGTC AGTCAGCAGG GAG...CACC
  223_6   ACAACCACCT CTACAAGCAA ATCTCCAGTC AGTCAGCAGG GAG...CACC
  223_7   ACAACCACCT CTACAAGCAA ATCTCCAGTC AGTCAGCAGG GAG...CACC
   A3_4   ATAATCACCT CTACAAGCAA ATCTCCA... GCGAATCGGG AGC...CACC
   A3_5   ATAATCACCT CTACAAGCAA ATCTCCA... GCGAATCGGG AGC...CACC
   A3_7   ATAATCGCCT CTACAAGCAA ATCTCCA... GCGAATCGGG AGC...CACC
   A3_3   ATAATCACCT CTACAAGCAA ATCTCCA... GCGAATCGGG AGC...CACC
  42_12   ACAACCACCT CTACAAGCAA ATCTCCAACG GGACATCGGG AGGAAGCACC
   AAV1   ATAACCACCT CTACAAGCAA ATCTCCAGTG CTTCAACGGG .GG..CCAGC
   AAV2   ACAACCACCT CTACAAACAA ATTTCCA... GCCAATCAGG AGC...CTCG
   AAV3   ACAACCATCT CTACAAGCAA ATCTCCA... GCCAATCAGG AGC...TTCA
   AAV8   ACAACCACCT CTACAAGCAA ATCTCCAACG GCACATCGGG AGGAGCCACC
   AAV9   ACAACCACCT CTACAAGCAA ATCTCCAATG GAACATCGGG AGGAAGCACC
   AAV7   ACAACCACCT CTACAAGCAA ATCTCCAGTG AAACTGCAGG TAG...TACC
  AAV10   ACAACCACAT CTACAAGCAA ATCTCCAGCG AGACAGGAGC CACCAACGAC
  AAV11   ACAACCACCT CTACAAACAA ATCTCCAGCG CTTCAACGGG GGCCAGCAAC
  AAV12   ACAACCACCT CTACAAGCAA ATCTCCAGCC AATCGGGTGC CACCAACGAC
   44_2   ACAACCACCT CTACAAGCAA ATCTCCAACG GGACTTCGGG AGGAAGCACC
```

FIG. 1AAJ

```
          3051                                                3100
  42_2    AACGACAACC ACTTCTTCGG CTACAGCACC CCCTGGGGCT ATTTTGACTT
  42_8    AACGACAACA CCTACTTCGG CTACAGCACC CCCTGGGGGT ATTTTGACTT
  42_15   AACGACAACA CCTACTTCGG CTACAGCACC CCCTGGGGGT ATTTTGACTT
  42_5b   AACGACAACA CCTACTTCGG CTACAGCACC CCCTGGGGGT ATTTTGACTT
  42_1b   AACGACAACA CCTACTTCGG CTACAGCACC CCCTGGGGGT ATTTTGACTT
  42_13   AACGACAACA CCTACTTCGG CTACAGCACC CCCTGGGGGT ATTTTGACTT
  42_3a   AACGACAACA CCTACTTCGG CTACAGCACC CCCTGGGGGT ATTTTGACTT
  42_4    AACGACAACC ACTTCTTCGG CTACAGCACC CCCTGGGGCT ATTTTGACTT
  42_5a   AACGACAACC ACTTCTTCGG CTACAGCACC CCCTGGGGCT ATTTTGACTT
  42_10   AACGACAACC ACTTCTTCGG CTACAGCACC CCCTGGGGCT ATTTTGACTT
  42_3b   AACGACAACC ACTTCTTCGG CTACAGCACC CCCTGGGGCT ATTTTGACTT
  42_11   AACGACAACC ACTTCTTCGG CTACAGCACC CCCTGGGGCT ATTTTGACTT
  42_6b   AACGACAACA CCTACTTCGG CTACAGCACC CCCTGGGGGT ATTTTGACTT
  43_1    AACGACAACA CCTACTTTGG CTACAGCACC CCCTGGGGGT ATTTTGACTT
  43_5    AACGACAACA CCTACTTTGG CTACAGCACC CCCTGGGGGT ATTTTGACTT
  43_12   AACGACAACA CCTACTTTGG CTACAGCACC CCCTGGGGGT ATTTTGACTT
  43_20   AACGACAACA CCTATTTTGG CTACAGCACC CCCTGGGGGT ATTTTGACTT
  43_21   AACGACAACA CCTATTTTGG CTACAGCACC CCCTGGGGGT ATTTTGACTT
  43_23   AACGACAACA CCTATTTTGG CTACAGCACC CCCTGGGGGT ATTTTGACTT
  43_25   AACGACAACA CCTATTTTGG CTACAGCACC CCCTGGGGGT ATTTTGACTT
  44_1    AACGACAACA CCTACTTCGG CTACAGCACC CCCTGGGGGT ATTTTGACTT
  44_5    AACGACAACA CCTACTTCGG CTACAGCACC CCCTGGGGGT ATTTTGACTT
  223_10  AACGATAACG TCTATTTCGG CTACAGCACC CCCTGGGGGT ATTTTGACTT
  223_2   AACGATAACG TCTATTTCGG CTACAGCACC CCCTGGGGGT ATTTTGACTT
  223_4   AACGATAACG TCTATTTCGG CTACAGCACC CCCTGGGGGT ATTTTGACTT
  223_5   AACGATAACG TCTATTTCGG CTACAGCACC CCCTGGGGGT ATTTTGACTT
  223_6   AACGATAACG TCTATTTCGG CTACAGCACC CCCTGGGGGT ATTTTGACTT
  223_7   AACGATAACG TCTATTTCGG CTACAGCACC CCCTGGGGGT ATTTTGACTT
  A3_4    AACGACAACC ACTACTTCGG CTACAGCACC CCCTGGGGGT ATTTTGACTT
  A3_5    AACGACAACC ACTACTTCGG CTACAGCACC CCCTGCGGGT ATTTTGACTT
  A3_7    AACGACAACC ACTACTTCGG CTACAGCACC CCCTGGGGGT ATTTTGACTT
  A3_3    AACGACAACC ACTACTTCGG CTACAGCACC CCCTGGGGGT ATTTTGACTT
  42_12   AACGACAACA CCTACTTCGG CTACAGCACC CCCTGGGGGT ATTTTGACTT
  AAV1    AACGACAACC ACTACTTCGG CTACAGCACC CCCTGGGGGT ATTTTGATTT
  AAV2    AACGACAATC ACTACTTTGG CTACAGCACC CCTTGGGGGT ATTTTGACTT
  AAV3    AACGACAACC ACTACTTTGG CTACAGCACC CCTTGGGGGT ATTTTGACTT
  AAV8    AACGACAACA CCTACTTCGG CTACAGCACC CCCTGGGGGT ATTTTGACTT
  AAV9    AACGACAACA CCTACTTTGG CTACAGCACC CCCTGGGGGT ATTTTGACTT
  AAV7    AACGACAACA CCTACTTCGG CTACAGCACC CCCTGGGGGT ATTTTGACTT
  AAV10   AACCACTACT TCGGCTACAG C......ACC CCCTGGGGGT ATTTTGACTT
  AAV11   ...GACAACC ACTACTTTGG CTACAGCACC CCCTGGGGGT ATTTTGACTT
  AAV12   AACCACTACT TCGGCTA... ...CAGCACC CCTTGGGGGT ATTTTGATTT
  44_2    AACGACAACA CCTACTTCGG CTACAGCACC CCCTGGGGGT ATTTTGACTT
```

FIG. 1AAK

```
        3101                                                    3150
 42_2   TAACAGATTC CACTGCCACT TCTCACCACG TGACTGGCAG CGACTCATCA
 42_8   TAACAGATTC CACTGCCACT TCTCACCACG TGACTGGCAG CGACTCATCA
 42_15  TAACAGATTC CACTGCCACT TCTCACCACG TGACTGGCAG CGACTCATCA
 42_5b  TAACAGATTC CACTGCCACT TCTCACCACG TGACTGGCAG CGACTCATCA
 42_1b  TAACAGATTC CACTGCCACT TCTCACCACG TGACTGGCAG CGACTCATCA
 42_13  TAACAGATTC CACTGCCACT TCTCACCACG TGACTGGCAG CGACTCATCA
 42_3a  TAACAGATTC CACTGCCACT TCTCACCACG TGACTGGCAG CGACTCATCA
 42_4   CAACAGATTC CACTGCCACT TCTCATCACG TGACTGGCAG CGACTCATCA
 42_5a  CAACAGATTC CACTGCCACT TCTCACCACG TGACTGGCAG CGACTCATCA
 42_10  CAACAGATTC CACTGCCACT TCTCACCACG TGACTGGCAG CGACTCATCA
 42_3b  CAACAGATTC CACTGCCACT TCTCACCACG TGACTGGCAG CGACTCATCA
 42_11  CAACAGATTC CACTGCCACT TCTCACCACG TGACTGGCAG CGACTCATCA
 42_6b  TAACAGATTC CACTGCCACT TCTCACCACG TGACTGGCAG CGACTCATCA
 43_1   CAACAGATTC CACTGCCACT TCTCACCACG TGACTGGCAG CGACTCATCA
 43_5   CAACAGATTC CACTGCCACT TCTCACCACG TGACTGGCAG CGACTCATCA
 43_12  CAACAGATTC CACTGCCACT TCTCACCACG TGACTGGCAG CGACTCATCA
 43_20  CAACAGATTC CACTGTCACT TTTCACCACG TGACTGGCAA CGACTCATCA
 43_21  CAACAGATTC CACTGTCACT TTTCACCACG TGACTGGCAA CGACTCATCA
 43_23  CAACAGATTC CACTGTCACT TTTCACCACG TGACTGGCAA CGACTCATCA
 43_25  CAACAGATTC CACTGTCACT TTTCACCACG TGACTGGCAA CGACTCATCA
 44_1   TAACAGATTC CACTGCCACT TCTCACCACG TGACTGGCAG CGACTCATCA
 44_5   TAACAGATTC CACTGCCACT TCTCACCACG TGACTGGCAG CGACTCATCA
223_10  CAACAGATTC CATTGCCACT TCTCACCACG TGACTGGCAG CGACTTATCA
223_2   CAACAGATTC CATTGCCACT TCTCACCACG TGACTGGCAG CGACTTATCA
223_4   CAACAGATTC CATTGCCACT TCTCACCACG TGACTGGCAG CGACTTATCA
223_5   CAACAGATTC CATTGCCACT TCTCACCACG TGACTGGCAG CGACTTATCA
223_6   CAACAGATTC CATTGCCACT TCTCACCACG TGACTGGCAG CGACTTATCA
223_7   CAACAGATTC CATTGCCACT TCTCACCACG TGACTGGCAG CGACTTATCA
 A3_4   TAACAGATTC CACTGTCACT TCTCACCACG TGACTGGCAG CGACTCATCA
 A3_5   TAACAGATTC CACTGTCACT TCTCACCACG TGACTGGCAG CGACTCATCA
 A3_7   TAACAGATTC CACTGTCACT TCTCACCACG TGACTGGCAG CGACTCATCA
 A3_3   TAACAGATTC CACTGTCACT TCTCACCACG TGACTGGCAG CGACTCATCA
 42_12  TAACAGATTC CACTGCCACT TCTCACCACG TGACTGGCAG CGACTCATCA
 AAV1   CAACAGATTC CACTGCCACT TTTCACCACG TGACTGGCAG CGACTCATCA
 AAV2   CAACAGATTC CACTGCCACT TTTCACCACG TGACTGGCAA AGACTCATCA
 AAV3   TAACAGATTC CACTGCCACT TCTCACCACG TGACTGGCAG CGACTCATTA
 AAV8   TAACAGATTC CACTGCCACT TTTCACCACG TGACTGGCAG CGACTCATCA
 AAV9   CAACAGATTC CACTGCCACT TCTCACCACG TGACTGGCAG CGACTCATCA
 AAV7   TAACAGATTC CACTGCCACT TCTCACCACG TGACTGGCAG CGACTCATCA
 AAV10  TAACAGATTC CACTGCCACT TTTCACCACG TGACTGGCAG CGACTCATCA
 AAV11  TAACAGATTC CACTGCCACT TCTCACCACG TGACTGGCAG CGACTCATCA
 AAV12  CAACAGATTC CACTGCCATT TCTCACCACG TGACTGGCAG CGACTCATCA
 44_2   TAACAGATTC CACTGCCACT TCTCACCACG TGACTGGCAG CGACTCATCA
```

FIG. 1AAL

```
          3151                                                    3200
   42_2   ACAACAACTG GGGATTCCGG CCCAGAAAGC TGCGGTTCAA GTTGTTCAAC
   42_8   ACAACAACTG GGGATTCCGG CCCAAGAGAC TCAACTTCAA GCTCTTCAAC
  42_15   ACAACAACTG GGGATTCCGG CCCAAGAGAC TCAACTTCAA GCTCTTCAAC
  42_5b   ACAACAACTG GGGATTCCGG CCCAAGAGAC TCAACTTCAA GCTCTTCAAC
  42_1b   ACAACAACTG GGGATTCCGG CCCAAGAGAC TCAACTTCAA GCTCTTCAAC
  42_13   ACAACAACTG GGGATTCCGG CCCAAGAGAC TCAACTTCAA GCTCTTCAAC
  42_3a   ACAACAGCTG GGGATTCCGG CCCAAGAGAC TCAACTTCAA GCTCTTCAAC
   42_4   ACAACAACTG GGGATTCCGG CCCAAGAGAC TCAACTTCAA GCTCTTCAAC
  42_5a   ACAACAACCG GGGATTCCGG CCCAGAAAGC TGCGGTTCAA GTTGTTCAAC
  42_10   ACAACAACTG GGGATTCCGG CCCAGAAAGC TGCGGTTCAA GTTGTTCAAC
  42_3b   ACAACAACTG GGGATTCCGG CCCAGAAAGC TGCGGTTCAA GTTGTTCAAC
  42_11   ACAACAACTG GGGATTCCGG CCCAGAAAGC TGCGGTTCAA GTTGTTCAAC
  42_6b   ACAACAACTG GGGATTCCGG CCCAGAAAGC TGCGGTTCAA GTTGTTCAAC
   43_1   ACAATAACTG GGGATTCCGG CCCAAGAGAC TCAACTTCAA GCTCTTCAAC
   43_5   ACAATAACTG GGGATTCCGG CCCAAGAGAC TCAACTTCAA GCTCTTCAAC
  43_12   ACAATAACTG GGGATTCCGG CCCAAGAGAC TCAACTTCAA GCTCTTCAAC
  43_20   ACAACAATTG GGGATTCCGG CCCAAAAGAC TCAACTTCAA GCTGTTCAAC
  43_21   ACAACAATTG GGGATTCCGG CCCAAAAGAC TCAACTTCAA GCTGTTCAAC
  43_23   ACAACAATTG GGGATTCCGG CCCAAAAGAC TCAACTTCAA GCTGTTCAAC
  43_25   ACAACAATTG GGGATTCCGG CCCAAAAGAC TCAACTTCAA GCTGTTCAAC
   44_1   ACAACAACTG GGGATTCCGG CCCAAGAGAC TCAACTTCAA GCTCTTCAAC
   44_5   ACAACAACTG GGGATTCCGG CCCAAGAGAC CCAACTTCAA GCTCTTCAAC
  223_10  ACAACAACTG GGGATTCCGG CCCAAGAAGC TCAACTTCAA GCTCTTCAAC
  223_2   ACAACAACTG GGGATTCCGG CCCAAGAAGC TCAACTTCAA GCTCTTCAAC
  223_4   ACAACAACTG GGGATTCCGG CCCAAGAAGC TCAACTTCAA GCTCTTCAAC
  223_5   ACAACAACTG GGGATTCCGG CCCAAGAAGC TCAACTTCAA GCTCTTCAAC
  223_6   ACAACAACTG GGGATTCCGG CCCAAGAAGC TCAACTTCAA GCTCTTCAAC
  223_7   ACAACAACTG GGGATTCCGG CCCAAGAAGC TCAACTTCAA GCTCTTCAAC
   A3_4   ACAACAACTG GGGATTTAGA CCCAAGAAAC TCAATTTCAA GCTCTTCAAC
   A3_5   ATAACAACTG GGGATTTAGA CCCAAGAAAC TCAATTTCAA GCTCTTCAAC
   A3_7   ACAACAACTG GGGATTTAGA CCCAAGAAAC TCAATTTCAA GCTCTTCAAC
   A3_3   ACAACAACTG GGGATTTAGA CCCAAGAAAC TCAATTTCAA GCTCTTCAAC
  42_12   ACAACAACTG GGGATTCCGG CCCAAGAGAC TCAACTTCAA GCTCTTCAAC
   AAV1   ACAACAATTG GGGATTCCGG CCCAAGAGAC TCAACTTCAA ACTCTTCAAC
   AAV2   ACAACAACTG GGGATTCCGA CCCAAGAGAC TCAACTTCAA GCTCTTTAAC
   AAV3   ACAACAACTG GGGATTCCGG CCCAAGAAAC TCAGCTTCAA GCTCTTCAAC
   AAV8   ACAACAACTG GGGATTCCGG CCCAAGAGAC TCAGCTTCAA GCTCTTCAAC
   AAV9   ACAACAACTG GGGATTCCGG CCAAAGAGAC TCAACTTCAA GCTGTTCAAC
   AAV7   ACAACAACTG GGGATTCCGG CCCAAGAAGC TGCGGTTCAA GCTCTTCAAC
  AAV10   ACAACAACTG GGGATTC
  AAV11   ACAACAACTG GGGATTC
  AAV12   ACAACAACTG GGGATTC
   44_2   ACAACAACTG GGGATTCCGG CCCAAGAGAC TCAACTTCAA GCTCTTCAAC
```

FIG. 1AAM

```
             3201                                                          3250
    42_2     ATCCAGGTCA AGGAGGTCAC GACGAACGAC GGCGTTACGA CCATCGCTAA
    42_8     ATCCAGGTCA AGGAGGTCAC GCAGAATGAA GGCACCAAGA CCATCGCCAA
   42_15     ATCCAGGTCA AGGAGGTCAC GCAGAATGAA GGCACCAAGA CCATCGCCAA
   42_5b     ATCCAGGTCA AGGAGGTCAC GCAGAATGAA GGCACCAAGA CCATCGCCAA
   42_1b     ATCCAGGTCA AGGAGGTCAC GCAGAATGAA GGCACCAAGA CCATCGCCAA
   42_13     ATCCAGGTCA AGGAGGTCAC GCAGAATGAA GGCACCAAGA CCATCGCCAA
   42_3a     ATCCAGGTCA AGGAGGTCAC GCAGAATGAA GGCACCAAGA CCATCGCCAA
    42_4     ATCCAGGTCA AGGAGGTCAC GCAGAATGAA GGCACCAAGA CCATCGCCAA
   42_5a     ATCCAGGTCA AGGAGGTCAC GACGAACGAC GGCGTTACGA CCATCGCTAA
   42_10     ATCCAGGTCA AGGAGGTCAC GACGAACGAC GGCGTTACGA CCATCGCCAA
   42_3b     ATCCAGGTCA AGGAGGTCAC GACGAACGAC GGCGTTACGA CCATCGCTAA
   42_11     ATCCAGGTCA AGGAGGTCAC GACGAACGAC GGCGTTACGA CCATCGCTAA
   42_6b     ATCCAGGTCA AGGAGGTCAC GACGGACGAC GGCGTTACGA CCATCGCTAA
    43_1     ATCCAGGTCA AGGAGGTCAC GCAGAATGAA GGCACCAAGA CCATCGCCAA
    43_5     ATCCAGGTCA AGGAGGTCAC GCAGAATGAA GGCACCAAGA CCATCGCCAA
   43_12     ATCCAGGTCA AGGAGGTCAC GCAGAATGAA GGCACCAAGA CCATCGCCAA
   43_20     ATCCAGGTCA AGGAAGTCAC GACGAACGAA GGCACCAAGA CCATCGCCAA
   43_21     ATCCAGGTCA AGGAAGTCAC GACGAACGAA GGCACCAAGA CCATCGCCAA
   43_23     ATCCAGGTCA AGGAAGTCAC GACGAACGAA GGCACCAAGA CCATCGCCAA
   43_25     ATCCAGGTCA AGGAAGTCAC GACGAACGAA GGCACCAAGA CCATCGCCAA
    44_1     ATCCAGGTCA AGGAGGTCAC GCAGAATGAA GGCACCAAGA CCATCGCCAA
    44_5     ATCCAGGTCA AGGAGGTCAC GCAGAATGAA GGCACCAAGA CCATCGCCAA
   223_10    ATCCAGGTCA AGGAGGTCAC GACGAATGAC GGTGTCACAA CCATCGCTAA
   223_2     ATCCAGGTCA AGGAGGTCAC GACGAATGAC GGTGTCACAA CCATCGCTAA
   223_4     ATCCAGGTCA AGGAGGTCAC GACGAATGAC GGCGTCACAA CCATCGCTAA
   223_5     ATCCAGGTCA AGGAGGTCAC GACGAATGAC GGCGTCACAA CCATCGCTAA
   223_6     ATCCAGGTCA AGGAGGTCAC GACGAATGAC GGTGTCACAA CCATCGCTAA
   223_7     ATCCAGGTCA AGGAGGTCAC GACGAATGAC GGCGTCACAA CCATCGCTAA
    A3_4     ATCCAAGTCA AGGAGGTCAC GCAGAATGAT GGAACCACGA CCATCGCCAA
    A3_5     ATCCAAGTCA AGGAGGTCAC GCAGAATGAT GGAACCACGA CCATCGCCAA
    A3_7     ATCCAAGTCA AGGAGGTCAC GCAGAATGAT GGAACCACGA CCATCGCCAA
    A3_3     ATCCAAGTCA AGGAGGTCAC GCAGAATGAT GGAACCACGA CCATCGCCAA
   42_12     ATCCAGGTCA AGGAGGTCAC GCAGAATGAA GGCACCAAGA CCATCGCCAA
    AAV1     ATCCAAGTCA AGGAGGTCAC GACGAATGAT GGCGTCACAA CCATCGCTAA
    AAV2     ATTCAAGTCA AAGAGGTCAC GCAGAATGAC GGTACGACGA CGATTGCCAA
    AAV3     ATCCAAGTTA GAGGGTCAC  GCAGAACGAT GGCACGACGA CTATTGCCAA
    AAV8     ATCCAGGTCA AGGAGGTCAC GCAGAATGAA GGCACCAAGA CCATCGCCAA
    AAV9     ATCCAGGTCA AGGAGGTTAC GACGAACGAA GGCACCAAGA CCATCGCCAA
    AAV7     ATCCAGGTCA AGGAGGTCAC GACGAATGAC GGCGTTACGA CCATCGCTAA
    44_2     ATCCAGGTCA AGGAGGTCAC GCAGAATGAA GGCACCAAGA CCATCGCCAA
```

FIG. 1AAN

```
           3251                                                        3300
  42_2     TAACCTTACC AGCACGATTC AGGTCTTCTC GGACTCGGAG TACCAACTGC
  42_8     TAACCTTACC AGCACGATTC AGGTCTTTAC GGACTCGGAA TACCAGCTCC
 42_15     TAACCTTACC AGCACGATTC AGGTCTTTAC GGACTCGGAA TACCAGCTCC
 42_5b     TAACCTTACC AGCACGATTC AGGTCTTTAC GGACTCGGAA TACCAGCTCC
 42_1b     TAACCTTACC AGCACGATTC AGGTCTTTAC GGACTCGGAA TACCAGCTCC
 42_13     TAACCTTACC AGCACGATTC AGGTCTTTAC GGACTCGGAA TACCAGCTCC
 42_3a     TAACCTTACC AGCACGATTC AGGTCTTTAC GGACTCGGAA TACCAGCTCC
  42_4     TAACCTTACC AGCACGATTC AGGTCTTTAC GGACTCGGAA TACCGGCTCC
 42_5a     TAACCTTACC AGCACGATTC AGGTCTTCTC GGACTCGGAG TACCAACTGC
 42_10     TAACCTTACC AGCACGATTC AGGTCTTCTC GGACTCGGAG TACCAACTGC
 42_3b     TAACCTTACC AGCACGATTC AGGTCTTCTC GGACTCGGAG TACCAACTGC
 42_11     TAACCTTACC AGCACGATTC AGGTCTTCTC GGACTCGGAG TACCAACTGC
 42_6b     TAACCTTACC AGCACGATTC AGGTCTTCTC GGACTCGGAG TACCAACTGC
  43_1     TAACCTTACC AGCACGATTC AGGTGTTTAC GGACTCGGAA TACCAGCTCC
  43_5     TAACCTTACC AGCACGATTC AGGTGTTTAC GGACTCGGAA TACCAGCTCC
 43_12     TAACCTTACC AGCACGATTC AGGTGTTTAC GGACTCGGAA TACCAGCTCC
 43_20     TAATCTCACC AGCACCGTGC AGGTCTTTAC GGACTCGGAG TACCAGTTAC
 43_21     TAATCTCACC AGCACCGTGC GGGTCTTTAC GGACTCGGAG TACCAGTTAC
 43_23     TAATCTCACC AGCACCGTGC AGGTCTTTAC GGACTTGGAG TACCAGTTAC
 43_25     TAATCTCACC AGCACCGTGC AGGTCTTTAC GGACTCGGAG TACCAGTTAC
  44_1     TAACCTTACC AGCACGATTC AGGTCTTTAC GGACTCGGAA TACCAGCTCC
  44_5     TAACCTTACC AGCACGATTC AGGTCTTTAC GGACTCGGAA TACCAGCTCC
 223_10    TAACCTTACC AGCACGGTTC AGGTCTTTTC GGACTCGGAA TATCAACTGC
 223_2     TAACCTTACC AGCACGGTTC AGGTCTTTTC GGACTCGGAA TATCAACTGC
 223_4     TAACCTTACC AGCACGGTTC AGGTCTTTTC GGACTCGGAA TATCAACTGC
 223_5     TAACCTTACC AGCACGGTTC AGGTCTTTTC GGACTCGGAA TATCAACTGC
 223_6     TAACCTTACC AGCACGGTTC AGGTCTTTTC GGACTCGGAA TATCAACTGC
 223_7     TAACCTTACC AGCACGGTTC AGGTCTTTTC GGACCCGGAA TATCAACTGC
  A3_4     TAACCTTACC AGCACGGTGC AGGTCTTCAC AGACTCTGAG TACCAGCTGC
  A3_5     TAACCTTACC AGCACGGTGC AGGTCTTCAC AGACTCTGAG TACCAGCTGC
  A3_7     TAACCTTACC AGCACGGTGC AGGTCTTCAC AGACTCTGAG TACCAGCTGC
  A3_3     TAACCTTACC AGCGCGGTGC AGGTCTTCAC AGACTCTGAG TACCAGCTGC
 42_12     TAACCTTACC AGCACGATTC AGGTCTTTAC GGACTCGGAA TACCAGCTCC
  AAV1     TAACCTTACC AGCACGGTTC AAGTCTTCTC GGACTCGGAG TACCAGCTTC
  AAV2     TAACCTTACC AGCACGGTTC AGGTGTTTAC TGACTCGGAG TACCAGCTCC
  AAV3     TAACCTTACC AGCACGGTTC AACTGTTTAC GGACTCGGAG TATCAGCTCC
  AAV8     TAACCTCACC AGCACCATCC AGGTGTTTAC GGACTCGGAG TACCAGCTGC
  AAV9     TAACCTTACC AGCACCGTCC AGGTCTTTAC GGACTCGGAG TACCAGCTAC
  AAV7     TAACCTTACC AGCACGATTC AGGTATTCTC GGACTCGGAA TACCAGCTGC
  44_2     TAACCTTACC AGCACGATTC AGGTCTTTAC GGACTCGGAA TACCAGCTCC
```

FIG. 1AAO

```
           3301                                                      3350
  42_2     CGTACGTCCT CGGCTCTGCG CACCAGGGCT GCCTCCCTCC GTTCCCTGCG
  42_8     CGTACGTCCT CGGCTCTGCG CACCAGGGCT GCCTGCCTCC GTTCCCGGCG
  42_15    CGTACGTCCT CGGCTCTGCG CACCAGGGCT GCCCGCCTCC GTTCCCGGCG
  42_5b    CGTACGTCCT CGGCTCTGCG CACCAGGGCT GCCTGCCTCC GTTCCCGGCG
  42_1b    CGTACGTCCT CGGCTCTGCG CACCAGGGCT GCCTGCCTCC GTTCCCGGCG
  42_13    CGTACGTCCT CGGCTCTGCG CACCAGGGCT GCCTGCCTCC GTTCCCGGCG
  42_3a    CGTACGTCCT CGGCTCTGCG CACCAGGGCT GCCTGCCTCC GTTCCCGGCG
  42_4     CGTACGTCCT CGGCTCTGCG CACCAGGGCT GCCTGCCTCC GTTCCCGGCG
  42_5a    CGTACGTCCT CGGCTCTGCG CACCAGGGCT GCCTCCCTCC GTTCCCTGCG
  42_10    CGTACGTCCT CGGCTCTGCG CACCAGGGCT GCCTCCCTCC GTTCCCTGCG
  42_3b    CGTACGTCCT CGGCTCTGCG CACCAGGGCT GCCTCCCTCC GTTCCCTGCG
  42_1     CGTACGTCCT CGGCTCTGCG CACCAGGGCT GCCTCCCTCC GTTCCCTGCG
  42_6b    CGTACGTCCT CGGCTCTGCG CACCAGGGCT GCCTCCCTCC GTTCCCTGCG
  43_1     CGTACGTCCC CGGCTCTGCG CACCAGGGCT GCCTCCCTCC GTTCCCGGCG
  43_5     CGTACGTCCT CGGCTCTGCG CACCAGGGCT GCCTCCCTCC GTTCCCGGCG
  43_12    CGTACGTCCT CGGCTCTGCG CACCAGGGCT GCCTCCCTCC GTTCCCGGCG
  43_20    CGTACGTGCT AGGATCCGCT CACCAGGGAT GTCTGCCTCC GTTCCCGGCG
  43_21    CGTACGTGCT AGGATCCGCT CACCAGGGAT GTCTGCCTCC GTTCCCGGCG
  43_23    CGTACGTGCT AGGATCCGCT CACCAGGGAT GTCTGCCTCC GTTCCCGGCG
  43_25    CGTACGTGCT AGGATCCGCT CACCAGGGAT GTCTGCCTCC GTTCCCGGCG
  44_1     CGTACGTCCT CGGCTCTGCG CACCAGGGCT GCCTGCCTCC GTTCCCGGCG
  44_5     CGTACGTCCT CGGCTCTGCG CACCAGGGCT GCCTGCCTCC GTTCCCGGCG
 223_10    CGTACGTCCT CGGCTCCGCG CACCAGGGCT GCCTGCCTCC GTTCCCGGCA
 223_2     CGTACGTCCT CGGCTCCGCG CACCAGGGCT GCCTGCCTCC GTTCCCGGCA
 223_4     CGTACGTCCT CGGCTCCGCG CACCAGGGCT GCCTGCCTCC GTTCCCGGCA
 223_5     CGTACGTCCT CGGCTCCGCG CACCAGGGCT GCCTGCCTCC GTTCCCGGCA
 223_6     CGTACGTCCT CGGCTCCGCG CACCAGGGCT GCCTGCCTCC GTTCCCGGCA
 223_7     CGTACGTCCT CGGCTCCGCG CACCAGGGCT GCCTGCCTCC GTTCCCGGCA
  A3_4     CCTACGTCCT CGGTTCGGCT CACCAGGGCT GCCTTCCGCC GTTCCCAGCA
  A3_5     CCTACGTCCT CGGTTCGGCT CACCAGGGCT GCCTTCCGCC GTTCCCAGCA
  A3_7     CCTACGTCCT CGGTTCGGCT CACCAGGGCT GCCTTCCGCC GTTCCCAGCA
  A3_3     CCTACGTCCT CGGTTCGGCT CACCAGGGCT GCCTTCCGCC GTTCCCAGCA
  42_12    CGTACGTCCT CGGCTCTGCG CACCAGGGCT GCCTGCCTCC GTTCCCGGCG
  AAV1     CGTACGTCCT CGGCTCTGCG CACCAGGGCT GCCTCCCTCC GTTCCCGGCG
  AAV2     CGTACGTCCT CGGCTCGGCG CATCAAGGAT GCCTCCCGCC GTTCCCAGCA
  AAV3     CGTACGTGCT CGGGTCGGCG CACCAAGGCT GTCTCCCGCC GTTTCCAGCA
  AAV8     CGTACGTTCT CGGCTCTGCC CACCAGGGCT GCCTGCCTCC GTTCCCGGCG
  AAV9     CGTACGTCCT AGGCTCTGCC CACCAAGGAT GCCTGCCACC GTTTCCTGCA
  AAV7     CGTACGTCCT CGGCTCTGCG CACCAGGGCT GCCTGCCTCC GTTCCCGGCG
  44_2     CGTACGTCCT CGGCTCTGCG CACCAGGGCT GCCTGCCTCC GTTCCCGGCG
```

FIG. 1AAP

```
              3351                                                              3400
    42_2      GACGTGTTCA TGATTCCTCA GTACGGATAT CTGACTCTAA ACAACGGCAG
    42_8      GACGTCTTCA TGATTCCTCA GTACGGGTAC CTGACTCTGA ACAACGGCAG
    42_15     GACGTCTTCA TGATTCCTCA GTACGGGTAC CTGACTCTGA ACAACGGCAG
    42_5b     GACGTCTTCA TGATTCCTCA GTACGGGTAC CTGACTCTGA ACAACGGCAG
    42_1b     GACGTCTTCA TGATTCCTCA GTACGGGTAC CTGACTCTGA ACAACGGCAG
    42_13     GACGTCTTCA TGATTCCTCA GTACGGGTAC CTGACTCTGA ACAACGGCAG
    42_3a     GACGTCTTCA TGATTCCTCA GTACGGGTAC CTGACTCTGA ACAACGGCAG
    42_4      GACGTCTTCA TGATTCCTCA GTACGGGTAC CTGACTCTGA ACAACGGCAG
    42_5a     GACGTGTTCA TGATTCCTCA GTACGGATAT CTGACTCTAA ACAACGGCAG
    42_10     GACGTGTTCA TGATTCCTCA GTACGGATAT CTGACTCTAA ACAACGGCAG
    42_3b     GACGTGTTCA TGATTCCTCA GTACGGATAT CTGACTCTAA ACAACGGCAG
    42_1      GACGTGTTCA TGATTCCTCA GTACGGATAT CTGACTCTAA ACAACGGCAG
    42_6b     GACGTGTTCA TGATTCCTCA GTACGGATAT CTGACTCTAA ACAACGGCAG
    43_1      GACGTCTTCA TGATTCCTCA GTACGGGTAT CTGACCCTAA ACAATGGCAG
    43_5      GACGTCTTCA TGATTCCTCA GTACGGGTAT CTGACCCTAA ACAATGGCAG
    43_12     GACGTCTTCA TGATTCCTCA GTACGGGTAT CTGACCCTAA ACAATGGCAG
    43_20     GACGTCTTCA CGGTTCCTCA GTACGGCTAT TTAACTTTAA ACAATGGAAG
    43_21     GACGTCTTCA TGGTTCCTCA GTACGGCTAT TTAACTTTAA ACAATGGAAG
    43_23     GACGTCTTCA TGGTTCCTCA GTACGGCTAT TTAACTTTAA ACAATGGAAG
    43_25     GACGTCTTCA TGGTTCCTCA GTACGGCTAT TTAACTTTAA ACAATGGAAG
    44_1      GACGTCTTCA TGATTCCTCA GTACGGGTAC CTGACTCTGA ACAATGGCAG
    44_5      GACGTCTTCA TGATTCCTCA GTACGGGTAC CTGACTCTGA ACAATGGCAG
    223_10    GACGTGTTCA TGATTCCGCA GTACGGATAC CTGACTCTGA ACAATGGCAG
    223_2     GACGTGTTCA TGATTCCGCA GTACGGATAC CTGACTCTGA ACAATGGCAG
    223_4     GACGTGTTCA TGATTCCGCA GTACGGATAC CTGACTCTGA ACAATGGCAG
    223_5     GACGTGTTCA TGATTCCGCA GTACGGATAC CTGACTCTGA ACAATGGCAG
    223_6     GACGTGTTCA TGATTCCGCA GTACGGATAC CTGACTCTGA ACAATGGCAG
    223_7     GACGTGTTCA TGATTCCGCA GTACGGATAC CTGACTCTGA ACAATGGCAG
    A3_4      GACGTCTTCA TGATTCCTCA GTACGGCTAC TTGACTCTGA ACAATGGCAG
    A3_5      GACGTCTTCA TGATTCCTCA GTACGGCTAC TTGACTCTGA ACAATGGCAG
    A3_7      GACGTCTTCA TGATTCCTCA GTACGGCTAC TTGACTCTGA ACAATGGCAG
    A3_3      GACGTCTTCA TGATTCCTCA GTACGGCTAC TTGACTCTGA ACAATGGCAG
    42_12     GACGTCTTCA TGATTCCTCA GTACGGGTAC CTGACTCTGA ACAACGGCAG
    AAV1      GACGTGTTCA TGATTCCGCA ATACGGCTAC CTGACGCTCA ACAATGGCAG
    AAV2      GACGTCTTCA TGGTGCCACA GTATGGATAC CTCACCCTGA ACAACGGGAG
    AAV3      GACGTCTTCA TGGTCCCTCA GTATGGATAC CTCACCCTGA ACAACGGAAG
    AAV8      GACGTGTTCA TGATTCCCCA GTACGGCTAC CTAACACTCA ACAACGGTAG
    AAV9      GACGTCTTCA TGGTTCCTCA GTACGGCTAC CTGACGCTCA ACAATGGAAG
    AAV7      GACGTCTTCA TGATTCCTCA GTACGGCTAC CTGACTCTCA ACAATGGCAG
    44_2      GACGTCTTCA TGATTCCTCA GTACGGGTAC CTGACTCTGA ACAATGGCAG
```

FIG. 1AAQ

```
          3401                                                      3450
  42_2    TCAGTCTGTG  GGACGTTCCT  CCTTCTACTG  CCTGGAGTAC  TTTCCTTCTC
  42_8    TCAGGCCGTG  GGCCGTTCCT  CCTTCTACTG  CCTGGAGTAC  TTTCCTTCTC
  42_15   TCAGGCCGTG  GGCCGTTCCT  CCTTCTACTG  CCTGGAGTAC  TTTCCTTCTC
  42_5b   TCAGGCCGTG  GGCCGTTCCT  CCTTCTACTG  CCTGGAGTAC  TTTCCTTCTC
  42_1b   TCAGGCCGTG  GGCCGTTCCT  CCTTCTACTG  CCTGGAGTAC  TTTCCTTCTC
  42_13   TCAGGCCGTG  GGCCGTTCCT  CCTTCTACTG  CCTGGAGTAC  TTTCCTTCTC
  42_3a   TCAGGCCGTG  GGCCGTTCCT  CCTTCTACTG  CCTGGAGTAC  TTTCCTTCTC
  42_4    TCAGGCCGTG  GGCCGTTCCT  CCTTCTACTG  CCTGGAGTAC  TTTCCTTCTC
  42_5a   TCAGTCTGTG  GGACGTTCCT  CCTTCTACTG  CCTGGAGTAC  TTTCCTTCTC
  42_10   TCAGTCTGTG  GGACGTTCCT  CCTTCTACTG  CCTGGAGTAC  TTTCCTTCTC
  42_3b   TCAGTCTGTG  GGACGTTCCT  CCTTCTACTG  CCTGGAGTAC  TTTCCTTCTC
  42_11   TCAGTCTGTG  GGACGTTCCT  CCTTCTACTG  CCTGGAGTAC  TTTCCTTCTC
  42_6b   TCAGTCTGTG  GGACGTTCCT  CCTTCTACTG  CCTGGAGTAC  TTTCCTTCTC
  43_1    TCAGGCTGTG  GGCCGTTCCT  CCTTCTACTG  CCTGGAATAC  TTCCCTTCTC
  43_5    TCAGGCTGTG  GGCCGTTCCT  CCTTCTACTG  CCTGGAATAC  TTCCCTTCTC
  43_12   TCAGGCTGTG  GGCCGTTCCT  CCTTCTACTG  CCTGGAATAC  TTCCCTTCTC
  43_20   CCAAGCCCTG  GGACGTTCCT  CCTTCTACTG  TCTGGAGTAT  TTCCCATCGC
  43_21   CCAAGCCCTG  GGACGTTCCT  CCTTCTACTG  TCTGGAGTAT  TTCCCATCGC
  43_23   CCAAGCCCTG  GGACGTTCCT  CCTTCTACTG  TCTGGAGTAT  TTCCCATCGC
  43_25   CCAAGCCCTG  GGACGTTCCT  CCTTCTACTG  TCTGGAGTAT  TTCCCATCGC
  44_1    TCAGGCCGTG  GGCCGTTCCT  CCTTCTACTG  CCTGGAGTAC  TTTCCTTCTC
  44_5    TCAGGCCGTG  GGCCGTTCCT  CCTTCTACTG  CCTGGAGTAC  TTTCCTTCTC
 223_10   CCAATCGGTA  GGCCGTTCCT  CCTTCTACTG  CCTGGAGTAC  TTTCCTTCTC
 223_2    CCAATCGGTA  GGCCGTTCCT  CCTTCTACTG  CCTGGAGTAC  TTTCCTTCTC
 223_4    CCAATCGGTA  GGCCGTTCCT  CCTTCTACTG  CCTGGAGTAC  TTTCCTTCTC
 223_5    CCAATCGGTA  GGCCGTTCCT  CCTTCTACTG  CCTGGAGTAC  TTTCCTTCTC
 223_6    CCAATCGGTA  GGCCGTTCCT  CCTTCTACTG  CCTGGAGTAC  TTTCCTTCTC
 223_7    CCAATCGGTA  GGCCGTTCCT  CCTTCTACTG  CCTGGAGTAC  TTTCCTTCTC
  A3_4    CCAAGCGGTA  GGACGTTCTT  CATTCTACTG  TCTAGAGTAT  TTTCCCTCTC
  A3_5    CCAAGCGGTA  GGACGTTCTT  CATTCTACTG  TCTAGAGTAT  TTTCCCTCTC
  A3_7    CCAAGCGGTA  GGACGTTCTT  CATTCTACTG  TCTAGAGTAT  TTTCCCTCTC
  A3_3    CCAAGCGGTA  GGACGTTCTT  CATTCTACTG  TCTAGAGTAT  TTTCCCTCTC
  42_12   TCAGGCCGTG  GGCCGTTCCT  CCTTCTACTG  CCTGGAGTAC  TTTCCTTCTC
  AAV1    CCAAGCCGTG  GGACGTTCAT  CCTTTACTG   CCTGGAATAT  TTCCCTTCTC
  AAV2    TCAGGCAGTA  GGACGCTCTT  CATTTACTG   CCTGGAGTAG  TTTCCTTCTC
  AAV3    TCAAGCGGTG  GGACGCTCAT  CCTTTACTG   CCTGGAGTAC  TTCCCTTCGC
  AAV8    TCAGGCCGTG  GGACGCTCCT  CCTTCTACTG  CCTGGAATAC  TTTCCTTCGC
  AAV9    TCAAGCGTTA  GGACGTTCTT  CTTTCTACTG  TCTGGAATAC  TTCCCTTCTC
  AAV7    TCAGTCTGTG  GGACGTTCCT  CCTTCTACTG  CCTGGAGTAC  TTCCCCTCTC
  44_2    TCAGGCCGTG  GGCCGTTCCT  CCTTCTACTG  CCTGGAGTAC  TTTCCTTCTC
```

FIG. 1AAR

```
         3451                                                    3500
 42_2    AGATGCTGAG AACGGGCAAT AACTTTGAAT TCAGCTACAC CTTTGAGGAA
 42_8    AAATGCTGAG AACGGGCAAC AACTTTGAGT TCAGCTACCA GTTTGAGGAC
 42_15   AAATGCGGAG AACGGGCAAC AACTTTGAGT TCAGCTACCA GTTTGAGGAC
 42_5b   AAATGCTGAG AACGGGCAAC AACTTTGAGT TCAGCTACCA GTTTGAGGAC
 42_1b   AAATGCTGAG AACGGGCAAC AACTTTGAGT TCAGCTACCA GTTTGAGGAC
 42_13   AAATGCTGAG AACGGGCAAC AACTTTGAGT TCAGCTACCA GTTTGAGGAC
 42_3a   AAATGCTGAG AACGGGCAAC AACTTTGAGT TCAGCTACCA GTTTGAGGAC
 42_4    AAATGCTGAG AACGGGCAAC AACTTTGAGT TCAGCTACCA GTTTGAGGAC
 42_5a   AGATGCTGAG AACGGGCAAT AACTTTGAAT TCAGCTACCA GTTTGAGGAC
 42_10   AGATGCTGAG AACGGGCAAT AACTTTGAAT TCAGCTACAC CTTTGAGGAA
 42_3b   AGATGCTGAG AACGGGCAAT AACTTTGAAT TCAGCTACAC CTTTGAGGAA
 42_11   AGATGCTGAG AACGGGCAAT AACTTTGAAT TCAGCTACAC CTTTGAGGAA
 42_6b   AGATGCTGAG AACGGGCAAT AACTTTGAAT TCAGCTACAC CTTTGAGGAA
 43_1    AAATGCTGAG GACGGGCAAC AACTTTGAAT TCAGCTACAC CTTCGAGGAC
 43_5    AAATGCTGAG GACGGGCAAC AACTTTGAAT TCAGCTACAC CTTCGAGGAC
 43_12   AAATGCTGAG GACGGGCAAC AACTTTGAAT TCAGCTACAC CTTCGAGGAC
 43_20   AGATGCTGAG AACCGGCAAC AACTTTCAGT TCAGCTACAC CTTCGAGGAC
 43_21   AGATGCTGAG AACCGGCAAC AACTTTCAGT TCAGCTACAC CTTCGAGGAC
 43_23   AGATGCCGAG AACCGGCAAC AACTTTCAGT TCAGCTACAC CTTCGAGGAC
 43_25   AGATGCTGAG AACCGGCAAC AACTTTCAGT TCAGCTACAC CTTCGAGGAC
 44_1    AAATGCTGAG AACGGGCAAC AACTTTGAGT TCAGCTACCA GTTTGAGGAC
 44_5    AAATGCTGAG AACGGGCAAC AACTTTGAGT TCAGCTACCA GTTTGAGGAC
 223_10  AGATGCTGAG AACGGGCAAC AACTTCACCT TTAGCTACAC CTTCGAGGAC
 223_2   AGATGCTGAG AACGGGCAAC AACTTCACCT TTAGCTACAC CTTCGAGGAC
 223_4   AGATGCTGAG AACGGGCAAC AACTTCACCT TTAGCTACAC CTTCGAGGAC
 223_5   AGATGCTGAG AACGGGCAAC AACTTCACCT TTAGCTACAC CTTCGAGGAC
 223_6   AGATGCTGAG AACGGGCAAC AACTTCACCT TTAGCTACAC CTTCGAGGAC
 223_7   AGATGCTGAG AACGGGCAAC AACTTCACCT TTAGCTACAC CTTCGAGGAC
 A3_4    AGATGCTGAG GACGGGAAAC AACTTCACCT TCAGCTACAC TTTTGAAGAC
 A3_5    AGATGCTGAG GACGGGAAAC AACTTCACCT TCAGCTACAC TTTTGAAGAC
 A3_7    AGATGCTGAG GACGGGAAAC AACTTCACCT TCAGCTACAC TTTTGAAGAC
 A3_3    AGATGCTGAG GACGGGAAAC AACTTCACCT TCAGCTACAC TTTTGAAGAC
 42_12   AAATGCTGAG AACGGGCAAC AACTTTGAGT TCAGCTACCA GTTTGAGGAC
 AAV1    AGATGCTGAG AACGGGCAAC AACTTTACCT TCAGCTACAC CTTTGAGGAA
 AAV2    AGATGCTGCG TACCGGAAAC AACTTTACCT TCAGCTACAC TTTTGAGGAC
 AAV3    AGATGCTAAG GACTGGAAAT AACTTCCAAT TCAGCTATAC CTTCGAGGAT
 AAV8    AGATGCTGAG AACCGGCAAC AACTTCCAGT TTACTTACAC CTTCGAGGAC
 AAV9    AGATGCTGAG AACCGGCAAC AACTTTCAGT TCAGCTACAC TTTCGAGGAC
 AAV7    AGATGCTGAG AACGGGCAAC AACTTTGAGT TCAGCTACAG CTTCGAGGAC
 44_2    AAATGCTGAG AACGGGCAAC AACTTTGAGT TCAGCTACCA GTTTGAGGAC
```

FIG. 1AAS

```
         3501                                                      3550
 42_2    GTGCCTTTCC ACAGCAGCTA TGCGCACAGC CAGAGCCTGG ACCGGCTGAT
 42_8    GTGCCTTTTC ACAGCAGCTA CGCGCACAGC CAAAGCCTGG ACCGGCTGAT
 42_15   GTGCCTTTTC ACAGCAGCTA CGCGCATAGC CAAAGCCTGG ACCGGCTGAT
 42_5b   GTGCCTTTTC ACAGCAGCTA CGCGCACAGC CAAAGCCTGG ACCGGCTGAT
 42_1b   GTGCCTTTTC ACAGCAGCTA TGCGCACAGC CAAAGCCTGG ACCGGCTGAT
 42_13   GTGCCTTTTC ACAGCAGCTA TGCGCACAGC CAAAGCCTGG ACCGGCTGAT
 42_3a   GTGCCTTTTC ACAGCAGCTA CGCGCACAGC CAAAGCCTGG ACCGGCTGAT
 42_4    GTGCCTTTTC ACAGCAGCTA CGCGCACAGC CAAAGCCTGG ACCGGCTGAT
 42_5a   GTGCCTTTC  ACAGCAGCTA CGCGCACAGC CAAAGCCTGG ACCGGCTGAT
 42_10   GTGCCTTTCC ACAGCAGCTA TGCGCACAGC CAGAGCCTGG ACCGGCTGAT
 42_3b   GTGCCTTTCC ACAGCAGCTA TGCGCACAGC CAGAGCCTGG ACCGGCTGAT
 42_11   GTGCCTTTCC ACAGCAGCTA TGCGCACAGC CAGAGCCTGG ACCGGCTGAT
 42_6b   GTGCCTTTCC ACAGCAGCTA TGCGCATAGC CAGAGCCTGG ACCGGCTGAT
 43_1    GTGCCTTTCC ACAGCAGCTA CGCGCACAGC CAGAGCCTGG ACCGGCTGAT
 43_5    GTGCCTTTCC ACAGCAGCTA CGCGCACAGC CAGAGCCTGG ACCGGCTGAT
 43_12   GTGCCTTTCC ACAGCAGCTA CGCGCACAGC CAGAGCCTGG ACCGGCTGAT
 43_20   GTGCCTTTCC ACAGCAGCTA CGCGCACAGC CAGAGCCTGG ACAGGCTGAT
 43_21   GTGCCTTTCC ACAGCAGCTA CGCGCACAGC CAGAGCCTGG ACAGGCTGAT
 43_23   GTGCCTTTCC ACAGCAGCTA CGCGCACAGC CAGAGCCTGG ACAGGCTGAT
 43_25   GTGCCTTTCC ACAGCAGCTA CGCGCACAGC CAGAGCCTGG ACAGGCTGAT
 44_1    GTGCCTTTTC ACAGCAGCTA CGCGCACAGC CAAAGCCTGG ACCGGCTGAT
 44_5    GTGCCTTTTC ACAGCAGCTA CGCGCACAGC CAAAGCCTGG ACCGGCTGAT
 223_10  GTGCCTTTCC ACAGCAGCTA CGCGCACAGC CAGAGTCTGG ACCGGCTGAT
 223_2   GTGCCTTTCC ACAGCAGCTA CGCGCACAGC CAGAGTCTGG ACCGGCTGAT
 223_4   GTGCCTTTCC ACAGCAGCTA CGCGCACAGC CAGAGTCTGG GCCGGCTGAT
 223_5   GTGCCTTTCC ACAGCAGCTA CGCGCACAGC CAGAGTCTGG GCCGGCTGAT
 223_6   GTGCCTTTCC ACAGCAGCTA CGCGCACAGC CAGAGTCTGG ACCGGCTGAT
 223_7   GTGCCTTTCC ACAGCAGCTA CGCGCACAGC CAGAGTCTGG ACCGGCTGAT
 A3_4    GTGCCTTTCC ACAGCAGCTA CGCGCACAGC CAGAGTCTGG ATCGGCTGAT
 A3_5    GTGCCTTTCC ACAGCAGCTA CGCGCACAGC CAGAGTCTGG ATCGGCTGAT
 A3_7    GTGCCTTTCC ACAGCAGCTA CGCGCACAGC CAGAGTCTGG ATCGGCTGAT
 A3_3    GTGCCTTTCC ACAGCAGCTA CGCGCACAGC CAGAGTCTGG ATCGGCTGAT
 42_12   GTGCCTTTTC ACAGCAGCTA CGCGCACAGC CAAAGCCTGG ACCGGCTGAC
 AAV1    GTGCCTTTCC ACAGCAGCTA CGCGCACAGC CAGACCCTGG ACCGGCTGAT
 AAV2    GTTCCTTTCC ACAGCAGCTA CGCTCACAGC CAGAGTCTGG ACCGTCTCAT
 AAV3    GTACCTTTTC ACAGCAGCTA CGCTCACAGC CAGAGTTTGG ATCGCTTGAT
 AAV8    GTGCCTTTCC ACAGCAGCTA CGCCCACAGC CAGAGCTTGG ACCGGCTGAT
 AAV9    GTGCCTTTCC ACAGCAGCTA CGCACACAGC CAGAGTCTAG ATCGACTGAT
 AAV7    GTGCCTTTCC ACAGCAGCTA CGCACACAGC CAGAGCCTGG ACCGGCTGAT
 44_2    GTGCCTTTTC ACAGCAGCTA CGCGCACAGC CAAAGCCTGG ACCGGCTGAT
```

FIG. 1AAT

```
         3551                                                          3600
  42_2   GAATCCCCTC ATCGACCAGT ACCTGTACTA CCTGGCCCGG ACCCAGAGCA
  42_8   GAACCCCCTC ATCGACCAGT ACCTGTACTA CCTGTCTCGG ACTCAGTCCA
  42_15  GAACCCCCTC ATCGACCAGT ACCTGTACTA CCTGTCTCGG ACTCAGTCCA
  42_5b  GAACCCCCTC ATCGACCAGT ACCTGTACTA CCTGTCTCGG ACTCAGTCCA
  42_1b  GAACCCCCTC ATCGACCAGT ACCTGTACTA CCTGTCTCGG ACTCAGTCCA
  42_13  GAACCCCCTC ATCGACCAGT ACCTGTACTA CCTGTCTCGG ACTCAGTCCA
  42_3a  GAACCCCCTC ATCGACCAGT ACCTGTACTA CCTGTCTCGG ACTCAGTCCA
  42_4   GAACCCCCTC ATCGACCAGT ACCTGTACTA CCTGTCTCGG ACTCAGTCCA
  42_5a  GAACCCCCTC ATCGACCAGT ACCTGTACTA CCTGTCTCGG ACTCAGTCCA
  42_10  GAATCCCCTC ATCGACCAGT ACCTGTACTA CCTGGCCCGG ACCCAGAGCA
  42_3b  GAATCCCCTC ATCGACCAGT ACCTGTACTA CCTGGCCCGG ACCCAGAGCA
  42_11  GAATCCCCTC ATCGACCAGT ACCTGTACTA CCTGGCCCGG ACCCAGAGCA
  42_6b  GAATCCCCTC ATCGACCAGT ACCTGTACTA CCTGGCCCGG ACCCAGAGCA
  43_1   GAACCCTCTC ATCGACCAGT ACCTGTATTA CTTATCCAGA ACTCAGTCCA
  43_5   GAACCCTCTC ATCGACCAGT ACCTGTATTA CTTATCCAGA ACTCAGTCCA
  43_12  GAACCCTCTC ATCGACCAGT ACCTGTATTA CTTATCCAGA ACTCAGTCCA
  43_20  GAATCCCCTC ATCGACCAGT ACCTGTACTA CCTGGTCAGA ACGCAAACGA
  43_21  GAATCCCCTC ATCGACCAGT ACCTGTACTA CCTGGTCAGA ACGCAAACGA
  43_23  GAATCCCCTC ATCGACCAGT ACCTGTACTA CCTGGTCAGA ACGCAAACGA
  43_25  GAATCCCCTC ATCGACCAGT ACCTGTACTA CCTGGTCAGA ACGCAAACGA
  44_1   GAACCCCCTC ATCGACCAGT ACCTGTACTA CCTGTCTCGG ACTCAGTCCA
  44_5   GAACCCCCTC ATCGACCAGT ACCTGTACTA CCTGTCTCGG ACTCAGTCCA
 223_10  GAATCCCCTC ATCGACCAGT ACCTGTACTA CTTGGCCAGA ACACAGAGCA
 223_2   GAATCCCCTC ATCGACCAGT ACCTGTACTA CTTGGCCAGA ACACAGAGCA
 223_4   GAATCCCCTC ATCGACCAGT ACCTGTACTA CTTGGCCAGA ACACAGAGCA
 223_5   GAATCCCCTC ATCGACCAGT ACCTGTACTA CTTGGCCAGA ACACAGAGCA
 223_6   GAATCCCCTC ATCGACCAGT ACCTGTACTA CTTGGCCAGA ACACAGAGCA
 223_7   GAATCCCCTC ATCGACCAGT ACCTGTACTA CTTGGCCAGA ACACAGAGCA
  A3_4   GAATCCTCTC ATTGACCAGT ACCTGTATTA CCTGAGCAAA ACTCAGGGTA
  A3_5   GAATCCTCTC ATTGACCAGT ACCTGTATTA CCTGAGCAAA ACTCAGGGTA
  A3_7   GAATCCTCTC ATTGACCAGT ACCTGTATTA CCTGAGCAAA ACTCAGGGTA
  A3_3   GAATCCTCTC ATTGACCAGT ACCTGTATTA CCTGAGCAAA ACTCAGGGTA
  42_12  GAACCCCCTC ATCGACCAGT ACCTGTACTA CCTGGCCCGG ACCCAGAGCA
  AAV1   GAATCCTCTC ATCGACCAAT ACCTGTATTA CCTGAACAGA ACTCAAA.AT
  AAV2   GAATCCTCTC ATCGACCAGT ACCTGTATTA CTTGAGCAGA ACAAACACTC
  AAV3   GAATCCTCTT ATTGATCAGT ATCTGTACTA CCTGAACAGA ACGCAAGGAA
  AAV8   GAATCCTCTG ATTGACCAGT ACCTGTACTA CTTGTCTCGG ACTCAAACAA
  AAV9   GAACCCCCTC ATCGACCAGT ACCTATACTA CCTGGTCAGA ACACAGACAA
  AAV7   GAATCCCCTC ATCGACCAGT ACTTGTACTA CCTGGCCAGA ACACAGAGTA
  44_2   GAACCCCCTC ATCGACCAGT ACCTGTACTA CCTGTCTCGG ACTCAGTCCA
```

FIG. 1AAU

```
         3601                                               3650
 42_2    CTACGG...GG TCCACAAGGG AGCTGCA.GT TCCA...... TCAGGCTGGG
 42_8    CGGGA...GG TACCGCAGGA ACTCAGCAGT TGCTATTTTC TCAGGCCGGG
 42_15   CGGGA...GG TACCGCAGGA ACTCAGCAGT TGCTATTTTC TCAGGCCGGG
 42_5b   CGGGA...GG TACCGCAGGA ACTCAGCAGT TGCTATTTTC TCAGGCCGGG
 42_1b   CGGGA...GG TACCGCAGGA ACTCAGCAGT TGCTATTTTC TCAGGCCGGG
 42_13   CGGGA...GG TACCGCAGGA ACTCAGCAGT TGCTATTTTC TCAGGCCGGG
 42_3a   CGGGA...GG TACCGCAGGA ACTCAGCAGT TGCTATTTTC TCAGGCCGGG
 42_4    CGGGA...GG TACCGCAGGA ACTCAGCAGT TGCTATTTTC TCAGGCCGGG
 42_5a   CGGGA...GG TACCGCAGGA ACTCAGCAGT TGCTATTTTC TCAGGCCGGG
 42_10   CTACG...GG GTCCACAAGG GAGCTGCAGT TCCA...... TCAGGCTGGG
 42_3b   CTACG...GG GTCCACAAGG GAGCTGCAGT TCCA...... TCAGGCTGGG
 42_11   CTACG...GG GTCCACAAGG GAGCTGCAGT TCCA...... TCAGGCTGGG
 42_6b   CTACG...GG GTCCACAAGG GAGCTGCAGT TCCA...... TCAGGCTGGG
 43_1    CAGGA...GG AACTCAAGGT ACTCAGCAAT TGTTATTTTC TCAAGCCGGG
 43_5    CAGGA...GG AACTCAAGGT ACTCAGCAAT TGTTATTTTC TCAAGCCGGG
 43_12   CAGGA...GG AACTCAAGGT ACTCAGCAAT TGTTATTTTC TCAAGCCGGG
 43_20   CT......GG AACTGGAGGG ACGCAGACTC TGGCATTCAG CCAAGCGGGT
 43_21   CT......GG AACTGGAGGG ACGCAGACTC TGGCATTCAG CCAAGCGGGT
 43_23   CT......GG AACTGGAGGG ACGCAGACTC TGGCATTCAG CCAAGCGGGT
 43_25   CT......GG AACTGGAGGG ACGCAGACTC TGGCATTCAG CCAAGCGGGT
 44_1    CGGGA...GG TACCGCAGGA ACTCAGCAGT TGCTATTTTC TCAGGCCGGG
 44_5    CGGGA...GG TACCGCAGGA ACTCAGCAGT TGCTATTTTC TCAGGCCGGG
 223_10  ACGCAGGAGG TACTGCTGGC AATCGGGAAC TGCAGTTTTA TCAGGGCGGA
 223_2   ACGCAGGAGG TACTGCTGGC AATCGGGAAC TGCAGTTTTA TCAGGGCGGA
 223_4   ACGCAGGAGG TACTGCTGGC AATCGGGAAC TGCAGTTTTA TCAGGGCGGA
 223_5   ACGCAGGAGG TACTGCTGGC AATCGGGAAC TGCAGTTTTA TCAGGGCGGA
 223_6   ACGCAGGAGG TACTGCTGGC AATCGGGAAC TGCAGTTTTA TCAGGGCGGA
 223_7   ACGCAGGAGG TACTGCTGGC AATCGGGAAC TGCAGTTTTA TCAGGGCGGA
 A3_4    CAAG...TGG AACAACGCAG CAATCGAGAC TGCAGTTCAG CCAAGCTGGG
 A3_5    CAAG...TGG AACAACGCAG CAATCGAGAC TGCAGTTCAA CCAAGCTGGG
 A3_7    CAAG...TGG AACAACGCAG CAATCGAGAC TGCAGTTCAG CCAAGCTGGG
 A3_3    CAAG...TGG AACAACGCAG CAATCGAGAC TGCAGTTCAG CCAAGCTGGG
 42_12   CTACG...GG GTCCACAAGG GGGCTGCAGT TCCA...... TCAGGCTGGG
 AAV1    CAGTCC..GG AAGTGCCCAA ACAAGGACT TGCTGTTTAG CCGTGGGTCT
 AAV2    CAAG...TGG AACCACCACG CAGTCAAGGC TTCAGTTTTC TCAGGCCGGA
 AAV3    CAACCTCTGG AACAACCAAC CAATCACGGC TGCTTTTTAG CCAGGCTGGG
 AAV8    CAGGAG..GC .ACGGCAAAT ACGCAGACTC TGGGCTTCAG CCAAGGTGGG
 AAV9    CTGGA..... .ACTGGGGGA ACTCAAACTT TGGCATTCAG CCAAGCAGGC
 AAV7    ACCCAGGAGG CACAGCTGGC AATCGGGAAC TGCAGTTTTA CCAGGGCGGG
 44_2    CGGGA...GG TACCGCAGGA ACTCAGCAGT TGCTATTTTC TCAGGCCGGG
```

FIG. 1AAV

```
            3651                                                              3700
   42_2    CCCAACACCA  TGGCCGAGCA  ATCAAAGAAC  TGGCTGCCCG  GACCCTGTTA
   42_8    CCTAATAACA  TGTCGGCTCA  GGCCAAAAAC  TGGCTACCCG  GGCCCTGCTA
  42_15    CCTAATAACA  TGTCGGCTCA  GGCCAAAAAC  TGGCTACCCG  GGCCCTGCTA
  42_5b    CCTAATAACA  TGTCGGCTCA  GGCCAAAAAC  TGGCTACCCG  GGCCCTGCTA
  42_1b    CCTAATAACA  TGTCGGCTCA  GGCCAAAAAC  TGGCTACCCG  GGCCCTGCTA
  42_13    CCTAATAACA  TGTCGGCTCA  GGCCAAAAAC  TGGCTACCCG  GGCCCTGCTA
  42_3a    CCTAATAACA  TGTCGGCTCA  GGCCAAAAAC  TGGCTACCCG  GGCCCTGCTA
   42_4    CCTAATAACA  TGTCGGCTCA  GGCCAAAAAC  TGGCTACCCG  GGCCCTGCTA
  42_5a    CCTAATAACA  TGTCGGCTCA  GGCCAAAAAC  TGGCTACCCG  GGCCCTGCTA
  42_10    CCCAACACCA  TGGCCGAGCA  ATCAAAGAAC  TGGCTGCCCG  GACCCTGTTA
  42_3b    CCCAACACCA  TGGCCGAGCA  ATCAAAGAAC  TGGCTGCCCG  GACCCTGTTA
  42_11    CCCAACACCA  TGGCCGAGCA  ATCAAAGAAC  TGGCTGCCCG  GACCCTGTTA
  42_6b    CCCAACACCA  TGGCCGAGCA  ATCAAAGAAC  TGGCTGCCCG  GACCCTGTTA
   43_1    CCCGCAAACA  TGTCGGCTCA  GGCCAAGAAC  TGGCTACCTG  GACCGTGTTA
   43_5    CCCGCAAACA  TGTCGGCTCA  GGCCAAGAAC  TGGCTACCTG  GACCGTGTTA
  43_12    CCCGCAAACA  TGTCGGCTCA  GGCCAAGAAC  TGGCTACCTG  GACCGTGTTA
  43_20    CCTAGCTCAA  TGGCCAACCA  GGCTAGAAAT  TGGGTGCCCG  GACCTTGCTA
  43_21    CCTAGCTCAA  TGGCCAACCA  GGCTAGAAAT  TGGGTGCCCG  GACCTTGCTA
  43_23    CCTAGCTCAA  TGGCCAACCA  GGCTAGAAAT  TGGGTGCCCG  GACCTTGCTA
  43_25    CCTAGCTCAA  TGGCCAACCA  GGCTAGAAAT  TGGGTGCCCG  GACCTTGCTA
   44_1    CCTAATAACA  TGTCGGCTCA  GGCCAAAAAC  TGGCTACCCG  GGCCCTGCTA
   44_5    CCTAATAACA  TGTCGGCTCA  GGCCAAAAAC  TGGCTACCCG  GGCCCTGCTA
  223_10   CCTACCACCA  TGGCCGAACA  AGCAAAGAAC  TGGCTGCCCG  GACCTTGCTT
  223_2    CCTACCACCA  TGGCCGAACA  AGCAAAGAAC  TGGCTGCCCG  GACCTTGCTT
  223_4    CCTACCACCA  TGGCCGAACA  AGCAAAGAAC  TGGCTGCCCG  GACCTTGCTT
  223_5    CCTACCACCA  TGGCCGAACA  AGCAAAGAAC  TGGCTGCCCG  GACCTTGCTT
  223_6    CCTACCACCA  TGGCCGAACA  AGCAAAGAAC  TGGCTGCCCG  GACCTTGCTT
  223_7    CCTACCACCA  TGGCCGAACA  AGCAAAGAAC  TGGCTGCCCG  GACCTTGCTT
   A3_4    CCTAGCTCCA  TGGCTCAGCA  GGCCAAAAAC  TGCCTACCGG  GACCCAGCTA
   A3_5    CCTAGCTCCA  TGGCTCAGCA  GGCCAAAAAC  TGCCTACCGG  GACCCAGCTA
   A3_7    CCTAGCTCCA  TGGCTCAGCA  GGCCAAAAAC  TGCCTACCGG  GACCCAGCTA
   A3_3    CCTAGCTCCA  TGGCTCAGCA  GGCCAAAAAC  TGCCTACCGG  GACCCAGCTA
  42_12    CCCAACACCA  TGGCCGAGCA  ATCAAAGAAC  TGGCTGCCCG  GACCCTGTTA
   AAV1    CCAGCTGGCA  TGTCTGTTCA  GCCCAAAAAC  TGGCTACCTG  GACCCTGTTA
   AAV2    GCGAGTGACA  TTCGGGACCA  GTCTAGGAAC  TGGCTTCCTG  GACCCTGTTA
   AAV3    CCTCAGTCTA  TGTCTTTGCA  GGCCAGAAAT  TGGCTACCTG  GGCCCTGCTA
   AAV8    CCTAATACAA  TGGCCAATCA  GGCAAAGAAC  TGGCTGCCAG  GACCCTGTTA
   AAV9    CCTAGCTCAA  TGGCCAATCA  GGCTAGAAAC  TGGGTACCCG  GGCCTTGCTA
   AAV7    CCTTCAACTA  TGGCCGAACA  AGCCAAGAAT  TGGTTACCTG  GACCTTGCTT
   44_2    CCTAATAACA  TGTCGGCTCA  GGCCAAAAAC  TGGCTACCCG  GGCCCTGCTA
```

FIG. 1AAW

```
              3701                                                    3750
     42_2    TCGGCAGCAG AGACTGTCAA AAAACATAGA CAGCAACAAC AACAGTAACT
     42_8    CCGGCAGCAA CGCGTCTCCA CGACACTGTC GCAAAATAAC AACAGCAACT
     42_15   CCGGCAGCAA CGCGTCTCCA CGACACTGTC GCAAAATAAC AACAGCAACT
     42_5b   CCGGCAGCAA CGCGTCTCCA CGACACTGTC GCAAAATAAC AACAGCAACT
     42_1b   CCGGCAGCAA CGCGTCTCCA CGACAGTGTC GCAAAATAAC AACAGCAACT
     42_13   CCGGCAGCAA CGCGTCTCCA CGACAGTGTC GCAAAATAAC AACAGCAACT
     42_3a   CCGGCAGCAA CGCGTCTCCA CGACACTGTC GCAAAATAAC AACAGCAACT
     42_4    CCGGCAGCAA CGCGTCTCCA CGACACTGTC GCAAAATAAC AACAGCAACT
     42_5a   CCGGCAGCAA CGCGTCTCCA CGACACTGTC GCAAAATAAC AACAGCAACT
     42_10   TCGGCAGCAG AGACTGTCAA AAAACATAGA CAGCAACAAC AACAGTAACT
     42_3b   TCGGCAGCAG AGACTGTCAA AAAACATAGA CAGCAACAAC ACCAGTAACT
     42_11   TCGGCGGCAG AGACTGTCAA AAGACATAGA CAGCAACAAC AACAGTAACT
     42_6b   TCGGCAGCAG AGACTGTCAA AAAACATAGA CAGCAACAAC AACAGTAACT
     43_1    CCGTCAGCAA CGAGTTTCCA CGACACTGTC GCAAACAAC  AACAGCAATT
     43_5    CCGTCAGCAA CGAGTTTCCA CGACACTGTC GCAAACAAC  AACAGCAATT
     43_12   CCGTCAGCAA CGAGTTTCCA CGACACTGTC GCAAACAAC  AACAGCAATT
     43_20   CCGGCAGCAG CGCGTCTCCA CGACAACCAA CCAGAACAAC AACAGCAACT
     43_21   CCGGCAGCAG CGCGTCTCCA CGACAACCAA CCAGAGCAAC AACAGCAACT
     43_23   CCGGCAGCAG CGCGTCTCCA CGACAACCAA CCAGAACAAC AACAGCAACT
     43_25   CCGGCAGCAG CGCGTCTCCA CGACAACCAA CCAGAACAAC AACAGCAACT
     44_1    CCGGCAGCAA CGCGTCTCCA CGACACTGTC GCAAAATAAC AACAGCAACT
     44_5    CCGGCAGCAA CGCGTCTCCA CGACACTGTC GCAAAATAAC AACAGCAACT
     223_10  CCGGCAACAG AGAGTATCCA AGACGCTGGA TCAAAATAAC AACAGCAACT
     223_2   CCGGCAACAG AGAGTATCCA AGACGCTGGA TCAAAATAAC AACAGCAACT
     223_4   CCGGCAACAG AGAGTATCCA AGACGCTGGA TCAAAATAAC AACAGCAACT
     223_5   CCGGCAACAG AGAGTATCCA AGACGCTGGA TCAAAATAAC AACAGCAACT
     223_6   CCGGCAACAG AGAGTATCCA AGACGCTGGA TCAAAATAAC AACAGCAACT
     223_7   CCGGCAACAG AGAGTATCCA AGACGCTGGA TCAAAATAAC AACAGCAACT
     A3_4    CCGACAGCAG CGAATGTCTA AGACGGCTAA TGACAACAAC AACAGTGAAT
     A3_5    CCGACAGCAG CGAATGTCTA AGACGGCTAA TGACAACAAC AACAGTGAAT
     A3_7    CCGACAGCAG CGAATGTCTA AGACGGCTAA TGACAACAAC AACAGTGAAT
     A3_3    CCGACAGCAG CGAATGTCTA AGACGGCTAA TGACAACAAC AACAGTGAAT
     42_12   TCGGCAGCAG AGACTGTCAA AAAACATAGA CAGCAACAAC AACAGTAACT
     AAV1    TCGGCAGCAG CGCGTTTCTA AAACAAAAAC AGACAACAAC AACAGCAATT
     AAV2    CCGCCAGCAG CGAGTATCAA AGACATCTGC GGATAACAAC AACAGTGAAT
     AAV3    CCGGCAACAG AGACTTTCAA AGACTGCTAA CGACAACAAC AACAGTAACT
     AAV8    CCGCCAACAA CGCGTCTCAA CGACAACCGG GCAAAACAAC AATAGCAACT
     AAV9    CCGTCAGCAG CGCGTCTCCA CAACCACCAA CCAAAATAAC AACAGCAACT
     AAV7    CCGGCAACAA AGAGTCTCCA AAACGCTGGA TCAAAACAAC AACAGCAACT
     44_2    CCGGCAGCAA CGCGTCTCCA CGACACTGTC GCAAAATAAC AACAGCAACT
```

FIG. 1AAX

```
              3751                                                                3800
    42_2     TTGCCTGGAC CGGGGCCACT AAATACCATC TGAATGGTAG AAATTCATTA
    42_8     TTGCTTGGAC CGGTGCCACC AAGTATCATC TGAATGGCAG AGACTCTCTG
    42_15    TTGCTTGGAC CGGTGCCACC AAGTATCATC TGAATGGCAG AGACTCTCTG
    42_5b    TTGCTTGGAC CGGTGCCACC AAGTATCATC TGAATGGCAG AGACTCTCTG
    42_1b    TTGCTTGGAC CGGTGCCACC AAGTATCATC TGAATGGCAG AGACTCTCTG
    42_13    TTGCTTGGAC CGGTGCCACC AAGTATCATC TGAATGGCAG AGACTCTCTG
    42_3a    TTGCTTGGAC CGGTGCCACC AAGTATCATC TGAATGGCAG AGACTCTCTG
    42_4     TTGCTTGGAC CGGTGCCACC AAGTATCATC TGAATGGCAG AGACTCTCTG
    42_5a    TTGCTTGGAC CGGTGCCACC AAGTATCATC TGAATGGCAG AGACTCTCTG
    42_10    TTGCCTGGAC CGGGGCCACT AAATACCATC TGAATGGTAG AAATTCATTA
    42_3b    TTGCCTGGAC CGGGGCCACT AAATACCATC TGAATGGTAG AAATTCATTA
    42_11    TTGCCTGGAC CGGGGCCACT AAATACCATC TGAATGGTAG AAATTCATTA
    42_6b    TTGCCTGGAC CGGGGCCACT AAATACCATC TGAATGGTAG AAATTCATTA
    43_1     TTGCTTGGAC CGGTGCCACC AAGTATCACC TGAATGGCAG AGACTCCCTG
    43_5     TTGCTTGGAC CGGTGCCACC AAGTATCACC TGAATGGCAG AGACTCCCTG
    43_12    TTGCTTGGAC CGGTGCCACC AAGTATCACC TGAATGGCAG AGACTCCCTG
    43_20    TTGCCTGGAC GGGAGCTGCC AAGTTTAAGC TGAACGGCCG AGACTCTCTA
    43_21    TTGCCTGGAC GGGAGCTGCC AAGTTTAAGC TGAACGGCCG AGACTCTCTA
    43_23    TTGCCTGGAC GGGAGCTGCC AAGTTTAAGC TGAACGGCCG AGACTCTCTA
    43_25    TTGCCTGGAC GGGAGCTGCC AAGTTTAAGC TGAACGGCCG AGACTCTCTA
    44_1     TTGCCTGGAC CGGTGCCACC AAGTATCATC TGAATGGCAG AGACTCTCTG
    44_5     TTGCCTGGAC CGGTGCCACC AAGTATCATC TGAATGGCAG AGACTCTCTG
    223_10   TTGCCTGGAC TGGTGCCACA AAATACCATT TAAATGNAAG AAATTCATTG
    223_2    TTGCCTGGAC TGGTGCCACA AAATACCATT TAAATGGAAG AAATTCATTG
    223_4    TTGCCTGGAC TGGTGCCACA AAATACCATT TAAATGGAAG AAATTCATTG
    223_5    TTGCCTGGAC TGGTGCCACA AAATACCATT TAAATGGAAG AAATTCATTG
    223_6    TTGCCTGGAC TGGTGCCACA AAATACCATT TAAATGGAAG AAATTCATTG
    223_7    TTGCCTGGAC TGGTGCCACA AAATACCATT TAAATGGAAG AAATTCATTG
    A3_4     TTGCTTGGAC TGCAGCCACC AAATATTACC TGAATGGAAG AAATTCTCTG
    A3_5     TTGCTTGGAC TGCAGCCACC AAATATTACC CGAATGGAAG AAATTCTCTG
    A3_7     TTGCTTGGAC TGCAGCCACC AAATATTACC TGAATGGAAG AAATTCTCTG
    A3_3     TTGCTTGGAC TGCAGCCACC AAATATTACC TGAATGGAAG AAATTCTCTG
    42_12    TTGCCTGGAC CGGGGCCACT AAATACCATC TGAATGGTAG AAATTCATTA
    AAV1     TTACCTGGAC TGGTGCTTCA AAATATAACC TCAATGGGCG TGAATCCATC
    AAV2     ACTCGTGGAC TGGAGCTACC AAGTACCACC TCAATGGCAG AGACTCTCTG
    AAV3     TTCCTTGGAC AGCGGCCAGC AAATATCATC TCAATGGCCG CGACTCGCTG
    AAV8     TTGCCTGGAC TGCTGGGACC AAATACCATC TGAATGGAAG AAATTCATTG
    AAV9     TTGCGTGGAC GGGAGCTGCT AAATTCAAGC TGAACGGGAG AGACTCGCTA
    AAV7     TTGCTTGGAC TGGTGCCACC AAATATCACC TGAACGGCAG AAACTCGTTG
    44_2     TTGCCTGGAC CGGTGCCACC AAGTATCATC TGAATGGCAG AGACTCTCTG
```

FIG. 1AAY

```
              3801                                                              3850
    42_2     ACCAACCCGG  GCGTAGCCAT  GGCCACCAAC  AAGGACGACG  AGGACCAGTT
    42_8     GTAAATCCCG  GTGTCGCTAT  GGCAACGCAC  AAGGACGACG  AAGAGCGATT
   42_15     GTAAATCCCG  GTGTCGCTAT  GGCAACGCAC  AAGGACGACG  AAGAGCGATT
   42_5b     GTAAATCCCG  GTGTCGCTAT  GGCAACGCAC  AAGGACGACG  AAGAGCGATT
   42_1b     GTAAATCCCG  GTGTCGCTAT  GGCAACGCAC  AAGGGCGACG  AAGAGCGATT
   42_13     GTAAATCCCG  GTGTCGCTAT  GGCAACGCAC  AAGGGCGACG  AAGAGCGATT
   42_3a     GTAAATCCCG  GTGTCGCTAT  GGCAACGCAC  AAGGACGACG  AAGAGCGATT
    42_4     GTAAATCCCG  GTGTCGCTAT  GGCAACGCAC  AAGGACGACG  AAGAGCGATT
   42_5a     GTAAATCCCG  GTGTCGCTAT  GGCAACGCAC  AAGGACGACG  AAGAGCGATT
   42_10     ACCAACCCGG  GCGTAGCCAT  GGCCACCAAC  AAGGACGACG  AGGACCAGTT
   42_3b     ACCAACCCGG  GCGTAGCCAT  GGCCACCAAC  AAGGACGACG  AGGACCAGTT
   42_11     ACCAACCCGG  GCGTAGCCAT  GGCCACCAAC  AAGGACGACG  AGGACCAGTT
   42_6b     ACCAACCCGG  GCGTAGCCAT  GGCCACCAAC  AAGGACGACG  AGGACCAGTT
    43_1     GTTAATCCCG  GCGTTGCCAT  GGCTACCCAC  AAGGACGACG  AGGAGCGCTT
    43_5     GTTAATCCCG  GCGTTGCCAT  GGCTACCCAC  AAGGACGACG  AGGAGCGCTT
   43_12     GTTAATCCCG  GCGTTGCCAT  GGCTACCCAC  AAGGACGACG  AGGAGCGCTT
   43_20     ATGAATCCGG  GCGTGGCAAT  GGCTTCCCAC  AAGGATGACG  ACGACCGCTT
   43_21     ATGAATCCGG  GCGTGGCAAT  GGCTTCCCAC  AAGGATGACG  ACGACCGCTT
   43_23     ATGAATCCGG  GCGTGGCAAT  GGCTTCCCAC  AAGGATGACG  ACGACCGCTT
   43_25     ATGAATCCGG  GCGTGGCAAT  GGCTTCCCAC  AAGGATGACG  ACGACCGCTT
    44_1     GTAAATCCCG  GTGTCGCTAT  GGCAACCCAC  AAGGACGACG  AAGAGCGATT
    44_5     GTAAATCCCG  GTGTCGCTAT  GGCAACCCAC  AAGGACGACG  AAGAGCGATT
  223_10     GTTAATCCCG  GTGTCGCCAT  GGCAACCCAC  AAGGACGACG  AGGAACGCTT
   223_2     GTTAATCCCG  GTGTCGCCAT  GGCAACCCAC  AAGGACGACG  AGGAACGCTT
   223_4     GTTAATCCCG  GTGTCGCCAT  GGCAACCCAC  AAGGACGACG  AGGAACGCTT
   223_5     GTTAATCCCG  GTGTCGCCAT  GGCAACCCAC  AAGGACGACG  AGGAACGCTT
   223_6     GTTAATCCCG  GTGTCGCCAT  GGCAACCCAC  AAGGACGACG  AGGAACGCTT
   223_7     GTTAATCCCG  GTGTCGCCAT  GGCAACCCAC  AAGGACGACG  AGGAACGCTT
    A3_4     GTCAATCCCG  GGCCCCCAAT  GGCCAGTCAC  AAGGACGATG  AGGAAAAGTA
    A3_5     GTCAATCCCG  GGCCCCCAAT  GGCCAGTCAC  AAGGACGATG  AGGAAAAGTA
    A3_7     GTCAATCCCG  GGCCCCCAAT  GGCCAGTCAC  AAGGACGATG  AGGAAAAGTA
    A3_3     GTCAATCCCG  GGCCCCCAGT  GGCCAGTCAC  AAGGACGATG  AGGAAAAGTA
   42_12     ACCAACCCGG  GCGTAGCCAT  GGCCACCAAC  AAGGACGACG  AGGACCAGTT
    AAV1     ATCAACCCTG  GCACTGCTAT  GGCCTCACAC  AAAGACGACG  AAGACAAGTT
    AAV2     GTGAATCC..  GGCC....AT  GGCAAGCCAC  AAGGACGATG  AAGAAAAGTT
    AAV3     GTGAATCCAG  GACCAGCTAT  GGCCAGTCAC  AAGGACGATG  AAGAAAAATT
    AAV8     GCTAATCCTG  GCATCGCTAT  GGCAACACAC  AAAGACGACG  AGGAGCGTTT
    AAV9     ATGAATCCTG  GCGTGGCTAT  GGCATCGCAC  AAAGACGACG  AGGACCGCTT
    AAV7     GTTAATCCCG  GCGTCGCCAT  GGCAACTCAC  AAGGACGACG  AGGACCGCTT
    44_2     GTAAATCCCG  GTGTCGCTAT  GGCAACCCAC  AAGGACGACG  AAGAGCGATT
```

FIG. 1AAZ

```
            3851                                                    3900
    42_2    CTTTCCCATC AACGGAGTGC TGGTTTTTGG CGAAACGGGG GCTGCCAACA
    42_8    TTTTCCATCC AGCGGAGTCT TGATGTTTGG GAAACAGGGA GCTGGAAA..
    42_15   TTTTCCATCC AGCGGAGTCT TGATGTTTGG GAAACAGGGA GCTGGAAA..
    42_5b   TTTTCCATCC AGCGGAGTCT TGATGTTTGG GAAACAGGGA GCTGGAAA..
    42_1b   TTTTCCATCC AGCGGAGTCT TGATGTTTGG GAAACAGGGA GCTGGAAA..
    42_13   TTTTCCATCC AGCGGAGTCT TGATGTTTGG GAAACAGGGA GCTGGAAA..
    42_3a   TTTTCCATCC AGCGGAGTCT TGATGTTTGG GAAACAGGGA GCTGGAAA..
    42_4    TTTTCCATCC AGCGGAGTCT TGATGTTTGG GAAACAGGGA GCTGGAAA..
    42_5a   TTTTCCATCC AGCGGAGTCT TGATGTTTGG GAAACAGGGA GCTGGAAA..
    42_10   CTTTCCCATC AACGGAGTGC TGGTTTTTGG CAAAACGGGG GCTGCCAACA
    42_3b   CTTTCCCATC AACGGAGTGC TGGTTTTTGG CAAAACGGGG GCTGCCAACA
    42_11   CTTTCCCATC AACGGAGTGC TGGTTTTTGG CAAAACGGGG GCTGCCAACA
    42_6b   CTTTCCCATC AACGGAGTGC TGGTTTTTGG CAAAACGGGG GCTGCCAACA
    43_1    CTTCCCGTCA AGCGGAGTTC TAATGTTTGG CAAGCAGGGG GCTGGAAA..
    43_5    CTTCCCGTCA AGCGGAGTTC TAATGTTTGG CAAGCAGGGG GCTGGAAA..
    43_12   CTTCCCGTCA AGCGGAGTTC TAATGTTTGG CAAGCAGGGG GCTGGAAA..
    43_20   CTTCCCTTCG AGCGGGGTCC TGATTTTTGG CAAGCAAGGA GCCGGGAA..
    43_21   CTTCCCTTCG AGCGGGGTCC TGATTTTTGG CAAGCAAGGA GCCGGGAA..
    43_23   CTTCCCTTCG AGCGGGGTCC TGATTTTTGG CAAGCAAGGA GCCGGGAA..
    43_25   CTTCCCTTCG AGCGGGGTCC TGATTTTTGG CAAGCAAGGA GCCGGGAA..
    44_1    TTTTCCGTCC AGCGGAGTCT TAATGTTTGG GAAACAGGCA GCTGGAAA..
    44_5    TTTTCCGTCC AGCGGAGTCT TAATGTTTGG GAAACAGGGA GCTGGAAA..
    223_10  CTTCCCTTCG AGCGGAGTTC TAATTTTTGG CAAAACTGGA GCAGCTAATA
    223_2   CTCCCCTTCG AGCGGAGTTC TAATTTTTGG CAAAACTGGA GCAGCTAATA
    223_4   CTTCCCTTCG AGCGGAGTTC TAATTTTTGG CAAAACTGGA GCAGCTAATA
    223_5   CTTCCCTTCG AGCGGAGTTC TAATTTTTGG CAAAACTGGA GCAGCTAATA
    223_6   CTTCCCTTCG AGCGGAGTTC TAATTTTTGG CAAAACTGGA GCAGCTAATA
    223_7   CTTCCCTTCG AGCGGAGTTC TAATTTTTGG CAAAACTGGA GCAGCTAATA
    A3_4    TTTCCCCATG CACGGAAATC TCATCTTTGG AAAACAAGGC ACAGGAAC..
    A3_5    TTTCCCCATG CACGGAAATC TCATCTTTGG AAAACAAGGC ACAGGAAC..
    A3_7    TTTCCCCATG CACGGAAATC TCATCTTTGG AAAACAAGGC ACAGGAAC..
    A3_3    TTTCCCCATG CACGGAAATC TCATCTTTGG AAAACAAGGC ACAGGAAC..
    42_12   CTTTCCCATC AACGGAGTGC TGGTTTTTGG CAAAACGGGG GCTGCCAACA
    AAV1    CTTTCCCATG AGCGGTGTCA TGATTTTTGG AAAAGAGAGC GCCGGAGC..
    AAV2    TTTTCCTCAG AGCGGGGTTC TCATCTTTGG GAAGCAAGGC TCAGAGAA..
    AAV3    TTTCCCTATG CACGGCAATC TAATATTTGG CAAAGAAGCG ACAACGGC..
    AAV8    TTTTCCAGT  AACGGGATCC TGATTTTTGG CAAACAAAAT GCTGCCAG..
    AAV9    CTTTCCATCA AGTGGCGTTC TCATATTTGG CAAGCAAGGA GCCGGGAA..
    AAV7    TTTCCCATCC AGCGGAGTCC TGATTTTTGG AAAAACTGGA GCAACTAACA
    44_2    TTTTCCGTCC AGCGGAGTCT TAATGTTTGG GAAACAGGGA GCTGGAAA..
```

FIG. 1AAAA

```
         3901                                                    3950
  42_2   AGACAACGCT GGAA...... AACGTGCTAA TGACCAGCGA GGAGGAGATC
  42_8   AGACAACG.T GGACTATAGC AGCGTTATGC TAACCAGTGA GGAAGAAATC
  42_15  AGACAACG.T GGACTATAGC AGCGTTATGC TAACCAGTGA GGAAGAAATC
  42_5b  AGACAACG.T GGACTATAGC AGCGTTATGC TAACCAGTGA GGAAGAAATC
  42_1b  AGACAACG.T AGACTATAGC AGCGTTATGC TAACCAGTGA GGAAGAAATC
  42_13  AGACAACG.T GGACTATAGC AGCGTTATGC TAACCAGTGA GGAAGAAATC
  42_3a  AGACAACG.T GGACTATAGC AGCGTTATGC TAACCAGTGA GGAAGAAATC
  42_4   AGACAACG.T GGACTATAGC AGCGTTATGC TAACCAGTGA GGAAGAAATC
  42_5a  AGACAACG.T GGACTATAGC AGCGTTATGC TAACCAGTGA GGAAGAAATC
  42_10  AGACAACGCT GGAA...... AACGTGCTAA TGACCAGCGA GGAGGAGATC
  42_3b  AGACAACGCT GGAA...... AACGTGCTAA TGACCAGCGA GGAGGAGATC
  42_11  AGACAACGCT GGAA...... AACGTGCTAA TGACCAGCGA GGAGGAGATC
  42_6b  AGACAACGCT GGAA...... AACGTGCTAA TGACCAGCGA GGAGGAGATC
  43_1   AGACAATG.T GGACTACAGC AGCGTGATGC TCACCAGCGA AGAAGAAATT
  43_5   AGACAATG.T GGACTACAGC AGCGTGATGC TCACCAGCGA AGAAGAAATT
  43_12  AGACAATG.T GGACTACAGC AGCGTGATGC TCACCAGCGA AGAAGAAATT
  43_20  CGATGGAG.T GGATTACAGC CAAGTGCTGA TTACAGATGA GGAAGAAATC
  43_21  CGATGGAG.T GGATTACAGC CAAGTGCTGA TTACAGATGA GGAAGAAATC
  43_23  CGATGGAG.T GGATTACAGC CAAGTGCTGA TTACAGATGA GGAAGAAATC
  43_25  CGATGGAG.T GGATTACAGC CAAGTGCTGA TTACAGATGA GGAAGAAATC
  44_1   AGACAACG.T GGACTATAGC AGCGTTATGC TAACCAGTGA GGAAGAAATT
  44_5   AGACAACG.T GGACTATAGC AGCGTTATGC TAACCAGTGA GGAAGAAATT
 223_10  AAACTACATT AGAA...... AACGTGCTCA TGACAAATGA AGAAGAAATT
 223_2   AAACTACATT AGAA...... AACGTGCTCA TGACAAATGA AGAAGAAATT
 223_4   AAACTACATT AGAA...... AACGTGCTCA TGACAAATGA AGAAGAAATT
 223_5   AAACTACATT AGAA...... AACGTGCTCA TGACAAATGA AGAAGAAATT
 223_6   AAACTACATT AGAA...... AACGTGCTCA TGACAAATGA AGAAGAAATT
 223_7   AAACTACATT AGAA...... AACGTGCTCA TGACAAATGA AGAAGAAATT
  A3_4   TACCAATG.T GGACATTGAA TCAGTGCTTA TTACAGACGA AGAAGAAATC
  A3_5   TACCAATG.T GGACATTGAA TCAGTGCTTA TTACAGACGA AGAAGAAATC
  A3_7   TACCAATG.T GGACATTGAA TCAGTGCTTA TTACAGACGA AGAAGAAATC
  A3_3   TACCAATG.T GGACATTGAA TCAGTGCTTA TTACAGACGA AGAAGAAATC
  42_12  AGACAACGCT GGAA...... AACGTGCTAA TGACCAGCGA GGAGGAGATC
  AAV1   TTCAAACA.C TGCATTGGAC AATGTCATGA TTACAGACGA AGAGGAAATT
  AAV2   AACAAATG.T GAACATTGAA AAGGTCATGA TTACAGACGA AGAGGAAATC
  AAV3   AAGTAACG.C AGAATTAGAT AATGTAATGA TTACGGATGA AGAACAGATT
  AAV8   AGACAATG.C GGATTACAGC GATGTCATGC TCACCAGCGA GGAAGAAATC
  AAV9   CGATGGAG.T CGACTACAGC CAGGTGCTGA TTACAGATGA GGAAGAAATT
  AAV7   AAACTACATT GGAA...... AATGTGTTAA TGACAAATGA AGAAGAAATT
  44_2   AGACAACG.T GGACTATAGC AGCGTTATGC TAACCAGTGA GGAAGAAATT
```

FIG. 1AAAB

```
         3951                                                                    4000
  42_2   AAAACCACCA  ATCCCGTGGC  TACAGAAGAA  TACGGTGTGG  TCTCCAGCAA
  42_8   AAAACCACCA  ACCCAGTGGC  CACAGAACAG  TACGGCGTGG  TGGCCGATAA
 42_15   AAAACCACCA  ACCCAGTGGC  CACAGAACAG  TACGGCGTGG  TGGCCGATAA
 42_5b   AAAACCACCA  ACCCAGTGGC  CACAGAACAG  TACGGCGTGG  TGGCCGATAA
 42_1b   AAAACCACCA  ACCCAGTGGC  CACAGAACAG  TACGGCGTGG  TGGCCGATAA
 42_13   AAAACCACCA  ACCCAGTGGC  CACAGAACAG  TACGGCGTGG  TGGCCGATAA
 42_3a   AAAACCACCA  ACCCAGTGGC  CACAGAACAG  TACGGCGTGG  TGGCCGATAA
  42_4   AAAACCACCA  ACCCAGTGGC  CACAGAACAG  TACGGCGTGG  TGGCCGATAA
 42_5a   AAAACCACCA  ACCCAGTGGC  CACAGAACAG  TACGGCGTGG  TGGCCGATAA
 42_10   AAAACCACCA  ATCCCGTGGC  TACAGAAGAA  TACGGTGTGG  TCTCCAGCAA
 42_3b   AAAACCACCA  ATCCCGTGGC  TACAGAACAG  TACGGTGTGG  TCTCCAGCAA
 42_11   AAAACCACCA  ATCCCGTGGC  TACAGAAGAA  TACGGTGTGG  TCTCCAGCAA
 42_6b   AAAACCACCA  ATCCCGTGGC  TACAGAAGAA  TACGGTGTGG  TCTCCAGCAA
  43_1   AAAACTACTA  ACCCAGTGGC  TACAGAGCAG  TATGGTGTGG  TGGCAGACAA
  43_5   AAAACTACTA  ACCCAGTGGC  TACAGAGCAG  TATGGTGTGG  TGGCAGACAA
 43_12   AAAACTACTA  ACCCAGTGGC  TACAGAGCAG  TATGGTGTGG  TGGCAGACAA
 43_20   AAGGCTACCA  ACCCCGTGGC  CACAGAAGAA  TATGGAGCAG  TGGCCATCAA
 43_21   AAGGCTACCA  ACCCCGTGGC  CACAGAAGAA  TATGGAGCAG  TGGCCATCAA
 43_23   AAGGCTACCA  ACCCCGTGGC  CACAGAAGAA  TATGGAGCAG  TGGCCATCAA
 43_25   AAGGCTACCA  ACCCCGTGGC  CACAGAAGAA  TATGGAGCAG  TGGCCATCAA
  44_1   AAAACCACCA  ACCCAGTGGC  CACGGAACAG  TACGGCGTGG  TGGCCGATAA
  44_5   AAAACCACCA  ACCCAGTGGC  CACAGAACAG  TACGGCGTGG  TGGCCGATAA
223_10   CGTCCTACCA  ACCCGGTAGC  TACCGAGGAA  TACGGGATTG  TAAGCAGCAA
 223_2   CGTCCTACCA  ACCCGGTAGC  TACCGAGGAA  TACGGGATTG  TAAGCAGCAA
 223_4   CGTCCTACCA  ACCCGGTAGC  TACCGAGGAA  TACGGGATTG  TAAGCAGCAA
 223_5   CGTCCTACCA  ACCCGGTAGC  TACCGAGGAA  TACGGGATTG  TAAGCAGCAA
 223_6   CGTCCTACCA  ACCCGGTAGC  TACCGAGGAA  TACGGGATTG  TAAGCAGCAA
 223_7   CGTCCTACCA  ACCCGGTAGC  TACCGAGGAA  TACGGGATTG  TAAGCAGCAA
  A3_4   AGAACAACTA  ATCCTGTGGC  TACAGAACAA  TACGGACAGG  TTGCCACCAA
  A3_5   AGAACGACTA  ATCCTGTGGC  TACAGAACAA  TACGGACAGG  TTGCCACCAA
  A3_7   AGAACAACTA  ATCCTGTGGC  TACAGAACAA  TACGGACAGG  TTGCCACCAA
  A3_3   AGAACAACTA  ATCCTGTGGC  TACAGAACAA  TACGGACAGG  TTGCCACCAA
 42_12   AAAACCACCA  ATCCCGTGGC  TACAGAAGAA  TACGGTGTGG  TCTCCAGCAA
  AAV1   AAAGCCACTA  ACCCTGTGGC  CACCGAAAGA  TTTGGGACCG  TGGCAGTCAA
  AAV2   GGAACAACCA  ATCCCGTGGC  TACGGAGCAG  TATGGTTCTG  TATCTACCAA
  AAV3   CGTACCACCA  ATCCTGTGGC  AACAGAGCAG  TATGGAACTG  TGGCAAATAA
  AAV8   AAAACCACTA  ACCCTGTGGC  TACAGAGGAA  TACGGTATCG  TGGCAGATAA
  AAV9   AAAGCCACCA  ACCCTGTAGC  CACAGAGGAA  TACGGAGCAG  TGGCCATCAA
  AAV7   CGTCCTACTA  ATCCTGTAGC  CACGGAAGAA  TACGGGATAG  TCAGCAGCAA
  44_2   AAAACCACCA  ACCAGTGGC   CACAGAACAG  TACGGCGTGG  TGGCCGATAA
```

FIG. 1AAAC

```
         4001                                                    4050
  42_2   CCTGCAATCG TCTACGGCCG GACCCCAGAC ACAGACTGTC AACAGCCAGG
  42_8   CCTGCAACAG CAAAACGCCG CTCCTATTGT AGGGGCCGTC AACAGTCAAG
 42_15   CCTGCAACAG CAAAACGCCG CTCCTATTGT AGGGGCCGTC AACAGTCAAG
 42_5b   CCTGCAACAG CAAAACGCCG CTCCTATTGT AGGGGCCGTC AACAGTCAAG
 42_1b   CCTGCAACAG CAAAACGCCG CTCCTATTGT AGGGGCCGTC AACAGTCAAG
 42_13   CCTGCAACAG CAAAACGCCG CTCCTATTGT AGGGGCCGTC AACAGTCAAG
 42_3a   CCTGCAACAG CAAAACGCCG CTCCTATTGT AGGGGCCGTC AACAGTCAAG
  42_4   CCTGCAACAG CAAAACGCCG CTCCTATTGT AGGGGCCGTC AACAGTCAAG
 42_5a   CCTGCAACAG CAAAACGCCG CTCCTATTGT AGGGGCCGTC AACAGTCAAG
 42_10   CCTGCAATCG TCTACGGCCG GACCCCAGAC ACAGACTGTC AACAGCCAGG
 42_3b   CCTGCAATCG TCTACGGCCG GACCCCAGAC ACAGACTGTC AACAGCCAGG
 42_11   CCTGCAATCG TCTACGGCCG GACCCCAGAC ACAGACTGTC AACAGCCAGG
 42_6b   CCTGCAATCG TCTACGGCCG GACCCCAGAC ACAGACTGTC AACAGCCAGG
  43_1   CCTGCAGCAG ACCAACGGAG CTCCCATTGT GGGAACTGTC AACAGCCAGG
  43_5   CCTGCAGCAG ACCAACGGAG CTCCCATTGT GGGAACTGTC AACAGCCAGG
 43_12   CCTGCAGCAG ACCAACGGAG CTCCCATTGT GGGAACTGTC AACAGCCAGG
 43_20   CAACCAGGCC GCCAATACGC AGGCGCAGAC CGGACTCGTG CACAACCAGG
 43_21   CAACCAGGCC GCCAATACGC AGGCGCAGAC CGGACTCGTG CACAACCAGG
 43_23   CAACCAGGCC GCCAATACGC AGGCGCAGAC CGGACTCGTG CACAACCAGG
 43_25   CAACCAGGCC GCCAATACGC AGGCGCAGAC CGGACTCGTG CACAACCAGG
  44_1   CCTGCAACAG CAAAACGCCG CTCCTATTGT AGGGGCCGTC AACAGTCAAG
  44_5   CCTGCAACAG CAAAACGCCG CTCCTATTGT AGGGGCCGTC AACAGTCAAG
 223_10  CTTGCAGGCG GCTAGCACCG CAGCCCAGAC ACAAGTTGTT AACAACCAGG
 223_2   CTTGCAGGCG GCTAGCACCG CAGCCCAGAC ACAAGTTGTT AACAACCAGG
 223_4   CTTGCAGGCG GCTAGCACCG CAGCCCAGAC ACAAGTTGTT AACAACCAGG
 223_5   CTTGCAGGCG GCTAGCACCG CAGCCCAGAC ACAAGTTGTT AACAACCAGG
 223_6   CTTGCAGGCG GCTAGCACCG CAGCCCAGAC ACAAGTTGTT AACAACCAGG
 223_7   CTTGCAGGCG GCTAGCACCG CAGCCCAGAC ACAAGTTGTT AACAACCAGG
  A3_4   CCATCAGAGT CAGGACACCA CAGCTTCCTA TGGAAGTGTG GACAGCCAGG
  A3_5   CCGTCAGAGT CAGAACACCA CAGCTTCCTA TGGAAGTGTG GACAGCCAGG
  A3_7   CCATCAGAGT CAGAACACCA CAGCTTCCTA TGGAAGTGTG GACAGCCAGG
  A3_3   CCATCAGAGT CAGAACACCA CAGCTTCCTA TGGAAGTGTG GACAGCCAGG
 42_12   CCTGCAATCG TCTACGGCCG GACCCCAGAC ACAGACTGTC AACAGCCAGG
  AAV1   TTTCCAGAGC AGCAGCACAG ACCCTGCGAC CGGAGATGTG CATGCTATGG
  AAV2   CCTCCAGAGA GGCAACAGAC AAGCAGCTAC CGCAGATGTC AACACACAAG
  AAV3   CTTGCAGAGC TCAAATACAG CTCCCACGAC TGGAACTGTC AATCATCAGG
  AAV8   CTTGCAGCAG CAAAACACGG CTCCTCAAAT TGGAACTGTC AACAGCCAGG
  AAV9   CAACCAGGCC GCTAACACGC AGGCGCAAAC TGGACTTGTG CATAACCAGG
  AAV7   CTTACAAGCG GCTAATACTG CAGCCCAGAC ACAAGTTGTC AACAACCAGG
  44_2   CCTGCAACAG CAAAACGCCG CTCCTATTGT AGGGGCCGTC AACAGTCAAG
```

FIG. 1AAAD

```
         4051                                                    4100
 42_2    GGGCTCTGCC CGGCATGGTC TGGCAGAACC GGGACGTGTA CCTGCAGGGT
 42_8    GAGCCTTACC TGGCATGGTC TGGCAGAACC GGGACGTGTA CCTGCAGGGT
 42_15   GAGCCTTACC TGGCATGGTC TGGCAGAACC GGGACGTGTA CCTGCAGGGT
 42_5b   GAGCCTTACC TGGCATGGTC TGGCAGAACC GGGACGTGTA CCTGCAGGGT
 42_1b   GAGCCTTACC TGGCATGGTC TGGCAGAACC GGGACGTGTA CCTGCAGGGT
 42_13   GAGCCTTACC TGGCATGGTC TGGCAGAACC GGGACGTGTA CCTGCAGGGT
 42_3a   GAGCCTTACC TGGCATGGTC TGGCAGAACC GGGACGTGTA CCTGCAGGGT
 42_4    GAGCCTTACC TGGCATGGTC TGGCAGAACC GGGACGTGTA CCTGCAGGGT
 42_5a   GAGCCTTACC TGGCATGGCC TGGCAGAACC GGGACGTGTA CCTGCAGGGT
 42_10   GGGCTCTGCC CGGCATGGTC TGGCAGAACC GGGACGTGTA CCTGCAGGGT
 42_3b   GGGCTCTGCC CGGCATGGTC TGGCAGAACC GGGACGTGTA CCTGCAGGGT
 42_11   GGGCTCTGCC CGGCATGGTC TGGCAGAACC GGGACGTGTA CCTGCAGGGT
 42_6b   GGGCTCTGCC CGGCATGGTC TGGCAGAACC GGGACGTGTA CCTGCAGGGT
 43_1    GGGCCTTACC TGGTATGGTC TGGCAAAACC GGGACGTGTA CCTGCAGGGC
 43_5    GGGCCTTACC TGGTATGGTC TGGCAAAACC GGGACGTGTA CCTGCAGGGC
 43_12   GGGCCTTACC TGGTATGGTC TGGCAAAACC GGGACGTGTA CCTGCAGGGC
 43_20   GGGTGATTCC CGGCATGGTG TGGCAGAATA GAGACGTGTA CCTGCAGGGT
 43_21   GGGTGATTCC CGGCATGGTG TGGCAGAATA GAGACGTGTA CCTGCAGGGT
 43_23   GGGTGATTCC CGGCATGGTG TGGCAGAATA GAGACGTGTA CCTGCAGGGT
 43_25   GGGTGATTCC CGGCATGGTG TGGCAGAATA GAGACGTGTA CCTGCAGGGT
 44_1    GAGCCTTACC TGGCATGGTC TGGCAGAACC GGGACGTGTA CCTGCAGGGT
 44_5    GAGCCTTACC TGGCATGGTC TGGCAGAACC GGGACGTGTA CCTGCAGGGT
 223_10  GAGCCTTACC TGGCATGGTC TGGCAGAACC GGGACGTGTA CCTGCAAGGT
 223_2   GAGCCTTACC TGGCATGGTC TGGCAGAACC GGGACGTGTA CCTGCAAGGT
 223_4   GAGCCTTACC TGGCATGGTC TGGCAGAACC GGGACGTGTA CCTGCAAGGT
 223_5   GAGCCTTACC TGGCATGGTC TGGCAGAACC GGGACGTGTA CCTGCAAGGT
 223_6   GAGCCTTACC TGGCATGGTC TGGCAGAACC GGGACGTGTA CCTGCAAGGT
 223_7   GAGCCTTACC TGGCATGGTC TGGCAGAACC GGGACGTGTA CCTGCAAGGT
 A3_4    GAATCTTACC TGGAATGGTG TGGCAGGACC GCGATGTCTA TCTTCAAGGT
 A3_5    GAATCTTACC TGGAATGGTG TGGCAGGACC GCGATGTCTA TCTTCAAGGT
 A3_7    GAATCTTACC TGGAATGGTG TGGCAGGACC GCGATGTCTA TCTTCAAGGT
 A3_3    GAATCTTACC TGGAATGGTG TGGCAGGACC GCGATGTCTA TCTTCAAGGT
 42_12   GGGCTCTGCC CGGCATGGTC TGGCAGAACC GGGACGTGTA CCTGCAGGGT
 AAV1    GAGCATTACC TGGCATGGTG TGGCAAGATA GAGACGTGTA CCTGCAGGGT
 AAV2    GCGTTCTTCC AGGCATGGTC TGGCAGGACA GAGATGTGTA CCTTCAGGGG
 AAV3    GGGCCTTACC TGGCATGGTG TGGCAAGATC GTGACGTGTA CCTTCAAGGA
 AAV8    GGGCCTTACC CGGTATCGTC TGGCAGAACC GGGACGTGTA CCTGCAGGGT
 AAV9    GAGTTATTCC TGGTATGGTC TGGCAGAACC GGGACGTGTA CCTGCAGGGC
 AAV7    GAGCCTTACC TGGCATGGTC TGGCAGAACC GGGACGTGTA CCTGCAGGGT
 44_2    GAGCCTTACC TGGCATGGTC TGGCAGAACC GGGACGTGTA CCTGCAGGGT
```

FIG. 1AAAE

```
            4101                                                      4150
   42_2     CCC.ATCTGG  GCCAAAATTC  CTCACACGGA  CGGCAACTTT  CACCCGTCTC
   42_8     CCT.ATCTGG  GCCAAGATTC  CTCACACGGA  CGGCAACTTT  CATCCTTCGC
   42_15    CCT.ATCTGG  GCCAAGATTC  CTCACACGGA  CGGCAACTTT  CATCCTTCGC
   42_5b    CCT.ATCTGG  GCCAAGATTC  CTCACACGGA  CGGCAACTTT  CATCCTTCGC
   42_1b    CCT.ATCTGG  GCCAAGATTC  CTCACACGGA  CGGCAACTTT  CATCCTTCGC
   42_13    CCT.ATCTGG  GCCAAGATTC  CTCACACGGA  CGGCAACTTT  CATCCTTCGC
   42_3a    CCT.ATCTGG  GCCAAGATTC  CTCACACGGA  CGGCAACTTT  CATCCTTCGC
   42_4     CCT.ATCTGG  GCCAAGATTC  CTCACACGGA  CGGCAACTTT  CATCCTTCGC
   42_5a    CCT.ATCTGG  GCCAAGATTC  CTCACACGGA  CGGCAACTTT  CATCCTTCGC
   42_10    CCC.ATCTGG  GCCAAAATTC  CTCACACGGA  CGGCAACTTT  CACCCGTCTC
   42_3b    CCC.ATCTGG  GCCAAAATTC  CTCACACGGA  CGGCAACTTT  CACCCGTCTC
   42_11    CCC.ATCTGG  GCCAAAATTC  CTCACACGGA  CGGCAACTTT  CACCCGTCTC
   42_6b    CCC.ATCTGG  GCCAAAATTC  CTCACACGGA  CGGCAACTTT  CACCCGTCTC
   43_1     CCC.ATCTGG  GCCAAAATTC  CTCACACGGA  CGGCAACTTT  CATCCTTCGC
   43_5     CCC.ATCTGG  GCCAAAATTC  CTCACACGGA  CGGCAACTTT  CATCCTTCGC
   43_12    CCC.ATCTGG  GCCAAAATTC  CTCACACGGA  CGGCAACTTT  CATCCTTCGC
   43_20    CCC.ATCTGG  GCCAAAATTC  CTCACACGGA  CGGCAACTTT  CACCCGTCTC
   43_21    CCC.ATCTGG  GCCAAAATTC  CTCACACGGA  CGGCAACTTT  CACCCGTCTC
   43_23    CCC.ATCTGG  GCCAAAATTC  CTCACACGGA  CGGCAACTTT  CACCCGTCTC
   43_25    CCC.ATCTGG  GCCAAAATTC  CTCACACGGA  CGGCAACTTT  CACCCGTCTC
   44_1     CCT.ATCTGG  GCCAAGATTC  CTCACACGGA  CGGAAACTTT  CATCCCTCGC
   44_5     CCT.ATCTGG  GCCAAGATTC  CTCACACGGA  CGGAAACTTT  CATCCCTCGC
   223_10   CCC.ATTTGG  GCCAAGATTC  CTCACACGGA  CGGCAACTTT  CACCCGTCTC
   223_2    CCC.ATTTGG  GCCAAGATTC  CTCACACGGA  CGGCAACTTT  CACCCGTCTC
   223_4    CCC.ATTTGG  GCCAAGATTC  CTCACACGGA  CGGCAACTTT  CACCCGTCTC
   223_5    CCC.ATTTGG  GCCAAGATTC  CTCACACGGA  CGGCAACTTT  CACCCGTCTC
   223_6    CCC.ATTTGG  GCCAAGATTC  CTCACACGGA  CGGCAACTTT  CACCCGTCTC
   223_7    CCC.ATTTGG  GCCAAGATTC  CTCACACGGA  CGGCAACTTT  CACCCGTCTC
   A3_4     CCC.ATTTGG  GCCAAAACTC  CTCACACGGA  CGGACACTTT  CATCCTTCTC
   A3_5     CCC.ATTTGG  GCCAAAACTC  CTCACACGGA  CGGACACTTT  CATCCTTCTC
   A3_7     CCC.ATTTGG  GCCAAAACTC  CTCACACGGA  CGGACACTTT  CATCCTTCTC
   A3_3     CCC.ATTTGG  GCCAAAACTC  CTCACACGGA  CGGACACTTT  CATCCTTCTC
   42_12    CCC.ATCTGG  GCCAAAATTC  CTCACACGGA  CGGCAACTTT  CACCCGTCTC
   AAV1     CCC.ATTTGG  GCCAAAATTC  CTCACACAGA  TGGACACTTT  CACCCGTCTC
   AAV2     CCC.ATCTGG  GCAAAGATTC  CACACACGGA  CGGACATTTT  CACCCCTCTC
   AAV3     CCT.ATCTGG  GCAAAGATTC  CTCACACGGA  TGGACACTTT  CATCCTTCTC
   AAV8     CCC.ATCTGG  GCCAAGATTC  CTCACACGGA  CGGCAACTTC  CACCCGTCTC
   AAV9     CCCTATTTGG  GCTAAAATAC  CTCACACAGA  TGGCAACTTT  CACCCGTCTC
   AAV7     CCC.ATCTGG  GCCAAGATTC  CTCACACGGA  TGGCAACTTT  CACCCGTCTC
   44_2     CCT.ATCTGG  GCCAAGATTC  CTCACACGGA  CGGAAACTTT  CATCCCTCGC
```

FIG. 1AAAF

```
            4151                                                          4200
   42_2   CCCTGATGGG CGGATTTGGA CTCAAACACC CGCCTCCTCA AATTCTCATC
   42_8   CGCTGATGGG AGGCTTTGGA CTGAAACACC CGCCTCCTCA GATCCTGATT
  42_15   CGCTGATGGG AGGCTTTGGA CTGAAACACC CGCCTCCTCA GATCCTGATT
  42_5b   CGCTGATGGG AGGCTTTGGA CTGAAACACC CGCCTCCTCA GATCCTGATT
  42_1b   CGCTGATGGG AGGCTTTGGA CTGAAACACC CGCCTCCTCA GATCCTGATT
  42_13   CGCTGATGGG AGGCTTTGGA CTGAAACACC CGCCTCCTCA GATCCTGATT
  42_3a   CGCTGATGGG AGGCTTTGGA CTGAAACACC CGCCTCCTCA GATCCTGATT
   42_4   CGCTGATGGG AGGCTTTGGA CTGAAACACC CGCCTCCTCA GATCCTGATT
  42_5a   CGCTGATGGG AGGCTTTGGA CTGAAACACC CGCCTCCTCA GATCCTGATT
  42_10   CCCTGATGGG CGGATTTGGA CTCAAACACC CGCCTCCTCA AATTCTCATC
  42_3b   CCCTGATGGG CGGATTTGGA CTCAAACACC CGCCTCCTCA AATTCTCATC
  42_11   CCCTGATGGG CGGATTTGGA CTCAAACACC CGCCTCCTCA AATTCTCATC
  42_6b   CCCTGATGGA CGGATTTGGA CTCAAACACC CGCCTCCTCA AATTCTCATC
   43_1   CGCTGATGGG AGGCTTTGGA CTGAAACACC CGCCTCCTCA GATCCTGGTG
   43_5   CGCTGATGGG AGGCTTTGGA CTGAAACACC CGCCTCCTCA GATCCTGGTG
  43_12   CGCTGATGGG AGGCTTTGGA CTGAAACACC CGCCTCCTCA GATCCTGGTG
  43_20   CCCTGATGGG CGGCTTTGGA CTGAAGCACC CGCCTCCTCA AATTCTCATC
  43_21   CCCTGATGGG CGGCTTTGGA CTGAAGCACC CGCCTCCTCA AATTCTCATC
  43_23   CCCTGATGGG CGGCTTTGGA CTGAAGCACC CGCCTCCTCA AATTCTCATC
  43_25   CCCTGATGGG CGGCTTTGGA CTGAAGCACC CGCCTCCTCA AATTCTCATC
   44_1   CGCTGATGGG AGGCTTTGGA CTGAAACACC CGCCTCCTCA GATCCTGATT
   44_5   CGCTGATGGG AGGCTTTGGA CTGAAACACC CGCCTCCTCA GATCCTGATT
 223_10   CTCTAATGGG TGGCTTTGGA CTGAAACACC CGCCTCCCCA GATCCTGATC
  223_2   CTCTAATGGG TGGCTTTGGA CTGAAACACC CGCCTCCCCA GATCCTGATC
  223_4   CTCTAATGGG TGGCTTTGGA CTGAAACACC CGCCTCCCCA GATCCTGATC
  223_5   CTCTAATGGG TGGCTTTGGA CTGAAACACC CGCCTCCCCA GATCCTGATC
  223_6   CTCTAATGGG TGGCTTTGGA CTGAAACACC CGCCTCCCCA GATCCTGATC
  223_7   CTCTAATGGG TGGCTTTGGA CTGAAACACC CGCCTCCCCA GATCCTGATC
   A3_4   CGCTCATGGG AGGCTTTGGA CTGAAACACC CTCCTCCCCA GATCCTGATC
   A3_5   CGCTCATGGG AGGCTTTGGA CTGAAACACC CTCCTCCCCA GATCCTGATC
   A3_7   CGCTCATGGG AGGCTTTGGA CTGAAACACC CTCCTCCCCA GATCCTGATC
   A3_3   CGCTCATGGG AGGCTTTGGA CTGAAACACC CTCCTCCCCA GATCCTGATC
  42_12   CCCTGATGGG CGGATTTGGA CTCAAACACC CGCCTCCTCA AATTCTCATC
   AAV1   CTCTTATGGG CGGCTTTGGA CTCAAGAACC CGCCTCCTCA GATCCTCATC
   AAV2   CCCTCATGGG TGGATTCGGA CTTAAACACC CTCCTCCACA GATTCTCATC
   AAV3   CTCTGATGGG AGGCTTTGGA CTGAAACATC CGCCTCCTCA AATCATGATC
   AAV8   CGCTGATGGG CGGCTTTGGC CTGAAACATC CTCCGCCTCA GATCCTGATC
   AAV9   CTCTGATGGG TGGATTTGGA CTGAAACACC CACCTCCACA GATTCTAATT
   AAV7   CTTTGATGGG CGGCTTTGGA CTTAAACATC CGCCTCCTCA GATCCTGATC
   44_2   CGCTGATGGG AGGCTTTGGA CTGAAACACC CGCCTCCTCA GATCCTGATT
```

FIG. 1AAAG

```
        4201                                                          4250
 42_2   AAAAACACCC CGGTACCTGC TAATCCTCCA GAGGTGTTTA CTCCTGCCAA
 42_8   AAGAATACAC CTGTTCCCGC GGATCCTCCA ACTACCTTCA GTCAAGCCAA
 42_15  AAGAATACAC CTGTTCCCGC GGATCCTCCA ACTACCTTCA GTCAAGCCAA
 42_5b  AAGAATACAC CTGTTCCCGC GGATCCTCCA ACTACCTTCA GTCAAGCCAA
 42_1b  AAGAATACAC CTGTTCCCGC GGATCCTCCA ACTACCTTCA GTCAAGCCAA
 42_13  AAGAATACAC CTGTTCCCGC GGATCCTCCA ACTACCTTCA GTCAAGCCAA
 42_3a  AAGAATACAC CTGTTCCCGC GGATCCTCCA ACTACCTTCA GTCAAGCCAA
 42_4   AAGAATACAC CTGTTCCCGC GGATCCTCCA ACTACCTTCA GTCAAGCCAA
 42_5a  AAGAATACAC CTGTTCCCGC GGATCCTCCA ACTACCTTCA GTCAAGCCAA
 42_10  AAAAACACCC CGGTACCTGC TAATCCTCCA GAGGTGTTTA CTCCTGCCAA
 42_3b  AAAAACACCC CGGTACCTGC TAATCCTCCA GAGGTGTTTA CTCCTGCCAA
 42_11  AAAAACACCC CGGTACCTGC TAATCCTCCA GAGGTGTTTA CTCCTGCCAA
 42_6b  AAAAACACCC CGGTACCTGC TAATCCTCCA GAGGTGTTTA CTCCTGCCAA
 43_1   AAAAACACTC CTGTTCCTGC GGATCCTCCG ACCACCTTCA GCCAGGCCAA
 43_5   AAAAACACTC CTGTTCCTGC GGATCCTCCG ACCACCTTCA GCCAGGCCAA
 43_12  AAAAACACTC CTGTTCCTGC GGATCCTCCG ACCACCTTCA GCCAGGCCAA
 43_20  AAGAACACAC CGGTTCCAGC GGACCCGCCG CTTACCTTCA ACCAGGCCAA
 43_21  AAGAACACAC CGGTTCCAGC GGACCCGCCG CTTACCTTCA ACCAGGCCAA
 43_23  AAGAACACAC CGGTTCCAGC GGACCCGCCG CTTACCTTCA ACCAGGCCAA
 43_25  AAGAACACAC CGGTTCCAGC GGACCCGCCG CTTACCTTCA ACCAGGCCAA
 44_1   AAGAATACAC CTGTTCCCGC GGATCCTCCA ACTACCTTCA GTCAAGCTAA
 44_5   AAGAATACAC CTGTTCCCGC GGATCCTCCA ACTACCTTCA GTCAAGCTAA
223_10  AAAAACACAC CGGTACCTGC TAATCCTCCA GAAGTGTTTA CTCCTGCCAA
223_2   AAAAACACGC CGGTACCTGC TAATCCTCCA GAAGTGTTTA CTCCTGCCAA
223_4   AAAAACACAC CGGTACCTGC TAATCCTCCA GAAGTGTTTA CTCCTGCCAA
223_5   AAAAACACAC CGGTACCTGC TAATCCTCCA GAAGTGTTTA CTCCTGCCAA
223_6   AAAAACACAC CGGTACCTGC TAATCCTCCA GAAGTGTTTA CTCCTGCCAA
223_7   AAAAACACAC CGGTACCTGC TAATCCTCCA GAAGTGTTTA CTCCTGCCAA
 A3_4   AAAAACACAC CTGTGCCAGC GAATCCCGCG ACCACTTTCA CTCCTGGAAA
 A3_5   AAAAACACAC CTGTGCCAGC GAATCCCGCG ACCACTTTCA CTCCTGGAAA
 A3_7   AAAAACACAC CTGTGCCAGC GAATCCCGCG ACCACTTTCA CTCCTGGAAA
 A3_3   AAAAACACAC CTGTGCCAGC GAATCCCGCG ACCACTTTCA CTCCTGGAAA
 42_12  A...A..... .......... .......... .......... ..........
 AAV1   AAAAACACGC CTGTTCCTGC GAATCCTCCG GCGGAGTTTT CAGCTACAAA
 AAV2   AAGAACACCC CGGTACCTGC GAATCCTTCG ACCACCTTCA GTGCGGCAAA
 AAV3   AAAAATACTC CGGTACCGGC AAATCCTCCG ACGACTTTCA GCCCGGCCAA
 AAV8   AAGAACACGC CTGTACCTGC GGATCCTCCG ACCACCTTCA ACCAGTCAAA
 AAV9   AAAAATACAC CAGTGCCGGC AGATCCTCCT CTTACCTTCA ATCAAGCCAA
 AAV7   AAGAACACTC CCGTTCCCGC TAATCCTCCG GAGGTGTTTA CTCCTGCCAA
 44_2   AAGAATACAC CTGTTCCCGC GGATCCTCCA ACTACCTTCA GTCAAGCTAA
```

FIG. 1AAAH

```
           4251                                                           4300
  42_2     GTTTGCCTCA TTTATCACGC AGTACAGCAC CGGCCA.GGT CAGCGTGGAG
  42_8     GCTGGCGTCG TTCATCACGC AGTACAGCAC CGGACA.GGT CAGCGTGGAA
  42_15    GCTGGCGTCG TTCATCACGC AGTACAGCAC CGGACA.GGT CAGCGTGGAA
  42_5b    GCTGGCGTCG TTCATCACGC AGTACAGCAC CGGACA.GGT CAGCGTGGAA
  42_1b    GCTGGCGTCG TTCATCACGC AGTACAGCAC CGGACA.GGT CAGCGTGGAA
  42_13    GCTGGCGTCG TTCATCACGC AGTACAGCAC CGGACA.GGT CAGCGTGGAA
  42_3a    GCTGGCGTCG TTCATCACGC AGTACAGCAC CGGACA.GGT CAGCGTGGAA
  42_4     GCCGGCGTCG TTCATCACGC AGTACAGCAC CGGACA.GGT CAGCGTGGAA
  42_5a    GCTGGCGTCG TTCATCACGC AGTACAGCAC CGGACA.GGT CAGCGTGGAA
  42_10    GTTTGCCTCA TTTATCACGC AGTACAGCAC CGGCCA.GGT CAGCGTGGAG
  42_3b    GTTTGCCTCA TTTATCACGC AGTACAGCAC CGGCCA.GGT CAGCGTGGAG
  42_11    GTTTGCCTCA TTTATCACGC AGTACAGCAC CGGCCA.GGT CAGCGTGGAG
  42_6b    GTTTGCCTCA TTTATCACGC AGTACAGCAC CGGCCA.GGT CAGCGTGGAG
  43_1     GCTGGCTTCT TTTATCACGC AGTACAGCAC CGGACA.GGT CAGCGTGGAA
  43_5     GCTGGCTTCT TTTATCACGC AGTACAGCAC CGGACA.GGT CAGCGTGGAA
  43_12    GCTGGCTTCT TTTATCACGC AGTACAGCAC CGGACA.GGT CAGCGTGGAA
  43_20    GCTGAACTCT TTCATCACGC AGTACAGCAC CGGACA.GGT CAGCGTGGAA
  43_21    GCTGAACTCT TTCATCACGC AGTACAGCAC CGGACA.GGT CAGCGTGGAA
  43_23    GCTGAACTCT TTCATCACGC AGTACAGCAC CGGACA.GGT CAGCGTGGAA
  43_25    GCTGAACTCT TTCATCACGC AGTACAGCAC CGGACA.GGT CAGCGTGGAA
  44_1     GCTGGCGTCG TTCATCACGC AGTACAGCAC CGGACA.GGT CAGCGTGGAA
  44_5     GCTGGCGTCG TTCATCACGC AGTACAGCAC CGGACA.GGT CAGCGTGGAA
  223_10   GTTGCTTCC  TTCATCACGC AGTACAGCAC CGGGCA.AGT CAGCGTTGAG
  223_2    GTTGCTTCC  TTCATCACGC AGTACAGCAC CGGGCA.AGT CAGCGTTGAG
  223_4    GTTGCTTCC  TTCATCACGC AGTACAGCAC CGGGCA.AGT CAGCGTTGAG
  223_5    GTTGCTTCC  TTCATCACGC AGTACAGCAC CGGGCA.AGT CAGCGTTGAG
  223_6    GCTTGCTTCC TTCATCACGC AGTACAGCAC CGGGCA.AGT CAGCGTTGAG
  223_7    GATTGCTTCC TTCATCACGC AGTACAGCAC CGGGCA.AGT CAGCGTTGAG
  A3_4     GTTGCTTCG  TTCATTACCC AGTATTCCAC CGGACA.GGT CAGCGTGGAA
  A3_5     GTTGCTTCG  TTCATTACCC AGTATTCCAC CGGACA.GGT CAGCGTGGAA
  A3_7     GTTTGCTTCG TTCATTACCC AGTATTCCAC CGGACA.GGT CAGCGTGGAA
  A3_3     GTTTGCTTCG TTCATTACCC AGTATTCCAC CGGACA.GGT CAGCGTGGAA
  42_12    .......... .......... .......... .......... ..........
  AAV1     GTTTGCTTCA TTCATCACCC AATACTCCAC AGGACA.AGT GAGTGTGGAA
  AAV2     GTTTGCTTCC TTCATCACAC AGTACTCCAC GGCACAGGT  CAGCGTGGAG
  AAV3     GTTTGCTTCA TTTATCACTC AGTACTCCAC TGGACA.GGT CAGCGTGGAA
  AAV8     GCTGAACTCT TTCATCACGC AATACAGCAC CGGACA.GGT CAGCGTGGAA
  AAV9     GCTGAACTCT TTCATCACGC AGTACAGCAC GGGACA.AGT CAGCGTGGAA
  AAV7     GTTTGCTTCG TTCATCACAC AGTACAGCAC CGGACA.AGT CAGCGTGGAA
  44_2     GCTGGCGTCG TTCATCACGC AGTACAGCAC CGGACA.GGT CAGCGTGGAA
```

FIG. 1AAAl

```
         4301                                                              4350
 42_2    ATCGAGTGGG  AACTGCAGAA  AGAAAACAGC  AAACGCTGGA  ATCCAGAGAT
 42_8    ATTGAATGGG  AGCTGCAGAA  AGAGAACAGC  AAGCGCTGGA  ACCCAGAGAT
 42_15   ATTGAATGGG  AGCTGCAGAA  AGAGAACAGC  AAGCGCTGGA  ACCCAGAGAT
 42_5b   ATTGAATGGG  AGCTGCAGAA  AGAGAACAGC  AAGCGCTGGA  ACCCAGAGAT
 42_1b   ATTGAATGGG  AGCTGCAGAA  AGAGAACAGC  AAGCGCTGGA  ACCCAGAGAT
 42_13   ATTGAATGGG  AGCTGCAGAA  AGAGAACAGC  AAGCGCTGGA  ACCCAGAGAT
 42_3a   ATTGAATGGG  AGCTGCAGAA  AGAGAACAGC  AAGCGCTGGA  ACCCAGAGAT
 42_4    ATTGAATGGG  AGCTGCAGAA  AGAGAACAGC  AAGCGCTGGA  ACCCAGAGAT
 42_5a   ATTGAATGGG  AGCTGCAGAA  AGAGAACAGC  AAGCGCTGGA  ACCCAGAGAT
 42_10   ATCGAGTGGG  AACTGCAGAA  AGAAAACAGC  AAACGCTGGA  ATCCAGAGAT
 42_3b   ATCGAGTGGG  AACTGCAGAA  AGAAAACAGC  AAACGCTGGA  ATCCAGAGAT
 42_11   ATCGAGTGGG  AACTGCAGAA  AGAGAACAGC  AAACGCTGGA  ATCCAGAGAT
 42_6b   ATCGAGTGGG  AACTGCAGAA  AGAAAACAGC  AAACGCTGGA  ATCCAGAGAT
 43_1    ATCGAATGGG  AGCTGCAGAA  AGAAAACAGC  AAGCGCTGGA  ACCCAGAGAT
 43_5    ATCGAATGGG  AGCTGCAGAA  AGAAAACAGC  AAGCGCTGGA  ACCCAGAGAT
 43_12   ATCGAATGGG  AGCTGCAGAA  AGAAAACAGC  AAGCGCTGGA  ACCCAGAGAT
 43_20   ATCGAGTGGG  AGCTGCAGAA  AGAAAACAGC  AAACGCTGGA  ATCCAGAGAT
 43_21   ATCGAGTGGG  AGCTGCAGAA  AGAAAACAGC  AAACGCTGGA  ATCCAGAGAT
 43_23   ATCGAGTGGG  AGCTGCAGAA  AGAAAACAGC  AAACGCTGGA  ATCCAGAGAT
 43_25   ATCGAGTGGG  AGCTGCAGAA  AGAAAACAGC  AAACGCTGGA  ATCCAGAGAT
 44_1    ATTGAATGGG  AGCTGCAGAA  AGAAAACAGC  AAACGCTGGA  ACCCAGAGAT
 44_5    ATTGAATGGG  AGCTGCAGAA  AGAAAACAGC  AAACGCTGGA  ACCCAGAGAT
 223_10  ATCGAGTGGG  AGCTGCAGAA  AGAGAACAGC  AAGCGCTGGA  ACCCAGAGAT
 223_2   ATCGAGTGGG  AGCTGCAGAA  AGAGAACAGC  AAGCGCTGGA  ACCCAGAGAT
 223_4   ATCGAATGGG  AGCTGCAGAA  AGAGAACAGC  AAGCGCTGGA  ACCCAGAGAT
 223_5   ATCGAATGGG  AGCTGCAGAA  AGAGAACAGC  AAGCGCTGGA  ACCCAGAGAT
 223_6   ATCGAGTGGG  AGCTGCAGAA  AGAGAACAGC  AAGCGCTGGA  ACCCAGAGAT
 223_7   ATCGAGTGGG  AGCTGCAGAA  AGAGAACAGC  AAGCGCTGGA  ACCCAGAGAT
 A3_4    ATAGAGTGGG  AGCTGCAGAA  AGAAAACAGC  AAACGCTGGA  ACCCAGAAAT
 A3_5    ATAGAGTGGG  AGCTGCAGAA  AGAAAACAGC  AAACGCTGGA  ACCCGGAAAT
 A3_7    ATAGAGTGGG  AGCTGCAGAA  AGAAAACAGC  AAACGCTGGA  ACCCAGAAAT
 A3_3    ATAGAGTGGG  AGCTGCAGAA  AGAAAACAGC  AAACGCTGGA  ACCCAGAAAT
 42_12   ..........  ..........  ..........  ..........  ..........
 AAV1    ATTGAATGGG  AGCTGCAGAA  AGAAAACAGC  AAGCGCTGGA  ATCCCGAAGT
 AAV2    ATCGAGTGGG  AGCTGCAGAA  GGAAAACAGC  AAACGCTGGA  ATCCCGAAAT
 AAV3    ATTGAGTGGG  AGCTACAGAA  AGAAAACAGC  AAACGTTGGA  ATCCAGAGAT
 AAV8    ATTGAATGGG  AGCTGCAGAA  GGAAAACAGC  AAGCGCTGGA  ACCCCGAGAT
 AAV9    ATCGAGTGGG  AGCTGCAGAA  AGAAAACAGC  AAGCGCTGGA  ATCCAGAGAT
 AAV7    ATCGAGTGGG  AGCTGCAGAA  GGAAAACAGC  AAGCGCTGGA  ACCCGGACAT
 44_2    ATTGAATGGG  AGCTGCAGAA  AGAAAACAGC  AAACGCTGGA  ACCCAGAGAT
```

FIG. 1AAAJ

```
        4351                                                                           4400
 42_2   TCAGTACACC TCAAATTATG CCAAGTCTAA TAAT.GTGGA ATTTGCTGTC
 42_8   TCAGTATACT TCCAACTACT ACAAATCTAC AAAT.GTGGA CTTTGCTGTC
 42_15  TCAGTATACT TCCAACTACT ACAAATCTAC AAAT.GTGGA CTTTGCTGTC
 42_5b  TCAGTATACT TCCAACTACT ACAAATCTAC AAAT.GTGGA CTTTGCTGTC
 42_1b  TCAGTATACT TCCAACTACT ACAAATCTAC AAAT.GTGGA CTTTGCTGTC
 42_13  TCAGTATACT TCCAACTACT ACAAATCTAC AAAT.GTGGA CTTTGCTGTC
 42_3a  TCAGTATACT TCCAACTACT ACAAATCTAC AAAT.GTGGA CTTTGCTGTC
 42_4   TCAGTATACT TCCAACTACT ACAAATCTAC AAAT.GTGGA CTTTGCTGTC
 42_5a  TCAGTATACT TCCAACTACT ACAAATCTAC AAAT.GTGGA CTTTGCTGTC
 42_10  TCAGTACACC TCAAATTATG CCAAGTCTAA TAAT.GTGGA ATTTGCTGTC
 42_3b  TCAGTACACC TCAAATTATG CCAAGTCTAA TAAT.GTGGA ATTTGCTGTC
 42_11  TCAGTACACC TCAAATTATG CCAAGTCTAA TAAT.GTGGA ATTTGCTGTC
 42_6b  TCAGTACACC TCAAATTATG CCAAGTCTAA TAAT.GTGGA ATTTGCTGTC
 43_1   TCAGTATACT TCCAACTACT ACAAATCTAC AAAT.GTGGA CTTTGCTGTC
 43_5   TCAGTATACT TCCAACTACT ACAAATCTAC AAAT.GTGGA CTTTGCTGTC
 43_12  TCAGTATACT TCCAACTACT ACAAATCTAC AAAT.GTGGA CTTTGCTGTC
 43_20  TCAATACACT TCCAACTACT ACAAATCTAC AAAT.GTGGA CTTTGCTGTC
 43_21  TCAATACACT TCCAACTACT ACAAATCTAC AAAT.GTGGA CTTTGCTGTC
 43_23  TCAATACACT TCCAACTACT ACAAATCTAC AAAT.GTGGA CTTTGCTGTC
 43_25  TCAATACACT TCCAACTACT ACAAATCTAC AAAT.GTGGA CTTTGCTGTC
 44_1   TCAATACACT TCCAACTACT ACAAATCTAC AAAT.GTGGA CTTCGCTGTT
 44_5   TCAATACACT TCCAACTACT ACAAATCTAC AAAT.GTGGA CTTTGCTGTT
223_10  TCAGTACACC TCCAACTTTG ACAAACAGAC TGGA.GTCGA CTTTGCTGTT
223_2   TCAGTACACC TCCAACTTTG ACAAACAGAC TGGA.GTGGA CTTTGCTGTT
223_4   TCAGTACACC TCCAACTTTG ACAAACAGAC TGGA.GTGGA CTTTGCTGTT
223_5   TCAGTACACC TCCAACTTTG ACAAACAGAC TGGA.GTGGA CTTTGCTGTT
223_6   TCAGTACACC TCCAACTTTG ACAAACAGAC TGGA.GTGGA CTTTGCTGTT
223_7   TCAGTACACC TCCAACTTTG ACAAACAGAC TGGA.GTGGA CTTTGCTGTT
 A3_4   TCAGTACACC TCCAACTACA ACAAGTCGGT GAAT.GTGGA GTTTACCGTG
 A3_5   TCAGTACACC TCCAACTACA ACAAGTCGGT GAAT.GTGGA GTTTACCGTG
 A3_7   TCAGTACACC TCCAACTACA ACAAGTCGGT GAAT.GTGGA GTTTACCGTG
 A3_3   TCAGTACACC TCCAACTACA ACAAGTCGGT GAAT.GTGGA GTTTACCGTG
 42_12  ...GTATACT TCCAACTACT ACAAATCTAC AAAT.GTGGA CTTTGCTGTC
 AAV1   GCAGTACACA TCCAATTATG CAAAATCTGC CAAC.GTTGA TTTTACTGTG
 AAV2   TCAGTACACT TCCAACTACA ACAAGTCTGT TAATCGTGGA CTT.ACCGTG
 AAV3   TCAGTACACT TCCAACTACA ACAAGTCTGT TAAT.GTGGA CTTTACTGTA
 AAV8   CCAGTACACC TCCAACTACT ACAAATCTAC AAGT.GTGGA CTTTGCTGTT
 AAV9   CCAGTATACT TCAAACTACT ACAAATCTAC AAAT.GTGGA CTTTGCTGTC
 AAV7   TCAGTACACC TCCAACTTTG AAAAGCAGAC TGGT.GTGGA CTTTGCCGTT
 44_2   TCAATACACT TCCAACTACT ACAAATCTAC AAAT.GTGGA CTTTGCTGTT
```

FIG. 1AAAK

```
           4401                                                        4450
  42_2     AACAACGAAG  GGGTTTATAC  TGAGCCTCGC  CCCATTGGCA  CCCGTTACCT
  42_8     AATACTGAGG  GTACTTATTC  AGAGCCTCGC  CCCATTGGCA  CCCGTTACCT
  42_15    AATACTGAGG  GTACTTATTC  AGAGCCTCGC  CCCATTGGCA  CCCGTTACCT
  42_5b    AATACTGAGG  GTACTTATTC  AGAGCCTCGC  CCCATTGGCA  CCCGTTACCT
  42_1b    AATACTGAGG  GTACTTATTC  AGAGCCTCGC  CCCATTGGCA  CCCGTTACCT
  42_13    AATACTGAGG  GTACTTATTC  AGAGCCTCGC  CCCATTGGCA  CCCGTTACCT
  42_3a    AATACTGAGG  GTACTTATTC  AGAGCCTCGC  CCCATTGGCA  CCCGTTACCT
  42_4     AATACTGAGG  GTACTTATTC  AGAGCCTCGC  CCCATTGGCA  CCCGTTACCT
  42_5a    AATACTGAGG  GTACTTATTC  AGAGCCTCGC  CCCATTGGCA  CCCGTTACCT
  42_10    AACAACGAAG  GGGTTTATAC  TGAGCCTCGC  CCCATTGGCA  CCCGTTACCT
  42_3b    AACAACGAAG  GGGTTTATAC  TGAGCCTCGC  CCCATTGGCA  CCCGTTACCT
  42_11    AACAACGAAG  GGGTTTATAC  TGAGCCTCGC  CCCATTGGCA  CCCGTTACCT
  42_6b    AACAACGAAG  GGGTTTATAC  TGAGCCTCGC  CCCATTGGCA  CCCGTTACCT
  43_1     AATACTGAGG  GTACTTATTC  AGAGCCTCGC  CCCATTGGCA  CTCGTTATCT
  43_5     AATACCGAGG  GTACTTATTC  AGAGCCTCGC  CCCATTGGCA  CTCGTTATCT
  43_12    AATACTGAGG  GTACTTATTC  AGAGCCTCGC  CCCATTGGCA  CTCGTTATCT
  43_20    AACACGGAAG  GAGTTTATAG  CGAGCCTCGC  CCCATTGGCA  CCCGTTACCT
  43_21    AACACGGAAG  GAGTTTATAG  CGAGCCTCGC  CCCATTGGCA  CCCGTTACCT
  43_23    AACACGGAAG  GAGTTTATAG  CGAGCCTCGC  CCCATTGGCA  CCCGTTACCT
  43_25    AACACGGAGG  GGGTTTATAG  CGAGCCTCGC  CCCATTGGCA  CCCGTTACCT
  44_1     AACACAGATG  GCACTTATTC  TGAGCCTCGC  CCCATTGGCA  CCCGTTACCT
  44_5     AACACAGATG  GCACTTATTC  TGAGCCTCGC  CCCATTGGCA  CCCGTTACCT
  223_10   GACAGCCAGG  GTGTTTACTC  TGAGCCT...  ..........  ..........
  223_2    GACAGCCAGG  GTGTTTACTC  TGAGCCT...  ..........  ..........
  223_4    GACAGCCAGG  GTGTTTACTC  TGAGCCT...  ..........  ..........
  223_5    GACAGCCAGG  GTGTTTACTC  TGAGCCT...  ..........  ..........
  223_6    GACAGCCAGG  GTGTTTACTC  TGAGCCT...  ..........  ..........
  223_7    GACAGCCAGG  GTGTTTACTC  TGAGCCT...  ..........  ..........
  A3_4     GACGCAAACG  GTGTTTATTC  TGAACCCCGC  CCTATTGGCA  CTCGTTACCT
  A3_5     GACGCAAACG  GTGTTTATTC  TGAACCCCGC  CCTATTGGCA  CTCGTTACCT
  A3_7     GACGCAAACG  GTGTTTATTC  TGAACCCCGC  CCTATTGGCA  CTCGTTACCT
  A3_3     GACGCAAACG  GTGTTTATTC  TGAACCCCGC  CCTATTGGCA  CTCGTTACCT
  42_12    AATACTGAGG  GTACTTATTC  AGAGCCTCGC  CCCATTGGCA  CCCGTTACCT
  AAV1     GACAACAATG  GACTTTATAC  TGAGCCTCGC  CCCATTGGCA  CCCGTTACCT
  AAV2     GATACTAATG  GCGTGTATTC  AGAGCCTCGC  CCCATTGGCA  CCAGATACCT
  AAV3     GACACTAATG  GTGTTTATAG  TGAACCTCGC  CCTATTGGAA  CCCGGTATCT
  AAV8     AATACAGAAG  GCGTGTACTC  TGAACCCCGC  CCCATTGGCA  CCCGTTACCT
  AAV9     AATACCGAAG  GTGTTACTC   TGAGCCTCGC  CCCATTGGTA  CTCGTTACCT
  AAV7     GACAGCCAGG  GTGTTTACTC  TGAGCCTCGC  CCTATTGGCA  CTCGTTACCT
  44_2     AACACAGATG  GCACTTATTC  TGAGCCTCGC  CCCATCGGCA  CCCGTTACCT
```

FIG. 1AAAL

```
           4451                                                           4500
                    VP1-3 stop       Poly A signal
   42_2     CACCCGTAAC CTGTAATTGC CTGTTAATCA ATAAACCGGT TAATTCGTTT
   42_8     CACCCGTAAC CTGTAATTGC CTGTTAATCA ATAAACCGGC TAATTCGTTT
   42_15    CACCCGTAAC CTGTAATTGC CTGTTAATCA ATAAACCGGT TAATTCGTTT
   42_5b    CACCCGTAAC CTGTAATTGC CTGTTAATCA ATAAACCGGT TAATTCGTTT
   42_1b    CACCCGTAAC CTGTAATTGC CTGTTAATCA ATAAACCGGT TGATTCGTTT
   42_13    CACCCGTAGC CTGTAATTGC CTGTTAATCA ATAAACCGGT TGATTCGTTT
   42_3a    CACCCGTAAC CTGTAATTGC CTGTTAATCA ATAAACCGGT TAATTCGTTT
   42_4     CACCCGTAAC CTGTAATTGC CTGTTAATCA ATAAACCGGT TAATTCGTTT
   42_5a    CACCCGTAAC CTGTAATTGC CTGTTAATCA ATAAACCGGT TAATTCGTTT
   42_10    CACCCGTAAC CTGTAATTGC CTGTTAATCA ATAAACCGGT TAATTCGTTT
   42_3b    CACCCGTAAC CTGTAATTGC CTGTTAATCA ATAAACCGGT TAATTCGTTT
   42_11    CACCCGTAAC CTGTAATTAC TTGTTAATCA ATAAACCGGT TGATTCGTTT
   42_6b    CACCCGTAAC CTGTAATTGC CTGTTAATCA ATAAACCGGT TAATTCGTTT
   43_1     CACCCGTAAT CTGTAATTGC TTGTTAATCA ATAAACCGGT ..........
   43_5     CACCCGTAAT CTGTAATTGC TTGTTAATCA ATAAACCGGT TAATTCGTTT
   43_12    CACCCGTAAT CTGTAATTGC TTGTTAATCA ATAAACCGGT TAATTCGTTT
   43_20    CACCCGCAAC CTGTAATTAC ATGTTAATCA ATAAACCGGT TAATTCGTTT
   43_21    CACCCGCAAC CTGTAATTAC ATGTTAATCA ATAAACCGGT TAATTCGTTT
   43_23    CACCCGCAAC CTGTAATTAC ATGTTAATCA ATAAACCGGT TAATTCGTTT
   43_25    CACCCGCAAC CTGTAATTAC ATGTTAATCA ATAAACCGGT TAATTCGTTT
   44_1     CACCCGTAAT CTGTAATTGC TCGTTAATCA ATAAACCGGT TGATTCGTTT
   44_5     CACCCGTAAT CTGTAATTGC TTGTTAATCA ATAAACCGGT TGATTCGTTT
   223_10   .......... .......... .......... .......... ..........
   223_2    .......... .......... .......... .......... ..........
   223_4    .......... .......... .......... .......... ..........
   223_5    .......... .......... .......... .......... ..........
   223_6    .......... .......... .......... .......... ..........
   223_7    .......... .......... .......... .......... ..........
   A3_4     TACCCGGAAC TTGTAATTTC CTGTTAATGA ATAAACCGAT TTATGCGTTT
   A3_5     TACCCGGAAC TTGTAATTTC CTGTTAATGA ATAAACCGAT TTATGCGTTT
   A3_7     TACCCGGAAC TTGTAATTTC CTGTTAATGA ATAAACCGAT TTATGCGTTT
   A3_3     TACCCGGAAC TTGTAATTTC CTGTTAATGA ATAAGCCGAT TTATGCGTTT
   42_12    CACCCGTAAC CTGTAATTGC CTGTTAATCA ATAAACCGGT TAATTCGTTT
   AAV1     TACCCGTCCC CTGTAATTAC GTGTTAATCA ATAAACCGGT TGATTCGTTT
   AAV2     GACTCGTAAT CTGTAATTGC TTGTTAATCA ATAAACCGTT TAATTCGTTT
   AAV3     CACACGAAAC TTGTGAATCC TGGTTAATCA ATAAACCGTT TAATTCGTTT
   AAV8     CACCCGTAAT CTGTAATTGC CTGTTAATCA ATAAACCGGT TGATTCGTTT
   AAV9     CACCCGTAAT TTGTAATTGC CTGTTAATCA ATAAACCGGT TAATTCGTTT
   AAV7     CACCCGTAAT CTGTAATTGC ATGTTAATCA ATAAACCGGT TGATTCGTTT
   44_2     CACCCGTAAT CTGTAATTGC TTGTTAATCA ATAAACCGGT TGATTCGTTT
                    vp1-3 stop        PolyA signal
```

FIG. 1AAAM

```
                 4501                                                      4550
     42_2        CAGTTGAACT TTGGTCTC.T GCGAAGGGCG AATTC..... ...........
     42_8        CAGTTGAACT TTGGTCTC.T GCGAAGGGCG AATTC..... ...........
     42_15       CAGTTGAACT TTGGTCTC.T GCGAAGGGCG AATTC..... ...........
     42_5b       CAGTTGAACT TTGGTCTC.T GCGAAGGGCG AATTCGTTTA AACCTGCAGG
     42_1b       CAGTTGAACT TTGGTCTC.. ...AAGGGCG AATTC..... ...........
     42_13       CAGTTGAACT TTGGTCTC.T GCGAAGGGCG AATTC..... ...........
     42_3a       CAGTTGAACT TTGGTCTC.T GCGAAGGGCG AATTC..... ...........
     42_4        CAGTTGAACT TTGGTCTC.T GCGAAGGGCG AATTC..... ...........
     42_5a       CAGTTGAACT TTGGTCTC.T GCGAAGGGCG AATTC..... ...........
     42_10       CAGTTGAACT TTGGTC.... ...AAGGGCG AATTC..... ...........
     42_3b       CAGTTGAACT TTGGTCTC.T GCGAAGGGCG AATTC..... ...........
     42_11       CAGTTGAACT TTGGTCTC.T GCGAAGGGCG AATTC..... ...........
     42_6b       CAGTTGAACT TTGGTCTC.T GCGAAGGGCG AATTC..... ...........
     43_1        .......... .......... .......... .......... ...........
     43_5        CAGTTGAACT TTGGTCTC.T GCGAAGGGCG AATTCGTTTA AACCTGCAGG
     43_12       CAGTTGAACT TTGGTCTC.T GCGAAGGGCG AATTC..... ...........
     43_20       CAGTTGAACT TTGGTCTC.T GCGAAGGGCG AATTC..... ...........
     43_21       CAGTTGAACT TTGGTCTC.T GCGAAGGGCG AATTC..... ...........
     43_23       CAGTTGAACT TTGGTCTC.T GCGAAGGGCG AATTC..... ...........
     43_25       CAGTTGAACT TTGGTCTC.T GCGAAGGGCG AATTC..... ...........
     44_1        CAGTTGAACT TTGGTCTC.T GCGAAGGGCG AATTC..... ...........
     44_5        CAGTTGAACT TTGGTCTC.T GCGAAGGGCG AATTC..... ...........
     223_10      .......... .......... .......... .......... ...........
     223_2       .......... .......... .......... .......... ...........
     223_4       .......... .......... .......... .......... ...........
     223_5       .......... .......... .......... .......... ...........
     223_6       .......... .......... .......... .......... ...........
     223_7       .......... .......... .......... .......... ...........
     A3_4        CAGTTGAACT TTGGTCTC.T GCGAAGGGCG AATTCGC.GG CCGCTA.....
     A3_5        CAGTTGAACT TTGGTCTC.T GCGAAGGGCG AATTC..... ...........
     A3_7        CAGTTGAACT TTGGTCTC.T GCGAAGGGCG AATTC..... ...........
     A3_3        CAGTTGAACT TTGGTCTC.T GCGAAGGGCG AATTCGT.TT AAACCT.....
     42_12       CAGTTGAACT TTGGTCTC.T GCGAAGGGCG AATTC..... ...........
     AAV1        CAGTTGAACT TTGGTCTCCT GTCCTTCTTA TCTTATCGGT TACCATGGTT
     AAV2        CAGTTGAACT TTGGTCTC.T GCGTATTTCT ..TTCTT.AT CTAGTTTCCA
     AAV3        CAGTTGAACT TTGGCTCT.T GTGCACTTCT TTATCTTTAT CTTGTTTCCA
     AAV8        CAGTTGAACT TTGGTCTC.T GCG....... .......... ...........
     AAV9        CAGTTGAACT TTGGTCTC.T GCG....... .......... ...........
     AAV7        CAGTTGAACT TTGGTCTCCT GTGCTTCTTA TCTTATCGGT TTCCATAGCA
     44_2        CAGTTGAACT TTGGTCTC.T GCGAAGGGCG AATTC..... ...........
```

FIG. 1AAAN

```
         4551                                                      4600
  42_2    ..........  ..........  ..........  ..........  ..........
  42_8    ..........  ..........  ..........  ..........  ..........
 42_15    ..........  ..........  ..........  ..........  ..........
 42_5b    ACTAGTCCCT  TTAGTGAGGG  TTAATTCTGA  G.........  ..........
 42_1b    ..........  ..........  ..........  ..........  ..........
 42_13    ..........  ..........  ..........  ..........  ..........
 42_3a    ..........  ..........  ..........  ..........  ..........
  42_4    ..........  ..........  ..........  ..........  ..........
 42_5a    ..........  ..........  ..........  ..........  ..........
 42_10    ..........  ..........  ..........  ..........  ..........
 42_3b    ..........  ..........  ..........  ..........  ..........
 42_11    ..........  ..........  ..........  ..........  ..........
 42_6b    ..........  ..........  ..........  ..........  ..........
  43_1    ..........  ..........  ..........  ..........  ..........
  43_5    AC........  ..........  ..........  ..........  ..........
 43_12    ..........  ..........  ..........  ..........  ..........
 43_20    ..........  ..........  ..........  ..........  ..........
 43_21    ..........  ..........  ..........  ..........  ..........
 43_23    ..........  ..........  ..........  ..........  ..........
 43_25    ..........  ..........  ..........  ..........  ..........
  44_1    ..........  ..........  ..........  ..........  ..........
  44_5    ..........  ..........  ..........  ..........  ..........
 223_10   ..........  ..........  ..........  ..........  ..........
 223_2    ..........  ..........  ..........  ..........  ..........
 223_4    ..........  ..........  ..........  ..........  ..........
 223_5    ..........  ..........  ..........  ..........  ..........
 223_6    ..........  ..........  ..........  ..........  ..........
 223_7    ..........  ..........  ..........  ..........  ..........
  A3_4    ..........  ..........  ..........  ..........  ..........
  A3_5    ..........  ..........  ..........  ..........  ..........
  A3_7    ..........  ..........  ..........  ..........  ..........
  A3_3    ..........  ..........  ..........  ..........  ..........
 42_12    ..........  ..........  ..........  ..........  ..........
  AAV1    ATAGCTTACA  CATTAACTGC  TTGGTTGCGC  T.........  ..........
  AAV2    TGGCTAC...  GTAGATAAGT  AGC.......  ..........  ..........
  AAV3    TGGCTACTGC  GTAGATAAGC  AGCGGCCTGC  GGCGCTTGCG  CTTCGCGGTT
  AAV8    ..........  ..........  ..........  ..........  ..........
  AAV9    ..........  ..........  ..........  ..........  ..........
  AAV7    ACTGGTTACA  CATTAACTGC  TTGGGTGCGC  TTCACGATAA  GAACACTGAC
  44_2    ..........  ..........  ..........  ..........  ..........
```

FIG. 1AAAO

```
       4601                                                    4650
 42_2  ..........  ..........  ..........  ..........  ..........
 42_8  ..........  ..........  ..........  ..........  ..........
42_15  ..........  ..........  ..........  ..........  ..........
42_5b  ....CTTGGC  GTAATCATGG  GTCATAG...  ..........  ..........
42_1b  ..........  ..........  ..........  ..........  ..........
42_13  ..........  ..........  ..........  ..........  ..........
42_3a  ..........  ..........  ..........  ..........  ..........
 42_4  ..........  ..........  ..........  ..........  ..........
42_5a  ..........  ..........  ..........  ..........  ..........
42_10  ..........  ..........  ..........  ..........  ..........
42_3b  ..........  ..........  ..........  ..........  ..........
42_11  ..........  ..........  ..........  ..........  ..........
42_6b  ..........  ..........  ..........  ..........  ..........
 43_1  ..........  ..........  ..........  ..........  ..........
 43_5  ..........  ..........  ..........  ..........  ..........
43_12  ..........  ..........  ..........  ..........  ..........
43_20  ..........  ..........  ..........  ..........  ..........
43_21  ..........  ..........  ..........  ..........  ..........
43_23  ..........  ..........  ..........  ..........  ..........
43_25  ..........  ..........  ..........  ..........  ..........
 44_1  ..........  ..........  ..........  ..........  ..........
 44_5  ..........  ..........  ..........  ..........  ..........
223_10 ..........  ..........  ..........  ..........  ..........
223_2  ..........  ..........  ..........  ..........  ..........
223_4  ..........  ..........  ..........  ..........  ..........
223_5  ..........  ..........  ..........  ..........  ..........
223_6  ..........  ..........  ..........  ..........  ..........
223_7  ..........  ..........  ..........  ..........  ..........
 A3_4  ..........  ..........  ..........  ..........  ..........
 A3_5  ..........  ..........  ..........  ..........  ..........
 A3_7  ..........  ..........  ..........  ..........  ..........
 A3_3  ..........  ..........  ..........  ..........  ..........
42_12  ..........  ..........  ..........  ..........  ..........
 AAV1  ....TCGCGA  TAAAAGACTT  ACGTCATCGG  GTTACCCCTA  GTGATGGAGT
 AAV2  ....ATGGCG  GGTTAATCAT  TAACTACAAG  GA.ACCCCTA  GTGATGGAGT
 AAV3  TACAACTGCT  GGTTAATATT  TAACTCTCGC  CATACCTCTA  GTGATGGAGT
 AAV8  ..........  ..........  ..........  ..........  ..........
 AAV9  ..........  ..........  ..........  ..........  ..........
 AAV7  ..........  ..........  ..GTCACCGC  GGTACCCCTA  GTGATGGAGT
 44_2  ..........  ..........  ..........  ..........  ..........
```

FIG. 1AAAP

```
        4651                                                                      4700
  42_2   .......... .......... .......... .......... ..........
  42_8   .......... .......... .......... .......... ..........
 42_15   .......... .......... .......... .......... ..........
 42_5b   .......... .......... .......... .......... ..........
 42_1b   .......... .......... .......... .......... ..........
 42_13   .......... .......... .......... .......... ..........
 42_3a   .......... .......... .......... .......... ..........
  42_4   .......... .......... .......... .......... ..........
 42_5a   .......... .......... .......... .......... ..........
 42_10   .......... .......... .......... .......... ..........
 42_3b   .......... .......... .......... .......... ..........
 42_11   .......... .......... .......... .......... ..........
 42_6b   .......... .......... .......... .......... ..........
  43_1   .......... .......... .......... .......... ..........
  43_5   .......... .......... .......... .......... ..........
 43_12   .......... .......... .......... .......... ..........
 43_20   .......... .......... .......... .......... ..........
 43_21   .......... .......... .......... .......... ..........
 43_23   .......... .......... .......... .......... ..........
 43_25   .......... .......... .......... .......... ..........
  44_1   .......... .......... .......... .......... ..........
  44_5   .......... .......... .......... .......... ..........
223_10   .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   .......... .......... .......... .......... ..........
  A3_5   .......... .......... .......... .......... ..........
  A3_7   .......... .......... .......... .......... ..........
  A3_3   .......... .......... .......... .......... ..........
 42_12   .......... .......... .......... .......... ..........
  AAV1   TGCCCACTCC CTCTCTGCGC GCTCGCTCGC TCGGTGGGGC CTGCGGACCA
  AAV2   TGGCCACTCC CTCTCTGCGC GCTCGCTCGC TCACTGAGGC CGGGCGACCA
  AAV3   TGGCCACTCC CTCTATGCGC ACTCGCTCGC TCGGTGGGGC CTGGCGACCA
  AAV8   .......... .......... .......... .......... ..........
  AAV9   .......... .......... .......... .......... ..........
  AAV7   TGGCCACTCC CTCTATGCGC GCTCGCTCGC TCGGTGGGGC CTGCGGACCA
  44_2   .......... .......... .......... .......... ..........
```

FIG. 1AAAQ

```
        4701                                                                      4750
 42_2   ..........  ..........  ..........  ..........  ..........
 42_8   ..........  ..........  ..........  ..........  ..........
 42_15  ..........  ..........  ..........  ..........  ..........
 42_5b  ..........  ..........  ..........  ..........  ..........
 42_1b  ..........  ..........  ..........  ..........  ..........
 42_13  ..........  ..........  ..........  ..........  ..........
 42_3a  ..........  ..........  ..........  ..........  ..........
 42_4   ..........  ..........  ..........  ..........  ..........
 42_5a  ..........  ..........  ..........  ..........  ..........
 42_10  ..........  ..........  ..........  ..........  ..........
 42_3b  ..........  ..........  ..........  ..........  ..........
 42_11  ..........  ..........  ..........  ..........  ..........
 42_6b  ..........  ..........  ..........  ..........  ..........
 43_1   ..........  ..........  ..........  ..........  ..........
 43_5   ..........  ..........  ..........  ..........  ..........
 43_12  ..........  ..........  ..........  ..........  ..........
 43_20  ..........  ..........  ..........  ..........  ..........
 43_21  ..........  ..........  ..........  ..........  ..........
 43_23  ..........  ..........  ..........  ..........  ..........
 43_25  ..........  ..........  ..........  ..........  ..........
 44_1   ..........  ..........  ..........  ..........  ..........
 44_5   ..........  ..........  ..........  ..........  ..........
 223_10 ..........  ..........  ..........  ..........  ..........
 223_2  ..........  ..........  ..........  ..........  ..........
 223_4  ..........  ..........  ..........  ..........  ..........
 223_5  ..........  ..........  ..........  ..........  ..........
 223_6  ..........  ..........  ..........  ..........  ..........
 223_7  ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
 42_12  ..........  ..........  ..........  ..........  ..........
 AAV1   AAGGTCCGCA  GACGGCAGAG  CTCTGCTCTG  CCGGCCCCAC  CGAGCGAGCG
 AAV2   AAGGTCGCCC  GACGCCCGGG  CTTTGCCCGG  GCGGCCTCAG  TGAGCGAGCG
 AAV3   AAGGTCGCCA  GACGGACGTG  CTTTGCACGT  CCGGCCCCAC  CGAGCGAGCG
 AAV8   ..........  ..........  ..........  ..........  ..........
 AAV9   ..........  ..........  ..........  ..........  ..........
 AAV7   AAGGTCCGCA  GACGGCAGAG  CTCTGCTCTG  CCGGCCCCAC  CGAGCGAGCG
 44_2   ..........  ..........  ..........  ..........  ..........
```

FIG. 1AAAR

```
            4751                          4774
  42_2      ..........   ..........  ....
  42_8      ..........   ..........  ....
  42_15     ..........   ..........  ....
  42_5b     ..........   ..........  ....
  42_1b     ..........   ..........  ....
  42_13     ..........   ..........  ....
  42_3a     ..........   ..........  ....
  42_4      ..........   ..........  ....
  42_5a     ..........   ..........  ....
  42_10     ..........   ..........  ....
  42_3b     ..........   ..........  ....
  42_11     ..........   ..........  ....
  42_6b     ..........   ..........  ....
  43_1      ..........   ..........  ....
  43_5      ..........   ..........  ....
  43_12     ..........   ..........  ....
  43_20     ..........   ..........  ....
  43_21     ..........   ..........  ....
  43_23     ..........   ..........  ....
  43_25     ..........   ..........  ....
  44_1      ..........   ..........  ....
  44_5      ..........   ..........  ....
  223_10    ..........   ..........  ....
  223_2     ..........   ..........  ....
  223_4     ..........   ..........  ....
  223_5     ..........   ..........  ....
  223_6     ..........   ..........  ....
  223_7     ..........   ..........  ....
  A3_4      ..........   ..........  ....
  A3_5      ..........   ..........  ....
  A3_7      ..........   ..........  ....
  A3_3      ..........   ..........  ....
  42_12     ..........   ..........  ....
  AAV1      AGCGCGCAGA   GAGGGAGTGG  GCAA
  AAV2      AGCGCGCAGA   GAGGGAGTGG  CCAA
  AAV3      AGTGCGCATA   GAGGGAGTGG  CCAA
  AAV8      ..........   ..........  ....
  AAV9      ..........   ..........  ....
  AAV7      AGCGCGCATA   GAGGGAGTGG  CCAA
  44_2      ..........   ..........  ....
```

```
                        10        20        30        40        50        60
                ....|....|....|....|....|....|....|....|....|....|....|....|
C1\VP1          MAADGYLPDWLEDNLSEGIREWWDLKPGAPKPKANQQKQDDGRGLVLPGYKYLGPFNGLD
C2\VP1          MAADGYLPDWLEDNLSEGIREWWDLKPGAPKLKANQQKQDDGRGLVLPGYKYLGPFEGLD
C5\VP1@2        MAADGYLPDWLEDNLSEGIREWWDLKPGAPKPKANQQKQDDGRGLVLPGYEYLGPFNGLD
AAV4\VP1        -MTDGYLPDWLEDNLSEGVREWWALQPGAPKPKANQQHQDNARGLVLPGYKYLGPGNGLD
AAV1            MAADGYLPDWLEDNLSEGIREWWDLKPGAPKPKANQQKQDDGRGLVLPGYKYLGPFNGLD
AAV6\VP1        MAADGYLPDWLEDNLSEGIREWWDLKPGAPKPKANQQKQDDGRGLVLPGYKYLGPFNGLD
A3_3            MAADGYLPDWLEDTLSEGIRQWWKLKPGPPPPKPNQQHRDDSRGLVLPGYKYLGPFNGLD
A3_7            MAADGYLPDWLEDTLSEGIRQWWKLKPGPPPPKPNQQHRDDSRGLVLPGYKYLGPFNGLD
A3_4            MAADGYLPDWLEDTLSEGIRQWWKLKPGPPPPKPNQQHRDDSRGLVLPGYKYLGPFNGLD
A3_5            MAADGYLPDWLEDTLSEGIRQWWKLKPGPPPPKPNQQHRDDSRGLVLPGYKYLGPFNGLD
AAV2            MAADGYLPDWLEDTLSEGIRQWWKLKPGPPPPKPAERHKDDSRGLVLPGYKYLGPFNGLD
AAV3            MAADGYLPDWLEDNLSEGIREWWALKPGVPQPKANQQHQDNRRGLVLPGYKYLGPGNGLD
13.3b\VP1       MAADGYLPDWLEDNLSEGIREWWDLKPGAPKPKANQQKQDNGRGLVLPGYKYLGPFNGLD
AAV7            MAADGYLPDWLEDNLSEGIREWWDLKPGAPKPKANQQKQDNGRGLVLPGYKYLGPFNGLD
223_4           ------------------------------------------------------------
223_5           ------------------------------------------------------------
223_10          ------------------------------------------------------------
223_2           ------------------------------------------------------------
223_7           ------------------------------------------------------------
223_6           ------------------------------------------------------------
44_1            MAADGYLPDWLEDNLSEGIREWWDLKPGAPKPKANQQKQDDGRGLVLPGYKYLGPFNGLD
44_5            MAADGYLPDWLEDNLSEGIREWWDLKPGAPKPKANQQKQDDGRGLVLPGYKYLGPFNGLD
44_2            MAADGYLPDWLEDNLSEGIREWWDLKPGAPKPKANQQKQDDGRGLVLPGYKYLGPFNGLD
29.3\VP1        MAADGYLPDWLEDNLSEGIREWWALKPGAPKPKANQQKQDDGRGLVLPGYKYLGPFNGLD
29.5\VP1        MAADGYLPDWLEDNLSEGIREWWALKPGAPKPKANQQKQDDGRGLVLPGYKYLGPFNGLD
42_15           MAADGYLPDWLEDNLSEGIREWWDLKPGAPKPKANQQKQDDGRGLVLPGYKYLGPFNGLD
42_8            MAADGYLPDWLEDNLSEGIREWWDLKPGAPKPKANQQKQDDGRGLVLPGYKYLGPFNGLD
42_13           MAADGYLPDWLEDNLSEGIREWWDLKPGAPKPKANQQKQDDGRGLVLPGYKYLGPFNGLD
42_3A           MAADGHLPDWLEDNLSEGIREWWDLKPGAPKPKANQQKQDDGRGLVLPGYKYLGPFNGLD
42_4            MAADGYLPDWLEDNLSEGIREWWDLKPGAPKPKANQQKQDDGRGLVLPGYKYLGPFNGLD
42_5A           MAADGYLPDWLEDNLSEGIREWWDLKPGAPKPKANQQKQDDGRGLVLPGYKYLGPFNGLD
42_1B           MAADGYLPDWLEDNLSEGIREWWDLRPGAPKPKANQQKQDDGRGLVLPGYKYLGPFNGLD
42_5B           MAADGYLPDWLEDNLSEGIREWWDLKPGAPKPKANQQKQDDGRGLVLPGYKYLGPFNGLD
43_1            MAADGYLPDWLEDNLSEGIREWWDLKPGAPKPKANQQKQDDGRGLVLPGYKYLGPFNGLD
43_12           MAADGYLPDWLEDNLSEGIREWWDLKPGAPKPKANQQKQDDGRGLVLPGYKYLGPFNGLD
43_5            MAADGYLPDWLEDNLSEGIREWWDLKPGAPKPKANQQKQDDGRGLVLPGYKYLGPFNGLD
AAV8            MAADGYLPDWLEDNLSEGIREWWALKPGAPKPKANQQKQDDGRGLVLPGYKYLGPFNGLD
43_21           MAADGYLPDWLEDNLSEGIREWWDLKPGAPKPKANQQKQDDGRGLVLPGYKYLGPFNGLD
43_25           MAADGYLPDWLEDNLSEGIREWWDLKPGAPKPKANQQKQDDGRGLVLPGYKYLGPFNGLD
43_23           MAADGYLPDWLEDNLSEGIREWWDLKPGAPKPKANQQKQDDGRGLVLPGYKYLGPFNGLD
43_20           MAADGYLPDWLEDNLSEGIREWWDLKPGAPKPKANQQKQDDGRGLVLPGYKYLGPFNGLD
AAV_9           MAADGYLPDWLEDNLSEGIREWWDLKPGAPKPKANQQKQDDGRGLVLPGYKYLGPFNGLD
24.1            MAADGYLPDWLEDNLSEGIREWWDLKPGAPKPKANQQKQDDGRGLVLPGYKYLRPFNGLD
42.2REAL        MAADGYLPDWLEDNLSEGIREWWDLKPGAPKPKANQQKQDDGRGLVLPGYKYLGPFNGLD
7.2\VP1         MAADGYLPDWLEGNLSEGIREWWDLKPGAPKPKANQQKQDDGRGLVLPGYRYLGPFNGLD
27.3\VP1        MAADGYLPDWLEDNLSEGIREWWDLKPGAPKPKANQQKQDDGRGLVLPGYKYLGPFNGLD
16.3\VP1        MAADGYLPDWLEDNLSEGIREWWDLKPGAPKPKANQQKQDDGRGLVLPGYKYLGPFNGLD
42_10           MAADGYLPDWLEDNLSEGIREWWDLKPGAPKPKANQQKQDDGRGLVLPGYKYLGPFNGLD
42_3B           MAADGYLPDWLEDTLSEGIREWWDLKPGAPKPKANQQKQDDGRGLVLPGYKYLGPFNGLD
42_11           MAADGYLPDWLEDTLSEGIREWWDLKPGAPKPKANQQKQDDGRGLVLPGYKYLGPFNGLD
F1\VP1          MAADGYLPDWLEDNLSEGIREWWDLKPGAPKPKANQQKQDDGRGLVLPGYKYLGPFNGLD
F5\VP1@3        MAADGYLPDWLEDNLSEGIREWWDLKPGAPKPKANQQKQDDGRGLVLPGYKYLGPFNGLD
F3\VP1          MAADGYLPDWLEDNLSEGIREWWDLKPGAPKPKANQQKQDDGRGLVLPGYKYLGPFNGLD
42_6B           MAADGYLPDWLEDNLSEGIREWWDLKPGAPKPKANQQKQDDGRGLVLPGYKYLGPFNGLD
42_12           MAADGYLPDWLEDNLSEGIREWWDLKPGAPKPKANQQKQDDGRGLVLPGYKYLGPFNGLD
AAV5\CAP        MSFVDHPPDWLEE-VGEGLREFLGLEAGPPKPKPNQQHQDQARGLVLPGYNYLGPGNGLD
```

FIG. 2A

```
                       70        80        90       100       110       120
                ....|....|....|....|....|....|....|....|....|....|....|....|
C1\VP1          KGEPVNAADAAALEHDKAYDQQLKAGDNPYLRYNHADAEFQERLQEDTSFGGNLGRAVFQ
C2\VP1          KGEPVNAADAAALEHDKAYDQQLKAGDNPYLRYNHADAEFQERLQEDTSFGGNLGRAVFQ
C5\VP1@2        KGEPVNAADAAALEHDKAYDQQLKAGDNPYLRYNHADAEFQERLQEDTSFGGNLGRAVFQ
AAV4\VP1        KGEPVNAADAAALEHDKAYDQQLKAGDNPYLKYNHADAEFQQRLQGDTSFGGNLGRAVFQ
AAV1            KGEPVNAADAAALEHDKAYDQQLKAGDNPYLRYNHADAEFQERLQEDTSFGGNLGRAVFQ
AAV6\VP1        KGEPVNAADAAALEHDKAYDQQLKAGDNPYLRYNHADAEFQERLQEDTSFGGNLGRAVFQ
A3_3            KGEPVNEADAAALEHDKAYDHQLKQGDNPYLKYNHADAEFQERLQEDTSFGGNLGRAVFQ
A3_7            KGEPVNEADAAALEHDKAYDHQLKQGDNPYLKYNHADAEFQERLQEDTSFGGNLGRAVFQ
A3_4            KGEPVNEADAAALEHDKAYDHQLKQGDNPYLKYNHADAEFQERLQEDTSFGGNLGRAVFQ
A3_5            KGEPVNEADAAALEHDKAYDHQLKQGDNPYLKYNHADAEFQERLQEDTSFGGNLGRAVFQ
AAV2            KGEPVNEADAAALEHDKAYDRQLDSGDNPYLKYNHADAEFQERLKEDTSFGGNLGRAVFQ
AAV3            KGEPVNEADAAALEHDKAYDQQLKAGDNPYLKYNHADAEFQERLQEDTSFGGNLGRAVFQ
13.3b\VP1       KGEPVNAADAAALEHDKAYDQQLNAGDNPYLRYNHADAEFQERLQEDTSFGGNLGRAVFQ
AAV7            KGEPVNAADAAALEHDKAYDQQLKAGDNPYLRYNHADAEFQERLQEDTSFGGNLGRAVFQ
223_4           ------------------KAYDQQLKAGDNPYLRYNHADAEFQERLQEDTSFGGNLGRAVFQ
223_5           ------------------KAYDQQLKAGDNPYLRYNHADAEFQERLQEDTSFGGNLGRAVFQ
223_10          ------------------KAYDQQLKAGDNPYLRYNHADAEFQERLQEDTSFGGNLGRAVFQ
223_2           ------------------KAYDQQLKAGDNPYLRYNHADAEFQECLQEDTSFGGNLGRAVFQ
223_7           ------------------KAYDQQLKAGDNPYLRYNHADAEFQERLQEDTSFGGNLGRAVFQ
223_6           ------------------KAYDQQLKAGDNPYLRYNHADAEFQERLQEDTSFGGNLGRAVFQ
44_1            KGEPVNAADAAALEHDKAYDQQLKAGDNPYLRYNHADAEFQERLQEDTSFGGNLGRAVFQ
44_5            KGEPVNAADAAALEHDKAYDQQLKAGDNPYLRYNHADAEFQERLQEDTSFGGNLGRAVFQ
44_2            KGEPVNAADAAALEHDKAYDQQLKAGDNPYLRYNHADAEFQERLQEDTSFGGNLGRAVFQ
29.3\VP1        KGEPVNAADAAALEHDKAYDQQLKAGDNPYLRYNHADAEFQERLQEDTSFGGNLGRAVFQ
29.5\VP1        KGEPVNAADAAALEHDKAYDQQLKAGDNPYLRYNHADAEFQERLQEDTSFGGNLGRAVFQ
42_15           KGEPVNAADAAALEHDKAYDQQLKAGDNPYLRYNHADAEFQERLQEDTSFGGNLGRAVFQ
42_8            KGEPVNAADAAALEHDKAYDQQLKAGDNPYLRYNHADAEFQERLQEDTSFGGNLGRAVFQ
42_13           KGEPVNAADAAALEHDKAYDQQLKAGDNPYLRYNHADAEFQERLQEDTSFGGNLGRAVFQ
42_3A           KGEPVNAADAAALEHDKAYDQQLKAGDNPYLRYNHADAEFQERLQEDTSFGGNLGRAVFQ
42_4            KGEPVNEADAAALEHDKAYDKQLEQGDNPYLKYNHADAEFQERLQEDTSFGGNLGRAVFQ
42_5A           KGEPVNEADAAALEHDKAYDKQLEQGDNPYLKYNHADAEFQERLQEDTSFGGNLGRAVFR
42_1B           KGEPVNEADAAALEHDKAYDKQLEQGDNPYLKYNHADAEFQERLQEDTSFGGNLGRAVFQ
42_5B           KGEPVNEADAAALEHDKAYDKQLEQGDNPYLKYNHADAEFQERLQEDTSFGGNLGRAVFQ
43_1            KGEPVNAADAAALEHDKAYDQQLKAGDNPYLRYNHADAEFQERLQEDTSFGGNLGRAVFQ
43_12           KGEPVNAADAAALEHDKAYDQQLKAGDNPYLRYNHADAEFQERLQEDTSFGGNLGRAVFQ
43_5            KGEPVNAADAAALEHDKAYDQQLKAGDNPYLRYNHADAEFQERLQEDTSFGGNLGRAVFQ
AAV8            KGEPVNAADAAALEHDKAYDQQLQAGDNPYLRYNHADAEFQERLQEDTSFGGNLGRAVFQ
43_21           KGEPVNAADAAALEHDKAYDQQLKAGDNPYLRYNHADAEFQERLQEDTSFGGNLGRAVFQ
43_25           KGEPVNAADAAALEHDKAYDQQLKAGDNPYLRYNHADAEFQERLQEDTSFGGNLGRAVFQ
43_23           KGEPVNAADAAALEHDKAYDQQLKAGDNPYLRYNHADAEFQERLQEDTSFGGNLGRAVFQ
43_20           KGEPVNAADAAALEHDKAYDQQLKAGDNPYLRYNHADAEFQERLQEDTSFGGNLGRAVFQ
AAV_9           KGEPVNAADAAALEHDKAYDQQLKAGDNPYLRYNHADAEFQERLQEDTSFGGNLGRAVFQ
24.1            KGEPVNEADAAALEHDKAYDKQLEQGDNPYLKYNHADAEFQERLQEDTSFGGNLGRAVFQ
42.2REAL        KGEPVNEADAAALEHDKAYDKQLEQGDNPYLKYNHADAEFQERLQEDTSFGGNLGRAVFQ
7.2\VP1         KGEPVNEADAAALEHDKAYDKQLEQGDNPYLKYNHADAEFQERLQEDTSFGGNLGRAVFQ
27.3\VP1        KGEPVNEADAAALEHDKAYDKQLEQGDNPYLKYNHADAEFQERLQEDTSFGGNLGRAVFQ
16.3\VP1        KGEPVNEADAAALEHDKAYDKQLEQGDNPYLKYNHADAEFQERLQEDTSFGGNLGRAVFQ
42_10           KGEPVNAADAAALEHDKAYDQQLKAGDNPYLRYNHADAEFQERLQEDTSFGGNLGRAVFQ
42_3B           KGEPVNEADAAALEHDKAYDKQLEQGDNPYLKYNHADAEFQERLQEDTSFGGNLGRAVFQ
42_11           KGEPVNAADAAALEHDKAYDQQLKAGDNPYLRYNHADAEFQERLQEDTSFGGNLGRAVFQ
F1\VP1          KGEPVNAADAAALEHDKAYDQQLKAGDNPYLRYNHADAEFQERLQEDTSFGGNLGRAVFQ
F5\VP1@3        KGEPVNAADAAALEHDKAYDQQLKAGDNPYLRYNHADAEFQERLQEDTSFGGNLGRAVFQ
F3\VP1          KGEPVNAADAAALEHDKAYDQQLKAGDNPYLRYNHADAEFQERLQEDTSFGGNLGRAVFQ
42_6B           KGEPVNEADAAALEHDKAYDKQLEQGDNPYLKYNHADAEFQERLQEDTSFGGNLGRAVFQ
42_12           KGEPVNEADAAALEHDKAYDKQLEQGDNPYLKYNHADAEFQERLQEDTSFGGNLGRAVFQ
AAV5\CAP        RGEPVNRADEVAREHDISYNEQLEAGDNPYLKYNHADAEFQEKLADDTSFGGNLGKAVFQ
```

FIG. 2B

```
                       130       140       150       160       170       180
                  ....|....|....|....|....|....|....|....|....|....|....|....|
    C1\VP1        AKKRVLEPLGLVEEGAKTAPGKKRP-LESPQ-EPDSSSGIGKKGKQPAKKRLNFEEDTGA
    C2\VP1        AKKRVLEPLGLVEEGAKTAPGKKRP-LESPQ-EPDSSSGIGKKGKQPAKKRLNFEEDTGA
    C5\VP1@2      AKKRVLEPLGLVEEGAKTAPGKKRP-LESPQ-EPDSSSGIGKKGKQPAKKRLNFEEDTGA
    AAV4\VP1      AKKRVLEPLGLVEQAGETAPGKKRPLIESPQ-QPDSSTGIGKKGKQPAKKKLVFEDETGA
    AAV1          AKKRVLEPLGLVEEGAKTAPGKKRPVEQSPQ-EPDSSSGIGKTGQQPAKKRLNFGQTGDS
    AAV6\VP1      AKKRVLEPFGLVEEGAKTAPGKKRPVEQSPQ-EPDSSSGIGKTGQQPAKKRLNFGQTGDS
    A3_3          AKKRVLEPLGLVEEAVKTAPGKKRPIEQSPA-EPDSSSGIGKSGQQPAKKRLNFGQTGDT
    A3_7          AKKRVLEPLGLVEEAVKTAPGKKRPIEQSPA-EPDSSSGIGKSGQQPAKKRLNFGQTGDT
    A3_4          AKKRVLEPLGLVEEAVKTAPGKKRPIEQSPA-EPDSSSGIGESGQQPAKKRLNFGQTGDT
    A3_5          AKKRVLEPLGLVEEAVKTAPGKKRPIEQSPA-EPDSSSGIGKSGQQPAKKRLNFGQTGDT
    AAV2          AKKRVLEPLGLVEEPVKTAPGKKKRPVEHSPV-EPDSSSGTGKAGQQPARKRLNFGQTGDA
    AAV3          AKKRILEPLGLVEEAAKTAPGKKGAVDQSPQ-EPDSSSGVGKSGKQPARKRLNFGQTGDS
    13.3b\VP1     AKKRVLEPLGLVEEGAKTAPAKKRPVEPSPQRSPDSSTGIGKKGQQPARKRLNFGQTGDS
    AAV7          AKKRVLEPLGLVEEGAKTAPAKKRPVEPSPQRSPDSSTGIGKKGQQPARKRLNFGQTGDS
    223_4         AKKRVLEPLGLVETPAKTAPGKKRPVD-----SPDSTSGIGKKGQQPAKKRLNFGQTGDS
    223_5         AKKRVLEPLGLVETPAKTAPGKKRPVD-----SPDSTSGIGKKGQQPAKKRLNFGQTGDS
    223_10        AKKRVLEPLGLVETPAKTAPGKKRPVD-----SPDSTSGIGKKGQQPAKKRLNFGQTGDS
    223_2         AKKRVLEPLGLVETPAKTAPGKKRPVD-----SPDSTSGIGKKGQQPAKKRLNFGQTGDS
    223_7         AKKRVLEPLGLVETPAKTAPGKKRPVD-----SPDSTSGIGKKGQQPAKKRLNFGQTGDS
    223_6         AKKRVLEPLGLVETPAKTAPGKKRPVD-----SPDSTSGIGKKGQQPAKKRLNFGQTGDS
    44_1          AKKRVLEPLGLVEEGAKTAPGKKRPVEPSPQRSPDSSTGIGKKGQQPAKKRLNFGQTGDS
    44_5          AKKRVLEPLGLVEEGAKTAPGKKRPVEPSPQRSPDSSTGIGKKGQQPAKKRLNFGQTGDS
    44_2          AKKRVLEPLGLVEEGAKTAPGKKRPVEPSPQRSPDSSTGIGKKGQQPAKKRLNFGQTGDS
    29.3\VP1      AKKRVLEPLGLVEEGAKTAPGKKRPVEPSPQRSPDSTTGIGKKGQQPAKKRLNFGQTGDS
    29.5\VP1      AKKRVLEPLGLVEEGAKTAPGKKRPVEPSPQRSPDSSTGIGKKGQQPAKKRLNFGQTGDS
    42_15         AKKRVLEPLGLVEEGAKTAPGKKRPVEPSPQRSPDSSTGIGKTGQQPAKKRLNFGQTGDS
    42_8          AKKRVLEPLGLVEEGAKTAPGKKRPVEPSPQRSPDSSTGIGKTGQQPAKKRLNFGQTGDS
    42_13         AKKRVLEPLGLVEEGAKTAPGKKRPIE-----SPDSSTGIGKKGQQPAKKKLNFGQTGDS
    42_3A         AKKRVLEPLGLVEEGAKTAPGKKRPIE-----SPDSSTGIGKKGQQPAKKKLNFGQTGDS
    42_4          AKKRVLEPLGLVEEGAKTAPGKKRPIE-----SPDSSTGIGKKGQQPAKKKLNFGQTGDS
    42_5A         AKKRVLEPLGLVEEGAKTAPGKKRPIE-----SPDSSTGIGKKGQQPAKKKLNFGQTGDS
    42_1B         AKKRVLEPLGLVEEGAKTAPGKKRPIE-----SPDSSTGIGKKGQQPAKKKLNFGQTGDS
    42_5B         AKKRVLEPLGLVEEGAKTAPGKKRPVEPSPQRSPDSSTGIGKTGQQPAKKRLNFGQTGDS
    43_1          AKKRVLEPLGLVEEGAKTAPGKKRPVEPSPQRSPDSSTGIGKKGHQPARKRLNFGQTGDS
    43_12         AKKRVLEPLGLVEEGAKTAPGKKRPVEPSPQRSPDSSTGIGKKGHQPARKRLNFGQTGDS
    43_5          AKKRVLEPLGLVEEGAKTAPGKKRPVEPSPQRSPDSSTGIGKKGHQPARKRLNFGQTGDS
    AAV8          AKKRVLEPLGLVEEGAKTAPGKKRPVEPSPQRSPDSSTGIGKKGQQPARKRLNFGQTGDS
    43_21         AKKRVLEPLGLVEEGAKTAPGKKRPVEQSPQ-EPDSSSGIGKTGQQPAKKRLNFGQTGDS
    43_25         AKKRVLEPLGLVEEGAKTAPGKKRPVEQSPQ-EPDSSSGIGKTGQQPAKKRLNFGQTGDS
    43_23         AKKRVLEPLGLVEEGAKTAPGKKRPVEQSPQ-EPDSSSGIGKTGQQPAKKRLNFGQTGDS
    43_20         AKKRVLEPLGLVEEGAKTAPGKKRLVEQSPQ-EPDSSSGIGKTGQQPAKKRLNFGQTGDS
    AAV_9         AKKRVLEPLGLVEEGAKTAPGKKRPVEQSPQ-EPDSSSGIGKSGQQPAKKRLNFGQTGDS
    24.1          AKKRVLEPLGLVEEVAKTAPGKKRPIE-----SPDSSTGIGKKGQQPAKKKLNFGQTGDS
    42.2REAL      AKKRVLEPLGLVEEGAKTAPGKKRPIE-----SPDSSTGIGKKGQQPAKKKLNFGQTGDS
    7.2\VP1       AKKRVLEPLGLVEEGAKTAPGKKRPIE-----SPDSSTGIGKNGQPPAKKKLNFGQTGDS
    27.3\VP1      AKKRVLEPLGLVEEGAKTASGKKRPIE-----SPDSSTGIGKKGQQPAKKKLNFGQTGDS
    16.3\VP1      AKKRVLEPLGLVEEGAKTAPGKKRPIE-----SPDSSTGIGKKGQQPAKKKLNFGQTGDS
    42_10         AKKRVLEPLGLVEEGAKTAPGKKRPIE-----SPDSSTGIGRKGQQPAKKKLVFGQTGDS
    42_3B         AKKRVLEPLGLVEEGAKTAPGKKRPIE-----SPDSSTGIGKKGQQPAKKKLNFGQTGDS
    42_11         AKKRVLEPLGLVEEGAKTAPGKKRPIE-----SPDSSTGIGKKGQQPAKKKLNFGQTGDS
    F1\VP1        AKKRVLEPLGLVEEGAKTAPGKKRPID-----SPDSSTGIGKKGQQPAKKKLNFGQTGDS
    F5\VP1@3      AKKRVLEPLGLVEEGAKTAPGKKRPID-----SPDSSTGIGKKGQQPAKKKLNFGQTGDS
    F3\VP1        AKKRVLEPLGLVEEGAKTAPGKKRPIG-----SPDSSTGIGKKGQQPAKKKLNFGQTGDS
    42_6B         AKKRVLEPLGLVEEGAKTAPGKKRPVEPSPQRSPDSSTGIGKTGQQPAKKRLNFGQTGDS
    42_12         AKKRVLEPLGLVEEGAKTAPGKKRPVEPSPQRSPDSSTGIGKTGQQPAKKRLNFGQTGDS
    AAV5\CAP      AKKRVLEPFGLVEEGAKTAPTGKR---------IDDHFPKRKKARTEEDSKP--STSSDA
```

FIG. 2C

```
                  190       200       210       220       230       240
             ....|....|....  ....|....|....|....|....|....|....|....|....
C1\VP1       GDGP----PEGSDTSAMS--SDIEMRAAPGGNAVDAGQGSDGVGNASGDWHCDSTWSEGK
C2\VP1       GDGP----PEGSDTSAMS--SDIEMRAAPGGNAVDAGQGSDGVGNASGDWHCDSTWSEGK
C5\VP1@2     GDGP----PEGSDTSAMS--SDIEMRAAPGGNAVDAGQGSDGVGNASGDWHCDSTWSEGK
AAV4\VP1     GDGP----PEGSTSGAMS---DDSEMRAAAGGAAVEGGQGADGVGNASGDWHCDSTWSEGH
AAV1         ESVPD-PQPLGEPPATPAAVGPTTMASGGGAPMADNNEGADGVGNASGNWHCDSTWLGDR
AAV6\VP1     ESVPD-PQPLGEPPATPAAVGPTTMASGGGAPMADNNEGADGVGNASGNWHCDSTWLGDR
A3_3         ESVPG-PQPIGEPPAAPSGVGSNTMASGGGAPMADNNEGADGVGNSSGNWHCDSTWMGDR
A3_7         ESVPD-PQPIGEPPAAPSGVGSNTMASGGGAPMADNNEGADGVGNSSGNWHCDSTWMGDR
A3_4         ESVPD-PQPIGEPPAAPSGVGSNTMASGGGAPMADDNEGADGVGNSSGNWHCDSTWMGDR
A3_5         ESVPD-PQPIGEPPAAPSGVGSNTMASGGGAPMADNNEGADGVGNSSGNWHCDSTWMGDR
AAV2         DSVPD-PQPLGQPPAAPSGLGTNTMATGSGAPMADNNEGADGVGNSSGNWHCDSTWMGDR
AAV3         ESVPD-PQPLGEPPAAPTSLGSNTMASGGGAPMADNNEGADGVGNSSGNWHCDSQWLGDR
13.3b\VP1    ESVPD-PQPLGEPPAAPSSVGSGTVAAGGGAPMADNNEGADGVGNASGNWHCDSTWLGDR
AAV7         ESVPD-PQPLGEPPAAPSSVGSGTVAAGGGAPMADNNEGADGVGNASGNWHCDSTWLGDR
223_4        EPVPD-PQPIGEPPAGPSGLGSGTMAAGGGAPMADNNEGADGVGNASGNWHCDSTRLGDR
223_5        EPVPD-PQPIGEPPAGPSGLGSGTMAAGGGAPMADNNEGADGVGNASGNWHCDSTRLGDR
223_10       ESVPD-PQPIGEPPAGPSGLGSGTMAAGGGAPMADNNEGADGVGNASGNWHCDSTWLGDR
223_2        ESVPD-PQPIGEPPAGPSGLGSGTMVAGGGAPMADNNEGADGVGNASGNWHCDSTWLGDR
223_7        ESVPD-PQPIGEPPAGPSGLGSGTMAAGGGAPMADNNEGADGVGNASGNWHCDSTWLGDR
223_6        ESVPD-PQPIGEPPAGPSGLGSGTMAAGGGAPMADNSEGADGVGNASGNWHCDSTWLGDR
44_1         ESVPD-PQPIGEPPAGPSGLGSGTMAAGGGAPMADNNEGADGVGSSSGNWHCDSTWLGDR
44_5         ESVPD-PQPIGEPPAGPSGLGSGTMAAGGGAPMADNNEGADGVGSSSGNWHCDSTWLGDR
44_2         ESVPD-PQPIGEPPAGPSGLGSGTMAAGGGAPMADNNEGADGVGSSSGNWHCDSTWLGDR
29.3\VP1     ESVPD-PQPIGEPPAGPSGLGSGTMAAGGGAPMADNNEGADGVGSSSGNWHCDSTWLGDR
29.5\VP1     ESVPD-PQPIGEPPAGPSGLGSGTMAAGGGAPMADNNEGADGVGSSSGNWHCDSTWLGDG
42_15        ESVPD-PQPIGEPPAGPSGLGSGTMAAGGGAPMADNNEGADGVGSSSGNWHCDSTWLGDR
42_8         ESVPD-PQPIGEPPAGPSGLGSGTMAAGGGAPMADNNEGADGVGSSSGNWHCDSTWLGDR
42_13        ESVPD-PQPIGEPPAGPSGLGSGTMAAGGGAPMADNNEGADGVGSSSGNWHCDSTWLGDR
42_3A        ESVPD-PQPIGEPPAGPSGLGSGTMAAGGGAPMADNNEGADGVGSSSGNWHCDSTWLGDR
42_4         ESVPD-PQPIGEPPAGPSGLGSGTMAAGGGAPMADNNEGADGVGNASGNWHCDSTWLGDR
42_5A        ESVPD-PQPLGEPPAAPSGLGSGTMAAGGGAPMADNNEGADGVGNASGNWHCDSTWLGDR
42_1B        ESVPD-PQPIGEPPAGPSGLGSGTMAAGGGAPMADNNEGADGVGSSSGNWHCDSTWLGDR
42_5B        ESVPD-PQPIGEPPAGPSGLGSGTMAAGGGAPMADNNEGADGVGSSSGNWHCDSTWLGDR
43_1         ESVPD-PQPIGEPPAGPSGLGSGTMAAGGGAPMADNNEGADGVGSSSGNWHCDSTWLGDR
43_12        ESVPD-PQPIGEPPAGPSGLGSGTMAAGGGAPMADNNEGADGVGSSSGNWHCDSTWLGDR
43_5         ESVPD-PQPIGEPPAGPSGLGSGTMAAGGGAPMADNNEGADGVGSSSGNWHCDSTWLGDR
AAV8         ESVPD-PQPLGEPPAAPSGVGPNTMAAGGGAPMADNNEGADGVGSSSGNWHCDSTWLGDR
43_21        ESVPD-PQPLGEPPAAPSGLGPNTMASGGGAPMADNNEGADGVGNSSGNWHCDSTWLGDR
43_25        ESVPD-PQPLGEPPAAPSGLGPNTMASGGGAPMADNNEGADGVGNSSGNWHCDSTWLGDR
43_23        ESVPD-PQPLGEPPAAPSGLGPNTMASGGGAPMADNNEGADGVGNSSGNWHCDSTWLGDR
43_20        ESVPD-PQPLGEPPAAPSGLGPNTMASGGGAPMADNNEGADGVGNSSGNWHCDSTWLGDR
AAV_9        ESVPD-PQPLGEPPEAPSGLGPNTMASGGGAPMADNNEGADGVGNSSGNWHCDSTWLGDR
24.1         ESVPD-PQPLGEPPAAPSGLGSGTMAAGGGAPMADNNEGADGVGNASGNWHCDSTWLGDR
42.2REAL     ESVPD-PQPLGEPPAAPSGLGSGTMAAGGGAPMADNNEGADGVGNASGNWHCDSTWLGDR
7.2\VP1      ESVPD-PQPLGEPPAAPSGLGSGTMAAGGGAPMADNNEGADGVGNASGNWHCDSTWLGDR
27.3\VP1     ESVPD-PQPLGEPPAAPSGLGSGTMAAGGGAPMADNNEGADGVGNASGNWHCDSTWLGDR
16.3\VP1     ESVPD-PQPLGEPPAAPSGLGSGTMAAGGGAPMADNNEGADGVGNASGNWHCDSTWLGDR
42_10        ESVPD-PQPIGEPPAGPSGLGSGTMAAGGGAPMADNNEGADGVGNASGNWHCDSTWLGDR
42_3B        ESVPD-PQPIGEPPAGPSGLGSGTMAAGGGAPMADNNEGADGVGNASGNWHCDSTWLGDR
42_11        ESVPD-PQPIGEPPAGPSGLGSGTMAAGGGAPMADNNEGADGVGNASGNWHCDSTWLGDR
F1\VP1       ESVPD-PQPLGEPPAAPSSVGSGTMAAGGGAPMADNNEGADGVGNASGNWHCDSTWLGDR
F5\VP1@3     ESVPD-PQPLGEPPAAPSSVGSGTMAAGGGAPTADNNEGADGVGNASGNWHCDSTWLGDR
F3\VP1       ESVPD-PQPLGEPPAAPSSVGSGTMAAGGGAPMADNNEGADGVGNASGNWHCDSTWLGDR
42_6B        ESVPD-PQPIGEPPAGPSGLGSGTMAAGGGAPMADNNEGADGVGSSSGNWHCDSTWLGDR
42_12        ESVPD-PQPIGEPPAGPSGLGSGTMAAGGGAPMADNNEGADGVGSSSGNWHCDSTWLGDR
AAV5\CAP     EAGPSGSQQLQIPAQPASSLGADTMSAGGGGPLGDNNQGADGVGNASGDWHCDSTWMGDR
```

FIG. 2D

```
                       250       260       270       280       290       300
                ....|....|....|....|....|....|....|....|....|....|....|....|
C1\VP1          VTTTSTRTWVLPTYNNHLYLRLG-----TTSNSNTYNGFSTPWGYFDFNRFHCHFSPRDW
C2\VP1          VTTTSTRTWVLPTYNNHLYLRLG-----TTSNSNTYNGFSTPWGYFDFNRFHCHFSPRDW
C5\VP1@2        VTTTSTRTWVLPTYNNHLYLRLG-----TTSNSNTYNGFSTPWGYFDFNRFHCHFSPRDW
AAV4\VP1        VTTTSTRTWVLPTYNNHLYKRLG-----ESLQSNTYNGFSTPWGYFDFNRFHCHFSPRDW
AAV1            VITTSTRTWALPTYNNHLYKQIS-SASTGASNDNHYFGYSTPWGYFDFNRFHCHFSPRDW
AAV6\VP1        VITTSTRTWALPTYNNHLYKQIS-SASTGASNDNHYFGYSTPWGYFDFNRFHCHFSPRDW
A3_3            VITTSTRTWALPTYNNHLYKQIS--SESGATNDNHYFGYSTPWGYFDFNRFHCHFSPRDW
A3_7            VITTSTRTWALPTYNNRLYKQIS--SESGATNDNHYFGYSTPWGYFDFNRFHCHFSPRDW
A3_4            VITTSTRTWALPTYNNHLYKQIS--SESGATNDNHYFGYSTPWGYFDFNRFHCHFSPRDW
A3_5            VITTSTRTWALPTYNNHLYKQIS--SESGATNDNHYFGYSTPWGYFDFNRFHCHFSPRDW
AAV2            VITTSTRTWALPTYNNHLYKQIS--SQSGASNDNHYFGYSTPWGYFDFNRFHCHFSPRDW
AAV3            VITTSTRTWALPTYNNHLYKQIS--SQSGASNDNHYFGYSTPWGYFDFNRFHCHFSPRDW
13.3b\VP1       VITTSTRTWALPTYNNHLYEQIS-SETAGSTNDNTYFGYSTPWGYFDFNRFHCHFSPRDW
AAV7            VITTSTRTWALPTYNNHLYKQIS-SETAGSTNDNTYFGYSTPWGYFDFNRFHCHFSPRDW
223_4           VITTSTRTWALPTYNNHLYKQIS-SQSAGSTNDNVYFGYSTPWGYFDFNRFHCHFSPRDW
223_5           VITTSTRTWALPTYNNHLYKQIS-SQSAGSTNDNVYFGYSTPWGYFDFNRFHCHFSPRDW
223_10          VITTSTRTWALPTYNNHLYKQIS-SQSAGSTNDNVYFGYSTPWGYFDFNRFHCHFSPRDW
223_2           VITTSTRTWALPTYNNHLYKQIS-SQSAGSTNDNVYFGYSTPWGYFDFNRFHCHFSPRDW
223_7           VITTSTRTWALPTYNNHLYKQIS-SQSAGSTNDNVYFGYSTPWGYFDFNRFHCHFSPRDW
223_6           VITTSTRTWALPTYNNHLYKQIS-SQSAGSTNDNVYFGYSTPWGYFDFNRFHCHFSPRDW
44_1            VITTSTRTWALPTYNNHLYKQISNGTSGGSTNDNTYFGYSTPWGYFDFNRFHCHFSPRDW
44_5            VITTSTRTWALPTYNNHLYKQISNGTSGGSTNDNTYFGYSTPWGYFDFNRFHCHFSPRDW
44_2            VITTSTRTWALPTYNNHLYKQISNGTSGGSTNDNTYFGYSTPWGYFDFNRFHCHFSPRDW
29.3\VP1        VITTSTRTWALPTYNNHLYKQISNGTSGGSTNDNTYFGYSTPWGYFDFNRFHCHFSPRDW
29.5\VP1        VITTSTRTWALPTYNNHLYKQISNGTSGGSTNDNTYFGYSTPWGYFDFNRFHCHFSPRDW
42_15           VITTSTRTWALPTYNNHLYKQISNGTSGGSTNDNTYFGYSTPWGYFDFNRFHCHFSPRDW
42_8            VITTSTRTWALPTYNNHLYKQISNGTSGGSTNDNTYFGYSTPWGYFDFNRFHCHFSPRDW
42_13           VITTSTRTWALPTYNNHLYKQISNGTSGGSTNDNTYFGYSTPWGYFDFNRFHCHFSPRDW
42_3A           VITTSTRTWALPTYNNHLYKQISNGTSGGSTNDNTYFGYSTPWGYFDFNRFHCHFSPRDW
42_4            VITTSTRTWALPTYNNHLYKQIS--SQSGATNDNHFFGYSTPWGYFDFNRFHCHFSSRDW
42_5A           VITTSTRTWALPTYNNHLYKQIS--SQSGATNDNHFFGYSTPWGYFDFNRFHCHFSPRDW
42_1B           VITTSTRTWALPTYNNHLYKQISNGTSGGSTNDNTYFGYSTPWGYFDFNRFHCHFSPRDW
42_5B           VITTSTRTWALPTYNNHLYKQISNGTSGGSTNDNTYFGYSTPWGYFDFNRFHCHFSPRDW
43_1            VITTSTRTWALPTYNNHLYKQISNGTSGGSTNDNTYFGYSTPWGYFDFNRFHCHFSPRDW
43_12           VITTSTRTWALPTYNNHLYKQISNGTSGGSTNDNTYFGYSTPWGYFDFNRFHCHFSPRDW
43_5            VITTSTRTWALPTYNNHLYKQISNGTSGGSTNDNTYFGYSTPWGYFDFNRFHCHFSPRDW
AAV8            VITTSTRTWALPTYNNHLYKQISNGTSGGATNDNTYFGYSTPWGYFDFNRFHCHFSPRDW
43_21           VITTSTRTWALPTYNNHLYKQISNGTSGGSTNDNTYFGYSTPWGYFDFNRFHCHFSPRDW
43_25           VITTSTRTWALPTYNNHLYKQISNGTSGGSTNDNTYFGYSTPWGYFDFNRFHCHFSPRDW
43_23           VITTSTRTWALPTYNNHLYKQISNGTSGGSTNDNTYFGYSTPWGYFDFNRFHCHFSPRDW
43_20           VITTSTRTWALPTYNNHLYKQISNGTSGGSTNDNTYFGYSTPWGYFDFNRFHCHFSPRDW
AAV_9           VITTSTRTWALPTYNNHLYKQISNGTSGGSTNDNTYFGYSTPWGYFDFNRFHCHFSPRDW
24.1            VITTSTRTWALPTYNNHLYKQIS-SQS-GATNDNHFFGYSTPWGYFDFNRFHCHFSPRDW
42.2REAL        VITTSTRTWALPTYNNHLYKQIS-SQS-GATNDNHFFGYSTPWGYFDFNRFHCHFSPRDW
7.2\VP1         VITTSTRTWALPTYNNHLYKQIS-SQS-GATNDNHFFGYSTPWGYFDFNRFHCHFSPRDW
27.3\VP1        VITTSTRTWALPTYNNHLYKQIS-SQS-GATNDNHFFGYSTPWGYFDFNRFHCHFSPRDW
16.3\VP1        VITTSTRTWALPTYNNHLYKQIS-SQS-GATNDNHFFGYSTPWGYFDFNRFHCHFSPRDW
42_10           VITTSTRTWALPTYNNHLYKQIS-SQS-GATNDNHFFGYSTPWGYFDFNRFHCHFSPRDW
42_3B           VITTSTRTWALPTYNNHLYKQIS-SQS-GATNDNHFFGYSTPWGYFDFNRFHCHFSPRDW
42_11           VITTSTRTWALPTYNNHLYKQIS-SQS-GATNDNHFFGYSTPWGYFDFNRFHCHFSPRDW
F1\VP1          VITTSTRTWALPTYNNHLYKQIS--SSSGATNDNHYFGYSTPWGYFDFNRFHCHFSPRDW
F5\VP1@3        VITTSTRTWALPTYNNHLYKQIS--SSSGATNDNHYFGYSTPWGYFDFNRFHCHFSPRDW
F3\VP1          VITTSTRTWALPTYNNHLYKQIS--SSSGATNDNHYFGYSTPWGYFDFNRFHCHFSPRDW
42_6B           VITTSTRTWALPTYNNHLYKQISNGTSGGSTNDNTYFGYSTPWGYFDFNRFHCHFSPRDW
42_12           VITTSTRTWALPTYNNHLYKQISNGTSGGSTNDNTYFGYSTPWGYFDFNRFHCHFSPRDW
AAV5\CAP        VVTKSTRTWVLPSYNNHQYREIK-SGSVDGSNANAYFGYSTPWGYFDFNRFHSHWSPRDW
```

FIG. 2E

```
                        310        320        330        340        350        360
               ....|....|....|....|....|....|....|....|....|....|....|....|
C1\VP1         QRLINNNWGLRPKAMRVKIFNIQVKEVTTSNGETTVANNLTSTVQIFADSSYELPYVMDA
C2\VP1         QRLINNNWGLRPKAMRVKIFNIQVKEVTTSNGETTVANNLTSTVQIFADSSYELPYVMDA
C5\VP1@2       QRLINNNWGLRPKAMRVKIFNIQVKEVTTSNGETTVANNLTSTVQIFADSSYELPYVMDA
AAV4\VP1       QRLINNNWGMRPKAMRVKIFNIQVKEVTTSNGETTVANNLTSTVQIFADSSYELPYVMDA
AAV1           QRLINNNWGFRPKRLNFKLFNIQVKEVTTNDGVTTIANNLTSTVQVFSDSEYQLPYVLGS
AAV6\VP1       QRLINNNWGFRPKRLNFKLFNIQVKEVTTNDGVTTIANNLTSTVQVFSDSEYQLPYVLGS
A3_3           QRLINNNWGFRPKKLNFKLFNIQVKEVTQNDGTTTIANNLTSAVQVFTDSEYQLPYVLGS
A3_7           QRLINNNWGFRPKKLNFKLFNIQVKEVTQNDGTTTIANNLTSTVQVFTDSEYQLPYVLGS
A3_4           QRLINNNWGFRPKKLNFKLFNIQVKEVTQNDGTTTIANNLTSTVQVFTDSEYQLPYVLGS
A3_5           QRLINNNWGFRPKKLNFKLFNIQVKEVTQNDGTTTIANNLTSTVQVFTDSEYQLPYVLGS
AAV2           QRLINNNWGFRPKRLNFKLFNIQVKEVTQNDGTTTIANNLTSTVQVFTDSEYQLPYVLGS
AAV3           QRLINNNWGFRPKKLSFKLFNIQVRGVTQNDGTTTIANNLTSTVQVFTDSEYQLPYVLGS
13.3b\VP1      QRLINNNWGFRPKKLRFKLFNIQVKEVTTNDGVTTIANNLTSTIQVFSDSEYQLPYVLGS
AAV7           QRLINNNWGFRPKKLRFKLFNIQVKEVTTNDGVTTIANNLTSTIQVFSDSEYQLPYVLGS
223_4          QRLINNNWGFRPKKLNFKLFNIQVKEVTTNDGVTTIANNLTSTVQVFSDSEYQLPYVLGS
223_5          QRLINNNWGFRPKKLNFKLFNIQVKEVTTNDGVTTIANNLTSTVQVFSDSEYQLPYVLGS
223_10         QRLINNNWGFRPKKLNFKLFNIQVKEVTTNDGVTTIANNLTSTVQVFSDSEYQLPYVLGS
223_2          QRLINNNWGFRPKKLNFKLFNIQVKEVTTNDGVTTIANNLTSTVQVFSDSEYQLPYVLGS
223_7          QRLINNNWGFRPKKLNFKLFNIQVKEVTTNDGVTTIANNLTSTVQVFSDPEYQLPYVLGS
223_6          QRLINNNWGFRPKKLNFKLFNIQVKEVTTNDGVTTIANNLTSTVQVFSDSEYQLPYVLGS
44_1           QRLINNNWGFRPKKLNFKLFNIQVKEVTQNEGTKTIANNLTSTIQVFTDSEYQLPYVLGS
44_5           QRLINNNWGFRPKRPNFKLFNIQVKEVTQNEGTKTIANNLTSTIQVFTDSEYQLPYVLGS
44_2           QRLINNNWGFRPKKLNFKLFNIQVKEVTQNEGTKTIANNLTSTIQVFTDSEYQLPYVLGS
29.3\VP1       QRLINNNWGFRPKRLNFKLFNIQVKEVTQNEGTKTIANNLTSTIQVFTDSEYQLPYVLGS
29.5\VP1       QRLINNNWGFRPKSLNFKLFNIQVKEVTQNEGTKTIANNLTSTIQVFTDSEYQLPYVLGS
42_15          QRLINNNWGFRPKRLNFKLFNIQVKEVTQNEGTKTIANNLTSTIQVFTDSEYQLPYVLGS
42_8           QRLINNNWGFRPKRLNFKLFNIQVKEVTQNEGTKTIANNLTSTIQVFTDSEYQLPYVLGS
42_13          QRLINNNWGFRPKRLNFKLFNIQVKEVTQNEGTKTIANNLTSTIQVFTDSEYQLPYVLGS
42_3A          QRLINNSWGFRPKRLNFKLFNIQVKEVTQNEGTKTIANNLTSTIQVFTDSEYQLPYVLGS
42_4           QRLINNNWGFRPKRLNFKLFNIQVKEVTQNEGTKTIANNLTSTIQVFTDSEYRLPYVLGS
42_5A          QRLINNNRGFRPRKLRFKLFNIQVKEVTTNDGVTTIANNLTSTIQVFSDSEYQLPYVLGS
42_1B          QRLINNNWGFRPKRLNFKLFNIQVKEVTQNEGTKTIANNLTSTIQVFTDSEYQLPYVLGS
42_5B          QRLINNNWGFRPKRLNFKLFNIQVKEVTQNEGTKTIANNLTSTIQVFTDSEYQLPYVLGS
43_1           QRLINNNWGFRPKRLNFKLFNIQVKEVTQNEGTKTIANNLTSTIQVFTDSEYQLPYVPGS
43_12          QRLINNNWGFRPKRLNFKLFNIQVKEVTQNEGTKTIANNLTSTIQVFTDSEYQLPYVLGS
43_5           QRLINNNWGFRPKRLNFKLFNIQVKEVTQNEGTKTIANNLTSTIQVFTDSEYQLPYVLGS
AAV8           QRLINNNWGFRPKRLSFKLFNIQVKEVTQNEGTKTIANNLTSTIQVFTDSEYQLPYVLGS
43_21          QRLINNNWGFRPKRLNFKLFNIQVKEVTTNEGTKTIANNLTSTVRVFTDSEYQLPYVLGS
43_25          QRLINNNWGFRPKRLNFKLFNIQVKEVTTNEGTKTIANNLTSTVQVFTDSEYQLPYVLGS
43_23          QRLINNNWGFRPKRLNFKLFNIQVKEVTTNEGTKTIANNLTSTVQVFTDLEYQLPYVLGS
43_20          QRLINNNWGFRPKRLNFKLFNIQVKEVTTNEGTKTIANNLTSTVQVFTDSEYQLPYVLGS
AAV_9          QRLINNNWGFRPKRLNFKLFNIQVKEVTTNEGTKTIANNLTSTVQVFTDSEYQLPYVLGS
24.1           QRLINNNWGFRPRKLRFKLFNIQVKEVTTNDGVTTIANNLTSTIQVFSDSEYQLPYVLGS
42.2REAL       QRLINNNWGFRPRKLRFKLFNIQVKEVTTNDGVTTIANNLTSTIQVFSDSEYQLPYVLGS
7.2\VP1        QRLINNNWGFRPRKLRFKLFNIQVKEVTTNDGVTTIANNLTSTIQVFSDSEYQLPYVLGS
27.3\VP1       QRLINNNWGFRPRKLRFKLFNIQVKEVTTNDGVTTIANNLTSTIQVFSDSEYQLPYVLGS
16.3\VP1       QRLINNNWGFRPRKLRFKLFNIQVKEVTTNDGVTTIANNLTSTIQVFSDSEYQLPYVLGS
42_10          QRLINNNWGFRPRKLRFKLFNIQVKEVTTNDGVTTIANNLTSTIQVFSDSEYQLPYVLGS
42_3B          QRLINNNWGFRPRKLRFKLFNIQVKEVTTNDGVTTIANNLTSTIQVFSDSEYQLPYVLGS
42_11          QRLINNNWGFRPRKLRFKLFNIQVKEVTTNDGVTTIANNLTSTIQVFSDSEYQLPYVLGS
F1\VP1         QRLINNNWGFRPKKLRFKLFNIQVKEVTTNDGVTTIANNLTSTVQVFSDSEYQLPYVLGS
F5\VP1@3       QRLINNNWGFRPKKLRFKLFNIQVKEVTTNDGVTTIANNLTSTVQVFSDSEYQLPYVLGS
F3\VP1         QRLINNNWGFRPKKLRFKLLNIQVKEVTTNDGVTTIANNLTSTVQVFSDSEYQLPYVLGS
42_6B          QRLINNNWGFRPRKLRFKLFNIQVKEVTTDDGVTTIANNLTSTIQVFSDSEYQLPYVLGS
42_12          QRLINNNWGFRPKRLNFKLFNIQVKEVTQNEGTKTIANNLTSTIQVFTDSEYQLPYVLGS
AAV5\CAP       QRLINNYWGFRPRSLRVKIFNIQVKEVTVQDSTTTIANNLTSTVQVFTDDDYQLPYVVGN
```

FIG. 2F

```
                    370        380        390        400        410        420
               ....|....|....|....|....|....|....|....|....|....|....|....|
C1\VP1         GQEGSLSPFPNDVFMVPQYGYCGIVTG-ENQNQTDRNAFYCLEYFPSQMLRTGNNFEMAY
C2\VP1         GQEGSLSPFPNDVFMVPQYGYCGIVTG-ENQNQTDRNAFYCLEYFPSQMLRTGNNFEMAY
C5\VP1@2       GQEGSLPPFPNDVFMVPQYGYCGIVTG-ENQNQTDRNAFYCLEYFPSQMLRTGNNFETAY
AAV4\VP1       GQEGSLPPFPNDVFMVPQYGYCGLVTGNTSQQQTDRNAFYCLEYFPSQMLRTGNNFEITY
AAV1           AHQGCLPPFPADVFMIPQYGYLTLNNG---SQAVGRSSFYCLEYFPSQMLRTGNNFTFSY
AAV6\VP1       AHQGCLPPFPADVFMIPQYGYLTLNNG---SQAVGRSSFYCLEYFPSQMLRTGNNFTFSY
A3_3           AHQGCLPPFPADVFMIPQYGYLTLNNG---SQAVGRSSFYCLEYFPSQMLRTGNNFTFSY
A3_7           AHQGCLPPFPADVFMIPQYGYLTLNNG---SQAVGRSSFYCLEYFPSQMLRTGNNFTFSY
A3_4           AHQGCLPPFPADVFMIPQYGYLTLNNG---SQAVGRSSFYCLEYFPSQMLRTGNNFTFSY
A3_5           AHQGCLPPFPADVFMIPQYGYLTLNNG---SQAVGRSSFYCLEYFPSQMLRTGNNFTFSY
AAV2           AHQGCLPPFPADVFMVPQYGYLTLNNG---SQAVGRSSFYCLEYFPSQMLRTGNNFTFSY
AAV3           AHQGCLPPFPADVFMVPQYGYLTLNNG---SQAVGRSSFYCLEYFPSQMLRTGNNFQFSY
13.3b\VP1      AHQGCLPPFPADVFMIPQYGYLTLNNG---SQSVGRSSFYCLEYFPSQMLRTGNNFEFSY
AAV7           AHQGCLPPFPADVFMIPQYGYLTLNNG---SQSVGRSSFYCLEYFPSQMLRTGNNFEFSY
223_4          AHQGCLPPFPADVFMIPQYGYLTLNNG---SQSVGRSSFYCLEYFPSQMLRTGNNFTFSY
223_5          AHQGCLPPFPADVFMIPQYGYLTLNNG---SQSVGRSSFYCLEYFPSQMLRTGNNFTFSY
223_10         AHQGCLPPFPADVFMIPQYGYLTLNNG---SQSVGRSSFYCLEYFPSQMLRTGNNFTFSY
223_2          AHQGCLPPFPADVFMIPQYGYLTLNNG---SQSVGRSSFYCLEYFPSQMLRTGNNFTFSY
223_7          AHQGCLPPFPADVFMIPQYGYLTLNNG---SQSVGRSSFYCLEYFPSQMLRTGNNFTFSY
223_6          AHQGCLPPFPADVFMIPQYGYLTLNNG---SQSVGRSSFYCLEYFPSQMLRTGNNFTFSY
44_1           AHQGCLPPFPADVFMIPQYGYLTLNNG---SQAVGRSSFYCLEYFPSQMLRTGNNFEFSY
44_5           AHQGCLPPFPADVFMIPQYGYLTLNNG---SQAVGRSSFYCLEYFPSQMLRTGNNFEFSY
44_2           AHQGCLPPFPADVFMIPQYGYLTLNNG---SQAVGRSSFYCLEYFPSQMLRTGNNFEFSY
29.3\VP1       ARQGCLPPFPADVFMIPQYGYLTLNNG---SQAVGRSSFYCLEYFPSQMLRTGNNFEFSY
29.5\VP1       AHQGCLPPFPADVFMIPQYGYLTLNNG---SQAVGRSSFYCLEYFPSQMLRTGNNFEFSY
42_15          AHQGCPPPFPADVFMIPQYGYLTLNNG---SQAVGRSSFYCLEYFPSQMRRTGNNFEFSY
42_8           AHQGCLPPFPADVFMIPQYGYLTLNNG---SQAVGRSSFYCLEYFPSQMLRTGNNFEFSY
42_13          AHQGCLPPFPADVFMIPQYGYLTLNNG---SQAVGRSSFYCLEYFPSQMLRTGNNFEFSY
42_3A          AHQGCLPPFPADVFMIPQYGYLTLNNG---SQAVGRSSFYCLEYFPSQMLRTGNNFEFSY
42_4           AHQGCLPPFPADVFMIPQYGYLTLNNG---SQAVGRSSFYCLEYFPSQMLRTGNNFEFSY
42_5A          AHQGCLPPFPADVFMIPQYGYLTLNNG---SQSVGRSSFYCLEYFPSQMLRTGNNFEFSY
42_1B          AHQGCLPPFPADVFMIPQYGYLTLNNG---SQAVGRSSFYCLEYFPSQMLRTGNNFEFSY
42_5B          AHQGCLPPFPADVFMIPQYGYLTLNNG---SQAVGRSSFYCLEYFPSQMLRTGNNFEFSY
43_1           AHQGCLPPFPADVFMIPQYGYLTLNNG---SQAVGRSSFYCLEYFPSQMLRTGNNFEFSY
43_12          AHQGCLPPFPADVFMIPQYGYLTLNNG---SQAVGRSSFYCLEYFPSQMLRTGNNFEFSY
43_5           AHQGCLPPFPADVFMIPQYGYLTLNNG---SQAVGRSSFYCLEYFPSQMLRTGNNFEFSY
AAV8           AHQGCLPPFPADVFMIPQYGYLTLNNG---SQAVGRSSFYCLEYFPSQMLRTGNNFQFTY
43_21          AHQGCLPPFPADVFMVPQYGYLTLNNG---SQALGRSSFYCLEYFPSQMLRTGNNFQFSY
43_25          AHQGCLPPFPADVFMVPQYGYLTLNNG---SQALGRSSFYCLEYFPSQMLRTGNNFQFSY
43_23          AHQGCLPPFPADVFMVPQYGYLTLNNG---SQALGRSSFYCLEYFPSQMPRTGNNFQFSY
43_20          AHQGCLPPFPADVFTVPQYGYLTLNNG---SQALGRSSFYCLEYFPSQMLRTGNNFQFSY
AAV_9          AHQGCLPPFPADVFMVPQYGYLTLNNG---SQALGRSSFYCLEYFPSQMLRTGNNFQFSY
24.1           AHQGCLPPFPADVFMIPQYGYLTLNNG---SQSVGRSSFYCLEYFPSQMLRTGNNFEFSY
42.2REAL       AHQGCLPPFPADVFMIPQYGYLTLNNG---SQSVGRSSFYCLEYFPSQMLRTGNNFEFSY
7.2\VP1        AHQGCLPPFPADVFMIPQYGYLTLNNG---SQSVGRSSFYCLEYFPSQMLRTGDNFEFSY
27.3\VP1       AHQGCLPPFPADVFMIPQYGYLTLNNG---SQSVGRSSFCCLEYFPSQMLRTGNNFEFSY
16.3\VP1       AHQGCLPPFPADVFMIPQYGYLTLNNG---SQSMGRSSFYCLEYFPSQMLRTGNNFEFSY
42_10          AHQGCLPPFPADVFMIPQYGYLTLNNG---SQSVGRSSFYCLEYFPSQMLRTGNNFEFSY
42_3B          AHQGCLPPFPADVFMIPQYGYLTLNNG---SQSVGRSSFYCLEYFPSQMLRTGNNFEFSY
42_11          AHQGCLPPFPADVFMIPQYGYLTLNNG---SQSVGRSSFYCLEYFPSQMLRTGNNFEFSY
F1\VP1         AHQGCLPPFPADVFMIPQYGYLTLNNG---SQSVGRSSFYCLEYFPSQMLRTGNNFEFSY
F5\VP1@3       AHQGCLPPFPADVFMIPQYGYLTLNNG---SQSVGRSSFYCLEYFPSQMLRTGNNFEFSY
F3\VP1         AHQGCLPPFPADVFMIPQYGYLTLDNG---SQSVGRSSFYCLEYFPSQMLRTGNNFEFSY
42_6B          AHQGCLPPFPADVFMIPQYGYLTLNNG---SQSVGRSSFYCLEYFPSQMLRTGNNFEFSY
42_12          AHQGCLPPFPADVFMIPQYGYLTLNNG---SQAVGRSSFYCLEYFPSQMLRTGNNFEFSY
AAV5\CAP       GTEGCLPAFPPQVFTLPQYGYATLNRD-NTENPTERSSFFCLEYFPSKMLRTGNNFEFTY
```

FIG. 2G

```
                    430       440       450       460       470       480
                ....|....|....|....|....|....|....|....|....|....|....|....|
C1\VP1          NFGKVPFHSMYAYSQSPDRLMNPLLDQYLWHLQSTTSGETLNQGNAATTFGKIRSGDFAF
C2\VP1          NFEKVPFHSMYAHSQSLDRLMNPLLDQYLWHLQSTTSGETLNQGNAATTFGKIRSGDFAF
C5\VP1@2        NFEKVPFHSMYAHSQSLDGLMNPLLDQYLWHLQSTTSGETLNQGNAATTFGKIRSGDFAF
AAV4\VP1        SFEKVPFHSMYAHSQSLDRLMNPLIDQYLWGLQSTTTGTTLNAGTATTNFTKLRPTNFSN
AAV1            TFEEVPFHSSYAHSQSLDRLMNPLIDQYLYYLNRTQNQSG-SAQNKDLLFSRGSPAGMSV
AAV6\VP1        TFEDVPFHSSYAHSQSLDRLMNPLIDQYLYYLNRTQNQSG-SAQNKDLLFSRGSPAGMSV
A3_3            TFEDVPFHSSYAHSQSLDRLMNPLIDQYLYYLSKTQ-GTSGTTQQSRLQFSQAGPSSMAQ
A3_7            TFEDVPFHSSYAHSQSLDRLMNPLIDQYLYYLSKTQ-GTSGTTQQSRLQFSQAGPSSMAQ
A3_4            TFEDVPFHSSYAHSQSLDRLMNPLIDQYLYYLSKTQ-GTSGTTQQSRLQFSQAGPSSMAQ
A3_5            TFEDVPFHSSYAHSQSLDRLMNPLIDQYLYYLSKTQ-GTSGTTQQSRLQFNQAGPSSMAQ
AAV2            TFEDVPFHSSYAHSQSLDRLMNPLIDQYLYYLSRTN-TPSGTTTQSRLQFSQAGASDIRD
AAV3            TFEDVPFHSSYAHSQSLDRLMNPLIDQYLYYLNRTQGTTSGTTNQSRLLFSQAGPQSMSL
13.3b\VP1       SFEDVPFHSSYAHSQSLDRLMNPLIDQYLYYLARTQSDPGGTAGNRELQFYQGGPSTMAE
AAV7            SFEDVPFHSSYAHSQSLDRLMNPLIDQYLYYLARTQSNPGGTAGNRELQFYQGGPSTMAE
223_4           TFEDVPFHSSYAHSQSLGRLMNPLIDQYLYYLARTQSNAGGTAGNRELQFYQGGPTTMAE
223_5           TFEDVPFHSSYAHSQSLGRLMNPLIDQYLYYLARTQSNAGGTAGNRELQFYQGGPTTMAE
223_10          TFEDVPFHSSYAHSQSLDRLMNPLIDQYLYYLARTQSNAGGTAGNRELQFYQGGPTTMAE
223_2           TFEDVPFHSSYAHSQSLDRLMNPLIDQYLYYLARTQSNAGGTAGNRELQFYQGGPTTMAE
223_7           TFEDVPFHSSYAHSQSLDRLMNPLIDQYLYYLARTQSNAGGTAGNRELQFYQGGPTTMAE
223_6           TFEDVPFHSSYAHSQSLDRLMNPLIDQYLYYLARTQSNAGGTAGNRELQFYQGGPTTMAE
44_1            QFEDVPFHSSYAHSQSLDRLMNPLIDQYLYYLSRTQSTGG-TAGTQQLLFSQAGPNNMSA
44_5            QFEDVPFHSSYAHSQSLDRLMNPLIDQYLYYLSRTQSTGG-TAGTQQLLFSQAGPNNMSA
44_2            QFEDVPFHSSYAHSQSLDRLMNPLIDQYLYYLSRTQSTGG-TAGTQQLLFSQAGPNNMSA
29.3\VP1        QFEDVPFHSSYAHSQSLDRLMNPLIDQYLYYLSRTQSTGG-TAGTQQLLFSQAGPNNMSA
29.5\VP1        QFEDVPFHSSYAHSQSLDRLMNPLIDQYLYYLSRTQSTGG-TAGTQQLLFSQAGPNNMSA
42_15           QFEDVPFHSSYAHSQSLDRLMNPLIDQYLYYLSRTQSTGG-TAGTQQLLFSQAGPNNMSA
42_8            QFEDVPFHSSYAHSQSLDRLMNPLIDQYLYYLSRTQSTGG-TAGTQQLLFSQAGPNNMSA
42_13           QFEDVPFHSSYAHSQSLDRLMNPLIDQYLYYLSRTQSTGG-TAGTQQLLFSQAGPNNMSA
42_3A           QFEDVPFHSSYAHSQSLDRLMNPLIDQYLYYLSRTQSTGG-TAGTQQLLFSQAGPNNMSA
42_4            QFEDVPFHSSYAHSQSLDRLMNPLIDQYLYYLSRTQSTGG-TAGTQQLLFSQAGPNNMSA
42_5A           QFEDVPFHSSYAHSQSLDRLMNPLIDQYLYYLSRTQSTGG-TAGTQQLLFSQAGPNNMSA
42_1B           QFEDVPFHSSYAHSQSLDRLMNPLIDQYLYYLSRTQSTGG-TAGTQQLLFSQAGPNNMSA
42_5B           QFEDVPFHSSYAHSQSLDRLMNPLIDQYLYYLSRTQSTGG-TAGTQQLLFSQAGPNNMSA
43_1            TFEDVPFHSSYAHSQSLDRLMNPLIDQYLYYLSRTQSTGG-TQGTQQLLFSQAGPANMSA
43_12           TFEDVPFHSSYAHSQSLDRLMNPLIDQYLYYLSRTQSTGG-TQGTQQLLFSQAGPANMSA
43_5            TFEDVPFHSSYAHSQSLDRLMNPLIDQYLYYLSRTQSTGG-TQGTQQLLFSQAGPANMSA
AAV8            TFEDVPFHSSYAHSQSLDRLMNPLIDQYLYYLSRTQTTGG-TANTQTLGFSQGGPNTMAN
43_21           TFEDVPFHSSYAHSQSLDRLMNPLIDQYLYYLVRTQTTG--TGGTQTLAFSQAGPSSMAN
43_25           TFEDVPFHSSYAHSQSLDRLMNPLIDQYLYYLVRTQTTG--TGGTQTLAFSQAGPSSMAN
43_23           TFEDVPFHSSYAHSQSLDRLMNPLIDQYLYYLVRTQTTG--TGGTQTLAFSQAGPSSMAN
43_20           TFEDVPFHSSYAHSQSLDRLMNPLIDQYLYYLVRTQTTG--TGGTQTLAFSQAGPSSMAN
AAV_9           TFEDVPFHSSYAHSQSLDRLMNPLIDQYLYYLVRTQTTG--TGGTQTLAFSQAGPSSMAN
24.1            TFEEVPFHSSYVHSQSLDRLMNPLIDQYLYYLARTQST---TGSTRELQFHQAGPNTMAE
42.2REAL        TFEEVPFHSSYAHSQSLDRLMNPLIDQYLYYLARTQST---TGSTRELQFHQAGPNTMAE
7.2\VP1         TFEEVPFHSSYAHSQSLDRLMNPLIDQYLYYLARTQST---TGSTRELQFHQAGPNTMAE
27.3\VP1        TFEEVPFHSSYAHSQSLDRLMNPLIDQYLYYLARTQST---TGSTRELQFHQAGPNTVAE
16.3\VP1        TFEEVPFHSSYAHSQSLDRLMNPLIDQYLYYLARTQST---TGSTRELQFHQAGPNTMAE
42_10           TFEEVPFHSSYAHSQSLDRLMNPLIDQYLYYLARTQST---TGSTRELQFHQAGPNTMAE
42_3B           TFEEVPFHSSYAHSQSLDRLMNPLIDQYLYYLARTQST---TGSTRELQFHQAGPNTMAE
42_11           TFEEVPFHSSYAHSQSLDRLMNPLIDQYLYYLARTQST---TGSTRELQFHQAGPNTMAE
F1\VP1          SFEDVPFHSSYAHSQSLDRLMNPLIDQYLYYLARTQST---TGSTRELQFHQAGPNTMAE
F5\VP1@3        SFEDVPFHSSYAHSQSLDRLMNPLIDQYLYYLARTQST---TGSTRELQFHQAGPNTMAE
F3\VP1          SFEDVPFHSSYAHSQSLDRLMNPLIDQYLYYLARTQST---TCSTRELQFHQACPNTMAE
42_6B           TFEEVPFHSSYAHSQSLDRLMNPLIDQYLYYLARTQST---TGSTRELQFHQAGPNTMAE
42_12           QFEDVPFHSSYAHSQSLDRLTNPLIDQYLYYLARTQST---TGSTRGLQFHQAGPNTMAE
AAV5\CAP        NFEEVPFHSSFAPSQNLFKLANPLVDQYLYRFVSTNNTGG-------VQFNKNLAGRYAN
```

FIG. 2H

```
                    490       500       510       520       530       540
              ....|....|....|....|....|....|....|....|....|....|....|....|
C1\VP1        YRKNWLPGPCVKQQRLSKTASQNYKIPASGGNALLKYDTHYTLNNRWSNIAPGPPMATAG
C2\VP1        YRKNWLPGPCVKQQRFSKTASQNYKIPASGGNALLKYDTHYTLNNRWSNIAPGPPMATAG
C5\VP1@2      YRKNWLPGPCVKQQRFSKTASQNYKIPASGGNALLKYDTHYTLNNRWSNIAPGPPMATAG
AAV4\VP1      FKKNWLPGPSIKQQGFSKTANQNYKIPATGSDSLIKYETHSTLDGRWSALTPGPPMATAG
AAV1          QPKNWLPGPCYRQQRVSKTKTDN-----NNSNFTWTGASKYNLNGRESIINPGTAMASHK
AAV6\VP1      QPKNWLPGPCYRQQRVSKTKTDN-----NNSNFTWTGASKYNLNGRESIINPGTAMASHK
A3_3          QAKNWLPGPSYRQQRMSKTANDN-----NNSEFAWTAATKYYLNGRNSLVNPGPPVASHK
A3_7          QAKNWLPGPSYRQQRMSKTANDN-----NNSEFAWTAATKYYLNGRNSLVNPGPPMASHK
A3_4          QAKNWLPGPSYRQQRMSKTANDN-----NNSEFAWTAATKYYLNGRNSLVNPGPPMASHK
A3_5          QAKNWLPGPSYRQQRMSKTANDN-----NNSEFAWTAATKYYPNGRNSLVNPGPPMASHK
AAV2          QSRNWLPGPCYRQQRVSKTSADN-----NNSEYSWTGATKYHLNGRDSLVNPGPAMASHK
AAV3          QARNWLPGPCYRQQRLSKTANDN-----NNSNFPWTAASKYHLNGRDSLVNPGPAMASHK
13.3b\VP1     QAKNWLPGPCFRQQRVSKTLDQN-----NNSNFAWTGATKYHLNGRNSLVNPGVAMATHK
AAV7          QAKNWLPGPCFRQQRVSKTLDQN-----NNSNFAWTGATKYHLNGRNSLVNPGVAMATHK
223_4         QAKNWLPGPCFRQQRVSKTLDQN-----NNSNFAWTGATKYHLNGRNSLVNPGVAMATHK
223_5         QAKNWLPGPCFRQQRVSKTLDQN-----NNSNFAWTGATKYHLNGRNSLVNPGVAMATHK
223_10        QAKNWLPGPCFRQQRVSKTLDQN-----NNSNFAWTGATKYHLNXRNSLVNPGVAMATHK
223_2         QAKNWLPGPCFRQQRVSKTLDQN-----NNSNFAWTGATKYHLNGRNSLVNPGVAMATHK
223_7         QAKNWLPGPCFRQQRVSKTLDQN-----NNSNFAWTGATKYHLNGRNSLVNPGVAMATHK
223_6         QAKNWLPGPCFRQQRVSKTLDQN-----NNSNFAWTGATKYHLNGRNSLVNPGVAMATHK
44_1          QAKNWLPGPCYRQQRVSTTLSQN-----NNSNFAWTGATKYHLNGRDSLVNPGVAMATHK
44_5          QAKNWLPGPCYRQQRVSTTLSQN-----NNSNFAWTGATKYHLNGRDSLVNPGVAMATHK
44_2          QAKNWLPGPCYRQQRVSTTLSQN-----NNSNFAWTGATKYHLNGRDSLVNPGVAMATHK
29.3\VP1      QAKNWLPGPCYRQQRVSTTLSQN-----NNSNFAWTGATKYHLNGRDSLVNPGVAMATHK
29.5\VP1      QAKNWLPGPCYRQQRVSTTLSQN-----DNSNFAWTGATKYHLNGRDSLVNPGVAMATHK
42_15         QAKNWLPGPCYRQQRVSTTLSQN-----NNSNFAWTGATKYHLNGRDSLVNPGVAMATHK
42_8          QAKNWLPGPCYRQQRVSTTLSQN-----NNSNFAWTGATKYHLNGRDSLVNPGVAMATHK
42_13         QAKNWLPGPCYRQQRVSTTVSQN-----NNSNFAWTGATKYHLNGRDSLVNPGVAMATHK
42_3A         QAKNWLPGPCYRQQRVSTTLSQN-----NNSNFAWTGATKYHLNGRDSLVNPGVAMATHK
42_4          QAKNWLPGPCYRQQRVSTTLSQN-----NNSNFAWTGATKYHLNGRDSLVNPGVAMATHK
42_5A         QAKNWLPGPCYRQQRVSTTLSQN-----NNSNFAWTGATKYHLNGRDSLVNPGVAMATHK
42_1B         QAKNWLPGPCYRQQRVSTTVSQN-----NNSNFAWTGATKYHLNGRDSLVNPGVAMATHK
42_5B         QAKNWLPGPCYRQQRVSTTLSQN-----NNSNFAWTGATKYHLNGRDSLVNPGVAMATHK
43_1          QAKNWLPGPCYRQQRVSTTLSQN-----NNSNFAWTGATKYHLNGRDSLVNPGVAMATHK
43_12         QAKNWLPGPCYRQQRVSTTLSQN-----NNSNFAWTGATKYHLNGRDSLVNPGVAMATHK
43_5          QAKNWLPGPCYRQQRVSTTLSQN-----NNSNFAWTGATKYHLNGRDSLVNPGVAMATHK
AAV8          QAKNWLPGPCYRQQRVSTTTGQN-----NNSNFAWTAGTKYHLNGRNSLANPGIAMATHK
43_21         QARNWVPGPCYRQQRVSTTTNQS-----NNSNFAWTGAAKFKLNGRDSLMNPGVAMASHK
43_25         QARNWVPGPCYRQQRVSTTTNQN-----NNSNFAWTGAAKFKLNGRDSLMNPGVAMASHK
43_23         QARNWVPGPCYRQQRVSTTTNQN-----NNSNFAWTGAAKFKLNGRDSLMNPGVAMASHK
43_20         QARNWVPGPCYRQQRVSTTTNQN-----NNSNFAWTGAAKFKLNGRDSLMNPGVAMASHK
AAV_9         QARNWVPGPCYRQQRVSTTTNQN-----NNSNFAWTGAAKFKLNGRDSLMNPGVAMASHK
24.1          QSKNWLPGPCYRQQRLSKNIDSN-----NNSNFAWTGATKYHLNGRNSLTNPGVAMATNK
42.2REAL      QSKNWLPGPCYRQQRLSKNIDSN-----NNSNFAWTGATKYHLNGRNSLTNPGVAMATNK
7.2\VP1       QSKNWLPGPCYRQQRLSKNIDSN-----NNSNFAWTGATKYHLNGRNSLTNPGVAMATNK
27.3\VP1      QSKNWLPGPCYRQQRLSKNIDSN-----NNSNFAWTGATKYHLNGRNSLTNPGVAMATNK
16.3\VP1      QSKNWLPGPCYRQQRLSKNIDSN-----NNSNFAWTGATKYHLNGRNSLTNPGVAMATNK
42_10         QSKNWLPGPCYRQQRLSKNIDSN-----NNSNFAWTGATKYHLNGRNSLTNPGVAMATNK
42_3B         QSKNWLPGPCYRQQRLSKNIDSN-----NTSNFAWTGATKYHLNGRNSLTNPGVAMATNK
42_11         QSKNWLPGPCYRQRLSKDIDSN------NNSNFAWTGATKYHLNGRNSLTNPGVAMATNK
F1\VP1        QSKNWLPGPCYRQQGLSKNLDFN-----NNSNFAWTAATKYELNGRNSLTNPGIPMATNK
F5\VP1@3      QSKNWLPGPCYRQQRLSKNLDFN-----NNSNFAWTAATKYELNGRNSLTNPGIPMATNK
F3\VP1        QSKNWLPGPCYRQQRLSKNLDFN-----NNSNFAWTAATKYELNGRNSLTNPGIPMATNK
42_6B         QSKNWLPGPCYRQQRLSKNIDSN-----NNSNFAWTGATKYHLNGRNSLTNPGVAMATNK
42_12         QSKNWLPGPCYRQQRLSKNIDSN-----NNSNFAWTGATKYHLNGRNSLTNPGVAMATNK
AAV5\CAP      TYKNWFPGPMGRTQGWNLGSGVN-----RASVSAFATTNRMELEGASYQVPPQPNGMTNN
```

FIG. 2I

```
                      550         560         570        580         590        600
              ....|....|....|....|....|....|....|....|....|....|....|....|
C1\VP1        PSDGDFS-NAQLIFPGPS--VTGNTTTSAN-NLLFTSEEEIAATNPRDTDMFGQIADNNQ
C2\VP1        PSDGDFS-NAQLIFPGPS--VTGNTTTSAN-NLLFTSEGEIAATNPRDTDMFGQIADNNQ
C5\VP1@2      PSDGDFS-NAQLIFPGPS--VTGNTTTSAN-NLLFTSEEEIAATNPRDTDMFGQIADNNQ
AAV4\VP1      PADSKFS-NSQLIFAGPK--QNGNTATVPG-TLIFTSEEELAATNATDTDMWGNLPGGDQ
AAV1          DDEDKFFPMSGVMIFGKE--SAGASNTALD-NVMITDEEEIKATNPVATERFGTVAVNFQ
AAV6\VP1      DDKDKFFPMSGVMIFGKE--SAGASNTALD-NVMITDEEEIKATNPVATERFGTVAVNLQ
A3_3          DDEEKYFPMHGNLIFGKQ--GTGTTNVDIE-SVLITDEEEIRTTNPVATEQYGQVATNHQ
A3_7          DDEEKYFPMHGNLIFGKQ--GTGTTNVDIE-SVLITDEEEIRTTNPVATEQYGQVATNHQ
A3_4          DDEEKYFPMHGNLIFGKQ--GTGTTNVDIE-SVLITDEEEIRTTNPVATEQYGQVATNHQ
A3_5          DDEEKYFPMHGNLIFGKQ--GTGTTNVDIE-SVLITDEEEIRTTNPVATEQYGQVATNRQ
AAV2          DDEEKFFPQSGVLIFGKQ--GSEKTNVDIE-KVMITDEEEIRTTNPVATEQYGSVSTNLQ
AAV3          DDEEKFFPMHGNLIFGKE--GTTASNAELD-NVMITDEEEIRTTNPVATEQYGTVANNLQ
13.3b\VP1     DDEDRFFPSSGVLIFGKT--GATN-KTTLE-NVLMTNEEEIRPTNPVATEEYGIVSSNLQ
AAV7          DDEDRFFPSSGVLIFGKT--GATN-KTTLE-NVLMTNEEEIRPTNPVATEEYGIVSSNLQ
223_4         DDEERFFPSSGVLIFGKT--GAAN-KTTLE-NVLMTNEEEIRPTNPVATEEYGIVSSNLQ
223_5         DDEERFFPSSGVLIFGKT--GAAN-KTTLE-NVLMTNEEEIRPTNPVATEEYGIVSSNLQ
223_10        DDEERFFPSSGVLIFGKT--GAAN-KTTLE-NVLMTNEEEIRPTNPVATEEYGIVSSNLQ
223_2         DDEERFSPSSGVLIFGKT--GAAN-KTTLE-NVLMTNEEEIRPTNPVATEEYGIVSSNLQ
223_7         DDEERFFPSSGVLIFGKT--GAAN-KTTLE-NVLMTNEEEIRPTNPVATEEYGIVSSNLQ
223_6         DDEERFFPSSGVLIFGKT--GAAN-KTTLE-NVLMTNEEEIRPTNPVATEEYGIVSSNLQ
44_1          DDEERFFPSSGVLMFGKQ--GAGKDNVDYS-SVMLTSEEEIKTTNPVATEQYGVVADNLQ
44_5          DDEERFFPSSGVLMFGKQ--GAGKDNVDYS-SVMLTSEEEIKTTNPVATEQYGVVADNLQ
44_2          DDEERFFPSSGVLMFGKQ--GAGKDNVDYS-SVMLTSEEEIKTTNPVATEQYGVVADNLQ
29.3\VP1      DDEERFFPSSGVLMFGKQ--GAGKGNVDYS-SVMLTSEEEIKTTNPVATEQYGVVADNLQ
29.5\VP1      DDEERFFPSSGVLMFGKQ--GAGKDNVDYS-SVMLTSEEEIKTTNPVATEQYGVVADNLQ
42_15         DDEERFFPSSGVLMFGKQ--GAGKDNVDYS-SVMLTSEEEIKTTNPVATEQYGVVADNLQ
42_8          DDEERFFPSSGVLMFGKQ--GAGKDNVDYS-SVMLTSEEEIKTTNPVATEQYGVVADNLQ
42_13         GDEERFFPSSGVLMFGKQ--GAGKDNVDYS-SVMLTSEEEIKTTNPVATEQYGVVADNLQ
42_3A         DDEERFFPSSGVLMFGKQ--GAGKDNVDYS-SVMLTSEEEIKTTNPVATEQYGVVADNLQ
42_4          DDEERFFPSSGVLMFGKQ--GAGKDNVDYS-SVMLTSEEEIKTTNPVATEQYGVVADNLQ
42_5A         DDEERFFPSSGVLMFGKQ--GAGKDNVDYS-SVMLTSEEEIKTTNPVATEQYGVVADNLQ
42_1B         GDEERFFPSSGVLMFGKQ--GAGKDNVDYS-SVMLTSEEEIKTTNPVATEQYGVVADNLQ
42_5B         DDEERFFPSSGVLMFGKQ--GAGKDNVDYS-SVMLTSEEEIKTTNPVATEQYGVVADNLQ
43_1          DDEERFFPSSGVLMFGKQ--GAGKDNVDYS-SVMLTSEEEIKTTNPVATEQYGVVADNLQ
43_12         DDEERFFPSSGVLMFGKQ--GAGKDNVDYS-SVMLTSEEEIKTTNPVATEQYGVVADNLQ
43_5          DDEERFFPSSGVLMFGKQ--GAGKDNVDYS-SVMLTSEEEIKTTNPVATEQYGVVADNLQ
AAV8          DDEERFFPSNGILIFGKQ--NAARDNADYS-DVMLTSEEEIKTTNPVATEEYGIVADNLQ
43_21         DDDDRFFPSSGVLIFGKQ--GAGNDGVDYS-QVLITDEEEIKATNPVATEEYGAVAINNQ
43_25         DDDDRFFPSSGVLIFGKQ--GAGNDGVDYS-QVLITDEEEIKATNPVATEEYGAVAINNQ
43_23         DDDDRFFPSSGVLIFGKQ--GAGNDGVDYS-QVLITDEEEIKATNPVATEEYGAVAINNQ
43_20         DDDDRFFPSSGVLIFGKQ--GAGNDGVDYS-QVLITDEEEIKATNPVATEEYGAVAINNQ
AAV_9         DDEDRFFPSSGVLIFGKQ--GAGNDGVDYS-QVLITDEEEIKATNPVATEEYGAVAINNQ
24.1          DDEDQFFPINGVLVFGKT--GAAN-KTTLE-NVLMTSEEEIKTTNPVATEEYGVVSSNLQ
42.2REAL      DDEDQFFPINGVLVFGET--GAAN-KTTLE-NVLMTSEEEIKTTNPVATEEYGVVSSNLQ
7.2\VP1       DDEDQFFPINGVLVFGKT--GAAN-KTTLE-NVLMTSEEEIKTTNPVATEEYGVVSSNLQ
27.3\VP1      DDEDQFLPINGVLVFGKT--GAAN-KTTLE-NVLMTSEEEIKTTNPVATEEYGVVSSNLQ
16.3\VP1      DDEGQFFPINGVLVFGKT--GAAN-KTTLE-NVLMTSEEEIKTTNPVATEEYGVVSSNLQ
42_10         DDEDQFFPINGVLVFGKT--GAAN-KTTLE-NVLMTSEEEIKTTNPVATEEYGVVSSNLQ
42_3B         DDEDQFFPINGVLVFGKT--GAAN-KTTLE-NVLMTSEEEIKTTNPVATEQYGVVSSNLQ
42_11         DDEDQFFPINGVLVFGKT--GAAN-KTTLE-NVLMTSEEEIKTTNPVATEEYGVVSSNLQ
F1\VP1        DDEDQFFPINGVLVFGKT--GAAN-KTTLE-NVLMTSEEEIKTTNPVATEEYGVVSSNLQ
F5\VP1@3      DDEDQFFPINGVLVFGKT--GAAN-KTTLE-NVLMTSEEEIKTTNPVATEEYGVVSSNLQ
F3\VP1        DDEDQFFPINGVLVFGKT--GAAN-KTTLE-NVLMTSEEEIKTTNPVATEEYGVVSSNLQ
42_6B         DDEDQFFPINGVLVFGKT--GAAN-KTTLE-NVLMTSEEEIKTTNPVATEEYGVVSSNLQ
42_12         DDEDQFFPINGVLVFGKT--GAAN-KTTLE-NVLMTSEEEIKTTNPVATEEYGVVSSNLQ
AAV5\CAP      LQGSNTYALENTMIFNSQPANPGTTATYLEGNMLITSESETQPVNRVAYNVGGQMATNNQ
```

FIG. 2J

```
                     610       620       630       640       650       660
                ....|....|....|....|....|....|....|....|....|....|....|....|
C1\VP1          NATTAPITGNVTAMGVLPGMVWQNRDIYYQGPIWAKIPHADGHFHPSPLIGGFGLKHPPP
C2\VP1          NATTAPITGNVTAMGVLPGMVWQNRDIYYQGPIWAKIPHADGHFHPSPLIGGFGLKHPPP
C5\VP1@2        NATTAPITGNVTAMGVLPGMVWQNRDIYYQGPIWAKIPHADGHFHPSPLIGGFGLKHPPP
AAV4\VP1        SNSNLPTVDRLTALGAVPGMVWQNRDIYYQGPIWAKIPHTDGHFHPSPLIGGFGLKHPPP
AAV1            SSSTDPATGDVHAMGALPGMVWQDRDVYLQGPIWAKIPHTDGHFHPSPLMGGFGLKNPPP
AAV6\VP1        SSSTDPATGDVHVMGALPGMVWQDRDVYLQGPIWAKIPHTDGHFHPSPLMGGFGLKHPPP
A3_3            SQNTTASYGSVDSQGILPGMVWQDRDVYLQGPIWAKTPHTDGHFHPSPLMGGFGLKHPPP
A3_7            SQNTTASYGSVDSQGILPGMVWQDRDVYLQGPIWAKTPHTDGHFHPSPLMGGFGLKHPPP
A3_4            SQDTTASYGSVDSQGILPGMVWQDRDVYLQGPIWAKTPHTDGHFHPSPLMGGFGLKHPPP
A3_5            SQNTTASYGSVDSQGILPGMVWQDRDVYLQGPIWAKTPHTDGHFHPSPLMGGFGLKHPPP
AAV2            RGNRQAATADVNTQGVLPGMVWQDRDVYLQGPIWAKIPHTDGHFHPSPLMGGFGLKHPPP
AAV3            SSNTAPTTGTVNHQGALPGMVWQDRDVYLQGPIWAKIPHTDGHFHPSPLMGGFGLKHPPP
13.3b\VP1       AANTAAQTQVVNNQGALPGMVWQNRDVYLQGPIWAKIPHTDGNFHPSPLMGGFGLKHPPP
AAV7            AANTAAQTQVVNNQGALPGMVWQNRDVYLQGPIWAKIPHTDGNFHPSPLMGGFGLKHPPP
223_4           AASTAAQTQVVNNQGALPGMVWQNRDVYLQGPIWAKIPHTDGNFHPSPLMGGFGLKHPPP
223_5           AASTAAQTQVVNNQGALPGMVWQNRDVYLQGPIWAKIPHTDGNFHPSPLMGGFGLKHPPP
223_10          AASTAAQTQVVNNQGALPGMVWQNRDVYLQGPIWAKIPHTDGNFHPSPLMGGFGLKHPPP
223_2           AASTAAQTQVVNNQGALPGMVWQNRDVYLQGPIWAKIPHTDGNFHPSPLMGGFGLKHPPP
223_7           AASTAAQTQVVNNQGALPGMVWQNRDVYLQGPIWAKIPHTDGNFHPSPLMGGFGLKHPPP
223_6           AASTAAQTQVVNNQGALPGMVWQNRDVYLQGPIWAKIPHTDGNFHPSPLMGGFGLKHPPP
44_1            QQNAAPIVGAVNSQGALPGMVWQNRDVYLQGPIWAKIPHTDGNFHPSPLMGGFGLKHPPP
44_5            QQNAAPIVGAVNSQGALPGMVWQNRDVYLQGPIWAKIPHTDGNFHPSPLMGGFGLKHPPP
44_2            QQNAAPIVGAVNSQGALPGMVWQNRDVYLQGPIWAKIPHTDGNFHPSPLMGGFGLKHPPP
29.3\VP1        QQNAAPIVGAVNSQGALPGMVWQNRDVYLQGPIWAKIPHTDGNFHPSPLMGGFGLKHPPP
29.5\VP1        QQNAAPIVGAVNSQGALPGMVWQNRDVYLQGPIWAKIPHTDGNFHPSPLMGGFGLKHPPP
42_15           QQNAAPIVGAVNSQGALPGMVWQNRDVYLQGPIWAKIPHTDGNFHPSPLMGGFGLKHPPP
42_8            QQNAAPIVGAVNSQGALPGMVWQNRDVYLQGPIWAKIPHTDGNFHPSPLMGGFGLKHPPP
42_13           QQNAAPIVGAVNSQGALPGMVWQNRDVYLQGPIWAKIPHTDGNFHPSPLMGGFGLKHPPP
42_3A           QQNAAPIVGAVNSQGALPGMVWQNRDVYLQGPIWAKIPHTDGNFHPSPLMGGFGLKHPPP
42_4            QQNAAPIVGAVNSQGALPGMVWQNRDVYLQGPIWAKIPHTDGNFHPSPLMGGFGLKHPPP
42_5A           QQNAAPIVGAVNSQGALPGMAWQNRDVYLQGPIWAKIPHTDGNFHPSPLMGGFGLKHPPP
42_1B           QQNAAPIVGAVNSQGALPGMVWQNRDVYLQGPIWAKIPHTDGNFHPSPLMGGFGLKHPPP
42_5B           QQNAAPIVGAVNSQGALPGMVWQNRDVYLQGPIWAKIPHTDGNFHPSPLMGGFGLKHPPP
43_1            QTNGAPIVGTVNSQGALPGMVWQNRDVYLQGPIWAKIPHTDGNFHPSPLMGGFGLKHPPP
43_12           QTNGAPIVGTVNSQGALPGMVWQNRDVYLQGPIWAKIPHTDGNFHPSPLMGGFGLKHPPP
43_5            QTNGAPIVGTVNSQGALPGMVWQNRDVYLQGPIWAKIPHTDGNFHPSPLMGGFGLKHPPP
AAV8            QQNTAPQIGTVNSQGALPGMVWQNRDVYLQGPIWAKIPHTDGNFHPSPLMGGFGLKHPPP
43_21           AANTQAQTGLVHNQGVIPGMVWQNRDVYLQGPIWAKIPHTDGNFHPSPLMGGFGLKHPPP
43_25           AANTQAQTGLVHNQGVIPGMVWQNRDVYLQGPIWAKIPHTDGNFHPSPLMGGFGLKHPPP
43_23           AANTQAQTGLVHNQGVIPGMVWQNRDVYLQGPIWAKIPHTDGNFHPSPLMGGFGLKHPPP
43_20           AANTQAQTGLVHNQGVIPGMVWQNRDVYLQGPIWAKIPHTDGNFHPSPLMGGFGLKHPPP
AAV_9           AANTQAQTGLVHNQGVIPGMVWQNRDVYLQGPIWAKIPHTDGNFHPSPLMGGFGLKHPPP
24.1            SSTAGPQTQTVNSQGALPGMVWQNRDVCLQGPIWAKIPHTDGNFHPSPLMGGFGLKHPPP
42.2REAL        SSTAGPQTQTVNSQGALPGMVWQNRDVYLQGPIWAKIPHTDGNFHPSPLMGGFGLKHPPP
7.2\VP1         SSTAGPQTQTVNSQGALPGMVWQNRDVYLQGPIWAKIPHTDGNFHPSPLMGGFGLKHPPP
27.3\VP1        SSTAGPRTQTVNSQGALPGMVWQNRDVYLQGPIWAEIPHTDGNFHPSPLMGGFGLKHPPP
16.3\VP1        SSTAGPQTQTVNSQGALPGMVWQNRDVYLQGPIWAKIPHTDGNFHPSPLMGGFGLKHPPP
42_10           SSTAGPQTQTVNSQGALPGMVWQNRDVYLQGPIWAKIPHTDGNFHPSPLMGGFGLKHPPP
42_3B           SSTAGPQTQTVNSQGALPGMVWQNRDVYLQGPIWAKIPHTDGNFHPSPLMGGFGLKHPPP
42_11           SSTAGPQTQTVNSQGALPGMVWQNRDVYLQGPIWAKIPHTDGNFHPSPLMGGFGLKHPPP
F1\VP1          PSTAGPQSQTINSQGALPGMVWQNRDVYLQGPIWAKIPHTDGNFHPSPLMGGFGLKHPPP
F5\VP1@3        SSTAGPQSQTINSQGALPGMVWQNRDVYLQGPIWAKIPHTDGNFHPSPLMGGFGLEHPPP
F3\VP1          SSTAGPQSQTINSQGALPGMVWQNRDVYLQGPIWAKIPHTDGNFHPSPLMGGFGLKHPPP
42_6B           SSTAGPQTQTVNSQGALPGMVWQNRDVYLQGPIWAKIPHTDGNFHPSPLMDGFGLKHPPP
42_12           SSTAGPQTQTVNSQGALPGMVWQNRDVYLQGPIWAKIPHTDGNFHPSPLMGGFGLKHPPP
AAV5\CAP        SSTTAPATGTYNLQEIVPGSVWMERDVYLQGPIWAKIPETGAHFHPSPAMGGFGLKHPPP
```

FIG. 2K

```
                          670       680       690       700       710       720
                 ....|.... ....|....|....|....|....|....|....|....|....|....|
C1\VP1           QIFIKNTPVPANPATTFTAARVDSFITQYSTGQVAVQIEWEIEKERSKRWNPEVQFTSNY
C2\VP1           QIFIKNTPVPANPATTFTAARVDSFITQYSTGQVAVQIEWEIEKERSKRRNPEVQFTSNY
C5\VP1@2         QIFIKNTPVPAYPATTFTAARVDSFITQYSTGQVAVQIEWEIEKERSKRWNPEVQFTSNC
AAV4\VP1         QIFIKNTPVPANPATTFSSTPVNSFITQYSTGQVSVQIDWEIQKERSKRWNPEVQFTSNY
AAV1             QILIKNTPVPANPPAEFSATKFASFITQYSTGQVSVEIEWELQKENSKRWNPEVQYTSNY
AAV6\VP1         QILIKNTPVPANPPAEFSATKFASFITQYSTGQVSVEIEWELQKENSKRWNPEVQYTSNY
A3_3             QILIKNTPVPANPATTFTPGKFASFITQYSTGQVSVEIEWELQKENSKRWNPEIQYTSNY
A3_7             QILIKNTPVPANPATTFTPGKFASFITQYSTGQVSVEIEWELQKENSKRWNPEIQYTSNY
A3_4             QILIKNTPVPANPATTFTPGKFASFITQYSTGQVSVEIEWELQKENSKRWNPEIQYTSNY
A3_5             QILIKNTPVPANPATTFTPGKFASFITQYSTGQVSVEIEWELQKENSKRWNPEIQYTSNY
AAV2             QILIKNTPVPANPSTTFSAAKFASFITQYSTGQVSVEIEWELQKENSKRWNPEIQYTSNY
AAV3             QIMIKNTPVPANPPTTFSPAKFASFITQYSTGQVSVEIEWELQKENSKRWNPEIQYTSNY
13.3b\VP1        QILIKNTPVPANPPEVFTPAKFASFITQYSTGQVSVEIEWELQKENSKRWDPEIQYTSNF
AAV7             QILIKNTPVPANPPEVFTPAKFASFITQYSTGQVSVEIEWELQKENSKRWNPEIQYTSNF
223_4            QILIKNTPVPANPPEVFTPAKFASFITQYSTGQVSVEIEWELQKENSKRWNPEIQYTSNF
223_5            QILIKNTPVPANPPEVFTPAKFASFITQYSTGQVSVEIEWELQKENSKRWNPEIQYTSNF
223_10           QILIKNTPVPANPPEVFTPAKFASFITQYSTGQVSVEIEWELQKENSKRWNPEIQYTSNF
223_2            QILIKNTPVPANPPEVFTPAKFASFITQYSTGQVSVEIEWELQKENSKRWNPEIQYTSNF
223_7            QILIKNTPVPANPPEVFTPAKIASFITQYSTGQVSVEIEWELQKENSKRWNPEIQYTSNF
223_6            QILIKNTPVPANPPEVFTPAKLASFITQYSTGQVSVEIEWELQKENSKRWNPEIQYTSNF
44_1             QILIKNTPVPADPPTTFSQAKLASFITQYSTGQVSVEIEWELQKENSKRWNPEIQYTSNY
44_5             QILIKNTPVPADPPTTFSQAKLASFITQYSTGQVSVEIEWELQKENSKRWNPEIQYTSNY
44_2             QILIKNTPVPADPPTTFSQAKLASFITQYSTGQVSVEIEWELQKENSKRWNPEIQYTSNY
29.3\VP1         QILIKNTPVPADPPTTFSQAKLASFITQYSTGQVSVEIEWELQKENSKRWNPEIQYTSNY
29.5\VP1         QILIKNTPVPADPPTTFSQAKLASFITQYSTGQVSVEIEWELQKENSKRWNPEIQYTSNY
42_15            QILIKNTPVPADPPTTFSQAKLASFITQYSTGQVSVEIEWELQKENSKRWNPEIQYTSNY
42_8             QILIKNTPVPADPPTTFSQAKLASFITQYSTGQVSVEIEWELQKENSKRWNPEIQYTSNY
42_13            QILIKNTPVPADPPTTFSQAKLASFITQYSTGQVSVEIEWELQKENSKRWNPEIQYTSNY
42_3A            QILIKNTPVPADPPTTFSQAKLASFITQYSTGQVSVEIEWELQKENSKRWNPEIQYTSNY
42_4             QILIKNTPVPADPPTTFSQAKPASFITQYSTGQVSVEIEWELQKENSKRWNPEIQYTSNY
42_5A            QILIKNTPVPADPPTTFSQAKLASFITQYSTGQVSVEIEWELQKENSKRWNPEIQYTSNY
42_1B            QILIKNTPVPADPPTTFSQAKLASFITQYSTGQVSVEIEWELQKENSKRWNPEIQYTSNY
42_5B            QILIKNTPVPADPPTTFSQAKLASFITQYSTGQVSVEIEWELQKENSKRWNPEIQYTSNY
43_1             QILVKNTPVPADPPTTFSQAKLASFITQYSTGQVSVEIEWELQKENSKRWNPEIQYTSNY
43_12            QILVKNTPVPADPPTTFSQAKLASFITQYSTGQVSVEIEWELQKENSKRWNPEIQYTSNY
43_5             QILVKNTPVPADPPTTFSQAKLASFITQYSTGQVSVEIEWELQKENSKRWNPEIQYTSNY
AAV8             QILIKNTPVPADPPTTFNQSKLNSFITQYSTGQVSVEIEWELQKENSKRWNPEIQYTSNY
43_21            QILIKNTPVPADPPLTFNQAKLNSFITQYSTGQVSVEIEWELQKENSKRWNPEIQYTSNY
43_25            QILIKNTPVPADPPLTFNQAKLNSFITQYSTGQVSVEIEWELQKENSKRWNPEIQYTSNY
43_23            QILIKNTPVPADPPLTFNQAKLNSFITQYSTGQVSVEIEWELQKENSKRWNPEIQYTSNY
43_20            QILIKNTPVPADPPLTFNQAKLNSFITQYSTGQVSVEIEWELQKENSKRWNPEIQYTSNY
AAV_9            QILIKNTPVPADPPLTFNQAKLNSFITQYSTGQVSVEIEWELQKENSKRWNPEIQYTSNY
24.1             QILIKNTPVPANPPEVFTPAKFASFITQYSTGQVSVEIEWELQKENSKRWNPEIQYTSNY
42.2REAL         QILIKNTPVPANPPEVFTPAKFASFITQYSTGQVSVEIEWELQKENSKRWNPEIQYTSNY
7.2\VP1          QILIKNTPVPANPPEVFTPAKFASFITQYSTGQVSVEIEWELQKENSKRWNPEIQYTSNY
27.3\VP1         QILIKNTPVPANPPEVFTPAKFASFITQYSTGQVSVEIEWELQKENSKRWNPEIQYTSNY
16.3\VP1         QILIKNTPVPANPPGVFTPALFASFITQYSTGQVSVEIEWELQKENSKRWNPEIQYTSNY
42_10            QILIKNTPVPANPPEVFTPAKFASFITQYSTGQVSVEIEWELQKENSKRWNPEIQYTSNY
42_3B            QILIKNTPVPANPPEVFTPAKFASFITQYSTGQVSVEIEWELQKENSKRWNPEIQYTSNY
42_11            QILIKNTPVPANPPEVFTPAKFASFITQYSTGQVSVEIEWELQKENSKRWNPEIQYTSNY
F1\VP1           QILIKNTPVPANPPEVFTPAKFASFITQYSTGQVSVEIEWELQKENSKRWNPEIQYTSNY
F5\VP1@3         QILIKNTPVPANPPEVFTPAKFASFITQYSTGQVSVEIEWELQKENSKRWNPEIQYTSNY
F3\VP1           QILIKNTPVPANPPEVFTPAKFASFITQYSTGQVSVEIEWELQKENSKRWNPEIQYTSNY
42_6B            QILIKNTPVPANPPEVFTPAKFASFITQYSTGQVSVEIEWELQKENSKRWNPEIQYTSNY
42_12            QILIK-------------------------------------------------YTSNY
AAV5\CAP         MMLIKNTPVPGN-ITSFSDVPVSSFITQYSTGQVTVEMEWELKKENSKRWNPEIQYTNNY
```

FIG. 2L

```
                        730       740       750
                 ....|....|....|....|....|....|.
C1\VP1           GNQSSMLWAPDTTGKYTEPRVIGSRYLTNHL
C2\VP1           GNQSSMLWAPDTTGKYTEPRVIGSRYLTNHL
C5\VP1@2         GNQSSMLWAPDTTGKYTEPRVIGSRYLTNHL
AAV4\VP1         GQQNSLLWAPDAAGKYTEPRAIGTRYLTHHL
AAV1             AKSANVDFTVDNNGLYTEPRPIGTRYLTRPL
AAV6\VP1         AKSANVDFTVDNNGLYTEPRPIGTRYLTRPL
A3_3             NKSVNVEFTVDANGVYSEPRPIGTRYLTRNL
A3_7             NKSVNVEFTVDANGVYSEPRPIGTRYLTRNL
A3_4             NKSVNVEFTVDANGVYSEPRPIGTRYLTRNL
A3_5             NKSVNVEFTVDANGVYSEPRPIGTRYLTRNL
AAV2             NKSVNVDFTVDTNGVYSEPRPIGTRYLTRNL
AAV3             NKSVNVDFTVDTNGVYSEPRPIGTRYLTRNL
13.3b\VP1        EKQTGVDFAVDSQGVYSEPRPIGTRYLTRNL
AAV7             EKQTGVDFAVDSQGVYSEPRPIGTRYLTRNL
223_4            DKQTGVDFAVDSQGVYSEP------------
223_5            DKQTGVDFAVDSQGVYSEP------------
223_10           DKQTGVDFAVDSQGVYSEP------------
223_2            DKQTGVDFAVDSQGVYSEP------------
223_7            DKQTGVDFAVDSQGVYSEP------------
223_6            DKQTGVDFAVDSQGVYSEP------------
44_1             YKSTNVDFAVNTDGTYSEPRPIGTRYLTRNL
44_5             YKSTNVDFAVNTDGTYSEPRPIGTRYLTRNL
44_2             YKSTNVDFAVNTDGTYSEPRPIGTRYLTRNL
29.3\VP1         YKSTNVDFAVNTDGTYSEPRPIGTRYLTRNL
29.5\VP1         YKSTNVDFAVNTDGTYSEPRPIGTRYLTRNL
42_15            YKSTNVDFAVNTEGTYSEPRPIGTRYLTRNL
42_8             YKSTNVDFAVNTEGTYSEPRPIGTRYLTRNL
42_13            YKSTNVDFAVNTEGTYSEPRPIGTRYLTRSL
42_3A            YKSTNVDFAVNTEGTYSEPRPIGTRYLTRNL
42_4             YKSTNVDFAVNTEGTYSEPRPIGTRYLTRNL
42_5A            YKSTNVDFAVNTEGTYSEPRPIGTRYLTRNL
42_1B            YKSTNVDFAVNTEGTYSEPRPIGTRYLTRNL
42_5B            YKSTNVDFAVNTEGTYSEPRPIGTRYLTRNL
43_1             YKSTNVDFAVNTEGTYSEPRPIGTRYLTRNL
43_12            YKSTNVDFAVNTEGTYSEPRPIGTRYLTRNL
43_5             YKSTNVDFAVNTEGTYSEPRPIGTRYLTRNL
AAV8             YKSTSVDFAVNTEGVYSEPRPIGTRYLTRNL
43_21            YKSTNVDFAVNTEGVYSEPRPIGTRYLTRNL
43_25            YKSTNVDFAVNTEGVYSEPRPIGTRYLTRNL
43_23            YKSTNVDFAVNTEGVYSEPRPIGTRYLTRNL
43_20            YKSTNVDFAVNTEGVYSEPRPIGTRYLTRNL
AAV_9            YKSTNVDFAVNTEGVYSEPRPIGTRYLTRNL
24.1             AKSNNVEFAVNNEGVYTEPRPIGTRYLTRNL
42.2REAL         AKSNNVEFAVNNEGVYTEPRPIGTRYLTRNL
7.2\VP1          AKSNNVEFAVNNEGVYTEPRPIGTRYLTRNL
27.3\VP1         AKSNNVEFAVNNEGVYTEPRPIGTRYLTRNL
16.3\VP1         AKSNNVEFAVNNEGVYTEPRPIGTRYLTRNL
42_10            AKSNNVEFAVNNEGVYTEPRPIGTRYLTRNL
42_3B            AKSNNVEFAVNNEGVYTEPRPIGTRYLTRNL
42_11            AKSNNVEFAVNNEGVYTEPRPIGTRYLTRNL
F1\VP1           AKSNNVEFAVNPDGVYTEPRPIGTRYLPRNL
F5\VP1@3         AKSNNVEFAVNPDGVYTEPRPIGTRYLTRNL
F3\VP1           AKSNNVEFAVNPDGVYTEPRPIGTRYLTRNL
42_6B            AKSNNVEFAVNNEGVYTEPRPIGTRYLTRNL
42_12            YKSTNVDFAVNTEGTYSEPRPIGTRYLTRNL
AAV5\CAP         NDPQFVDFAPDSTGEYRTTRPIGTRYLTRPL
```

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
            50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
            85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
            115                 120                 125

Pro Asn Trp Phe Ala Val Thr Lys Thr Arg Asn Gly Ala Gly Gly Gly
            130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
            165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
            210                 215                 220
```

Fig. 3B

```
Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
            245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
            275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445
```

Fig. 3C

```
Glu Leu Thr Arg Arg Leu Glu His Asp Phe Gly Lys Val Thr Lys Gln
    450                 455                 460
Glu Val Lys Glu Phe Phe Arg Trp Ala Ser Asp His Val Thr Glu Val
465                 470                 475                 480
Ala His Glu Phe Tyr Val Arg Lys Gly Gly Ala Ser Lys Arg Pro Ala
                485                 490                 495
Pro Asp Asp Ala Asp Ile Ser Glu Pro Lys Arg Ala Cys Pro Ser Val
            500                 505                 510
Ala Asp Pro Ser Thr Ser Asp Ala Glu Gly Ala Pro Val Asp Phe Ala
        515                 520                 525
Asp Arg Tyr Gln Asn Lys Cys Ser Arg His Ala Gly Met Ile Gln Met
    530                 535                 540
Leu Phe Pro Cys Lys Thr Cys Glu Arg Met Asn Gln Asn Phe Asn Ile
545                 550                 555                 560
Cys Phe Thr His Gly Val Arg Asp Cys Leu Glu Cys Phe Pro Gly Val
                565                 570                 575
Ser Glu Ser Gln Pro Val Val Arg Lys Lys Thr Tyr Arg Lys Leu Cys
            580                 585                 590
Ala Ile His His Leu Leu Gly Arg Ala Pro Glu Ile Ala Cys Ser Ala
        595                 600                 605
Cys Asp Leu Val Asn Val Asp Leu Asp Asp Cys Val Ser Glu Gln
    610                 615                 620
```

METHOD OF DETECTING AND/OR IDENTIFYING ADENO-ASSOCIATED VIRUS (AAV) SEQUENCES AND ISOLATING NOVEL SEQUENCES IDENTIFIED THEREBY

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recent studies suggest that AAV vectors may be the preferred vehicle for gene therapy. To date, there have been 6 different serotypes of AAVs isolated from human or non-human primates (NHP) and well characterized. Among them, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B.

What are desirable are AAV-based constructs for gene delivery.

SUMMARY OF THE INVENTION

In one aspect, the invention provides a novel method of detecting and identifying AAV sequences from cellular DNAs of various human and non-human primate (NHP) tissues using bioinformatics analysis, PCR based gene amplification and cloning technology, based on the nature of latency and integration of AAVs in the absence of helper virus co-infection.

In another aspect, the invention provides method of isolating novel AAV sequences detected using the above described method of the invention. The invention further comprises methods of generating vectors based upon these novel AAV serotypes, for serology and gene transfer studies solely based on availability of capsid gene sequences and structure of rep/cap gene junctions.

In still another aspect, the invention provides a novel method for performing studies of serology, epidemiology, biodistribution and mode of transmission, using reagents according to the invention, which include generic sets of primers/probes and quantitative real time PCR.

In yet another aspect, the invention provides a method of isolating complete and infectious genomes of novel AAV serotypes from cellular DNA of different origins using RACE and other molecular techniques.

In a further aspect, the invention provides a method of rescuing novel serotypes of AAV genomes from human and NHP cell lines using adenovirus helpers of different origins.

In still a further aspect, the invention provides novel AAV serotypes, vectors containing same, and methods of using same.

These and other aspects of the invention will be readily apparent from the following detailed description of the invention.

BRIEF DESCRIPTION OF THE DRAWINGS

FIGS. 2A through 2M are an alignment of the amino acid sequences of the proteins of the vp1 capsid proteins of previously published AAV serotypes 1 [SEQ ID NO:64], AAV2 [SEQ ID NO:70], AAV3 [SEQ ID NO: 71], AAV4 [SEQ ID NO:63], AAV5 [SEQ ID NO:114], and AAV6 [SEQ ID NO:65] and novel AAV sequences of the invention, including: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], 42-12 [SEQ ID NO: 113]. Novel serotypes AAV8

Figure 1B:
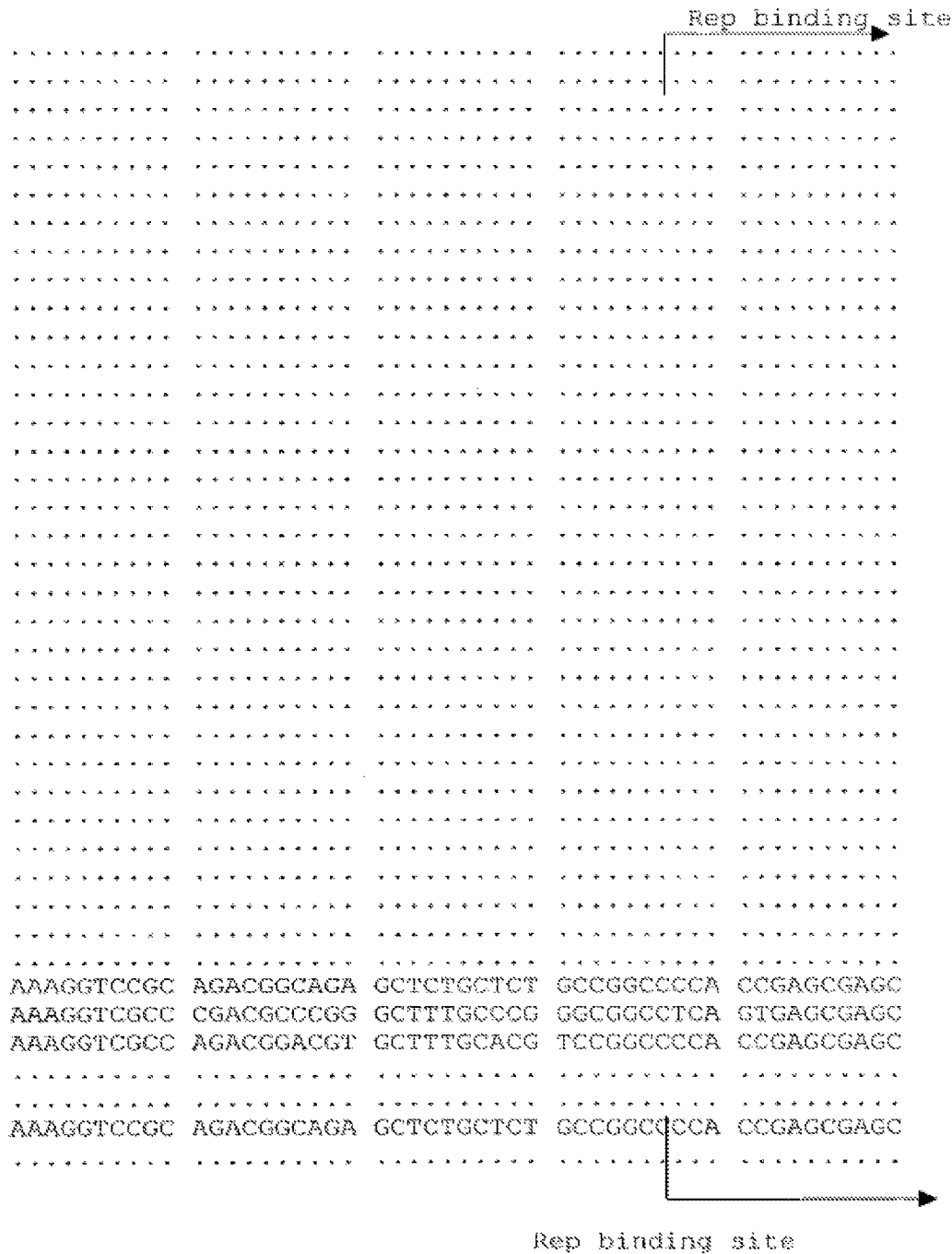
FIGS. 1A through 1AAAR provide an alignment of the nucleic acid sequences encoding at least the cap proteins for the AAV serotypes. The full-length sequences including the ITRs, the rep region, and the capsid region are provided for novel AAV serotype 7 [SEQ ID NO:1], and for previously published AAV1 [SEQ IN NO:6], AAV2 [SEQ ID NO:7]; and AAV3 [SEQ ID NO:8]. Novel AAV serotypes AAV8 [SEQ ID NO:4] and AAV9 [SEQ ID NO:5] are the subject of co-filed applications. The other novel clones of the invention provided in this alignment include: 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], 44.2 [SEQ ID NO: 59]. The nucleotide sequences of the signature regions of AAV10 [SEQ ID NO: 117], AAV11 [SEQ ID NO: 118] and AAV12 [SEQ ID NO:119] are provided in this figure. Critical landmarks in the structures of AAV genomes are shown. Gaps are demonstrated by dots. The 3' ITR of AAV1 [SEQ ID NO:6] is shown in the same configuration as in the published sequences. TRS represents terminal resolution site. Notice that AAV7 is the only AAV reported that uses GTG as the initiation codon for VP3.

[SEQ ID NO:95] and AAV9 [SEQ ID NO:100] are the subject of co-filed patent applications.

FIGS. 3A through 3C provide the amino acid sequences of the AAV7 rep proteins [SEQ ID NO:3].

DETAILED DESCRIPTION OF THE INVENTION

In the present invention, the inventors have found a method which takes advantage of the ability of adeno-associated virus (AAV) to penetrate the nucleus, and, in the absence of a helper virus co-infection, to integrate into cellular DNA and establish a latent infection. This method utilizes a polymerase chain reaction (PCR)-based strategy for detection, identification and/or isolation of sequences of AAVs from DNAs from tissues of human and non-human primate origin as well as from other sources. Advantageously, this method is also suitable for detection, identification and/or isolation of other integrated viral and non-viral sequences, as described below.

The invention further provides nucleic acid sequences identified according to the methods of the invention. One such adeno-associated virus is of a novel serotype, termed herein serotype 7 (AAV7). Other novel adeno-associated virus serotypes provided herein include AAV10, AAV11, and AAV12. Still other novel AAV serotypes identified according to the methods of the invention are provided in the present specification. See, Figures and Sequence Listing, which is incorporated by reference.

Also provided are fragments of these AAV sequences. Among particularly desirable AAV fragments are the cap proteins, including the vp1, vp2, vp3, the hypervariable regions, the rep proteins, including rep 78, rep 68, rep 52, and rep 40, and the sequences encoding these proteins. Each of these fragments may be readily utilized in a variety of vector systems and host cells. Such fragments may be used alone, in combination with other AAV sequences or fragments, or in combination with elements from other AAV or non-AAV viral sequences. In one particularly desirable embodiment, a vector contains the AAV cap and/or rep sequences of the invention.

As described herein, alignments are performed using any of a variety of publicly or commercially available Multiple Sequence Alignment Programs, such as AClustal W≅, accessible through Web Servers on the internet. Alternatively, Vector NTI utilities are also used. There are also a number of algorithms known in the art which can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similar programs are available for amino acid sequences, e.g., the "Clustal X" program. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The term "substantial homology" or "substantial similarity," when referring to amino acids or fragments thereof, indicates that, when optimally aligned with appropriate amino acid insertions or deletions with another amino acid, there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

The AAV sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV sequences of the invention.

As described herein, the vectors of the invention containing the AAV capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below. As used throughout this specification and the claims, the terms A comprising≅ and "including" and their variants are inclusive of other components, elements, integers, steps and the like. Conversely, the term "consisting" and its variants is exclusive of other components, elements, integers, steps and the like.

I. Methods of the Invention

A. Detection of Sequences Via Molecular Cloning

In one aspect, the invention provides a method of detecting and/or identifying target nucleic acid sequences in a sample. This method is particularly well suited for detection of viral sequences which are integrated into the chromosome of a cell, e.g., adeno-associated viruses (AAV) and retroviruses, among others. The specification makes reference to AAV, which is exemplified herein. However, based on this information, one of skill in the art may readily perform the methods of the invention on retroviruses [e.g., feline leukemia virus (FeLV), HTLVI and HTLVII], and lentivirinae [e.g., human immunodeficiency virus (HIV), simian immunodeficiency virus (SIV), feline immunodeficiency virus (FIV), equine infectious anemia virus, and spumavirinal)], among others. Further, the method of the invention may also be used for detection of other viral and non-viral sequences, whether integrated or non-integrated into the genome of the host cell.

As used herein, a sample is any source containing nucleic acids, e.g., tissue, tissue culture, cells, cell culture, and biological fluids including, without limitation, urine and blood. These nucleic acid sequences may be DNA or RNA from plasmids, natural DNA or RNA from any source, including bacteria, yeast, viruses, and higher organisms such as plants or animals. DNA or RNA is extracted from the sample by a variety of techniques known to those of skill in the art, such as those described by Sambrook, Molecular Cloning: A Laboratory Manual (New York: Cold Spring Harbor Laboratory). The origin of the sample and the method by which the nucleic acids are obtained for application of the method of the invention is not a limitation of the present invention. Optionally, the method of the invention can be performed directly on the source of DNA, or on nucleic acids obtained (e.g., extracted) from a source.

The method of the invention involves subjecting a sample containing DNA to amplification via polymerase chain reaction (PCR) using a first set of primers specific for a first region of double-stranded nucleic acid sequences, thereby obtaining amplified sequences.

As used herein, each of the Aregions≈ is predetermined based upon the alignment of the nucleic acid sequences of at least two serotypes (e.g., AAV) or strains (e.g., lentiviruses), and wherein each of said regions is composed of sequences having a 5' end which is highly conserved, a middle which is preferably, but necessarily, variable, and a 3' end which is highly conserved, each of these being conserved or variable relative to the sequences of the at least two aligned AAV serotypes. Preferably, the 5' and/or 3' end is highly conserved over at least about 9, and more preferably, at least 18 base pairs (bp). However, one or both of the sequences at the 5= or 3=end may be conserved over more than 18 bp, more than 25 bp, more than 30 bp, or more than 50 bp at the 5' end. With respect to the variable region, there is no requirement for conserved sequences, these sequences may be relatively conserved, or may have less than 90, 80, or 70% identity among the aligned serotypes or strains.

Each of the regions may span about 100 bp to about 10 kilobase pairs in length. However, it is particularly desirable that one of the regions is a Asignature region≈, i.e., a region which is sufficiently unique to positively identify the amplified sequence as being from the target source. For example, in one embodiment, the first region is about 250 bp in length, and is sufficiently unique among known AAV sequences, that it positively identifies the amplified region as being of AAV origin. Further, the variable sequences within this region are sufficiently unique that can be used to identify the serotype from which the amplified sequences originate. Once amplified (and thereby detected), the sequences can be identified by performing conventional restriction digestion and comparison to restriction digestion patterns for this region in any of AAV1, AAV2, AAV3, AAV4, AAV5, or AAV6, or that of AAV7, AAV10, AAV11, AAV12, or any of the other novel serotypes identified by the invention, which is predetermined and provided by the present invention.

Given the guidance provided herein, one of skill in the art can readily identify such regions among other integrated viruses to permit ready detection and identification of these sequences. Thereafter, an optimal set of generic primers located within the highly conserved ends can be designed and tested for efficient amplification of the selected region from samples. This aspect of the invention is readily adapted to a diagnostic kit for detecting the presence of the target sequence (e.g., AAV) and for identifying the AAV serotype, using standards which include the restriction patterns for the AAV serotypes described herein or isolated using the techniques described herein. For example, quick identification or molecular serotyping of PCR products can be accomplished by digesting the PCR products and comparing restriction patterns.

Figure 1E:
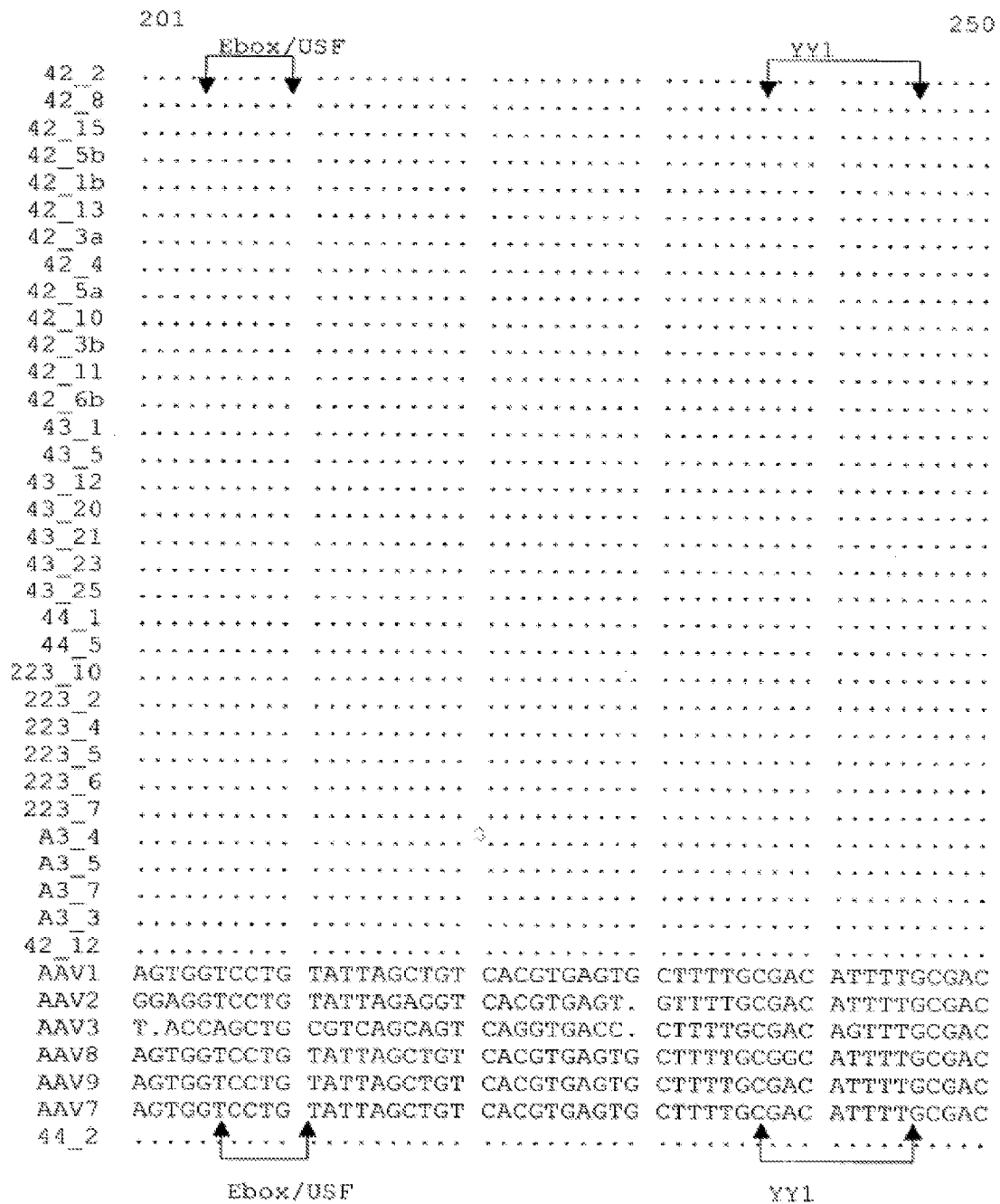
Figure 1F:
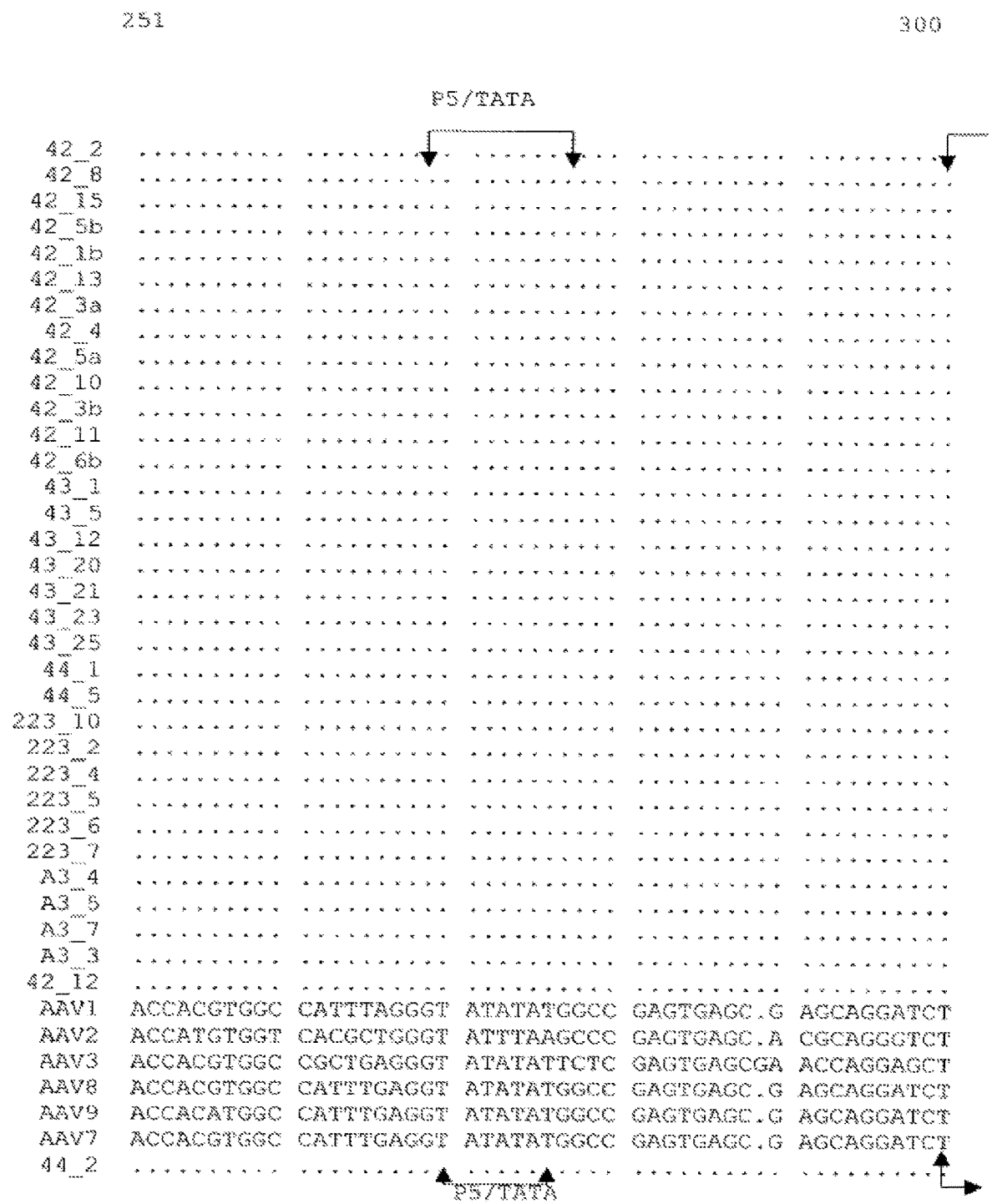
Figure 1G:
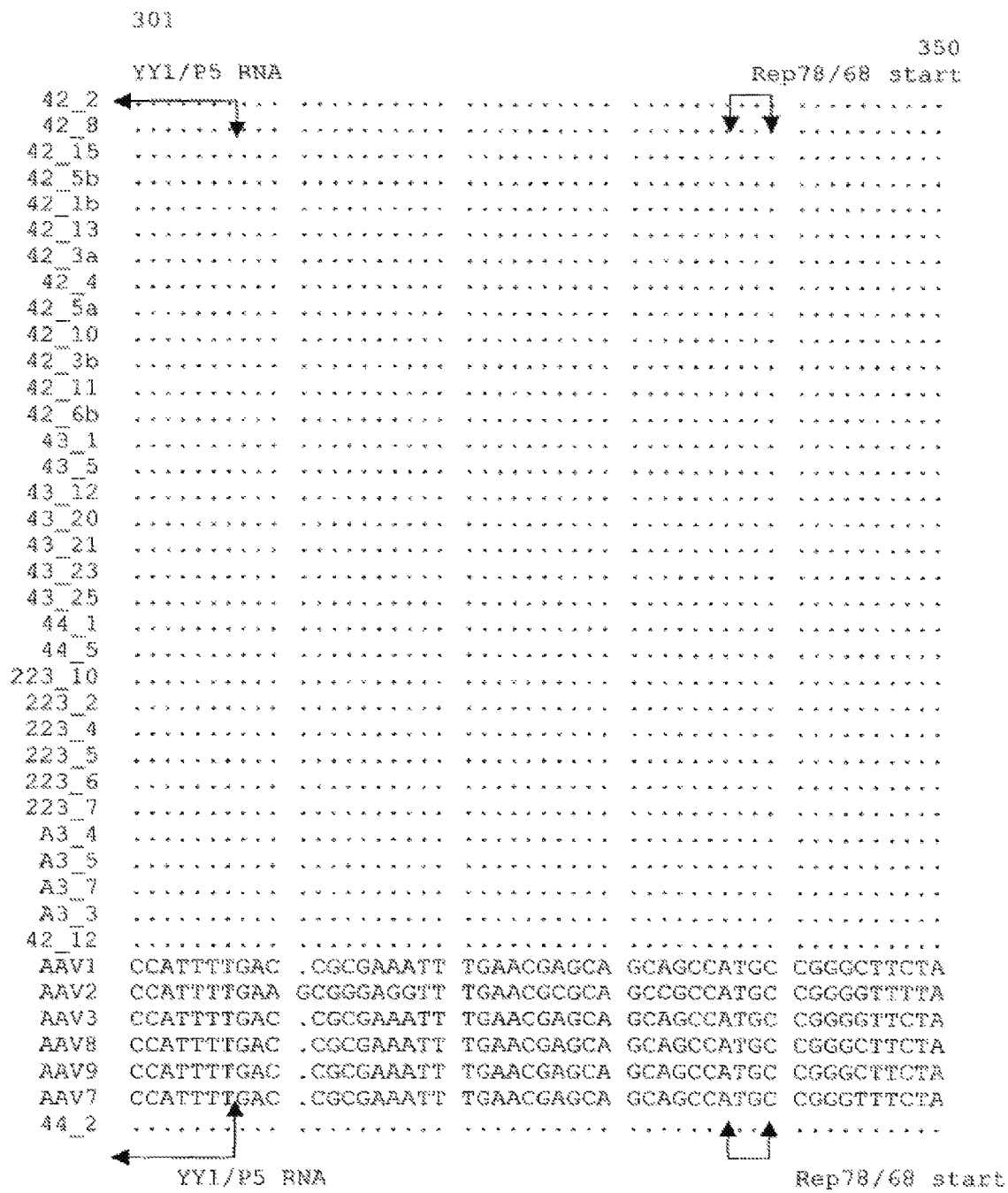

Thus, in one embodiment, the "signature region" for AAV spans about bp 2800 to about 3200 of AAV 1 [SEQ ID NO:6], and corresponding base pairs in AAV 2, AAV3, AAV4, AAV5, and AAV6. More desirably, the region is about 250 bp, located within bp 2886 to about 3143 bp of AAV 1 [SEQ ID NO:6], and corresponding base pairs in AAV 2 [SEQ ID NO:7], AAV3 [SEQ ID NO8], and other AAV serotypes. See, FIG. 1. To permit rapid detection of AAV in the sample, primers which specifically amplify this signature region are utilized. However, the present invention is not limited to the exact sequences identified herein for the AAV signature region, as one of skill in the art may readily alter this region to encompass a shorter fragment, or a larger fragment of this signature region.

The PCR primers are generated using techniques known to those of skill in the art. Each of the PCR primer sets is composed of a 5' primer and a 3' primer. See, e.g., Sambrook et al, cited herein. The term "primer" refers to an oligonucleotide which acts as a point of initiation of synthesis when placed under conditions in which synthesis of a primer extension product which is complementary to a nucleic acid strand is induced. The primer is preferably single stranded. However, if a double stranded primer is utilized, it is treated to separate its strands before being used to prepare extension products. The primers may be about 15 to 25 or more nucleotides, and preferably at least 18 nucleotides. However, for certain applications shorter nucleotides, e.g., 7 to 15 nucleotides are utilized.

The primers are selected to be sufficiently complementary to the different strands of each specific sequence to be amplified to hybridize with their respective strands. Therefore, the primer sequence need not reflect the exact sequence of the region being amplified. For example, a non-complementary nucleotide fragment may be attached to the 5' end of the primer, with the remainder of the primer sequence being completely complementary to the strand. Alternatively, non-complementary bases or longer sequences can be interspersed into the primer, provided that the primer sequence has sufficient complementarity with the sequence of the strand to be amplified to hybridize therewith and form a template for synthesis of the extension product of the other primer.

The PCR primers for the signature region according to the invention are based upon the highly conserved sequences of two or more aligned sequences (e.g., two or more AAV serotypes). The primers can accommodate less than exact identity among the two or more aligned AAV serotypes at the 5' end or in the middle. However, the sequences at the 3' end of the primers correspond to a region of two or more aligned AAV serotypes in which there is exact identity over at least five, preferably, over at least nine base pairs, and more preferably, over at least 18 base pairs at the 3' end of the primers. Thus, the 3' end of the primers is composed of sequences with 100% identity to the aligned sequences over at least five nucleotides. However, one can optionally utilize one, two, or more degenerate nucleotides at the 3' end of the primer.

For example, the primer set for the signature region of AAV was designed based upon a unique region within the AAV capsid, as follows. The 5' primer was based upon nt 2867-2891 of AAV2 [SEQ ID NO:7], 5'-GGTAATTCCTC-CGGAAATTGGCATT3'. See, FIG. 1. The 3' primer was designed based upon nt 3096-3122 of AAV2 [SEQ ID NO:7], 5'-GACTCATCAACAACAACTGGGGATTC-3'. However, one of skill in the art may have readily designed the primer set based upon the corresponding regions of AAV 1, AAV3, AAV4, AAV5, AAV6, or based upon the information provided herein, AAV7, AAV10, AAV11, AAV12, or another novel AAV of the invention. In addition, still other primer sets can be readily designed to amplify this signature region, using techniques known to those of skill in the art.

B. Isolation of Target Sequences

As described herein, the present invention provides a first primer set which specifically amplifies the signature region of the target sequence, e.g., an AAV serotype, in order to permit detection of the target. In a situation in which further sequences are desired, e.g., if a novel AAV serotype is identified, the signature region may be extended. Thus, the invention may further utilize one or more additional primer sets.

Suitably, these primer sets are designed to include either the 5' or 3' primer of the first primer set and a second primer unique to the primer set, such that the primer set amplifies a region 5' or 3' to the signature region which anneals to either the 5' end or the 3' end of the signature region. For example, a first primer set is composed of a 5' primer, P1 and a 3' primer P2 to amplify the signature region. In order to extend the signature region on its 3' end, a second primer set is composed of primer P1 and a 3' primer P4, which amplifies the signature region and contiguous sequences downstream of the signature region. In order to extend the signature region on its 5' end, a third primer set is composed of a 5' primer, P5, and primer P2, such that the signature region and contiguous sequences upstream of the signature region are amplified. These extension steps are repeated (or performed at the same time), as needed or desired. Thereafter, the products results from these amplification steps are fused using conventional steps to produce an isolated sequence of the desired length.

The second and third primer sets are designed, as with the primer set for the signature region, to amplify a region having highly conserved sequences among the aligned sequences. Reference herein to the term "second" or "third" primer set is for each of discussion only, and without regard to the order in which these primers are added to the reaction mixture, or used for amplification. The region amplified by the second primer set is selected so that upon amplification it anneals at its 5' end to the 3' end of the signature region. Similarly, the region amplified by the third primer set is selected so that upon amplification it anneals at its 3' end anneals to the 5' end of the signature region. Additional primer sets can be designed such that the regions which they amplify anneal to the either the 5' end or the 3' end of the extension products formed by the second or third primer sets, or by subsequent primer sets.

For example, where AAV is the target sequence, a first set of primers (P1 and P2) are used to amplify the signature region from the sample. In one desirable embodiment, this signature region is located within the AAV capsid. A second set of primers (P1 and P4) is used to extend the 3' end of the signature region to a location in the AAV sequence which is just before the AAV 3' ITR, i.e., providing an extension product containing the entire 3' end of the AAV capsid when using the signature region as an anchor. In one embodiment, the P4 primer corresponds to nt 4435 to 4462 of AAV2 [SEQ ID NO:7], and corresponding sequences in the other AAV serotypes. This results in amplification of a region of about 1.6 kb, which contains the 0.25 kb signature region. A third set of primers (P3 and P2) is used to extend the 5' end of signature region to a location in the AAV sequences which is in the 3' end of the rep genes, i.e., providing an extension product containing the entire 5' end of the AAV capsid when using the signature region as an anchor. In one embodiment, the P3 primer corresponds to nt 1384 to 1409 of AAV2 [SEQ ID NO:7], and corresponding sequences in the other AAV serotypes. This results in amplification of a region of about 1.7 kb, which contains the 0.25 kb signature region. Optionally, a fourth set of primers are used to further extend the extension product containing the entire 5' end of the AAV capsid to also include the rep sequences. In one embodiment, the primer designated P5 corresponds to nt 108 to 133 of AAV2 [SEQ ID NO:7], and corresponding sequences in the other AAV serotypes and is used in conjunction with the P2 primer.

Following completion of the desired number of extension steps, the various extension products are fused, making use of the signature region as an anchor or marker, to construct an intact sequence. In the example provided herein, AAV sequences containing, at a minimum, an intact AAV cap gene are obtained. Larger sequences may be obtained, depending upon the number of extension steps performed.

Suitably, the extension products are assembled into an intact AAV sequence using methods known to those of skill in the art. For example, the extension products may be digested with DraIII, which cleaves at the DraIII site located within the signature region, to provide restriction fragments which are re-ligated to provide products containing (at a minimum) an intact AAV cap gene. However, other suitable techniques for assembling the extension products into an intact sequence may be utilized. See, generally, Sambrook et al, cited herein.

As an alternative to the multiple extension steps described above, another embodiment of the invention provides for direct amplification of a 3.1 kb fragment which allows isolation of full-length cap sequences. To directly amplify a 3.1 kb full-length cap fragment from NHP tissue and blood DNAs, two other highly conserved regions were identified in AAV genomes for use in PCR amplification of large fragments. A primer within a conserved region located in the middle of the rep gene is utilized (AV1ns: 5' GCTGCGT-CAACTGGACCAATGAGAAC 3', nt of SEQ ID NO:6) in combination with the 3' primer located in another conserved region downstream of the Cap gene (AV2cas: 5' CGCAGA-GACCAAAGTTCAACTGAAACGA 3', SEQ ID NO: 7) for amplification of AAV sequences including the full-length AAV cap. Typically, following amplification, the products are cloned and sequence analysis is performed with an accuracy of ≥99.9%. Using this method, the inventors have isolated at least 50 capsid clones which have subsequently been characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5). These clones are identified elsewhere in the specification, together with the species of animal from which they were identified and the tissues in that animal these novel sequences have been located.

C. Alternative Method for Isolating Novel AAV

In another aspect, the invention provides an alternative method for isolating novel AAV from a cell. This method involves infecting the cell with a vector which provides helper functions to the AAV; isolating infectious clones containing AAV; sequencing the isolated AAV; and comparing the sequences of the isolated AAV to known AAV serotypes, whereby differences in the sequences of the isolated AAV and known AAV serotypes indicates the presence of a novel AAV.

In one embodiment, the vector providing helper functions provides essential adenovirus functions, including, e.g., E1a, E1b, E2a, E4ORF6. In one embodiment, the helper functions are provided by an adenovirus. The adenovirus may be a wild-type adenovirus, and may be of human or non-human origin, preferably non-human primate (NHP) origin. The DNA sequences of a number of adenovirus types are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified human types [see, e.g., Horwitz, cited above]. Similarly adenoviruses known to infect non-human animals (e.g., chimpanzees) may also be employed in the vector constructs of this invention. See, e.g., U.S. Pat. No. 6,083,716. In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. The selection of the adenovirus type is not anticipated to limit the following invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

In another alternative, infectious AAV may be isolated using genome walking technology (Siebert et al., 1995, *Nucleic Acid Research*, 23:1087-1088, Friezner-Degen et al., 1986, *J. Biol. Chem.* 261:6972-6985, BD Biosciences Clontech, Palo Alto, Calif.). Genome walking is particularly well suited for identifying and isolating the sequences adjacent to the novel sequences identified according to the method of the invention. For example, this technique may be useful for isolating inverted terminal repeat (ITRs) of the novel AAV serotype, based upon the novel AAV capsid and/or rep sequences identified using the methods of the invention. This technique is also useful for isolating sequences adjacent to other AAV and non-AAV sequences identified and isolated according to the present invention. See, Examples 3 and 4.

The methods of the invention may be readily used for a variety of epidemiology studies, studies of biodistribution, monitoring of gene therapy via AAV vectors and vector derived from other integrated viruses. Thus, the methods are well suited for use in pre-packaged kits for use by clinicians, researchers, and epidemiologists.

II. Diagnostic Kit

In another aspect, the invention provides a diagnostic kit for detecting the presence of a known or unknown adeno-associated virus (AAV) in a sample. Such a kit may contain a first set of 5' and 3' PCR primers specific for a signature region of the AAV nucleic acid sequence. Alternatively, or additionally, such a kit can contain a first set of 5' and 3' PCR primers specific for the 3.1 kb fragment which includes the full-length AAV capsid nucleic acid sequence identified herein (e.g., the AV1ns and AV2cas primers.) Optionally, a kit of the invention may further contain two or more additional sets of 5' and 3' primers, as described herein, and/or PCR probes. These primers and probes are used according to the present invention amplify signature regions of each AAV serotype, e.g., using quantitative PCR.

The invention further provides a kit useful for identifying an AAV serotype detected according to the method of the invention and/or for distinguishing novel AAV from known AAV. Such a kit may further include one or more restriction enzymes, standards for AAV serotypes providing their "signature restriction enzyme digestions analyses", and/or other means for determining the serotype of the AAV detected.

In addition, kits of the invention may include, instructions, a negative and/or positive control, containers, diluents and buffers for the sample, indicator charts for signature comparisons, disposable gloves, decontamination instructions, applicator sticks or containers, and sample preparator cups, as well as any desired reagents, including media, wash reagents and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

The kits provided by the present invention are useful for performing the methods described herein, and for study of biodistribution, epidemiology, mode of transmission of novel AAV serotypes in human and NHPs.

Thus, the methods and kits of the invention permit detection, identification, and isolation of target viral sequences, particularly integrated viral sequences. The methods and kits are particularly well suited for use in detection, identification and isolation of AAV sequences, which may include novel AAV serotypes.

In one notable example, the method of the invention facilitated analysis of cloned AAV sequences by the inventors, which revealed heterogeneity of proviral sequences between cloned fragments from different animals, all of which were distinct from the known six AAV serotypes, with the majority of the variation localized to hypervariable regions of the capsid protein. Surprising divergence of AAV sequences was noted in clones isolated from single tissue sources, such as lymph node, from an individual rhesus monkey. This heterogeneity is best explained by apparent evolution of AAV sequence within individual animals due, in part, to extensive homologous recombination between a limited number of co-infecting parenteral viruses. These studies suggest sequence evolution of widely disseminated virus during the course of a natural AAV infection that presumably leads to the formation of swarms of quasispecies which differ from one another in the array of capsid hypervariable regions. This is the first example of rapid molecular evolution of a DNA virus in a way that formerly was thought to be restricted to RNA viruses.

Sequences of several novel AAV serotypes identified by the method of the invention and characterization of these serotypes is provided.

III. Novel AAV Serotypes

A. Nucleic Acid Sequences

Nucleic acid sequences of novel AAV serotypes identified by the methods of the invention are provided. See, SEQ ID NO:1, 9-59, and 117-120, which are incorporated by reference herein. See also, FIG. 1 and the sequence listing.

For novel serotype AAV7, the full-length sequences, including the AAV 5' ITRs, capsid, rep, and AAV 3' ITRs are provided in SEQ ID NO:1.

For other novel AAV serotypes of the invention, the approximately 3.1 kb fragment isolated according to the method of the invention is provided. This fragment contains sequences encoding full-length capsid protein and all or part of the sequences encoding the rep protein. These sequences include the clones identified below.

For still other novel AAV serotypes, the signature region encoding the capsid protein is provided. For example, the AAV10 nucleic acid sequences of the invention include those illustrated in FIG. 1 [See, SEQ ID NO:117, which spans 255 bases]. The AAV11 nucleic acid sequences of the invention include the DNA sequences illustrated in FIG. 1 [See, SEQ ID NO:118 which spans 258 bases]. The AAV12 nucleic acid sequences of the invention include the DNA sequences illustrated in FIG. 1 [See, SEQ ID NO:119, which consists of 255 bases]. Using the methodology described above, further AAV10, AAV11 and AAV12 sequences can be readily identified and used for a variety of purposes, including those described for AAV7 and the other novel serotypes herein.

FIG. 1 provides the non-human primate (NHP) AAV nucleic acid sequences of the invention in an alignment with the previously published AAV serotypes, AAV 1 [SEQ ID NO:6], AAV2 [SEQ ID NO:7], and AAV3 [SEQ ID NO:8]. These novel NHP sequences include those provided in the following Table I, which are identified by clone number:

TABLE 1

| AAV Cap Sequence | Clone Number | Source Species | Tissue | SEQ ID NO (DNA) |
|---|---|---|---|---|
| Rh. 1 | Clone 9 (AAV9) | Rhesus | Heart | 5 |
| Rh. 2 | Clone 43.1 | Rhesus | MLN | 39 |
| Rh. 3 | Clone 43.5 | Rhesus | MLN | 40 |
| Rh. 4 | Clone 43.12 | Rhesus | MLN | 41 |
| Rh. 5 | Clone 43.20 | Rhesus | MLN | 42 |
| Rh. 6 | Clone 43.21 | Rhesus | MLN | 43 |
| Rh. 7 | Clone 43.23 | Rhesus | MLN | 44 |
| Rh. 8 | Clone 43.25 | Rhesus | MLN | 45 |
| Rh. 9 | Clone 44.1 | Rhesus | Liver | 46 |
| Rh. 10 | Clone 44.2 | Rhesus | Liver | 59 |
| Rh. 11 | Clone 44.5 | Rhesus | Liver | 47 |
| Rh. 12 | Clone 42.1B | Rhesus | MLN | 30 |
| Rh. 13 | 42.2 | Rhesus | MLN | 9 |
| Rh. 14 | Clone 42.3A | Rhesus | MLN | 32 |
| Rh. 15 | Clone 42.3B | Rhesus | MLN | 36 |
| Rh. 16 | Clone 42.4 | Rhesus | MLN | 33 |
| Rh. 17 | Clone 42.5A | Rhesus | MLN | 34 |
| Rh. 18 | Clone 42.5B | Rhesus | MLN | 29 |
| Rh. 19 | Clone 42.6B | Rhesus | MLN | 38 |
| Rh. 20 | Clone 42.8 | Rhesus | MLN | 27 |
| Rh. 21 | Clone 42.10 | Rhesus | MLN | 35 |
| Rh. 22 | Clone 42.11 | Rhesus | MLN | 37 |
| Rh. 23 | Clone 42.12 | Rhesus | MLN | 58 |
| Rh. 24 | Clone 42.13 | Rhesus | MLN | 31 |
| Rh. 25 | Clone 42.15 | Rhesus | MLN | 28 |
| Rh. 26 | Clone 223.2 | Rhesus | Liver | 49 |
| Rh. 27 | Clone 223.4 | Rhesus | Liver | 50 |
| Rh. 28 | Clone 223.5 | Rhesus | Liver | 51 |
| Rh. 29 | Clone 223.6 | Rhesus | Liver | 52 |
| Rh. 30 | Clone 223.7 | Rhesus | Liver | 53 |
| Rh. 31 | Clone 223.10 | Rhesus | Liver | 48 |
| Rh. 32 | Clone C1 | Rhesus | Spleen, Duo, Kid & Liver | 19 |
| Rh. 33 | Clone C3 | Rhesus | | 20 |
| Rh. 34 | Clone C5 | Rhesus | | 21 |
| Rh. 35 | Clone F1 | Rhesus | Liver | 22 |
| Rh. 36 | Clone F3 | Rhesus | | 23 |
| Rh. 37 | Clone F5 | Rhesus | | 24 |
| Cy. 1 | Clone 1.3 | Cyno | Blood | 14 |
| Cy. 2 | Clone 13.3B | Cyno | Blood | 15 |
| Cy. 3 | Clone 24.1 | Cyno | Blood | 16 |
| Cy. 4 | Clone 27.3 | Cyno | Blood | 17 |
| Cy. 5 | Clone 7.2 | Cyno | Blood | 18 |
| Cy. 6 | Clone 16.3 | Cyno | Blood | 10 |
| bb. 1 | Clone 29.3 | Baboon | Blood | 11 |
| bb. 2 | Clone 29.5 | Baboon | Blood | 13 |
| Ch. 1 | Clone A3.3 | Chimp | Blood | 57 |
| Ch. 2 | Clone A3.4 | Chimp | Blood | 54 |
| Ch. 3 | Clone A3.5 | Chimp | Blood | 55 |
| Ch. 4 | Clone A3.7 | Chimp | Blood | 56 |

A novel NHP clone was made by splicing capsids fragments of two chimp adenoviruses into an AAV2 rep construct. This new clone, A3.1, is also termed Ch.5 [SEQ ID NO:20]. Additionally, the present invention includes two human AAV sequences, termed H6 [SEQ ID NO:25] and H2 [SEQ ID NO:26].

The AAV nucleic acid sequences of the invention further encompass the strand which is complementary to the strands provided in the sequences provided in FIG. 1 and the Sequence Listing [SEQ ID NO:1, 9-59, 117-120], nucleic acid sequences, as well as the RNA and cDNA sequences corresponding to the sequences provided in FIG. 1 and the Sequence Listing [SEQ ID NO:1, 9-59, 117-120], and their complementary strands. Also included in the nucleic acid sequences of the invention are natural variants and engineered modifications of the sequences of FIG. 1 and the Sequence Listing [SEQ ID NO:1, 9-59, 117-120], and their complementary strands. Such modifications include, for example, labels which are known in the art, methylation, and substitution of one or more of the naturally occurring nucleotides with a degenerate nucleotide.

Further included in this invention are nucleic acid sequences which are greater than 85%, preferably at least about 90%, more preferably at least about 95%, and most preferably at least about 98 to 99% identical or homologous to the sequences of the invention, including FIG. 1 and the Sequence Listing [SEQ ID NO:1, 9-59, 117-120]. These terms are as defined herein.

Also included within the invention are fragments of the novel AAV sequences identified by the method described herein. Suitable fragments are at least 15 nucleotides in length, and encompass functional fragments, i.e., fragments which are of biological interest. In one embodiment, these fragments are fragments of the novel sequences of FIG. 1 and the Sequence Listing [SEQ ID NO:1, 9-59, 117-120], their complementary strands, cDNA and RNA complementary thereto.

Examples of suitable fragments are provided with respect to the location of these fragments on AAV1, AAV2, or AAV7. However, using the alignment provided herein (obtained using the Clustal W program at default settings), or similar techniques for generating an alignment with other novel serotypes of the invention, one of skill in the art can readily identify the precise nucleotide start and stop codons for desired fragments.

Examples of suitable fragments include the sequences encoding the three variable proteins (vp) of the AAV capsid which are alternative splice variants: vp1 [e.g., nt 825 to 3049 of AAV7, SEQ ID NO: 1]; vp2 [e.g., nt 1234-3049 of AAV7, SEQ ID NO: 1]; and vp 3 [e.g., nt 1434-3049 of AAV7, SEQ ID NO:1]. It is notable that AAV7 has an unusual GTG start codon. With the exception of a few house-keeping genes, such a start codon has not previously been reported in DNA viruses. The start codons for vp1, vp2 and vp3 for other AAV serotypes have been believed to be such that they permit the cellular mechanism of the host cell in which they reside to produce vp1, vp2 and vp3 in a ratio of 10%:10%:80%, respectively, in order to permit efficient assembly of the virion. However, the AAV7 virion has been found to assemble efficiently even with this rare GTG start codon. Thus, the inventors anticipate this it is desirable to alter the start codon of the vp3 of other AAV serotypes to contain this rare GTG start codon, in order to improve packaging efficiency, to alter the virion structure and/or to alter location of epitopes (e.g., neutralizing antibody epitopes) of other AAV serotypes. The start codons may be altered using conventional techniques including, e.g., site directed mutagenesis. Thus, the present invention encompasses altered AAV virions of any selected serotype, composed of a vp 3, and/or optionally, vp1 and/or vp2 having start codons altered to GTG.

Other suitable fragments of AAV, include a fragment containing the start codon for the AAV capsid protein [e.g., nt 468 to 3090 of AAV7, SEQ ID NO:1, nt 725 to 3090 of AAV7, SEQ ID NO: 1, and corresponding regions of the other AAV serotypes]. Still other fragments of AAV7 and the other novel AAV serotypes identified using the methods described herein include those encoding the rep proteins, including rep 78 [e.g., initiation codon 334 of FIG. 1 for AAV7], rep 68 [initiation codon nt 334 of FIG. 1 for AAV7], rep 52 [initiation codon 1006 of FIG. 1 for AAV7], and rep 40 [initiation codon 1006 of FIG. 1 for AAV7] Other fragments of interest may include the AAV 5' inverted terminal repeats ITRs, [nt 1 to 107 of FIG. 1 for AAV7]; the AAV 3' ITRs [nt 4704 to 4721 of FIG. 1 for AAV7], P19 sequences, AAV P40 sequences, the rep binding site, and the terminal resolute site (TRS). Still other suitable fragments will be readily apparent to those of skill in the art. The corresponding regions in the other novel serotypes of the invention can be readily determined by reference to FIG. 1, or by utilizing conventional alignment techniques with the sequences provided herein.

In addition to including the nucleic acid sequences provided in the figures and Sequence Listing, the present invention includes nucleic acid molecules and sequences which are designed to express the amino acid sequences, proteins and peptides of the AAV serotypes of the invention. Thus, the invention includes nucleic acid sequences which encode the following novel AAV amino acid sequences: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113], and artificial AAV serotypes generated using these sequences and/or unique fragments thereof.

As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

B. AAV Amino Acid Sequences, Proteins and Peptides

The invention provides proteins and fragments thereof which are encoded by the nucleic acid sequences of the novel AAV serotypes identified herein, including, e.g., AAV7 [nt 825 to 3049 of AAV7, SEQ ID NO: 1] the other novel serotypes provided herein. Thus, the capsid proteins of the novel serotypes of the invention, including: H6 [SEQ ID NO: 25], H2 [SEQ ID NO: 26], 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], and 44.2 [SEQ ID NO: 59], can be readily generated using conventional techniques from the open reading frames provided for the above-listed clones.

The invention further encompasses AAV serotypes generated using sequences of the novel AAV serotypes of the invention, which are generated using synthetic, recombinant or other techniques known to those of skill in the art. The invention is not limited to novel AAV amino acid sequences, peptides and proteins expressed from the novel AAV nucleic acid sequences of the invention and encompasses amino acid sequences, peptides and proteins generated by other methods known in the art, including, e.g., by chemical synthesis, by other synthetic techniques, or by other methods. For example, the sequences of any of C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113] by be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.,* 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Particularly desirable proteins include the AAV capsid proteins, which are encoded by the nucleotide sequences identified above. The sequences of many of the capsid proteins of the invention are provided in an alignment in FIG. 2 and/or in the Sequence Listing, SEQ ID NO: 2 and 60 to 115, which is incorporated by reference herein. The AAV capsid is composed of three proteins, vp1, vp2 and vp3, which are alternative splice variants. The full-length sequence provided in these figures is that of vp1. Based on the numbering of the AAV7 capsid [SEQ ID NO:2], the sequences of vp2 span amino acid 138-737 of AAV7 and the sequences of vp3 span amino acids 203-737 of AAV7. With this information, one of skill in the art can readily determine the location of the vp2 and vp3 proteins for the other novel serotypes of the invention.

Other desirable proteins and fragments of the capsid protein include the constant and variable regions, located between hypervariable regions (HPV) and the sequences of the HPV regions themselves. An algorithm developed to determine areas of sequence divergence in AAV2 has yielded 12 hypervariable regions (HVR) of which 5 overlap or are part of the four previously described variable regions. [Chiorini et al, *J. Virol,* 73:1309-19 (1999); Rutledge et al, *J. Virol.,* 72:309-319] Using this algorithm and/or the alignment techniques described herein, the HVR of the novel AAV serotypes are determined. For example, with respect to the number of the AAV2 vp1 [SEQ ID NO:70], the HVR are located as follows: HVR1, aa 146-152; HVR2, aa 182-186; HVR3, aa 262-264; HVR4, aa 381-383; HVR5, aa 450-474; HVR6, aa 490-495; HVR7, aa500-504; HVR8, aa 514-522; HVR9, aa 534-555; HVR10, aa 581-594; HVR11, aa 658-667; and HVR12, aa 705-719. Utilizing an alignment prepared in accordance with conventional methods and the novel sequences provided herein [See, e.g., FIG. 2], one can readily determine the location of the HVR in the novel AAV serotypes of the invention. For example, utilizing FIG. 2, one can readily determine that for AAV7 [SEQ ID NO:2]. HVR1 is located at aa 146-152; HVR2 is located at 182-187; HVR3 is located at aa 263-266, HVR4 is located at aa 383-385, HVR5 is located at aa 451-475; HVR6 is located at aa 491-496 of AAV7; HVR7 is located at aa 501-505; HVR8 is located at aa 513-521; HVR9 is located at 533-554; HVR10 is located at aa 583-596; HVR11 is located at aa 660-669; HVR12 is located at aa 707-721. Using the information provided herein, the HVRs for the other novel serotypes of the invention can be readily determined.

In addition, within the capsid, amino acid cassettes of identity have been identified. These cassettes are of particular interest, as they are useful in constructing artificial serotypes, e.g., by replacing a HVR1 cassette of a selected serotype with an HVR1 cassette of another serotype. Certain of these cassettes of identity are noted in FIG. 2. See, FIG. 2, providing the Clustal X alignment, which has a ruler is displayed below the sequences, starting at 1 for the first residue position. The line above the ruler is used to mark strongly conserved positions. Three characters (*, : , .) are used. "*" indicates positions which have a single, fully conserved residue. ":" indicates that a "strong" group is fully conserved "." Indicates that a "weaker" group is fully conserved. These are all the positively scoring groups that occur in the Gonnet Pam250 matrix. The strong groups are defined as a strong score >0.5 and the weak groups are defined as weak score <0.5.

Additionally, examples of other suitable fragments of AAV capsids include, with respect to the numbering of AAV2 [SEQ ID NO:70], aa 24-42, aa 25-28; aa 81-85; aa133-165; aa 134-165; aa 137-143; aa 154-156; aa 194-208; aa 261-274; aa 262-274; aa 171-173; aa 413-417; aa 449-478; aa 494-525; aa 534-571; aa 581-601; aa 660-671; aa 709-723. Still other desirable fragments include, for example, in AAV7, amino acids 1 to 184 of SEQ ID NO:2, amino acids 199 to 259; amino acids 274 to 446; amino acids 603 to 659; amino acids 670 to 706; amino acids 724 to 736; aa 185 to 198; aa 260 to 273; aa447 to 477; aa495 to 602; aa660 to 669; and aa707 to 723. Still other desirable regions, based on the numbering of AAV7 [SEQ ID NO:2], are selected from among the group consisting of aa 185 to 198; aa 260 to 273; aa447 to 477; aa495 to 602; aa660 to 669; and aa707 to 723. Using the alignment provided herein performed using the Clustal X program at default settings, or using other commercially or publicly available alignment programs at default settings, one of skill in the art can readily determine corresponding fragments of the novel AAV capsids of the invention.

Other desirable proteins are the AAV rep proteins [aa 1 to 623 of SEQ ID NO:3 for AAV7] and functional fragments thereof, including, e.g., aa 1 to 171, aa 172 to 372, aa 373 to 444, aa 445 to 623 of SEQ ID NO:3, among others. Suitably, such fragments are at least 8 amino acids in length. See, FIG. 3. Comparable regions can be identified in the proteins of the other novel AAV of the invention, using the techniques described herein and those which are known in the art. In addition, fragments of other desired lengths may be readily utilized. Such fragments may be produced recombinantly or by other suitable means, e.g., chemical synthesis.

The sequences, proteins, and fragments of the invention may be produced by any suitable means, including recombinant production, chemical synthesis, or other synthetic means. Such production methods are within the knowledge of those of skill in the art and are not a limitation of the present invention.

IV. Production of rAAV with Novel AAV Capsids

The invention encompasses novel, wild-type AAV serotypes identified by the invention, the sequences of which wild-type AAV serotypes are free of DNA and/or cellular material with these viruses are associated in nature. In another aspect, the present invention provides molecules which utilize the novel AAV sequences of the invention, including fragments thereof, for production of molecules useful in delivery of a heterologous gene or other nucleic acid sequences to a target cell.

The molecules of the invention which contain sequences of a novel AAV serotype of the invention include any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain sequences encoding a novel AAV capsid of the invention (e.g., AAV7 capsid, AAV 44-2 (rh.10), an AAV10 capsid, an AAV11 capsid, an AAV12 capsid), or a fragment of one or more of these AAV capsids. Alternatively, the vectors may contain the capsid protein, or a fragment thereof, itself.

Optionally, vectors of the invention may contain sequences encoding AAV rep proteins. Such rep sequences may be from the same AAV serotype which is providing the cap sequences. Alternatively, the present invention provides vectors in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are expressed from the same source as the cap sequences. In this embodiment, the rep sequences may be fused in frame to cap sequences of a different AAV serotype to form a chimeric AAV vector. Optionally, the vectors of the invention further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV serotype (e.g., AAV7 or another novel AAV). Alternatively, these vectors contain sequences encoding artificial capsids which contain one or more fragments of the AAV7 (or another novel AAV) capsid fused to heterologous AAV or non-AAV capsid proteins (or fragments thereof). These artificial capsid proteins are selected from non-contiguous portions of the AAV7 (or another novel AAV) capsid or from capsids of other AAV serotypes. For example, it may be desirable to modify the coding regions of one or more of the AAV vp1, e.g., in one or more of the hypervariable regions (i.e., HPV1-12), or vp2, and/or vp3. In another example, it may be desirable to alter the start codon of the vp3 protein to GTG. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having an AAV serotype 7 (or another novel AAV) capsid, or a portion thereof. Such a method involves culturing a host cell which contains a nucleic acid sequence encoding an adeno-associated virus (AAV) serotype 7 (or another novel AAV) capsid protein, or fragment thereof, as defined herein; a functional rep gene; a minigene composed of, at a minimum, AAV inverted terminal repeats (ITRs) and a transgene; and sufficient helper functions to permit packaging of the minigene into the AAV7 (or another novel AAV) capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.*, 70:520-532 (1993) and U.S. Pat. No. 5,478,745.

A. The Minigene

The minigene is composed of, at a minimum, a transgene and its regulatory sequences, and 5= and 3=AAV inverted terminal repeats (ITRs). It is this minigene which is packaged into a capsid protein and delivered to a selected host cell.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the plateletderived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Viral.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner which permits its transcription, translation and/or expression in a cell transfected with the plasmid vector or infected with the virus produced by the invention. As used herein, Aoperably linked≡ sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracyclineinducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor a chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5= and 3=ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 μg to about 100 μg DNA, and preferably about 10 to about 50 μg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

B. Rep and Cap Sequences

In addition to the minigene, the host cell contains the sequences which drive expression of the novel AAV capsid protein (e.g., AAV7 or other novel AAV capsid or an artificial capsid protein comprising a fragment of one or more of these capsids) in the host cell and rep sequences of the same serotype as the serotype of the AAV ITRs found in the minigene. The AAV cap and rep sequences may be independently obtained from an AAV source as described above and may be introduced into the host cell in any manner known to one in the art as described above. Additionally, when pseudotyping a novel AAV capsid of the invention, the sequences encoding each of the essential rep proteins may be supplied by the same AAV serotype, or the sequences encoding the rep proteins may be supplied by different AAV serotypes (e.g., AAV1, AAV2, AAV3, AAV4, AAV5, AAV6, or one of the novel serotypes identified herein). For example, the rep78/68 sequences may be from AAV2, whereas the rep52/40 sequences may from AAV1.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By Aadenoviral DNA which expresses the E1a gene product≡, it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

D. Host Cells and Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The most desirable cells do not carry any adenovirus gene other than E1, E2a and/or E4 ORF6; nor do they contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6. Yet other cell lines can be constructed using the novel AAV rep and/or novel AAV cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

These novel AAV-based vectors which are generated by one of skill in the art are beneficial for gene delivery to selected host cells and gene therapy patients since no neutralization antibodies to AAV7 have been found in the human population. Further, early studies show no neutralizing antibodies in cyno monkey and chimpanzee populations, and less than 15% cross-reactivity of AAV 7 in rhesus monkeys, the species from which the serotype was isolated. One of skill in the art may readily prepare other rAAV viral vectors containing the AAV7 capsid proteins provided herein using a variety of techniques known to those of skill in the art. One may similarly prepare still other rAAV viral vectors containing AAV7 sequence and AAV capsids of another serotype. Similar advantages are conferred by the vectors based on the other novel AAV of the invention.

Thus, one of skill in the art will readily understand that the AAV7 sequences of the invention can be readily adapted for use in these and other viral vector systems for in vitro, ex vivo or in vivo gene delivery. Similarly, one of skill in the art can readily select other fragments of the novel AAV genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

V. Recombinant Viruses and Uses Thereof

Using the techniques described herein, one of skill in the art may generate a rAAV having a capsid of a novel serotype of the invention, or a novel capsid containing one or more novel fragments of an AAV serotype identified by the method of the invention. In one embodiment, a full-length capsid from a single serotype, e.g., AAV7 [SEQ ID NO: 2] can be utilized. In another embodiment, a full-length capsid may be generated which contains one or more fragments of a novel serotype of the invention fused in frame with sequences from another selected AAV serotype. For example, a rAAV may contain one or more of the novel hypervariable region sequences of an AAV serotype of the invention. Alternatively, the unique AAV serotypes of the invention may be used in constructs containing other viral or non-viral sequences.

It will be readily apparent to one of skill in the art one embodiment, that certain serotypes of the invention will be particularly well suited for certain uses. For example, vectors based on AAV7 capsids of the invention are particularly well suited for use in muscle; whereas vectors based on rh.10 (44-2) capsids of the invention are particularly well suited for use in lung. Uses of such vectors are not so limited and one of skill in the art may utilize these vectors for delivery to other cell types, tissues or organs. Further, vectors based upon other capsids of the invention may be used for delivery to these or other cells, tissues or organs.

A. Delivery of Transgene

In another aspect, the present invention provides a method for delivery of a transgene to a host which involves transfecting or infecting a selected host cell with a vector generated with the sequences of the AAV of the invention. Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences which direct expression thereof and AAV capsid proteins.

Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W. C. Manning et al, *Human Gene Therapy*, 9:477-485 (Mar. 1, 1998). The results of this assay may be used to determine which AAV vector containing capsid proteins of a particular serotype are preferred for delivery, e.g., by the absence of neutralizing antibodies specific for that capsid serotype.

In one aspect of this method, the delivery of vector with a selected AAV capsid proteins may precede or follow delivery of a gene via a vector with a different serotype AAV capsid protein. Similarly, the delivery of vector with other novel AAV capsid proteins of the invention may precede or follow delivery of a gene via a vector with a different serotype AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of serotypes which differ from the first vector. For example, if a first vector has AAV7 capsid proteins [SEQ ID NO:2], subsequently administered vectors may have capsid proteins selected from among the other serotypes, including AAV1, AAV2, AAV3A, AAV3B, AAV4, AAV6, AAV10, AAV11, and AAV12, or any of the other novel AAV capsids identified herein including, without limitation: A3.1, H2, H6, C1, C2, C5, A3-3, A3-7, A3-4, A3-5, 3.3b, 223.4, 223-5, 223-10, 223-2, 223-7, 223-6, 44-1, 44-5, 44-2, 42-15, 42-8, 42-13, 42-3A, 42-4, 42-5A, 42-1B, 42-5B, 43-1, 43-12, 43-5, 43-21, 43-25, 43-20, 24.1, 42.2, 7.2, 27.3, 16.3, 42.10, 42-3B, 42-11, F1, F5, F3, 42-6B, and/or 42-12.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 1 ml to about 100 ml of solution containing concentrations of from about $1 \times 10^9$ to $1 \times 10^{16}$ genomes virus vector. A preferred human dosage may be about $1 \times 10^{13}$ to $1 \times 10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGF β, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, IL-2, IL-4, IL-12, and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce Aself≅-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Transgenes

Alternatively, or in addition, the vectors of the invention may contain AAV sequences of the invention and a transgene encoding a peptide, polypeptide or protein which induces an immune response to a selected immunogen. For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, Ross-River virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncoriviral which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Between the HIV and SIV, many suitable antigens have been described and can readily be selected. Examples of suitable HIV and SIV antigens include, without limitation the gag, pol, Vif, Vpx, VPR, Env, Tat and Rev proteins, as well as various fragments thereof. In addition, a variety of modifications to these antigens have been described. Suitable antigens for this purpose are known to those of skill in the art. For example, one may select a sequence encoding the gag, pol, Vif, and Vpr, Env, Tat and Rev, amongst other proteins. See, e.g., the modified gag protein which is described in U.S. Pat. No. 5,972,596. See, also, the HIV and SIV proteins described in D. H. Barouch et al, J. Virol., 75(5):2462-2467 (March 2001), and R. R. Amara, et al, Science, 292:69-74 (6 Apr. 2001). These proteins or subunits thereof may be delivered alone, or in combination via separate vectors or from a single vector.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek=s disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; *pseudomonas*, acinetobacteria and eikenella; melioidosis; *salmonella; shigella; haemophilus; moraxella; H. ducreyi* (which causes chancroid); *brucella; Franisella tularensis* (which causes tularemia); *yersinia* (*pasteurella*); *streptobacillus moniliformis* and spirillum; Gram-positive bacilli include *listeria monocytogenes; erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *mycoplasma* and chlamydial infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Depaitment of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fever, all of which are currently classified as Category A agents; *Coxiella burnetti* (Q fever); *Brucella* species (brucellosis), *Burkholderia mallei* (glanders), *Ricinus communis* and its toxin (ricin toxin), *Clostridium perfringens* and its toxin (epsilon toxin), *Staphylococcus* species and their toxins (enterotoxin B), all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of T cell receptors (TCRs) which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a nucleic acid molecule that encodes at least one of these polypeptides will elicit an immune response that will target T cells involved in scleroderma.

Optionally, vectors containing AAV sequences of the invention may be delivered using a prime-boost regimen. A variety of such regimens have been described in the art and may be readily selected. See, e.g., WO 00/11140, published Mar. 2, 2000, incorporated by reference.

Such prime-boost regimens typically involve the administration of a DNA (e.g., plasmid) based vector to prime the immune system to second, booster, administration with a traditional antigen, such as a protein or a recombinant virus carrying the sequences encoding such an antigen. In one embodiment, the invention provides a method of priming and boosting an immune response to a selected antigen by delivering a plasmid DNA vector carrying said antigen, followed by boosting, e.g., with a vector containing AAV sequences of the invention.

In one embodiment, the prime-boost regimen involves the expression of multiproteins from the prime and/or the boost vehicle. See, e.g., R. R. Amara, Science, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one or example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming vaccine may be administered at various sites in the body in a dose dependent manner, which depends on the antigen to which the desired immune response is being targeted. The invention is not limited to the amount or situs of injection(s) or to the pharmaceutical carrier. Rather, the priming step encompasses treatment regimens which include a single dose or dosage which is administered hourly, daily, weekly or monthly, or yearly. As an example, the mammals may receive one or two priming injection containing between about 10 μg to about 50 μg of plasmid in carrier. A desirable priming amount or dosage of the priming DNA vaccine composition ranges between about 1 μg to about 10,000 μg of the DNA vaccine. Dosages may vary from about 1 μg to 1000 μg DNA per kg of subject body weight. The amount or site of injection is desirably selected based upon the identity and condition of the mammal being vaccinated.

The dosage unit of the DNA vaccine suitable for delivery of the antigen to the mammal is described herein. The DNA vaccine is prepared for administration by being suspended or dissolved in a pharmaceutically or physiologically acceptable carrier such as isotonic saline, isotonic salts solution or other formulations which will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes.

Optionally, the priming step of this invention also includes administering with the priming DNA vaccine composition, a suitable amount of an adjuvant, such as are defined herein.

Preferably, a boosting composition is administered about 2 to about 27 weeks after administering the priming DNA vaccine to the mammalian subject. The administration of the boosting composition is accomplished using an effective amount of a boosting vaccine composition containing or capable of delivering the same antigen as administered by the priming DNA vaccine. The boosting composition may be composed of a recombinant viral vector derived from the same viral source or from another source. Alternatively, the "boosting composition" can be a composition containing the same antigen as encoded in the priming DNA vaccine, but in the form of a protein or peptide, which composition induces an immune response in the host. In another embodiment, the boosting vaccine composition includes a composition containing a DNA sequence encoding the antigen under the control of a regulatory sequence directing its expression in a mammalian cell, e.g., vectors such as well-known bacterial or viral vectors. The primary requirements of the boosting vaccine composition are that the antigen of the vaccine composition is the same antigen, or a cross-reactive antigen, as that encoded by the DNA vaccine.

Suitably, the vectors of the invention are also well suited for use in regimens which use non-AAV vectors as well as proteins, peptides, and/or other biologically useful therapeutic or immunogenic compounds. These regimens are particularly well suited to gene delivery for therapeutic poses and for immunization, including inducing protective immunity. Such uses will be readily apparent to one of skill in the art.

Further, a vector of the invention provides an efficient gene transfer vehicle which can deliver a selected transgene to a selected host cell in vivo or ex vivo even where the organism has neutralizing antibodies to one or more AAV serotypes. In one embodiment, the vector (e.g., an rAAV) and the cells are mixed ex vivo; the infected cells are cultured using conventional methodologies; and the trans-duced cells are re-infused into the patient. Further, the vectors of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

EXAMPLES

Example 1: PCR Amplification, Cloning and Characterization of Novel AAV Sequences Tissues from nonhuman primates were screened for AAV sequences using a PCR method based on oligonucleotides to highly conserved regions of known AAVs. A stretch of AAV sequence spanning 2886 to 3143 bp of AAV1 [SEQ ID NO:6] was selected as a PCR amplicon in which a hypervariable region of the capsid protein (Cap) that is unique to each known AAV serotype, which is termed herein a "signature region," is flanked by conserved sequences. In later analysis, this signature region was shown to be located between conserved residues spanning hypervariable region 3.

An initial survey of peripheral blood of a number of nonhuman primate species revealed detectable AAV in a subset of animals from species such as rhesus macaques, cynomologous macaques, chimpanzees and baboons. However, there were no AAV sequences detected in some other species tested, including Japanese macaques, pig-tailed macaques and squirrel monkeys. A more extensive analysis of vector distribution was conducted in tissues of rhesus monkeys of the University of Pennsylvania and Tulane colonies recovered at necropsy. This revealed AAV sequence throughout a wide array of tissues.

A. Amplification of an AAV Signature Region

DNA sequences of AAV1-6 and AAVs isolated from Goose and Duck were aligned to each other using "Clustal W" at default settings. The alignment for AAV1-6, and including the information for the novel AAV7, is provided in FIG. 1. Sequence similarities among AAVs were compared.

In the line of study, a 257 bp region spanning 2886 bp to 3143 bp of AAV 1 [SEQ ID NO: 6], and the corresponding region in the genomes of AAV 2-6 genomes [See, FIG. 1], was identified by the inventors. This region is located with the AAV capsid gene and has highly conserved sequences among at both 5' and 3' ends and is relatively variable sequence in the middle. In addition, this region contains a DraIII restriction enzyme site (CACCACGTC, SEQ ID NO:15). The inventors have found that this region serves as specific signature for each known type of AAV DNA. In other words, following PCR reactions, digestion with endonucleases that are specific to each known serotypes and gel electrophoresis analysis, this regions can be used to definitively identify amplified DNA as being from serotype 1, 2, 3, 4, 5, 6, or another serotype.

The primers were designed, validated and PCR conditions optimized with AAV1, 2 and 5 DNA controls. The primers were based upon the sequences of AAV2: 5' primer, 1S: bp 2867-2891 of AAV2 (SEQ ID NO:7) and 3' primer, 18as, bp 3095-3121 of AAV2 (SEQ ID NO:7).

Cellular DNAs from different tissues including blood, brain, liver, lung, testis, etc. of different rhesus monkeys were studied utilizing the strategy described above. The results revealed that DNAs from different tissues of these monkeys gave rise to strong PCR amplifications. Further restriction analyses of PCR products indicated that they were amplified from AAV sequences different from any published AAV sequences.

PCR products (about 255 bp in size) from DNAs of a variety of monkey tissues have been cloned and sequenced. Bioinformatics study of these novel AAV sequences indicated that they are novel AAV sequences of capsid gene and distinct from each other. FIG. 1 includes in the alignment the novel AAV signature regions for AAV10-12 [SEQ ID NO:117, 118 and 119, respectively]. Multiple sequence alignment analysis was performed using the Clustal W (1.81) program. The percentage of sequence identity between the signature regions of AAV 1-7 and AAV 10-12 genomes is provided below.

TABLE 2

| Sequences for Analysis | | |
|---|---|---|
| Sequence # | AAV Serotype | Size (bp) |
| 1 | AAV1 | 258 |
| 2 | AAV2 | 255 |
| 3 | AAV3 | 255 |
| 4 | AAV4 | 246 |
| 5 | AAV5 | 258 |
| 6 | AAV6 | 258 |
| 7 | AAV7 | 258 |
| 10 | AAV10 | 255 |
| 11 | AAV11 | 258 |
| 12 | AAV12 | 255 |

TABLE 3

| Pairwise Alignment (Percentage of Identity) | | | | | | | | | |
|---|---|---|---|---|---|---|---|---|---|
| | AAV2 | AAV3 | AAV4 | AAV5 | AAV6 | AAV7 | AAV10 | AAV11 | AAV12 |
| AAV1 | 90 | 90 | 81 | 76 | 97 | 91 | 93 | 94 | 93 |
| AAV2 | | 93 | 79 | 78 | 90 | 90 | 93 | 93 | 92 |
| AAV3 | | | 80 | 76 | 90 | 92 | 92 | 92 | 92 |
| AAV4 | | | | 76 | 81 | 84 | 82 | 81 | 79 |
| AAV5 | | | | | 75 | 78 | 79 | 79 | 76 |
| AAV6 | | | | | | 91 | 92 | 94 | 94 |
| AAV7 | | | | | | | 94 | 92 | 92 |
| AAV10 | | | | | | | | 95 | 93 |
| AAV11 | | | | | | | | | 94 |

Over 300 clones containing novel AAV serotype sequences that span the selected 257 bp region were isolated and sequenced. Bioinformatics analysis of these 300+ clones suggests that this 257 bp region is critical in serving as a good land marker or signature sequence for quick isolation and identification of novel AAV serotype.

B. Use of the Signature Region for PCR Amplification.

The 257 bp signature region was used as a PCR anchor to extend PCR amplifications to 5' of the genome to cover the junction region of rep and cap genes (1398 bp-3143 bp, SEQ ID NO:6) and 3' of the genome to obtain the entire cap gene sequence (2866 bp-4600 bp, SEQ ID NO:6). PCR amplifications were carried out using the standard conditions, including denaturing at 95° C. for 0.5-1 min, annealing at 60-65° C. for 0.5-1 min and extension at 72° C. for 1 min per kb with a total number of amplification cycles ranging from 28 to 42.

Using the aligned sequences as described in "A", two other relative conserved regions were identified in the sequence located in 3' end of rep genes and 5' to the 257 bp region and in the sequence down stream of the 257 bp fragment but before the AAV' 3 ITR. Two sets of new primers were designed and PCR conditions optimized for recovery of entire capsid and a part of rep sequences of novel AAV serotypes. More specifically, for the 5' amplification, the 5' primer, AV1Ns, was GCTGCGTCAACTG-GACCAATGAGAAC [nt 1398-1423 of AAV1, SEQ ID NO:6] and the 3' primer was 18as, identified above. For the 3' amplification, the 5' primer was 1s, identified above, and the 3' primer was AV2Las, TCGTTTCAGTTGAACTTTG-GTCTCTGCG [nt 4435-4462 of AAV2, SEQ ID NO:7].

In these PCR amplifications, the 257 bp region was used as a PCR anchor and land marker to generate overlapping fragments to construct a complete capsid gene by fusion at the DraIII site in the signature region following amplification of the 5' and 3' extension fragments obtained as described herein. More particularly, to generate the intact AAV7 cap gene, the three amplification products (a) the sequences of the signature region; (b) the sequences of the 5' extension; and (c) the sequences of the 3' extension were cloned into a pCR4-Topo [Invitrogen] plasmid backbone according to manufacturer's instructions. Thereafter, the plasmids were digested with DraIII and recombined to form an intact cap gene.

In this line of work, about 80% of capsid sequences of AAV7 and AAV 8 were isolated and analyzed. Another novel serotype, AAV9, was also discovered from Monkey #2.

Using the PCR conditions described above, the remaining portion of the rep gene sequence for AAV7 is isolated and cloned using the primers that amplify 108 bp to 1461 bp of AAV genome (calculated based on the numbering of AAV2, SEQ ID NO:7). This clone is sequenced for construction of a complete AAV7 genome without ITRs.

C. Direct Amplification of 3.1 kb Cap Fragment

To directly amplify a 3.1 kb full-length Cap fragment from NHP tissue and blood DNAs, two other highly conserved regions were identified in AAV genomes for use in PCR amplification of large fragments. A primer within a conserved region located in the middle of the rep gene was selected (AV1ns: 5' GCTGCGTCAACTGGACCAAT-GAGAAC 3', nt 1398-1423 of SEQ ID NO:6) in combination with the 3' primer located in another conserved region downstream of the Cap gene (AV2cas: 5' CGCAGAGAC-CAAAGTTCAACTGAAACGA 3', SEQ ID NO:7) for amplification of full-length cap fragments. The PCR products were Topo-cloned according to manufacturer's directions (Invitrogen) and sequence analysis was performed by Qiagengenomics (Qiagengenomics, Seattle, Wash.) with an accuracy of ≥99.9%. A total of 50 capsid clones were isolated and characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5).

To rule out the possibility that sequence diversity within the novel AAV family was not an artifact of the PCR, such as PCR-mediated gene splicing by overlap extension between different partial DNA templates with homologous sequences, or the result of recombination process in bacteria, a series of experiments were performed under identical conditions for VP1 amplification using total cellular DNAs. First, intact AAV7 and AAV8 plasmids were mixed at an equal molar ratio followed by serial dilutions. The serially diluted mixtures were used as templates for PCR amplification of 3.1 kb VP1 fragments using universal primers and identical PCR conditions to that were used for DNA amplifications to see whether any hybrid PCR products were generated. The mixture was transformed into bacteria and isolated transformants to look for hybrid clones possibly derived from recombination process in bacterial cells. In a different experiment, we restricted AAV7 and AAV8 plasmids with Msp I, Ava I and HaeI, all of which cut both genomes multiple times at different positions, mixed the digestions in different combinations and used them for PCR amplification of VP1 fragments under the same conditions to test whether any PCR products could be generated through overlap sequence extension of partial AAV sequences. In another experiment, a mixture of gel purified 5' 1.5 kb AAV7 VP1 fragment and 3' 1.7 kb AAV8 VP1 fragment with overlap in the signature region was serially diluted and used for PCR amplification in the presence and absence of 200 ng cellular DNA extracted from a monkey cell line that was free of AAV sequences by TaqMan analysis. None of these experiments demonstrated efficient PCR-mediated overlap sequence production under the conditions of the genomic DNA Cap amplification (data not shown). As a further confirmation, 3 pairs of primers were designed, which were located at different HVRs, and were sequence specific to the variants of clone 42s from Rhesus macaque F953, in different combinations to amplify shorter fragments from mesenteric lymph node (MLN) DNA from F953 from which clone 42s were isolated. All sequence variations identified in full-length Cap clones were found in these short fragments (data not shown).

Example 2: Adeno-Associated Viruses Undergo Substantial Evolution in Primates During Natural Infections Sequence analysis of selected AAV isolates revealed divergence throughout the genome that is most concentrated in hypervariable regions of the capsid proteins. Epidemiologic data indicate that all known serotypes are endemic to primates, although isolation of clinical isolates has been restricted to AAV2 and AAV3 from anal and throat swabs of human infants and AAV5 from a human condylomatous wart. No known clinical sequalae have been associated with AAV infection.

In an attempt to better understand the biology of AAV, nonhuman primates were used as models to characterize the sequalae of natural infections. Tissues from nonhuman primates were screened for AAV sequences using the PCR method of the invention based on oligonucleotides to highly conserved regions of known AAVs (see Example 1). A stretch of AAV sequence spanning 2886 to 3143 bp of AAV1 [SEQ ID NO:6] was selected as a PCR amplicon in which conserved sequences are flanked by a hypervariable region that is unique to each known AAV serotype, termed herein a "signature region."

An initial survey of peripheral blood of a number of nonhuman primate species including rhesus monkeys, cynomologous monkeys, chimpanzees, and baboons revealed detectable AAV in a subset of animals from all species. A more extensive analysis of vector distribution was conducted in tissues of rhesus monkeys of the University of Pennsylvania and Tulane colonies recovered at necropsy. This revealed AAV sequence throughout a wide array of tissues.

The amplified signature sequences were subcloned into plasmids and individual transformants were subjected to sequence analysis. This revealed substantial variation in nucleotide sequence of clones derived from different animals. Variation in the signature sequence was also noted in clones obtained within individual animals. Tissues harvested from two animals in which unique signature sequences were identified (i.e., colon from 98E044 and heart from 98E056) were further characterized by expanding the sequence amplified by PCR using oligonucleotides to highly conserved sequences. In this way, complete proviral structures were reconstructed for viral genomes from both tissues as described herein. These proviruses differ from the other known AAVs with the greatest sequence divergence noted in regions of the Cap gene.

Additional experiments were performed to confirm that AAV sequences resident to the nonhuman primate tissue represented proviral genomes of infectious virus that is capable of being rescued and form virions. Genomic DNA from liver tissue of animal 98E056, from which AAV8 signature sequence was detected, was digested with an endonuclease that does not have a site within the AAV sequence and transfected into 293 cells with a plasmid containing an E1 deleted genome of human adenovirus serotype 5 as a source of helper functions. The resulting lysate was passaged on 293 cells once and the lysate was recovered and analyzed for the presence of AAV Cap proteins using a broadly reacting polyclonal antibody to Cap proteins and for the presence and abundance of DNA sequences from the PCR amplified AAV provirus from which AAV8 was derived. Transfection of endonuclease restricted heart DNA and the adenovirus helper plasmid yielded high quantities of AAV8 virus as demonstrated by the detection of Cap proteins by Western blot analysis and the presence of $10^4$ AAV8 vector genomes per 293 cell. Lysates were generated from a large-scale preparation and the AAV was purified by cesium sedimentation. The purified preparation demonstrated 26 nm icoshedral structures that look identical to those of AAV serotype 2. Transfection with the adenovirus helper alone did not yield AAV proteins or genomes, ruling out contamination as a source of the rescued AAV.

To further characterize the inter and intra animal variation of AAV signature sequence, selected tissues were subjected to extended PCR to amplify entire Cap open reading frames.

The resulting fragments were cloned into bacterial plasmids and individual transformants were isolated and fully sequenced. This analysis involved mesenteric lymph nodes from three rhesus monkeys (Tulane/V223—6 clones; Tulane/T612—7 clones; Tulane/F953—14 clones), liver from two rhesus monkeys (Tulane/V251—3 clones; Penn/ 00E033—3 clones), spleen from one rhesus monkey (Penn/ 97E043—3 clones), heart from one rhesus monkey (IHGT/ 98E046—1 clone) and peripheral blood from one chimpanzee (New Iberia/X133—5 clones), six cynomologous macaques (Charles River/A1378, A3099, A3388, A3442, A2821, A3242—6 clones total) and one Baboon (SFRB/8644—2 clones). Of the 50 clones that were sequenced from 15 different animals, 30 were considered non-redundant based on the finding of at least 7 amino acid differences from one another. The non-redundant VP1 clones are numbered sequentially as they were isolated, with a prefix indicating the species of non-human primate from which they were derived. The structural relationships between these 30 non-redundant clones and the previously described 8 AAV serotypes were determined using the SplitsTree program [Huson, D. H. SplitsTree: analyzing and visualizing evolutionary data. *Bioinformatics* 14, 68-73 (1998)] with implementation of the method of split decomposition. The analysis depicts homoplasy between a set of sequences in a tree-like network rather than a bifurcating tree. The advantage is to enable detection of groupings that are the result of convergence and to exhibit phylogenetic relationships even when they are distorted by parallel events. Extensive phylogenetic research will be required in order to elucidate the AAV evolution, whereas the intention here only is to group the different clones as to their sequence similarity.

To confirm that the novel VP1 sequences were derived from infectious viral genomes, cellular DNA from tissues with high abundance of viral DNA was restricted with an endonuclease that should not cleave within AAV and transfected into 293 cells, followed by infection with adenovirus. This resulted in rescue and amplification of AAV genomes from DNA of tissues from two different animals (data not shown).

VP1 sequences of the novel AAVs were further characterized with respect to the nature and location of amino acid sequence variation. All 30 VP1 clones that were shown to differ from one another by greater than 1% amino acid sequence were aligned and scored for variation at each residue. An algorithm developed to determine areas of sequence divergence yielded 12 hypervariable regions (HVR) of which 5 overlap or are part of the 4 previously described variable regions [Kotin, cited above; Rutledge, cited above]. The three-fold-proximal peaks contain most of the variability (HVR5-10). Interestingly the loops located at the 2 and 5 fold axis show intense variation as well. The HVRs 1 and 2 occur in the N-terminal portion of the capsid protein that is not resolved in the X-ray structure suggesting that the N-terminus of the VP1 protein is exposed on the surface of the virion.

Real-time PCR was used to quantify AAV sequences from tissues of 21 rhesus monkeys using primers and probes to highly conserved regions of Rep (one set) and Cap (two sets) of known AAVs. Each data point represents analysis from tissue DNA from an individual animal. This confirmed the wide distribution of AAV sequences, although the quantitative distribution differed between individual animals. The source of animals and previous history or treatments did not appear to influence distribution of AAV sequences in rhesus macaques. The three different sets of primers and probes used to quantify AAV yielded consistent results. The highest levels of AAV were found consistently in mesenteric lymph nodes at an average of 0.01 copies per diploid genome for 13 animals that were positive. Liver and spleen also contained high abundance of virus DNA. There were examples of very high AAV, such as in heart of rhesus macaque 98E056, spleen of rhesus macaque 97E043 and liver of rhesus macaque RQ4407, which demonstrated 1.5, 3 and 20 copies of AAV sequence per diploid genome respectively. Relatively low levels of virus DNA were noted in peripheral blood mononuclear cells, suggesting the data in tissue are not due to resident blood components (data not shown). It should be noted that this method would not necessarily capture all AAVs resident to the nonhuman primates since detection requires high homology to both the oligonucleotides and the real time PCR probe. Tissues from animals with high abundance AAV DNA was further analyzed for the molecular state of the DNA, by DNA hybridization techniques, and its cellular distribution, by in situ hybridization.

The kind of sequence variation revealed in AAV proviral fragments isolated from different animals and within tissues of the same animals is reminiscent of the evolution that occurs for many RNA viruses during pandemics or even within the infection of an individual. In some situations the notion of a wild-type virus has been replaced by the existence of swarms of quasispecies that evolve as a result of rapid replication and mutations in the presence of selective pressure. One example is infection by HIV, which evolves in response to immunologic and pharmacologic pressure. Several mechanisms contribute to the high rate of mutations in RNA viruses, including low fidelity and lack of proof reading capacity of reverse transcriptase and non-homologous and homologous recombination.

Evidence for the formation of quasispecies of AAV was illustrated in this study by the systematic sequencing of multiple cloned proviral fragments. In fact, identical sequences could not be found within any extended clones isolated between or within animals. An important mechanism for this evolution of sequence appears to be a high rate of homologous recombination between a more limited number of parenteral viruses. The net result is extensive swapping of hypervariable regions of the Cap protein leading to an array of chimeras that could have different tropisms and serologic specificities (i.e., the ability to escape immunologic responses especially as it relates to neutralizing antibodies). Mechanisms by which homologous recombination could occur are unclear. One possibility is that + and − strands of different single stranded AAV genomes anneal during replication as has been described during high multiplicity of infections with AAV recombinants. It is unclear if other mechanisms contribute to sequence evolution in AAV infections. The overall rate of mutation that occurs during AAV replication appears to be relatively low and the data do not suggest high frequencies of replication errors. However, substantial rearrangements of the AAV genome have been described during lytic infection leading to the formation of defective interfering particles. Irrespective of the mechanisms that lead to sequence divergence, with few exceptions, vp1 structures of the quasispecies remained intact without frameshifts or nonsense mutations suggesting that competitive selection of viruses with the most favorable profile of fitness contribute to the population dynamics.

These studies have implications in several areas of biology and medicine. The concept of rapid virus evolution, formerly thought to be a property restricted to RNA viruses, should be considered in DNA viruses, which classically have been characterized by serologic assays. It will be important in terms of parvoviruses to develop a new method for describing virus isolates that captures the complexity of its structure and biology, such as with HIV, which are categorized as general families of similar structure and function called Clades. An alternative strategy is to continue to categorize isolates with respect to serologic specificity and develop criteria for describing variants within serologic groups.

Example 3: Vectorology of Recombinant AAV Genomes Equipped with AAV2 ITRs Using Chimeric Plasmids Containing AAV2 Rep and Novel AAV Cap Genes for Serological and Gene Transfer Studies in Different Animal Models Chimeric packaging constructs are generated by fusing AAV2 rep with cap sequences of novel AAV serotypes. These chimeric packaging constructs are used, initially, for pseudotyping recombinant AAV genomes carrying AAV2 ITRs by triple transfection in 293 cell using Ad5 helper plasmid. These pseudotyped vectors are used to evaluate performance in transduction-based serological studies and evaluate gene transfer efficiency of novel AAV serotypes in different animal models including NHP and rodents, before intact and infectious viruses of these novel serotypes are isolated.

A. pAAV2GFP

The AAV2 plasmid which contains the AAV2 ITRs and green fluorescent protein expressed under the control of a constitutive promoter. This plasmid contains the following elements: the AAV2 ITRs, a CMV promoter, and the GFP coding sequences.

B. Cloning of Trans Plasmid

To construct the chimeric trans-plasmid for production of recombinant pseudotyped AAV7 vectors, p5E18 plasmid (Xiao et al., 1999, *J. Virol* 73:3994-4003) was partially digested with Xho I to linearize the plasmid at the Xho I site at the position of 3169 bp only. The Xho I cut ends were then filled in and ligated back. This modified p5E18 plasmid was restricted with Xba I and Xho I in a complete digestion to remove the AAV2 cap gene sequence and replaced with a 2267 bp Spe I/Xho I fragment containing the AAV7 cap gene which was isolated from pCRAAV7 6-5+15-4 plasmid.

The resulting plasmid contains the AAV2 rep sequences for Rep78/68 under the control of the AAV2 P5 promoter, and the AAV2 rep sequences for Rep52/40 under the control of the AAV2 P19 promoter. The AAV7 capsid sequences are under the control of the AAV2 P40 promoter, which is located within the Rep sequences. This plasmid further contains a spacer 5′ of the rep ORF.

C. Production of Pseudotyped rAAV

The rAAV particles (AAV2 vector in AAV7 capsid) are generated using an adenovirus-free method. Briefly, the cis plasmid (pAAV2.1 lacZ plasmid containing AAV2 ITRs), and the trans plasmid pCRAAV7 6-5+15-4 (containing the AAV2 rep and AAV7 cap) and a helper plasmid, respectively, were simultaneously co-transfected into 293 cells in a ratio of 1:1:2 by calcium phosphate precipitation.

For the construction of the pAd helper plasmids, pBG10 plasmid was purchased from Microbix (Canada). A RsrII fragment containing L2 and L3 was deleted from pBHG10, resulting in the first helper plasmid, pAdΔF13. Plasmid AdΔ F1 was constructed by cloning Asp700/SalI fragment with a PmeI/SgfI deletion, isolating from pBHG10, into Bluescript. MLP, L2, L2 and L3 were deleted in the pAdΔF1. Further deletions of a 2.3 kb NruI fragment and, subsequently, a 0.5 kb RsrII/NruI fragment generated helper plasmids pAdΔF5 and pAdΔF6, respectively. The helper plasmid, termed pΔF6, provides the essential helper functions of E2a and E4 ORF6 not provided by the E1-expressing helper cell, but is deleted of adenoviral capsid proteins and functional E1 regions).

Typically, 50 µg of DNA (cis:trans:helper) was transfected onto a 150 mm tissue culture dish. The 293 cells were harvested 72 hours post-transfection, sonicated and treated with 0.5% sodium deoxycholate (37EC for 10 min) Cell lysates were then subjected to two rounds of a CsCl gradient. Peak fractions containing rAAV vector are collected, pooled and dialyzed against PBS.

Example 4: Creation of Infectious Clones Carrying Intact Novel AAV Serotypes for Study of Basic Virology in Human and NHP Derived Cell Lines and Evaluation of Pathogenesis of Novel AAV Serotypes in NHP and Other Animal Models To achieve this goal, the genome walker system is employed to obtain 5′ and 3′ terminal sequences (ITRs) and complete construction of clones containing intact novel AAV serotype genomes.

Briefly, utilizing a commercially available Universal Genome Walker Kit [Clontech], genomic DNAs from monkey tissues or cell lines that are identified as positive for the presence of AAV7 sequence are digested with Dra I, EcoR V, Pvu II and Stu I endonucleases and ligated to Genome Walker Adaptor to generate 4 individual Genome Walker Libraries (GWLs). Using DNAs from GWLs as templates, AAV7 and adjacent genomic sequences will be PCR-amplified by the adaptor primer 1 (AP1, provided in the kit) and an AAV7 specific primer 1, followed by a nested PCR using the adaptor primer 2 (AP2) and another AAV7 specific primer 2, both of which are internal to the first set of primers. The major PCR products from the nested PCR are cloned and characterized by sequencing analysis.

In this experiment, the primers covering the 257 bp or other signature fragment of a generic AAV genome are used for PCR amplification of cellular DNAs extracted from Human and NHP derived cell lines to identify and characterize latent AAV sequences. The identified latent AAV genomes are rescued from the positive cell lines using adenovirus helpers of different species and strains.

To isolate infectious AAV clones from NHP derived cell lines, a desired cell line is obtained from ATCC and screened by PCR to identify the 257 bp amplicon, i.e., signature region of the invention. The 257 bp PCR product is cloned and serotyped by sequencing analysis. For these cell lines containing the AAV7 sequence, the cells are infected with SV-15, a simian adenovirus purchased from ATCC, human Ad5 or transfected with plasmid construct housing the human Ad genes that are responsible for AAV helper functions. At 48 hour post infection or transfection, the cells are harvested and Hirt DNA is prepared for cloning of AAV7 genome following Xiao et al., 1999, J. Virol, 73:3994-4003.

Example 5—Production of AAV Vectors

A pseudotyping strategy similar to that of Example 3 for AAV1/7 was employed to produce AAV2 vectors packaged with AAV1, AAV5 and AAV8 capsid proteins. Briefly, recombinant AAV genomes equipped with AAV2 ITRs were packaged by triple transfection of 293 cells with cis-plasmid, adenovirus helper plasmid and a chimeric packaging construct where the AAV2 rep gene is fused with cap genes of novel AAV serotypes. To create the chimeric packaging constructs, the Xho I site of p5E18 plasmid at 3169 bp was ablated and the modified plasmid was restricted with Xba I and Xho I in a complete digestion to remove the AAV2 cap gene and replace it with a 2267 bp Spe I/Xho I fragment containing the AAV8 cap gene [Xiao, W., et al., (1999) *J Virol* 73, 3994-4003]. A similar cloning strategy was used for creation of chimeric packaging plasmids of AAV2/1 and AAV2/5. All recombinant vectors were purified by the standard $CsCl_2$ sedimentation method except for AAV2/2, which was purified by single step heparin chromatography.

Genome copy (GC) titers of AAV vectors were determined by TaqMan analysis using probes and primers targeting SV40 poly A region as described previously [Gao, G., et al., (2000) *Hum Gene Ther* 11, 2079-91].

Vectors were constructed for each serotype for a number of in vitro and in vivo studies. Eight different transgene cassettes were incorporated into the vectors and recombinant virions were produced for each serotype. The recovery of virus, based on genome copies, is summarized in Table 4 below. The yields of vector were high for each serotype with no consistent differences between serotypes. Data presented in the table are average genome copy yields with standard deviation×$10^{13}$ of multiple production lots of 50 plate (150 mm) transfections.

TABLE 4

Production of Recombinant Vectors

|   |   | AAV2/1 | AAV2/2 | AAV2/5 | AAV2/7 | AAV2/8 |
|---|---|---|---|---|---|---|
| CMV | LacZ | 7.30 ± 4.33 (n = 9) | 4.49 ± 2.89 (n = 6) | 5.19 ± 5.19 (n = 8) | 3.42 (n = 1) | 0.87 (n = 1) |
| CMV | EGFP | 6.43 ± 2.42 (n = 2) | 3.39 ± 2.42 (n = 2) | 5.55 ± 6.49 (n = 4) | 2.98 ± 2.66 (n = 2) | 3.74 ± 3.88 (n = 2) |
| TBG | LacZ | 4.18 (n = 1) | 0.23 (n = 1) | 0.704 ± 0.43 (n = 2) | 2.16 (n = 1) | 0.532 (n = 1) |
| Alb | A1AT | 4.67 ± 0.75 (n = 2) | 4.77 (n = 1) | 4.09 (n = 1) | 5.04 (n = 1) | 2.02 (n = 1) |
| CB | A1AT | 0.567 (n = 1) | 0.438 (n = 1) | 2.82 (n = 1) | 2.78 (n = 1) | 0.816 ± 0.679 (n = 2) |
| TBG | rhCG | 8.51 ± 6.65 (n = 6) | 3.47 ± 2.09 (n = 5) | 5.26 ± 3.85 (n = 4) | 6.52 ± 3.08 (n = 4) | 1.83 ± 0.98 (n = 5) |
| TBG | cFIX | 1.24 ± 1.29 (n = 3) | 0.63 ± 0.394 (n = 6) | 3.74 ± 2.48 (n = 7) | 4.05 (n = 1) | 15.8 ± 15.0 (n = 5) |

Example 6—Serologic Analysis of Pseudotyped Vectors

C57BL/6 mice were injected with vectors of different serotypes of AAVCBA1AT vectors intramuscularly ($5 \times 10^{11}$ GC) and serum samples were collected 34 days later. To test neutralizing and cross-neutralizing activity of sera to each serotype of AAV, sera was analyzed in a transduction based neutralizing antibody assay [Gao, G. P., et al., (1996) *J Virol* 70, 8934-43]. More specifically, the presence of neutralizing antibodies was determined by assessing the ability of serum to inhibit transduction of 84-31 cells by reporter viruses (AAVCMVEGFP) of different serotypes. Specifically, the reporter virus AAVCMVEGFP of each serotype [at multiplicity of infection (MOI) that led to a transduction of 90% of indicator cells] was pre-incubated with heat-inactivated serum from animals that received different serotypes of AAV or from naïve mice. After 1-hour incubation at 37° C., viruses were added to 84-31 cells in 96 well plates for 48 or 72-hour, depending on the virus serotype. Expression of GFP was measured by FluoroImagin (Molecular Dynamics) and quantified by Image Quant Software. Neutralizing antibody titers were reported as the highest serum dilution that inhibited transduction to less than 50%.

The availability of GFP expressing vectors simplified the development of an assay for neutralizing antibodies that was based on inhibition of transduction in a permissive cell line (i.e., 293 cells stably expressing E4 from Ad5). Sera to selected AAV serotypes were generated by intramuscular injection of the recombinant viruses. Neutralization of AAV transduction by 1:20 and 1:80 dilutions of the antisera was evaluated (See Table 5 below). Antisera to AAV1, AAV2, AAV5 and AAV8 neutralized transduction of the serotype to which the antiserum was generated (AAV5 and AAV8 to a lesser extent than AAV1 and AAV2) but not to the other serotype (i.e., there was no evidence of cross neutralization suggesting that AAV 8 is a truly unique serotype).

TABLE 5

Serological Analysis of New AAV Serotypes.

| | | % Infection on 84-31 cells with AAVCMVEGFP virus: | | | | | | | | |
|---|---|---|---|---|---|---|---|---|---|---|
| | | AAV2/1 Serum dilution: | | AAV2/2 Serum dilution: | | AAV2/5 Serum dilution: | | AAV2/7 Serum dilution: | | AAV2/8 Serum dilution: | |
| Sera: | Immunization Vector | 1/20 | 1/80 | 1/20 | 1/80 | 1/20 | 1/80 | 1/20 | 1/80 | 1/20 | 1/80 |
| Group 1 | AAV2/1 | 0 | 0 | 100 | 100 | 100 | 100 | 100 | 100 | 100 | 100 |
| Group 2 | AAV2/2 | 100 | 100 | 0 | 0 | 100 | 100 | 100 | 100 | 100 | 100 |
| Group 3 | AAV2/5 | 100 | 100 | 100 | 100 | 16.5 | 16.5 | 100 | 100 | 100 | 100 |
| Group 4 | AAV2/7 | 100 | 100 | 100 | 100 | 100 | 100 | 61.5 | 100 | 100 | 100 |
| Group 5 | AAV2/8 | 100 | 100 | 100 | 100 | 100 | 100 | 100 | 100 | 26.3 | 60 |

Human sera from 52 normal subjects were screened for neutralization against selected serotypes. No serum sample was found to neutralize AAV2/7 and AAV2/8 while AAV2/2 and AAV2/1 vectors were neutralized in 20% and 10% of sera, respectively. A fraction of human pooled IgG representing a collection of 60,000 individual samples did not neutralize AAV2/7 and AAV2/8, whereas AAV2/2 and AAV2/1 vectors were neutralized at titers of serum equal to 1/1280 and 1/640, respectively.

Example 7—In Vivo Evaluation of Different Serotypes of AAV Vectors

In this study, 7 recombinant AAV genomes, AAV2CBhA1AT, AAV2AlbhA1AT, AAV2CMVrhCG, AAV2TBGrhCG, AAV2TBGcFIX, AAV2CMVLacZ and AAV2TBGLacZ were packaged with capsid proteins of different serotypes. In all 7 constructs, minigene cassettes were flanked with AAV2 ITRs. cDNAs of human α-antitrypsin (A1AT) [Xiao, W., et al., (1999) J Virol 73, 3994-4003] β-subunit of rhesus monkey choriogonadotropic hormone (CG) [Zoltick, P. W. & Wilson, J. M. (2000) Mol Ther 2, 657-9] canine factor IX [Wang, L., et al., (1997) Proc Nati Acad Sci USA 94, 11563-6] and bacterial β-glactosidase (i.e., Lac Z) genes were used as reporter genes. For liver-directed gene transfer, either mouse albumin gene promoter (Alb) [Xiao, W. (1999), cited above] or human thyroid hormone binding globulin gene promoter (TBG) [Wang (1997), cited above] was used to drive liver specific expression of reporter genes. In muscle-directed gene transfer experiments, either cytomegalovirus early promoter (CMV) or chicken β-actin promoter with CMV enhancer (CB) was employed to direct expression of reporters.

For muscle-directed gene transfer, vectors were injected into the right tibialis anterior of 4-6 week old NCR nude or C57BL/6 mice (Taconic, Germantown, N.Y.). In liver-directed gene transfer studies, vectors were infused intraportally into 7-9 week old NCR nude or C57BL/6 mice (Taconic, Germantown, N.Y.). Serum samples were collected intraorbitally at different time points after vector administration. Muscle and liver tissues were harvested at different time points for cryosectioning and Xgal histochemical staining from animals that received the lacZ vectors. For the re-administration experiment, C56BL/6 mice initially received AAV2/1, 2/2, 2/5, 2/7 and 2/8CBA1AT vectors intramuscularly and followed for A1AT gene expression for 7 weeks. Animals were then treated with AAV2/8TBGcFIX intraportally and studied for cFIX gene expression.

ELISA based assays were performed to quantify serum levels of hA1AT, rhCG and cFIX proteins as described previously [Gao, G. P., et al., (1996) J Virol 70, 8934-43; Zoltick, P. W. & Wilson, J. M. (2000) Mol Ther 2, 657-9; Wang, L., et al., Proc Natl Acad Sci USA 94, 11563-6]. The experiments were completed when animals were sacrificed for harvest of muscle and liver tissues for DNA extraction and quantitative analysis of genome copies of vectors present in target tissues by TaqMan using the same set of primers and probe as in titration of vector preparations [Zhang, Y., et al., (2001) Mol Ther 3, 697-707].

The performance of vectors base on the new serotypes were evaluated in murine models of muscle and liver-directed gene transfer and compared to vectors based on the known serotypes AAV1, AAV2 and AAV5. Vectors expressing secreted proteins (alpha-antitrypsin (A1AT) and chorionic gonadotropin (CG)) were used to quantitate relative transduction efficiencies between different serotypes through ELISA analysis of sera. The cellular distribution of transduction within the target organ was evaluated using lacZ expressing vectors and X-gal histochemistry.

The performance of AAV vectors in skeletal muscle was analyzed following direct injection into the tibialis anterior muscles. Vectors contained the same AAV2 based genome with the immediate early gene of CMV or a CMV enhanced β-actin promoter driving expression of the transgene. Previous studies indicated that immune competent C57BL/6 mice elicit limited humoral responses to the human A1AT protein when expressed from AAV vectors [Xiao, W., et al., (1999) J Virol 73, 3994-4003].

In each strain, AAV2/1 vector produced the highest levels of A1AT and AAV2/2 vector the lowest, with AAV2/7 and AAV2/8 vectors showing intermediate levels of expression. Peak levels of CG at 28 days following injection of nu/nu NCR mice showed the highest levels from AAV2/7 and the lowest from AAV2/2 with AAV2/8 and AAV2/1 in between. Injection of AAV2/1 and AAV2/7 lacZ vectors yielded gene expression at the injection sites in all muscle fibers with substantially fewer lacZ positive fibers observed with AAV2/2 and AAV 2/8 vectors. These data indicate that the efficiency of transduction with AAV2/7 vectors in skeletal muscle is similar to that obtained with AAV2/1, which is the most efficient in skeletal muscle of the previously described serotypes [Xiao, W. (1999), cited above; Chao, H., et al., (2001) Mol Ther 4, 217-22; Chao, H., et al., (2000) Mol Ther 2, 619-23].

Similar murine models were used to evaluate liver-directed gene transfer. Identical doses of vector based on genome copies were infused into the portal veins of mice that were analyzed subsequently for expression of the transgene. Each vector contained an AAV2 based genome using previously described liver-specific promoters (i.e., albumin or thyroid hormone binding globulin) to drive expression of the transgene. More particularly, CMVCG and TBGCG minigene cassettes were used for muscle and liver-directed gene transfer, respectively. Levels of rhCG were defined as relative units (RUs×$10^3$). The data were from assaying serum samples collected at day 28, post vector administration (4 animals per group). As shown in Table 3, the impact of capsid proteins on the efficiency of transduction of A1AT vectors in nu/nu and C57BL/6 mice and CG vectors in C57BL/6 mice was consistent (See Table 6).

TABLE 6

Expression of β-unit of Rhesus Monkey Chorionic Gonadotropin (rhCG)

| Vector | Muscle | Liver |
|---|---|---|
| AAV2/1 | 4.5 ± 2.1 | 1.6 ± 1.0 |
| AAV2 | 0.5 ± 0.1 | 0.7 ± 0.3 |
| AAV2/5 | ND* | 4.8 ± 0.8 |
| AAV2/7 | 14.2 ± 2.4 | 8.2 ± 4.3 |
| AAV2/8 | 4.0 ± 0.7 | 76.0 ± 22.8 |

*Not determined in this experiment.

In all cases, AAV2/8 vectors yielded the highest levels of transgene expression that ranged from 16 to 110 greater than what was obtained with AAV2/2 vectors; expression from AAV2/5 and AAV2/7 vectors was intermediate with AAV2/7 higher than AAV2/5. Analysis of X-Gal stained liver sections of animals that received the corresponding lacZ vectors showed a correlation between the number of transduced cells and overall levels of transgene expression. DNAs extracted from livers of C57BL/6 mice who received the A1AT vectors were analyzed for abundance of vector DNA using real time PCR technology.

The amount of vector DNA found in liver 56 days after injection correlated with the levels of transgene expression (See Table 7). For this experiment, a set of probe and primers targeting the SV40 polyA region of the vector genome was used for TaqMan PCR. Values shown are means of three individual animals with standard deviations. The animals were sacrificed at day 56 to harvest liver tissues for DNA extraction. These studies indicate that AAV8 is the most efficient vector for liver-directed gene transfer due to increased numbers of transduced hepatocytes.

TABLE 7

Real Time PCR Analysis for Abundance of AAV Vectors in nu/nu Mouse Liver Following Injection of 1 × $10^{11}$ Genome Copies of Vector.

| AAV vectors/Dose | Genome Copies per Cell |
|---|---|
| AAV2/1AlbA1AT | 0.6 ± 0.36 |
| AAV2AlbA1AT | 0.003 ± 0.001 |
| AAV2/5AlbA1AT | 0.83 ± 0.64 |
| AAV2/7AlbA1AT | 2.2 ± 1.7 |
| AAV2/8AlbA1AT | 18 ± 11 |

The serologic data described above suggest that AAV2/8 vector should not be neutralized in vivo following immunization with the other serotypes. C57BL/6 mice received intraportal injections of AAV2/8 vector expressing canine factor IX ($10^{11}$ genome copies) 56 days after they received intramuscular injections of A1AT vectors of different serotypes. High levels of factor IX expression were obtained 14 days following infusion of AAV2/8 into naïve animals (17±2 μg/ml, n=4) which were not significantly different that what was observed in animals immunized with AAV2/1 (31±23 μg/ml, n=4), AAV2/2 (16 μg/ml, n=2), and AAV2/7 (12 μg/ml, n=2). This contrasts to what was observed in AAV2/8 immunized animals that were infused with the AAV2/8 factor IX vector in which no detectable factor IX was observed (<0.1 μg/ml, n=4).

Oligonucleotides to conserved regions of the cap gene did amplify sequences from rhesus monkeys that represented unique AAVs. Identical cap signature sequences were found in multiple tissues from rhesus monkeys derived from at least two different colonies. Full-length rep and cap open reading frames were isolated and sequenced from single sources. Only the cap open reading frames of the novel AAVs were necessary to evaluate their potential as vectors because vectors with the AAV7 or AAV8 capsids were generated using the ITRs and rep from AAV2. This also simplified the comparison of different vectors since the actual vector genome is identical between different vector serotypes. In fact, the yields of recombinant vectors generated using this approach did not differ between serotypes.

Vectors based on AAV7 and AAV8 appear to be immunologically distinct (i.e., they are not neutralized by antibodies generated against other serotypes). Furthermore, sera from humans do not neutralize transduction by AAV7 and AAV8 vectors, which is a substantial advantage over the human derived AAVs currently under development for which a significant proportion of the human population has pre-existing immunity that is neutralizing [Chirmule, N., et al., (1999) Gene Ther 6, 1574-83].

The tropism of each new vector is favorable for in vivo applications. AAV2/7 vectors appear to transduce skeletal muscle as efficiently as AAV2/1, which is the serotype that confers the highest level of transduction in skeletal muscle of the primate AAVs tested to date [Xiao, W., cited above; Chou (2001), cited above, and Chou (2000), cited above]. Importantly, AAV2/8 provides a substantial advantage over the other serotypes in terms of efficiency of gene transfer to liver that until now has been relatively disappointing in terms of the numbers of hepatocytes stably transduced. AAV2/8 consistently achieved a 10 to 100-fold improvement in gene transfer efficiency as compared to the other vectors. The basis for the improved efficiency of AAV2/8 is unclear, although it presumably is due to uptake via a different receptor that is more active on the basolateral surface of hepatocytes. This improved efficiency will be quite useful in the development of liver-directed gene transfer where the number of transduced cells is critical, such as in urea cycle disorders and familial hypercholesterolemia.

Thus, the present invention provides a novel approach for isolating new AAVs based on PCR retrieval of genomic sequences. The amplified sequences were easily incorporated into vectors and tested in animals. The lack of pre-existing immunity to AAV7 and the favorable tropism of the vectors for muscle indicates that AAV7 is suitable for use as a vector in human gene therapy and other in vivo applications. Similarly, the lack of pre-existing immunity to the AAV serotypes of the invention, and their tropisms, renders them useful in delivery of therapeutic molecules and other useful molecules.

Example 9—Tissue Tropism Studies

In the design of a high throughput functional screening scheme for novel AAV constructs, a non-tissue specific and highly active promoter, CB promoter (CMV enhanced chicken β actin promoter) was selected to drive an easily detectable and quantifiable reporter gene, human α antitrypsin gene. Thus only one vector for each new AAV clone needs to be made for gene transfer studies targeting 3 different tissues, liver, lung and muscle to screen for tissue tropism of a particular AAV construct. The following table summarizes data generated from 4 novel AAV vectors in the tissue tropism studies (AAVCBA1AT), from which a novel AAV capsid clone, 44.2, was found to be a very potent gene transfer vehicle in all 3 tissues with a big lead in the lung tissue particularly. Table 8 reports data obtained (in μg A1AT/mL serum) at day 14 of the study.

TABLE 8

| Vector | Target Tissue | | |
|---|---|---|---|
| | Lung | Liver | Muscle |
| AAV2/1 | ND | ND | 45 ± 11 |
| AAV2/5 | 0.6 ± 0.2 | ND | ND |
| AAV2/8 | ND | 84 ± 30 | ND |
| AAV2/rh. 2 (43.1) | 14 ± 7 | 25 ± 7.4 | 35 ± 14 |
| AAV2/rh. 10 (44.2) | 23 ± 6 | 53 ± 19 | 46 ± 11 |
| AAV2/rh. 13 (42.2) | 3.5 ± 2 | 2 ± 0.8 | 3.5 ± 1.7 |
| AAV2/rh. 21 (42.10) | 3.1 ± 2 | 2 ± 1.4 | 4.3 ± 2 |

A couple of other experiments were then performed to confirm the superior tropism of AAV 44.2 in lung tissue. First, AAV vector carried CC10hA1AT minigene for lung specific expression were pseudotyped with capsids of novel AAVs were given to Immune deficient animals (NCR nude) in equal volume (50 μl each of the original preps without dilution) via intratracheal injections as provided in the following table. In Table 9, 50 μl of each original prep per mouse, NCR Nude, detection limit ≥0.033 μg/ml, Day 28

TABLE 9

| Vector | Total GC in 50 μl vector | μg of A1AT/ml with 50 μl vector | μg of A1AT/ml with 1 × 10¹¹ vector | Relative Gene transfer as compared to rh. 10 (clone 44.2) |
|---|---|---|---|---|
| 2/1 | 3 × 10¹² | 2.6 ± 0.5 | 0.09 ± 0.02 | 2.2 |
| 2/2 | 5.5 × 10¹¹ | <0.03 | <0.005 | <0.1 |
| 2/5 | 3.6 × 10¹² | 0.65 ± 0.16 | 0.02 ± 0.004 | 0.5 |
| 2/7 | 4.2 × 10¹² | 1 ± 0.53 | 0.02 ± 0.01 | 0.5 |
| 2/8 | 7.5 × 10¹¹ | 0.9 ± 0.7 | 0.12 ± 0.09 | 2.9 |
| 2/ch. 5 (A.3.1) | 9 × 10¹² | 1 ± 0.7 | 0.01 ± 0.008 | 0.24 |
| 2/rh. 8 (43.25) | 4.6 × 10¹² | 26 ± 21 | 0.56 ± 0.46 | 13.7 |
| 2/rh. 10 (44.2) | 2.8 × 10¹² | 115 ± 38 | 4.1 ± 1.4 | 100 |
| 2/rh. 13 (42.2) | 6 × 10¹² | 7.3 ± 0.8 | 0.12 ± 0.01 | 2.9 |
| 2/rh. 21 (42.10) | 2.4 × 10¹² | 9 ± 0.9 | 0.38 ± 0.04 | 9.3 |
| 2/rh. 22 (42.11) | 2.6 × 10¹² | 6 ± 0.4 | 0.23 ± 0.02 | 5.6 |
| 2/rh. 24 (42.13) | 1.1 × 10¹¹ | 0.4 ± 0.3 | 0.4 ± 0.3 | 1 |

The vectors were also administered to immune competent animals (C57BL/6) in equal genome copies (1×10¹¹ GC) as shown in the Table 10. (1×10¹¹ GC per animal, C57BL/6, day 14, detection limit ≥0.033 μg/ml)

TABLE 10

| AAV Vector | μg of A1AT/ml with 1 × 10¹¹ vector | Relative Gene transfer as compared to rh. 10 (clone 44.2) |
|---|---|---|
| 2/1 | 0.076 ± 0.031 | 2.6 |
| 2/2 | 0.1 ± 0.09 | 3.4 |
| 2/5 | 0.0840.033 | 2.9 |
| 2/7 | 0.33 ± 0.01 | 11 |
| 2/8 | 1.92 ± 1.3 | 2.9 |
| 2/ch. 5 (A.3.1) | 0.048 ± 0.004 | 1.6 |

TABLE 10-continued

| AAV Vector | μg of A1AT/ml with 1 × 10¹¹ vector | Relative Gene transfer as compared to rh. 10 (clone 44.2) |
|---|---|---|
| 2/rh. 8 (43.25) | 1.7 ± 0.7 | 58 |
| 2/rh. 10 (44.2) | 2.93 ± 1.7 | 100 |
| 2/rh. 13 (42.2) | 0.45 ± 0.15 | 15 |
| 2/rh. 21 (42.10) | 0.86 ± 0.32 | 29 |
| 2/rh. 22 (42.11) | 0.38 ± 0.18 | 13 |
| 2/rh. 24 (42.13) | 0.3 ± 0.19 | 10 |

The data from both experiments confirmed the superb tropism of clone 44.2 in lung-directed gene transfer.

Interestingly, performance of clone 44.2 in liver and muscle directed gene transfer was also outstanding, close to that of the best liver transducer, AAV8 and the best muscle transducer AAV1, suggesting that this novel AAV has some intriguing biological significance.

To study serological properties of those novel AAVs, pseudotyped AAVGFP vectors were created for immunization of rabbits and in vitro transduction of 84-31 cells in the presence and absence of antisera against different capsids. The data are summarized below:

TABLE 11a

| Cross-NAB assay in 8431 cells and adenovirus (Adv) coinfection | | | | |
|---|---|---|---|---|
| Infection in 8431 cells (coinfected with Adv) with: | | | | |
| Serum from rabbit immunized with: | 10⁹ GC rh. 13 AAV2/ 42.2 | 10⁹ GC rh. 21 AAV2/ 42.10 | 10⁹ GC rh. 22 AAV2/ 42.11 | 10¹⁰ GC rh. 24 AAV2/ 42.13 |
| AAV2/1 | 1/20 | 1/20 | 1/20 | No NAB |
| AAV2/2 | 1/640 | 1/1280 | 1/5120 | No NAB |
| AAV2/5 | No NAB | 1/40 | 1/160 | No NAB |
| AAV2/7 | 1/81920 | 1/81920 | 1/40960 | 1/640 |
| AAV2/8 | 1/640 | 1/640 | 1/320 | 1/5120 |
| Ch.5 AAV2/A3 | 1/20 | 1/160 | 1/640 | 1/640 |
| rh. 8 AAV2/43.25 | 1/20 | 1/20 | 1/20 | 1/320 |
| rh. 10 AAV2/44.2 | No NAB | No NAB | No NAB | 1/5120 |
| rh. 13 AAV2/42.2 | 1/5120 | 1/5120 | 1/5120 | No NAB |
| rh. 21 AAV2/42.10 | 1/5120 | 1/10240 | 1/5120 | 1/20 |
| rh. 22 AAV2/42.11 | 1/20480 | 1/20480 | 1/40960 | No NAB |
| rh. 24 AAV2/42.13 | No NAB | 1/20 | 1/20 | 1/5120 |

TABLE 11b

Cross-NAB assay in 8431 cells and Adv coinfection
Infection in 8431 cells (coinfected with Adv) with:

| Serum from rabbit immunized with: | $10^9$ GC rh. 12 AAV2/42.1B | $10^{10}$ GC ch. 5 AAV2/A3 | $10^{10}$ GC rh. 8 AAV2/43.25 | $10^9$ GC rh. 10 AAV2/44.2 | $10^9$ GC rh. 20 AAV2/42.8.2 |
|---|---|---|---|---|---|
| AAV2/1 | No NAB | 1/20480 | No NAB | 1/80 | ND |
| AAV2/2 | 1/20 | No NAB | No NAB | No NAB | ND |
| AAV2/5 | No NAB | 1/320 | No NAB | No NAB | ND |
| AAV2/7 | 1/2560 | 1/640 | 1/160 | 1/81920 | ND |
| AAV2/8 | 1/10240 | 1/2560 | 1/2560 | 1/81920 | ND |
| ch. 5 AAV2/A3 | 1/1280 | 1/10240 | ND | 1/5120 | 1/320 |
| rh. 8 AAV2/43.25 | 1/1280 | ND | 1/20400 | 1/5120 | 1/2560 |
| rh. 10 AAV2/44.2 | 1/5120 | ND | ND | 1/5120 | 1/5120 |
| rh. 13 AAV2/42.2 | 1/20 | ND | ND | No NAB | 1/320 |
| rh. 21 AAV2/42.10 | 1/20 | ND | ND | 1/40 | 1/80 |
| rh. 22 AAV2/42.11 | No NAB | ND | ND | ND | No NAB |
| rh. 24 AAV2/42.13 | 1/5120 | ND | ND | ND | 1/2560 |

TABLE 12

| | Titer of rabbit sera | | Titer after |
|---|---|---|---|
| | Vector | Titer d21 | Boosting |
| ch. 5 | AAV2/A3 | 1/10,240 | 1/40,960 |
| rh. 8 | AAV2/43.25 | 1/20,400 | 1/163,840 |
| rh. 10 | AAV2/44.2 | 1/10,240 | 1/527,680 |
| rh. 13 | AAV2/42.2 | 1/5,120 | 1/20,960 |
| rh. 21 | AAV2/42.10 | 1/20,400 | 1/81,920 |
| rh. 22 | AAV2/42.11 | 1/40,960 | ND |
| rh. 24 | AAV2/42.13 | 1/5,120 | ND |

TABLE 13a

Infection in 8431 cells (coinfected with Adv) with GFP

| | $10^9$ GC/well AAV2/1 | $10^9$ GC/well AAV2/2 | $10^9$ GC/well AAV2/5 | $10^9$ GC/well AAV2/7 | $10^9$ GC/well AAV2/8 | $10^9$ GC/well ch.5 AAV2/A3 |
|---|---|---|---|---|---|---|
| # GFU/field | 128 | >200 | 95 | 56 | 13 | 1 |
| | 83 | >200 | 65 | 54 | 11 | 1 |

TABLE 13b

Infection in 8431 cells (coinfected with Adv) with GFP

| | $10^9$ GC/well rh.8 AAV2/43.25 | $10^9$ GC/well rh.10 AAV2/44.2 | $10^9$ GC/well rh.13 AAV2/42.2 | $10^9$ GC/well rh.21 AAV2/42.10 | $10^9$ GC/well rh.22 AAV2/42.11 | $10^9$ GC/well rh.24 AAV2/42.13 | $10^9$ GC/well rh.12 AAV2/42.1B |
|---|---|---|---|---|---|---|---|
| # GFU/field | 3 | 13 | 54 | 62 | 10 | 3 | 18 |
| | 2 | 12 | 71 | 60 | 14 | 2 | 20 |
| | | | 48 | 47 | 16 | 3 | 12 |

Example 10—Mouse Model of Familial Hypercholesterolemia

The following experiment demonstrates that the AAV2/7 construct of the invention delivers the LDL receptor and express LDL receptor in an amount sufficient to reduce the levels of plasma cholesterol and triglycerides in animal models of familial hypercholesterolemia.

A. Vector Construction

AAV vectors packaged with AAV7 or AAV8 capsid proteins were constructed using a pseudotyping strategy [Hildinger M, et al., J. Virol 2001; 75:6199-6203]. Recombinant AAV genomes with AAV2 inverted terminal repeats (ITR) were packaged by triple transfection of 293 cells with the cis-plasmid, the adenovirus helper plasmid and a chimeric packaging construct, a fusion of the capsids of the novel AAV serotypes with the rep gene of AAV2. The chimeric packaging plasmid was constructed as previously described [Hildinger et al, cited above]. The recombinant vectors were purified by the standard $CsCl_2$ sedimentation method. To determine the yield TaqMan (Applied Biosystems) analysis was performed using probes and primers targeting the SV40 poly(A) region of the vectors [Gao G P, et al., Hum Gene Ther. 2000 October 10; 11(15):2079-91]. The resulting vectors express the transgene under the control of the human thyroid hormone binding globulin gene promoter (TBG).

B. Animals

LDL receptor deficient mice on the C57Bl/6 background were purchased from the Jackson Laboratory (Bar Harbor, Me., USA) and maintained as a breeding colony. Mice were given unrestricted access to water and obtained a high fat Western Diet (high % cholesterol) starting three weeks prior vector injection. At day −7 as well at day 0, blood was obtained via retroorbital bleeds and the lipid profile evaluated. The mice were randomly divided into seven groups. The vector was injected via an intraportal injection as previously described ([Chen S J et al., *Mol Therapy* 2000; 2(3), 256-261]. Briefly, the mice were anaesthetized with ketamine and xylazine. A laparotomy was performed and the portal vein exposed. Using a 30 g needle the appropriate dose of vector diluted in 100 ul PBS was directly injected into the portal vein. Pressure was applied to the injection site to ensure a stop of the bleeding. The skin wound was closed and draped and the mice carefully monitored for the following day. Weekly bleeds were performed starting at day 14 after liver directed gene transfer to measure blood lipids. Two animals of each group were sacrificed at the time points week 6 and week 12 after vector injection to examine atherosclerotic plaque size as well as receptor expression. The remaining mice were sacrificed at week 20 for plaque measurement and determination of transgene expression.

TABLE 14

| | Vector | dose | n |
|---|---|---|---|
| Group 1 | AAV2/7-TBG-hLDLr | $1 \times 10^{12}$ gc | 12 |
| Group 2 | AAV2/7-TBG-hLDLr | $3 \times 10^{11}$ gc | 12 |
| Group 3 | AAV2/7-TBG-hLDLr | $1 \times 10^{11}$ gc | 12 |
| Group 4 | AAV2/8-TBG-hLDLr | $1 \times 10^{12}$ gc | 12 |
| Group 5 | AAV2/8-TBG-hLDLr | $3 \times 10^{11}$ gc | 12 |
| Group 6 | AAV2/8-TBG-hLDLr | $1 \times 10^{11}$ gc | 12 |
| Group 7 | AAV2/7-TBG-LacZ | $1 \times 10^{11}$ gc | 16 |

C. Serum Lipoprotein and Liver Function Analysis

Blood samples were obtained from the retroorbital plexus after a 6 hour fasting period. The serum was separated from the plasma by centrifugation. The amount of plasma lipoproteins and liver transaminases in the serum were detected using an automatized clinical chemistry analyzer (ACE, Schiapparelli Biosystems, Alpha Wassermann)

D. Detection of Transgene Expression

LDL receptor expression was evaluated by immunofluorescence staining and Western blotting. For Western Blot frozen liver tissue was homogenized with lysis buffer (20 mM Tris, pH7.4, 130 mM NaCl, 1% Triton X 100, proteinase inhibitor (complete, EDTA-free, Roche, Mannheim, Germany). Protein concentration was determined using the Micro BCA Protein Assay Reagent Kit (Pierce, Rockford, Ill.). 40 μg of protein was resolved on 4-15% Tris-HCl Ready Gels (Biorad, Hercules, Calif.) and transferred to a nitrocellulose membrane (Invitrogen,). To generate Anti-hLDL receptor antibodies a rabbit was injected intravenously with an AdhLDLr prep ($1 \times 10^{13}$ GC). Four weeks later the rabbit serum was obtained and used for Western Blot. A 1:100 dilution of the serum was used as a primary antibody followed by a HRP-conjugated anti-rabbit IgG and ECL chemiluminescent detection (ECL Western Blot Detection Kit, Amersham, Arlington Heights, Ill.).

E. Immunocytochemistry

For determination of LDL receptor expression in frozen liver sections immunohistochemistry analyses were performed. 10 um cryostat sections were either fixed in acetone for 5 minutes, or unfixed. Blocking was obtained via a 1 hour incubation period with 10% of goat serum. Sections were then incubated for one hour with the primary antibody at room temperature. A rabbit polyclonal antibody anti-human LDL (Biomedical Technologies Inc., Stoughton, Mass.) was used diluted accordingly to the instructions of the manufacturer. The sections were washed with PBS, and incubated with 1:100 diluted fluorescein goat anti-rabbit IgG (Sigma, St Louis, Mo.). Specimens were finally examined under fluorescence microscope Nikon Microphot-FXA. In all cases, each incubation was followed by extensive washing with PBS. Negative controls consisted of preincubation with PBS, omission of the primary antibody, and substitution of the primary antibody by an isotype-matched non-immune control antibody. The three types of controls mentioned above were performed for each experiment on the same day.

F. Gene Transfer Efficiency

Liver tissue was obtained after sacrificing the mice at the designated time points. The tissue was shock frozen in liquid nitrogen and stored at −80° C. until further processing. DNA was extracted from the liver tissue using a QIAamp DNA Mini Kit (QIAGEN GmbH, Germany) according to the manufacturers protocol. Genome copies of AAV vectors in the liver tissue were evaluated using Taqman analysis using probes and primers against the SV40 poly(A) tail as described above.

G. Atherosclerotic Plaque Measurement

For the quantification of the atherosclerotic plaques in the mouse aorta the mice were anaesthetized (10% ketamine and xylazine, ip), the chest opened and the arterial system perfused with ice-cold phosphate buffered saline through the left ventricle. The aorta was then carefully harvested, slit down along the ventral midline from the aortic arch down to the femoral arteries and fixed in formalin. The lipid-rich atherosclerotic plaques were stained with Sudan IV (Sigma, Germany) and the aorta pinned out flat on a black wax surface. The image was captured with a Sony DXC-960 MD color video camera. The area of the plaque as well as of the complete aortic surface was determined using Phase 3 Imaging Systems (Media Cybernetics).

H. Clearance of $I^{125}$ LDL

Two animals per experimental group were tested. A bolus of $I^{125}$-labeled LDL (generously provided by Dan Rader, U Penn) was infused slowly through the tail vein over a period of 30 sec (1,000,000 counts of [$I^{125}$]-LDL diluted in 100 μl sterile PBS/animal). At time points 3 min, 30 min, 1.5 hr, 3 hr, 6 hr after injection a blood sample was obtained via the retro-orbital plexus. The plasma was separated off from the whole blood and 10 μl plasma counted in the gamma counter. Finally the fractional catabolic rate was calculated from the lipoprotein clearance data.

I. Evaluation of Liver Lipid Accumulation

Oil Red Staining of frozen liver sections was performed to determine lipid accumulation. The frozen liver sections were briefly rinsed in distilled water followed by a 2 minute incubation in absolute propylene glycol. The sections were then stained in oil red solution (0.5% in propylene glycol) for 16 hours followed by counterstaining with Mayer's hematoxylin solution for 30 seconds and mounting in warmed glycerin jelly solution.

For quantification of the liver cholesterol and triglyceride content liver sections were homogenized and incubated in chloroform/methanol (2:1) overnight. After adding of 0.05% $H_2SO_4$ and centrifugation for 10 minutes, the lower layer of each sample was collected, divided in two aliquots and dried under nitrogen. For the cholesterol measurement the dried lipids of the first aliquot were dissolved in 1% Triton X-100 in chloroform. Once dissolved, the solution was dried under nitrogen. After dissolving the lipids in $ddH_2O$ and incubation for 30 minutes at 37° C. the total cholesterol concentration was measured using a Total Cholesterol Kit (Wako Diagnostics). For the second aliquot the dried lipids were dissolved in alcoholic KOH and incubated at 60° C. for 30 minutes. Then 1M $MgCl_2$ was added, followed by incubation on ice for 10 minutes and centrifugation at 14,000 rpm for 30 minutes. The supernatant was finally evaluated for triglycerides (Wako Diagnostics).

All of the vectors pseudotyped in an AAV2/8 or AAV2/7 capsid lowered total cholesterol, LDL and triglycerides as compared to the control. These test vectors also corrected phenotype of hypercholesterolemia in a dose-dependent manner. A reduction in plaque area for the AAV2/8 and AAV2/7 mice was observed in treated mice at the first test (2 months), and the effect was observed to persist over the length of the experiment (6 months).

Example 10—Functional Factor IX Expression and Correction of Hemophilia

A. Knock-Out Mice

Functional canine factor IX (FIX) expression was assessed in hemophilia B mice. Vectors with capsids of AAV1, AAV2, AAV5, AAV7 or AAV8 were constructed to deliver AAV2 5' ITR-liver-specific promoter [LSP]-canine FIX-woodchuck hepatitis post-regulatory element (WPRE)-AAV2 3' ITR. The vectors were constructed as described in Wang et al, 2000, *Molecular Therapy* 2: 154-158), using the appropriate capsids.

Knock-out mice were generated as described in Wang et al, 1997. *Proc. Natl. Acad. Sci. USA* 94: 11563-11566. This model closely mimic the phenotypes of hemophilia B in human.

Vectors of different serotypes (AAV1, AAV2, AAV5, AAV7 and AAV8) were delivered as a single intraportal injection into the liver of adult hemophiliac C57Bl/6 mice in a dose of $1\times10^{11}$ GC/mouse for the five different serotypes and one group received an AAV8 vector at a lower dose, $1\times10^{10}$ GC/mouse. Control group was injected with $1\times10^{11}$ GC of AAV2/8 TBG LacZ3. Each group contains 5-10 male and female mice. Mice were bled bi-weekly after vector administration.

1. ELISA

The canine FIX concentration in the mouse plasma was determined by an ELISA assay specific for canine factor IX, performed essentially as described by Axelrod et al, 1990, *Proc. Natl. Acad. Sci. USA*, 87:5173-5177 with modifications. Sheep anti-canine factor IX (Enzyme Research Laboratories) was used as primary antibody and rabbit anti-canine factor IX ((Enzyme Research Laboratories) was used as secondary antibody. Beginning at two weeks following injection, increased plasma levels of cFIX were detected for all test vectors. The increased levels were sustained at therapeutic levels throughout the length of the experiment, i.e., to 12 weeks. Therapeutic levels are considered to be 5% of normal levels, i.e., at about 250 ng/mL.

The highest levels of expression were observed for the AAV2/8 (at $10^{11}$) and AAV2/7 constructs, with sustained superphysiology levels cFIX levels (ten-fold higher than the normal level). Expression levels for AAV2/8 ($10^{11}$) were approximately 10 fold higher than those observed for AAV2/2 and AAV2/8 ($10^{10}$). The lowest expression levels, although still above the therapeutic range, were observed for AAV2/5.

2. In Vitro Activated Partial Thromboplastin Time (aPTT) Assay

Functional factor IX activity in plasma of the FIX knock-out mice was determined by an in vitro activated partial thromboplastin time (aPTT) assay-Mouse blood samples were collected from the retro-orbital plexus into 1/10 volume of citrate buffer. The aPTT assay was performed as described by Wang et al, 1997, *Proc. Natl. Acad. Sci. USA* 94: 11563-11566.

Clotting times by aPTT on plasma samples of all vector injected mice were within the normal range (approximately 60 sec) when measured at two weeks post-injection, and sustained clotting times in the normal or shorter than normal range throughout the study period (12 weeks).

Lowest sustained clotting times were observed in the animals receiving AAV2/8 ($10^{11}$) and AAV2/7. By week 12, AAV2/2 also induced clotting times similar to those for AAV2/8 and AAV2/7. However, this lowered clotting time was not observed for AAV2/2 until week 12, whereas lowered clotting times (in the 25-40 sec range) were observed for AAV2/8 and AAV2/7 beginning at week two.

Immuno-histochemistry staining on the liver tissues harvested from some of the treated mice is currently being performed. About 70-80% of hepatocytes are stained positive for canine FIX in the mouse injected with AAV2/8.cFIX vector.

B. Hemophilia B Dogs

Dogs that have a point mutation in the catalytic domain of the F.IX gene, which, based on modeling studies, appears to render the protein unstable, suffer from hemophilia B [Evans et al, 1989, Proc. Natl. Acad. Sci. USA, 86:10095-10099). A colony of such dogs has been maintained for more than two decades at the University of North Carolina, Chapel Hill. The homeostatic parameters of these dogs are well described and include the absence of plasma F.IX antigen, whole blood clotting times in excess of 60 minutes, whereas normal dogs are 6-8 minutes, and prolonged activated partial thromboplastin time of 50-80 seconds, whereas normal dogs are 13-28 seconds. These dogs experience recurrent spontaneous hemorrhages. Typically, significant bleeding episodes are successfully managed by the single intravenous infusion of 10 ml/kg of normal canine plasma; occasionally, repeat infusions are required to control bleeding.

Four dogs are injected intraportally with AAV.cFIX according to the schedule below. A first dog receives a single injection with AAV2/2.cFIX at a dose of $3.7\times10^{11}$ genome copies (GC)/kg. A second dog receives a first injection of AAV2/2.cFIX ($2.8\times10^{11}$ GC/kg), followed by a second injection with AAV2/7.cFIX ($2.3\times10^{13}$ GC/kg) at day 1180. A third dog receives a single injection with AAV2/2.cFIX at a dose of $4.6\times10^{12}$ GC/kg. The fourth dog receives an injection with AAV2/2.cFIX ($2.8\times10^{12}$ GC/kg) and an injection at day 995 with AAV2/7.cFIX ($5\times10^{12}$ GC/kg).

The abdomen of hemophilia dogs are aseptically and surgically opened under general anesthesia and a single infusion of vector is administered into the portal vein. The animals are protected from hemorrhage in the pen-operative period by intravenous administration of normal canine plasma. The dog is sedated, intubated to induce general anesthesia, and the abdomen shaved and prepped. After the abdomen is opened, the spleen is moved into the operative field. The splenic vein is located and a suture is loosely placed proximal to a small distal incision in the vein. A needle is rapidly inserted into the vein, then the suture loosened and a 5 F cannula is threaded to an intravenous location near the portal vein threaded to an intravenous location near the portal vein bifurcation. After hemostasis is secured and the catheter balloon inflated, approximately 5.0 ml of vector diluted in PBS is infused into the portal vein over a 5 minute interval. The vector infusion is followed by a 5.0 ml infusion of saline. The balloon is then deflated, the callula removed and venous hemostasis is secured. The spleen is then replaced, bleeding vessels are cauterized and the operative wound is closed. The animal is extubated having tolerated the surgical procedure well. Blood samples are analyzed as described. [Wang et al, 2000, *Molecular Therapy* 2: 154-158]

Results showing correction or partial correction are anticipated for AAV2/7.

All publications cited in this specification including priority applications, U.S. patent application Ser. No. 14/956,934, U.S. patent application Ser. No. 13/633,971, U.S. patent application Ser. No. 12/962,793, U.S. patent application Ser. No. 10/291,583, and U.S. provisional patent application Nos. 60/386,675, 60/377,066, 60/341,117, and 60/350,607, are incorporated herein by reference. While the invention has been described with reference to particularly preferred embodiments, it will be appreciated that modifications can be made without departing from the spirit of the invention. Such modifications are intended to fall within the scope of the claims.

The invention claimed is:

1. A recombinant adeno-associated virus (AAV) comprising an AAV capsid comprising vp1 proteins having the sequence of amino acids 1 to 738 of SEQ ID NO: 81 or a sequence at least 95% identical to the full length of amino acids 1 to 738 of SEQ ID NO: 81, AAV vp2 proteins, and AAV vp3 proteins, wherein the recombinant AAV further comprises, packaged within the capsid, a nucleic acid molecule comprising at least one AAV inverted terminal repeat (ITR), and a non-AAV nucleic acid sequence encoding a gene product operably linked to sequences which direct expression of the product in a host cell wherein the gene product is ornithine transcarbamylase, glucose-6-phosphatase, phenylalanine hydroxylase, argininosuccinate synthetase or a dystrophin protein.

2. The recombinant AAV according to claim 1, wherein the sequence of the vp1 proteins is at least 97% identical to the full length of amino acids 1 to 738 of SEQ ID NO: 81.

3. The recombinant AAV according to claim 1, wherein the sequence of the vp1 proteins is at least 99% identical to the full-length of amino acids 1 to 738 of SEQ ID NO: 81.

4. The recombinant AAV according to claim 1, wherein the sequence of the vp1 proteins is the full-length of amino acids 1 to 738 of SEQ ID NO: 81.

5. A recombinant adeno-associated virus (AAV) having an AAV capsid comprising AAV vp1 proteins, AAV vp2 proteins having a sequence of amino acids 138 to 738 of SEQ ID NO:81 (rh.10) or a sequence at least 95% identical to the full-length of amino acids 138 to 738 of SEQ ID NO: 81, and AAV vp3 proteins, wherein the recombinant AAV further comprises, packaged within the capsid, a nucleic acid molecule comprising at least one AAV inverted terminal repeat (ITR) and a non-AAV nucleic acid sequence encoding a gene product operably linked to sequences which direct expression of the product in a host cell, wherein the gene product is ornithine transcarbamylase, glucose-6-phosphatase, phenylalanine hydroxylase, argininosuccinate synthetase or a dystrophin protein.

6. The recombinant AAV according to claim 5, wherein the sequence of the vp2 proteins is at least 97% identical to the full length of amino acids 138 to 738 of SEQ ID NO: 81.

7. The recombinant AAV according to claim 5, wherein the sequence of the vp2 proteins is at least 99% identical to the full-length of amino acids 138 to 738 of SEQ ID NO: 81.

8. The recombinant AAV according to claim 5, wherein the sequence of the vp2 proteins is the full-length of amino acids 138 to 738 of SEQ ID NO: 81.

9. A recombinant adeno-associated virus (AAV) having an AAV capsid comprising AAV vp1 proteins, AAV vp2 proteins, and AAV vp3 proteins having a sequence of amino acids 204 to 738 of SEQ ID NO:81 (rh.10) or a sequence at least 95% identical to the full-length of amino acids 204 to 738 of SEQ ID NO: 81, wherein the recombinant AAV further comprises, packaged within the capsid, a nucleic acid molecule comprising at least one AAV inverted terminal repeat (ITR) and a non-AAV nucleic acid sequence encoding a gene product operably linked to sequences which direct expression of the product in a host cell, wherein the gene product is ornithine transcarbamylase, glucose-6-phosphatase, phenylalanine hydroxylase, argininosuccinate synthetase or a dystrophin protein.

10. The recombinant AAV according to claim 9, wherein the sequence of the vp3 proteins is at least 97% identical to the full length of amino acids 204 to 738 of SEQ ID NO: 81.

11. The recombinant AAV according to claim 9, wherein the sequence of the vp3 proteins is at least 99% identical to the full-length of amino acids 204 to 738 of SEQ ID NO: 81.

12. The recombinant AAV according to claim 9, wherein the sequence of the vp3 proteins is the full-length of amino acids 204 to 738 of SEQ ID NO: 81.

13. The recombinant AAV according to claim 9, wherein the AAV ITR is from AAV2.

14. A composition comprising a pharmaceutically compatible carrier and at least the recombinant AAV according to claim 1.

15. A composition comprising a pharmaceutically compatible carrier and at least the recombinant AAV according to claim 5.

16. A composition comprising a pharmaceutically compatible carrier and at least the recombinant AAV according to claim 9.

17. A method for delivering a transgene product to a subject, said method comprising administering the adeno-associated virus (AAV) according to claim 5.

18. A method for delivering a transgene product to a subject, said method comprising administering the adeno-associated virus (AAV) according to claim 9.

19. The recombinant AAV according to claim 1, wherein the gene product is ornithine transcarbamylase.

20. The recombinant AAV according to claim 1, wherein the gene product is glucose-6-phosphatase.

21. The recombinant AAV according to claim 1, wherein the gene product is phenylalanine hydroxylase.

22. The recombinant AAV according to claim 1, wherein the gene product is argininosuccinate synthetase.

23. The recombinant AAV according to claim 1, wherein the gene product is a dystrophin protein.

24. The recombinant AAV according to claim 5, wherein the gene product is ornithine transcarbamylase.

25. The recombinant AAV according to claim 5, wherein the gene product is glucose-6-phosphatase.

26. The recombinant AAV according to claim 5, wherein the gene product is, phenylalanine hydroxylase.

27. The recombinant AAV according to claim 5, wherein the gene product is argininosuccinate synthetase.

28. The recombinant AAV according to claim 5, wherein the gene product is a dystrophin protein.

29. The recombinant AAV according to claim 9, wherein the gene product is ornithine transcarbamylase.

30. The recombinant AAV according to claim 9, wherein the gene product is glucose-6-phosphatase.

31. The recombinant AAV according to claim 9, wherein the gene product is, phenylalanine hydroxylase.

32. The recombinant AAV according to claim 9, wherein the gene product is argininosuccinate synthetase.

33. The recombinant AAV according to claim 9, wherein the gene product is a dystrophin protein.

34. A method for delivering a transgene product to a subject, said method comprising administering the adeno-associated virus (AAV) according to claim 1.

* * * * *

SEQUENCE LISTING

```
<160> NUMBER OF SEQ ID NOS: 120

<210> SEQ ID NO 1
<211> LENGTH: 4721
<212> TYPE: DNA
<213> ORGANISM: Unknown
<220> FEATURE:
<223> OTHER INFORMATION: adeno-associated virus serotype 7

<400> SEQUENCE: 1
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taccgcgaag cgcctcccac gctgccgcgt cagcgctgac     180
gtaaatcacg tcataggga gtggtcctgt attagctgtc acgtgagtgc ttttgcgaca      240
ttttgcgaca ccacgtggcc atttgaggta tatatggccg agtgagcgag caggatctcc     300
attttgaccg cgaaatttga acgagcagca gccatgccgg gtttctacga gatcgtgatc     360
aaggtgccga gcgacctgga cgagcacctg ccgggcattt ctgactcgtt tgtgaactgg     420
gtggccgaga aggaatggga gctgccccg gattctgaca tggatctgaa tctgatcgag      480
caggcacccc tgaccgtggc cgagaagctg cagcgcgact tcctggtcca atggcgccgc     540
gtgagtaagg ccccggaggc cctgttcttt gttcagttcg agaagggcga gagctacttc     600
caccttcacg ttctggtgga gaccacgggg gtcaagtcca tggtgctagg ccgcttcctg     660
agtcagattc gggagaagct ggtccagacc atctaccgcg gggtcgagcc cacgctgccc     720
aactggttcg cggtgaccaa gacgcgtaat ggcgccggcg gggggaacaa ggtggtggac     780
gagtgctaca tccccaacta cctcctgccc aagacccagc ccgagctgca gtgggcgtgg     840
actaacatgg aggagtatat aagcgcgtgt ttgaacctgg ccgaacgcaa acggctcgtg     900
gcgcagcacc tgacccacgt cagccagacg caggagcaga acaaggagaa tctgaacccc     960
aattctgacg cgcccgtgat caggtcaaaa acctccgcgc gctacatgga gctggtcggg    1020
tggctggtgg accggggcat cacctccgag aagcagtgga tccaggagga ccaggcctcg    1080
tacatctcct tcaacgccgc ctccaactcg cggtcccaga tcaaggccgc gctggacaat    1140
gccggcaaga tcatggcgct gaccaaatcc gcgcccgact acctggtggg gcccctcgctg   1200 cccgcggaca ttaaaaccaa ccgcatctac cgcatcctgg agctgaacgg gtacgatcct    1260
gcctacgccg gctccgtctt tctcggctgg gcccagaaaa agttcgggaa gcgcaacacc    1320
atctggctgt tgggcccgc caccaccggc aagaccaaca ttgcggaagc catcgcccac    1380
gccgtgccct tctacggctg cgtcaactgg accaatgaga actttcccct caacgattgc    1440
gtcgacaaga tggtgatctg gtgggaggag ggcaagatga cggccaaggt cgtggagtcc    1500
gccaaggcca ttctcggcgg cagcaaggtg cgcgtggacc aaaagtgcaa gtcgtccgcc    1560
cagatcgacc ccacccccgt gatcgtcacc tccaacacca catgtgcgc cgtgattgac    1620 gggaacagca ccaccttcga gcaccagcag ccgttgcagg accggatgtt caaatttgaa    1680
ctcacccgcc gtctggagca cgactttggc aaggtgacga agcaggaagt caaagagttc    1740
```

```
ttccgctggg ccagtgatca cgtgaccgag gtggcgcatg agttctacgt cagaaagggc    1800
ggagccagca aaagacccgc ccccgatgac gcggatataa gcgagcccaa gcgggcctgc    1860
ccctcagtcg cggatccatc gacgtcagac gcggaaggag ctccggtgga ctttgccgac    1920
aggtaccaaa acaaatgttc tcgtcacgcg ggcatgattc agatgctgtt tccctgcaaa    1980
acgtgcgaga gaatgaatca gaatttcaac atttgcttca cacacggggt cagagactgt    2040
ttagagtgtt tccccggcgt gtcagaatct caaccggtcg tcagaaaaaa gacgtatcgg    2100
aaactctgcg cgattcatca tctgctgggg cgggcgcccg agattgcttg ctcggcctgc    2160
gacctggtca acgtggacct ggacgactgc gtttctgagc aataaatgac ttaaaccagg    2220
tatggctgcc gatggttatc ttccagattg gctcgaggac aacctctctg agggcattcg    2280
cgagtggtgg gacctgaaac ctggagcccc gaaacccaaa gccaaccagc aaaagcagga    2340
caacggccgg ggtctggtgc ttcctggcta caagtacctc ggacccttca acggactcga    2400 caaggggag cccgtcaacg cggcggacg agcggccctc gagcacgaca aggcctacga    2460
ccagcagctc aaagcgggtg acaatccgta cctgcggtat aaccacgccg acgccgagtt    2520
tcaggagcgt ctgcaagaag atacgtcatt tgggggcaac ctcgggcgag cagtcttcca    2580
ggccaagaag cgggttctcg aacctctcgg tctggttgag gaaggcgcta agacggctcc    2640
tgcaaagaag agaccggtag agccgtcacc tcagcgttcc cccgactcct ccacgggcat    2700
cggcaagaaa ggccagcagc ccgccagaaa gagactcaat ttcggtcaga ctggcgactc    2760
agagtcagtc cccgacccctc aacctctcgg agaacctcca gcagcgccct ctagtgtggg    2820
atctggtaca gtggctgcag gcggtggcgc accaatggca gacaataacg aaggtgccga    2880
cggagtgggt aatgcctcag gaaattggca ttgcgattcc acatggctgg gcgacagagt    2940
cattaccacc agcaccccgaa cctgggccct gcccacctac aacaaccacc tctacaagca    3000
aatctccagt gaaactgcag gtagtaccaa cgacaacacc tacttcggct acagcacccc    3060
ctgggggtat tttgactta acagattcca ctgccacttc tcaccacgtg actggcagcg    3120
actcatcaac aacaactggg gattccggcc caagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa ctttgagttc agctacagct cgaggacgt    3480 gcctttccac agcagctacg cacacagcca gagcctggac cggctgatga atcccctcat    3540
cgaccagtac ttgtactacc tggccagaac acagagtaac ccaggaggca cagctggcaa    3600
tcgggaactg cagttttacc agggcgggcc ttcaactatg gccgaacaag ccaagaattg    3660
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780
taatcccggc gtcgccatgg caactcacaa ggacgacgag gaccgctttt tcccatccag    3840
cggagtcctg atttttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctggcagaa ccggacgtg tacctgcagg gtcccatctg    4080
```

-continued

```
ggccaagatt cctcacacgg atggcaactt tcacccgtct cctttgatgg gcggctttgg      4140
acttaaacat ccgcctcctc agatcctgat caagaacact cccgttcccg ctaatcctcc      4200
ggaggtgttt actcctgcca gtttgcttc gttcatcaca cagtacagca ccggacaagt       4260
cagcgtggaa atcgagtggg agctgcagaa ggaaaacagc aagcgctgga acccggagat      4320
tcagtacacc tccaactttg aaaagcagac tggtgtggac tttgccgttg acagccaggg      4380
tgtttactct gagcctcgcc ctattggcac tcgttacctc acccgtaatc tgtaattgca      4440
tgttaatcaa taaaccggtt gattcgtttc agttgaactt tggtctcctg tgcttcttat      4500
cttatcggtt tccatagcaa ctggttacac attaactgct tgggtgcgct tcacgataag      4560
aacactgacg tcaccgcggt acccctagtg atggagttgg ccactccctc tatgcgcgct      4620
cgctcgctcg gtggggcctg cggaccaaag gtccgcagac ggcagagctc tgctctgccg      4680 gcccaccga gcgagcgagc gcgcatagag ggagtggcca a                           4721
```

<210> SEQ ID NO 2
<211> LENGTH: 737
<212> TYPE: PRT
<213> ORGANISM: Unknown
<220> FEATURE:
<223> OTHER INFORMATION: capsid protein of adeno-associated virus
      serotpye 7

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
```

```
                  245                 250                 255
Leu Tyr Lys Gln Ile Ser Ser Glu Thr Ala Gly Ser Thr Asn Asp Asn
            260                 265                 270
Thr Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
                    325                 330                 335
Asn Leu Thr Ser Thr Ile Gln Val Phe Ser Asp Ser Glu Tyr Gln Leu
                340                 345                 350
Pro Tyr Val Leu Gly Ser Ala His Gln Gly Cys Leu Pro Pro Phe Pro
                355                 360                 365
Ala Asp Val Phe Met Ile Pro Gln Tyr Gly Tyr Leu Thr Leu Asn Asn
            370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
                        405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ala
            435                 440                 445
Arg Thr Gln Ser Asn Pro Gly Gly Thr Ala Gly Asn Arg Glu Leu Gln
        450                 455                 460
Phe Tyr Gln Gly Gly Pro Ser Thr Met Ala Glu Gln Ala Lys Asn Trp
465                 470                 475                 480
Leu Pro Gly Pro Cys Phe Arg Gln Gln Arg Val Ser Lys Thr Leu Asp
                    485                 490                 495
Gln Asn Asn Asn Ser Asn Phe Ala Trp Thr Gly Ala Thr Lys Tyr His
                500                 505                 510
Leu Asn Gly Arg Asn Ser Leu Val Asn Pro Gly Val Ala Met Ala Thr
            515                 520                 525
His Lys Asp Asp Glu Asp Arg Phe Phe Pro Ser Ser Gly Val Leu Ile
        530                 535                 540
Phe Gly Lys Thr Gly Ala Thr Asn Lys Thr Thr Leu Glu Asn Val Leu
545                 550                 555                 560
Met Thr Asn Glu Glu Glu Ile Arg Pro Thr Asn Pro Val Ala Thr Glu
                    565                 570                 575
Glu Tyr Gly Ile Val Ser Ser Asn Leu Gln Ala Ala Asn Thr Ala Ala
                580                 585                 590
Gln Thr Gln Val Val Asn Asn Gln Gly Ala Leu Pro Gly Met Val Trp
            595                 600                 605
Gln Asn Arg Asp Val Tyr Leu Gln Gly Pro Ile Trp Ala Lys Ile Pro
        610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                    645                 650                 655
Ala Asn Pro Pro Glu Val Phe Thr Pro Ala Lys Phe Ala Ser Phe Ile
                660                 665                 670
```

```
Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
            690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 3
<211> LENGTH: 623
<212> TYPE: PRT
<213> ORGANISM: Unknown
<220> FEATURE:
<223> OTHER INFORMATION: rep protein of adeno-associated virus serotype
      7

<400> SEQUENCE: 3

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
                100                 105                 110

Arg Glu Lys Leu Val Gln Thr Ile Tyr Arg Gly Val Glu Pro Thr Leu
            115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
        210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ser
            275                 280                 285
```

Leu Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Ile Gln Met
530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
                565                 570                 575

Ser Glu Ser Gln Pro Val Val Arg Lys Lys Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
610                 615                 620

<210> SEQ ID NO 4
<211> LENGTH: 4393
<212> TYPE: DNA
<213> ORGANISM: Unknown
<220> FEATURE:
<223> OTHER INFORMATION: adeno-associated virus serotype 8

<400> SEQUENCE: 4
cagagaggga gtggccaact ccatcactag gggtagcgcg aagcgcctcc cacgctgccg     60
cgtcagcgct gacgtaaatt acgtcatagg ggagtggtcc tgtattagct gtcacgtgag    120
tgcttttgcg gcattttgcg acaccacgtg gccatttgag gtatatatgg ccgagtgagc    180

```
gagcaggatc tccattttga ccgcgaaatt tgaacgagca gcagccatgc cgggcttcta    240
cgagatcgtg atcaaggtgc cgagcgacct ggacgagcac ctgccgggca tttctgactc    300
gtttgtgaac tgggtggccg agaaggaatg ggagctgccc ccggattctg acatggatcg    360
gaatctgatc gagcaggcac ccctgaccgt ggccgagaag ctgcagcgcg acttcctggt    420
ccaatggcgc cgcgtgagta aggccccgga ggccctcttc tttgttcagt tcgagaaggg    480
cgagagctac tttcacctgc acgttctggt cgagaccacg ggggtcaagt ccatggtgct    540
aggccgcttc ctgagtcaga ttcgggaaaa gcttggtcca gaccatctac ccgcggggtc    600
gagccccacc ttgcccaact ggttcgcggt gaccaaagac gcggtaatgg cgccggcggg    660
ggggaacaag gtggtggacg agtgctacat ccccaactac ctcctgccca agactcagcc    720
cgagctgcag tgggcgtgga ctaacatgga ggagtatata agcgcgtgct tgaacctggc    780
cgagcgcaaa cggctcgtgg cgcagcacct gacccacgtc agccagacgc aggagcagaa    840
caaggagaat ctgaacccca attctgacgc gcccgtgatc aggtcaaaaa cctccgcgcg    900
ctatatggag ctggtcgggt ggctggtgga ccggggcatc acctccgaga agcagtggat    960
ccaggaggac caggcctcgt acatctcctt caacgccgcc tccaactcgc ggtcccagat   1020
caaggccgcg ctggacaatg ccggcaagat catggcgctg accaaatccg cgcccgacta   1080
cctggtgggg ccctcgctgc ccgcggacat tacccagaac cgcatctacc gcatcctcgc   1140
tctcaacggc tacgaccctg cctacgccgg ctccgtcttt ctcggctggg ctcagaaaaa   1200
gttcgggaaa cgcaacacca tctggctgtt tggacccgcc accaccggca agaccaacat   1260
tgcggaagcc atcgcccacg ccgtgccctt ctacggctgc gtcaactgga ccaatgagaa   1320
cttttccttc aatgattgcg tcgacaagat ggtgatctgg tgggaggagg caagatgac   1380 ggccaaggtc gtggagtccg ccaaggccat tctcggcggc agcaaggtgc gcgtggacca   1440
aaagtgcaag tcgtccgccc agatcgaccc caccccgtg atcgtcacct ccaacaccaa   1500
catgtgcgcc gtgattgacg ggaacagcac caccttcgag caccagcagc ctctccagga   1560
ccggatgttt aagttcgaac tcacccgccg tctggagcac gactttggca aggtgacaaa   1620
gcaggaagtc aaagagttct tccgctgggc cagtgatcac gtgaccgagg tgcgcatga   1680 gttttacgtc agaaagggcg gagccagcaa aagacccgcc cccgatgacg cggataaaag   1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctgggc gggctcccga   2040 gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gacccttcaa cggactcgac aagggggagc cgtcaacgc ggcggacgca gcggccctcg   2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
```

| | |
|---|---|
| aaggcgctaa gacggctcct ggaaagaaga gaccggtaga gccatcaccc cagcgttctc | 2580 |
| cagactcctc tacgggcatc ggcaagaaag gccaacagcc cgccagaaaa agactcaatt | 2640 |
| ttggtcagac tggcgactca gagtcagttc cagaccctca acctctcgga gaacctccag | 2700 |
| cagcgccctc tggtgtggga cctaatacaa tggctgcagg cggtggcgca ccaatggcag | 2760 |
| acaataacga aggcgccgac ggagtgggta gttcctcggg aaattggcat tgcgattcca | 2820 |
| catggctggg cgacagagtc atcaccacca gcacccgaac ctgggccctg cccacctaca | 2880 |
| acaaccacct ctacaagcaa atctccaacg ggacatcggg aggagccacc aacgacaaca | 2940 |
| cctacttcgg ctacagcacc ccctgggggt attttgactt taacagattc cactgccact | 3000 |
| tttcaccacg tgactggcag cgactcatca acaacaactg gggattccgg cccaagagac | 3060 |
| tcagcttcaa gctcttcaac atccaggtca aggaggtcac gcagaatgaa ggcaccaaga | 3120 |
| ccatcgccaa taacctcacc agcaccatcc aggtgtttac ggactcggag taccagctgc | 3180 |
| cgtacgttct cggctctgcc caccagggct gcctgcctcc gttcccggcg gacgtgttca | 3240 |
| tgattcccca gtacggctac ctaacactca acaacggtag tcaggccgtg ggacgctcct | 3300 |
| ccttctactg cctggaatac tttccttcgc agatgctgag aaccggcaac aacttccagt | 3360 |
| ttacttacac cttcgaggac gtgcctttcc acagcagcta cgcccacagc cagagcttgg | 3420 |
| accggctgat gaatcctctg attgaccagt acctgtacta cttgtctcgg actcaaacaa | 3480 |
| caggaggcac ggcaaatacg cagactctgg gcttcagcca aggtgggcct aatacaatgg | 3540 |
| ccaatcaggc aaagaactgg ctgccaggac cctgttaccg ccaacaacgc gtctcaacga | 3600 |
| caaccgggca aaacaacaat agcaactttg cctggactgc tgggaccaaa taccatctga | 3660 |
| atggaagaaa ttcattggct aatcctggca tcgctatggc aacacacaaa gacgacgagg | 3720 |
| agcgtttttt tcccagtaac gggatcctga ttttttggcaa acaaaatgct gccagagaca | 3780 |
| atgcggatta cagcgatgtc atgctcacca gcgaggaaga aatcaaaacc actaaccctg | 3840 |
| tggctacaga ggaatacggt atcgtggcag ataacttgca gcagcaaaac acggctcctc | 3900 |
| aaattggaac tgtcaacagc caggggggcct acccggtat ggtctggcag aaccgggacg | 3960 |
| tgtacctgca gggtcccatc tgggccaaga ttcctcacac ggacggcaac ttccaccgt | 4020 |
| ctccgctgat gggcggcttt ggcctgaaac atcctccgcc tcagatcctg atcaagaaca | 4080 |
| cgcctgtacc tgcggatcct ccgaccacct caaccagtc aaagctgaac tctttcatca | 4140 |
| cgcaatacag caccggacag gtcagcgtgg aaattgaatg ggagctgcag aaggaaaaca | 4200 |
| gcaagcgctg gaaccccgag atccagtaca cctccaacta ctacaaatct acaagtgtgg | 4260 |
| actttgctgt taatacagaa ggcgtgtact ctgaaccccg ccccattggc acccgttacc | 4320 |
| tcacccgtaa tctgtaattg cctgttaatc aataaaccgg ttgattcgtt tcagttgaac | 4380 |
| tttggtctct gcg | 4393 |

```
<210> SEQ ID NO 5
<211> LENGTH: 4385
<212> TYPE: DNA
<213> ORGANISM: Unknown
<220> FEATURE:
<223> OTHER INFORMATION: adeno-associated virus serotype 9

<400> SEQUENCE: 5
```

| | |
|---|---|
| cagagaggga gtggccaact ccatcactag gggtaatcgc gaagcgcctc ccacgctgcc | 60 |
| gcgtcagcgc tgacgtagat tacgtcatag gggagtggtc ctgtattagc tgtcacgtga | 120 |
| gtgcttttgc gacattttgc gacaccacat ggccatttga ggtatatatg gccgagtgag | 180 |

```
cgagcaggat ctccattttg accgcgaaat ttgaacgagc agcagccatg ccgggcttct    240
acgagattgt gatcaaggtg ccgagcgacc tggacgagca cctgccgggc atttctgact    300
cttttgtgaa ctgggtggcc gagaaggaat gggagctgcc cccggattct gacatggatc    360
ggaatctgat cgagcaggca cccctgaccg tggccgagaa gctgcagcgc gacttcctgg    420
tccaatggcg ccgcgtgagt aaggccccgg aggccctctt ctttgttcag ttcgagaagg    480
gcgagagcta ctttcacctg cacgttctgg tcgagaccac gggggtcaag tccatggtgc    540
taggccgctt cctgagtcag attcgggaga agctggtcca gaccatctac cgcgggatcg    600
agccgaccct gcccaactgg ttcgcggtga ccaagacgcg taatggcgcc ggcgggggga    660
acaaggtggt ggacgagtgc tacatcccca actacctcct gcccaagact cagcccgagc    720
tgcagtgggc gtggactaac atggaggagt atataagcgc gtgcttgaac ctggccgagc    780
gcaaacggct cgtggcgcag cacctgaccc acgtcagcca gacgcaggag cagaacaagg    840
agaatctgaa ccccaattct gacgcgcccc tgatcaggtc aaaaacctcc gcgcgctaca    900
tggagctggt cgggtggctg gtggaccggg gcatcaccct cgagaagcag tggatccagg    960
aggaccaggc tcgtacatc tccttcaacg ccgcctccaa ctcgcggtcc cagatcaagg   1020
ccgcgctgga caatgccggc aagatcatgg cgctgaccaa atccgcgccc gactacctgg   1080
taggcccttc acttccggtg gacattacgc agaaccgcat ctaccgcatc ctgcagctca   1140
acggctacga ccctgcctac gccggctccg tctttctcgg ctgggcacaa aagaagttcg   1200
ggaaacgcaa caccatctgg ctgtttgggc cggccaccac gggaaagacc aacatcgcag   1260
aagccattgc ccacgccgtg cccttctacg gctgcgtcaa ctggaccaat gagaactttc   1320
ccttcaacga ttgcgtcgac aagatggtga tctggtggga ggagggcaag atgacggcca   1380
aggtcgtgga gtccgccaag gccattctcg gcggcagcaa ggtgcgcgtg accaaaagt   1440 gcaagtcgtc cgcccagatc gaccccactc ccgtgatcgt cacctccaac accaacatgt   1500
gcgccgtgat tgacgggaac agcaccacct tcgagcacca gcagcctctc caggaccgga   1560
tgtttaagtt cgaactcacc cgccgtctgg agcacgactt tggcaaggtg acaaagcagg   1620
aagtcaaaga gttcttccgc tgggccagtg atcacgtgac cgaggtggcg catgagtttt   1680
acgtcagaaa gggcgcgagcc agcaaaaagac ccgcccccga tgacgcggat aaaagcgagc   1740
ccaagcgggc ctgcccctca gtcgcggatc catcgacgtc agacgcggaa ggagctccgg   1800
tggactttgc cgacaggtac caaaacaaat gttctcgtca cgcgggcatg cttcagatgc   1860
tgcttccctg caaaacgtgc gagagaatga atcagaattt caacatttgc ttcacacacg   1920
gggtcagaga ctgctcagag tgtttccccg gcgtgtcaga atctcaaccg gtcgtcagaa   1980
agaggacgta tcggaaactc tgtgcgattc atcatctgct ggggcgggct cccgagattg   2040
cttgctcggc ctgcgatctg gtcaacgtgg acctggatga ctgtgtttct gagcaataaa   2100
tgacttaaac caggtatggc tgccgatggt tatcttccag attggctcga ggacaacctc   2160
tctgagggca ttcgcgagtg gtgggcgctg aaacctggag ccccgaagcc aaaagccaac   2220
cagcaaaagc aggacgacgg ccggggtctg gtgcttcctg gctacaagta cctcggaccc   2280
ttcaacggac tcgacaaggg ggagcccgtc aacgcgcgg acgcagcggc cctcgagcac   2340
ggcaaggcct acgaccagca gctgcaggcg ggtgacaatc cgtacctgcg gtataaccac   2400
gccgacgccg agtttcagga gcgtctgcaa gaagatacgt cttttggggg caacctcggg   2460
cgagcagtct tccaggccaa gaagcgggtt ctcgaacctc tcggtctggt tgaggaaggc   2520
```

| | |
|---|---|
| gctaagacgg ctcctggaaa gaagagaccg gtagagccat caccccagcg ttctccagac | 2580 |
| tcctctacgg gcatcggcaa gaaaggccaa cagcccgcca gaaaaagact caattttggt | 2640 |
| cagactggcg actcagagtc agttccagac cctcaacctc tcggagaacc tccagcagcg | 2700 |
| ccctctggtg tgggacctaa tacaatggct gcaggcggtg gcgcaccaat ggcagacaat | 2760 |
| aacgaaggcg ccgacggagt gggtaattcc tcgggaaatt ggcattgcga ttccacatgg | 2820 |
| ctgggggaca gagtcatcac caccagcacc cgaacctggg cattgcccac ctacaacaac | 2880 |
| cacctctaca gcaaatctc caatggaaca tcgggaggaa gcaccaacga caacacctac | 2940 |
| tttggctaca gcaccccctg ggggtatttt gacttcaaca gattccactg ccacttctca | 3000 |
| ccacgtgact ggcagcgact catcaacaac aactgggat tccggccaaa gagactcaac | 3060 |
| ttcaagctgt tcaacatcca ggtcaaggag gttacgacga acgaaggcac caagaccatc | 3120 |
| gccaataacc ttaccagcac cgtccaggtc tttacggact cggagtacca gctaccgtac | 3180 |
| gtcctaggct ctgcccacca aggatgcctg ccaccgtttc ctgcagacgt cttcatggtt | 3240 |
| cctcagtacg gctacctgac gctcaacaat ggaagtcaag cgttaggacg ttcttctttc | 3300 |
| tactgtctgg aatacttccc ttctcagatg ctgagaaccg gcaacaactt tcagttcagc | 3360 |
| tacactttcg aggacgtgcc tttccacagc agctacgcac acagccagag tctagatcga | 3420 |
| ctgatgaacc ccctcatcga ccagtaccta tactacctgg tcagaacaca gaacactgga | 3480 |
| actgggggaa ctcaaacttt ggcattcagc caagcaggcc ctagctcaat ggccaatcag | 3540 |
| gctagaaaact gggtacccgg gccttgctac cgtcagcagc gcgtctccac aaccaccaac | 3600 |
| caaaataaca acagcaactt tgcgtggacg ggagctgcta aattcaagct gaacgggaga | 3660 |
| gactcgctaa tgaatcctgg cgtggctatg gcatcgcaca agacgacga ggaccgcttc | 3720 |
| tttccatcaa gtggcgttct catatttggc aagcaaggag ccgggaacga tggagtcgac | 3780 |
| tacagccagg tgctgattac agatgaggaa gaaattaaag ccaccaaccc tgtagccaca | 3840 |
| gaggaatacg gagcagtggc catcaacaac caggccgcta cacgcaggc gcaaactgga | 3900 |
| cttgtgcata ccagggagt tattcctggt atggtctggc agaaccggga cgtgtacctg | 3960 |
| cagggcccta tttgggctaa aatacctcac acagatggca actttcaccc gtctcctctg | 4020 |
| atgggtggat ttggactgaa acacccacct ccacagattc taattaaaaa tacaccagtg | 4080 |
| ccggcagatc ctcctcttac cttcaatcaa gccaagctga actctttcat cacgcagtac | 4140 |
| agcacgggac aagtcagcgt ggaaatcgag tgggagctgc agaaagaaaa cagcaagcgc | 4200 |
| tggaatccag agatccagta tacttcaaac tactacaaat ctacaaatgt ggactttgct | 4260 |
| gtcaatacca aaggtgttta ctctgagcct cgccccattg gtactcgtta cctcacccgt | 4320 |
| aatttgtaat gcctgttaa tcaataaacc ggttaattcg tttcagttga actttggtct | 4380 |
| ctgcg | 4385 |

```
<210> SEQ ID NO 6
<211> LENGTH: 4718
<212> TYPE: DNA
<213> ORGANISM: Unknown
<220> FEATURE:
<223> OTHER INFORMATION: adeno-associated virus serotype 1

<400> SEQUENCE: 6
```

| | |
|---|---|
| ttgcccactc cctctctgcg cgctcgctcg ctcggtgggg cctgcggacc aaaggtccgc | 60 |
| agacggcaga gctctgctct gccggcccca ccgagcgagc gagcgcgcag agagggagtg | 120 |
| ggcaactcca tcactagggg taatcgcgaa gcgcctccca cgctgccgcg tcagcgctga | 180 |

```
cgtaaattac gtcataggqq agtggtcctg tattagctgt cacgtgagtg cttttgcgac    240
attttgcgac accacgtggc catttagggt atatatggcc gagtgagcga gcaggatctc    300
cattttgacc gcgaaatttg aacgagcagc agccatgccg ggcttctacg agatcgtgat    360
caaggtgccg agcgacctgg acgagcacct gccgggcatt tctgactcgt tgtgagctg    420 ggtggccgag aaggaatggg agctgccccc ggattctgac atggatctga atctgattga    480
gcaggcaccc ctgaccgtgg ccgagaagct gcagcgcgct tcctggtcc aatggcgccg    540 cgtgagtaag gccccggagg ccctcttctt tgttcagttc gagaagggcg agtcctactt    600
ccacctccat attctggtgg agaccacggg ggtcaaatcc atggtgctgg ccgcttcct    660 gagtcagatt agggacaagc tggtgcagac catctaccgc gggatcgagc cgaccctgcc    720
caactggttc gcggtgacca agacgcgtaa tggcgccgga gggggaaca aggtggtgga    780 cgagtgctac atccccaact acctcctgcc caagactcag cccgagctgc agtgggcgtg    840
gactaacatg gaggagtata taagcgcctg tttgaacctg gccgagcgca aacggctcgt    900
ggcgcagcac ctgacccacg tcagccagac ccaggagcag aacaaggaga atctgaaccc    960
caattctgac gcgcctgtca tccggtcaaa aacctccgcg cgctacatgg agctggtcgg    1020
gtggctggtg gaccggggca tcacctccga gaagcagtgg atccaggagg accaggcctc    1080
gtacatctcc ttcaacgccg cttccaactc gcggtcccag atcaaggccg ctctggacaa    1140
tgccggcaag atcatggcgc tgaccaaatc cgcgcccgac tacctggtag gccccgctcc    1200
gcccgcggac attaaaacca accgcatcta ccgcatcctg gagctgaacg gctacgaacc    1260
tgcctacgcc ggctccgtct ttctcggctg ggcccagaaa aggttcggga agcgcaacac    1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acggccaagg tcgtggagtc    1500
cgccaaggcc attctcggcg gcagcaaggt gcgcgtggac caaaagtgca agtcgtccgc    1560
ccagatcgac cccaccccg tgatcgtcac ctccaacacc aacatgtgcg ccgtgattga    1620
cgggaacagc accaccttcg agcaccagca gccgttgcag gaccggatgt tcaaatttga    1680
actcacccgc cgtctggagc atgactttgg caaggtgaca aagcaggaag tcaaagagtt    1740
cttccgctgg gcgcaggatc acgtgaccga ggtggcgcat gagttctacg tcagaaaggg    1800
tggagccaac aaaagacccg ccccgatga cgcggataaa agcgagccca agcgggcctg    1860
cccctcagtc gcggatccat cgacgtcaga cgcggaagga gctccggtgg actttgccga    1920
caggtaccaa aacaaatgtt ctcgtcacgc gggcatgctt cagatgctgt ttccctgcaa    1980
gacatgcgag agaatgaatc agaatttcaa catttgcttc acgcacggga cgagagactg    2040
ttcagagtgc ttccccggcg tgtcagaatc tcaaccggtc gtcagaaaga ggacgtatcg    2100
gaaactctgt gccattcatc atctgctggg gcgggctccc gagattgctt gctcggcctg    2160
cgatctggtc aacgtggacc tggatgactg tgtttctgag caataaatga cttaaaccag    2220
gtatggctgc cgatggttat cttccagatt ggctcgagga caacctctct gagggcattc    2280
gcgagtggtg ggacttgaaa cctggagccc cgaagcccaa agccaaccag caaaagcagg    2340
acgacggccg gggtctggtg cttcctggct acaagtacct cggacccttc aacggactcg    2400 acaagggggga gccgtcaac gcggcggacg cagcggccct cgagcacgac aaggcctacg    2460
accagcagct caaagcgggt gacaatccgt acctgcggta taaccacgcc gacgccgagt    2520
```

```
ttcaggagcg tctgcaagaa gatacgtctt ttgggggcaa cctcgggcga gcagtcttcc    2580
aggccaagaa gcgggttctc gaacctctcg gtctggttga ggaaggcgct aagacggctc    2640
ctggaaagaa acgtccggta gagcagtcgc cacaagagcc agactcctcc tcgggcatcg    2700
gcaagacagg ccagcagccc gctaaaaaga gactcaattt tggtcagact ggcgactcag    2760
agtcagtccc cgatccacaa cctctcggag aacctccagc accccccgct gctgtgggac    2820
ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag cacccgcacc tgggccttgc ccacctacaa taaccacctc tacaagcaaa    3000
tctccagtgc ttcaacgggg gccagcaacg acaaccacta cttcggctac agcaccccct    3060
gggggtattt tgatttcaac agattccact gccacttttc accacgtgac tgcagcgac     3120 tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat tccgcaatac ggctacctga    3360
cgctcaacaa tggcagccaa gccgtgggac gttcatcctt ttactgcctg gaatatttcc    3420
cttctcagat gctgagaacg ggcaacaact ttaccttcag ctacacctt gaggaagtgc     3480 ctttccacag cagctacgcg cacagccaga gcctggaccg gctgatgaat cctctcatcg    3540
accaatacct gtattacctg aacagaactc aaaatcagtc cggaagtgcc caaacaagg     3600 acttgctgtt tagccgtggg tctccagctg gcatgtctgt tcagcccaaa aactggctac    3660
ctggaccctg ttatcggcag cagcgcgttt ctaaaacaaa aacagacaac aacaacagca    3720
attttacctg gactggtgct tcaaaatata acctcaatgg cgtgaatcc atcatcaacc     3780 ctggcactgc tatggcctca cacaaagacg acgaagacaa gttctttccc atgagcggtg    3840
tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
ccaaaattcc tcacacagat ggacactttc accgtctcc tcttatgggc ggctttggac     4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttaccttac ccgtccctg taattacgtg     4440 ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                            4718

<210> SEQ ID NO 7
<211> LENGTH: 4675
<212> TYPE: DNA
<213> ORGANISM: adeno-associated virus 2
```

<400> SEQUENCE: 7

```
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctggagg ggtggagtcg tgacgtgaat tacgtcatag   180
ggttagggag gtcctgtatt agaggtcacg tgagtgtttt gcgacatttt gcgacaccat   240
gtggtcacgc tgggtattta agcccgagtg agcacgcagg gtctccattt tgaagcggga   300
ggtttgaacg cgcagccgcc atgccggggt tttacgagat tgtgattaag gtccccagcg   360
accttgacgg gcatctgccc ggcatttctg acagctttgt gaactgggtg ccgagaagg    420
aatgggagtt gccgccagat tctgacatgg atctgaatct gattgagcag gcacccctga   480
ccgtggccga aagctgcag cgcgactttc tgacggaatg cgccgtgtg agtaaggccc    540
cggaggccct tttctttgtg caatttgaga agggagagag ctacttccac atgcacgtgc   600
tcgtggaaac caccggggtg aaatccatgg ttttgggacg tttcctgagt cagattcgcg   660
aaaaactgat tcagagaatt taccgcggga tcgagccgac tttgccaaac tggttcgcgg   720
tcacaaagac cagaaatggc gccggaggcg ggaacaaggt ggtggatgag tgctacatcc   780
ccaattactt gctccccaaa acccagcctg agctccagtg ggcgtggact aatatggaac   840
agtatttaag cgcctgtttg aatctcacgg agcgtaaacg gttggtggcg cagcatctga   900
cgcacgtgtc gcagacgcag gagcagaaca aagagaatca gaatcccaat tctgatgcgc   960
cggtgatcag atcaaaaact tcagccaggt acatggagct ggtcgggtgg ctcgtggaca  1020
aggggattac ctcggagaag cagtggatcc aggaggacca ggcctcatac atctccttca  1080
atgcggcctc caactcgcgg tcccaaatca aggctgcctt ggacaatgcg ggaaagatta  1140
tgagcctgac taaaaccgcc cccgactacc tggtgggcca gcagcccgtg gaggacattt  1200
ccagcaatcg gatttataaa attttggaac taaacgggta cgatcccaa tatgcggctt  1260
ccgtctttct gggatgggcc acgaaaaagt tcggcaagag gaacaccatc tggctgtttg  1320
ggcctgcaac taccgggaag accaacatcg cggaggccat agcccacact gtgcccttct  1380
acgggtgcgt aaactggacc aatgagaact ttcccttcaa cgactgtgtc gacaagatgg  1440
tgatctggtg ggaggagggg aagatgaccg ccaaggtcgt ggagtcggcc aaagccattc  1500
tcggaggaag caaggtgcgc gtggaccaga aatgcaagtc ctcggcccag atagacccga  1560
ctcccgtgat cgtcacctcc aacaccaaca tgtgcgccgt gattgacggg aactcaacga  1620
ccttcgaaca ccagcagccg ttgcaagacc ggatgttcaa atttgaactc acccgccgtc  1680
tggatcatga ctttgggaag gtcaccaagc aggaagtcaa agacttttc cggtgggcaa  1740
aggatcacgt ggttgaggtg gagcatgaat tctacgtcaa aaagggtgga gccaagaaaa  1800
gacccgcccc cagtgacgca gatataagtg agcccaaacg ggtgcgcgag tcagttgcgc  1860
agccatcgac gtcagacgcg gaagcttcga tcaactacgc agacaggtac caaaacaaat  1920
gttctcgtca cgtgggcatg aatctgatgc tgtttccctg cagacaatgc gagagaatga  1980
atcagaattc aaatatctgc ttcactcacg gacagaaaga ctgtttagag tgctttcccg  2040
tgtcagaatc tcaacccgtt tctgtcgtca aaaaggcgta tcagaaactg tgctacattc  2100
atcatatcat gggaaaggtg ccagacgctt gcactgcctg cgatctggtc aatgtggatt  2160
tggatgactg catctttgaa caataaatga tttaaatcag gtatgctgc cgatggttat  2220
cttccagatt ggctcgagga cactctctct gaaggaataa gacagtggtg gaagctcaaa  2280
```

```
cctggcccac caccaccaaa gcccgcagag cggcataagg acgacagcag gggtcttgtg    2340
cttcctgggt acaagtacct cggacccttc aacggactcg acaagggaga gccggtcaac    2400
gaggcagacg ccgcggccct cgagcacgta caaagcctac gaccggcagc tcgacagcgg    2460
agacaacccg tacctcaagt acaaccacgc cgacgcggag tttcaggagc gccttaaaga    2520
agatacgtct tttgggggca acctcggacg agcagtcttc caggcgaaaa agagggttct    2580
tgaacctctg ggcctggttg aggaacctgt taagacggct ccgggaaaaa agaggccggt    2640
agagcactct cctgtggagc cagactcctc ctcgggaacc ggaaaggcgg ccagcagcc    2700 tgcaagaaaa agattgaatt ttggtcgac tggagacgca gactcagtac ctgaccccca    2760
gcctctcgga cagccaccag cagcccctc tggtctggga actaatacga tggctacagg    2820
cagtggcgca ccaatggcag acaataacga gggcgccgac ggagtgggta attcctccgg    2880
aaattggcat tgcgattcca catggatggg cgacagagtc atcaccacca gcacccgaac    2940
ctgggccctg cccacctaca caaccacct ctacaaacaa atttccagcc aatcaggagc    3000
ctcgaacgac aatcactact ttggctacag cacccccttgg gggtattttg acttcaacag    3060
attccactgc cacttttcac cacgtgactg gcaaagactc atcaacaaca actgggatt    3120 ccgacccaag agactcaact tcaagctctt taacattcaa gtcaaagagg tcacgcagaa    3180
tgacggtacg acgacgattg ccaataacct taccagcacg gttcaggtgt ttactgactc    3240
ggagtaccag ctcccgtacg tcctcggctc ggcgcatcaa ggatgcctcc cgccgttccc    3300
agcagacgtc ttcatggtgc cacagtatgg atacctcacc ctgaacaacg ggagtcaggc    3360
agtaggacgc tcttcatttt actgcctgga gtactttcct tctcagatgc tgcgtaccgg    3420
aaacaacttt accttcagct acacttttga ggacgttcct ttccacagca gctacgctca    3480
cagccagagt ctgaccgtc tcatgaatcc tctcatcgac cagtacctgt attacttgag    3540
cagaacaaac actccaagtg gaaccaccac gcagtcaagg cttcagtttt ctcaggccgg    3600
agcgagtgac attcgggacc agtctaggaa ctggcttcct ggaccctgtt accgccagca    3660
gcgagtatca aagacatctg cggataacaa caacagtgaa tactcgtgga ctggagctac    3720
caagtaccac ctcaatggca gagactctct ggtgaatccg gccatggcaa gccacaagga    3780
cgatgaagaa aagtttttc ctcagagcgg ggttctcatc tttgggaagc aaggctcaga    3840
gaaaacaaat gtgaacattg aaaaggtcat gattacagac gaagaggaaa tcggaacaac    3900
caatcccgtg gctacggagc agtatggttc tgtatctacc aacctccaga gaggcaacag    3960
acaagcagct accgcagatg tcaacacaca aggcgttctt ccaggcatgg tctggcagga    4020
cagagatgtg taccttcagg ggcccatctg ggcaaagatt ccacacacgg acggacattt    4080
tcacccctct cccctcatgg gtggattcgg acttaaacac cctcctccac agattctcat    4140
caagaacacc ccggtacctg cgaatccttc gaccaccttc agtgcggcaa gtttgcttc    4200 cttcatcaca cagtactcca cgggacacg tcagcgtgga gatcgagtgg agctgcaga    4260 aggaaaacag caaacgctgg aatcccgaaa ttcagtacac ttccaactac aacaagtctg    4320
ttaatcgtgg acttaccgtg gatactaatg gcgtgtattc agagcctcgc cccattggca    4380
ccagatacct gactcgtaat ctgtaattgc ttgttaatca ataaaccgtt taattcgttt    4440
cagttgaact ttggtctctg cgtatttctt tcttatctag tttccatggc tacgtagata    4500
agtagcatgg cgggttaatc attaactaca aggaaccct agtgatggag ttggccactc    4560
cctctctgcg cgctcgctcg ctcactgagg ccgggcgacc aaaggtcgcc cgacgcccgg    4620
gctttgcccg ggcggcctca gtgagcgagc gagcgcgcag agagggagtg gccaa         4675
```

<210> SEQ ID NO 8
<211> LENGTH: 4726
<212> TYPE: DNA
<213> ORGANISM: adeno-associated virus 3

<400> SEQUENCE: 8

```
ttggccactc cctctatgcg cactcgctcg ctcggtgggg cctggcgacc aaaggtcgcc        60
agacggacgt gctttgcacg tccggcccca ccgagcgagc gagtgcgcat agagggagtg       120
gccaactcca tcactagagg tatggcagtg acgtaacgcg aagcgcgcga agcgagacca       180
cgcctaccag ctgcgtcagc agtcaggtga ccctttttgcg acagtttgcg acaccacgtg      240
gccgctgagg gtatatattc tcgagtgagc gaaccaggag ctccattttg accgcgaaat       300
ttgaacgagc agcagccatg ccggggttct acgagattgt cctgaaggtc ccagtgacc        360
tggacgagcg cctgccgggc atttctaact cgtttgttaa ctgggtggcc gagaaggaat       420
gggacgtgcc gccggattct gacatggatc cgaatctgat tgagcaggca cccctgaccg       480
tggccgaaaa gcttcagcgc gagttcctgg tggagtggcg ccgcgtgagt aaggccccgg       540
aggccctctt ttttgtccag ttcgaaaagg gggagaccta cttccacctg cacgtgctga       600
ttgagaccat cggggtcaaa tccatggtgg tcggccgcta cgtgagccag attaaagaga       660
agctggtgac ccgcatctac cgcggggtcg agccgcagct tccgaactgg ttcgcggtga       720
ccaaaacgcg aaatggcgcc gggggcggga caaggtggt ggacgactgc tacatcccca       780
actacctgct ccccaagacc cagcccgagc tccagtgggc gtggactaac atggaccagt       840
atttaagcgc ctgtttgaat ctcgcggagc gtaaacggct ggtggcgcag catctgacgc       900
acgtgtcgca gacgcaggag cagaacaaag agaatcagaa ccccaattct gacgcgccgg       960
tcatcaggtc aaaaacctca gccaggtaca tggagctggt cgggtggctg gtggaccgcg      1020
ggatcacgtc agaaaagcaa tggattcagg aggaccaggc ctcgtacatc tccttcaacg      1080
ccgcctccaa ctcgcggtcc cagatcaagg ccgcgctgga caatgcctcc aagatcatga      1140
gcctgacaaa gacggctccg gactacctgg tgggcagcaa cccgccggag gacattacca      1200
aaaatcggat ctaccaaatc ctggagctga acgggtacga tccgcagtac gcggcctccg      1260
tcttcctggg ctgggcgcaa aagaagttcg gaagaggaa caccatctgg ctctttgggc      1320
cggccacgac gggtaaaacc aacatcgcgg aagccatcgc ccacgccgtg cccttctacg      1380
gctgcgtaaa ctggaccaat gagaactttc ccttcaacga ttgcgtcgac aagatggtga      1440
tctggtggga ggagggcaag atgacggcca aggtcgtgga gagcgccaag gccattctgg      1500
gcggaagcaa ggtgcgcgtg gaccaaaagt gcaagtcatc ggcccagatc gaacccactc      1560
ccgtgatcgt cacctccaac accaacatgt gcgccgtgat tgacgggaac agcaccacct      1620
tcgagcatca gcagccgctg caggaccgga tgtttgaatt tgaacttacc cgccgtttgg      1680
accatgactt tgggaaggtc accaaacagg aagtaaagga cttttttcgg tgggcttccg      1740
atcacgtgac tgacgtggct catgagttct acgtcagaaa gggtggagct aagaaacgcc      1800
ccgcctccaa tgacgcggat gtaagcgagc caaaacggga gtgcacgtca cttgcgcagc      1860
cgacaacgtc agacgcggaa gcaccggcgg actacgcgga caggtaccaa aacaaatgtt      1920
ctcgtcacgt gggcatgaat ctgatgcttt ttcctgtaa acatgcgag agaatgaatc      1980
aaatttccaa tgtctgtttt acgcatggtc aaagagactg tggggaatgc ttccctggaa      2040
tgtcagaatc tcaacccgtt tctgtcgtca aaagaagac ttatcagaaa ctgtgtccaa      2100
```

```
ttcatcatat cctgggaagg gcacccgaga ttgcctgttc ggcctgcgat ttggccaatg    2160
tggacttgga tgactgtgtt tctgagcaat aaatgactta aaccaggtat ggctgctgac    2220
ggttatcttc cagattggct cgaggacaac ctttctgaag gcattcgtga gtggtgggct    2280
ctgaaacctg gagtccctca acccaaagcg aaccaacaac accaggacaa ccgtcggggt    2340
cttgtgcttc cgggttacaa atacctcgga cccggtaacg gactcgacaa aggagagccg    2400
gtcaacgagg cggacgcggc agccctcgaa cacgacaaag cttacgacca gcagctcaag    2460
gccggtgaca acccgtacct caagtacaac cacgccgacg ccgagtttca ggagcgtctt    2520
caagaagata cgtctttggg gggcaacctt ggcagagcag tcttccaggc caaaaagagg    2580
atccttgagc ctcttggtct ggttgaggaa gcagctaaaa cggctcctgg aaagaagggg    2640
gctgtagatc agtctcctca ggaaccggac tcatcatctg gtgttggcaa atcgggcaaa    2700
cagcctgcca gaaaaagact aaatttcggt cagactggag actcagagtc agtcccagac    2760
cctcaacctc tcggagaacc accagcagcc cccacaagtt tgggatctaa tacaatggct    2820
tcaggcggtg gcgcaccaat ggcagacaat aacgagggtg ccgatggagt gggtaattcc    2880
tcaggaaatt ggcattgcga ttcccaatgg ctgggcgaca gagtcatcac caccagcacc    2940
agaacctggg ccctgcccac ttacaacaac catctctaca agcaaatctc cagccaatca    3000
ggagcttcaa cgacaaacca ctactttggc tacagcaccc cttgggggta ttttgacttt    3060
aacagattcc actgccactt ctcaccacgt gactggcagc gactcattaa caacaactgg    3120
ggattccggc ccaagaaact cagcttcaag ctcttcaaca tccaagttag aggggtcacg    3180
cagaacgatg gcacgacgac tattgccaat aaccttacca gcacggttca agtgtttacg    3240
gactcggagt atcagctccc gtacgtgctc gggtcggcgc accaaggctg tctcccgccg    3300
tttccagcgg acgtcttcat ggtccctcag tatggatacc tcaccctgaa caacggaagt    3360
caagcggtgg gacgctcatc cttttactgc ctggagtact cccttcgca gatgctaagg    3420 actggaaata acttccaatt cagctatacc ttcgaggatg taccttttca cagcagctac    3480
gctcacagcc agagtttgga tcgcttgatg aatcctctta ttgatcagta tctgtactac    3540
ctgaacagaa cgcaaggaac aacctctgga acaaccaacc aatcacggct gcttttttagc    3600 caggctgggc ctcagtctat gtcttttgcag gccagaaatt ggctacctgg gccctgctac    3660
cggcaacaga gactttcaaa gactgctaac gacaacaaca cagtaacttt ccttggaca    3720 gcggccagca aatatcatct caatggccgc gactcgctgg tgaatccagg accagctatg    3780
gccagtcaca aggacgatga agaaaaattt ttccctatgc acggcaatct aatatttggc    3840
aaagaaggga caacggcaag taacgcagaa ttagataatg taatgattac ggatgaagaa    3900
gagattcgta ccaccaatcc tgtggcaaca gagcagtatg gaactgtggc aaataacttg    3960
cagagctcaa atacagctcc cacgactgga actgtcaatc atcaggggc cttacctggc    4020 atggtgtggc aagatcgtga cgtgtacctt caaggaccta tctgggcaaa gattcctcac    4080
acggatggac actttcatcc ttctcctctg atgggaggct ttggactgaa acatccgcct    4140
cctcaaatca tgatcaaaaa tactccggta ccggcaaatc ctccgacgac tttcagcccg    4200
gccaagtttg cttcatttat cactcagtac tccactggac aggtcagcgt ggaaattgag    4260
tgggagctac agaaagaaaa cagcaaacgt tggaatccag agattcagta cacttccaac    4320
tacaacaagt ctgttaatgt ggactttact gtagacacta atggtgttta tagtgaacct    4380
cgccctattg gaacccggta tctcacacga aacttgtgaa tcctggttaa tcaataaacc    4440
gtttaattcg tttcagttga actttggctc ttgtgcactt ctttatcttt atcttgtttc    4500
```

```
catggctact gcgtagataa gcagcggcct gcggcgcttg cgcttcgcgg tttacaactg    4560
ctggttaata tttaactctc gccatacctc tagtgatgga gttggccact ccctctatgc    4620
gcactcgctc gctcggtggg gcctggcgac caaaggtcgc cagacggacg tgctttgcac    4680
gtccggcccc accgagcgag cgagtgcgca tagagggagt ggccaa                   4726

<210> SEQ ID NO 9
<211> LENGTH: 3098
<212> TYPE: DNA
<213> ORGANISM: Unknown
<220> FEATURE:
<223> OTHER INFORMATION: AAV serotype, clone 42.2

<400> SEQUENCE: 9
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tcccaccccc gtgatcgtca cttccaacac caacatgtgc gctgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gccccgatg acgcggataa aagcgagccc aagcgggcct     480
gcccctcagt cgcggatcca tcgacgtcag acgcggaagg agctccggtg actttgccg      540 acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg tttccccggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgacc gtgtttctga caataaatg acttaaacca      840 ggtatggctg ccgatggtta tcttccagat tggctcgagg acaacctctc tgagggcatt     900
cgcgagtggt gggacttgaa acctggagcc ccgaaaccca agccaaccca gcaaaagcag     960
gacgacggcc ggggtctggt gcttcctggc tacaagtacc tcggacccct caacggactc    1020
gacaagggag agccggtcaa cgaggcagac gccgcgccc tcgagcacga caaggcctac    1080
gacaagcagc tcgagcaggg ggacaacccg tacctcaagt acaaccacgc cgacgccgag    1140
tttcaggagc gtcttcaaga agatacgtct tttgggggca acctcgggcg agcagtcttc    1200
caggccaaga agcgggttct cgaacctctc ggtctggttg aggaaggcgc taagacggct    1260
cctggaaaga agagacccat agaatccccc gactcctcca cgggcatcgg caagaaaggc    1320
cagcagcccg ctaaaaagaa gctcaacttt ggcagactg gcgactcaga gtcagtgccc    1380
gacccccaac ctcccggaga acctcccgcc gcgccctcag gtctgggatc tggtacaatg    1440
gctgcaggcg gtggcgcacc aatggcagac aataacgaag gcgccgacgg agtgggtaat    1500
gcctccggaa attggcattg cgattccaca tggctgggcg acagagtcat caccaccagc    1560
acccgcacct gggcctgcc cacctacaac aaccacctct acaagcagat atcaagtcag    1620
agcggggcta ccaacgacaa ccacttcttc ggctacagca cccctgggg ctattttgac    1680 ttcaacagat tccactgcca cttctcacca cgtgactggc agcgactcat caacaacaac    1740
tggggattcc ggcccagaa gctgcggttc aagttgttca acatccaggt caaggaggtc    1800
```

| | |
|---|---|
| acgacgaacg acggcgttac gaccatcgct aataaccttg ccagcacgat tcaggtcttc | 1860 |
| tcggactcgg agtaccaact gccgtacgtc ctcggctctg cgcaccaggg ctgcctccct | 1920 |
| ccgttccctg cggacgtgtt catgattcct cagtacggat atctgactct aaacaacggc | 1980 |
| agtcagtctg tgggacgttc ctccttctac tgcctggagt actttccttc tcagatgctg | 2040 |
| agaacgggca ataactttga attcagctac acctttgagg aagtgccttt ccacagcagc | 2100 |
| tatgcgcaca gccagagcct ggaccggctg atgaatcccc tcatcgacca gtacctgtac | 2160 |
| tacctggccc ggacccagag cactacgggg tccacaaggg agctgcagtt ccatcaggct | 2220 |
| gggcccaaca ccatggccga gcaatcaaag aactggctgc ccggaccctg ttatcggcag | 2280 |
| cagagactgt caaaaaacat agacagcaac aacaacagta actttgcctg gaccggggcc | 2340 |
| actaaatacc atctgaatgg tagaaattca ttaaccaacc cgggcgtagc catggccacc | 2400 |
| aacaaggacg acgaggacca gttctttccc atcaacggag tgctggtttt tggcgaaacg | 2460 |
| ggggctgcca acaagacaac gctggaaaac gtgctaatga ccagcgagga ggagatcaaa | 2520 |
| accaccaatc ccgtggctac agaagaatac ggtgtggtct ccagcaacct gcaatcgtct | 2580 |
| acggccggac cccagacaca gactgtcaac agccaggggg ctctgcccgg catggtctgg | 2640 |
| cagaaccggg acgtgtacct gcagggtccc atctgggcca aaattcctca cacggacggc | 2700 |
| aactttcacc cgtctcccct gatgggcgga tttggactca acacccgcc tcctcaaatt | 2760 |
| ctcatcaaaa acaccccggt acctgctaat cctccagagg tgtttactcc tgccaagttt | 2820 |
| gcctcattta tcacgcagta cagcaccggc caggtcagcg tggagatcga gtgggaactg | 2880 |
| cagaaagaaa acagcaaacg ctggaatcca gagattcagt acacctcaaa ttatgccaag | 2940 |
| tctaataatg tggaatttgc tgtcaacaac gaaggggttt atactgagcc tcgccccatt | 3000 |
| ggcacccgtt acctcacccg taacctgtaa ttgcctgtta atcaataaac cggttaattc | 3060 |
| gtttcagttg aactttggtc tctgcgaagg gcgaattc | 3098 |

<210> SEQ ID NO 10
<211> LENGTH: 3098
<212> TYPE: DNA
<213> ORGANISM: Unknown
<220> FEATURE:
<223> OTHER INFORMATION: AAV serotype, clone 16.3

<400> SEQUENCE: 10

| | |
|---|---|
| gaattcgccc ttcgcagaga ccaaagttca actgaaacga atcaaccggt ttattgatta | 60 |
| acaagtaatt acaggttacg ggtgaggtaa cgggtgccaa tggggcgagg ctcagtataa | 120 |
| acccccttcgt tgttgacagc aaattccaca ttattagact tggcataatt tgaggtgtac | 180 |
| tgaatctctg gattccagcg tttgctgttt tctttctgca gttcccactc gatctccacg | 240 |
| ctgacctggc cggtgctgta ctgcgtgata aatgaggcaa actaggcagg agtaaacacc | 300 |
| cctggaggat tagcaggtac cggggtgttt tgatgagaa tttgaggagg cgggtgtttg | 360 |
| agtccaaatc cgcccatcag gggagacggg tgaaagttgc cgtccgtgtg aggaattttg | 420 |
| gcccagatgg gaccctgcag gtacacgtcc cggttctgcc agaccatgcc gggcagagcc | 480 |
| ccctggctgt tgacagtctg tgtctggggt ccggccgtag acgattgcag gttgctggag | 540 |
| accacaccgt attcttctgt agccacggga ttggtggttt tgatctcctc ctcgctggtc | 600 |
| attagcacgt tttccagcgt tgtccttgttg gcagccccg ttttgccaaa aaccagcact | 660 |
| ccgttgatgg gaaagaactg gccctcgtcg tccttgttgg tggccatggc tacgcccggg | 720 |
| ttggttaatg aatttctacc attcagatgg tatttagtgg ccccggtcca ggcaaagtta | 780 |

```
ctgttgttgt tgctgtctat gtttttttgac agtctctgct gccgataaca gggtccgggc    840
agccagttct ttgattgctc ggccatggtg ttgggcccag cctgatggaa ctgcagctcc     900
cttgtggacc ccgtagtgct ctgggtccgg gccaggtagt acaggtactg gtcgatgagg     960
ggattcatca gccggtccag gctctggctg tgcgcatagc tgctgtggaa aggcacttcc    1020
tcaaaggtgt agctgaattc aaagttattg cccgttctca gcatctgaga aggaaagtac    1080
tccaggcagt agaaggagga acgtcccata gactgactgc cgttgtttag agtcagatat    1140
ccgtactgag gaatcatgaa cacgtccgca gggaacggag ggaggcagcc ctggtgcgca    1200
gagccgagga cgtacggcag ttggtactcc gagtccgaga agacctgaat cgtgctggta    1260
aggttattag cgatggtcgt aacgccgtcg ttcgtcgtga cctccttgac ctggatgttg    1320
aacaacttga accgcagctt tctgggccgg aatccccagt tgttgttgat gagtcgctgc    1380
cagtcacgtg gtgagaagtg gcagtggaat ctgttgaagt caaaatagcc ccaggggtg    1440 ctgtagccga agaagtggtt gtcgttggta gccccgctct gacttgatat ctgcttgtag    1500
aggtggttgt tgtaggtggg cagggcccag gtgcgggtgc tggtggtgat gactctgtcg    1560
cccagccatg tggaatcgca atgccaattt ccggaggcat tacccactcc gtcggcgcct    1620
tcgttattgt ctgccattgg tgcgccaccg cctgcagcca ttgtaccaga tcccagacct    1680
gagggcgcgg cgggaggttc tccgagaggt tggggtcgg gcactgactc tgagtcgcca     1740
gtctgcccaa agttgagctt cttttttagcg ggctgctggc ctttcttgcc gatgcccgtg   1800
gaggagtcgg gggattctat gggtctcttc tttccaggag ccgtcttagc gccttcctca    1860
accagaccga gaggttcgag aacccgcttc ttggcctgga agactgctcg cccgaggttg    1920
cccccaaaag acgtatcttc ttgaagacgc tcctgaaact cagcgtcggc gtggttgtac    1980
ttgaggtacg ggttgtcccc ctgctcgagc tgcttgtcgt aggccttgtc gtgctcgagg    2040
gccgcggcgt ctgcctcgtt gaccggctct cccttgtcga gtccgttgaa gggtccgagg    2100
tacttgtagc caggaagcac cagacccggg ccgtcgtcct gcttttgctg gttggctttg    2160
ggtttcgggg ctccaggttt caagtcccac cactcgcgaa tgccctcaga gaggttgtcc    2220
tcgagccaat ctggaagata accatcggca gccatacctg gtttaagtca tttattgctc    2280
agaaacacag tcatccaggt ccacgttgac cagatcgcag gccgagcaag caatctcggg    2340
agcccgcccc agcagatgat gaatggcaca gagtttccga tacgtcctct ttctgacgac    2400
cggttgagat tctgacacgc cggggaaaca ttctgaacag tctctggtcc cgtgcgtgaa    2460
gcaaatgttg aaattctgat tcattctctc gcatgtcttg cagggaaaca gcatctgaag    2520
catgcccgcg tgacgagaac atttgttttg gtacctgtcg gcaaagtcca ccggagctcc    2580
ttccgcgtct gacgtcgatg gatccgcgac tgaggggcag gcccgcttgg gctcgctttt    2640
atccgcgtca tcggggcgg gcctcttgtt ggctccaccc tttctgacgt agaactcatg     2700
cgccacctcg gtcacgtgat cctgcgccca gcggaagaac tctttgactt cctgctttgt    2760
caccttgcca aagtcctgct ccagacggcg ggtgagttca aatttgaaca tccggtcttg    2820
taacggctgc tggtgctcga aggtggtgct gttcccgtca atcacggcgc acatgttggt    2880
gttggaagtg acgatcacgg gggtgggatc gatctgggcg gacgacttgc acttttggtc    2940
cacgcgcacc ttgctgccgc cgagaatggc cttggcggac tccacgacct tggccgtcat    3000
cttgccctcc tccaccagag tcaccatctt gtcgacgcaa tcgttgaagg gaaagttctc    3060
attggtccag ttgacgcagc cgtagaaagg gcgaattc                            3098
```

<210> SEQ ID NO 11
<211> LENGTH: 3121
<212> TYPE: DNA
<213> ORGANISM: Unknown
<220> FEATURE:
<223> OTHER INFORMATION: AAV serotype, clone 29.3

<400> SEQUENCE: 11

```
gaattcgccc ttcgcagaga ccaaagttca actgaaacga atcaaccggt ttattgatta      60
acaagcaatt acagattacg ggtgaggtaa cgggtgccga tggggcgagg ctcagaataa     120
gtgccatctg tgttaacagc aaagtccaca tttgtagatt tgtagtagtt ggaagtgtat     180
tgaatctctg ggttccagcg tttgctgttt tctttctgca gctcccattc aatttccacg     240
ctgacctgtc cggtgctgta ctgcgtgatg aacgacgcca gcttagcttg actgaaggta     300
gttggaggat ccgcgggaac aggtgtattc ttaatcagga tctgaggagg cgggtgtttc     360
agtccaaagc cccccatcag cggcgaggga tgaaagtttc cgtccgtgtg aggaatcttg     420
gcccagatag gaccctgcag gtacacgtcc cggttctgcc agaccatgcc aggtaaggct     480
ccttgactgt tgacggcccc tacaatagga gcggcgtttt gctgttgcag gttatcggcc     540
accacgccgt actgttctgt ggccactggg ttggtggttt taatttcttc ctcactggtt     600
agcataacgc tgctatagtc cacgttgcct tttccagctc cctgtttccc aaacattaag     660
actccgctgg acgaaaaaaa tcgctcttcg tcgtccttgt gggttgccat agcgacaccg     720
ggatttacca gagagtctct gccattcaga tgatacttgg tggcaccggt ccaggcaaag     780
ttgctgttgt tattttgcga cagtgtcgtg agacgcgtt gctgccggta gcagggcccg     840
ggtagccagt ttttggcctg agccgacatg ttattaggcc cggcctgaga aaatagcaac     900
tgctgagttc ctgcggtacc tcccgtggac tgagtccgag acaggtagta caggtactgg     960
tcgatgaggg ggttcatcag ccggtccagg cttt ggctgt gcgcgtagct gctgtgaaaa    1020
ggcacgtcct caaactggta gctgaactca aagttgttgc ccgttctcag catttgagaa    1080
ggaaagtact ccaggcagta aaggaggaa cggcccacgg cctgactgcc attgttcaga    1140
gtcaggtacc cgtactgagg aatcatgaag acgtccgccg ggaacggagg caggcagccc    1200
tggcgcgcag agccgaggac gtacgggagc tggtattccg agtccgtaaa gacctgaatc    1260
gtgctggtaa ggttattggc gatggtcttg gtgccttcat tctgcgtgac ctccttgacc    1320
tggatgttga agagcttgaa gttgagtctc ttgggccgga atccccagtt gttgttgatg    1380
agtcgctgcc agtcacgtgg tgagaagtgg cagtggaatc tgttaaagtc aaaatacccc    1440
caggggtgc tgtagccgaa gtaggtgttg tcgttggtgc ttcctcccga agtcccgttg    1500
gagatttgct tgtagaggtg gttgttgtag gtggggaggg cccaggttcg ggtgctggtg    1560
gtgatgactc tgtcgcccag ccatgtggaa tcgcaatgcc aatttcctga ggaactaccc    1620
actccgtcgg cgccttcgtt attgtctgcc attggagcgc caccgcctgc agccattgta    1680
ccagatccca gaccagaggg gcctgcgggg ggttctccga ttggttgagg gtcgggcact    1740
gactctgagt cgccagtctg cccaaagttg agtctctttt tcgcgggctg ctggcctttc    1800
ttgccgatgc ccgtagtgga gtctggagaa cgctggggtg atggctctac cggtctcttc    1860
tttccaggag ccgtcttagc gccttcctca accagaccga gaggttcgag aacccgcttc    1920
ttggcctgga agactgctcg tccgaggttg cccccaaaag acgtatcttc ttgcagacgc    1980
tcctgaaact cggcgtcggc gtggttatac cgcaggtacg gattgtcacc cgctttgagc    2040
tgctggtcgt aggccttgtc gtgctcgagg gccgctgcgt ccgccgcgtt gacgggctcc    2100
```

```
cccttgtcga gtccgttgaa gggtccgagg tacttgtagc caggaagcac cagaccccgg   2160
ccgtcgtcct gcttttgctg gttggcttg ggcttcgggg ctccaggttt cagcgcccac    2220
cactcgcgaa tgccctcaga gaggttgtcc tcgagccaat ctggaagata accatcggca   2280
gccatacctg atctaaatca tttattgttc aaagatgcag tcatccaaat ccacattgac   2340
cagatcgcag gcagtgcaag cgtctggcac ctttcccatg atatgatgaa tgtagcacag   2400
tttctgatac gccttttga cgacagaaac gggttgagat tctgacacgg gaaagcactc    2460
taaacagtct ttctgtccgt gagtgaagca gatatttgaa ttctgattca ttctctcgca   2520
ttgtctgcag ggaaacagca tcagattcat gcccacgtga cgagaacatt tgttttggta   2580
cctgtccgcg tagttgatcg aagcttccgc gtctgacgtc gatggctgcg caactgactc   2640
gcgcacccgt ttgggctcac ttatatctgc gtcactgggg gcgggtcttt tcttggctcc   2700
accctttttg acgtagaatt catgctccac ctcaaccacg tgatcctttg cccaccggaa   2760
aaagtctttg acttcctgct tggtgacctt cccaaagtca tgatccagac ggcgggtgag   2820
ttcaaatttg aacatccggt cttgcaacgg ctgctggtgt tcgaaggtcg ttgagttccc   2880
gtcaatcacg gcgcacatgt tggtgttgga ggtgacgatc acgggagtcg ggtctatctg   2940
ggccgaggac ttgcatttct ggtccacgcg caccttgctt cctccgagaa tggctttggc   3000
cgactccacg accttggcgg tcatcttccc ctcctcccac cagatcacca tcttgtcgac   3060
acagtcgttg aagggaaagt tctcattggt ccagttgacg cagccgtaga agggcgaatt   3120
c                                                                  3121

<210> SEQ ID NO 12
<211> LENGTH: 3121
<212> TYPE: DNA
<213> ORGANISM: Unknown
<220> FEATURE:
<223> OTHER INFORMATION: AAV serotype, clone 29.4

<400> SEQUENCE: 12
gaattcgccc ttctacggct gcgtcaactg gaccaatgag aactttccct tcaacgactg     60
tgtcgacaag atggtgatct ggtgggagga ggggaagatg accgccaagg tcgtggagtc    120
ggccaaagcc attctcggag gaagcaaggt gcgcgtggac cagaaatgca agtcctcggc    180
ccagatagac ccgactcccg tgatcgtcac ctccaacacc aacatgtgcg ccgtgattga    240
cgggaactca acgaccttcg aacaccagca gccgttgcaa gaccggatgt tcaaatttga    300
actcacccgc cgtctggatc atgactttgg gaaggtcacc aagcaggaag tcaaagactt    360
tttccggtgg gcaaaggatc acgtggttga ggtggagcac gaattctacg tcaaaaaggg    420
tggagccaag aaaagaccg cccccagtga cgcagatata agtgagccca acgggtgcg     480 cgagtcagtt gcgcagccat cgacgtcaga cgcggaagct tcgatcaact acgcagacag   540
gtaccaaaac aaatgttctc gtcacgcggg catgaatctg atgctgtttc cctgcagaca   600
atgcgagaga atgaatcaga attcaaatat ctgcttcact cacggacaga aagactgttt   660
agagtgcttt cccgtgtcag aatctcaacc cgtttctgtc gtcaaaaagg cgtatcagaa   720
actgtgctac attcatcata tcatgggaaa ggtgccagac gcttgcactg cctgcgatct   780
ggtcgatgtg gatttggatg actgcatctt tgaacaataa atgatttaaa tcaggtatgg   840
ctgccgatgg ttatcttcca gattggctcg aggacaacct ctctgagggc attcgcgagt   900
ggtgggcgct gaaacctgga gccccgaagc ccaaagccaa ccagcaaaag caggacggcg   960
```

```
gccggggtct ggtgcttcct ggctacaagt acctcggacc cttcaacgga ctcgacaagg      1020
gggagcccgt caacgcggcg gacgcagcgg ccctcgagca cgacaaggcc tacgaccagc      1080
agctcaaagc gggtgacaat ccgtacctgc ggtataacca cgccgacgcc gagtttcagg      1140
agcgtctgca agaagatacg tcttttgggg caacctcgg gcgagcagtc ttccaggcca       1200
agaagcgggt tctcgaacct ctcggtctgg ttgaggaagg cgctaagacg gctcctggaa      1260
agaagagacc ggtagagcca tcaccccagc gttctccaga ctcctctacg ggcatcggca      1320
agaaaggcca gcagcccgcg aaaaagagac tcaactttgg gcagactggc gactcagagt      1380
cagtgcccga ccctcaacca atcggagaac ccccgcagg ccctctggt ctgggatctg        1440
gtacaatggc tgcaggcggt ggcgctccaa tggcagacaa taacgaaggc gccgacggag      1500
tgggtagttc ctcaggaaat tggcattgcg attccacatg gctgggcgac tgagtcatca      1560
ccaccagcac ccgaacctgg gccctcccca cctacaacaa ccacctctac aagcaaatct      1620
ccaacgggac ttcgggagga agcaccaacg acaacaccta cttcggctac agcacccct       1680
gggggtattt tgactttaac agattccact gccacttctc accacgtgac tggcagcgac      1740
tcatcaacaa caactgggga ttccggccca agagactcaa cttcaagctc ttcaacatcc      1800
aggtcaagga ggtcacgcag aatgaaggca ccaagaccat cgccaataac cttaccagca      1860
cgattcaggt cttacgggac tcggaatacc agctcccgta cgtcctcggc tctgcgcacc      1920
agggctgcct gcctccgttc ccggcggacg tcttcatgat tcctcagtac gggtacctga      1980
ctctgaacaa tggcagtcag gccgtgggcc gttcctcctt ctactgcctg gagtactttc      2040
cttctcaaat gctgagaacg ggcaacaact ttgagttcag ctaccagttt gaggacgtgc      2100
cttttcacag cagctacgcg cacagccaaa gcctggaccg gctgatgaac cccctcatcg      2160
accagtacct gtactacctg tctcggactc agtccacggg aggtaccgca ggaactcagc      2220
agttgctatt ttctcaggcc gggcctaata acatgtcggc tcaggccaaa aactggctac      2280
ccgggccctg ctaccggcag taacgcgtct ccacgacact gtcgcaaaat aacaacagca      2340
actttgtctg gaccggtgcc accaagtatc atctgaatgg cagagactct ctggtagatc      2400
ccggtgtcgc tatggcaacc cacaaggacg acgaagagcc attttttccg tccagcggag      2460
tcataatgtt tgggaaacag ggagctggaa agacaacgt ggactatagc agcgtcatgc       2520
taaccagtga ggaagaaatt aaaaccacca cccagtggc cacagaacag tacgcgtgg       2580
tggccgataa cctgcaacag caaaacgccg ctcctattgt aggggccgtc aacagtcaag      2640
gagccttacc tggcatggtc tggcagaacc gggacgtgta cctgcagggt cctacctggg      2700
ccaagattcc tcacacggac ggaaactttc atccctcgcc gctgatggga ggctttggac      2760
tgaaacaccc gcctcctcag atcctgatta agaatacacc tgttcccgcg gatcctccaa      2820
ctaccttcag tcaagctaag ctggcgtcgt tcatcacgca gtacagcacc ggacaggtca      2880
gcgtggaaat tgaatgggag ctgcaggaag aaaacagcaa acgctggaac ccagagattc      2940
aatacacttc caactactac aaatctacaa atgtggactt gctgttaac acagatggca       3000
cttattctga gcctcgcccc atcggcaccc gttacctcac ccgtaatctg taattgcttg      3060
ttaatcaata aaccggttga ttcgtttcag ttgaactttg gtctctgcga agggcgaatt      3120
c                                                                      3121

<210> SEQ ID NO 13
<211> LENGTH: 3121
<212> TYPE: DNA
<213> ORGANISM: Unknown
```

<220> FEATURE:
<223> OTHER INFORMATION: AAV serotype, clone 29.5

<400> SEQUENCE: 13

```
gaattcgccc ttcgcgagac caaagttcaa ctgaaacgaa tcaaccggtt tattgattaa     60
caagcaatta cagattacgg gtgaggtaac gggtgccgat ggggcgaggc tcagaataag    120
tgccatctgt gttaacagca aagtccacat ttgtagattt gtagtagttg aagtgtatt    180
gaatctctgg gttccagcgt ttgctgtttt ctttctgcag ctcccattca atttccacgc    240
tgacctgtcc ggtgctgtac tgcgtgatga acgacgccag cttagcttga ctgaaggtag    300
ttggaggatc cgcgggaaca ggtgtattct taatcaggat ctgaggaggc gggtgtttca    360
gtccaaagcc tcccatcagc ggcgagggat gaaagtttcc gtccgtgtga ggaatcttgg    420
cccagatagg accctgcagg tacacgtccc ggttctgcca gaccatgcca ggtaaggctc    480
cttgactgtt gacggcccct acaataggag cggcgttttg ctgttgcagg ttatcggcca    540
ccacgccgta ctgttctgtg gccactgggt tggtggtttt aatttcttcc tcactggtta    600
gcataacgct gctatagtcc acgttgtctt ttccagctcc ctgtttccca acattaaga    660
ctccgctgga cggaaaaaat cgctcttcgt cgtccttgtg ggttgccata gcgacaccgg    720
gatttaccag agagtctctg ccattcagat gatacttggt ggcaccggtc caggcaaagt    780
tgctgttgtc attttgcgac agtgtcgtgg agacgcgttg ctgccggtag cagggcccgg    840
gtagccagtt tttggcctga ccgacatgt tattaggccc ggcctgagaa aatagcaact    900
gctgagttcc tgcggtacct cccgtggact gagtccgaga caggtagtac aggtactggt    960
cgatgagggg gttcatcagc cggtccaggc tttggctgtg cgcgtagctg ctgtgaaaag   1020
gcacgtcctc aaactggtag ctgaactcaa agttgttgcc cgttctcagc atttgagaag   1080
gaaagtactc caggcagtag aaggaggaac ggcccacggc ctgactgcca ttgttcagag   1140
tcaggtaccc gtactgagga atcatgaaga cgtccgccgg gaacggaggc aggcagccct   1200
ggtgcgcaga gccgaggacg tacgggagct ggtattccga gtccgtaaag acctgaatcg   1260
tgctggtaag gttattggcg atggtcttgg tgccttcatt ctgcgtgacc tccttgacct   1320
ggatgttgaa gagcttgaag ttgaggctct tgggccggaa tccccagttg ttgttgatga   1380
gtcgctgcca gtcacgtggt gagaagtggc agtggaatct gttaaagtca aaatacccc   1440
agggggtgct gtagccgaag taggtgttgt cgttggtgct tcctcccgaa gtcccgttgg   1500
agatttgctt gtagaggtgg ttgttgtagg tggggagggc ccaggttcgg gtgctggtgg   1560
tgatgactcc gtcgcccagc catgtggaat cgcaatgcca atttcctgag gaactaccca   1620
ctccgtcggc gccttcgtta ttgtctgcca ttggagcgcc accgcctgca gccattgtac   1680
cagatcccag accagagggg cctgcggggg ttctccgat tggttgaggg tcgggcactg   1740
actctgagtc gccagtctgc ccaaagttga gtctcttttt cgcgggctgc tggccttttct   1800
tgccgatgcc cgtagaggag tctggagaac gctggggtga tggctctacc ggtctcttct   1860
ttccaggagc cgtcttagcg ccttcctcaa ccagaccgag aggttcgaga accgcttct   1920
tggcctggaa gactgctcgc ccgaggttgc ccccaaaaga cgtatcttct tgcagacgct   1980
cctgaaactc ggcgtcggcg tggttatacc gcaggtacga attgtcaccc gctttgagct   2040
gctggtcgta ggccttgtcg tgctcgaggg ccgctgcgtc cgccgcgttg acgggctccc   2100
ccttgtcgag tccgttgaag gtccgaggt acttgtagcc aggaagcacc agaccccggc   2160
cgtcgtcctg cttttgctgg ttggctttgg gcttcggggc tccaggtttc agcgcccacc   2220
```

| | |
|---|---|
| actcgcgaat gccctcagag aggttgtcct cgagccaatc tggaagataa ccatcggcag | 2280 |
| ccatacctga tttaaatcat ttattgttca aagatgcagt catccaaatc cacattgacc | 2340 |
| agatcgcagg cagtgcaagc gtctggcacc tttcccatga tatgatgaat gtagcacagt | 2400 |
| ttctgatacg ccttttgac dacagaaacg ggttgagatt ctgacacggg aaagcactct | 2460 |
| aaacagtctt tctgtccgtg agtgaagcag atatttgaat tctgattcat tctctcgcat | 2520 |
| tgtctgcagg gaaacagcat cagattcatg cccacgtgac gagaacattt gttttggtac | 2580 |
| ctgtctgcgt agttgatcga agcttccgcg tctgacgtcg atggctgcgc aactgactcg | 2640 |
| cgcacccgtt tgggctcact tatatctgcg tcactggggg cgggtctttt cttggctcca | 2700 |
| cccttttga cgtagaattc atgctccacc tcaaccacgt gatcctttgc ccaccggaaa | 2760 |
| aagtctttga cttcctgctt ggtgaccttc ccaaagtcat gatccagacg gcgggtgagt | 2820 |
| tcaaatttga acatccggtc ttgcaacggc tgctggtgtt cgaaggtcgt tgagttcccg | 2880 |
| tcaatcacgg cgcacatgtt ggtgttggag gtgacgatca cgggagtcgg gtctatctgg | 2940 |
| gccgaggact tgcatttctg gtccacgcgc accttgcttc ctccgagaat ggctttggcc | 3000 |
| gactccacga ccttggcggt catcttcccc tcctcccacc agatcaccat cttgtcgaca | 3060 |
| cagtcgttga agggaaagtt ctcattggtc cagttgacgc agccgtagaa agggcgaatt | 3120 |
| c | 3121 |

<210> SEQ ID NO 14
<211> LENGTH: 3131
<212> TYPE: DNA
<213> ORGANISM: Unknown
<220> FEATURE:
<223> OTHER INFORMATION: AAV serotype, clone 1-3

<400> SEQUENCE: 14

| | |
|---|---|
| gcggccgcga attcgccctt ggctgcgtca actggaccaa tgagaacttt cccttcaatg | 60 |
| attgcgtcga caagatggtg atctggtggg aggagggcaa gatgacggcc aaggtcgtgg | 120 |
| agtccgccaa ggccattctc ggcggcagca aggtgcgcgt ggaccaaaag tgcaagtcgt | 180 |
| ccgcccagat cgaccccacc cccgtgatcg tcacctccaa caccaacatg tgcgccgtga | 240 |
| ttgacgggaa cagcaccacc ttcgagcacc agcagcctct ccaggaccgg atgtttaagt | 300 |
| tcgaactcac ccgccgtctg gagcacgact ttggcaaggt gacaaagcag gaagtcaaag | 360 |
| agttcttccg ctgggccagt gatcacgtga ccgaggtggc gcatgagttt tacgtcagaa | 420 |
| agggcggagc cagcaaaaga cccgccccg atgacgcgga taaaagcgag cccaagcggg | 480 |
| cctgcccctc agtcgcggat ccatcgacgt cagacgcgga aggagctccg gtggactttg | 540 |
| ccgacaggta ccaaaacaaa tgttctcgtc acgcgggcat gcttcagatg ctgtttccct | 600 |
| gcaaaacgtg cgagagaatg aatcggaatt tcaacatttg cttcacacac ggggtcagag | 660 |
| actgctcaga gtgttttcccc ggcgtgtcag aatctcaacc ggtcgtcaga aagaggacgt | 720 |
| atcggaaact ccgtgcgatt catcatctgc tggggcgggc tcccgagatt gcttgctcgg | 780 |
| cctgcgatct ggtcaacgtg gacctggatg actgtgtttc tgagcaataa atgacttaaa | 840 |
| ccaggtatgg ctgccgatgg ttatcttcca gattggctcg aggacaacct ctctgagggc | 900 |
| attcgcgagt ggtgggcgct gaaacctgga gccccgaagc caaagccaa ccagcaaaag | 960 |
| caggacgacg gccggggtct ggtgcttcct ggctacaagt acctcggacc cttcaacgga | 1020 |
| ctcgacaagg gggagcccgt caacgcgcg gacgcagcgg ccctcgagca cgacaaggct | 1080 |
| tacgaccagc agctgcaggc gggtgacaat ccgtacctgc ggtataacca cgccgacgcc | 1140 |

-continued

```
gagtttcagg agcgtctgca agaagatacg tcttttgggg gcaacctcgg gcgagcagtc    1200
ttccaggcca agaagcgggt tctcgaacct ctcggtctgg ttgaggaagg cgctaagacg    1260
gctcctggaa agaagagacc ggtagagcca tcaccccagc gttctccaga ctcctctacg    1320
ggcatcggca agaaaggcca acagcccgcc agaaaaagac tcaattttgg tcagactggc    1380
gactcagagt cagttccaga ccctcaacct ctcggagaac ctccagcagc gccctctggt    1440
gtgggaccta atacaatggc tgcaggcggt ggcgcaccaa tggcagacaa taacgaaggc    1500
gccgacggag tgggtagttc ctcgggaaat tggcattgcg attccacatg gctgggcgac    1560
agagtcatca ccaccagcac ccgaacctgg gccctgccca cctacaacaa ccacctctac    1620
aagcaaatct ccaacgggac atcgggagga gccaccaacg acaacaccta cttcggctac    1680
agcaccccct gggggtattt tgactttaac agattccact gccacctttc caccgtgac    1740 tggcagcgac tcatcaacaa caactgggga ttccaccca agagactcag cttcaagctc    1800
ttcaacatcc aggtcaagga ggtcacgcag aatgaaggca ccaagaccat cgccaataac    1860
ctcaccagca ccatccaggt gtttacggac tcggagtacc agctgccgta cgttctcggc    1920
tctgtccacc agggctgcct gcctccgttc ccggcggacg tgttcatgat tccccagtac    1980
ggctacctaa cactcaacaa cggtagtcag gccgtgggac gctcctcctt ctactgcctg    2040
gaatactttc cttcgcagat gctgagaacc ggcaacaact tccagtttac ttacaccttc    2100
gaggacgtgc ctttccacag cagctacgcc cacagctaga gcttggaccg gctgatgaat    2160
cctctgattg accagtacct gtactacttg tctcggactc aaacaacagg aggcacggca    2220
aatacgcaga ctctgggctt cagccaaggt gggcctaata caatggccaa tcaggcaaag    2280
aactggctgc caggaccctg ttaccgccaa caacgcgtct caacgacaac cgggcaaaac    2340
aacaatagca actttgcctg gactgctggg accaaatacc atctgaatgg aagaaattca    2400
ttggctaatc ctggcatcgc tatggcaaca cacaaagacg acgaggagcg ttttttttccc    2460 agtaacggga tcctgatttt tggcaaacaa aatgctgcca gagacaatgc ggattacagc    2520
gatgtcatgc tcaccagcga ggaagaaatc aaaaccacta accctgtggc tacagaggaa    2580
tacggtatcg tggcagataa cttgcagcag caaaacacgg ctcctcaaat tggaactgtc    2640
aacagccagg gggccttacc cggtatggtc tggcagaacc gggacgtgta cctgcagggt    2700
cccatctggg ccaagattcc tcacacggac ggcaacttcc acccgtctcc gctgatgggc    2760
ggctttggcc tgaaacatcc tccgcctcag atcctgatca gaacacgcc tgtacctgcg    2820 gatcctccga ccaccttcaa ccagtcaaag ctgaactctt tcatcacgca atacagcacc    2880
ggacaggtca gcgtggaaat tgaatgggag ctgcagaagg aaaacagcaa gcgctggaac    2940
cccgagatca gtacacctc caactactac aaatctataa gtgtggactt tgctgttaat    3000
acagaaggcg tgtactctga accccgcccc attggcaccc gttacctcac ccgtaatctg    3060
taattgcctg ttaatcaata aaccggttga ttcgtttcag ttgaactttg gtctctgcga    3120
agggcgaatt c                                                        3131
```

<210> SEQ ID NO 15
<211> LENGTH: 3127
<212> TYPE: DNA
<213> ORGANISM: Unknown
<220> FEATURE:
<223> OTHER INFORMATION: AAV serotype, clone 13-3b

<400> SEQUENCE: 15

```
gcggccgcga attcgccctt cgcagagacc aaagttcaac tgaaacgaat caaccggttt      60
attgattaac atgcaattac agattacggg tgaggtaacg agtgccaata gggcgaggct     120
cagagtaaac accctggctg tcaacggcaa agtccacacc agtctgcttt tcaaagttgg     180
aggtgtactg aatctccggg tcccagcgct tgctgttttc cttctgcagc tcccactcga     240
tttccacgct gacttgtccg gtgctgtact gtgtgatgaa cgaagcaaac ttggcaggag     300
taaacacctc cggaggatta gcgggaacgg gagtgttctt gatcaggatc tgaggaggcg     360
gatgtttaag tccaaagccg cccatcaaag gagacgggtg aaagttgcca tccgtgtgag     420
gaatcttggc ccagatggga ccctgcaggt acacgtcccg gttctgccag accatgccag     480
gtaaggctcc ctggttgttg acaacttgtg tctgggctgc agtattagcc gcttgtaagt     540
tgctgctgac tatcccgtat tcttccgtgg ctacaggatt agtaggacga atttcttctt     600
catttgtcat taacacattt tccaatgtag ttttgttagt tgctccagtt tttccaaaaa     660
tcaggactcc gctggatggg aaaaagcggt cctcgtcgtc cttgtgagtt gccatggcga     720
cgccgggatt aaccaacgag tttctgccgt tcaggtgata tttggtggca ccagtccaag     780
caaagttgct gttgttgttt tgatccagcg ttttggagac cctttgttgc cggaagcagg     840
gtccaggtaa ccaattcttg gcttgttcgg ccatagttga aggcccgccc tggtaaaact     900
gcagttcccg attgccagct gtgcctcctg ggtcactctg tgttctggcc aggtagtaca     960
agtactggtc gatgagggga ttcatcagcc ggtccaggct ctggctgtgt gcgtagctgc    1020
tgtggaaagg cacgtcctcg aagctgtagc tgaactcaaa gttgttgccc gttctcagca    1080
tctgagaggg gaagtactcc aggcagtaga aggaggaacg tcccacagac tgactgccat    1140
tgttgagagt caggtagccg tactgaggaa tcatgaagac gtccgccggg aacggaggca    1200
ggcagccctg gtgcgcagag ccgaggacgt acggcagctg gtattccgag tccgagaata    1260
cctgaatcgt gctggtaagg ttattagcga tggtcgtaac gccgtcattc gtcgtgacct    1320
ccttgacctg gatgttgaag agcttgaacc gcagcttctt gggccggaat ccccagttgt    1380
tgttgatgag tcgctgccag tcacgtggtg agaagtggca gtggaatctg ttaaagtcaa    1440
aataccccca gggggtgctg tagccgaagt aggtgttgtc gttggtacta cctgcagttt    1500
cactggagat ttgctcgtag aggtggttgt tgtaggtggg cagggcccag gttcgggtgc    1560
tggtggtaat gactctgtcg cccagccatg tggaatcgca atgccaattt cctgaggcat    1620
tacccactcc gtcggcacct tcgttattgt ctgccattgg tgcgccaccg cctgcagcca    1680
ctgtaccaga tcccacacta gagggcgctg ctggaggttc tccgagaggt tgagggtcgg    1740
ggactgactc tgagtcgcca gtctgaccga aattgagtct ctttctggcg ggctgctggc    1800
ccttcttgcc gatgcccgtg gaggagtcgg gggaacgctg aggtgacggc tctaccggtc    1860
tcttctttgc aggagccgtc ttagcgcctt cctcaaccag accgagaggt tcgagaaccc    1920
gcttcttggc ctggaagact gctcgcccga ggttgccccc aaatgacgta tcttcttgca    1980
gacgctcctg aaactcggcg tcggcgtggt tataccgcag gtacgggttg tcacccgcat    2040
tgagctgctg gtcgtaggcc ttgtcgtgct cgagggccgc tgcgtccgcc gcgttgacgg    2100
gctccccctt gtcgagtccg ttgaagggtc cgaggtactt gtagccagga agcaccagac    2160
cccggccgtt gtcctgcttt tgctggttgg ctttgggttt cggggctcca ggtttcaggt    2220
cccaccactc gcgaatgccc tcagagaggt tgtcctcgag ccaatctgga agataaccat    2280
cggcagccat acctgatttta aatcatttat tgttcaaaga tgcagtcatc caaatccaca    2340
ttgaccagat cgcaggcagt gcaagcgtct ggcacctttc ccatgatatg atgaatgtag    2400
```

```
cacagtttct gatacgcctt tttgacgaca gaaacgggtt tagattctga cacgggaaag    2460
cactctaaac agtctttctg tccgtgagtg aagcagatat ttgaattctg attcattctc    2520
tcgcattgtc tgcagggaaa cagcatcaga ttcatgccca cgtgacgaga acatttgttt    2580
tggtacctgt ctgcgtagtt gatcgaagct tccgcgtctg acgtcgatgg ctgcgcaact    2640
gactcgcgca cccgtttggg ctcacttata tctgcgtcac tggggggcggg tcttttcttg    2700 gctccacccct ttttgacgta gaattcatgc tccacctcaa ccacgtaatc ctttgcccac    2760
cggaaaaagt ctttgacttc ctgcttggtg accttcccaa agtcatgatc cagacggcgg    2820
gtgagttcaa atttgaacat ccggtcttgc aacggctgct ggtgttcgaa ggtcgttgag    2880
ttcccgtcga tcacggcgca catgttggtg ttggagatga cgatcgcggg agtcgggtct    2940
atctgggccg aggacttgca tttctggtcc acgcgcacct tgcttcctcc gagaatggct    3000
ttggccgact ccacgacctt ggcggtcatc ttcccctcct cccaccagat caccatcttg    3060
tcgacacagt cgttgaaggg aaagttctca ttggtccagt tgacgcagcc gtagaaaggg    3120
cgaattc                                                              3127

<210> SEQ ID NO 16
<211> LENGTH: 3106
<212> TYPE: DNA
<213> ORGANISM: Unknown
<220> FEATURE:
<223> OTHER INFORMATION: AAV serotype, clone 24-1

<400> SEQUENCE: 16
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac cccttcgttg ttgacagcaa attccacatt attagacttg cataatttg     180 aggtgtactg aatctctgga ttccagcgtt tgctgttttc tttctgcagt tcccactcga     240
tctccacgct gacctggccg gtgctgtact gcgtgataaa tgaggcaaac ttggcaggag     300
taaacacctc tggaggatta gcaggtaccg gggtgttttt gatgagaatt tgaggaggcg     360
ggtgtttgag tccaaatccg cccatcaggg gagacgggtg aaagttgccg tccgtgtgag     420
gaattttggc ccagatggga ccctgcaggc acacgtcccg gttctgccag accatgccgg     480
gcagagcccc ctggctgttg acagtctgtg tctgggtcc ggccgtagac gattgcaggt     540
tgctggagac cacaccgtat tcttctgtag ccacgggatt ggtggttttg atctcctcct     600
cgctggtcat tagcacgttt tccagcgttg tcttgttggc agccccgtt ttgccaaaaa      660 ccagcactcc gttgatggga agaactggt cctcgtcgtc cttgttggtg gccatggcta     720
cgcccgggtt ggttaatgaa tttctaccat tcagatggta tttagtggcc ccggtccagg     780
caaagttact gttgttgttg ctgtctatgt tttttgacag tctctgctgc cgataacagg     840
gtccgggcag ccagttcttt gattgctcgg ccatggtgtt gggcccagcc tgatggaact     900
gcagctccct tgtggacccc gtagtgctct gggtccgggc caggtagtac aggtactggt     960
cgatgagggg attcatcagc cggtctaggc tctggctgtg cacatagctg ctgtggaaag    1020
gcacttcctc aaaggtgtag ctgaattcaa agttattgcc cgttctcagc atctgagaag    1080
gaaagtactc caggcagtag aaggaggaac gtcccacaga ctgactgccg ttgtttagag    1140
tcagatatcc gtactgagga atcatgaaca cgtccgcagg gaacggaggg aggcagcccct    1200 ggtgcgcaga gccgaggacg tacggcagtt ggtactccga gtccgagaag acctgaatcg    1260
```

```
tgctggtaag gttattagcg atggtcgtaa cgccgtcgtt cgtcgtgacc tccttgacct    1320
ggatgttgaa caacttgaac cgcagctttc tgggccggaa tccccagttg ttgttgatga    1380
gtcgctgcca gtcacgtggt gagaagtggc agtggaatct gttgaagtca aatagcccc    1440
aggggggtgct gtagctgaag aagtggttgt cgttggtagc cccgctctga cttgatatct    1500
gcttgtagag gtggttgttg taggtgggca gggcccaggt gcgggtgctg gtggtgatga    1560
ctctgtcgcc cagccatgtg gaatcgcaat gccaatttcc ggaggcatta cccactccgt    1620
cggcgccttc gttattgtct gccattggtg cgccaccgcc tgcagccatt gtaccagatc    1680
ccagacctga gggcgcggcg ggaggttctc gagaggttg ggggtcgggc actgactctg    1740
agtcgccagt ctgcccaaag ttgagcttct ttttagcggg ctgctggcct tcttgccga    1800
tgcccgtgga ggagtcgggg gattctatgg gtctcttctt tccaggagcc gtcttagcga    1860
cttcctcaac cagaccgaga ggttcgagaa cccgcttctt ggcctggaag actgctcgcc    1920
cgaggttgcc cccaaaagac gtatcttctt gaagacgctc ctgaaactcg gcgtcggcgt    1980
ggttgtactt gaggtacggg ttgtccccct gctcgagctg cttgtcgtag gccttgtcgt    2040
gctcgagggc cgcggcgtct gcctcgttga ccggctctcc cttgtcgagt ccgttgaagg    2100
gtctgaggta cttgtagcca ggaagcacca gaccccggcc gtcgtcctgc ttttgctggt    2160
tggctttggg tttcggggct ccaggtttca gtcccacca ctcgcgaatg ccctcagaga    2220
ggttgtcctc gagccaatct ggaagataac catcggcagc cacctggt ttaagtcatt    2280
tattgctcag aaacacagtc atccaggtcc acgttgacca gatcgcaggc cgagcaagca    2340
atctcgggag cccgccccag cagatgatga atggcacaga gtttccgata cgtcctcttt    2400
ctgacgaccg gttgagattc tgacacgccg gggaaacatt ctgaacagtc tctggtcccg    2460
tgcgtgaagc aaatgttgaa attctgattc actctctcgc atgtcttgca gggaaacagc    2520
atctgaagca tgcccgcgtg acgagaacat ttgttttggt acctgtcggc aaagtccacc    2580
ggagctcctt ccgcgtctga cgtcgatgga ttcgcgactg aggggcaggc ccgcttgggc    2640
tcgctttat ccgcgtcatc gggggcgggt ctcttgttgg ccccacccctt tctgacgtag    2700
aacccatgcg ccacctcgt cacgtgatcc tgcgcccagc ggaagaacct tttgacttcc    2760
tgctttgtca ccttgccaaa gttatgctcc agacggcggg tgggttcaaa tttgaacatc    2820
cggtcctgca acggctgctg gtgctcgaag gtggcgctgt tcccgtcaat cacggcgcac    2880
atgttggtgt tggaggtgac ggtcacgggg gtggggtcga tctgggcgga cgacttgcac    2940
ttttggtcca cgcgcacctt gctgccgccg agaatggcct tggcggactc cacgaccttg    3000
gccgtcatct tgccctcctc ccaccagatc accatcttgt cggcgcaatc gttgaaggga    3060
aagttctcat tggtccagtt gacgcagccg tagaaagggc gaattc                  3106
```

<210> SEQ ID NO 17
<211> LENGTH: 3102
<212> TYPE: DNA
<213> ORGANISM: Unknown
<220> FEATURE:
<223> OTHER INFORMATION: AAV serotype, clone 27-3

<400> SEQUENCE: 17

```
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac ccccttcgttg ttgacagcaa attccacatt attagacttg cataatttg     180
aggtgtactg aatctctgga ttccagcgtt tgctgttttc tttctgcagt tcccactcga     240
```

-continued

```
tctccacgct gacctggccg gtgctgtact gcgtgataaa tgaggcaaac ttggcaggag    300
taaacacctc tggaggatta gcaggtaccg gggtgttttt gatgagaatt tgaggaggcg    360
ggtgtttgag tccaaatccg cccatcaggg gagacgggtg aaagttgccg tccgtgtgag    420
gaatttcggc ccagatggga ccctgcaggt acacgtcccg gttctgccag accatgccgg    480
gcagagcccc ctggctgttg acagtctgtg tccggggtcc ggccgtagac gattgcaggt    540
tgctggagac cacaccgtat tcttctgtag ccacgggatt ggtggttttg atctcctcct    600
cgctggtcat tagcacgttt tccagcgttg tcttgttggc agccccgtt ttgccaaaaa     660 ccagcactcc gttgatggga aggaactggt cctcgtcgtc cttgttggtg gccatggcta    720
cgcccgggtt ggttaatgaa tttctaccat tcagatggta tttagtggcc ccggtccagg    780
caaagttact gttgttgttg ctgtctatgt tttttgacag tctctgctgc cgataacagg    840
gtccgggcag ccagttcttt gattgctcgg ccacggtgtt gggcccagcc tgatggaact    900
gcagctccct tgtggacccc gtagtgctct gggtccgggc caggtagtac aggtactggt    960
cgatgagggg attcatcagc cggtccaggc tctggctgtg cgcatagctg ctgtggaaag   1020
gcacttcctc aaaggtgtag ctgaattcaa agttattgcc cgttctcagc atctgagaag   1080
gaaagtactc caggcagcag aaggaggaac gtcccacaga ctgactgccg ttgtttagag   1140
tcagatatcc gtactgagga atcatgaaca cgtccgcagg gaacggaggg aggcagccct   1200
ggtgcgcaga gccgaggacg tacggcagtt ggtactccga gtccgagaag acctgaatcg   1260
tgctggtaag gttattagcg atggtcgtaa cgccgtcgtt cgtcgtgacc tccttgacct   1320
ggatgttgaa caacttgaac cgcagctttc tgggccggaa tccccagttg ttgttgatga   1380
gtcgctgcca gtcacgtggt gagaagtggc agtggaatct gttgaagtca aaatagcccc   1440 aggggggtgct gtagccgaag aagtggttgt cgttggtagc cccgctctga cttgatatct   1500
gcttgtagag gtggttgttg taggtgggca gggcccaggt gcgggtgctg gtggtgatga   1560
ctctgtcgcc cagccatgtg gaatcgcaat gccaatttcc ggaggcatta cccactccgt   1620
cggcgccttc gttattgtct gccattggtg cgccaccgcc tgcagccatt gtaccagatc   1680
ccagacctga gggcgcggcg ggaggttctc cgagaggttg ggggtcgggc actgactctg   1740
agtcgccagt ctgcccaaag ttgagcttct ttttagcggg ctgctggcct ttcttgccga   1800
tgcccgtgga ggagtcgggg gattctatgg gtctcttctt tccggaagcc gtcttagcgc   1860
cttcctcaac cagaccgaga ggttcgagaa cccgcttctt ggcctggaag actgctcgcc   1920
cgaggttgcc cccaaaagac gtatcttctt gaagacgctc ctgaaactcg gcgtcggcgt   1980
ggttgtactt gaggtacggg ttgtcccccct gctcgagctg cttgtcgtag gccttgtcgt   2040
gctcgagggc cgcggcgtct gcctcgttga ccggctctcc cttgtcgagt ccgttgaagg   2100
gtccgaggta cttgtagcca ggaagcacca gaccccggcc gtcgtcctgc ttttgctggt   2160
tggctttggg tttcggggct ccaggtttca agtcccacca ctcgcgaatg ccctcagaga   2220
ggttgtcctc gagccaatct ggaagataac catcggcagc catacctggt ttaagtcatt   2280
tattgctcag aaacacagtc atccaggtcc acgttgacca gatcgcaggc cgagcaagca   2340
atctcgggag cccgccccag cagatgatga atggcacaga gtttccgata cgtcctcttt   2400
ctgacgaccg gttgagattc tgacacgccg gggaaacatt ctgaacagtc tctggtcccg   2460
tgcgtgaagc aaatgttgaa attctgattc attctctcgc atgtcttgca gggaaacagc   2520
atctgaagca tgcccgcgtg acgagaacat ttgttttggt acctgtcggc aaagtccacc   2580
```

```
ggagctcctt ccgcgtctga cgtcgatgga tccgcgactg aggggcaagc ccgcttgggc      2640
tcgcttttat ccgcgtcatc gggggcgggt ctcttgttgg ctccacccct tctgacgtag      2700
aactcatgcg ccacctcggt cacgtgatcc tgcgcccagc ggaagaactc tttgacttcc      2760
tgctttgtca ccttgccaaa gtcatgctcc agacggcggg tgagttcaaa tttgaacatc      2820
cggtcttgta acggctgctg gtgctcgaag gtggtgctgt tcccgtcaat cacggcgcac      2880
atgttggtgt tggaagtgac gatcacgggg gtgggatcga tctgggcgga cgacttgcac      2940
ttttggtcca cgcgcacctt gctgccgccg agaatggcct tggcggactc cacgaccttg      3000
gccgtcatct tgccctcctc ccaccagatc accatcttgt cgacgcaatc gttgaaggga      3060
aagttctcat tggtccagtt gacgcagccg aagggcgaat tc                         3102

<210> SEQ ID NO 18
<211> LENGTH: 3106
<212> TYPE: DNA
<213> ORGANISM: Unknown
<220> FEATURE:
<223> OTHER INFORMATION: AAV serotype, clone 7-2

<400> SEQUENCE: 18
gcggccgcga attcgccctt cgcagagacc aaagttcaac tgaaacgaat cagccggttt        60
attgattaac aagtaattac aggttacggg tgaggtaacg ggtgccaatg gggcgaggct       120
cagtataaac cccttcgttg ttgacagcaa attccacatt attagacttg cataatttg        180 aggtgtactg aatctctgga ttccagcgtt tgctgttttc tttctgcagt tcccactcga       240
tctccacgct gacctggccg gtgctgtact gcgtgataaa tgaggcaaac ttggcaggag       300
taaacacctc tggaggatta gcaggtaccg gggtgttttt gatgagaatt tgaggaggcg       360
ggtgtttgag tccaaatccg cccatcaggg gagacgggtg aaagttgccg tccgtgtgag       420
gaattttggc ccagatggga ccctgcaggt acacgtcccg gttctgccag accatgccgg       480
gcagagcccc ctggctgttg acagtctgtg tctggggtcc ggccgtagac gattgcaggt       540
tgctggagac cacaccgtat tcttctgtag ccacgggatt ggtggttttg atctcctcct       600
cgctggtcat tagcacgttt tccagcgttg tcttgttggc agccccgtt ttgccaaaaa        660 ccagcactcc gttgatggga agaactggt cctcgtcgtc cttgttggtg gccatggcta       720
cgcccgggtt ggttaatgaa tttctaccat tcagatggta tttagtgcc ccggtccagg        780 caaagttact gttgttgttg ctgtctatgt tttttgacag tctctgctgc cgataacagg       840
gtccgggcag ccagttcttt gattgctcgg ccatggtgtt gggcccagcc tgatggaact       900
gcagctccct tgtggacccc gtagtgctct gggtccgggc caggtagtac aggtactggt       960
cgatgagggg attcatcagc cggtccaggc tctggctgtg cgcatagctg ctgtggaaag      1020
gcacttcctc aaaggtgtag ctgaattcaa agttatcgcc cgttctcagc atctgagaag      1080
gaaagtactc caggcagtag aaggaggaac gtcccacaga ctgactgccg ttgtttagag      1140
tcagatatcc gtactgagga atcatgaaca cgtccgcagg gaacgagggg aggcagccct      1200
ggtgcgcaga gccgaggacg tacggcagtt ggtactccga gtccgagaag acctgaatcg      1260
tgctggtaag gttattagcg atggtcgtaa cgccgtcgtt cgtcgtgacc tccttgacct      1320
ggatgttgaa caacttgaac cgcagctttc tgggccggaa tccccagttg ttgttgatga      1380
gtcgctgcca gtcacgtggt gagaagtggc agtggaatct gttgaagtca aaatagcccc      1440 aggggggtgct gtagccgaag aagtggttgt cgttggtagc cccgctctga cttgatatct      1500
gcttgtagag gtggttgttg taggtgggca gggcccaggt gcgggtgctg gtggtgatga      1560
```

```
ctctgtcgcc cagccatgtg gaatcgcaat gccaatttcc ggaggcatta cccactccgt    1620
cggcgccttc gttattgtct gccattggtg cgccaccgcc tgcagccatt gtaccagatc    1680
ccagacctga gggcgcggcg ggaggttctc cgagaggttg ggggtcgggc actgactctg    1740
agtcgccagt ctgcccaaag ttgagcttct ttttagcggg cggctggccg ttcttgccga    1800
tgcccgtgga ggagtcgggg gattctatgg gtctcttctt tccaggagcc gtcttagcgc    1860
cttcctcaac cagaccgaga ggttcgagaa cccgcttctt ggcctggaag actgctcgcc    1920
cgaggttgcc cccaaaagac gtatcttctt gaagacgctc ctgaaactcg cgtcggcgt    1980 ggttgtactt gaggtacggg ttgtcccct gctcgagctg cttgtcgtag ccttgtcgt    2040 gctcgagggc cgcggcgtct gcctcgttga ccggctctcc cttgtcgagt ccgttgaagg    2100
gtccgaggta cctgtagcca ggaagcacca gaccccggcc gtcgtcctgc ttttgctggt    2160
tggctttggg tttcggggct ccaggtttca gtcccacca ctcgcgaatg ccctcagaga    2220
ggttgccctc gagccaatct ggaagataac catcggcagc catacctggt ttaagtcatt    2280
tattgctcag aaacacagtc atccaggtcc acgttggcca gatcgcaggc cgagcaagca    2340
atctcgggag cccgccccag cagatgatga atggcacaga gtttccgata cgtcctcttt    2400
ctgacgaccg gttgagattc tgacacgccg gggaaacatt ctgaacagtc tctggtcccg    2460
tgcgtgaagc aaatgttgaa attctgattc attctctcgc atgtcttgca ggggaacagc    2520
atctgaagca tgcccgcgtg acgagaacat tgttttggt acctgtcggc aaagtccacc    2580
ggagctcctt ccgcgtctga cgtcgatgga tccgcgactg aggggcaggc ccgcttgggc    2640
tcgcttttat ccgcgtcatc gggggcgggt ctcttgttgg ctccacctt tctgacgtag    2700 aactcatacg ccacctcggt cacgtgatcc tgcgcccagc ggaagaactc tttgacttcc    2760
tgctttgtca ccttgccaaa gtcatgctcc agacggcggg tgagttcaaa tttgaacatc    2820
cggtcttgta acggctgctg gtgctcgaag gtggtgctgt tcccgtcaat cacgcgcac    2880 atgttggtgt tggaagtgac gatcacgggg gtgggatcga tctgggcgga cgacttgcac    2940
ttttggtcca cgcgcacctt gctgccgcca agaatggcct tggcggactc cacgaccttg    3000
gccgtcatcc tgccctcctc ccaccagatc accatcttgt cgacgcaatc gttgaaggga    3060
aagttctcat tggtccagtt gacgcagccg tagaaagggc gaattc                 3106
```

<210> SEQ ID NO 19
<211> LENGTH: 3105
<212> TYPE: DNA
<213> ORGANISM: Unknown
<220> FEATURE:
<223> OTHER INFORMATION: AAV serotype, clone C1

<400> SEQUENCE: 19

```
gaattcgccc ttgctgcgtc aactggacca atgagaactt tcccttcaac gattgcgtcg      60
acaagatggt gatctggtgg gaggagggca agatgaccgc caaggtcgtg gagtccgcca     120
aggccattct gggcggaagc aaggtgcgcg tggaccaaaa gtgcaagtca tcggcccaga     180
tcgaccccac gcccgtgatc gtcacctcca acaccaacat gtgcgccgtg atcgacggga     240
acagcaccac cttcgagcac cagcagccgc tgcaggacca catgttcaag ttcgagctca     300
cccgccgtct ggagcacgac tttggcaagg tgaccaagca ggaagtcaaa gagttcttcc     360
gctgggctca ggatcacgtg actgaggtgg cgcatgagtt ctacgtcaga aagggcgga     420 ccaccaaaag acccgccccc agtgacgcgg atataagcga gcccaagcgg gcctgcccct     480
```

```
cagttgcgga gccatcgacg tcagacgcgg aagcaccggt ggactttgcg gacaggtacc    540
aaaacaaatg ttctcgtcac gcgggcatgc ttcagatgct gtttccctgc aagacatgcg    600
agagaatgaa tcagaattte aacgtctgct tcacgcacgg ggtcagagac tgctcagagt    660
gcttccccgg cgcgtcagaa tctcaacccg tcgtcagaaa aaagacgtat cagaaactgt    720
gcgcgattca tcatctgctg gggcgggcac ccgagattgc gtgttcggcc cgcgatctcg    780
tcaacgtgga cttggatgac tgtgtttctg agcaataaat gacttaaacc aggtatggct    840
gctgacggtt atcttccaga ttggctcgag gacaacctct ctgagggcat cgcgagtgg    900 tgggacctga aacctggagc ccccaagccc aaggccaacc agcagaagca ggacgacggc    960
cggggtctgg tgcttcctgg ctacaagtac ctcggaccct tcaacggact cgacaagggg   1020
gagcccgtca acgcggcgga cgcagcggcc ctcgagcacg acaaggccta cgaccagcag   1080
ctcaaagcgg gtgacaatcc gtacctgcgg tataaccacg ccgacgccga gtttcaggag   1140
cgtctgcaag aagatacgtc ttttgggggc aacctcgggc gagcagtctt ccaggccaag   1200
aagagggtac tcgaacctct gggcctggtt gaagaaggtg ctaagacggc tcctggaaag   1260
aagagaccgt tagagtcacc acaagagccc gactcctcct caggaatcgg caaaaaggc   1320 aaacaaccag ccaaaaagag actcaacttt gaagaggaca ctggagccgg agacggaccc   1380
cctgaaggat cagataccag cgccatgtct tcagacattg aaatgcgtgc agcaccgggc   1440
ggaaatgctg tcgatgcggg acaaggttcc gatggagtgg gtaatgcctc gggtgattgg   1500
cattgcgatt ccacctggtc tgagggcaag gtcacaacaa cctcgaccag aacctgggtc   1560
ttgcccacct acaacaacca cttgtacctg cggctcggaa caacatcaaa cagcaacacc   1620
tacaacggat tctccacccc ctggggatac tttgacttta acagattcca ctgtcacttc   1680
tcaccacgtg actggcaaag actcatcaac aacaactggg gactacgacc aaaagccatg   1740
cgcgttaaaa tcttcaatat ccaagttaag gaggtcacaa cgtcgaacgg cgagactacg   1800
gtcgctaata accttaccag cacgttcag atatttgcgg actcgtcgta tgagctcccg   1860
tacgtgatgg acgctggaca agagggaagt ctgtctcctt tccccaatga cgtcttcatg   1920
gtgcctcaat atggctactg tggcattgtg actggcgaaa atcagaacca gacgacagaa   1980
aatgctttct actgcctgga gtattttcct tcacaaatgc tgagaactgg caataacttt   2040
gaaatggctt acaactttgg gaaggtgccg ttccactcaa tgtatgctta cagccagagc   2100
ccggacagac tgatgaatcc cctcctggac cagtacctgt ggcacttaca gtcgaccacc   2160
tctggagaga ctctgaatca aggcaatgca gcaaccacat ttggaaaaat caggagtgga   2220
gactttgcct tttacagaaa gaactggctg cctgggcctt gtgttaaaca gcagagactc   2280
tcaaaaactg ccagtcaaaa ttacaagatt cctgccagcg ggggcaacgc tctgttaaag   2340
tatgacaccc actatacctt aaacaaccgc tggagcaaca tagcgcctgg acctccaatg   2400
gcaacagctg accttcaga tggggacttc agcaacgccc agctcatctt ccctggacca   2460
tcagtcaccg gaaacacaac aacctcagca acaatctgt tgtttacatc agaagaagaa   2520
attgctgcca ccaacccaag agacacggac atgtttggtc agattgctga caataatcag   2580
aatgctacaa ctgctcccat aaccggcaac gtgactgcta gggagtgct tcctggcatg   2640 gtgtggcaaa acagagacat ttactaccaa gggccaattt gggccaagat cccacacgcg   2700
gacggacatt tcatccttc accgctaatt ggcggttttg gactgaaaca tccgcctccc   2760
cagatattta tcaaaaacac ccccgtacct gccaatcctg cgacaacctt cactgcagcc   2820
agagtggact cttcatcac acaatacagc accggccagg tcgctgttca gattgaatgg   2880
```

```
gaaatcgaaa aggaacgctc caaacgctgg aatcctgaag tgcagtttac ttcaaactat   2940
gggaaccagt cttctatgtt gtgggctccc gatacaactg ggaagtatac agagccgcgg   3000
gttattggct ctcgttattt gactaatcat ttgtaactgc ctagttaatc aataaaccgt   3060
gtgattcgtt tcagttgaac tttggtctct gcgaagggcg aattc                  3105

<210> SEQ ID NO 20
<211> LENGTH: 3105
<212> TYPE: DNA
<213> ORGANISM: Unknown
<220> FEATURE:
<223> OTHER INFORMATION: AAV serotype, clone C3

<400> SEQUENCE: 20
gaattcgccc ttgctgcgtc aactggacca atgagaactt tcccttcaac gattgcgtcg     60
acaagatggt gatctggtgg gaggagggca agatgaccgc caaggtcgtg gagtccgcca    120
aggccattct gggcggaagc aaggtgcgcg tggaccaaaa gtgcaagtca tcggcccaga    180
tcgaccccac gcccgtgatc gtcacctcca acaccaacat gtgcgccgtg atcgacggga    240
acagcaccac cttcgagcac cagcagccgc tgcaggaccg catgttcaag ttcgagctca    300
cccgccgtct ggagcacgac tttggcaagg tgaccaagca ggaagtcaaa gagttcttcc    360
gctgggctca ggatcacgtg actgaggtgg cgcatgagtt ctacgtcaga aagggcggag    420
ccaccaaaag acccgccccc agtgacgcgg atataagcga gcccaagcgg gcctgcccct    480
cagttgcgga gccatcgacg tcagacgcgg aagcaccggt ggactttgcg gacaggtacc    540
aaaacaaatg ttctcgtcac gcgggcatgc ttcagatgct gtttccctgc aagacatgcg    600
agagaatgaa tcagaatttc aacgtctgct tcacgcacgg ggtcagagac tgctcagagt    660
gcttccccgg cgcgtcagaa tctcaacccg tcgtcagaaa aaagacgtat cagaaactgt    720
gcgcgattca tcatctgctg gggcgggcac ccgagattgc gtgttcggcc tgcgatctcg    780
tcaacgtgga cttggatgac tgtgtttctg agcaataaat gacttaaacc aggtatggct    840
gctgacggtt atcttccaga ttggctcgag gacaacctct ctgagggcat tcgcgagtgg    900
tgggacctga aacctggagc ccccaagctc aaggccaacc agcagaagca ggacgacggc    960
cggggtctgg tgcttcctgg ctacaagtac ctcggaccct tccacggact cgacaagggg   1020
gagcccgtca acgcggcgga cgcagcggcc ctcgagcacg acaaggccta cgaccagcag   1080
ctcaaagcgg gtgacaatcc gtacctgcgg tataaccacg ccgacgccga gtttcaggag   1140
cgtctgcaaa aagatacgtc ttttgggggc aacctcgggc gagcagtctt ccaggccaag   1200
aagagggtac tcgaaccact gggcctggtt gaagaaggtg ctaagacggc tcctggaaag   1260
aagagaccgt tagagtcacc acaagagccc gactcctcct caggaatcgg caaaaaaggc   1320
aaacaaccag ccaaaaagag actcaacttt gaagaggaca ctggagccgg agacggaccc   1380
cctgaaggat cagataccag cgccatgtct tcagacattg aaatgcgtgc agcaccgggc   1440
ggaaatgctg tcgatgcggg acaaggttcc gatggagtgg gtaatgcctc gggtgattgg   1500
cattgcgatt ccacctggtc tgagggcaag gtcacaacaa cctcgaccag aacctgggtc   1560
ttgcccacct acaacaacca cttgtacctg cggctcggaa acatcaaa cagcaacacc   1620 tacaacggat tctccacccc ctggggatac tttgacttta acagattcca ctgtcacttc   1680
tcaccacgtg actggcaaag actcatcaac aacaactggg gactacgacc aaaagccatg   1740
cgcgttaaaa tcttcaatat ccaagttaag gaggtcacaa cgtcgaacgg cgagactacg   1800
```

-continued

```
gtcgctaata accttaccag cacggttcag atatttgcgg actcgtcgta tgagctcccg    1860
tacgtgatgg acgctggaca agagggaagt ctgcctcctt tccccaatga cgtcttcatg    1920
gtgcctcaat atggctactg tggcattgtg actggcgaaa atcagaacca gacggacaga    1980
aatgctttct actgcctgga gtattttcct tcacaaatgc tgagaactgg caataacttt    2040
gaaatggctt acaactttga aaggtgccg ttccactcaa tgtatgctca cagccagagc    2100
ctggacagac tgatgaatcc cctcctggac cagtacctgt ggcacttaca gtcgaccacc    2160
tctggagaga ctctgaatca aggcaatgca gcaaccacat ttggaaaaat caggagtgga    2220
gactttgcct tttacagaaa gaactggctg cctgggcctt gtgttaaaca gcagagattc    2280
tcaaaaactg ccagtcaaaa ttacaagatt cctgccagcg ggggcaacgc tctgttaaag    2340
tatgacaccc actatacctt aaacaaccgc tggagcaaca tagcgcctgg acctccaatg    2400
gcaacagctg gaccttcaga tgggacttc agcaacgccc agctcatctt ccctggacca    2460
tcagtcaccg aaacacaac aacctcagca acaatctgt tgtttacatc agaaggagaa    2520
attgctgcca ccaacccaag agacacggac atgtttggtc agattgctga caataatcag    2580
aatgctacaa ctgctcccat aaccggcaac gtgactgcta tgggagtgct tcctggcatg    2640
gtgtggcaaa acagagacat ttactaccaa gggccaattt gggccaagat cccacacgcg    2700
gacggacatt ttcatccttc accgctaatt ggcggttttg gactgaaaca tccgcctccc    2760
cagatattta tcaaaaacac ccccgtacct gccaatcctg cgacaacctt cactgcagcc    2820
agagtggact ctttcatcac acaatacagc accggccagg tcgctgttca gattgaatgg    2880
gaaatcgaaa aggaacgctc caaacgccgg aatcctgaag tgcagtttac ttcaaactat    2940
gggaaccagt cttctatgtt gtgggctccc gatacaactg gaagtatac agagccgcgg    3000 gttattggct ctcgttattt gactaatcat ttgtaactgc ctagttaatc aataaaccgt    3060
gtgattcgtt tcagttgaac tttggtctct gcgaagggcg aattc              3105
```

<210> SEQ ID NO 21
<211> LENGTH: 3105
<212> TYPE: DNA
<213> ORGANISM: Unknown
<220> FEATURE:
<223> OTHER INFORMATION: AAV serotype, clone C5

<400> SEQUENCE: 21

```
gaattcgccc ttcgcagaga ccaaagttca actgaaacga atcacacggt ttattgatta     60
actaggcagt acaaaatgat tagtcaaata acgagagcca ataacccgcg gctctgtata    120
cttcccagtt gtatcgggag cccacaacat agaagactgg ttcccacagt tgaagtaaa    180 ctgcacttca ggattccagc gtttggagcg ttccttttcg atttcccatt caatctgaac    240
agcgacctgg ccggtgctgt attgtgtgat gaaagagtcc actctggctg cagtgaaggt    300
tgtcgcagga taggcaggta cggggggtgtt tttgataaat atctggggag gcggatgttt    360
cagtccaaaa ccgccaatta gcggtgaagg atgaaaatgt ccgtccgcgt gtgggatctt    420
ggcccaaatt ggcccttggt agtaaatgtc tctgttttgc cacaccatgc caggaagcac    480
tcccatagca gtcacgttgc cggttatggg agcagttgta gcattctgat tatttgtcagc    540 aatctgacca acatgtccg tgtctcttgg gttggtggca gcaatttctt cttctgatgt    600
aaacaacaga ttgttttgctg aggttgttgt gtttccggtg actgatggtc cagggaagat    660
gagctgggcg ttgctgaagt ccccatctga aggtccagct gttgccattg gaggtccagg    720
cgctatgttg ctccagcggt tgtttaaggt atagtgggtg tcatacttta acagagcgtt    780
```

```
gcccccgctg gcaggaatct tgtaattttg actggcagtt tttgagaatc tctgctgttt     840
aacacaaggc ccaggcagcc agttctttct gtaaaaggca aagtctccac tcctgatttt     900
tccaaatgtg gttgctgcat tgccttgatt cagagtctct ccagaggtgg tcgactgtaa     960
gtgccacagg tactggtcca ggaggggatt catcagtccg tccaggctct ggctgtgagc    1020
atacattgag tggaacggca ccttctcaaa gttgtaagcc gtttcaaagt tattgccagt    1080
tctcagcatt tgtgaaggaa aatactccag gcagtagaaa gcatttctgt ccgtctggtt    1140
ctgattttcg ccagtcacaa tgccacagta gccatattga ggcaccatga agacgtcatt    1200
ggggaaagga ggcagacttc cctcttgtcc agcgtccatc acgtacggga gctcatacga    1260
cgagtccgca aatatctgaa ccgtgctggt aaggttatta gcgaccgtag tctcgccgtt    1320
cgacgttgtg acctccttaa cttggatatt gaagatttta acgcgcatgg cttttggtcg    1380
tagtccccag ttgttgttga tgagtctttg ccagtcacgt ggtgagaagt gacagtggaa    1440
tctgttaaag tcaaagtatc cccagggggt ggagaatccg ttgtaggtgt tgctgtttga    1500
tgttgttccg agccgcaggt acaagtggtt gttgtaggtg ggcaagaccc aggttctggt    1560
cgaggttgtt gtgaccttgc cctcagacca ggtggaatcg caatgccaat cacccgaggc    1620
attacccact ccatcggaac cttgtcccgc atcgacagca tttccgcccg gtgctgcacg    1680
catttcaatg tctgaagaca tggcgctggt atctgatcct tcaggggtc cgtctccggc    1740 tccagtgtcc tcttcaaagt tgagtctctt tttggctggt tgtttgcctt ttttgccgat    1800
tcctgaggag gagtcgggct cttgtggtga ctctaacggt ctcttctttc caggagccgt    1860
cttagcacct tcttcaacca ggcccagagg ttcgagtacc ctcttcttgg cctggaagac    1920
tgctcgcccg aggttgcccc caaaagacgt atcttcttgc agacgctcct gaaactcggc    1980
gtcggcgtgg ttataccgca ggtacggatt gtcacccgct ttgagctgct ggtcgtaggc    2040
cttgtcgtgc tcgagggccg ctgcgtccgc cgcgttgacg ggctcccct tgtcgagtcc    2100 gttgaagggt ccgaggtact cgtagccagg aagcaccaga ccccggccgt cgtcctgctt    2160
ctgctggttg gccttgggct tggggctcc aggtttcagg tcccaccact cgcgaatgcc    2220
ctcagagagg ttgtcctcga gccaatctgg aagataaccg tcagcagcca tacctggttt    2280
aagtcattta ttgctcagaa acacagtcat ccaagtccac gttgacgaga tcgcaggccg    2340
aacacgcaat ctcgggtgcc cgccccagca gatgatgaat cgcgcacagt ttctgatacg    2400 tctttttct gacgacgggt tgagattctg acgcgccggg aagcactct gagcagtctc    2460 tgaccccgtg cgtgaagcag acgttgaaat tctgattcat tctctcgcat gtcttgcagg    2520
gaaacagcat ctgaagcatg cccgcgtgac gagaacattt gttttggtac ctgtccgcaa    2580
ggtccaccgg tgcttccgcg tctgacgtcg atggctccgc aactgagggg caggcccgct    2640
tgggctcgct tatatccgcg tcactgggg cgggtctttt ggtggctccg ccctttctga    2700
cgtagaactc atgcgccacc tcagtcacgt gatcctgagc ccagcggaag aactctttga    2760
cttcctgctt ggtcaccttg ccaaagtcgt gctccagacg gcgggtgagc tcgaacttga    2820
acatgcggtc ctgcagcggc tgctggtgct cgaaggtggt gctgttccg tcgatcacgg    2880 cgcacatgtt ggtgttggag gtgacgatca cgggcgtggg gtcgatctgg gccgatgact    2940
tgcacttttg gtccacgcgc accttgcttc cgcccagaat ggccttggcg gactccacga    3000
ccttggcggt catcttgccc tcctcccacc agatcaccat cttgtcgacg caatcgttga    3060
agggaaagtt ctcattggtc cagttgacgc agcaagggcg aattc                    3105
```

<210> SEQ ID NO 22
<211> LENGTH: 3094
<212> TYPE: DNA
<213> ORGANISM: Unknown
<220> FEATURE:
<223> OTHER INFORMATION: AAV serotype, clone F1

<400> SEQUENCE: 22

| | | | | | |
|---|---|---|---|---|---|
| gaattcgccc | ttgctgcgtc | aactggacca | agagaacttt | cccttcaacg | attgcgtcga | 60 |
| caagatggtg | atctggtggg | aggagggcaa | gatgacggcc | aaggtcgtgg | agtccgccaa | 120 |
| agccattctg | ggcggaagca | aggtgcgcgt | cgaccaaaag | tgcaagtcct | cggcccagat | 180 |
| cgatcccacc | cccgtgatcg | tcacctccaa | caccaacatg | tgcgccgtga | tcgacgggaa | 240 |
| cagcaccacc | ttcgagcacc | agcagccgtt | gcaggaccgg | atgttcaaat | ttgaactcac | 300 |
| ccgccgtctg | gaacacgact | tggcaaggt | gaccaagcag | gaagtcaaag | agttcttccg | 360 |
| ctgggctagt | gatcacgtga | ctgaggtgac | gcatgagttc | tacgtcagaa | agggcggagc | 420 |
| cagcaaaaga | cccgcccccg | atgacgcgga | tataagcgag | cccaagcggg | cctgtccctc | 480 |
| agtcacggac | ccatcgacgt | cagacgcgga | aggagctccg | gtggactttg | ccgacaggta | 540 |
| ccaaaacaaa | tgttctcgtc | acgcgggcat | gcttcagatg | ctgtttcct | gcaaaacgtg | 600 |
| cgagagaatg | aatcagaatt | tcaacatttg | cttcacgcac | ggggtcagag | actgtttaga | 660 |
| atgtttcccc | ggcgtgtcag | aatctcaacc | ggtcgtcaga | aaaagacgt | atcggaagct | 720 |
| gtgtgcgatt | catcatctgc | tggggcgggc | acccgagatt | gcttgctcgg | cctgcgacct | 780 |
| ggtcaacgtg | gacctggacg | actgtgtttc | tgagcaataa | atgacttaaa | ccgggtatgg | 840 |
| ctgccgatgg | ttatcttcca | gattggctcg | aggacaacct | ctctgagggc | attcgcgagt | 900 |
| ggtgggacct | gaaacctgga | gccccgaaac | ccaaagccaa | ccagcaaaag | caggacgacg | 960 |
| gccggggtct | ggtgcttcct | ggctacaagt | acctcggacc | cttcaacgga | ctcgacaagg | 1020 |
| gggagcccgt | caacgcggcg | gacgcagcgg | ccctcgagca | cgacaaggcc | tacgaccagc | 1080 |
| agctcaaagc | gggtgacaat | ccgtacctgc | ggtataacca | cgccgacgcc | gagtttcagg | 1140 |
| agcgtctgca | agaagatacg | tcatttgggg | gcaacctcgg | gcgagcagtc | ttccaggcca | 1200 |
| agaagcgggt | tctcgaacct | ctcggtctgg | ttgaggaagg | cgctaagacg | gctcctggaa | 1260 |
| agaagagacc | catagactct | ccagactcct | ccacgggcat | cggcaaaaaa | ggccagcagc | 1320 |
| ccgctaaaaa | gaagctcaat | tttggtcaga | ctggcgactc | agagtcagtc | cccgaccctc | 1380 |
| aacctcttgg | agaacctcca | gcagcgccct | ctagtgtggg | atctggtaca | atggctgcag | 1440 |
| gcggtggcgc | accaatggca | gacaataacg | aaggtgccga | cggagtgggt | aatgcctcag | 1500 |
| gaaattggca | ttgcgattcc | acatggctgg | gcgacagagt | catcaccacc | agcaccagaa | 1560 |
| cctgggccct | ccccacctac | aacaaccacc | tctacaagca | aatctccagc | agcagctcag | 1620 |
| gagccaccaa | tgacaaccac | tacttcggct | acagcacccc | ctgggggtat | tttgactta | 1680 |
| acagattcca | ctgccacttc | tcaccacgtg | actggcagcg | actcatcaac | aacaactggg | 1740 |
| gattccggcc | caagaagctg | cggttcaagc | tcttcaacat | ccaggtcaag | gaggtcacaa | 1800 |
| cgaatgacgg | cgtcacgacc | atcgctaata | accttaccag | cacggttcag | gtcttctcgg | 1860 |
| actcggaata | ccagctgccg | tacgtcctcg | gctctgcgca | ccagggctgc | ctgcctccgt | 1920 |
| tcccggcgga | cgtcttcatg | attcctcagt | acggctacct | gactctgaac | aacggcagcc | 1980 |
| aatcggtggg | ccgttcctcc | ttctactgcc | tggaatattt | cccctctcaa | atgctgagaa | 2040 |
| cgggcaacaa | ctttgagttc | agttacagct | tcgaggacgt | gcctttccac | agcagctacg | 2100 |

```
cgcacagcca gagcctagac cggctgatga accctctcat cgaccagtac ctgtactacc    2160
tggcccggac ccagagcacc acgggttcca ccagggaact gcaatttcat caagctgggc    2220
ccaatactat ggccgagcag tcaaagaact ggctgcctgg accctgctat aggcaacagg    2280
gactgtcaaa gaacttggac tttaacaaca acagcaattt tgcctggact gctgccacta    2340
aatatcatct gaatggcaga aactctttga ccaatcctgg cattcccatg caaccaaca     2400 aggatgatga ggaccagttc tttcccatca acggggtact ggttttggc aagacgggag     2460 ctgccaacaa aactacgctg gaaaacgttc tgatgaccag cgaggaggag atcaagacca    2520
ctaaccctgt ggctacagaa gaatacggtg tggtctccag caacctgcag ccgtctacag    2580
ccgggcctca atcacagact atcaacagcc agggagcact gcctggcatg gtctggcaga    2640
accgggacgt gtatctgcag ggtcccatct gggccaaaat tcctcacacg gatggcaact    2700
ttcacccgtc tcctctgatg ggcggttttg gactcaaaca cccgcctcca cagatcctga    2760
tcaaaaacac acctgtacct gctaatcctc cggaggtgtt tactcctgcc aagtttgcct    2820
ccttcatcac gcagtacagc accggacaag tcagcgtgga aatcgagtgg gagctgcaga    2880
aagaaaacag caagcgctgg aacccagaaa ttcagtatac ttccaattat gccaagtcta    2940
ataatgttga atttgctgtg aaccctgatg tgtttatac tgagcctcgc cccattggca    3000
ctcgttacct cccccgtaat ctgtaattgc ttgttaatca ataaaccggt tgattcgttt    3060
cagttgaact ttggtctctg cgaagggcga attc                                3094
```

<210> SEQ ID NO 23
<211> LENGTH: 3095
<212> TYPE: DNA
<213> ORGANISM: Unknown
<220> FEATURE:
<223> OTHER INFORMATION: AAV serotype, clone F3

<400> SEQUENCE: 23

```
gaattcgccc ttcgcagaga ccaaagttca actgaaacga atcaaccggt ttattgatta     60
acaagcaatt acagattacg ggtgaggtaa cgagtgccaa tggggcgagg ctcagtataa    120
acaccatcag ggttcacagc aaattcaaca ttattagact tggcataatt ggaagtatac    180
tgaatttctg ggttccagcg cttgctgttt tctttctgca gctcccactc gatttccacg    240
ctgacttgtc cggtgctgta ctgcgtgatg aaggaggcaa acttggcagg agtaaacacc    300
tccggaggat tagcaggtac aggtgtgttt ttgatcagga tctgtggagg cgggtgtttg    360
agtccaaaac cgcccatcag aggagacggg tgaaagttgc catccgtgtg aggaattttg    420
gcccagatgg gaccctgcag atacacgtcc cggttctgcc agaccatgcc aggcagtgct    480
ccctggctgt tgatagtctg tgattgaggc ccggctgtag acgactgcag gttgctggag    540
accacaccgt attcttctgt agccacaggg ttagtggtct tgatctcctc ctcgctggtc    600
atcagaacgt tttccagcgt agttttgttg gcagctcccg tcttgccaaa accagtacc    660 ccgttgatgg gaaagaactg gtcctcatca tccttgttgg ttgccatggg aatgccagga    720
ttggtcaaag agtttctgcc attcagatga tatttagtgg cagcagtcca ggcaaaattg    780
ctgttgttgt taaagtccaa gttctttgac agtctctgtt gcctatagca gggtccaggc    840
agccagttct tgactgctc ggccatagta ttgggcccag cttgatgaaa ttgcagttcc    900
ctggtggaac ccgtggtgct ctgggtccgg ccaggtagt acaggtactg gtcgatgaga    960
gggttcatca gccggtctag gctctggctg tgcgcgtagc tgctgtggaa aggcacgtcc   1020
```

```
tcgaagctgt aactgaactc aaagttgttg cccgttctca gcatttgaga ggggaaatat    1080
tccaggcagt agaaggagga acggcccacc gattggctgc cgttgtccag agtcaggtag    1140
ccgtactgag gaatcatgaa gacgtccgcc gggaacggag gcaggcagcc ctggtgcgca    1200
gagccgagga cgtacggcag ctggtattcc gagtccgaga agacctgaac cgtgctggta    1260
aggttattag cgatggtcgt gacgccgtca ttcgttgtga cctccttgac ctggatgttg    1320
aggagcttga accgcagctt cttgggccgg aatccccagt tgttgttgat gagtcgctgc    1380
cagtcacgtg gtgagaagtg gcagtggaat ctgttaaagt caaaataccc ccagggggtg    1440
ctgtagccga agtagtggtt gtcattggtg gctcctgagc tgctgctgga gatttgcttg    1500
tagaggtggt tgttgtaggt ggggagggcc caggttctgg tgctggtggt gatgactctg    1560
tcgcccagcc atgtgaatc gcaatgccaa tttcctgagg cattacccac tccgtcggca    1620
ccttcgttat tgtctgccat tggtgcgcca ccgcctgcag ccattgtacc agatcccaca    1680
ctagagggcg ctgctggagg ttctccaaga ggttgagggt cggggactga ctctgagtcg    1740
ccagtctgac caaaattgag cttcttttta gcgggctgct ggccttttt gccgatgccc     1800 gtggaggagt ctggagagcc tatgggtctc ttctttccag gagccgtctt agcgccttcc    1860
tcaaccagac cgagaggttc gagaacccgc ttcttggcct ggaagactgc tcgcccgagg    1920
ttgcccccaa atgacgtatc ttcttgcaga cgctcctgaa actcggcgtc ggcgtggtta    1980
taccgcaggt acgattgtc acccgctttg agctgctggt cgtaggcctt gtcgtgctcg    2040
agggccgctg cgtccgccgc gttgacgggc tccccttgt cgagtccgtt gaagggtccg     2100
aggtacttgt agccaggaag caccagaccc ggccgtcgt cctgcttttg ctggttggct     2160
ttgggtttcg gggctccagg tttcaggtcc caccactcgc gaatgccctc agagaggttg    2220
tcctcgagcc aatctggaag ataaccatcg gcagccatac ctggtttaag tcatttattg    2280
ctcagaaaca cagtcgtcca ggtccacgtt gaccaggtcg caggccgagc aagcaatctc    2340
gggtgcccgc cccagcagat gatgaatcgc acacagcttc cgatacgtct tttttctgac    2400
gaccggttga gattctgaca cgccggggaa acattctaaa cagtctctga ccccgtgcgt    2460
gaagcaaatg ttgaaattct gattcattct ctcgcacgtt ttgcagggaa acagcacctg    2520
aagcatgccc gcgtgacgag aacatttgtt ttggtacctg tcggcaaagt ccaccggagc    2580
tccttccgcg tctgacgtcg atgggtccgt gactgaggga cgggcccgct gggctcgct    2640 tatatccgcg tcatcggggg cgggtctttt gctggctccg ccctttctga cgtagaactc    2700
atgcgtcacc tcagtcacgt gatcactagc ccagcggaag aactctttga cttcctgctt    2760
tgtcaccttg ccaaagtcgt gttccagacg gcgggtgagt tcaaatttga acatccggtc    2820
ctgcaacggt tgctggtgct cgaaggtggt gctgttcccg tcgatcacgg cgcacatgtt    2880
ggtgttggag gtgacgatca cggggtggg atcgatctgg gcggacgact tgcacttttg    2940
gtccacgcgc accttgctgc cgccgagaat ggccttggcg gactccacga ccttggccgt    3000
catcttgccc tcctcccacc agatcaccat cttgtcgacg caatcgttga agggaaagtt    3060
ctcattggtc cagttgacgc agcaagggcg aattc                              3095
```

<210> SEQ ID NO 24
<211> LENGTH: 3095
<212> TYPE: DNA
<213> ORGANISM: Unknown
<220> FEATURE:
<223> OTHER INFORMATION: AAV serotype, clone F5

<400> SEQUENCE: 24

```
gaattcgccc ttcgcagaga ccaaagttca actgaaacga atcaaccggt ttattgatta    60
acaagcaatt acagattacg ggtgaggtaa cgagtgccaa tggggcgagg ctcagtataa   120
acaccatcag ggttcacagc aaattcaaca ttattagact tggcataatt ggaagtatac   180
tgaatttctg ggttccagcg cttgctgttt tctttctgca gctcccactc gatttccacg   240
ctgacttgtc cggtgctgta ctgcgtgatg aaggaggcaa acttggcagg agtaaacacc   300
tccggaggat tagcaggtac aggtgtgttt ttgatcagga tctgtggagg cgggtgttcg   360
agtccaaaac cgcccatcag aggagacggg tgaaagttgc catccgtgtg aggaattttg   420
gcccagatgg gaccctgcag atacacgtcc cggttctgcc agaccatgcc aggcagtgct   480
ccctggctgt tgatagtctg tgattgaggc ccggctgtag acgactgcag gttgctggag   540
accacaccgt attcttctgt agccacaggg ttagtggtct tgatctcctc ctcgctggtc   600
atcagaacgt tttccagcgt agttttgttg gcagctcccg tcttgccaaa aaccagtacc   660
ccgttgatgg gaaagaactg gtcctcatca tccttgttgg ttgccatggg aatgccagga   720
ttggtcaaag agtttctgcc attcagatga tatttagtgg cagcagtcca ggcaaaattg   780
ctgttgttgt taaagtccaa gttctttgac agtctctgtt gcctatagca gggtccaggc   840
agccagttct ttgactgctc ggccatagta ttgggcccag cttgatgaaa ttgcagttcc   900
ctggtggaac ccgtggtgct ctgggtccgg gccaggtagt acaggtactg gtcgatgaga   960
gggttcatca gccggtctag gctctggctg tgcgcgtagc tgctgtggaa aggcacgtcc  1020
tcgaagctgt aactgaactc aaagttgttg cccgttctca gcatttgaga ggggaaatat  1080
tccaggcagt agaaggagga acggcccacc gattggctgc cgttgttcag agtcaggtag  1140
ccgtactgag gaatcatgaa gacgtccgcc gggaacggag gcaggcagcc ctggtgcgca  1200
gagccgagga cgtacggcag ctggtattcc gagtccgaga agacctgaac cgtgctggta  1260
aggttattag cgatggtcgt gacgccgtca ttcgttgtga cctccttgac ctggatgttg  1320
aagagcttga accgcagctt cttgggccgg aatccccagt tgttgttgat gagtcgctgc  1380
cagtcacgtg gtgagaagtg gcagtggaat ctgttaaagt caaaataccc ccagggggtg  1440
ctgtagccga agtagtggtt gtcattggtg gctcctgagc tgctgctgga gatttgcttg  1500
tagaggtggt tgttgtaggt ggggagggcc caggttctgg tgctggtggt gatgactctg  1560
tcgcccagcc atgtggaatc gcaatgccaa tttcctgagg cattacccac tccgtcggca  1620
ccttcgttat tgtctgccgt tggtgcgcca ccgcctgcag ccattgtacc agatcccaca  1680
ctagagggcg ctgctggagg ttctccaaga ggttgagggt cggggactga ctctgagtcg  1740
ccagtctgac caaaattgag cttctttta gcgggctgct ggccttttttt gccgatgccc  1800
gtggaggagt ctggagagtc tatgggtctc ttctttccag gagccgtctt agcgccttcc  1860
tcaaccagac cgagaggttc gagaacccgc ttcttggcct ggaagactgc tcgcccgagg  1920
ttgcccccaa atgacgtatc ttcttgcagg cgctcctgaa actcggcgtc ggcgtggtta  1980
taccgcaggt acgattgtc accccgctttg agctgctggt cgtaggcctt gtcgtgctcg  2040
agggccgctg cgtccgccgc gttgacgggc tcccccttgt cgagtccgtt gaagggtccg  2100
aggtacttgt agccaggaag caccagaccc cggccgtcgt cctgcttttg ctggttggct  2160
ttgggtttcg gggctccagg tttcaggtcc caccactcgc gaatgccctc agagaggttg  2220
tcctcgagcc aatctggaag ataaccatcg gcagccatac ctggtttaag ccatttattg  2280
ctcagaaaca cagtcgtcca ggtccacgtt gaccaggtcg caggccgagc aggcaatctc  2340
```

| | |
|---|---|
| gggtgcccgc cccagcagat gatgaatcgc acacagcttc cgatacgtct tttttctgac | 2400 |
| gaccggttga gattctgaca cgccggggaa acattctaaa cagtctctga ccccgtgcgt | 2460 |
| gaagcaaatg ttgaaattct gattcattct ctcgcacgtt ttgcagggaa acagcatctg | 2520 |
| aagcatgccc gcgtggcgag aacatttgtt ttggtacctg tcggcaaagt ccaccggagc | 2580 |
| tccttccgcg tctgacgtcg atgggtccgt gactgaggga caggcccgct tgggctcgct | 2640 |
| tatatccgcg tcatcggggg cgggtctttt gctggctccg ccctttctga cgtagaactc | 2700 |
| atgcgtcacc tcagtcacgt gatcactagc ccagcggaag aactctttga cttcctgctt | 2760 |
| tgtcaccttg ccaaagtcgt gttccagacg gcgggtgagt tcaaatttga acatccggtc | 2820 |
| ctgcaacggc tgctggtgct cgaaggtggt gctgttcccg tcgatcacgg cgcgcatgtt | 2880 |
| ggtgttggag gtgacgatca cggggtgggg atcgatctgg gcggacgact tgcactttg | 2940 |
| gtccacgcgc accttgctgc cgccgagaat ggccttggcg gactccacga ccttggccgt | 3000 |
| catcttgccc tcctcccacc agatcaccat cttgtcgacg caatcgttga agggaaagtt | 3060 |
| ctcattggtc cagttgacgc agcaagggcg aattc | 3095 |

<210> SEQ ID NO 25
<211> LENGTH: 3142
<212> TYPE: DNA
<213> ORGANISM: Unknown
<220> FEATURE:
<223> OTHER INFORMATION: AAV serotype, clone H6

<400> SEQUENCE: 25

| | |
|---|---|
| aaaacgacgg gccagtgatt gtaatacgac tcactatagg gcgaaattga aattagcggc | 60 |
| cgcgaattcg cctttcgcag agaccaaagt tcaactgaaa cgaattaaac ggtttattga | 120 |
| ttaacaagca attacagatt acgagtcagg tatctggtgc caatgggcg aggctctgaa | 180 |
| tacacaccat tagtgtccac agtaaagtcc acattaacag acttgttgta gttggaagtg | 240 |
| tactgaattt cgggattcca gcgtttgctg ttctccttct gcagctccca ctcgatctcc | 300 |
| acgctgacct gtcccgtgga atactgtgtg atgaaagaag caaacttggc agaactgaag | 360 |
| tttgtgggag gattggctgg aacgggagtg ttttttgatca tgatctgagg aggcgggtgt | 420 |
| ttgagtccaa aacctcccat cagtggagaa ggatgaaagt gtccatcggt gtgaggaatc | 480 |
| ttggcccaaa tgggtccctg caggtacacg tctcgatcct gccacaccat accaggtaac | 540 |
| gctccttggt gattgacagt tccagtagtt ggaccagtgt ttgagttttg caaattattt | 600 |
| gacacagtcc cgtactgctc cgtagccacg ggattggtgg ccctgatttc ttcttcatct | 660 |
| gtaatcatga cattttccaa atccgcgtcg ttggcatttg ttccttgttt accaaatatc | 720 |
| agggttccat gcatggggaa aaacttttct tcgtcatcct tgtgactggc catagctggt | 780 |
| cctggattaa ccaacgagtc ccggccattt agatgatact ttgtagctgc agtccaggga | 840 |
| aagttgctgt tgttgttgtc gtttgcctgt tttgacagac gctgctgtct gtagcaaggt | 900 |
| ccaggcagcc agttttttagc ttgaagagac atgttggttg gtccagcttg ctaaacagt | 960 |
| agccgagact gctgaagagt tccactattt gtttgtgtct tgttcagata atacaggtac | 1020 |
| tggtcgatca gaggattcat cagccgatcc agactctggc tgtgagcgta gctgctgtgg | 1080 |
| aaaggcacgt cttcaaaagt gtagctgaac tgaaagttgt ttccagtacg cagcatctga | 1140 |
| gaaggaaagt actccaggca gtaaaaggaa gagcgtccta ccgcctgact cccgttgttc | 1200 |
| agggtgaggt atccatactg tgggaccatg aagacgtccg ctggaaacgg cgggaggcat | 1260 |
| ccttgatgcg ccgagcccag gacgtacggg agctggtact ccgagtcagt aaacacctga | 1320 |

```
accgtgctgg taaggttatt ggcaatcgtc gtcgtaccgt cattctgcgt gacctctttg    1380
acttgaatat taaagagctt gaagttgagt cttttgggcc ggaatcccg gttgttgttg     1440 acgagtcttt gccagtcacg tggtgaaaag tggcagtgga atctgttgaa gtcaaaatac    1500 ccccagggg tgctgtagcc aaagtagtgg ttgtcgttgc tggctcctga ttggctggag     1560
atttgcttgt agaggtggtt gttgtatgtg ggcagggccc aggttcgggt gctggtggtg    1620
atgactctgt cgcccagcca ttgggaatcg caatgccaat ttcctgagga attacccact    1680
ccatcggcac cctcgttatt gtctgccatt ggtgcgccac tgcctgtagc cattgtagta    1740
gatcccagac cagaggggc tgctggtggc tgtccgagag ctgggggtc aggtacggag      1800 tctgcgtctc cagtctgacc aaaatttaat cttttcttg caggctgctg cccgcttt       1860 ccggttcccg aggaggagtc tggctccaca ggagagtgct ctaccggcct ctttttccc     1920 ggagccgtct taacaggctc ctcaaccagg cccagaggtt caagaaccct cttttcgcc     1980 tggaagactc tcgtccgag gttgcccca aaagacgtat cttctttaag gcgctcctga     2040
aactctgcgt cggcgtggtt gtacttgagg tacgggttgt ctccgctgtc gagctgccgg    2100
tcgtaggcct tgtcgtgctc gagggccgcg gcgtctgcct cgttgaccgg ctccccttg     2160 tcgagtccgt tgaagggtcc gaggtacttg tacccaggaa gcacaagacc cctgctgtcg    2220
tccttatgcc gctctgcggg ctttggtggt ggtgggccag gttgagctt ccaccactgt    2280 cttattcctt cagagagagt gtcctcgagc caatctggaa gataaccatc ggcagccata    2340
cctgatttaa atcatttatt gttcagagat gcagtcatcc aaatccacat tgaccagatc    2400
gcaggcagtg caagcgtctg gcacctttcc catgatatga tgaatgtagc acagtttctg    2460
atacgccttt ttgacgacag aaacggggttg agattctgac acgggaaagc actctaaaca    2520
gtctttctgt ccgtgagtga agcagatatt tgaattctga ttcattctct cgcattgtct    2580
gcagggaaac agcatcagat tcatgcccac gtgacgagaa catttgtttt ggtacctgtc    2640
cgcgtagttg atcgaagctt ccgcgtctga cgtcgatggc tgcgcaactg actcgcgcgc    2700
ccgtttgggc tcacttatat ctgcgtcact ggggcgggt cttttcttag ctccacccttt    2760 tttgacgtag aattcatgct ccacctcaac cacgtgatcc tttgcccacc ggaaaaagtc    2820
tttcacttcc tgcttggtga ccttttccaaa gtcatgatcc agacggcggg taagttcaaa    2880
tttgaacatc cggtcttgca acggctgctg gtgctcgaag gtcgttgagt tcccgtcaat    2940
cacggcgcac atgttggtgt tggaggtgac gatcacggga gtcgggtcta tctgggccga    3000
ggacttgcat ttctggtcca cacgcacctt gcttcctcca agaatggctt tggccgactc    3060
cacgaccttg gcggtcatct tcccctcctc ccaccagatc accatcttgt cgacgcaatg    3120
gtaaaaggaa agttctcatt gg                                              3142
```

<210> SEQ ID NO 26
<211> LENGTH: 3075
<212> TYPE: DNA
<213> ORGANISM: Unknown
<220> FEATURE:
<223> OTHER INFORMATION: AAV serotype, clone H2

<400> SEQUENCE: 26

```
tgagaacttt cctttcaacg attgcgtcgg acaagatggt gatctggtgg gaggagggga     60
agatgaccgc caaggtcgtg gagtcggcca aagccattct tggaggaagc aaggtgcgtg    120
tggaccagaa atgcaagtcc tcggcccaga tagacccgac tcccgtgatc gtcacctcca    180
```

-continued

```
acaccaacat gtgcgccgtg attgacggga actcaacgac cttcgagcac cagcagccgt    240
tgcaagaccg gatgttcaaa tttgaactta cccgccgtct ggatcatgac tttggaaagg    300
tcaccaagca ggaagtgaaa gacttttttcc ggtgggcaaa ggatcacgtg gttgaggtgg    360
agcatgaatt ctacgtcaaa aagggtggag ctaagaaaag acccgccccc agtgacgcag    420
atataagtga gcccaaacgg gcgcgcgagt cagttgcgca gccatcaacg tcagacgcgg    480
aagcttcgat caactacgcg gacaggtacc aaaaacaaat gttctcgtca cgtgggcatg    540
aatctgatgc tgtttccctg cagacaatgc gagagaatga atcagaattc aaatatctgc    600
ttcactcacg gacagaaaga ctgtttagag tgctttcccg tgtcagaatc tcaacccgtt    660
tctgtcgtca aaaaggcgta tcagaaactg tgctacattc atcatatcat gggaaaggtg    720
ccagacgctt gcactgcctg cgatctggtc aatgtggatt tggatgactg catctctgaa    780
caataaatga tttaaatcag gtatggctgc cgatggttat cctccagatt ggctcgagga    840
cactctctct gaagggataa gacagtggtg gaagctcaaa cctggcccac caccaccaaa    900
gcccgcagag cggcataagg acgacagcag gggtcttgtg cttcctgggt acaagtacct    960
cggacccttc aacggactcg acaaggggga gccggtcaac gaggcagacg ccgcggccct   1020
cgagcacgac aaggcctacg accggcagct cgacagcgga gacaacccgt acctcaagta   1080
caaccacgcc gacgcagagt ttcaggagcg ccttaaagaa gatacgtctt ttgggggcaa   1140
cctcggacga gcagtcttcc aggcgaaaaa gagggttctt gaacctctgg gcctggttga   1200
ggaacctgtt aagacggctc cgggaaaaaa gaggccggta gagcactctc ctgtggagcc   1260
agactcctcc tcgggaaccg gaaaagcggg ccagcggcct gcaagaaaaa gattaaattt   1320
tggtcagact ggagacgcag actccgtacc tgaccccag cctctcggac agccaccagc   1380
agccccctct ggtctgggat ctactacaat ggctacaggc agtggcgcac caatggcaga   1440
caataacgag ggtgccgatg gagtgggtaa ttcctcagga aattggcatt gcgattccca   1500
atggctgggc gacagagtca tcaccaccag cacccgaacc tgggccctgc ccacatacaa   1560
caaccacctc tacaagcaaa tctccagcca atcaggagcc agcaacgaca ccactactt   1620 tggctacagc acccccgggg ggtattttga cttcaacaga ttccactgcc actttttcacc   1680 acgtgactgg caaagactca tcaacaacaa ctggggattc cggcccaaaa gactcaactt   1740
caagctcttt aatattcaag tcaaagaggt cacgcagaat gacggtacga cgacgattgc   1800
caataacctt accagcacgg ttcaggtgtt tactgactcg gagtaccagc tcccgtacgt   1860
cctgggctcg gcgcatcaag gatgcctccc gccgtttcca gcggacgtct tcatggtccc   1920
acagtatgga tacctcaccc tgaacaacgg gagtcaggcg gtaggacgct cttccttta   1980 ctgcctggag tactttcctt ctcagatgct gcgtactgga aacaactttc agttcagcta   2040
cacttttgaa gacgtgcctt tccacagcag ctacgctcac agccagagtc tggatcggct   2100
gatgaatcct ctgatcgacc agtacctgta ttatctgaac aagacacaaa caaatagtgg   2160
aactcttcag cagtctcggc tactgttag ccaagctgga ccaaccaaca tgtctcttca   2220
agctaaaaac tggctgcctg gaccttgcta cagacagcag cgtctgtcaa acaggcaaa   2280 cgacaacaac aacagcaact ttccctggac tgcagctaca aagtatcatc taaatggccg   2340
ggactcgttg gttaatccag gaccagctat ggccagtcac aaggatgacg aagaaaagtt   2400
tttccccatg catggaaccc tgatatttgg taaacaagga acaaatgcca acgacgcgga   2460
tttggaaaat gtcatgatta cagatgaaga agaaatcagg gccaccaatc ccgtggctac   2520
ggagcagtac gggactgtgt caaataattt gcaaaactca aacactggtc caactactgg   2580
```

```
aactgtcaat cgccaaggag cgttacctgg tatggtgtgg caggatcgag acgtgtacct    2640
gcagggaccc atttgggcca agattcctca caccgatgga cactttcatc cttctccact    2700
gatgggaggt tttggactca aacacccgcc tcctcagatc atgatcaaaa acactcccgt    2760
tccagccaat cctcccacaa acttcagttc tgccaagttt gcttctttca tcacacagta    2820
ttccacggga caggtcagcg tggagatcga gtgggagctg cagaaggaga acagcaaacg    2880
ctggaatccc gaaattcagt acacttccaa ctacaacaag tctgttaatg tggactttac    2940
tgtggacact aatggtgtgt attcagagcc tcgccccatt ggcaccagat acctgactcg    3000
taatctgtaa ttgcttgtta atcaataaac cgtttaattc gtttcagttg aactttggtc    3060
tctgcgaagg gcgaa                                                     3075

<210> SEQ ID NO 27
<211> LENGTH: 3128
<212> TYPE: DNA
<213> ORGANISM: Unknown
<220> FEATURE:
<223> OTHER INFORMATION: AAV serotype, clone 42.8

<400> SEQUENCE: 27
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tcccaccccc gtgatcgtca cttccaacac caacatgtgc gccgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gccccgatg acgcggataa agcgagccc aagcgggcct     480 gccccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg tttccccggc gtgtcagaat ctcaaccggt cgtcagaaag aggacgtatc     720
ggaaactctg tgccattcat catctgctag ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatt     900
cgcgagtggt gggacttgaa acctggagcc ccgaaaccca agccaacca gcaaaagcag     960 gacgacggcc ggggtctggt gcttcctggc tacaagtacc tcggaccctt caacggactc    1020
gacaaggggg agcccgtcaa cgcggcggac gcagcggccc tcgagcacga caaggcctac    1080
gaccagcagc tcaaagcggg tgacaatccg tacctgcgt ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260 cctgaaaga agagaccggt agagccatca ccccagcgtt ctccagactc ctctacgggc    1320
atcggcaaga caggccagca gcccgcgaaa aagagactca actttgggca gactggcgac    1380
tcagagtcag tgcccgaccc tcaaccaatc ggagaacccc ccgcaggccc ctctggtctg    1440
ggatctggta caatggctgc aggcggtggc gctccaatgg cagacaataa cgaaggcgcc    1500
```

```
gacggagtgg gtagttcctc aggaaattgg cattgcgatt ccacatggct gggcgacaga    1560
gtcatcacca ccagcacccg aacctgggcc ctccccacct acaacaacca cctctacaag    1620
caaatctcca acgggacatc ggaggaagc accaacgaca cacctactt cggctacagc     1680 accccctggg ggtatttga ctttaacaga ttccactgcc acttctcacc acgtgactgg    1740
cagcgactca tcaacaacaa ctggggattc cggcccaaga gactcaactt caagctcttc    1800
aacatccagg tcaaggaggt cacgcagaat gaaggcacca agaccatcgc caataacctt    1860
accagcacga ttcaggtctt tacggactcg gaataccagc tcccgtacgt cctcggctct    1920
gcgcaccagg gctgcctgcc tccgttcccg gcggacgtct tcatgattcc tcagtacggg    1980
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt ttcacagcag ctacgcgcac agccaaagcc tggaccggct gatgaacccc    2160
ctcatcgacc agtacctgta ctacctgtct cggactcagt ccacgggagg taccgcagga    2220
actcagcagt tgctattttc tcaggccggg cctaataaca tgtcggctca ggccaaaaac    2280
tggctacccg gcccctgcta ccggcagcaa cgcgtctcca cgacactgtc gcaaaataac    2340
aacagcaact ttgcttggac cggtgccacc aagtatcatc tgaatggcag agactctctg    2400
gtaaatcccg gtgtcgctat ggcaacgcac aaggacgacg aagagcgatt ttttccatcc    2460
agcggagtct tgatgtttgg gaaacaggga gctggaaaag acaacgtgga ctatagcagc    2520
gttatgctaa ccagtgagga gaaatcaaa accaccaacc cagtggccac agaacagtac    2580
ggcgtggtgg ccgataacct gcaacagcaa acgccgctc ctattgtagg ggccgtcaac    2640
agtcaaggag ccttacctgg catggtctgg cagaaccggg acgtgtacct gcagggtcct    2700
atctgggcca agattcctca cacggacggc aactttcatc cttcgccgct gatgggaggc    2760
tttggactga aacacccgcc tcctcagatc ctgattaaga atacacctgt tcccgcggat    2820
cctccaacta ccttcagtca agccaagctg gcgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgcccattg gcaccccgtt acctcacccg taacctgtaa    3060
ttgcctgtta atcaataaac cggctaattc gtttcagttg aactttggtc tctgcgaagg    3120
gcgaattc                                                            3128

<210> SEQ ID NO 28
<211> LENGTH: 3128
<212> TYPE: DNA
<213> ORGANISM: Unknown
<220> FEATURE:
<223> OTHER INFORMATION: AAV serotype, clone 42.15

<400> SEQUENCE: 28
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccacccc gtgatcgtca cctccaacac caacatgtgc gccgtgattg      240
acggaaacag caccaccttc gagcaccagc agccgttgca ggaccggatg ttcaaatttg     300
aactcacccg ccgtctggag catgactttg gcaaggtgac aaagcaggaa gtcaaagagt     360
tcttccgctg gcgcaggat cacgtgaccg aggtggcgca tgagttctac gtcagaaagg     420
```

```
gtggagccaa caagagaccc gcccccgatg acgcggataa aagcgagccc aagcgggcct      480 gccccctcagt cgcggatcca tcgacgtcag acgcggaagg agctccggtg gactttgccg     540
acaggtacca aaacaaatgt tctcgtcacg cgggcatgct tcagatgctg tttccctgca      600
agacatgcga gagaatgaat cagaatttca acatttgctt cacgcgcggg accagagact      660
gttcagaatg tttcccgggc gtgtcagaat ctcaaccggt cgtcagaaag aggacgtatc      720
ggaaactctg tgccattcat catctgctgg ggcgggctcc cgagattgct tgctcggcct      780
gcgatctggt caacgtggac ctggatgact gtgtttctga gcaataaatg acttaaacca      840
ggtatggctg ccgatggtta tcttccagat tggctcgagg acaacctctc tgagggcatt      900
cgcgagtggt gggacttgaa acctggagcc cgaaaccca aagccaacca gcaaaagcag       960
gacgacggcc ggggtctggt gcttcctggc tacaagtacc tcggacccct caacggactc     1020 gacaagggg agcccgtcaa cgcggcggac gcagcggccc tcgagcacga caaggcctac     1080
gaccagcagc tcaaagcggg tgacaatccg tacctgcgt ataaccacgc cgacgccgag      1140
tttcaggagc gtctgcaaga agatacgtct tttgggggca acctcgggcg agcagtcttc     1200
caggccaaga agcgggttct cgaacctctc ggtctggttg aggaaggcgc taagacggct     1260
cctggaaaga agagaccggt agagccatca ccccagcgtt ctccagactc ctctacgggc     1320
atcggcaaga caggccagca gcccgcgaaa aagagactca actttgggca gactggcgac     1380
tcagagtcag tgcccgaccc tcaaccaatc ggagaacccc cgcaggcccc ctctggtctg     1440
ggatctggta caatggctgc aggcggtggc gctccaatgg cagacaataa cgaaggcgcc     1500
gacggagtgg gtagttcctc aggaaattgg cattgcgatt ccacatggct gggcgacaga     1560
gtcatcacca ccagcacccg aacctgggcc ctccccacct acaacaacca cctctacaag     1620
caaatctcca acgggacatc gggaggaagc accaacgaca cacctactt cggctacagc      1680 accccctggg ggtatttga ctttaacaga ttccactgcc acttctcacc acgtgactgg     1740
cagcgactca tcaacaacaa ctgggggattc cggcccaaga gactcaactt caagctcttc    1800
aacatccagg tcaaggaggt cacgcagaat gaaggcacca agaccatcgc caataacctt    1860
accagcacga ttcaggtctt tacggactcg gaataccagc tcccgtacgt cctcggctct    1920
gcgcaccagg gctgcccgcc tccgttcccg gcggacgtct tcatgattcc tcagtacggg    1980
tacctgactc tgaacaacgg cagtcaggcc gtgggccgtt cctccttcta ctgcctggag   2040
tactttcctt ctcaaatgcg gagaacgggc aacaactttg agttcagcta ccagtttgag    2100
gacgtgcctt tcacagcag ctacgcgcat agccaaagcc tggaccggct gatgaacccc     2160
ctcatcgacc agtacctgta ctacctgtct cggactcagt ccacgggagg taccgcagga    2220
actcagcagt tgctatttc tcaggccggg cctaataaca gtcggctca ggccaaaaac      2280 tggctacccg ggccctgcta ccggcagcaa cgcgtctcca cgacactgtc gcaaaataac    2340
aacagcaact tgcttggac cggtgccacc aagtatcatc tgaatggcag agactctctg      2400
gtaaatcccg gtgtcgctat ggcaacgcac aaggacgacg aagagcgatt ttttccatcc    2460
agcggagtct tgatgtttgg gaaacaggga gctggaaaag acaacgtgga ctatagcagc    2520
gttatgctaa ccagtgagga gaaatcaaa accaccaacc cagtggccac agaacagtac    2580
ggcgtggtgg ccgataacct gcaacagcaa aacgccgctc ctattgtagg ggccgtcaac    2640
agtcaaggag ccttacctgg catggtctgg cagaaccggg acgtgtacct gcagggtcct   2700 atctggggcca agattcctca cacggacggc aactttcatc cttcgccgct gatgggaggc    2760
```

-continued

| | |
|---|---|
| tttggactga aacacccgcc tcctcagatc ctgattaaga atacacctgt tcccgcggat | 2820 |
| cctccaacta ccttcagtca agccaagctg gcgtcgttca tcacgcagta cagcaccgga | 2880 |
| caggtcagcg tggaaattga atgggagctg cagaaagaga acagcaagcg ctggaaccca | 2940 |
| gagattcagt atacttccaa ctactacaaa tctacaaatg tggactttgc tgtcaatact | 3000 |
| gagggtactt attcagagcc tcgccccatt ggcacccgtt acctcacccg taacctgtaa | 3060 |
| ttgcctgtta atcaataaac cggttaattc gtttcagttg aactttggtc tctgcgaagg | 3120 |
| gcgaattc | 3128 |

<210> SEQ ID NO 29
<211> LENGTH: 3197
<212> TYPE: DNA
<213> ORGANISM: Unknown
<220> FEATURE:
<223> OTHER INFORMATION: AAV serotype. clone 42.5b

<400> SEQUENCE: 29

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaagg tgcgcgtgga ccaaaagtgc aagtcgtccg | 180 |
| cccagatcga ccccaccccc gtgatcgtca cctccaacac caacatgtgc gccgtgattg | 240 |
| acgggaacag caccaccttc gagcaccagc agccgttaca agaccggatg ttcaaatttg | 300 |
| aactcacccg ccgtctggag cacgactttg gcaaggtgac aaagcaggaa gtcaaagagt | 360 |
| tcttccgctg ggcgcaggat cacgtgaccg aggtggcgca tgagttctac gtcagaaagg | 420 |
| gtggagccaa caagagaccc gcccccgatg acgcggataa agcgagccc aagcgggcct | 480 |
| gcccctcagt cgcggatcca tcgacgtcag acgcggaagg agctccggtg gactttgccg | 540 |
| acaggtacca aaacaaatgt tctcgtcacg cgggcatgct tcagatgctg tttccctgca | 600 |
| agacatgcga gagaatgaat cagaatttca acatttgctt cacgcacggg accagagact | 660 |
| gttcagaatg tttccccggc gtgtcagaat ctcaaccggt cgtcagaaag aggacgtatc | 720 |
| ggaaactctg tgccattcat catctgctgg ggcgggctcc cgagattgct tgctcggcct | 780 |
| gcgatctggt caacgtggac ctggatgact gtgtttctga gcaataaatg acttaaacca | 840 |
| ggtatggctg ccgatggtta tcttccagat tggctcgagg acaacctctc tgagggcatt | 900 |
| cgcgagtggt gggacttgaa acctggagcc ccgaaaccca agccaaccag caaaagcag | 960 |
| gacgacggcc ggggtctggt gcttcctggc tacaagtacc tcggaccctt caacggactc | 1020 |
| gacaagggag agccggtcaa cgaggcagac gccgcggccc tcgagcacga caaggcctac | 1080 |
| gacaagcagc tcgagcaggg ggacaacccg tacctcaagt acaaccacgc cgacgccgag | 1140 |
| tttcaggagc gtcttcaaga agatacgtct tttgggggca acctcgggcg agcagtcttc | 1200 |
| caggccaaga agcgggttct cgaacctctc ggtctggttg aggaaggcgc taagacggct | 1260 |
| cctggaaaga gagaccgggt agagccatca ccccagcgtt ctccagactc ctctacgggc | 1320 |
| atcggcaaga caggccagca gcccgcgaaa aagagactca actttgggca gactggcgac | 1380 |
| tcagagtcag tgcccgaccc tcaaccaatc ggagaacccc ccgcaggccc ctctggtctg | 1440 |
| ggatctggta caatggctgc aggcggtggc gctccaatgg cagacaataa cgaaggcgcc | 1500 |
| gacggagtgg gtagttcctc aggaaattgg cattgcgatt ccacatggct gggcgacaga | 1560 |
| gtcatcacca ccagcacccg aacctgggcc ctccccacct acaacaacca cctctacaag | 1620 |
| caaatctcca acgggacatc gggaggaagc accaacgaca cacctactt cggctacagc | 1680 |

-continued

```
acccccctggg ggtattttga ctttaacaga ttccactgcc acttctcacc acgtgactgg    1740
cagcgactca tcaacaacaa ctggggattc cggcccaaga gactcaactt caagctcttc    1800
aacatccagg tcaaggaggt cacgcagaat gaaggcacca agaccatcgc caataacctt    1860
accagcacga ttcaggtctt tacggactcg gaataccagc tcccgtacgt cctcggctct    1920
gcgcaccagg gctgcctgcc tccgttcccg gcggacgtct tcatgattcc tcagtacggg    1980
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt tcacagcag ctacgcgcac agccaaagcc tggaccggct gatgaacccc    2160
ctcatcgacc agtacctgta ctacctgtct cggactcagt ccacgggagg taccgcagga    2220
actcagcagt tgctattttc tcaggccggg cctaataaca tgtcggctca ggccaaaaac    2280
tggctacccg ggccctgcta ccggcagcaa cgcgtctcca cgacactgtc gcaaaataac    2340
aacagcaact ttgcttggac cggtgccacc aagtatcatc tgaatggcag agactctctg    2400
gtaaatcccg gtgtcgctat ggcaacgcac aaggacgacg aagagcgatt ttttccatcc    2460
agcggagtct tgatgtttgg gaaacaggga gctggaaaag acaacgtgga ctatagcagc    2520
gttatgctaa ccagtgagga gaaaatcaaa accaccaacc cagtggccac agaacagtac    2580
ggcgtggtgg ccgataacct gcaacagcaa acgccgctc ctattgtagg ggccgtcaac    2640
agtcaaggag ccttacctgg catggtctgg cagaaccggg acgtgtacct gcagggtcct    2700
atctgggcca agattcctca cacggacggc aactttcatc cttcgccgct gatgggaggc    2760
tttggactga acacccgcc tcctcagatc ctgattaaga atacacctgt tcccgcggat    2820
cctccaacta ccttcagtca agccaagctg gcgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgccccatt ggcacccgtt acctcacccg taacctgtaa    3060
ttgcctgtta atcaataaac cggttaattc gtttcagttg aactttggtc tctgcgaagg    3120
gcgaattcgt ttaaacctgc aggactagtc cctttagtga gggttaattc tgagcttggc    3180
gtaatcatgg gtcatag                                                    3197
```

<210> SEQ ID NO 30
<211> LENGTH: 2501
<212> TYPE: DNA
<213> ORGANISM: Unknown
<220> FEATURE:
<223> OTHER INFORMATION: AAV serotype, clone 42.1b

<400> SEQUENCE: 30

```
gaattcgccc ttggctgcgt caactggacc aatgagaact ttcccttcaa cgattgcgtc     60
gacaagatgg tgatctggtg ggaggagggc aagatgacgg ccaaggtcgt ggagtccgcc    120
aaggccattc atcatctgct ggggcgggct cccgagattg cttgctcggc ctgcgatctg    180
gtcaacgtgg acctggatga ctgtgtttct gagcaataaa tgacttaaac caggtatggc    240
tgccgatggt tatcttccag attggctcga ggacaacctc tctgagggca ttcgcgagtg    300
gtgggacttg agacctggag ccccgaaacc caaagccaac cagcaaaagc aggacgacgg    360
ccggggtctg gtgcttcctg gctacaagta ccctcggaccc ttcaacggac tcgacaaggg    420
agagccggtc aacgaggcag acgccgcggc cctcgagcac gacaaggcct acgacaagca    480
```

```
gctcgagcag ggggacaacc cgtacctcaa gtacaaccac gccgacgccg agtttcagga    540
gcgtcttcaa gaagatacgt cttttggggg caacctcggg cgagcagtct tccaggccaa    600
gaagcgggtt ctcgaacctc tcggtctggt tgaggaaggc gctaagacgg ctcctggaaa    660
gaagagaccc atagaatccc ccgactcctc cacgggcatc ggcaagaaag ccagcagcc    720 cgctaaaaag agactcaact ttgggcagac tggcgactca gagtcagtgc ccgaccctca    780
accaatcgga gaaccccccg caggcccctc tggtctggga tctggcacaa tggctgcagg    840
cggtggcgct ccaatggcag acaataacga aggcgccgac ggagtgggta gttcctcagg    900
aaattggcat tgcgattcca catggctggg cgacagagtc atcaccacca gcacccgaac    960
ctgggccctc cccacctaca caaccaccct ctacaagcaa atctccaacg ggacatcggg   1020
aggaagcacc aacgacaaca cctacttcgg ctacagcacc ccctgggggt attttgactt   1080
taacagattc cactgccact tctcaccacg tgactggcag cgactcatca acaacaactg   1140
gggattccgg cccaagagac tcaacttcaa gctcttcaac atccaggtca aggaggtcac   1200
gcagaatgaa ggcaccaaga ccatcgccaa taaccttacc agcacgattc aggtctttac   1260
ggactcggaa taccagctcc cgtacgtcct cggctctgcg caccagggct gcctgcctcc   1320
gttcccggcg gacgtcttca tgattcctca gtacgggtac ctgactctga caacggcag   1380 tcaggccgtg ggccgttcct ccttctactg cctggagtac tttccttctc aaatgctgag   1440
aacgggcaac aactttgagt tcagctacca gtttgaggac gtgccttttc acagcagcta   1500
tgcgcacagc caaagcctgg accggctgat gaaccccctc atcgaccagt acctgtacta   1560
cctgtctcgg actcagtcca cgggaggtac cgcaggaact cagcagttgc tattttctca   1620
ggccgggcct aataacatgt cggctcaggc caaaaactgg ctaccgggc cctgctaccg   1680 gcagcaacgc gtctccacga cagtgtcgca aaataacaac agcaactttg cttggaccgg   1740
tgccaccaag tatcatctga atggcagaga ctctctggta aatcccggtg tcgctatggc   1800
aacgcacaag ggcgacgaag agcgattttt tccatccagc ggagtcttga tgtttgggaa   1860
acagggagct ggaaaagaca acgtagacta tagcagcgtt atgctaacca gtgaggaaga   1920
aatcaaaacc accaacccag tggccacaga acagtacggc gtggtggccg ataacctgca   1980
acagcaaaac gccgctccta ttgtagggc cgtcaacagt caaggagcct acctggcat   2040 ggtctggcag aaccgggacg tgtacctgca gggtcctatc tgggccaaga ttcctcacac   2100
ggacggcaac tttcatcctt cgccgctgat gggaggcttt ggactgaaac accgcctcc   2160 tcagatcctg attaagaata cacctgttcc cgcggatcct ccaactacct tcagtcaagc   2220
caagctggcg tcgttcatca cgcagtacag caccggacag gtcagcgtgg aaattgaatg   2280
ggagctgcag aaagagaaca gcaagcgctg gaacccagag attcagtata cttccaacta   2340
ctacaaatct acaaatgtgg actttgctgt caatactgag ggtacttatt cagagcctcg   2400
ccccattggc acccgttacc tcacccgtaa cctgtaattg cctgttaatc aataaaccgg   2460
ttgattcgtt tcagttgaac tttggtctca agggcgaatt c                      2501
```

<210> SEQ ID NO 31
<211> LENGTH: 3113
<212> TYPE: DNA
<213> ORGANISM: Unknown
<220> FEATURE:
<223> OTHER INFORMATION: AAV serotype, clone 42.13

<400> SEQUENCE: 31

```
gaattcgccc tttctacggc tgcgtcaact ggaccaatga gaactttccc ttcaacgatt     60
```

```
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga tcccacccc  gtgatcgtca cttccaacac caacatgtgc gccgtgattg    240
acgggaacag caccaccttc gagcaccagc agccgttaca agaccggatg ttcaaatttg    300
aactcacccg ccgtctggag catgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gccccgatg  acgcggataa aagcgagccc aagcgggcct    480 gccctcagt  cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc cgaaaccca  aagccaacca gcaaaagcag    960
gacgacggcc ggggtctggt gcttcctggc tacaagtacc tcggacccct caacggactc    1020 gacaagggg  agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtcttcaaga agatacgtct tttgggggca acctcgggcg agcagtcttc    1200
caggccaaga agcgggttct cgaacctctc ggtctggttg aggaaggcgc taagacggct    1260
cctggaaaga agagacccat agaatccccc gactcctcca cgggcatcgg caagaaaggc    1320
cagcagcccg ctaaaaagaa gctcaacttt gggcagactg gcgactcaga gtcagtgccc    1380
gaccctcaac caatcggaga accccccgca ggcccctctg gtctgggatc tggtacaatg    1440
gctgcaggcg gtggcgctcc aatggcagac aataacgaag gcgccgacgg agtgggtagt    1500
tcctcaggaa attggcattg cgattccaca tggctgggcg acagagtcat caccaccagc    1560
acccgaacct gggccctccc cacctacaac aaccacctct acaagcaaat ctccaacggg    1620
acatcgggag gaagcaccaa cgacaacacc tacttcggct acagcacccc ctgggggtat    1680 tttgactta  acagattcca ctgccacttc tcaccacgtg actggcagcg actcatcaac    1740
aacaactggg gattccggcc caagagactc aacttcaagc tcttcaacat ccaggtcaag    1800
gaggtcacgc agaatgaagg caccaagacc atcgccaata accttaccag cacgattcag    1860 gtctttacg  actcggaata ccagctcccg tacgtcctcg gctctgcgca ccagggctgc    1920
ctgcctccgt tcccggcgga cgtcttcatg attcctcagt acgggtacct gactctgaac    1980
aacggcagtc aggccgtggg ccgttcctcc ttctactgcc tggagtactt tccttctcaa    2040
atgctgagaa cgggcaacaa ctttgagttc agctaccagt ttgaggacgt gccttttcac    2100
agcagctatg cgcacagcca aagcctggac cggctgatga accccctcat cgaccagtac    2160
ctgtactacc tgtctcggac tcagtccacg ggaggtaccg caggaactca gcagttgcta    2220
ttttctcagg ccgggcctaa taacatgtcg gctcaggcca aaaactggct acccgggccc    2280
tgctaccggc agcaacgcgt ctccacgaca gtgtcgcaaa ataacaacag caactttgct    2340
tggaccggtg ccaccaagta tcatctgaat ggcagagact ctctggtaaa tcccggtgtc    2400
```

```
gctatggcaa cgcacaaggg cgacgaagag cgatttttc catccagcgg agtcttgatg    2460
tttgggaaac agggagctgg aaaagacaac gtggactata gcagcgttat gctaaccagt    2520
gaggaagaaa tcaaaaccac caacccagtg gccacagaac agtacggcgt ggtggccgat    2580
aacctgcaac agcaaaacgc cgctcctatt gtaggggccg tcaacagtca aggagcctta    2640
cctggcatgg tctggcagaa ccgggacgtg tacctgcagg gtcctatctg ggccaagatt    2700
cctcacacgg acggcaactt tcatccttcg ccgctgatgg gaggctttgg actgaaacac    2760
ccgcctcctc agatcctgat taagaataca cctgttcccg cggatcctcc aactaccttc    2820
agtcaagcca agctggcgtc gttcatcacg cagtacagca ccggacaggt cagcgtggaa    2880
attgaatggg agctgcagaa agagaacagc aagcgctgga acccagagat tcagtatact    2940
tccaactact acaaatctac aaatgtggac tttgctgtca atactgaggg tacttattca    3000
gagcctcgcc ccattggcac ccgttacctc acccgtagcc tgtaattgcc tgttaatcaa    3060
taaaccggtt gattcgtttc agttgaactt tggtctctgc gaagggcgaa ttc          3113

<210> SEQ ID NO 32
<211> LENGTH: 3113
<212> TYPE: DNA
<213> ORGANISM: Unknown
<220> FEATURE:
<223> OTHER INFORMATION: AAV serotype, clone 42.3a

<400> SEQUENCE: 32
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga tcccaccccc gtgatcgtca cttccaacac caacatgtgc gccgtgattg     240
acgggaacag caccaccttc gagcaccagc agccgttaca agaccggatg ttcaaatttg     300
aactcacccg ccgtctggag catgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gccccgatg acgcggataa aagcgagccc aagcgggcct     480 gccctcagt cgcggatcca tcgacgtcag acgcggaagg agctccggtg gactttgccg     540
acaggtacca aaacaaatgt ctcgtcacg cgggcatgct tcagatgctg cttccctgca     600
agacatgcga gagaatgaat cagaatttca gcatttgctt cacgcacggg accagagact     660
gttcagaatg ttttccccggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgact gtgtttctga gcaataaatg acttaaacca     840
ggtatggctg ccgatggtca tcttccagat ggctcgagg acaacctctc tgagggcatt     900
cgcgagtggt gggacttgaa acctggagcc ccgaaaccca agccaaccaa gcaaaagcag     960
gacgacggcc ggggtctggt gcttcctggc tacaagtacc tcggacccctt caacggactc    1020 gacaaggggg agcccgtcaa cgcggcggac gcagcggccc tcgagcacga caaggcctac    1080
gaccagcagc tcaaagcggg tgacaatccg tacctgcgt ataaccacgc cgacgccgag    1140
tttcaggagc gtcttcaaga agatacgtct tttggggggca acctcgggcg agcagtcttc    1200
caggccaaga agcgggttct cgaacctctc ggtctggttg aggaaggcgc taagacggct    1260
cctggaaaga gagacccat agaatccccc gactcctcca cgggcatcgg caagaaaggc    1320
cagcagcccg ctaaaaagaa gctcaacttt gggcagactg gcgactcaga gtcagtgccc    1380
```

```
gaccctcaac caatcggaga accccccgca ggcccctctg gtctgggatc tggtacaatg    1440
gctgcaggcg gtggcgctcc aatggcagac aataacgaag gcgccgacgg agtgggtagt    1500
tcctcaggaa attggcattg cgattccaca tagctgggcg acagagtcat caccaccagc    1560
acccgaacct gggccctccc cacctacaac aaccacctct acaagcaaat ctccaacggg    1620
acatcgggag gaagcaccaa cgacaacacc tacttcggct acagcacccc ctgggggtat    1680
tttgacttta acagattcca ctgccacttc tcaccacgtg actggcagcg actcatcaac    1740
aacagctggg gattccggcc caagagactc aacttcaagc tcttcaacat ccaggtcaag    1800
gaggtcacgc agaatgaagg caccaagacc atcgccaata accttaccag cacgattcag    1860
gtctttacgg actcggaata ccagctcccg tacgtcctcg gctctgcgca ccagggctgc    1920
ctgcctccgt tcccggcgga cgtcttcatg attcctcagt acgggtacct gactctgaac    1980
aacggcagtc aggccgtggg ccgttcctcc ttctactgcc tggagtactt ccttctcaa     2040 atgctgagaa cgggcaacaa ctttgagttc agctaccagt tgaggacgt gccttttcac     2100 agcagctacg cgcacagcca aagcctggac cggctgatga cccccctcat cgaccagtac    2160
ctgtactacc tgtctcggac tcagtccacg ggaggtaccg caggaactca gcagttgcta    2220
ttttctcagg ccgggcctaa taacatgtcg gctcaggcca aaaactggct acccgggccc    2280
tgctaccggc agcaacgcgt ctccacgaca ctgtcgcaaa ataacaacag caactttgct    2340
tggaccggtg ccaccaagta tcatctgaat ggcagagact ctctggtaaa tcccggtgtc    2400
gctatggcaa cgcacaagga cgacgaagag cgatttttc catccagcgg agtcttgatg    2460
tttgggaaac agggagctgg aaaagacaac gtggactata gcagcgttat gctaaccagt    2520
gaggaagaaa tcaaaaccac caacccagtg gccacagaac agtacggcgt ggtggccgat    2580
aacctgcaac agcaaaacgc cgctcctatt gtaggggccg tcaacagtca aggagcctta    2640
cctggcatgg tctggcagaa ccgggacgtg tacctgcagg gtcctatctg ggccaagatt    2700
cctcacacgg acggcaactt tcatccttcg ccgctgatgg gaggctttgg actgaaacac    2760
ccgcctcctc agatcctgat taagaataca cctgttcccg cggatcctcc aactaccttc    2820
agtcaagcca agctggcgtc gttcatcacg cagtacagca ccgacaggt cagcgtggaa    2880 attgaatggg agctgcagaa agagaacagc aagcgctgga acccagagat tcagtatact    2940
tccaactact acaaatctac aaatgtggac tttgctgtca atactgaggg tacttattca    3000
gagcctcgcc ccattggcac ccgttacctc acccgtaacc tgtaattgcc tgttaatcaa    3060
taaaccggtt aattcgtttc agttgaactt tggtctctgc gaagggcgaa ttc           3113
```

<210> SEQ ID NO 33
<211> LENGTH: 2504
<212> TYPE: DNA
<213> ORGANISM: Unknown
<220> FEATURE:
<223> OTHER INFORMATION: AAV serotype, clone 42.4

<400> SEQUENCE: 33

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattcatcat ctgctggggc gggctcccga gattgcttgc tcggcctgcg     180
atctggtcaa cgtggacctg gatgactgtg tttctgagca ataaatgact taaaccaggt     240
atggctgccg atggttatct tccagattgg ctcgaggaca acctctctga gggcattcgc     300
```

```
gagtggtggg acttgaaacc tggagccccg aaacccaaag ccaaccagca aaagcaggac    360
gacggccggg gtctggtgct tcctggctac aagtacctcg gacccttcaa cggactcgac    420
aagggagagc cggtcaacga ggcagacgcc gcggccctcg agcacgacaa ggcctacgac    480
aagcagctcg agcaggggga caacccgtac ctcaagtaca accacgccga cgccgagttt    540
caggagcgtc ttcaagaaga tacgtctttt gggggcaacc tcgggcgagc agtcttccag    600
gccaagaagc gggttctcga acctctcggt ctggttgagg aaggcgctaa gacggctcct    660
ggaaagaaga gacccataga atcccccgac tcctccacgg gcatcggcaa gaaaggccag    720
cagcccgcta aaagaagct caactttggg cagactggcg actcagagtc agtgcccgac    780
cctcaaccaa tcggagaacc ccccgcaggc ccctctggtc tgggatctgg tacaatggct    840
gcaggcggtg gcgctccaat ggcagacaat aacgaaggcg ccgacggagt gggtaatgcc    900
tccggaaatt ggcattgcga ttccacatgg ctgggcgaca gagtcatcac caccagcacc    960
cgcacctggg ccctgcccac ctacaacaac cacctctaca agcagatatc aagtcagagc   1020
ggggctacca acgacaacca cttcttcggc tacagcaccc cctggggcta ttttgacttc   1080
aacagattcc actgccactt ctcatcacgt gactggcagc gactcatcaa caacaactgg   1140
ggattccggc caagagact caacttcaag ctcttcaaca tccaggtcaa ggaggtcacg   1200
cagaatgaag gcaccaagac catcgccaat aaccttacca gcacgattca ggtctttacg   1260
gactcggaat accggctccc gtacgtcctc ggctctgcgc accagggctg cctgcctccg   1320
ttcccggcgg acgtcttcat gattcctcag tacgggtacc tgactctgaa caacggcagt   1380
caggccgtgg gccgttcctc cttctactgc ctggagtact tccttctca aatgctgaga   1440
acgggcaaca actttgagtt cagctaccag tttgaggacg tgccttttca cagcagctac   1500
gcgcacagcc aaagcctgga ccggctgatg aaccccctca tcgaccagta cctgtactac   1560
ctgtctcgga ctcagtccac gggaggtacc gcaggaactc agcagttgct atttttctcag  1620
gccgggccta ataacatgtc ggctcaggcc aaaaactggc tacccgggcc ctgctaccgg   1680
cagcaacgcg tctccacgac actgtcgcaa ataacaaca gcaactttgc ttggaccggt    1740
gccaccaagt atcatctgaa tggcagagac tctctggtaa atcccggtgt cgctatggca    1800
acgcacaagg acgacgaaga gcgatttttt ccatccagcg gagtcttgat gtttgggaaa    1860
cagggagctg gaaaagacaa cgtggactat agcagcgtta tgctaaccag tgaggaagaa    1920
atcaaaacca ccaacccagt ggccacagaa cagtacggcg tggtggccga taacctgcaa    1980
cagcaaaacg ccgctcctat tgtagggcc gtcaacagtc aaggagcctt acctggcatg    2040
gtctggcaga accgggacgt gtacctgcag gtcctatct gggccaagat tcctcacacg    2100
gacggcaact ttcatcctc gccgctgatg ggaggctttg gactgaaaca cccgcctcct    2160
cagatcctga ttaagaatac acctgttccc gcggatcctc aactacctt cagtcaagcc    2220
aagccggcgt cgttcatcac gcagtacagc accggacagg tcagcgtgga aattgaatgg    2280
gagctgcaga aagagaacag caagcgctgg aacccagaga ttcagtatac ttccaactac    2340
tacaaatcta caaatgtgga ctttgctgtc aatactgagg gtacttattc agagcctcgc    2400
cccattggca cccgttacct cacccgtaac ctgtaattgc ctgttaatca ataaaccggt    2460
taattcgttt cagttgaact ttggtctctg cgaagggcga attc                    2504
```

<210> SEQ ID NO 34
<211> LENGTH: 3106
<212> TYPE: DNA
<213> ORGANISM: Unknown

<220> FEATURE:
<223> OTHER INFORMATION: AAV serotype, clone 42.5a

<400> SEQUENCE: 34

```
gaattcgccc ttctacggct gcgtcaactg gaccaatgag aactttccct tcaacgattg    60
cgtcgacaag atggtgatct ggtgggagga gggcaagatg acggccaagg tcgtggagtc   120
cgccaaggcc attctcggcg gcagcaaggt gcgcgtggac caaaagtgca agtcgtccgc   180
ccagatcgac cccaccccg tgatcgtcac ctccaacacc aacatgtgcg ccgtgattga   240
cgggaacagc accaccttcg agcaccagca gccgttgcag gaccggatgt tcaaatttga   300
actcacccgc cgtctggagc atgactttgg caaggcgaca aagcaggaag tcaaagagtt   360
cttccgctgg gcgcaggatc acgtgaccga ggtggcgcat gagttctacg tcagaaaggg   420
tggagccaac aagagacccg ccccgatga cgcggataaa agcgagccca gcgggcccg   480
cccctcagtc gcggatccat cgacgtcaga cgcggaagga gctccggtgg actttgccga   540
caggtaccaa aacaaatgtt ctcgtcacgc gggcatgctt cagatgctgt ttccctgcaa   600
aacatgcgag agaatgaatc agaatttcaa catttgcttc acgcacggga ccagagactg   660
ttcagaatgt ttccccggcg tgtcagaatc tcaaccggtc gtcagaaaga ggacgtatcg   720
gaaactctgt gccattcatc atctgctggg gcgggctccc gagattgctt gctcggcctg   780
cgatctggtc aacgtggacc tggatgactg tgtttctgag caataaatga cttaaaccag   840
gtatggctgc cgatggttat cttccagatt ggctcgagga caacctctct gagggcattc   900
gcgagtggtg ggacttgaaa cctggagccc cgaaacccaa agccaaccag caaaagcagg   960
acgacggccg gggtctggtg cttcctggct acaagtacct cggacccttc aacggactcg  1020
acaagggaga gccggtcaac gaggcagacg ccgcggccct cgagcacgac aaggcctacg  1080
acaagcagct cgagcagggg gacaacccgt acctcaagta caaccacgcc gacgccgagt  1140
ttcaggagcg tcttcaagaa gatacgtctt ttggggcaa cctcgggcga gcagtcttcc  1200
gggccaagaa gcgggttctc gaacctctcg gtctggttga ggaaggcgct aagacggctc  1260
ctggaaagaa gagacccata gaatccccg actcctccac gggcatcggc aagaaaggcc  1320
agcagcccgc taaaaagaag ctcaactttg gcagactgg cgactcagag tcagtgcccg  1380
accccccaacc tctcggagaa cctccgccg cgccctcagg tctgggatct ggtacaatgg  1440
ctgcaggcgg tggcgcacca atggcagaca ataacgaagg cgccgacgga gtgggtaatg  1500
cctccggaaa ttggcattgc gattccacat ggctgggcga cagagtcatc accaccagca  1560
cccgcacctg ggccctgccc acctacaaca accacctcta aagcagata tcaagtcaga  1620
gcggggctac caacgacaac cacttcttcg gctacagcac ccctggggc tatttttgact  1680
tcaacagatt ccactgccac ttctcaccac gtgactggca gcgactcatc aacaacaacc  1740
ggggattccg gcccagaaag ctgcggttca gttgttcaa catccaggtc aaggaggtca  1800
cgacgaacga cggcgttacg accatcgcta ataaccttac cagcacgatt caggtcttct  1860
cggactcgga gtaccaactg ccgtacgtcc tcggctctgc gcaccagggc tgcctccctc  1920
cgttccctgc ggacgtgttc atgattcctc agtacggata tctgactcta aacaacggca  1980
gtcagtctgt gggacgttcc tccttctact gcctggagta ctttccttct cagatgctga  2040
gaacgggcaa taactttgaa ttcagctacc agtttgagga cgtgccctt cacagcagct  2100
acgcgcacag ccaaagccctg gaccggctga tgaacccct catcgaccag tacctgtact  2160
acctgtctcg gactcagtcc acgggaggta ccgcaggaac tcagcagttg ctattttctc  2220
```

```
aggccgggcc taataacatg tcggctcagg ccaaaaactg gctacccggg ccctgctacc    2280
ggcagcaacg cgtctccacg acactgtcgc aaaataacaa cagcaacttt gcttggaccg    2340
gtgccaccaa gtatcatctg aatggcagag actctctggt aaatcccggt gtcgctatgg    2400
caacgcacaa ggacgacgaa gagcgatttt ttccatccag cggagtcttg atgtttggga    2460
aacagggagc tggaaaagac aacgtggact atagcagcgt tatgctaacc agtgaggaag    2520
aaatcaaaac caccaaccca gtggccacag aacagtacgg cgtggtggcc gataacctgc    2580
aacagcaaaa cgccgctcct attgtagggg ccgtcaacag tcaaggagcc ttacctggca    2640
tggcctggca gaaccgggac gtgtacctgc agggtcctat ctgggccaag attcctcaca    2700
cggacggcaa ctttcatcct tcgccgctga tgggaggctt tggactgaaa cacccgcctc    2760
ctcagatcct gattaagaat acacctgttc ccgcggatcc tccaactacc ttcagtcaag    2820
ccaagctggc gtcgttcatc acgcagtaca gcaccggaca ggtcagcgtg gaaattgaat    2880
gggagctgca gaaagagaac agcaagcgct ggaacccaga gattcagtat acttccaact    2940
actacaaatc tacaaatgtg gactttgctg tcaatactga gggtacttat tcagagcctc    3000
gccccattgg cacccgttac ctcacccgta acctgtaatt gcctgttaat caataaaccg    3060
gttaattcgt ttcagttgaa ctttggtctc tgcgaagggc gaattc                  3106
```

<210> SEQ ID NO 35
<211> LENGTH: 2489
<212> TYPE: DNA
<213> ORGANISM: Unknown
<220> FEATURE:
<223> OTHER INFORMATION: AAV serotype, clone 42.10

<400> SEQUENCE: 35

```
gaattcgccc tttctacggc tgcgtcaact ggaccaatga gaactttccc ttcaacgatt      60
gcgtcgacaa gatggtgatc tggtgggagg agggcaagat gacggccaag gtcgtgaagt     120
ccgccaaggc cattcatcat ctgctggggc gggctcccga gattgcttgc tcggcctgcg     180
atctggtcaa cgtggacctg atgactgtg tttctgagca ataaatgact taaaccaggt     240
atggctgccg atggttatct tccagattgg ctcgaggaca acctctctga gggcattcgc     300
gagtggtggg acttgaaacc tggagccccg aaacccaaag ccaaccagca aaagcaggac     360
gacgccgggg tctggtgct tcctggctac aagtacctcg gacccttcaa cggactcgac     420
aagggagagc cggtcaacga ggcagacgcc gcggccctcg agcacgacaa ggcctacgac     480
aagcagctcg agcagggga caacccgtac ctcaagtaca accacgccga cgccgagttt     540
caggagcgtc ttcaagaaga tacgtctttt gggggcaacc tcgggcgagc agtcttccag     600
gccaagaagc gggttctcga acctctcggt ctggttgagg aaggcgctaa gacggctcct     660
ggaaagaaga gacccataga atccccgac tcctccacgg gcatcggcag gaaaggccag     720
cagcccgcta aaaagaagct caactttggg cagactggcg actcagagtc agtgcccgac     780
cctcaaccaa tcggagaacc ccccgcaggc ccctctggtc tgggatctgg tacaatggct     840
gcaggcggtg gcgctccaat ggcagacaat aacgaaggcg ccgacggagt gggtaatgcc     900
tccggaaatt ggcattgcga ttccacatgg ctgggcgaca gagtcatcac caccagcacc     960
cgcacctggg ccctgcccac ctacaacaac cacctctaca agcagatatc aagtcagagc    1020
ggggctacca acgacaacca cttcttcggc tacagcaccc cctggggcta ttttgacttc    1080
aacagattcc actgccactt ctcaccacgt gactggcagc gactcatcaa caacaactgg    1140
ggattccggc ccagaaagct gcggttcaag ttgttcaaca tccaggtcaa ggaggtcacg    1200
```

```
acgaacgacg gcgttacgac catcgccaat aaccttacca gcacgattca ggtcttctcg   1260
gactcggagt accaactgcc gtacgtcctc ggctctgcgc accagggctg cctccctccg   1320
ttccctgcgg acgtgttcat gattcctcag tacggatatc tgactctaaa caacggcagt   1380
cagtctgtgg gacgttcctc cttctactgc ctggagtact tccttctca gatgctgaga    1440
acgggcaata actttgaatt cagctacacc tttgaggaag tgccttttcca cagcagctat   1500
gcgcacagcc agagcctgga ccggctgatg aatcccctca tcgaccagta cctgtactac   1560
ctggcccgga cccagagcac tacggggtcc acaagggagc tgcagttcca tcaggctggg   1620
cccaacacca tggccgagca atcaaagaac tggctgcccg accctgtta tcggcagcag    1680
agactgtcaa aaacatagea cagcaacaac acagtaact ttgcctggac cggggccact     1740
aaataccatc tgaatggtag aaattcatta accaacccgg gcgtagccat ggccaccaac   1800
aaggacgacg aggaccagtt cttteccate aacggagtgc tggttttgg caaaacgggg    1860
gctgccaaca agacaacgct ggaaaacgtg ctaatgacca gcgaggagga gatcaaaacc   1920
accaatcccg tggctacaga agaatacggt gtggtctcca gcaacctgca atcgtctacg   1980
gccgaccccc agacacagac tgtcaacagc caggggggctc tgcccggcat ggtctggcag   2040
aaccgggacg tgtacctgca gggtcccatc tgggccaaaa ttcctcacac ggacggcaac   2100
tttcacccgt ctcccctgat gggcggattt ggactcaaac accgcctcc tcaaattctc    2160
atcaaaaaca ccccggtacc tgctaatcct ccagaggtgt ttactcctgc caagtttgcc   2220
tcatttatca cgcagtacag caccggccag gtcagcgtgg agatcgagtg gaactgcag    2280
aaagaaaaca gcaaacgctg gaatccagag attcagtaca cctcaaatta tgccaagtct   2340
aataatgtgg aatttgctgt caacaacgaa ggggtttata ctgagcctcg ccccattggc   2400
acccgttacc tcacccgtaa cctgtaattg cctgttaatc aataaaccgg ttaattcgtt   2460
tcagttgaac tttggtcaag gcgaattc                                       2489
```

<210> SEQ ID NO 36
<211> LENGTH: 2495
<212> TYPE: DNA
<213> ORGANISM: Unknown
<220> FEATURE:
<223> OTHER INFORMATION: AAV serotype, clone 42.3b

<400> SEQUENCE: 36

```
gaattcgccc tttctacggc tgcgtcaact agaccaatga gaactttccc ttcaacgatt    60
gcgtcgacaa gatggtgatc tggtgggagg agggcaagat gacggccaag gtcgtggagt   120
ccgccaaggc cattcatcat ctgctggggc gggctcccga gattgcttgc tcggcctgcg   180
atctggtcaa cgtggacctg gatgactgtg tttctgagca ataaatgact taaaccaggt   240
atggctgccg atggttatct tccagattgg ctcgaggaca acctctctga gggcattcgc   300
gagtggtggg acttgaaacc tggagccccg aaacccaaag ccaaccagca aaagcaggac   360
gacggccggg gtctggtgct tcctggctac aagtacctcg gaccctttcaa cggactcgac   420
aagggagagc cggtcaacga ggcagacgcc gcggccctcg agcacgacaa ggcctacgac   480
aagcagctcg agcaggggga caacccgtac ctcaagtaca accacgccga cgccgagttt   540
caggagcgtc ttcaagaaga tacgtctttt gggggcaacc tcgggcgagc agtcttccag   600
gccaagaagc gggttctcga acctctcggt ctggttgagg aaggcgctaa gacggctcct   660
ggaaagaaga gacccataga atccccgac tcctccacgg gcatcggcaa gaaaggccag   720
```

```
cagcccgcta aaaagaagct caactttggg cagactggcg actcagagtc agtgcccgac      780
cctcaaccaa tcggagaacc ccccgcaggc ccctctggtc tgggatctgg tacaatggct      840
gcaggcggtg gcgctccaat ggcagacaat aacgaaggcg ccgacggagt gggtaatgcc      900
tccggaaatt ggcattgcga ttccacatgg ctgggcgaca gagtcatcac caccagcacc      960
cgcacctggg ccctgcccac ctacaacaac cacctctaca agcagatatc aagtcagagc     1020
ggggctacca cgacaaccac cttcttcggc tacagcaccc cctggggcta ttttgacttc     1080
aacagattcc actgccactt ctcaccacgt gactggcagc gactcatcaa caacaactgg     1140
ggattccggc cagaaagct gcggttcaag ttgttcaaca tccaggtcaa ggaggtcacg     1200
acgaacgacg gcgttacgac catcgctaat aaccttacca gcacgattca ggtcttctcg     1260
gactcggagt accaactgcc gtacgtcctc ggctctgcgc accagggctg cctccctccg     1320
ttccctgcgg acgtgttcat gattcctcag tacggatatc tgactctaaa caacggcagt     1380
cagtctgtgg gacgttcctc cttctactgc ctggagtact ttccttctca gatgctgaga     1440
acgggcaata actttgaatt cagctacacc tttgaggaag tgccttttcca cagcagctat     1500 gcgcacagcc agagcctgga ccggctgatg aatccccctca tcgaccagta cctgtactac     1560
ctggcccgga cccagagcac tacggggtcc acaaggggag tgcagttcca tcaggctggg     1620
cccaacacca tggccgagca atcaaagaac tggctgcccg accctgtta tcggcagcag     1680 agactgtcaa aaaacataga cagcaacaac accagtaact tgcctggac cggggccact     1740 aaataccatc tgaatggtag aaattcatta accaacccgg gcgtagccat ggccaccaac     1800
aaggacgacg aggaccagtt cttttccatc aacggagtgc tggtttttgg caaaacgggg     1860
gctgccaaca gacaacgct ggaaaacgtg ctaatgacca gcgaggagga gatcaaaacc     1920
accaatcccg tggctacaga acagtacggt gtggtctcca gcaacctgca atcgtctacg     1980
gccggacccc agacacagac tgtcaacagc caggggctc tgcccggcat ggtctggcag     2040
aaccgggacg tgtacctgca gggtcccatc tgggccaaaa ttcctcacac ggacggcaac     2100
tttcacccgt ctcccctgat gggcggattt ggactcaaac accccgcctcc tcaaattctc     2160 atcaaaaaca ccccggtacc tgctaatcct ccagaggtgt ttactcctgc caagtttgcc     2220
tcatttatca cgcagtacag caccggccag gtcagcgtgg agatcgagtg ggaactgcag     2280
aaagaaaaca gcaaacgctg gaatccagag attcagtaca cctcaaatta tgccaagtct     2340
aataatgtgg aatttgctgt caacaacgaa ggggtttata ctgagcctcg ccccattggc     2400
acccgttacc tcacccgtaa cctgtaattg cctgttaatc aataaaccgg ttaattcgtt     2460
tcagttgaac tttggtctct gcgaagggcg aattc                                2495
```

<210> SEQ ID NO 37
<211> LENGTH: 3098
<212> TYPE: DNA
<213> ORGANISM: Unknown
<220> FEATURE:
<223> OTHER INFORMATION: AAV serotype, clone 42.11

<400> SEQUENCE: 37

```
gaattcgccc tttctacggc tgcgtcaact ggaccaatga aactttccc ttcaacgatt       60 gcgtcgacaa gatggtgatc tggtgggagg agggcaagat gacggccaag gtcgtggagt      120
ccgccaaggc cattctcggc ggcagcaagg tgcgcgtgga ccaaaagtgc aagtcttccg      180
cccagatcga tccacccccc gtgatcgtca cttccaacac caacatgtgc gccgtgattg      240
acgggaacag caccaccttc gagcaccagc agccgttaca agaccggatg ttcaaatttg      300
```

```
aactcacccg ccgtctggag cacgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gccccgatg acgcggataa aagcgagccc aagcgggcct    480
gccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accggagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca aagccaacca gcaaaagcag    960
gacgacggcc ggggtctggt gcttcctggc tacaagtacc tcggacccct caacggactc   1020
gacaagggag agccggtcaa cgcggcggac gcagcggccc tcgagcacga caaggcctac   1080
gaccagcagc tcaaagcggg tgacaatccg tacctgcgt ataaccacgc cgacgccgag   1140
tttcaggagc gtcttcaaga agatacgtct tttgggggca acctcgggcg agcagtcttc   1200
caggccaaga agcgggttct cgaacctctc ggtctggttg aggaaggcgc taagacggct   1260
cctggaaaga agagacccat agaatccccc gactcctcca cgggcatcgg caagaaaggc   1320
cagcagcccg ctaaaaagaa gctcaacttt gggcagactg gcgactcaga gtcagtgccc   1380
gaccctcaac caatcggaga accccccgca ggccctctg gtctgggatc tggtacaatg   1440
gctgcaggcg gtggcgctcc aatggcagac aataacgaag gcgccgacgg agtgggtaat   1500
gcctccggaa attggcattg cgattccaca tggctgggcg acagagtcat caccaccagc   1560
acccgcacct gggcctgcc cacctacaac aaccacctct acaagcagat atcaagtcag   1620
agcggggcta ccaacgacaa ccacttcttc ggctacagca cccctgggg ctatttgac   1680
ttcaacagat tccactgcca cttctcacca cgtgactggc agcgactcat caacaacaac   1740
tggggattcc ggcccagaaa gctgcggttc aagttgttca acatccaggt caaggaggtc   1800
acgacgaacg acggcgttac gaccatcgct aataacctta ccagcacgat tcaggtcttc   1860
tcggactcgg agtaccaact gccgtacgtc ctcggctctg cgcaccaggg ctgcctccct   1920
ccgttccctg cggacgtgtt catgattcct cagtacggat atctgactct aaacaacggc   1980
agtcagtctg tgggacgttc ctccttctac tgcctggagt actttccttc tcagatgctg   2040
agaacgggca ataactttga attcagctac acctttgagg aagtgccttt ccacagcagc   2100
tatgcgcaca gccagagcct ggaccggctg atgaatcccc tcatcgacca gtacctgtac   2160
tacctggccc ggacccagag cactacgggg tccacaaggg agctgcagtt ccatcaggct   2220
gggcccaaca ccatggccga gcaatcaaag aactggctgc ccgaccctg ttatcggcgg   2280
cagagactgt caaaagacat agacagcaac aacaacagta actttgcctg gaccggggcc   2340
actaaatacc atctgaatgg tagaaattca ttaaccaacc cgggcgtagc catggccacc   2400
aacaaggacg acgaggacca gttcttccc atcaacggag tgctggtttt tggcaaaacg   2460
ggggctgcca acaagacaac gctggaaaac gtgctaatga ccagcgagga ggagatcaaa   2520
accaccaatc ccgtggctac agaagaatac ggtgtggtct ccagcaacct gcaatcgtct   2580
acggccggac cccagacaca gactgtcaac agccagggg ctctgcccgg catggtctgg   2640
```

-continued

| | |
|---|---|
| cagaaccggg acgtgtacct gcagggtccc atctgggcca aaattcctca cacggacggc | 2700 |
| aactttcacc cgtctcccct gatgggcgga tttggactca acacccgcc tcctcaaatt | 2760 |
| ctcatcaaaa acaccccggt acctgctaat cctccagagg tgtttactcc tgccaagttt | 2820 |
| gcctcattta tcacgcagta cagcaccggc caggtcagcg tggagatcga gtgggaactg | 2880 |
| cagaaagaga acagcaaacg ctggaatcca gagattcagt acacctcaaa ttatgccaag | 2940 |
| tctaataatg tggaatttgc tgtcaacaac gaagggttt atactgagcc tcgcccatt | 3000 |
| ggcacccgtt acctcacccg taacctgtaa ttacttgtta atcaataaac cggttgattc | 3060 |
| gtttcagttg aactttggtc tctgcgaagg gcgaattc | 3098 |

<210> SEQ ID NO 38
<211> LENGTH: 3276
<212> TYPE: DNA
<213> ORGANISM: Unknown
<220> FEATURE:
<223> OTHER INFORMATION: AAV serotype, clone 42.6a

<400> SEQUENCE: 38

| | |
|---|---|
| gaattcgccc ttcgcagaga ccaaagttca actgaaacga attaaccggt ttattgatta | 60 |
| acaggcaatt acaggttacg ggtgaggtaa cgggtgccaa tggggcgagg ctcagtataa | 120 |
| accccttcgt tgttgacagc aaattccaca ttattagact tggcataatt tgaggtgtac | 180 |
| tgaatctctg gattccagcg tttgctgttt tctttctgca gttcccactc gatctccacg | 240 |
| ctgacctggc cggtgctgta ctgcgtgata aatgaggcaa acttggcagg agtaaacacc | 300 |
| tctggaggat tagcaggtac cggggtgttt ttgatgagaa tttgaggagg cgggtgtttg | 360 |
| agtccaaatc cgtccatcag gggagacggg tgaaagttgc cgtccgtgtg aggaattttg | 420 |
| gcccagatgg gaccctgcag gtacacgtcc cggttctgcc agaccatgcc gggcagagcc | 480 |
| ccctggctgt tgacagtctg tgtctggggt ccggccgtag acgattgcag gttgctggag | 540 |
| accacaccgt attcttctgt agccacggga ttggtggttt tgatctcctc ctcgctggtc | 600 |
| attagcacgt tttccagcgt tgtcttgttg gcagcccccg ttttgccaaa aaccagcact | 660 |
| ccgttgatgg gaaagaactg gtcctcgtcg tccttgttgg tggccatggc tacgcccggg | 720 |
| ttggttaatg aatttctacc attcagatgg tatttagtgg ccccggtcca ggcaaagtta | 780 |
| ctgttgttgt tgctgtctat gttttttgac agtctctgct gccgataaca gggtccgggc | 840 |
| agccagttct ttgattgctc ggccatggtg ttgggcccag cctgatggaa ctgcagctcc | 900 |
| cttgtggacc ccgtagtgct ctgggtccgg gccaggtagt acaggtactg gtcgatgagg | 960 |
| ggattcatca gccggtccag gctctggcta tgcgcatagc tgctgtggaa aggcacttcc | 1020 |
| tcaaggtgt agctgaattc aaagttattg cccgttctca gcatctgaga aggaaagtac | 1080 |
| tccaggcagt agaaggagga acgtcccaca gactgactgc cgttgtttag agtcagatat | 1140 |
| ccgtactgag gaatcatgaa cacgtccgca gggaacggag ggaggcagcc ctggtgcgca | 1200 |
| gagccgagga cgtacggcag ttggtactcc gagtccgaga agacctgaat cgtgctggta | 1260 |
| aggttattag cgatggtcgt aacgccgtcg tccgtcgtga cctccttgac ctggatgttg | 1320 |
| aacaacttga accgcagctt tctgggccgg aatccccagt tgttgttgat gagtcgctgc | 1380 |
| cagtcacgtg gtgagaagtg gcagtggaat ctgttaaagt caaatacccc caggggggtg | 1440 |
| ctgtagccga agtaggtgtt gtcgttggtg cttcctcccg atgtcccgtt ggagatttgc | 1500 |
| ttgtagaggt ggttgttgta ggtgggaggg gcccaggttc gggtgctggt ggtgatgact | 1560 |
| ctgtcgccca gccatgtgga atcgcaatgc caatttcctg aggaactacc cactccgtcg | 1620 |

-continued

```
gcgccttcgt tattgtctgc cattggagcg ccaccgcctg cagccattgt accagatccc    1680
agaccagagg ggcctgcggg gggttctccg attggttgag ggtcgggcac tgactctgag    1740
tcgccagtct gcccaaagtt gagtctcttt ttcgcgggct gctggcctgt cttgccgatg    1800
cccgtagagg agtctggaga acgctggggt gatggctcta ccggtctctt ctttccagga    1860
gccgtcttag cgccttcctc aaccagaccg agaggttcga gaacccgctt cttggcctgg    1920
aagactgctc gcccgaggtt gcccccaaaa gacgtatctt cttgaagacg ctcctgaaac    1980
tcggcgtcgg cgtggttgta cttgaggtac gggttgtccc cctgctcgag ctgcttgtcg    2040
taggccttgt cgtgctcgag ggccgcgcg tctgcctcgt tgaccggctc tcccttgtcg    2100
agtccgttga agggtccgag gtacttgtag ccaggaagca ccagaccccg gccgtcgtcc    2160
tgcttttgct ggttggcttt gggtttcggg gctccaggtt tcaagtccca ccactcgcga    2220
atgccctcag agaggttgtc ctcgagccaa tctggaagat aaccatcggc agccatacct    2280
ggtttaagtc atttattgct cagaaacaca gtcatccagg tccacgttga ccagatcgca    2340
ggccgagcaa gcaatctcgg gagcccgccc cagcagatga tgaatggcac agagtttccg    2400
atacgtcctc tttctgacga ccggttgaga ttctgcacg ccggggaaac attctgaaca    2460
gtctctggtc ccgtgcgtga agcaaatgtt gaaattctga ttcattctct cgcatgtctt    2520
gcagggaaac agcatctgaa gcatgcccgc gtgacgagaa cacttgtttt ggtacctgtc    2580
ggcaaagtcc accggagctc cttccgcgtc tgacgtcgat ggatgcaaaa tgtcgcaaaa    2640
gcactcacgt gacagctaat acaggaccac tcccctatga cgtgatttac gtcagcgcta    2700
tgcccgcgtg acgagaacat ttgttttggt acctgtcggc aaagtccacc ggagctcctt    2760
ccgcgtctga cgtcgatgga tccgcgactg aggggcaggc ccgcttgggc tcgcttttat    2820
ccgcgtcatc gggggcgggt ctcttgttgg ctccacccct tctgacgtag aactcatgcg    2880
ccacctcggt cacgtgatcc tgcgcccagc ggaagaactc tttgacttcc tgctttgtca    2940
ccttgccaaa gtcatgctcc agacggcggg tgagttcaaa tttgaacatc cggtcctgca    3000
acggctgctg gtgctcgaag gtggtgctgt tcccgtcaat cacggcgcac atgttggtgt    3060
tggaagtgac gatcacgggg gtgggatcga tctgggcgga agacttgcac ttttggtcca    3120
cgcgcacctt gctgccgccg agaatggcct tggcggactc cacgaccttg gccgtcatct    3180
tgccctcctc ccaccagatc accatcttgt cgacgcaatc gttgaaggga aagttctcat    3240
tggtccagtt gacgcagccg tagaaagggc gaattc                              3276
```

<210> SEQ ID NO 39
<211> LENGTH: 3084
<212> TYPE: DNA
<213> ORGANISM: Unknown
<220> FEATURE:
<223> OTHER INFORMATION: AAV serotype, clone 43.1

<400> SEQUENCE: 39

```
gaattcgccc tttctacggc tgcatcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga ccccacccc gtgatcgtca cctccaacac caacatgtgc gccgtgattg    240
acgggaacag caccaccttc gagcaccagc agccgttgca ggaccggatg ttcaagttcg    300
aactcacccg ccgtctggag cacgactttg gcaaggtgac caagcaggaa gtcaaagagt    360
```

```
tcttccgctg gcgcaggat cacgtgaccg aggtggcgca tgagttctac gtcagaaagg    420
gcggagccag caaaagaccc gcccccgatg acgcggatat aagcgagccc aagcgggcct    480
gccccctcagt cgcggatcca tcgacgtcag acgcggaagg agctccggtg gactttgccg    540
acaggtacca aaacaaatgt tctcgtcacg cgggcatgct tcagatgctg tttccctgca    600
aaacgtgcga gaaatgaat cagaatttca acatttgctt cacgcacggg gtcagagact    660
gctcagaatt ttccccggt gcatcagaat ctcaaccggt cgtcagaaaa aaacgtatc     720
agaaactgtg tgccattcat catctgctgg ggcgggcacc cgagattgct tgctcggcct    780
gcgatctggt caacgtggac ctggacgact gtgtttctga gcaataaatg acttaaacca    840
ggtatggctg ccgatggtta tcttccagat tggcttgagg acaacctctc tgagggcatt    900
cgcgagtggt gggacctgaa acctggagcc ccgaaaccca agccaaccca gcaaaagcag    960
gacgacggcc ggggtctggt gcttcctggc tacaagtacc tcggacccttt caacggactc    1020
gacaagggg agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtctgcaaga agatacgtct tttgggggca acctcggcg agcagtcttc    1200
caggccaaga agcgggttct cgaacctctc ggtctggttg aggaaggcgc taagacggct    1260
cctggaaaga agagaccggt agagccatca cctcagcgtt ccccccgactc ctccacgggc    1320
atcggcaaga aaggccacca gcccgcgaga aagagactga actttgggca gactggcgac    1380
tcggagtcag tccccgaccc tcaaccaatc ggagaaccac cagcaggccc ctctggtctg    1440
ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctgcccacct acaacaacca tctctacaag    1620
caaatctcca cgggacatc gggaggaagc actaacgaca cacctactt tggctacagc    1680
accccctggg ggtattttga cttcaacaga ttccactgcc acttctcacc acgtgactgg    1740
cagcgactca tcaacaataa ctggggattc cggcccaaga gactcaactt caagctcttc    1800
aacatccagg tcaaggaggt cacgcagaat gaaggcacca agaccatcgc caataacctt    1860
accagcacga ttcaggtgtt tacggactcg gaataccagc tcccgtacgt ccccggctct    1920
gcgcaccagg gctgcctccc tccgttcccg gcggacgtct tcatgattcc tcagtacggg    1980
tatctgaccc taaacaatgg cagtcaggct gtgggccgtt cctccttcta ctgcctggaa    2040
tacttcccttt ctcaaatgct gaggacgggc aacaactttg aattcagcta caccttcgag    2100
gacgtgcctt tccacagcag ctacgcgcac agccagagcc tggaccggct gatgaaccct    2160
ctcatcgacc agtacctgta ttacttatcc agaactcagt ccacaggagg aactcaaggt    2220
actcagcaat tgttattttc tcaagccggg cccgcaaaca tgtcggctca ggccaagaac    2280
tggctacctg gaccgtgtta ccgtcagcaa cgagttttcca cgacactgtc gcaaaacaac    2340
aacagcaatt ttgcttggac cggtgccacc aagtatcacc tgaatggcag agactccctg    2400
gttaatccccg gcgttgccat ggctacccac aaggacgacg aggagcgctt cttcccgtca    2460
agcggagttc taatgtttgg caagcagggg gctggaaaag acaatgtgga ctacagcagc    2520
gtgatgctca ccagcgaaga agaaattaaa actactaacc cagtggctac agagcagtat    2580
ggtgtggtgg cagacaacct gcagcagacc aacggagctc ccattgtggg aactgtcaac    2640
agccaggggg ccttacctgg tatggtctgg caaaaccggg acgtgtacct gcagggcccc    2700
atctgggcca aaattcctca cacggacggc aactttcatc cttcgccgct gatgggaggc    2760
```

```
tttggactga aacacccgcc tcctcagatc ctggtgaaaa acactcctgt tcctgcggat    2820
cctccgacca ccttcagcca ggccaagctg gcttctttta tcacgcagta cagcaccgga    2880
caggtcagcg tggaaatcga atgggagctg cagaaagaaa acagcaagcg ctggaaccca    2940
gagattcagt atacttccaa ctactacaaa tctacaaatg tggactttgc tgtcaatact    3000
gagggtactt attcagagcc tcgccccatt ggcactcgtt atctcacccg taatctgtaa    3060
ttgcttgtta atcaataaac cggt                                          3084

<210> SEQ ID NO 40
<211> LENGTH: 2370
<212> TYPE: DNA
<213> ORGANISM: Unknown
<220> FEATURE:
<223> OTHER INFORMATION: AAV serotype, clone 43.5

<400> SEQUENCE: 40
gaattcgccc tttctacggc tgcgtcaact ggaccaatga aactttccc ttcaacgatt      60 gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga ccccaccccc gtgatcgtca cctccaacac caacatgtgc gccgtgattg    240
acgggaacag caccaccttc gagcaccagc agccgttgca ggaccggatg ttcaagttcg    300
aactcacccg ccgtctggag cacgactttg gcaaggtgac caagcaggaa gtcaaagagt    360
tcttccgctg ggcgcaggat cacgtgaccg aggtggcgca tgagttctac gtcagaaagg    420
gcggagccag caaaagaccc gcccccgatg acgcggatat aagcgagccc aagcgggcct    480 gccctcagt cgcggatcca tcgacgtcag acgcggaagg agctccggtg gactttgccg    540
acaggtacca aaacaaatgt tctcgtcacg cgggcatgct tcagacgctg tttccctgca    600
aaacgtgcga gaatgaat cagaatttca acatttgctt cacgcacggg gtcagagact    660
gctcagaatg tttccccggt gcatcagaat ctcaaccggt cgtcagaaaa aaaacgtatc    720
agaaactgtg tgccattcat catctgctgg ggcgggcacc cgagattgct tgctcggcct    780
gcgatctggt caacgtggac ctggacgact gtgtttctga gcaataaatg acttaaacca    840
ggtatggctg ccgatggtta tcttccagat tggcttgagg acaacctctc tgagggcatt    900
cgcgagtggt gggacctgaa acctggagcc ccgaaaccca agccaaccag caaaagcag    960 gacgacggcc ggggtctggt gcttcctggc tacaagtacc tcggaccctt caacggactc   1020
gacaaggggg agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtctgcaaga agatacgtct ttggggggca acctcgggcg agcagtcttc   1200
caggccaaga agcgggttct cgaacctctc ggtctggttg aggaaggcgc taagacggct   1260
cctggaaaga gagaccggt agagccatca cctcagcgtt ccccgactc ctccacgggc   1320 atcggcaaga aaggccacca gcccgcgaga aagagactga actttggca gactggcgac   1380 tcggagtcag tccccgaccc tcaaccaatc ggagaaccac cagcaggccc ctctggtctg   1440 ggatctgta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctggccc ctgcccacct acaacaacca tctctacaag   1620
caaatctcca acgggacatc gggaggaagc actaacgaca caccactt tggctacagc   1680
```

| | |
|---|---|
| acccccctggg ggtattttga cttcaacaga ttccactgcc acttctcacc acgtgactgg | 1740 |
| cagcgactca tcaacaataa ctggggattc cggcccaaga gactcaactt caagctcttc | 1800 |
| aacatccagg tcaaggaggt cacgcagaat gaaggcacca agaccatcgc caataacctt | 1860 |
| accagcacga ttcaggtgtt tacggactcg gaataccagc tcccgtacgt cctcggctct | 1920 |
| gcgcaccagg gctgcctccc tccgttcccg gcggacgtct tcatgattcc tcagtacggg | 1980 |
| tatctgaccc taaacaatgg cagtcaggct gtgggccgtt cctccttcta ctgcctggaa | 2040 |
| tacttcccctt ctcaaatgct gaggacgggc aacaactttg aattcagcta caccttcgag | 2100 |
| gacgtgcctt tccacagcag ctacgcgcac agccagagcc tggaccggct gatgaaccct | 2160 |
| ctcatcgacc agtacctgta ttacttatcc agaactcagt ccacaggagg aactcaaggt | 2220 |
| actcagcaat tgttattttc tcaagccggg cccgcaaaca tgtyggctca ggccaagaac | 2280 |
| tggctacctg gaccgtgtta ccgtcagcaa cgagtttcca cgacactgtc gcaaaacaac | 2340 |
| aacagcaatt ttgctggacc ggtgccacca | 2370 |

<210> SEQ ID NO 41
<211> LENGTH: 3123
<212> TYPE: DNA
<213> ORGANISM: Unknown
<220> FEATURE:
<223> OTHER INFORMATION: AAV serotype, clone 43.12

<400> SEQUENCE: 41

| | |
|---|---|
| gaattcgccc ttggctgcgt caactggacc aatgagaact ttcccttcaa cgattgcgtc | 60 |
| gacaagatgg tgatctggtg ggaggagggc aagatgacgg ccaaggtcgt ggagtccgcc | 120 |
| aaggccattc tcggcggcag caaggtgcgc gtggaccaaa agtgcaagtc gtccgcccag | 180 |
| atcgacccca cccccgtgat cgtcacctcc aacaccaaca tgtgcgccgt gattgacggg | 240 |
| aacagcacca ccttcgagca ccagcagccg ttgcaggacc ggatgttcaa gttcgaactc | 300 |
| acccgccgtc tggagcacga cttttggcaag gtgaccaagc aggaagtcaa agagttcttc | 360 |
| cgctgggcgc aggatcacgt gaccgaggtg gcgcatgagt tctacgtcag aaagggcgga | 420 |
| gccagcaaaa gacccgcccc cgatgacgcg gatataagcg agcccaagcg ggcctgcccc | 480 |
| tcagtcgcgg atccatcgac gtcagacgcg gaaggagctc cggtggactt tgccgacagg | 540 |
| taccaaaaca aatgttctcg tcacgcgggc atgctccaga tgctgttccc ctgcaaaacg | 600 |
| tgcgagagaa tgaatcagaa tttcaacatt tgcttcacgc acggggtcag agactgctca | 660 |
| gaatgtttcc ccggtgcatc agaatctcaa ccggtcgtca gaaaaaaaac gtatcagaaa | 720 |
| ctgtgtgcca ttcatcatct gctggggcgg gcacccgaga ttgcttgctc ggcctgcgat | 780 |
| ctggtcaacg tggacctgga cgactgtgtt tctgagcaat aaatgactta aaccaggtat | 840 |
| ggctgccgat ggttatcttc cagattggct tgaggacaac ctctctgagg gcattcgcga | 900 |
| gtggtgggac ctgaaacctg gagccccgaa acccaaagcc aaccagcaaa agcaggacga | 960 |
| cggccggggt ctggtgcttc ctggctacaa gtacctcgga cccttcaacg gactcgacaa | 1020 |
| gggggagccc gtcaacgcgg cggacgcagc ggccctcgag cacgacaagg cctacgacca | 1080 |
| gcagctcaaa gcgggtgaca atccgtacct gcggtataac cacgccgacg ccgagtttca | 1140 |
| ggagcgtctg caagaagata cgtcttttgg gggcaacctc gggcgagcag tcttccaggc | 1200 |
| caagaagcgg gttctcgaac ctctcggtct ggttgaggaa ggcgctaaga cggctcctgg | 1260 |
| aaagaagaga ccggtagagc catcacctca gcgttccccc gactcctcca cgggcatcgg | 1320 |
| caagaaaggc caccagcccg cgagaaagag actgaacttt gggcagactg gcgactcgga | 1380 |

```
gtcagtcccc gaccctcaac caatcggaga accaccagca ggcccctctg gtctgggatc    1440
tggtacaatg gctgcaggcg gtggcgctcc aatggcagca aataacgaag cgccgacgg     1500 agtgggtagt tcctcaggaa attggcattg cgattccaca tggctgggcg acagagtcat   1560
caccaccagc acccgaacct gggccctgcc cacctacaac aaccatctct acaagcaaat   1620
ctccaacggg acatcgggag gaagcactaa cgacaacacc tactttggct acagcacccc   1680
ctgggggtat tttgacttca acagattcca ctgccacttc tcaccacgtg actggcagcg   1740
actcatcaac aataactggg gattccggcc caagagactc aacttcaagc tcttcaacat   1800
ccaggtcaag gaggtcacgc agaatgaagg caccaagacc atcgccaata accttaccag   1860
cacgattcag gtgtttacgg actcggaata ccagctcccg tacgtcctcg gctctgcgca   1920
ccagggctgc ctccctccgt tcccggcgga cgtcttcatg attcctcagt acggtatct    1980 gaccctaaac aatggcagtc aggctgtggg ccgttcctcc ttctactgcc tggaatactt   2040
cccttctcaa atgctgagga cgggcaacaa ctttgaattc agctacacct tcgaggacgt   2100 gccttttccac agcagctacg cgcacagcca gagcctggac cggctgatga ccctctcat   2160 cgaccagtac ctgtattact tatccagaac tcagtccaca ggaggaactc aaggtactca   2220
gcaattgtta tttctcaag ccgggcccgc aaacatgtcg gctcaggcca gaactggct    2280 acctggaccg tgttaccgtc agcaacgagt ttccacgaca ctgtcgcaaa caacaacag    2340 caatttttgct tggaccggtg ccaccaagta tcacctgaat ggcagagact ccctggttaa   2400
tcccggcgtt gccatggcta cccacaagga cgacgaggag cgcttcttcc cgtcaagcgg   2460
agttctaatg tttggcaagc aggggggctgg aaaagacaat gtggactaca gcagcgtgat   2520
gctcaccagc gaagaagaaa ttaaaactac taacccagtg gctacagagc agtatggtgt   2580
ggtggcagac aacctgcagc agaccaacgg agctcccatt gtgggaactg tcaacagcca   2640
gggggcctta cctggtatgg tctggcaaaa ccgggacgtg tacctgcagg gccccatctg   2700
ggccaaaatt cctcacacgg acggcaactt tcatccttcg ccgctgatgg gaggctttgg   2760
actgaaacac ccgccctcc agatcctggt gaaaaacact cctgttcctg cggatcctcc    2820
gaccaccttc agccaggcca agctggcttc ttttatcacg cagtacagca ccggacaggt   2880
cagcgtggaa atcgaatggg agctgcagaa agaaaacagc aagcgctgga acccagagat   2940
tcagtatact tccaactact acaaatctac aaatgtggac tttgctgtca atactgaggg   3000
tacttattca gagcctcgcc ccattggcac tcgttatctc acccgtaatc tgtaattgct   3060
tgttaatcaa taaaccggtt aattcgtttc agttgaactt tggtctctgc gaagggcgaa   3120
ttc                                                                 3123

<210> SEQ ID NO 42
<211> LENGTH: 3122
<212> TYPE: DNA
<213> ORGANISM: Unknown
<220> FEATURE:
<223> OTHER INFORMATION: AAV serotype, clone 43.20

<400> SEQUENCE: 42
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgtgtgga ccaaaagtgc aagtcttccg    180
cccagatcga tcccaccccc gtgatcgtca cctccaacac caacatgtgc gccgtgattg    240
```

```
acgggaacag cgccaccttc gagcaccagc agccgttgca ggaccggatg ttcaaatttg    300
aactcacccg ccgtctggag catgactttg gcaaggtgac gaagcaggaa gtcaaagagt    360
tcttccgctg ggcgcaggat cacgtgaccg aggtggcgca tgagttccac gtcagaaagg    420
gtggagccaa caagagaccc gccccgatg acgcggatat aagcgagccc aagcgggcct     480 gccccctcagt cgcggatcca tcgacgtcag acgcggaagg agctccggtg actttgccg    540 acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag gggacgtatc    720
ggaaactctg tgcgattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggacccctt caacggactc    1020 gacaaggggg agcccgtcaa cgcggcggac gcagcggccc tcgagcacga caaagcctac    1080
gaccagcagc tcaaagcggg tgacaatccg tacctgcgtg taatcacgc cgacgccgag     1140 tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga agagactggt agagcagtcg ccacaagagc cagactcctc ctcgggcatc    1320
ggcaagacag gccagcagcc cgctaaaaag agactcaatt ttggtcagac tggcgactca    1380
gagtcagtcc ccgacccaca acctctcgga gaacctccag cagcccctc aggtctggga     1440 cctaatacaa tggcttcagg cggtggcgct ccaatggcag acaataacga aggcgccgac    1500
ggagtgggta attcctcggg aaattggcat tgcgattcca catggctggg ggacagagtc    1560
atcaccacca gcacccgaac ctgggccctg cccacctaca caaccaccct ctacaagcaa    1620
atctccaacg gcacctcggg aggaagcacc aacgacaaca cctattttgg ctacagcacc    1680
ccctgggggt atttttgactt caacagattc cactgtcact tttcaccacg tgactggcaa    1740
cgactcatca acaacaattg gggattccgg cccaaaagac tcaacttcaa gctgttcaac    1800
atccaggtca aggaagtcac gacgaacgaa ggcaccaaga ccatcgccaa taatctcacc    1860
agcaccgtgc aggtctttac ggactcggag taccagttac cgtacgtgct aggatccgct    1920
caccagggat gtctgcctcc gttcccggcg gacgtcttca cggttcctca gtacggctat    1980
ttaactttaa caatggaag ccaagccctg gacgttcct ccttctactg tctggagtat       2040
ttcccatcgc agatgctgag aaccggcaac aactttcagt tcagctacac cttcgaggac    2100
gtgcctttcc acagcagcta cgcgcacagc cagagcctgg acaggctgat gaatcccctc    2160
atcgaccagt acctgtacta cctggtcaga acgcaaacga ctggaactgg agggacgcag    2220
actctggcat tcagccaagc gggtcctagc tcaatggcca accaggctag aaattgggtg    2280 cccggaccttt gctaccggca gcagcgcgtc tccacgacaa ccaaccagaa caacaacagc    2340
aactttgcct ggacgggagc tgccaagttt aagctgaacg gccgagactc tctaatgaat    2400
ccgggcgtgg caatggcttc ccacaaggat gacgacgacc gcttcttccc ttcgagcggg    2460
gtcctgattt ttggcaagca aggagccggg aacgatggag tggattacag ccaagtgctg    2520
attacagatg aggaagaaat caaggctacc aaccccgtgg ccacagaaga atatggagca    2580
gtggccatca caaccaggc cgccaatacg caggcgcaga ccggactcgt gcacaaccag    2640
```

| | |
|---|---:|
| ggggtgattc ccggcatggt gtggcagaat agagacgtgt acctgcaggg tcccatctgg | 2700 |
| gccaaaattc ctcacacgga cggcaacttt cacccgtctc ccctgatggg cggctttgga | 2760 |
| ctgaagcacc cgcctcctca aattctcatc aagaacacac cggttccagc ggacccgccg | 2820 |
| cttaccttca accaggccaa gctgaactct ttcatcacgc agtacagcac cggacaggtc | 2880 |
| agcgtggaaa tcgagtggga gctgcagaaa gaaaacagca aacgctggaa tccagagatt | 2940 |
| caatacactt ccaactacta caaatctaca aatgtggact tgctgtcaa cacggaagga | 3000 |
| gtttatagcg agcctcgccc cattggcacc cgttacctca cccgcaacct gtaattacat | 3060 |
| gttaatcaat aaaccggtta attcgtttca gttgaacttt ggtctctgcg aagggcgaat | 3120 |
| tc | 3122 |

<210> SEQ ID NO 43
<211> LENGTH: 3117
<212> TYPE: DNA
<213> ORGANISM: Unknown
<220> FEATURE:
<223> OTHER INFORMATION: AAV serotype, clone 43.21

<400> SEQUENCE: 43

| | |
|---|---:|
| gaattcgccc ttggctgcgt caactggacc aatgagaact ttcccttcaa cgattgcgtc | 60 |
| gacaagatgg tgatctggtg ggaggagggc aagatgacgg ccaaggtcgt ggagtccgcc | 120 |
| aaggccattc tcggcggcag caaggtgcgt gtggaccaaa agtgcaagtc ttccgcccag | 180 |
| atcgatccca cccccgtgat cgtcacctcc aacaccaaca tgtgcgccgt gattgacggg | 240 |
| aacagcacca ccttcgagca ccagcagccg ttgcaggacc ggatgttcaa atttgaactc | 300 |
| acccgccgtc tggagcatga ctttggcaag gtgacgaagc aggaagtcaa agagttcttc | 360 |
| cgctgggcgc aggatcacgt gaccgaggtg gcgcatgagt tccacgtcag aaagggtgga | 420 |
| gccaacaaga gacccgcccc cgatgacgcg gatataagcg agcccaagcg ggcctgcccc | 480 |
| tcagtcgcgg atccatcgac gtcagacgcg gaaggagctc cggtggactt tgccgacagg | 540 |
| taccaaaaca aatgttctcg tcacgcgggc atgcttcaga tgctgtttcc ctgcaagaca | 600 |
| tgcgagagaa tgaatcagaa tttcaacatt tgcttcacgc acgggaccag agactgttca | 660 |
| gaatgtttcc ccggcgtgtc agaatctcaa ccggtcgtca gaaagaggac gtatcggaaa | 720 |
| ctctgtgcga ttcatcatct gctggggcgg gctcccgaga ttgcttgctc ggcctgcgat | 780 |
| ctggtcaacg tggacctgga tgactgtgtt tctgagcaat aaatgactta aaccaggtat | 840 |
| ggctgccgat ggttatcttc cagattggct cgaggacaac ctctctgagg cattcgcga | 900 |
| gtggtgggac ttgaaacctg gagccccgaa acccaaagcc aaccagcaaa agcaggacga | 960 |
| cggccggggt ctggtgcttc ctggctacaa gtacctcgga cccttcaacg gactcgacaa | 1020 |
| ggggagccc gtcaacgcgg cggacgcagc ggccctcgag cacgacaaag cctacgacca | 1080 |
| gcagctcaaa gcgggtgaca atccgtacct gcggtataat cacgccgacg ccgagtttca | 1140 |
| ggagcgtctg caagaagata cgtctttttgg gggcaacctc gggcgagcag tcttccaggc | 1200 |
| caagaagcgg gttctcgaac ctctcggtct ggttgaggaa ggcgctaaga cggctcctgg | 1260 |
| aaagaagaga ccggtagagc agtcgccaca agagccagac cctcctcgg gcatcggcaa | 1320 |
| gacaggccag cagcccgcta aaaagagact caattttggt cagactggcg actcagagtc | 1380 |
| agtccccgac ccacaacctc tcggagaacc tccagcagcc cctcaggtc tgggacctaa | 1440 |
| tacaatggct tcaggcggtg gcgctccaat ggcagacaat aacgaaggcg ccgacggagt | 1500 |

-continued

| | |
|---|---|
| gggtaattcc tcgggaaatt ggcattgcga ttccacatgg ctgggggaca gagtcatcac | 1560 |
| caccagcacc cgaacctggg ccctgcccac ctacaacaac cacctctaca agcaaatctc | 1620 |
| caacggcacc tcgggaggaa gcaccaacga caacacctat tttggctaca gcaccccctg | 1680 |
| ggggtatttt gacttcaaca gattccactg tcactttca ccacgtgact ggcaacgact | 1740 |
| catcaacaac aattggggat tccggcccaa aagactcaac ttcaagctgt tcaacatcca | 1800 |
| ggtcaaggaa gtcacgacga acgaaggcac caagaccatc gccaataatc tcaccagcac | 1860 |
| cgtgcgggtc tttacggact cggagtacca gttaccgtac gtgctaggat ccgctcacca | 1920 |
| gggatgtctg cctccgttcc cggcggacgt cttcatggtt cctcagtacg gctatttaac | 1980 |
| tttaaacaat ggaagccaag ccctgggacg ttcctccttc tactgtctgg agtatttccc | 2040 |
| atcgcagatg ctgagaaccg gcaacaactt tcagttcagc tacaccttcg aggacgtgcc | 2100 |
| tttccacagc agctacgcgc acagccagag cctggacagg ctgatgaatc ccctcatcga | 2160 |
| ccagtacctg tactacctgg tcagaacgca aacgactgga actggaggga cgcagactct | 2220 |
| ggcattcagc caagcgggtc ctagctcaat ggccaaccag gctagaaatt gggtgcccgg | 2280 |
| accttgctac cggcagcagc gcgtctccac gacaaccaac cagagcaaca acagcaactt | 2340 |
| tgcctggacg ggagctgcca gtttaagct gaacggccga gactctctaa tgaatccggg | 2400 |
| cgtggcaatg gcttcccaca aggatgacga cgaccgcttc ttcccttcga gcggggtcct | 2460 |
| gattttggc aagcaaggag ccgggaacga tggagtggat tacagccaag tgctgattac | 2520 |
| agatgaggaa gaaatcaagg ctaccaaccc cgtggccaca aagaatatg agcagtggc | 2580 |
| catcaacaac caggccgcca atcgcaggc gcagaccgga ctcgtgcaca ccagggggt | 2640 |
| gattcccggc atggtgtggc agaatagaga cgtgtacctg cagggtccca tctgggccaa | 2700 |
| aattcctcac acgacggca actttcaccc gtctcccctg atgggcggct ttggactgaa | 2760 |
| gcacccgcct cctcaaattc tcatcaagaa cacaccggtt ccagcggacc cgccgcttac | 2820 |
| cttcaaccag gccaagctga actctttcat cacgcagtac agcaccggac aggtcagcgt | 2880 |
| ggaaatcgag tgggagctgc agaaagaaaa cagcaaacgc tggaatccag agattcaata | 2940 |
| cacttccaac tactacaaat ctacaaatgt ggactttgct gtcaacacgg aaggagttta | 3000 |
| tagcgagcct cgccccattg gcacccgtta cctcacccgc aacctgtaat tacatgttaa | 3060 |
| tcaataaaacc ggttaattcg tttcagttga actttggtct ctgcgaaggg cgaattc | 3117 |

<210> SEQ ID NO 44
<211> LENGTH: 3121
<212> TYPE: DNA
<213> ORGANISM: Unknown
<220> FEATURE:
<223> OTHER INFORMATION: AAV serotype, clone 43.23

<400> SEQUENCE: 44

| | |
|---|---|
| gaattcgccc ttctacggct gcgtcaactg gaccaatgag aactttccct tcaacgattg | 60 |
| cgtcgacaag atggtgatct ggtgggagga gggcaagatg acggccaagg tcgtggagtc | 120 |
| cgccaaggcc attctcggcg gcagcaaggt gcgtgtggac caaaagtgca agtcttccgc | 180 |
| ccagatcgat cccaccccg tgatcgtcac ctccaacacc aacatgtgcg ccgtgattga | 240 |
| cgggaacagc accaccttcg agcaccagca gccgttgcag gaccggatgt tcaaatttga | 300 |
| actcacccgc gtctctggagc atgactttgg caaggtgacg aagcaggaag tcaaagagtt | 360 |
| cttccgctgg gcgcaggatc acgtgaccga ggtggcgcat gagttccacg tcagaaaggg | 420 |
| tggcgccaac aagagacccg cccccgatga cgcggatata agcgagccca gcggggcctg | 480 |

```
ccgctcagtc gcggatccat cgacgtcaga cgcggaagga gctccggtgg actttgccga    540
caggtaccaa aacaaatgtt ctcgtcacgc gggcatgctt cagatgctgt ttccctgcaa    600
gacatgcgag agaatgaatc agaatttcaa catttgcttc acgcacggga ccagagactg    660
ttcagaatgt ttccccggcg tgtcagaatc tcaaccggtc gtcagaaaga ggacgtatcg    720
gaaactctgt gcgattcatc atctgctggg gcgggctccc gagattgctt gctcggcctg    780
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacggccg gggtctggtg cttcctggct acaagtacct cggacccttc aacggactcg   1020
acaaggggga gcccgtcaac gcggcggacg cagcggccct cgagcacgac aaagcctacg   1080
accagcagct caaagcgggt gacaatccgt acctgcggta taatcacgcc gacgccgagt   1140
ttcaggagcg tctgcaagaa gatacgtcct ttgggggcaa cctcgggcga gcagtcttcc   1200
aggccaagaa gcgggttctc gaacctctcg gtctggttga ggaaggcgct aagacggctc   1260
ctggaaagaa gagaccggta gagcagtcgc acaagagcc agactcctcc tcgggcatcg   1320
gcaagacagg ccagcagccc gctaaaaaga gactcaattt tggtcagact ggcgactcag   1380
agtcagtccc cgaccacaa cctctcggag aacctccagc agcccctca ggtctgggac   1440
ctaatacaat ggcttcaggc ggtggcgctc aatggcaga caataacgaa ggcgccgacg   1500
gagtgggtaa ttcctcggga aattggcatt gcgattccac atggctgggg acagagtca   1560
tcaccaccag cacccgaacc tgggccctgc ccacctacaa caaccacctc tacaagcaaa   1620
tctccaacgg cacctcggga ggaagcacca acgacaacac ctattttggc tacagcaccc   1680
cctgggggta ttttgacttc aacagattcc actgtcactt tcaccacgt gactggcaac   1740
gactcatcaa caacaattgg ggattccggc ccaaaagact caacttcaag ctgttcaaca   1800
tccaggtcaa ggaagtcacg acgaacgaag gcaccaagac catcgccaat aatctcacca   1860
gcaccgtgca ggtctttacg gacttggagt accagttacc gtacgtgcta ggatccgctc   1920
accagggatg tctgcctccg ttcccggcgg acgtcttcat ggttcctcag tacggctatt   1980
taactttaaa caatggaagc caagccctgg acgttcctc cttctactgt ctggagtatt   2040
tcccatcgca gatgccagaa accggcaaca actttcagtt cagctacacc ttcgaggacg   2100
tgcctttcca cagcagctac gcgcacagcc agagcctgga caggctgatg aatcccctca   2160
tcgaccagta cctgtactac ctggtcagaa cgcaaacgac tggaactgga gggacgcaga   2220
ctctggcatt cagccaagcg gtcctagct caatggccaa ccaggctaga aattgggtgc   2280
ccggaccttg ctaccggcag cagcgcgtct ccacgacaac caaccagaac aacaacagca   2340
actttgcctg gacgggagct gccaagtta gctgaacgg ccgagactct ctaatgaatc   2400
cgggcgtggc aatggcttcc cacaaggatg acgacgaccg cttcttccct tcgagcgggg   2460
tcctgatttt tggcaagcaa ggagccggga acgatggagt ggattacagc caagtgctga   2520
ttacagatga ggaagaaatc aaggctacca accccgtggc cacagaagaa tatggagcag   2580
tggccatcaa caaccaggcc gccaatacgc aggcgcagac cggactcgtg cacaaccagg   2640
gggtgattcc cggcatggtg tggcagaata gagacgtgta cctgcagggt cccatctggg   2700
ccaaaattcc tcacacggac ggcaactttc accgtctcc cctgatgggc ggctttggac   2760
tgaagcaccc gcctcctcaa attctcatca agaacacacc ggttccagcg gacccgccgc   2820
```

```
ttaccttcaa ccaggccaag ctgaactctt tcatcacgca gtacagcacc ggacaggtca    2880
gcgtggaaat cgagtgggag ctgcagaaag aaaacagcaa acgctggaat ccagagattc    2940
aatacacttc caactactac aaatctacaa atgtggactt tgctgtcaac acggaaggag    3000
tttatagcga gcctcgcccc attggcaccc gttacctcac ccgcaacctg taattacatg    3060
ttaatcaata aaccggttaa ttcgtttcag ttgaactttg gtctctgcga agggcgaatt    3120
c                                                                    3121
```

```
<210> SEQ ID NO 45
<211> LENGTH: 3122
<212> TYPE: DNA
<213> ORGANISM: Unknown
<220> FEATURE:
<223> OTHER INFORMATION: AAV serotype, clone 43.25

<400> SEQUENCE: 45
```

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgtgtgga ccaaaagtgc aagtcttccg     180
cccagatcga tccacccccc gtgatcgtca cctccaacac caacatgtgc gccgtgattg     240
acgggaacag caccaccttc gagcaccagc agccgttgca ggaccggatg ttcaaatttg     300
aactcacccg ccgtctggag catgactttg gcaaggtgac gaagcaggaa gtcaaagggt     360
tcttccgctg ggcgcaggat cacgtgaccg aggtggcgca tgagttccac gtgcgagccc     420
aagcgggcct gccccctcagt cgcggatcca tcgacgtcag accagaaagg gtggagccaa     480
caagagaccc gccccgatg acgcggatat aagcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatt ttttccccggc gtgtcagaat ctcaaccggt cgtcagaaag aggacgtatc     720
ggaaactctg tgcgattcat catctgctgg ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatt     900
cgcgagtggt gggacttgaa acctggagcc ccgaaaccca agccaaccca gcaaaagcag     960
gacgacggcc ggggtctggt gcttcctggc tacaagtacc tcggaccctt caacggactc    1020 gacaagggggg agcccgtcaa cgcggcggac gcagcggccc tcgagcacga caaagcctac    1080
gaccagcagc tcaaagcggg tgacaatccg tacctgcggt ataatcacgc cgacgccgag    1140
tttcaggagc gtctgcaaga agatacgtct ttgggggggca acctcgggcg agcagtcttc    1200
caggccaaga agcgggttct cgaacctctc ggtctggttg aggaaggcgc taagacggct    1260
cctggaaaga gagaccggt agagcagtcg ccacaagagc cagactcctc ctcgggcatc    1320
ggcaagacag gccagcagcc cgctaaaaag agactcaatt ttggtcagac tggcgactca    1380
gagtcagtcc ccgacccaca acctctcgga gaacctccag cagcccctc aggtctggga    1440 cctaatacaa tggcttcagg cggtggcgct ccaatggcag acaataacga aggcgccgac    1500
ggagtgggta ttcctcggg aaattggcat tgcgattcca catggctggg ggacagagtc    1560
atcaccacca gcacccgaac ctgggcccctg cccacctaca caaccaccct ctacaagcaa    1620
atctccaacg gcacctcggg aggaagcacc aacgacaaca cctatttttgg ctacagcacc    1680 ccctgggggt attttgactt caacagattc cactgtcact tttcaccacg tgactggcaa    1740
```

```
cgactcatca acaacaattg gggattccgg cccaaaagac tcaacttcaa gctgttcaac    1800
atccaggtca aggaagtcac gacgaacgaa ggcaccaaga ccatcgccaa taatctcacc    1860
agcaccgtgc aggtctttac ggactcggag taccagttac cgtacgtgct aggatccgct    1920
caccagggat gtctgcctcc gttcccggcg gacgtcttca tggttcctca gtacggctat    1980
ttaactttaa acaatggaag ccaagccctg ggacgttcct ccttctactg tctggagtat    2040
ttcccatcgc agatgctgag aaccggcaac aactttcagt tcagctacac cttcgaggac    2100 gtgccttttcc acagcagcta cgcgcacagc cagagcctgg acaggctgat gaatcccctc    2160
atcgaccagt acctgtacta cctggtcaga acgcaaacga ctggaactgg agggacgcag    2220
actctggcat tcagccaagc gggtcctagc tcaatggcca accaggctag aaattgggtg    2280
cccggacctt gctaccggca gcagcgcgtc tccacgacaa ccaaccagaa caacaacagc    2340
aactttgcct ggacgggagc tgccaagttt aagctgaacg gccgagactc tctaatgaat    2400
ccgggcgtgg caatggcttc ccacaaggat gacgacgacc gcttcttccc ttcgagcggg    2460
gtcctgattt ttggcaagca aggagccggg aacgatggag tggattacag ccaagtgctg    2520
attacagatg aggaagaaat caaggctacc aaccccgtgg ccacagaaga atatggagca    2580
gtggccatca caaccaggc cgccaatacg caggcgcaga ccggactcgt gcacaaccag    2640
ggggtgattc ccggcatggt gtggcagaat agagacgtgt acctgcaggg tcccatctgg    2700
gccaaaattc ctcacacgga cggcaacttt cacccgtctc ccctgatggg cggctttgga    2760
ctgaagcacc cgcctcctca aattctcatc aagaacacac cggttccagc ggacccgccg    2820
cttaccttca accaggccaa gctgaactct ttcatcacgc agtacagcac cggacaggtc    2880
agcgtggaaa tcgagtggga gctgcagaaa gaaaacagca acgctggaaa tccagagatt    2940
caatacactt ccaactacta caaatctaca aatgtggact tgctgtcaa cacggagggg    3000 gtttatagcg agcctcgccc cattggcacc cgttacctca cccgcaacct gtaattacat    3060
gttaatcaat aaaccggtta attcgtttca gttgaacttt ggtctctgcg aagggcgaat    3120
tc                                                                   3122
```

<210> SEQ ID NO 46
<211> LENGTH: 3128
<212> TYPE: DNA
<213> ORGANISM: Unknown
<220> FEATURE:
<223> OTHER INFORMATION: AAV serotype, clone 44.1

<400> SEQUENCE: 46

```
gaattcgccc tttctacggc tgcgtcaact ggaccaatga gaactttccc ttcaacgatt     60
gcgtcgacaa gatgttgatc tggtggggagg agggcaagat gacggccaag gtcgtggagt    120
ccgccaaggc cattctcggc ggcagcaaag tgcgcgtgga ccaaaagtgc aagccgtccg    180
cccagatcga ccccacccc gtgatcgtca cctccaacac caacatgtgc gccgtgattg    240
acgggaacag caccaccttc gagcaccagc agccgttgcg ggaccggatg ttcaagtttg    300
aactcacccg ccgtctggag cacgactttg gcaaggtgac aaagcaggaa gtcagagagt    360
tcttccgctg ggcgcaggat cacgtgaccg aggtggcgca cgagttctac gtcagaaagg    420
gtggagccaa caagagaccc gcccccgatg acgcggataa agcgagccc aagcgggcct    480 gccccctcagt cgccggatcca tcgacgtcag acgcggaagg agctccggtg gactttgccg    540
acaggtacca aaacaaatgt ctctcgtcacg cgggcatgct tcagatgctg tttcctgca    600
```

```
aaacatgcga gagaatgaat cagaatttca acatttgctt cacgcacggg accagagact    660
gttcagaatg tttccccggc gtgtcagaat ctcaaccggt cgtcagaaaa agacgtatc    720 ggaaactctg tgcgattcat catctgctgg ggcgggcacc cgagattgct tgctcggcct    780
gcgatctggt caacgtggac ctagatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccca gcaaaagcag    960
gacgacggcc ggggtctggt gcttcctggc tacaagtacc tcggacccct caacggactc   1020
gacaagggga agcccgtcaa cgcggcggac gcagcggccc tcgagcacga caaggcctac   1080
gaccagcagc tcaaagcggg tgacaatccg tacctgcggt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagccatca ccccagcgtt ctccagactc ctctacgggc   1320
atcggcaaga aaggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacttc gggaggaagc accaacgaca cacctactt cggctacagc   1680 accccctggg ggtatttttga ctttaacaga ttccactgcc acttctcacc acgtgactgg   1740
cagcgactca tcaacaacaa ctggggattc cggcccaaga gactcaactt caagctcttc   1800
aacatccagg tcaaggaggt cacgcagaat gaaggcacca agaccatcgc caataacctt   1860
accagcacga ttcaggtctt tacggactcg aataccagc tcccgtacgt cctcggctct   1920
gcgcaccagg gctgcctgcc tccgttcccg cggacgtct tcatgattcc tcagtacggg   1980
tacctgactc tgaacaatgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gatgaacccc   2160
ctcatcgacc agtacctgta ctacctgtct cggactcagt ccacgggagg taccgcagga    2220
actcagcagt tgctattttc tcaggccggg cctaataaca tgtcggctca ggccaaaaac   2280
tggctacccg ggccctgcta ccggcagcaa cgcgtctcca cgacactgtc gcaaaataac   2340
aacagcaact gtaaatcccg tgtcgctat ggcaacccac aaggacgacg aagagcgatt   2400
ttgcctggac cggtgccacc aagtatcatc tgaatggcag agactctctg ttttccgtcc   2460
agcggagtct taatgtttgg gaaacaggga gctggaaaag acaacgtgga ctatagcagc   2520
gttatgctaa ccagtgagga agaaattaaa accaccaacc cagtggccac ggaacagtac   2580
ggcgtggtgg ccgataacct gcaacagcaa acgccgctc ctattgtagg ggccgtcaac   2640
agtcaaggag ccttacctgg catggtctgg cagaaccggg acgtgtacct gcagggtcct   2700
atctgggcca agattcctca cacggacgga aactttcatc cctcgccgct gatgggaggc   2760
tttggactga aacacccgcc tcctcagatc ctgattaaga atacacctgt tcccgcggat   2820
cctccaacta ccttcagtca agctaagctg gcgtcgttca tcacgcagta cagcaccgga   2880
caggtcagcg tggaaattga atgggagctg cagaaagaaa acagcaaacg ctggaaccca   2940
gagattcaat acacttccaa ctactacaaa tctacaaatg tggacttcgc tgttaacaca   3000
```

| | |
|---|---:|
| gatggcactt attctgagcc tcgccccatt ggcaccegtt acctcacccg taatctgtaa | 3060 |
| ttgctcgtta atcaataaac cggttgattc gtttcagttg aactttggtc tctgcgaagg | 3120 |
| gcgaattc | 3128 |

<210> SEQ ID NO 47
<211> LENGTH: 3128
<212> TYPE: DNA
<213> ORGANISM: Unknown
<220> FEATURE:
<223> OTHER INFORMATION: AAV serotype, clone 44.5

<400> SEQUENCE: 47

| | |
|---|---:|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtggagt | 120 |
| ccgccaaggc cattctcggc ggcagcaaag tgcgcgtgga ccaaaagtgc aagtcgtccg | 180 |
| cccagatcga ccccaccccc gtgatcgtca cctccaacac caacatgtgc gccgtgattg | 240 |
| acgggaacag caccaccttc gagcaccagc agccgttgca ggaccggatg ttcaagtttg | 300 |
| aactcacccg ccgtctggag cacgactttg gcaaggtgac aaagcaggaa gtcagagagt | 360 |
| tcttccgctg ggcgcaggat cacgtgaccg aggtggcgca cgagttctac gtcagaaagg | 420 |
| gtggagccaa caagagaccc gcccccgatg acgcggataa aagcgagccc aagcgggcct | 480 |
| gcccctcagt cgcggatcca tcgacgtcag acgcggaagg agctccggtg gactttgccg | 540 |
| acaggtacca aaacaaatgt tctcgtcacg cgggcatgct tcagatgctg tttccctgca | 600 |
| aaacatgcga gagaatgaat cagaatttca acatttgctt cacgcacggg accagagact | 660 |
| gttcagaatg tttccccggc gtgtcagaat ctcaaccggt tgtcagaaaa aagacgtatc | 720 |
| ggaaactctg tgcgattcat catctgctgg ggcgggcacc cgagattgct tgctcggcct | 780 |
| gcgatctggt caacgtggac ctagatgact gtgtttctga gcaataaatg acttaaacca | 840 |
| ggtatggctg ccgatggtta tcttccagat tggctcgagg acaacctctc tgagggcatt | 900 |
| cgcgagtggt gggacttgaa acctggagcc ccgaaaccca agccaaccag caaaagcag | 960 |
| gacgacggcc ggggtctggt gcttcctggc tacaagtacc tcggaccctt caacggactc | 1020 |
| gacaaggggg agcccgtcaa cgcggcggac gcagcggccc tcgagcacga caaggcctac | 1080 |
| gaccagcagc tcaaagcggg tgacaatccg tacctgcgt ataaccacgc cgacgccgag | 1140 |
| tttcaggagc gtctgcaaga agatacgtct tttggggggca acctcggcg agcagtcttc | 1200 |
| caggccaaga gcgggttctc gaacctctc ggtctggttg aggaaggcgc taagacggct | 1260 |
| cctggaaaga gagaccggt agagccatca ccccagcgtt ctccagactc ctctacgggc | 1320 |
| atcggcaaga aggccagca gcccgcgaaa aagagactca actttgggca gactggcgac | 1380 |
| tcagagtcag tgcccgaccc tcaaccaatc ggagaaccc cgcaggccc ctctggtctg | 1440 |
| ggatctggta caatggctgc aggcggtggc gctccaatgg cagacaataa cgaaggcgcc | 1500 |
| gacggagtgg gtagttcctc aggaaattgg cattgcgatt ccacatggct gggcgacaga | 1560 |
| gtcatcacca ccagcacccg aacctgggcc ctccccacct acaacaacca cctctacaag | 1620 |
| caaatctcca cgggacttc gggaggaagc accaacgaca cacctactt cggctacagc | 1680 |
| accccctggg ggtattttga ctttaacaga ttccactgcc acttctcacc acgtgactgg | 1740 |
| cagcgactca tcaacaacaa ctgggggattc cggcccaaga gacccaactt caagctcttc | 1800 |
| aacatccagg tcaaggaggt cacgcagaat gaaggcacca agaccatcgc caataacctt | 1860 |

| | |
|---|---|
| accagcacga ttcaggtctt tacggactcg aataccagc tcccgtacgt cctcggctct | 1920 |
| gcgcaccagg gctgcctgcc tccgttcccg gcggacgtct tcatgattcc tcagtacggg | 1980 |
| tacctgactc tgaacaatgg cagtcaggcc gtgggccgtt cctccttcta ctgcctggag | 2040 |
| tactttcctt ctcaaatgct gagaacgggc aacaactttg agttcagcta ccagtttgag | 2100 |
| gacgtgcctt ttcacagcag ctacgcgcac agccaaagcc tggaccggct gatgaacccc | 2160 |
| ctcatcgacc agtacctgta ctacctgtct cggactcagt ccacggggag taccgcagga | 2220 |
| actcagcagt tgctatttc tcaggccggg cctaataaca tgtcggctca ggccaaaaac | 2280 |
| tggctacccg ggccctgcta ccggcagcaa cgcgtctcca cgacactgtc gcaaaataac | 2340 |
| aacagcaact ttgcctggac cggtgccacc aagtatcatc tgaatggcag agactctctg | 2400 |
| gtaaatcccg gtgtcgctat ggcaacccac aaggacgacg aagagcgatt ttttccgtcc | 2460 |
| agcggagtct taatgtttgg gaaacaggga gctggaaaag acaacgtgga ctatagcagc | 2520 |
| gttatgctaa ccagtgagga agaaattaaa accaccaacc cagtggccac agaacagtac | 2580 |
| ggcgtggtgg ccgataacct gcaacagcaa acgccgctc ctattgtagg ggccgtcaac | 2640 |
| agtcaaggag ccttacctgg catggtctgg cagaaccggg acgtgtacct gcagggtcct | 2700 |
| atctgggcca agattcctca cacggacgga aactttcatc cctcgccgct gatgggaggc | 2760 |
| tttggactga acacccgcc tcctcagatc ctgattaaga atacacctgt tcccgcggat | 2820 |
| cctccaacta ccttcagtca agctaagctg gcgtcgttca tcacgcagta cagcaccgga | 2880 |
| caggtcagcg tggaaattga atgggagctg cagaaagaaa acagcaaacg ctggaaccca | 2940 |
| gagattcaat acacttccaa ctactacaaa tctacaaatg tggactttgc tgttaacaca | 3000 |
| gatggcactt attctgagcc tcgccccatt ggcacccgtt acctcacccg taatctgtaa | 3060 |
| ttgcttgtta atcaataaac cggttgattc gtttcagttg aactttggtc tctgcgaagg | 3120 |
| gcgaattc | 3128 |

<210> SEQ ID NO 48
<211> LENGTH: 1933
<212> TYPE: DNA
<213> ORGANISM: Unknown
<220> FEATURE:
<223> OTHER INFORMATION: AAV serotype, clone 223.10
<220> FEATURE:
<221> NAME/KEY: misc_feature
<222> LOCATION: (1302)..(1302)
<223> OTHER INFORMATION: can be a, c, g or t

<400> SEQUENCE: 48

| | |
|---|---|
| caaggcctac gaccagcagc tcaaagcggg tgacaatccg tacctgcggt ataaccacgc | 60 |
| cgacgccgag tttcaggagc gtcttcaaga agatacgtct tttggggca acctcgggcg | 120 |
| agcagtcttc caggccaaaa agcgggttct cgaacctctt ggtctggttg agacgccagc | 180 |
| taagacggca cctggaaaga agcgaccggt agactcgcca gactccacct cgggcatcgg | 240 |
| caagaaaggc cagcagcccg cgaaaaagag actcaacttt gggcagactg gcgactcaga | 300 |
| gtcagtcccc gaccctcaac caatcggaga accaccagca ggccctctg tctgggatc | 360 |
| tggtacaatg gctgcaggcg gtggcgcacc aatggctgac aataacgagg gcgccgacgg | 420 |
| agtgggtaat gcctcaggaa attggcattg cgattccaca tggctgggcg acagagtcat | 480 |
| caccaccagc acccgaacct gggccctgcc cacctacaac aaccacctct acaagcaaat | 540 |
| ctccagtcag tcagcaggga gcaccaacga taacgtctat ttcggctaca gcaccccctg | 600 |
| ggggtatttt gacttcaaca gattccattg ccacttctca ccacgtgact ggcagcgact | 660 |

```
tatcaacaac aactggggat tccggcccaa gaagctcaac ttcaagctct tcaacatcca    720
ggtcaaggag gtcacgacga atgacggtgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
ttctcagatg ctgagaacgg gcaacaactt cacctttagc tacaccttcg aggacgtgcc   1020
tttccacagc agctacgcgc acagccagag tctggaccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat gnaagaaatt cattggttaa   1320
tcccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acgggattgt   1500
aagcagcaac ttgcaggcgg ctagcaccgc agcccagaca caagttgtta caaccagggg   1560
agccttacct ggcatggtct ggcagaaccg ggacgtgtac ctgcaaggtc ccatttgggc   1620
caagattcct cacacggacg gcaactttca cccgtctcct ctaatgggtg gctttggact   1680
gaaacacccg cctccccaga tcctgatcaa aaacacaccg gtacctgcta atcctccaga   1740
agtgtttact cctgccaagt tgcttccttt catcacgcag tacagcaccg ggcaagtcag   1800
cgttgagatc gagtgggagc tgcagaaaga aacagcaag cgctggaacc cagagattca   1860
gtacacctcc aactttgaca aacagactgg agtggacttt gctgttgaca gccagggtgt   1920
ttactctgag cct                                                      1933
```

<210> SEQ ID NO 49
<211> LENGTH: 1933
<212> TYPE: DNA
<213> ORGANISM: Unknown
<220> FEATURE:
<223> OTHER INFORMATION: AAV serotype, clone 223.2

<400> SEQUENCE: 49

```
caaggcctac gaccagcagc tcaaagcggg tgacaatccg tacctgcggt ataaccacgc     60
cgacgccgag tttcaggagt gtcttcaaga agatacgtct tttgggggca acctcgggcg    120
agcagtcttc caggccaaaa agcgggttct cgaacctctt ggtctggttg agacgccagc    180
taagacggca cctggaaaga agcgaccggt agactcgcca gactccacct cgggcatcgg    240
caagaaaggc cagcagcccg cgaaaaagag actcaacttt gggcagactg gcgactcaga    300
gtcagtcccc gaccctcaac caatcggaga accaccagca ggcccctctg gtctgggatc    360
tggtacaatg gttgcaggcg gtggcgcacc aatggctgac aataacgagg gcgccgacgg    420
agtgggtaat gcctcaggaa attggcattg cgattccaca tggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcaccccctg    600
ggggtatttt gacttcaaca gattccattg ccacttctca ccacgtgact ggcagcgact    660
tatcaacaac aactggggat tccggcccaa gaagctcaac ttcaagctct tcaacatcca    720
```

```
ggtcaaggag gtcacgacga atgacggtgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
ttctcagatg ctgagaacgg gcaacaactt caccttagc tacaccttcg aggacgtgcc   1020
tttccacagc agctacgcgc acagccgag tctggaccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tcccggtgtc gccatggcaa cccacaagga cgacgaggaa cgcttctccc cttcgagcgg   1380
agttctaatt tttggcaaaa ctggagcagc taataaaact acattagaaa acgtgctcat   1440
gacaaatgaa gaagaaattc gtcctaccaa cccggtagc accgaggaat acgggattgt   1500
aagcagcaac ttgcaggcgg ctagcaccgc agcccagaca caagttgtta acaaccaggg   1560
agccttacct ggcatggtct ggcagaaccg ggacgtgtac ctgcaaggtc ccatttgggc   1620
caagattcct cacacggacg gcaactttca cccgtctcct ctaatgggtg gctttggact   1680
gaaacacccg cctccccaga tcctgatcaa aaacacgccg gtacctgcta atcctccaga   1740
agtgtttact cctgccaagt ttgcttcctt catcacgcag tacagcaccg ggcaagtcag   1800
cgttgagatc gagtgggagc tgcagaaaga gaacagcaag cgctggaacc cagagattca   1860
gtacaccctcc aactttgaca aacagactgg agtggacttt gctgttgaca gccagggtgt   1920
ttactctgag cct                                                       1933

<210> SEQ ID NO 50
<211> LENGTH: 1933
<212> TYPE: DNA
<213> ORGANISM: Unknown
<220> FEATURE:
<223> OTHER INFORMATION: AAV serotype, clone 223.4

<400> SEQUENCE: 50
caaggcctac gaccagcagc tcaaagcggg tgacaatccg tacctgcggt ataaccacgc     60
cgacgccgag tttcaggagc gtcttcaaga agatacgtct tttgggggca acctcgggcg    120
agcagtcttc caggccaaaa agcgggttct cgaacctctt ggtctggttg agacgccagc    180
taagacggca cctggaaaga agcgaccggt agactcgcca gactccacct cgggcatcgg    240
caagaaaggc cagcagcccg cgaaaaagag actcaacttt gggcagactg gcgactcaga    300
gccagtcccc gaccctcaac caatcggaga accaccagca ggcccctctg gtctgggatc    360
tggtacaatg gctgcaggcg gtggcgcacc aatggctgac aataacgagg cgccgacgg    420
agtgggtaat gcctcaggaa attggcattg cgattccaca cggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcacccctg    600
ggggtatttt gacttcaaca gattccattg ccacttctca ccacgtgact ggcagcgact    660
tatcaacaac aactgggat ccggcccaa gaagctcaac ttcaagctct tcaacatcca    720
ggtcaaggag gtcacgacga atgacggtgt cacaaccatc gctaataacc ttaccagcac    780
ggttcaggtc ttttcggact cggaatatca actgccgtac gtcctcggct ccgcgcacca    840
```

-continued

```
gggctgcctg cctccgttcc cggcagacgt gttcatgatt ccgcagtacg ataccctgac    900
tctgaacaat ggcagccaat cggtaggccg ttcctccttc tactgcctgg agtactttcc    960
ttctcagatg ctgagaacgg gcaacaactt cacctttagc tacaccttcg aggacgtgcc   1020
tttccacagc agctacgcgc acagccagag tctgggccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tcccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acgggattgt   1500
aagcagcaac ttgcaggcgg ctagcaccgc agcccagaca caagttgtta caaccaggg    1560
agccttacct ggcatggtct ggcagaaccg ggacgtgtac ctgcaaggtc ccatttgggc   1620
caagattcct cacacggacg gcaactttca cccgtctcct ctaatgggtg ctttggact    1680
gaaacacccg cctccccaga tcctgatcaa aaacacaccg gtacctgcta atcctccaga   1740
agtgttact  cctgccaagt ttgcttcctt catcacgcag tacagcaccg ggcaagtcag   1800
cgttgagatc gaatgggagc tgcagaaaga gaacagcaag cgctggaacc cagagattca   1860
gtacaccctcc aactttgaca aacagactgg agtggacttt gctgttgaca gccagggtgt  1920
ttactctgag cct                                                     1933
```

<210> SEQ ID NO 51
<211> LENGTH: 1933
<212> TYPE: DNA
<213> ORGANISM: Unknown
<220> FEATURE:
<223> OTHER INFORMATION: AAV serotype, clone 223.5

<400> SEQUENCE: 51

```
caaggcctac gaccagcagc tcaaagcggg tgacaatccg tacctgcggt ataaccacgc     60
cgacgccgag tttcaggagc gtcttcaaga agatacgtct tttggggggca acctcgggcg    120
agcagtcttc caggccaaaa agcgggttct cgaacctctt ggtctggttg agacgccagc    180
taagacggca cctggaaaga agcgaccggt agactcgcca gactccacct cgggcatcgg    240
caagaaaggc cagcagcccg cgaaaaagag actcaacttt gggcagactg gcgactcaga    300
gccagtcccc gaccctcaac caatcggaga accaccagca ggcccctctg gtctgggatc    360
tggtacaatg gctgcaggcg gtggcgcacc aatggctgac aataacgagg gcgccgacgg    420
agtgggtaat gcctcaggaa attggcattg cgattccaca cggctgggcg acagagtcat    480
caccaccagc acccgaacct gggcctgcc cacctacaac aaccacctct acaagcaaat    540
ctccagtcag tcagcaggga gcaccaacga taacgtctat ttcggctaca gcacccctg    600
ggggtatttt gacttcaaca gattccatg ccacttctca ccacgtgact ggcagcgact    660
tatcaacaac aactggggat ccggcccaa gaagctcaac ttcaagctct caacatcca    720
ggtcaaggag gtcacgacga atgacggcgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg ataccctgac    900
```

```
tctgaacaat ggcagccaat cggtaggccg ttcctccttc tactgcctgg agtactttcc    960
ttctcagatg ctgagaacgg gcaacaactt caccttttagc tacaccttcg aggacgtgcc   1020
tttccacagc agctacgcgc acagccagag tctgggccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tcccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acggggattgt   1500
aagcagcaac ttgcaggcgg ctagcaccgc agcccagaca caagttgtta acaaccaggg   1560
agccttacct ggcatggtct ggcagaaccg ggacgtgtac ctgcaaggtc ccatttgggc   1620
caagattcct cacacggacg gcaactttca cccgtctcct ctaatgggtg ctttggact    1680
gaaacacccg cctcccccaga tcctgatcaa aaacacaccg gtacctgcta atcctccaga   1740
agtgttact cctgccaagt tgcttccctt catcacgcag tacagcaccg ggcaagtcag   1800
cgttgagatc gaatgggagc tgcagaaaga gaacagcaag cgctggaacc cagagattca   1860
gtacacctcc aactttgaca aacagactgg agtggacttt gctgttgaca gccagggtgt   1920
ttactctgag cct                                                       1933

<210> SEQ ID NO 52
<211> LENGTH: 1933
<212> TYPE: DNA
<213> ORGANISM: Unknown
<220> FEATURE:
<223> OTHER INFORMATION: AAV serotype, clone 223.6

<400> SEQUENCE: 52
caaggcctac gaccagcagc tcaaagcggg tgacaatccg tacctgcggt ataaccacgc     60
cgacgccgag tttcaggagc gtcttcaaga agatacgtct tttggggca acctcgggcg   120
agcagtcttc caggccaaaa agcgggttct cgaacctctt ggtctggttg agacgccagc   180
taagacggca cctggaaaga agcgaccggt agactcgcca gactccacct cgggcatcgg   240
caagaaaggc cagcagcccg cgaaaaagag actcaacttt gggcagactg gcgactcaga   300
gtcagtcccc gaccctcaac caatcggaga accaccagca ggcccctctg gtctgggatc   360
tggtacaatg gctgcaggcg gtggcgcacc aatggctgac aatagcgagg gcgccgacgg   420
agtgggtaat gcctcaggaa attggcattg cgattccaca tggctgggcg acagagtcat   480
caccaccagc acccgaacct gggccctgcc cacctacaac aaccacctct acaagcaaat   540
ctccagtcag tcagcaggga gcaccaacga taacgtctat ttcggctaca gcaccccctg   600
gggtattttt gacttcaaca gattccattg ccacttctca ccacgtgact ggcagcgact   660
tatcaacaac aactgggggat tccggcccaa gaagctcaac ttcaagctct tcaacatcca   720
ggtcaaggag gtcacgacga atgacggtgt cacaaccatc gctaataacc ttaccagcac   780
ggttcaggtc ttttcggact cggaatatca actgccgtac gtcctcggct ccgcgcacca   840
gggctgcctg cctccgttcc cggcagacgt gttcatgatt ccgcagtacg gatacctgac   900
tctgaacaat ggcagccaat cggtaggccg ttcctccttc tactgcctgg agtactttcc    960
ttctcagatg ctgagaacgg gcaacaactt caccttttagc tacaccttcg aggacgtgcc   1020
```

```
tttccacagc agctacgcgc acagccagag tctggaccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tcccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acgggattgt   1500
aagcagcaac ttgcaggcgg ctagcaccgc agcccagaca caagttgtta acaaccaggg   1560
agccttacct ggcatggtct ggcagaaccg ggacgtgtac ctgcaaggtc ccatttgggc   1620
caagattcct cacacggacg gcaactttca cccgtctcct ctaatgggtg ctttggact   1680
gaaacacccg cctcccccaga tcctgatcaa aaacacaccg gtacctgcta atcctccaga   1740
agtgtttact cctgccaagc ttgcttcctt catcacgcag tacagcaccg ggcaagtcag   1800
cgttgagatc gagtgggagc tgcagaaaga gaacagcaag cgctggaacc cagagattca   1860
gtacacctcc aactttgaca aacagactgg agtggacttt gctgttgaca gccagggtgt   1920
ttactctgag cct                                                       1933

<210> SEQ ID NO 53
<211> LENGTH: 1933
<212> TYPE: DNA
<213> ORGANISM: Unknown
<220> FEATURE:
<223> OTHER INFORMATION: AAV serotype, clone 223.7

<400> SEQUENCE: 53
caaggcctac gaccagcagc tcaaagcggg tgacaatccg tacctgcggt ataaccacgc     60
cgacgccgag tttcaggagc gtcttcaaga agatacgtct tttggggggca acctcgggcg   120
agcagtcttc caggccaaaa agcgggttct cgaacctctt ggtctggttg agacgccagc   180
taagacggca cctggaaaga agcgaccggt agactcgcca gactccacct cgggcatcgg   240
caagaaaggc cagcagcccg cgaaaaagag actcaacttt gggcagactg gcgactcaga   300
gtcagtcccc gaccctcaac caatcggaga accaccagca ggcccctctg gtctgggatc   360
tggtacaatg gctgcaggcg gtggcgcacc aatggctgac aataacgagg gcgccgacgg   420
agtgggtaat gcctcaggaa attggcattg cgattccaca tggctgggcg acagagtcat   480
caccaccagc acccgaacct gggccctgcc cacctacaac aaccacctct acaagcaaat   540
ctccagtcag tcagcaggga gcaccaacga taacgtctat ttcggctaca gcacccctg   600
ggggtatttt gacttcaaca gattccattg ccacttctca ccacgtgact ggcagcgact   660
tatcaacaac aactggggat tccggcccaa gaagctcaac ttcaagctct caacatcca   720
ggtcaaggag gtcacgacga atgacggcgt cacaaccatc gctaataacc ttaccagcac   780
ggttcaggtc ttttcggacc cggaatatca actgccgtac gtcctcggct ccgcgcacca   840
gggctgcctg cctccgttcc cggcagacgt gttcatgatt ccgcagtacg gatacctgac   900
tctgaacaat ggcagccaat cggtaggccg ttcctccttc tactgcctgg agtactttcc   960
ttctcagatg ctgagaacgg caacaacttc accttagc tacaccttcg aggacgtgcc  1020
tttccacagc agctacgcgc acagccagag tctggaccgg ctgatgaatc ccctcatcga  1080
```

| | |
|---|---|
| ccagtacctg tactacttgg ccagaacaca gagcaacgca ggaggtactg ctggcaatcg | 1140 |
| ggaactgcag ttttatcagg gcggacctac caccatggcc aacaagcaa agaactggct | 1200 |
| gcccggacct tgcttccggc aacagagagt atccaagacg ctggatcaaa ataacaacag | 1260 |
| caactttgcc tggactggtg ccacaaaata ccatttaaat ggaagaaatt cattggttaa | 1320 |
| tcccggtgtc gccatggcaa cccacaagga cgacgaggaa cgcttcttcc cttcgagcgg | 1380 |
| agttctaatt tttggcaaaa ctggagcagc taataaaact acattagaaa acgtgctcat | 1440 |
| gacaaatgaa gaagaaattc gtcctaccaa cccggtagct accgaggaat acgggattgt | 1500 |
| aagcagcaac ttgcaggcgg ctagcaccgc agcccagaca caagttgtta acaaccaggg | 1560 |
| agccttacct ggcatggtct ggcagaaccg ggacgtgtac ctgcaaggtc ccatttgggc | 1620 |
| caagattcct cacacggacg gcaactttca cccgtctcct ctaatgggtg ctttggact | 1680 |
| gaaacacccg cctccccaga tcctgatcaa aaacacaccg gtacctgcta atcctccaga | 1740 |
| agtgtttact cctgccaaga ttgcttcctt catcacgcag tacagcaccg gcaagtcag | 1800 |
| cgttgagatc gagtgggagc tgcagaaaga gaacagcaag cgctggaacc cagagattca | 1860 |
| gtacacctcc aactttgaca aacagactgg agtggacttt gctgttgaca gccagggtgt | 1920 |
| ttactctgag cct | 1933 |

<210> SEQ ID NO 54
<211> LENGTH: 3123
<212> TYPE: DNA
<213> ORGANISM: Unknown
<220> FEATURE:
<223> OTHER INFORMATION: AAV serotype, clone A3.4

<400> SEQUENCE: 54

| | |
|---|---|
| gaattcgccc tttctacggc tgcgtcaact ggaccaatga aaactttccc ttcaacgatt | 60 |
| gcgtcgacaa gatggtgatc tggtgggagg agggaaagat gaccgccaag gtcgtggaat | 120 |
| ctgccaaagc cattctgggt ggaagcaagg ttcgtgtgga ccagaaatgc aagtcttcgg | 180 |
| cccagatcga cccgactccg gtgattgtca cctctaacac caacatgtgc gccgtgattg | 240 |
| acggaaactc gaccaccttc gagcaccagc agccgttgca agaccggatg ttcaaatttg | 300 |
| aacttacccg ccgtttggat catgactttg gaaggtcac caagcaggaa gtcaaagact | 360 |
| ttttccggtg ggctcaagat cacgtgactg aggtggagca tgagttctac gtcaaaaagg | 420 |
| gtggagccaa gaaaaggccc gccccgatg atgtatatat aaatgagccc aagcgggcgc | 480 |
| gcgagtcagt tgcgcagcca tcgacgtcag acgcggaagc ttcgataaac tacgcgggca | 540 |
| ggtaccaaaa caaatgttct cgtcacgtgg gcatgaatct gatgctgttt ccctgtcgac | 600 |
| aatgcgaaag aatgaatcag aattcaaata tctgcttcac acacgggcaa aaagactgtt | 660 |
| tggaatgctt tcccgtgtca gaatctcaac ccgtttctgt cgtcagaaaa acgtatcaga | 720 |
| aactttgtta cattcatcat atcatgggaa aagaaccaga cgcctgcact gcctgcgacc | 780 |
| tggtaaatgt ggacttggat gactgtattt ctgagcaata aatgacttaa atcaggtatg | 840 |
| gctgctgacg gttatcttcc agattggctc gaggacactc tctctgaagg aatcagacag | 900 |
| tggtggaagc tcaaacctgg cccaccaccg ccgaaaccta accaacaaca ccgggacgac | 960 |
| agtaggggtc ttgtgcttcc tgggtacaag tacctcggac ccttcaacgg actcgacaaa | 1020 |
| ggagagccgg tcaacgaggc agacgccgcg gccctcgagc acgacaaagc ctacgaccac | 1080 |
| cagctcaagc aaggggacaa cccgtacctc aaatacaacc acgcggacgc tgaatttcag | 1140 |
| gagcgtcttc aagaagatac gtctttcggg ggcaacctcg gcgagcagt cttccaggcc | 1200 |

```
aaaaagaggg tactcgagcc tcttggtctg gttgaggaag ctgttaagac ggctcctgga    1260
aaaaagagac ctatagagca gtctcctgca gaaccggact cttcctcggg catcggcgaa    1320
tcaggccagc agcccgctaa gaaaagactc aattttggtc agactggcga cacagagtca    1380
gtcccagacc ctcaaccaat cggagaaccc cccgcagccc cctctggtgt gggatctaat    1440
acaatggctt caggcggtgg ggcaccaatg gcagacgata cgaaggcgc cgacggagtg     1500 ggtaattcct cggaaattg gcattgcgat tccacatgga tgggcgacag agttatcacc     1560
accagcacaa gaacctgggc cctccccacc tacaataatc acctctacaa gcaaatctcc    1620
agcgaatcgg gagccaccaa cgacaaccac tacttcggct acagcacccc ctgggggtat    1680
tttgacttta acagattcca ctgtcacttc tcaccacgtg actggcagcg actcatcaac    1740
aacaactggg gatttagacc caagaaactc aatttcaagc tcttcaacat ccaagtcaag    1800
gaggtcacgc agaatgatgg aaccacgacc atcgccaata accttaccag cacggtgcag    1860
gtcttcacag actctgagta ccagctgccc tacgtcctcg gttcggctca ccagggctgc    1920
cttccgccgt tcccagcaga cgtcttcatg attcctcagt acggctactt gactctgaac    1980
aatggcagcc aagcggtagg acgttcttca ttctactgtc tagagtattt tccctctcag    2040
atgctgagga cggaaacaa cttcaccttc agctacactt ttgaagacgt gccttccac      2100 agcagctacg cgcacagcca gagtctggat cggctgatga atcctctcat tgaccagtac    2160
ctgtattacc tgagcaaaac tcagggtaca agtggaacaa cgcagcaatc gagactgcag    2220
ttcagccaag ctgggcctag ctccatggct cagcaggcca aaaactggct accgggaccc    2280
agctaccgac agcagcgaat gtctaagacg gctaatgaca caacaacag tgaatttgct     2340 tggactgcag ccaccaaata ttacctgaat ggaagaaatt ctctggtcaa tcccgggccc    2400
ccaatggcca gtcacaagga cgatgaggaa aagtatttcc ccatgcacgg aaatctcatc    2460
tttggaaaac aaggcacagg aactaccaat gtggacattg aatcagtgct tattacagac    2520
gaagaagaaa tcagaacaac taatcctgtg gctacagaac aatacggaca ggttgccacc    2580
aaccatcaga gtcaggacac cacagcttcc tatggaagtg tggacagcca gggaatctta    2640
cctggaatgg tgtggcagga ccgcgatgtc tatcttcaag gtcccatttg ggccaaaact    2700
cctcacacgg acggacactt tcatccttct ccgctcatgg gaggctttgg actgaaacac    2760
cctcctcccc agatcctgat caaaacaca cctgtgccag cgaatcccgc gaccactttc    2820
actcctggaa agtttgcttc gttcattacc cagtattcca ccggacaggt cagcgtggaa    2880
atagagtggg agctgcagaa agaaaacagc aaacgctgga acccagaaat tcagtacacc    2940
tccaactaca acaagtcggt gaatgtggag tttaccgtgg acgcaaacgg tgtttattct    3000
gaaccccgcc ctattggcac tcgttacctt acccggaact tgtaatttcc tgttaatgaa    3060
taaaccgatt tatgcgtttc agttgaactt tggtctctgc gaagggcgaa ttcgcggccg    3120
cta                                                                 3123
```

<210> SEQ ID NO 55
<211> LENGTH: 3113
<212> TYPE: DNA
<213> ORGANISM: Unknown
<220> FEATURE:
<223> OTHER INFORMATION: AAV serotype, clone A3.5

<400> SEQUENCE: 55

```
gaattcgccc tttctacggc tgcgtcaact ggaccaatga aaactttccc ttcaacgatt      60
```

```
gcgtcgacaa gatggtgatc tggtgggagg agggaaagat gaccgccaag gtcgtggaat    120
ctgccaaagc cattctgggt ggaagcaagg ttcgtgtgga ccagaaatgc aagtcttcgg    180
cccagatcga cccgactccg gtgattgtca cctctaacac caacatgtgc gccgtgattg    240
acggaaactc gaccaccttc gagcaccagc agccgttgca agaccggatg ttcaaatttg    300
aacttacccg ccgtttggat catgactttg ggaaggtcac caagcaggaa gtcaaagact    360
ttttccggtg ggctcaagat cacgtgactg aggtggagca tgagttctac gtcaaaaagg    420
gtggagccaa gaaaaggccc gcccccgatg atgtatatat aaatgagccc aagcgggcgc    480
gcgagtcagt tgcgcagcca tcgacgtcag acgcggaagc ttcgataaac tacgcggaca    540
ggtaccaaaa caaatgttct cgtcacgtgg gcatgaatct gatgctgttt ccctgtcgac    600
aatgcgaaag aatgaatcag aattcaaata tctgcttcac acacgggcaa aaagactgtt    660
tggaatgctt tcccgtgtca gaatctcaac ccgttcctgt cgtcagaaaa acgtatcaga    720
aactttgtta cattcatcat atcatgggaa aagtaccaga cgcctgcact gcctgcgacc    780
tggtaaatgt ggacttggat gactgtattt ctgagcaata aatgacttaa atcaggtatg    840
gctgctgacg gttatcttcc agattggctc gaggacactc tctctgaagg aatcagacag    900
tggtggaagc tcaaacctgg cccaccaccg ccgaaaccta ccaacaaca ccgggacgac    960
agtaggggtc ttgtgcttcc tgggtacaag tacctcggac ccttcaacgg actcgacaaa    1020
ggagagccgt caacgaggc agacgccgcg gccctcgagc acgacaaagc ctacgaccac    1080
cagctcaagc aaggggacaa cccgtacctc aaatacaacc acgcggacgc tgaatttcag    1140
gagcgtcttc aagaagatac gtctttcggg ggcaacctcg ggcgagcagt cttccaggcc    1200
aaaaagaggg tactcgagcc tcttggtctg gttgaggaag ctgttaagac ggctcctgga    1260
aaaagagac ctatagagca gtcctcctgca gaaccggact cttcctcggg catcggcaaa    1320
tcaggccagc agcccgctaa gaaaagactc aattttggtc agactggcga cacagagtca    1380
gtcccagacc ctcaaccaat cggagaaccc ccgcagcccc cctctggtgt gggatctaat    1440
acaatggctt caggcggtgg ggcaccaatg gcagacaata cgaaggcgc cgacggagtg    1500
ggtaattcct cggaaattg gcattgcgat tccacatgga tgggcgacag agttatcacc    1560
accagcacaa gaacctgggc cctccccacc tacaataatc acctctacaa gcaaatctcc    1620
agcgaatcgg gagccaccaa cgacaaccac tacttcggct acagcaccc ctgggggtat    1680
tttgactta acagattcca ctgtcacttc tcaccacgtg actggcagcg actcatcaat    1740
aacaactggg gatttagacc caagaaactc aatttcaagc tcttcaacat ccaagtcaag    1800
gaggtcacgc agaatgatgg aaccacgacc atcgccaata accttaccag cacggtgcag    1860
gtcttcacag actctgagta ccagctgccc tacgtcctcg gttcggctca ccagggctgc    1920
cttccgccgt tcccagcaga cgtcttcatg attcctcagt acggctactt gactctgaac    1980
aatggcagcc aagcggtagg acgttcttca ttctactgtc tagagtattt tccctctcag    2040
atgctgagga cggaaacaa cttcacccttc agctacactt ttgaagacgt gccttttcac    2100
agcagctacg cgcacagcca gagtctggat cggctgatga atcctctcat tgaccagtac    2160
ctgtattacc tgagcaaaac tcagggtaca agtggaacaa cgcagcaatc gagactgcag    2220
ttcaaccaag ctgggcctag ctccatggct cagcaggcca aaaactggct accgggaccc    2280
agctaccgac agcagcgaat gtctaagacg gctaatgaca caacaacag tgaatttgct    2340
tggactgcag ccaccaaata ttacccgaat ggaagaaatt ctctggtcaa tcccgggccc    2400
ccaatggcca gtcacaagga cgatgaggaa aagtatttcc ccatgcacgg aaatctcatc    2460
```

| | |
|---|---:|
| tttggaaaac aaggcacagg aactaccaat gtggacattg aatcagtgct tattacagac | 2520 |
| gaagaagaaa tcagaacgac taatcctgtg gctacagaac aatacggaca ggttgccacc | 2580 |
| aaccgtcaga gtcagaacac cacagcttcc tatggaagtg tggacagcca gggaatctta | 2640 |
| cctggaatgg tgtggcagga ccgcgatgtc tatcttcaag gtcccatttg gccaaaaact | 2700 |
| cctcacacgg acggacactt tcatccttct ccgctcatgg gaggctttgg actgaaacac | 2760 |
| cctcctcccc agatcctgat caaaacaca cctgtgccag cgaatcccgc gaccactttc | 2820 |
| actcctggaa gtttgcttc gttcattacc cagtattcca ccggacaggt cagcgtggaa | 2880 |
| atagagtggg agctgcagaa agaaaacagc aaacgctgga acccggaaat tcagtacacc | 2940 |
| tccaactaca acaagtcggt gaatgtggag tttaccgtgg acgcaaacgg tgtttattct | 3000 |
| gaaccccgcc ctattggcac tcgttacctt acccggaact tgtaatttcc tgttaatgaa | 3060 |
| taaaccgatt tatgcgtttc agttgaactt tggtctctgc gaagggcgaa ttc | 3113 |

<210> SEQ ID NO 56
<211> LENGTH: 3122
<212> TYPE: DNA
<213> ORGANISM: Unknown
<220> FEATURE:
<223> OTHER INFORMATION: AAV serotype, clone A3.7

<400> SEQUENCE: 56

| | |
|---|---:|
| agcggccgcg aattcgccct ttctacggct gcgtcaactg gaccaatgaa aactttccct | 60 |
| tcaacgattg cgtcgacaag atggtgatct ggtgggagga gggaaagatg accgccaagg | 120 |
| tcgtggaatc tgccaaagcc attctgggtg gaagcaaggt tcgtgtggac cagaaatgca | 180 |
| ggtcttcggc ccagatcgac ccgactccgg tgattgtcac ctctaacacc aacatgtgcg | 240 |
| ccgtgattga cggaaactcg accaccttcg agcaccagca gccgttgcaa gaccggatgt | 300 |
| tcaaatttga acttacccgc cgtttggatc atgactttgg gaaggtcacc aagcaggaag | 360 |
| tcaaagactt tttccggtgg gctcaagatc acgtgactga ggtggagcat gagttctacg | 420 |
| tcaaaaaggg tggagccaag aaaaggcccg ccccgatga tgtatatata aatgagccca | 480 |
| agcgggcgcg cgagtcagtt gcgcagccat cgacgtcaga cgcggaagct tcgataaact | 540 |
| acgcggacag gtaccaaaac aaatgttctc gtcacgtggg catgaatctg atgctgtttc | 600 |
| cctgtcgaca atgcgaaaga tgaatcaga attcaaatat ctgcttcaca cacgggcaaa | 660 |
| aagactgttt ggaatgcttt cccgtgtcag aatctcaacc cgtttctgtc gtcagaaaaa | 720 |
| cgtatcagaa actttgttac attcatcata tcatgggaaa agtaccagac gcctgcactg | 780 |
| cctgcgacct ggtaaatgtg gacttggatg actgtatttc tgagcaataa atgacttaaa | 840 |
| tcaggtatgg ctgctgacgg ttatcttcca gattggctcg aggacactct ctctgaagga | 900 |
| atcagacagt ggtggaagct caaacctggc ccaccaccgc cgaaacctaa ccaacaacac | 960 |
| cgggacgaca gtagggtct tgtgcttcct gggtacaagt acctcggacc cttcaacgga | 1020 |
| ctcgacaaag gagagccggt caacgaggca gacgccgcgg ccctcgagca cgacaaagcc | 1080 |
| tacgaccacc agctcaagca aggggacaac ccgtacctca atacaaccca cgcggacgct | 1140 |
| gaatttcagg agcgtcttca agaagatacg tctttcgggg caacctcgg gcgagcagtc | 1200 |
| ttccaggcca aaagagggt actcgagcct cttggtctgg ttgaggaagc tgttaagacg | 1260 |
| gctcctggaa aaagagacc tatagagcag tctcctgcag aaccggactc ttcctcgggc | 1320 |
| atcggcaaat caggccagca gcccgctaag aaaagactca attttggtca gactggcgac | 1380 |

```
acagagtcag tcccagaccc tcaaccaatc ggagaacccc ccgcagcccc ctctggtgtg    1440
ggatctaata caatggcttc aggcggtggg gcaccaatgg cagacaataa cgaaggcgcc    1500
gacggagtgg gtaattcctc gggaaattgg cattgcgatt ccacatggat gggcgacaga    1560
gttatcacca ccagcacaag aacctgggcc ctccccacct acaataatcg cctctacaag    1620
caaatctcca gcgaatcggg agccaccaac gacaaccact acttcggcta cagcaccccc    1680
tgggggtatt ttgactttaa cagattccac tgtcacttct caccacgtga ctggcagcga    1740
ctcatcaaca caactgggg atttagaccc aagaaactca atttcaagct cttcaacatc    1800
caagtcaagg aggtcacgca gaatgatgga accacgacca tcgccaataa ccttaccagc    1860
acggtgcagg tcttcacaga ctctgagtac cagctgccct acgtcctcgg ttcggctcac    1920
cagggctgcc ttccgccgtt cccagcagac gtcttcatga ttcctcagta cggctacttg    1980
actctgaaca atggcagcca gcggtagga cgttcttcat tctactgtct agagtatttt    2040
ccctctcaga tgctgaggac gggaaacaac ttcaccttca gctacacttt tgaagacgtg    2100
cctttccaca gcagctacgc gcacagccag agtctggatc ggctgatgaa tcctctcatt    2160
gaccagtacc tgtattacct gagcaaaact cagggtacaa gtggaacaac gcagcaatcg    2220
agactgcagt tcagccaagc tgggcctagc tccatggctc agcaggccaa aaactggcta    2280
ccgggaccca gctaccgaca gcagcgaatg tctaagacgg ctaatgacaa caacaacagt    2340
gaatttgctt ggactgcagc caccaaatat acctgaatg gaagaaattc tctggtcaat    2400
cccgggcccc caatggccag tcacaaggac gatgaggaaa agtatttccc catgcacgga    2460
aatctcatct ttggaaaaca aggcacagga actaccaatg tggacattga atcagtgctt    2520
attacagacg aagaagaaat cagaacaact aatcctgtgg ctacagaaca atacggacag    2580
gttgccacca ccatcagag tcagaacacc acagcttcct atggaagtgt ggacagccag    2640
ggaatcttac ctggaatggt gtggcaggac cgcgatgtct atcttcaagg tcccatttgg    2700
gccaaaactc ctcacgga cggacacttt catccttctc cgctcatggg aggctttgga    2760
ctgaaacacc ctcctcccca gatcctgatc aaaaacacac ctgtgccagc gaatcccgcg    2820
accactttca ctcctggaaa gtttgcttcg ttcattaccc agtattccac cggacaggtc    2880
agcgtggaaa tagagtggga gctgcagaaa gaaaacagca acgctggaa cccagaaatt    2940 cagtacacct ccaactacaa caagtcgtg aatgtggagt ttaccgtgga cgcaaacggt    3000
gtttattctg aaccccgccc tattggcact cgttacctta cccggaactt gtaatttcct    3060
gttaatgaat aaaccgattt atgcgtttca gttgaacttt ggtctctgcg aagggcgaat    3120
tc                                                                   3122
```

<210> SEQ ID NO 57
<211> LENGTH: 3123
<212> TYPE: DNA
<213> ORGANISM: Unknown
<220> FEATURE:
<223> OTHER INFORMATION: AAV serotype, clone A3.3

<400> SEQUENCE: 57

```
gaattcgccc tttctacggc tgcgtcaact ggaccaatga aaactttccc ttcaacgatt      60
gcgtcgacaa gatggtgatc tggtgggagg agggaaagat gaccgccaag gtcgtggaat     120
ctgccaaagc cattctgggt ggaggcaagg ttcgtgtgga ccagaaatgc aagtcttcgg     180
cccagatcga cccgactccg gtgattgtca cctctaacac caacatgtgc gccgtgattg     240
acggaaactc gaccaccttc gagcaccagc agccgttgca agaccggatg ttcaaatttg     300
```

```
aacttacccg ccgtttggat catgactttg ggaaggtcac caagcaggaa gtcaaagact    360 tttccggtg  ggctcaagat cacgtgactg aggtggagca tgagttctac gtcaaaaagg    420
gtggagccaa gaaaaggccc gcccccgatg atgtatatat aaatgagccc aagcgggcgc    480
gcgagtcagt tgcgcagcca tcgacgtcag acgcggaagc ttcgataaac tacgcggaca    540
ggtaccaaaa caaatgttct cgtcacgtgg gcatgaatct gatgctgttt ccctgtcgac    600
aatgcgaaag aatgaatcag aattcaaata tctgcttcac acacgggcaa aaagactgtt    660
tggaatgctt tcccgtgtca gaatctcaac ccgtttctgt cgtcagaaaa acgtatcaga    720
aactttgtta cattcatcat atcatgggaa aagtaccaga cgcctgcact gcctgcgacc    780
tggtaaatgt ggacttggat gactgtattt ctgagcaata aatgacttaa atcaggtatg    840
gctgctgacg gttatcttcc agattggctc gaggacactc tctctgaagg aatcagacag    900
tggtggaagc tcaaacctgg cccaccaccg ccgaaaccta accaacaaca ccgggacgac    960 agtagggggtc ttgtgcttcc tgggtacaag tacctcggac ccttcaacgg actcgacaaa   1020
ggagagccgg tcaacgaggc agacgccgcg gccctcgagc acgacaaagc ctacgaccac   1080
cagctcaagc aaggggacaa cccgtacctc aaatacaacc acgcggacgc tgaatttcag   1140
gagcgtcttc aagaagatac gtctttcggg ggcaacctcg ggcgagcagt cttccaggcc   1200
aaaaagaggg tactcgagcc tcttggtctg gttgaggaag ctgttaagac ggctcctgga   1260 aaaagagac  ctatagagca gtctcctgca gaaccggact cttcctcggg catcggcaaa   1320
tcaggccagc agcccgctaa gaaaagactc aattttggtc agactggcga cacagagtca   1380
gtcccaggcc ctcaaccaat cggagaaccc cccgcagccc cctctggtgt gggatctaat   1440
acaatggctt caggcggtgg ggcaccaatg gcagacaata acgaaggcgc cgacggagtg   1500
ggtaattcct cgggaaattg gcattgcgat tccacatgga tgggcgacag agttatcacc   1560
accagcacaa gaacctgggc cctccccacc tacaataatc acctctacaa gcaaatctcc   1620
agcgaatcgg gagccaccaa cgacaaccac tacttcggct acagcacccc ctgggggtat   1680 tttgactta  acagattcca ctgtcacttc tcaccacgtg actggcagcg actcatcaac   1740
aacaactggg gatttagacc caagaaactc aatttcaagc tcttcaacat ccaagtcaag   1800
gaggtcacgc agaatgatgg aaccacgacc atcgccaata accttaccag cgcggtgcag   1860
gtcttcacag actctgagta ccagctgccc tacgtcctcg gttcggctca ccagggctgc   1920
cttccgccgt tcccagcaga cgtcttcatg attcctcagt acggctactt gactctgaac   1980 aatgcagcc  aagcggtagg acgttcttca ttctactgtc tagagtattt tccctctcag   2040
atgctgagga cgggaaacaa cttcaccttc agctacactt ttgaagacgt gccttccac    2100 agcagctacg cgcacagcca gagtctggat cggctgatga atcctctcat tgaccagtac   2160
ctgtattacc tgagcaaaac tcagggtaca agtggaacaa cgcagcaatc gagactgcag   2220
ttcagccaag ctgggcctag ctccatggct cagcaggcca aaaactggct accgggaccc   2280
agctaccgac agcagcgaat gtctaagacg gctaatgaca acaacaacag tgaatttgct   2340
tggactgcag ccaccaaata ttacctgaat ggaagaaatt ctctggtcaa tcccgggccc   2400
ccagtggcca gtcacaagga cgatgaggaa aagtatttcc ccatgcacgg aaatctcatc   2460
tttggaaaac aaggcacagg aactaccaat gtggacattg aatcagtgct tattacagac   2520
gaagaagaaa tcgaacaac  taatcctgtg gctacagaac aatacggaca ggttgccacc   2580
aaccatcaga gtcagaacac cacacagctt cc tatggaagtg tggacagcca gggaatctta   2640
```

```
cctggaatgg tgtggcagga ccgcgatgtc tatcttcaag gtcccatttg ggccaaaact    2700
cctcacacgg acggacactt tcatccttct ccgctcatgg gaggctttgg actgaaacac    2760
cctcctcccc agatcctgat caaaaacaca cctgtgccag cgaatcccgc gaccactttc    2820
actcctggaa agtttgcttc gttcattacc cagtattcca cctgacaggt cagcgtggaa    2880
atagagtggg agctgcagaa agaaaacagc aaacgctgga acccagaaat tcagtacacc    2940
tccaactaca acaagtcggt gaatgtggag tttaccgtgg acgcaaacgg tgtttattct    3000 gaacccccgcc ctattggcac tcgttacctt acccggaact tgtaatttcc tgttaatgaa    3060
taagccgatt tatgcgtttc agttgaactt tggtctctgc gaagggcgaa ttcgtttaaa    3120
cct                                                                 3123
```

<210> SEQ ID NO 58
<211> LENGTH: 2969
<212> TYPE: DNA
<213> ORGANISM: Unknown
<220> FEATURE:
<223> OTHER INFORMATION: AAV serotype, clone 42.12

<400> SEQUENCE: 58

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa aagcgagccc aagcgggcct     480 gccccctcagt cgcggatcca tcgacgtcag acgcggaagg agctccggtg gactttgccg     540
acaggtacca aaacaaatgt tctcgtcacg cgggcatgct tcagatgctg tttcccctgca    600 agacatgcga gaatgaat cagaatttca acatttgctt cacgcacggg accagagact       660
gttcagaatg tttccccggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatc     900
cgcgagtggt gggacttgaa acctggagcc ccgaaaccca agccaaccag caaaagcag     960 gacgacggcc ggggtctggt gcttcctggc tacaagtacc tcggaccctt caacggactc    1020
gacaagggag agccggtcaa cgaggcagac gccgcggccc tcgagcacga caaggcctac    1080
gacaagcagc tcgagcaggg ggacaacccg tacctcaagt acaaccacgc cgacgccgag    1140
tttcaggagc gtcttcaaga agatacgtct tttggggcca acctcggcgc agcagtcttc    1200
caggccaaga agcgggttct cgaacctctc ggtctggttg aggaaggcgc taagacggct    1260
cctgaaagaa agagaccggt agagccatca ccccagcgtt ctccagactc ctctacgggc    1320
atcggcaaga caggccagca gccgcgaaaa aagagactca actttgggca gactggcgac    1380
tcagagtcag tgcccgaccc tcaaccaatc ggagaacccc ccgcaggccc ctctggtctg    1440
ggatctggta caatgctgc aggcggtggc gctccaatgg cagacaataa cgaaggcgcc    1500
gacggagtgg gtagttcctc aggaaattgg cattgcgatt ccacatggct gggcgacaga    1560
```

```
gtcatcacca ccagcacccg aacctgggcc ctccccacct acaacaacca cctctacaag    1620
caaatctcca acgggacatc gggaggaagc accaacgaca cacctactt cggctacagc     1680 accccctggg ggtattttga ctttaacaga ttccactgcc acttctcacc acgtgactgg    1740
cagcgactca tcaacaacaa ctggggattc cggcccaaga gactcaactt caagctcttc    1800
aacatccagg tcaaggaggt cacgcagaat gaaggcacca agaccatcgc caataacctt    1860
accagcacga ttcaggtctt tacgactcg gaataccagc tcccgtacgt cctcggctct     1920
gcgcaccagg gctgcctgcc tccgttcccg gcggacgtct tcatgattcc tcagtacggg    1980
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt tcacagcag ctacgcgcac agccaaagcc tggaccggct gacgaacccc     2160
ctcatcgacc agtacctgta ctacctggcc cggacccaga gcactacggg gtccacaagg    2220
gggctgcagt ccatcaggc tgggcccaac accatggccg agcaatcaaa gaactggctg     2280
cccggaccct gttatcggca gcagagactg tcaaaaaaca tagacagcaa caacaacagt    2340
aactttgcct ggaccggggc cactaaatac catctgaatg gtagaaattc attaaccaac    2400
ccgggcgtag ccatggccac caacaaggac gacgaggacc agttctttcc catcaacgga    2460
gtgctggttt ttggcaaaac gggggctgcc aacaagacaa cgctgaaaaa cgtgctaatg    2520
accagcgagg aggagatcaa aaccaccaat cccgtggcta cagaagaata cggtgtggtc    2580
tccagcaacc tgcaatcgtc tacggccgga ccccagacac agactgtcaa cagccagggg    2640
gctctgcccg gcatggtctg gcagaaccgg gacgtgtacc tgcagggtcc catctgggcc    2700
aaaattcctc acacggacgg caactttcac ccgtctcccc tgatgggcgg atttggactc    2760
aaacacccgc ctcctcaaat tctcatcaag tatacttcca actactacaa atctacaaat    2820
gtggactttg ctgtcaatac tgagggtact tattcagagc ctcgccccat tggcacccgt    2880
tacctcaccc gtaacctgta attgcctgtt aatcaataaa ccggttaatt cgtttcagtt    2940
gaactttggt ctctgcgaag ggcgaattc                                      2969
```

<210> SEQ ID NO 59
<211> LENGTH: 3129
<212> TYPE: DNA
<213> ORGANISM: Unknown
<220> FEATURE:
<223> OTHER INFORMATION: AAV serotype, clone 44.2

<400> SEQUENCE: 59

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaaag tgcgcgtgga ccaaaagtgc aagtcgtccg    180
cccagatcga ccccacccc gtgatcgtca cctccaacac caacatgtgc gccgtgattg    240
acgggaacag caccaccttc gagcaccagc agccgttgca ggaccggatg ttcaagtttg    300
aactcacccg ccgtctggag cacgactttg gcaaggtgac aaagcaggaa gtcagagagt    360
tcttccgctg ggcgcaggat cacgtgaccg aggtggcgca cgagttctac gtcagaaagg    420
gtggagccaa caagagaccc gccccgatg acgcggataa agcgagccc aagcgggcct      480 gcccctcagt cgcggatcca tcgacgtcag acgcggaagg agctccggtg gactttgccg    540
acaggtacca aaacaaatgt tctcgtcacg cgggcatgct tcagatgctg tttcctgca    600
```

```
aaacatgcga gagaatgaat cagaatttca acatttgctt cacgcacggg accagagact    660
gttcagaatg tttccccggc gtgtcagaat ctcaaccggt cgtcagaaaa agacgtatc    720
ggaaactctg tgcgattcat catctgctgg gggcgggcac ccgagattgc ttgctcggcc    780
tgcgatctgg tcaacgtgga cctagatgac tgtgtttctg agcaataaat gacttaaacc    840
aggtatggct gccgatggtt atcttccaga ttggctcgag acaacctctc tgagggcat    900
tcgcgagtgg tgggacttga aacctggagc cccgaaaccc aaagccaacc agcaaaagca    960
ggacgacggc cggggtctgg tgcttcctgg ctacaagtac ctcggaccct tcaacggact   1020
cgacaagggg gagcccgtca acgcggcgga cgcagcggcc ctcgagcacg acaaggccta   1080
cgaccagcag ctcaaagcgg gtgacaatcc gtacctgcgg tataaccacg ccgacgccga   1140
gtttcaggag cgtctgcaag aagatacgtc ttttgggggc aacctcgggc gagcagtctt   1200
ccaggccaag aagcgggttc tcgaacctct cggtctggtt gaggaaggcg ctaagacggc   1260
tcctggaaag aagagaccgg tagagccatc accccagcgt tctccagact cctctacggg   1320
catcggcaag aaaggccagc agcccgcgaa aaagagactc aactttgggc agactggcga   1380
ctcagagtca gtgcccgacc ctcaaccaat cggagaaccc cccgcaggcc cctctggtct   1440
gggatctggt acaatggctg caggcggtgg cgctccaatg gcagacaata acgaaggcgc   1500
cgacggagtg ggtagttcct caggaaattg gcattgcgat ccacatggc tgggcgacag    1560
agtcatcacc accagcaccc gaacctgggc cctcccacc tacaacaacc acctctacaa    1620
gcaaatctcc aacgggactt cgggaggaag caccaacgac aacacctact cggctacag    1680
cacccctgg gggtattttg actttaacag attccactgc cacttctcac cacgtgactg    1740
gcagcgactc atcaacaaca actggggatt ccggcccaag agactcaact tcaagctctt   1800
caacatccag gtcaaggagg tcacgcagaa tgaaggcacc aagaccatcg ccaataacct   1860
taccagcacg attcaggtct ttacggactc ggaataccag ctcccgtacg tcctcggctc   1920
tgcgcaccag gctgcctgc ctccgttccc ggcggacgtc ttcatgattc ctcagtacgg    1980
gtacctgact ctgaacaatg gcagtcaggc cgtgggccgt tcctccttct actgcctgga   2040
gtactttcct tctcaaatgc tgagaacggg caacaacttt gagttcagct accagtttga   2100
ggacgtgcct tttcacagca gctacgcgca gccaaagc ctggaccggc tgatgaaccc     2160
cctcatcgac cagtacctgt actacctgtc tcggactcag tccacgggag gtaccgcagg   2220
aactcagcag ttgctatttt tcaggccgg gcctaataac atgtcggctc aggccaaaaa    2280
ctggctaccc gggcccctgct accggcagca acgcgtctcc acgacactgt cgcaaaataa   2340
caacagcaac tttgcctgga ccggtgccac caagtatcat ctgaatggca gagactctct   2400
ggtaaatccc ggtgtcgcta tggcaaccca caggacgac gaagagcgat tttttccgtc     2460
cagcggagtc ttaatgtttg ggaaacaggg agctggaaaa dacaacgtgg actatagcag   2520
cgttatgcta accagtgagg aagaaattaa aaccaccaac ccagtggcca cagaacagta    2580
cggcgtggtg gccgataacc tgcaacagca aaacgccgct cctattgtag gggccgtcaa   2640
cagtcaagga gccttacctg gcatggtctg gcagaaccgg gacgtgtacc tgcagggtcc   2700
tatctgggcc aagattcctc acacggacgg aaactttcat ccctcgccgc tgatgggagg   2760
ctttggactg aaacacccgc ctcctcagat cctgattaag aatacacctg ttcccgcgga   2820
tcctccaact accttcagtc aagctaagct ggcgtcgttc atcacgcagt acagcaccgg   2880
acaggtcagc gtggaaattg aatgggagct gcagaaagaa aacagcaaac gctggaaccc   2940
agagattcaa tacacttcca actactacaa atctacaaat gtggactttg ctgttaacac   3000
```

```
agatggcact tattctgagc ctcgccccat cggcacccgt tacctcaccc gtaatctgta   3060
attgcttgtt aatcaataaa ccggttgatt cgtttcagtt gaactttggt ctctgcgaag   3120
ggcgaattc                                                          3129
```

<210> SEQ ID NO 60
<211> LENGTH: 733
<212> TYPE: PRT
<213> ORGANISM: Unknown
<220> FEATURE:
<223> OTHER INFORMATION: capsid protein of AAV serotype, clone C1VP1

<400> SEQUENCE: 60

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335
```

Ser Ser Tyr Glu Leu Pro Tyr Val Met Asp Ala Gly Gln Glu Gly Ser
            340                 345                 350

Leu Ser Pro Phe Pro Asn Asp Val Phe Met Val Pro Gln Tyr Gly Tyr
            355                 360                 365

Cys Gly Ile Val Thr Gly Glu Asn Gln Asn Thr Asp Arg Asn Ala
370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Gly Lys Val Pro Phe His Ser Met
                405                 410                 415

Tyr Ala Tyr Ser Gln Ser Pro Asp Arg Leu Met Asn Pro Leu Leu Asp
            420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
            450                 455                 460

Ala Phe Tyr Arg Lys Asn Trp Leu Pro Gly Pro Cys Val Lys Gln Gln
465                 470                 475                 480

Arg Leu Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
            515                 520                 525

Asp Gly Asp Phe Ser Asn Ala Gln Leu Ile Phe Pro Gly Pro Ser Val
            530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Tyr Gly Asn
            690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 61
<211> LENGTH: 733

<212> TYPE: PRT
<213> ORGANISM: Unknown
<220> FEATURE:
<223> OTHER INFORMATION: capsid protein of AAV serotype, clone C2VP1

<400> SEQUENCE: 61

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Leu
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe His Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
            165                 170                 175

Gly Ala Gly Asp Gly Pro Pro Glu Gly Ser Asp Thr Ser Ala Met Ser
        180                 185                 190

Ser Asp Ile Glu Met Arg Ala Ala Pro Gly Gly Asn Ala Val Asp Ala
    195                 200                 205

Gly Gln Gly Ser Asp Gly Val Gly Asn Ala Ser Gly Asp Trp His Cys
210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
            245                 250                 255

Thr Ser Asn Ser Asn Thr Tyr Asn Gly Phe Ser Thr Pro Trp Gly Tyr
        260                 265                 270

Phe Asp Phe Asn Arg Phe His Cys His Phe Ser Pro Arg Asp Trp Gln
    275                 280                 285

Arg Leu Ile Asn Asn Trp Gly Leu Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
            325                 330                 335

Ser Ser Tyr Glu Leu Pro Tyr Val Met Asp Ala Gly Gln Glu Gly Ser
        340                 345                 350

Leu Pro Pro Phe Pro Asn Asp Val Phe Met Val Pro Gln Tyr Gly Tyr
    355                 360                 365

Cys Gly Ile Val Thr Gly Glu Asn Gln Asn Gln Thr Asp Arg Asn Ala
    370                 375                 380
```

```
Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
        405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
            515                 520                 525

Asp Gly Asp Phe Ser Asn Ala Gln Leu Ile Phe Pro Gly Pro Ser Val
530                 535                 540

Thr Gly Asn Thr Thr Thr Ser Ala Asn Asn Leu Leu Phe Thr Ser Glu
545                 550                 555                 560

Gly Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
        610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Ile Glu Lys Glu Arg
        675                 680                 685

Ser Lys Arg Arg Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730
```

<210> SEQ ID NO 62
<211> LENGTH: 733
<212> TYPE: PRT
<213> ORGANISM: Unknown
<220> FEATURE:
<223> OTHER INFORMATION: capsid protein of AAV serotype, clone C5VP1[@0002]

<400> SEQUENCE: 62

```
Met Ala Ala Asp Gly Tyr Leu Pro Asp Trp Leu Glu Asp Asn Leu Ser
1               5                   10                  15
```

```
Glu Gly Ile Arg Glu Trp Trp Asp Leu Lys Pro Gly Ala Pro Lys Pro
         20                  25                  30

Lys Ala Asn Gln Gln Lys Gln Asp Asp Gly Arg Gly Leu Val Leu Pro
             35                  40                  45

Gly Tyr Glu Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
         115                 120                 125

Leu Gly Leu Val Glu Glu Gly Ala Lys Thr Ala Pro Gly Lys Lys Arg
     130                 135                 140

Pro Leu Glu Ser Pro Gln Glu Pro Asp Ser Ser Gly Ile Gly Lys
145                 150                 155                 160

Lys Gly Lys Gln Pro Ala Lys Lys Arg Leu Asn Phe Glu Glu Asp Thr
                 165                 170                 175

Gly Ala Gly Asp Gly Pro Pro Glu Gly Ser Asp Thr Ser Ala Met Ser
             180                 185                 190

Ser Asp Ile Glu Met Arg Ala Ala Pro Gly Gly Asn Ala Val Asp Ala
         195                 200                 205

Gly Gln Gly Ser Asp Gly Val Gly Asn Ala Ser Gly Asp Trp His Cys
     210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                 245                 250                 255

Thr Ser Asn Ser Asn Thr Tyr Asn Gly Phe Ser Thr Pro Trp Gly Tyr
             260                 265                 270

Phe Asp Phe Asn Arg Phe His Cys His Phe Ser Pro Arg Asp Trp Gln
         275                 280                 285

Arg Leu Ile Asn Asn Asn Trp Gly Leu Arg Pro Lys Ala Met Arg Val
     290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                 325                 330                 335

Ser Ser Tyr Glu Leu Pro Tyr Val Met Asp Ala Gly Gln Glu Gly Ser
             340                 345                 350

Leu Pro Pro Phe Pro Asn Asp Val Phe Met Val Pro Gln Tyr Gly Tyr
         355                 360                 365

Cys Gly Ile Val Thr Gly Glu Asn Gln Asn Gln Thr Asp Arg Asn Ala
     370                 375                 380

Phe Tyr Cys Leu Glu Tyr Phe Pro Ser Gln Met Leu Arg Thr Gly Asn
385                 390                 395                 400

Asn Phe Glu Thr Ala Tyr Asn Phe Glu Lys Val Pro Phe His Ser Met
                 405                 410                 415

Tyr Ala His Ser Gln Ser Leu Asp Gly Leu Met Asn Pro Leu Leu Asp
             420                 425                 430

Gln Tyr Leu Trp His Leu Gln Ser Thr Thr Ser Gly Glu Thr Leu Asn
```

```
            435                 440                 445
Gln Gly Asn Ala Ala Thr Thr Phe Gly Lys Ile Arg Ser Gly Asp Phe
    450                 455                 460
Ala Phe Tyr Arg Lys Asn Trp Leu Pro Gly Pro Cys Val Lys Gln Gln
465                 470                 475                 480
Arg Phe Ser Lys Thr Ala Ser Gln Asn Tyr Lys Ile Pro Ala Ser Gly
                485                 490                 495
Gly Asn Ala Leu Leu Lys Tyr Asp Thr His Tyr Thr Leu Asn Asn Arg
                500                 505                 510
Trp Ser Asn Ile Ala Pro Gly Pro Met Ala Thr Ala Gly Pro Ser
            515                 520                 525
Asp Gly Asp Phe Ser Asn Ala Gln Leu Ile Phe Pro Gly Pro Ser Val
    530                 535                 540
Thr Gly Asn Thr Thr Thr Ser Ala Asn Asn Leu Leu Phe Thr Ser Glu
545                 550                 555                 560
Glu Glu Ile Ala Ala Thr Asn Pro Arg Asp Thr Asp Met Phe Gly Gln
                565                 570                 575
Ile Ala Asp Asn Asn Gln Asn Ala Thr Thr Ala Pro Ile Thr Gly Asn
                580                 585                 590
Val Thr Ala Met Gly Val Leu Pro Gly Met Val Trp Gln Asn Arg Asp
            595                 600                 605
Ile Tyr Tyr Gln Gly Pro Ile Trp Ala Lys Ile Pro His Ala Asp Gly
    610                 615                 620
His Phe His Pro Ser Pro Leu Ile Gly Gly Phe Gly Leu Lys His Pro
625                 630                 635                 640
Pro Pro Gln Ile Phe Ile Lys Asn Thr Pro Val Pro Ala Tyr Pro Ala
                645                 650                 655
Thr Thr Phe Thr Ala Ala Arg Val Asp Ser Phe Ile Thr Gln Tyr Ser
                660                 665                 670
Thr Gly Gln Val Ala Val Gln Ile Glu Trp Glu Ile Glu Lys Glu Arg
            675                 680                 685
Ser Lys Arg Trp Asn Pro Glu Val Gln Phe Thr Ser Asn Cys Gly Asn
    690                 695                 700
Gln Ser Ser Met Leu Trp Ala Pro Asp Thr Thr Gly Lys Tyr Thr Glu
705                 710                 715                 720
Pro Arg Val Ile Gly Ser Arg Tyr Leu Thr Asn His Leu
                725                 730

<210> SEQ ID NO 63
<211> LENGTH: 734
<212> TYPE: PRT
<213> ORGANISM: Unknown
<220> FEATURE:
<223> OTHER INFORMATION: capsid protein of AAV serotype, clone AAV4VP1

<400> SEQUENCE: 63

Met Thr Asp Gly Tyr Leu Pro Asp Trp Leu Glu Asp Asn Leu Ser Glu
1               5                   10                  15
Gly Val Arg Glu Trp Trp Ala Leu Gln Pro Gly Ala Pro Lys Pro Lys
            20                  25                  30
Ala Asn Gln Gln His Gln Asp Asn Ala Arg Gly Leu Val Leu Pro Gly
        35                  40                  45
Tyr Lys Tyr Leu Gly Pro Gly Asn Gly Leu Asp Lys Gly Glu Pro Val
    50                  55                  60
Asn Ala Ala Asp Ala Ala Ala Leu Glu His Asp Lys Ala Tyr Asp Gln
```

```
                65                  70                  75                  80
Gln Leu Lys Ala Gly Asp Asn Pro Tyr Leu Lys Tyr Asn His Ala Asp
                    85                  90                  95
Ala Glu Phe Gln Gln Arg Leu Gln Gly Asp Thr Ser Phe Gly Gly Asn
                100                 105                 110
Leu Gly Arg Ala Val Phe Gln Ala Lys Lys Arg Val Leu Glu Pro Leu
                115                 120                 125
Gly Leu Val Glu Gln Ala Gly Glu Thr Ala Pro Gly Lys Lys Arg Pro
            130                 135                 140
Leu Ile Glu Ser Pro Gln Pro Asp Ser Ser Thr Gly Ile Gly Lys
145                 150                 155                 160
Lys Gly Lys Gln Pro Ala Lys Lys Leu Val Phe Glu Asp Glu Thr
                165                 170                 175
Gly Ala Gly Asp Gly Pro Pro Glu Gly Ser Thr Ser Gly Ala Met Ser
            180                 185                 190
Asp Asp Ser Glu Met Arg Ala Ala Gly Gly Ala Ala Val Glu Gly
            195                 200                 205
Gly Gln Gly Ala Asp Gly Val Gly Asn Ala Ser Gly Asp Trp His Cys
        210                 215                 220
Asp Ser Thr Trp Ser Glu Gly His Val Thr Thr Ser Thr Arg Thr
225                 230                 235                 240
Trp Val Leu Pro Thr Tyr Asn Asn His Leu Tyr Lys Arg Leu Gly Glu
                245                 250                 255
Ser Leu Gln Ser Asn Thr Tyr Asn Gly Phe Ser Thr Pro Trp Gly Tyr
                260                 265                 270
Phe Asp Phe Asn Arg Phe His Cys His Phe Ser Pro Arg Asp Trp Gln
            275                 280                 285
Arg Leu Ile Asn Asn Asn Trp Gly Met Arg Pro Lys Ala Met Arg Val
            290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
            340                 345                 350
Leu Pro Pro Phe Pro Asn Asp Val Phe Met Val Pro Gln Tyr Gly Tyr
            355                 360                 365
Cys Gly Leu Val Thr Gly Asn Thr Ser Gln Gln Gln Thr Asp Arg Asn
        370                 375                 380
Ala Phe Tyr Cys Leu Glu Tyr Phe Pro Ser Gln Met Leu Arg Thr Gly
385                 390                 395                 400
Asn Asn Phe Glu Ile Thr Tyr Ser Phe Glu Lys Val Pro Phe His Ser
                405                 410                 415
Met Tyr Ala His Ser Gln Ser Leu Asp Arg Leu Met Asn Pro Leu Ile
                420                 425                 430
Asp Gln Tyr Leu Trp Gly Leu Gln Ser Thr Thr Thr Gly Thr Thr Leu
            435                 440                 445
Asn Ala Gly Thr Ala Thr Thr Asn Phe Thr Lys Leu Arg Pro Thr Asn
        450                 455                 460
Phe Ser Asn Phe Lys Lys Asn Trp Leu Pro Gly Pro Ser Ile Lys Gln
465                 470                 475                 480
Gln Gly Phe Ser Lys Thr Ala Asn Gln Asn Tyr Lys Ile Pro Ala Thr
            485                 490                 495
```

```
Gly Ser Asp Ser Leu Ile Lys Tyr Glu Thr His Ser Thr Leu Asp Gly
            500                 505                 510

Arg Trp Ser Ala Leu Thr Pro Gly Pro Met Ala Thr Ala Gly Pro
        515                 520                 525

Ala Asp Ser Lys Phe Ser Asn Ser Gln Leu Ile Phe Ala Gly Pro Lys
        530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
        610                 615                 620

Gly His Phe His Pro Ser Pro Leu Ile Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
        690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 64
<211> LENGTH: 736
<212> TYPE: PRT
<213> ORGANISM: Unknown
<220> FEATURE:
<223> OTHER INFORMATION: capsid protein of AAV serotype, clone AAV1

<400> SEQUENCE: 64

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540
```

-continued

```
Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 65
<211> LENGTH: 736
<212> TYPE: PRT
<213> ORGANISM: Unknown
<220> FEATURE:
<223> OTHER INFORMATION: capsid protein of AAV serotype, clone AAV6VP1

<400> SEQUENCE: 65

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175
```

-continued

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
```

```
            595                 600                 605
Asp Arg Asp Val Tyr Leu Gln Gly Pro Ile Trp Ala Lys Ile Pro His
610                 615                 620

Thr Asp Gly His Phe His Pro Ser Pro Leu Met Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
                690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 66
<211> LENGTH: 735
<212> TYPE: PRT
<213> ORGANISM: Unknown
<220> FEATURE:
<223> OTHER INFORMATION: capsid protein of AAV serotype, clone A3.3

<400> SEQUENCE: 66

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Asn Gln Gln His Arg Asp Asp Ser Arg Gly Leu Val Leu Pro
                35                  40                  45

Gly Tyr Lys Tyr Leu Gly Pro Phe Asn Gly Leu Asp Lys Gly Glu Pro
50                  55                  60

Val Asn Glu Ala Asp Ala Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Ala Val Lys Thr Ala Pro Gly Lys Lys Arg
130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Gly Pro Gln Pro Ile Gly Glu Pro Pro
                180                 185                 190

Ala Ala Pro Ser Gly Val Gly Ser Asn Thr Met Ala Ser Gly Gly Gly
                195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
```

```
            225                 230                 235                 240
        Thr Thr Ser Thr Arg Thr Trp Ala Leu Pro Thr Tyr Asn Asn His Leu
                        245                 250                 255

Tyr Lys Gln Ile Ser Ser Glu Ser Gly Ala Thr Asn Asp Asn His Tyr
                        260                 265                 270

Phe Gly Tyr Ser Thr Pro Trp Gly Tyr Phe Asp Phe Asn Arg Phe His
                        275                 280                 285

Cys His Phe Ser Pro Arg Asp Trp Gln Arg Leu Ile Asn Asn Asn Trp
                        290                 295                 300

Gly Phe Arg Pro Lys Lys Leu Asn Phe Lys Leu Phe Asn Ile Gln Val
        305                 310                 315                 320

Lys Glu Val Thr Gln Asn Asp Gly Thr Thr Thr Ile Ala Asn Asn Leu
                        325                 330                 335

Thr Ser Ala Val Gln Val Phe Thr Asp Ser Glu Tyr Gln Leu Pro Tyr
                        340                 345                 350

Val Leu Gly Ser Ala His Gln Gly Cys Leu Pro Pro Phe Pro Ala Asp
                        355                 360                 365

Val Phe Met Ile Pro Gln Tyr Gly Tyr Leu Thr Leu Asn Asn Gly Ser
                        370                 375                 380

Gln Ala Val Gly Arg Ser Ser Phe Tyr Cys Leu Glu Tyr Phe Pro Ser
        385                 390                 395                 400

Gln Met Leu Arg Thr Gly Asn Asn Phe Thr Phe Ser Tyr Thr Phe Glu
                        405                 410                 415

Asp Val Pro Phe His Ser Ser Tyr Ala His Ser Gln Ser Leu Asp Arg
                        420                 425                 430

Leu Met Asn Pro Leu Ile Asp Gln Tyr Leu Tyr Tyr Leu Ser Lys Thr
                        435                 440                 445

Gln Gly Thr Ser Gly Thr Thr Gln Gln Ser Arg Leu Gln Phe Ser Gln
                        450                 455                 460

Ala Gly Pro Ser Ser Met Ala Gln Gln Ala Lys Asn Trp Leu Pro Gly
        465                 470                 475                 480

Pro Ser Tyr Arg Gln Gln Arg Met Ser Lys Thr Ala Asn Asp Asn Asn
                        485                 490                 495

Asn Ser Glu Phe Ala Trp Thr Ala Ala Thr Lys Tyr Tyr Leu Asn Gly
                        500                 505                 510

Arg Asn Ser Leu Val Asn Pro Gly Pro Val Ala Ser His Lys Asp
                        515                 520                 525

Asp Glu Glu Lys Tyr Phe Pro Met His Gly Asn Leu Ile Phe Gly Lys
        530                 535                 540

Gln Gly Thr Gly Thr Thr Asn Val Asp Ile Glu Ser Val Leu Ile Thr
        545                 550                 555                 560

Asp Glu Glu Ile Arg Thr Thr Asn Pro Val Ala Thr Glu Gln Tyr
                        565                 570                 575

Gly Gln Val Ala Thr Asn His Gln Ser Gln Asn Thr Thr Ala Ser Tyr
                        580                 585                 590

Gly Ser Val Asp Ser Gln Gly Ile Leu Pro Gly Met Val Trp Gln Asp
                        595                 600                 605

Arg Asp Val Tyr Leu Gln Gly Pro Ile Trp Ala Lys Thr Pro His Thr
                        610                 615                 620

Asp Gly His Phe His Pro Ser Pro Leu Met Gly Gly Phe Gly Leu Lys
        625                 630                 635                 640

His Pro Pro Pro Gln Ile Leu Ile Lys Asn Thr Pro Val Pro Ala Asn
                        645                 650                 655
```

```
Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
        690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 67
<211> LENGTH: 735
<212> TYPE: PRT
<213> ORGANISM: Unknown
<220> FEATURE:
<223> OTHER INFORMATION: capsid protein of AAV serotype, clone A3.7

<400> SEQUENCE: 67

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn Arg Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290                 295                 300
Gly Phe Arg Pro Lys Lys Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Ile Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Lys Thr
            435                 440                 445
Gln Gly Thr Ser Gly Thr Thr Gln Gln Ser Arg Leu Gln Phe Ser Gln
450                 455                 460
Ala Gly Pro Ser Ser Met Ala Gln Gln Ala Lys Asn Trp Leu Pro Gly
465                 470                 475                 480
Pro Ser Tyr Arg Gln Gln Arg Met Ser Lys Thr Ala Asn Asp Asn Asn
                485                 490                 495
Asn Ser Glu Phe Ala Trp Thr Ala Ala Thr Lys Tyr Tyr Leu Asn Gly
                500                 505                 510
Arg Asn Ser Leu Val Asn Pro Gly Pro Pro Met Ala Ser His Lys Asp
            515                 520                 525
Asp Glu Glu Lys Tyr Phe Pro Met His Gly Asn Leu Ile Phe Gly Lys
530                 535                 540
Gln Gly Thr Gly Thr Thr Asn Val Asp Ile Glu Ser Val Leu Ile Thr
545                 550                 555                 560
Asp Glu Glu Glu Ile Arg Thr Thr Asn Pro Val Ala Thr Glu Gln Tyr
                565                 570                 575
Gly Gln Val Ala Thr Asn His Gln Ser Gln Asn Thr Thr Ala Ser Tyr
                580                 585                 590
Gly Ser Val Asp Ser Gln Gly Ile Leu Pro Gly Met Val Trp Gln Asp
            595                 600                 605
Arg Asp Val Tyr Leu Gln Gly Pro Ile Trp Ala Lys Thr Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ala Thr Thr Phe Thr Pro Gly Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
690                 695                 700
```

```
Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 68
<211> LENGTH: 735
<212> TYPE: PRT
<213> ORGANISM: Unknown
<220> FEATURE:
<223> OTHER INFORMATION: capsid protein of AAV serotype, clone A3.4

<400> SEQUENCE: 68

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
130                 135                 140

Pro Ile Glu Gln Ser Pro Ala Glu Pro Asp Ser Ser Ser Gly Ile Gly
145                 150                 155                 160

Glu Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asp Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Lys Thr
        435                 440                 445

Gln Gly Thr Ser Gly Thr Thr Gln Gln Ser Arg Leu Gln Phe Ser Gln
    450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Ala Thr Lys Tyr Tyr Leu Asn Gly
            500                 505                 510

Arg Asn Ser Leu Val Asn Pro Gly Pro Pro Met Ala Ser His Lys Asp
        515                 520                 525

Asp Glu Glu Lys Tyr Phe Pro Met His Gly Asn Leu Ile Phe Gly Lys
    530                 535                 540

Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
                565                 570                 575

Gly Gln Val Ala Thr Asn His Gln Ser Gln Asp Thr Thr Ala Ser Tyr
            580                 585                 590

Gly Ser Val Asp Ser Gln Gly Ile Leu Pro Gly Met Val Trp Gln Asp
        595                 600                 605

Arg Asp Val Tyr Leu Gln Gly Pro Ile Trp Ala Lys Thr Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 69
<211> LENGTH: 735
<212> TYPE: PRT

<213> ORGANISM: Unknown
<220> FEATURE:
<223> OTHER INFORMATION: capsid protein of AAV serotype, clone A3.5

<400> SEQUENCE: 69

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser

```
                385                 390                 395                 400
        Gln Met Leu Arg Thr Gly Asn Asn Phe Thr Phe Ser Tyr Thr Phe Glu
                        405                 410                 415
        Asp Val Pro Phe His Ser Ser Tyr Ala His Ser Gln Ser Leu Asp Arg
                        420                 425                 430
        Leu Met Asn Pro Leu Ile Asp Gln Tyr Leu Tyr Tyr Leu Ser Lys Thr
                        435                 440                 445
        Gln Gly Thr Ser Gly Thr Thr Gln Gln Ser Arg Leu Gln Phe Asn Gln
                450                 455                 460
        Ala Gly Pro Ser Ser Met Ala Gln Gln Ala Lys Asn Trp Leu Pro Gly
        465                 470                 475                 480
        Pro Ser Tyr Arg Gln Gln Arg Met Ser Lys Thr Ala Asn Asp Asn Asn
                        485                 490                 495
        Asn Ser Glu Phe Ala Trp Thr Ala Ala Thr Lys Tyr Tyr Pro Asn Gly
                        500                 505                 510
        Arg Asn Ser Leu Val Asn Pro Gly Pro Pro Met Ala Ser His Lys Asp
                        515                 520                 525
        Asp Glu Glu Lys Tyr Phe Pro Met His Gly Asn Leu Ile Phe Gly Lys
                530                 535                 540
        Gln Gly Thr Gly Thr Thr Asn Val Asp Ile Glu Ser Val Leu Ile Thr
        545                 550                 555                 560
        Asp Glu Glu Glu Ile Arg Thr Thr Asn Pro Val Ala Thr Glu Gln Tyr
                        565                 570                 575
        Gly Gln Val Ala Thr Asn Arg Gln Ser Gln Asn Thr Thr Ala Ser Tyr
                        580                 585                 590
        Gly Ser Val Asp Ser Gln Gly Ile Leu Pro Gly Met Val Trp Gln Asp
                        595                 600                 605
        Arg Asp Val Tyr Leu Gln Gly Pro Ile Trp Ala Lys Thr Pro His Thr
                610                 615                 620
        Asp Gly His Phe His Pro Ser Pro Leu Met Gly Gly Phe Gly Leu Lys
        625                 630                 635                 640
        His Pro Pro Pro Gln Ile Leu Ile Lys Asn Thr Pro Val Pro Ala Asn
                        645                 650                 655
        Pro Ala Thr Thr Phe Thr Pro Gly Lys Phe Ala Ser Phe Ile Thr Gln
                        660                 665                 670
        Tyr Ser Thr Gly Gln Val Ser Val Glu Ile Glu Trp Glu Leu Gln Lys
                        675                 680                 685
        Glu Asn Ser Lys Arg Trp Asn Pro Glu Ile Gln Tyr Thr Ser Asn Tyr
                690                 695                 700
        Asn Lys Ser Val Asn Val Glu Phe Thr Val Asp Ala Asn Gly Val Tyr
        705                 710                 715                 720
        Ser Glu Pro Arg Pro Ile Gly Thr Arg Tyr Leu Thr Arg Asn Leu
                        725                 730                 735

<210> SEQ ID NO 70
<211> LENGTH: 735
<212> TYPE: PRT
<213> ORGANISM: Unknown
<220> FEATURE:
<223> OTHER INFORMATION: capsid protein of AAV serotype, clone AAV2

<400> SEQUENCE: 70

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
```

-continued

```
                    20                  25                  30
Lys Pro Ala Glu Arg His Lys Asp Asp Ser Arg Gly Leu Val Leu Pro
                35                  40                  45
Gly Tyr Lys Tyr Leu Gly Pro Phe Asn Gly Leu Asp Lys Gly Glu Pro
            50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
        435                 440                 445
```

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 71
<211> LENGTH: 736
<212> TYPE: PRT
<213> ORGANISM: Unknown
<220> FEATURE:
<223> OTHER INFORMATION: capsid protein of AAV serotype, clone AAV3

<400> SEQUENCE: 71

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

-continued

```
Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495
```

```
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
    530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Gly Thr Val Asn His Gln Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                725                 730                 735

<210> SEQ ID NO 72
<211> LENGTH: 737
<212> TYPE: PRT
<213> ORGANISM: Unknown
<220> FEATURE:
<223> OTHER INFORMATION: capsid protein of AAV serotype, clone 3.3bVP1

<400> SEQUENCE: 72

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asn Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Asn Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
            195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Glu Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asp Pro Gly Gly Thr Ala Gly Asn Arg Glu Leu Gln
450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
530                 535                 540

Phe Gly Lys Thr Gly Ala Thr Asn Lys Thr Thr Leu Glu Asn Val Leu
```

```
                545                 550                 555                 560
Met Thr Asn Glu Glu Glu Ile Arg Pro Thr Asn Pro Val Ala Thr Glu
                            565                 570                 575
Glu Tyr Gly Ile Val Ser Ser Asn Leu Gln Ala Ala Asn Thr Ala Ala
                    580                 585                 590
Gln Thr Gln Val Val Asn Asn Gln Gly Ala Leu Pro Gly Met Val Trp
                595                 600                 605
Gln Asn Arg Asp Val Tyr Leu Gln Gly Pro Ile Trp Ala Lys Ile Pro
            610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                        645                 650                 655
Ala Asn Pro Pro Glu Val Phe Thr Pro Ala Lys Phe Ala Ser Phe Ile
                660                 665                 670
Thr Gln Tyr Ser Thr Gly Gln Val Ser Val Glu Ile Glu Trp Glu Leu
                    675                 680                 685
Gln Lys Glu Asn Ser Lys Arg Trp Asp Pro Glu Ile Gln Tyr Thr Ser
        690                 695                 700
Asn Phe Glu Lys Gln Thr Gly Val Asp Phe Ala Val Asp Ser Gln Gly
705                 710                 715                 720
Val Tyr Ser Glu Pro Arg Pro Ile Gly Thr Arg Tyr Leu Thr Arg Asn
                        725                 730                 735
Leu

<210> SEQ ID NO 73
<211> LENGTH: 644
<212> TYPE: PRT
<213> ORGANISM: Unknown
<220> FEATURE:
<223> OTHER INFORMATION: capsid protein of AAV serotype, clone 223-4

<400> SEQUENCE: 73

Lys Ala Tyr Asp Gln Gln Leu Lys Ala Gly Asp Asn Pro Tyr Leu Arg
1               5                   10                  15
Tyr Asn His Ala Asp Ala Glu Phe Gln Glu Arg Leu Gln Glu Asp Thr
                    20                  25                  30
Ser Phe Gly Gly Asn Leu Gly Arg Ala Val Phe Gln Ala Lys Lys Arg
            35                  40                  45
Val Leu Glu Pro Leu Gly Leu Val Glu Thr Pro Ala Lys Thr Ala Pro
    50                  55                  60
Gly Lys Lys Arg Pro Val Asp Ser Pro Asp Ser Thr Ser Gly Ile Gly
65                  70                  75                  80
Lys Lys Gly Gln Gln Pro Ala Lys Lys Arg Leu Asn Phe Gly Gln Thr
                85                  90                  95
Gly Asp Ser Glu Pro Val Pro Asp Pro Gln Pro Ile Gly Glu Pro Pro
                    100                 105                 110
Ala Gly Pro Ser Gly Leu Gly Ser Gly Thr Met Ala Ala Gly Gly Gly
            115                 120                 125
Ala Pro Met Ala Asp Asn Asn Glu Gly Ala Asp Gly Val Gly Asn Ala
    130                 135                 140
Ser Gly Asn Trp His Cys Asp Ser Thr Arg Leu Gly Asp Arg Val Ile
145                 150                 155                 160
Thr Thr Ser Thr Arg Thr Trp Ala Leu Pro Thr Tyr Asn Asn His Leu
                165                 170                 175
```

```
Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Gly
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
    530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
            580                 585                 590
```

```
Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
        610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 74
<211> LENGTH: 644
<212> TYPE: PRT
<213> ORGANISM: Unknown
<220> FEATURE:
<223> OTHER INFORMATION: capsid protein of AAV serotype, clone 223-5

<400> SEQUENCE: 74

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Pro Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
```

```
            305                 310                 315                 320
Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Gly
                340                 345                 350

Arg Leu Met Asn Pro Leu Ile Asp Gln Tyr Leu Tyr Tyr Leu Ala Arg
                355                 360                 365

Thr Gln Ser Asn Ala Gly Gly Thr Ala Gly Asn Arg Glu Leu Gln Phe
                370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
                420                 425                 430

Asn Gly Arg Asn Ser Leu Val Asn Pro Gly Val Ala Met Ala Thr His
                435                 440                 445

Lys Asp Asp Glu Glu Arg Phe Phe Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
                500                 505                 510

Thr Gln Val Val Asn Asn Gln Gly Ala Leu Pro Gly Met Val Trp Gln
                515                 520                 525

Asn Arg Asp Val Tyr Leu Gln Gly Pro Ile Trp Ala Lys Ile Pro His
                530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
                580                 585                 590

Gln Tyr Ser Thr Gly Gln Val Ser Val Glu Ile Glu Trp Glu Leu Gln
                595                 600                 605

Lys Glu Asn Ser Lys Arg Trp Asn Pro Glu Ile Gln Tyr Thr Ser Asn
                610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 75
<211> LENGTH: 644
<212> TYPE: PRT
<213> ORGANISM: Unknown
<220> FEATURE:
<223> OTHER INFORMATION: capsid protein of AAV serotype, clone 223-10
<220> FEATURE:
<221> NAME/KEY: MISC_FEATURE
<222> LOCATION: (434)..(434)
<223> OTHER INFORMATION: can be any amino acid

<400> SEQUENCE: 75

Lys Ala Tyr Asp Gln Gln Leu Lys Ala Gly Asp Asn Pro Tyr Leu Arg
```

-continued

```
1               5                   10                  15
Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
            35                  40                  45

Val Leu Glu Pro Leu Gly Leu Val Glu Thr Pro Ala Lys Thr Ala Pro
 50                  55                  60

Gly Lys Lys Arg Pro Val Asp Ser Pro Asp Ser Thr Ser Gly Ile Gly
 65                  70                  75                  80

Lys Lys Gly Gln Gln Pro Ala Lys Lys Arg Leu Asn Phe Gly Gln Thr
                    85                  90                  95

Gly Asp Ser Glu Ser Val Pro Asp Pro Gln Pro Ile Gly Glu Pro Pro
                100                 105                 110

Ala Gly Pro Ser Gly Leu Gly Ser Gly Thr Met Ala Ala Gly Gly Gly
                115                 120                 125

Ala Pro Met Ala Asp Asn Asn Glu Gly Ala Asp Gly Val Gly Asn Ala
130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
                180                 185                 190

Tyr Phe Gly Tyr Ser Thr Pro Trp Gly Tyr Phe Asp Phe Asn Arg Phe
                195                 200                 205

His Cys His Phe Ser Pro Arg Asp Trp Gln Arg Leu Ile Asn Asn Asn
            210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
                260                 265                 270

Tyr Val Leu Gly Ser Ala His Gln Gly Cys Leu Pro Pro Phe Pro Ala
            275                 280                 285

Asp Val Phe Met Ile Pro Gln Tyr Gly Tyr Leu Thr Leu Asn Asn Gly
            290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
            340                 345                 350

Arg Leu Met Asn Pro Leu Ile Asp Gln Tyr Leu Tyr Tyr Leu Ala Arg
            355                 360                 365

Thr Gln Ser Asn Ala Gly Gly Thr Ala Gly Asn Arg Glu Leu Gln Phe
 370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
                420                 425                 430
```

```
Asn Xaa Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
    530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
                580                 585                 590

Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
        610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 76
<211> LENGTH: 644
<212> TYPE: PRT
<213> ORGANISM: Unknown
<220> FEATURE:
<223> OTHER INFORMATION: capsid protein of AAV serotype, clone 223-2

<400> SEQUENCE: 76

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Cys Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Val Ala Gly Gly Gly
        115                 120                 125

Ala Pro Met Ala Asp Asn Asn Glu Gly Ala Asp Gly Val Gly Asn Ala
    130                 135                 140
```

```
Ser Gly Asn Trp His Cys Asp Ser Thr Trp Leu Gly Asp Arg Val Ile
145                 150                 155                 160
Thr Thr Ser Thr Arg Thr Trp Ala Leu Pro Thr Tyr Asn Asn His Leu
            165                 170                 175
Tyr Lys Gln Ile Ser Ser Gln Ser Ala Gly Ser Thr Asn Asp Asn Val
        180                 185                 190
Tyr Phe Gly Tyr Ser Thr Pro Trp Gly Tyr Phe Asp Phe Asn Arg Phe
    195                 200                 205
His Cys His Phe Ser Pro Arg Asp Trp Gln Arg Leu Ile Asn Asn Asn
210                 215                 220
Trp Gly Phe Arg Pro Lys Lys Leu Asn Phe Lys Leu Phe Asn Ile Gln
225                 230                 235                 240
Val Lys Glu Val Thr Thr Asn Asp Gly Val Thr Thr Ile Ala Asn Asn
            245                 250                 255
Leu Thr Ser Thr Val Gln Val Phe Ser Asp Ser Glu Tyr Gln Leu Pro
        260                 265                 270
Tyr Val Leu Gly Ser Ala His Gln Gly Cys Leu Pro Pro Phe Pro Ala
    275                 280                 285
Asp Val Phe Met Ile Pro Gln Tyr Gly Tyr Leu Thr Leu Asn Asn Gly
290                 295                 300
Ser Gln Ser Val Gly Arg Ser Ser Phe Tyr Cys Leu Glu Tyr Phe Pro
305                 310                 315                 320
Ser Gln Met Leu Arg Thr Gly Asn Asn Phe Thr Phe Ser Tyr Thr Phe
            325                 330                 335
Glu Asp Val Pro Phe His Ser Ser Tyr Ala His Ser Gln Ser Leu Asp
        340                 345                 350
Arg Leu Met Asn Pro Leu Ile Asp Gln Tyr Leu Tyr Tyr Leu Ala Arg
    355                 360                 365
Thr Gln Ser Asn Ala Gly Gly Thr Ala Gly Asn Arg Glu Leu Gln Phe
370                 375                 380
Tyr Gln Gly Gly Pro Thr Thr Met Ala Glu Gln Ala Lys Asn Trp Leu
385                 390                 395                 400
Pro Gly Pro Cys Phe Arg Gln Gln Arg Val Ser Lys Thr Leu Asp Gln
            405                 410                 415
Asn Asn Asn Ser Asn Phe Ala Trp Thr Gly Ala Thr Lys Tyr His Leu
        420                 425                 430
Asn Gly Arg Asn Ser Leu Val Asn Pro Gly Val Ala Met Ala Thr His
    435                 440                 445
Lys Asp Asp Glu Glu Arg Phe Ser Pro Ser Ser Gly Val Leu Ile Phe
450                 455                 460
Gly Lys Thr Gly Ala Ala Asn Lys Thr Thr Leu Glu Asn Val Leu Met
465                 470                 475                 480
Thr Asn Glu Glu Glu Ile Arg Pro Thr Asn Pro Val Ala Thr Glu Glu
            485                 490                 495
Tyr Gly Ile Val Ser Ser Asn Leu Gln Ala Ala Ser Thr Ala Ala Gln
        500                 505                 510
Thr Gln Val Val Asn Asn Gln Gly Ala Leu Pro Gly Met Val Trp Gln
    515                 520                 525
Asn Arg Asp Val Tyr Leu Gln Gly Pro Ile Trp Ala Lys Ile Pro His
530                 535                 540
Thr Asp Gly Asn Phe His Pro Ser Pro Leu Met Gly Gly Phe Gly Leu
545                 550                 555                 560
Lys His Pro Pro Pro Gln Ile Leu Ile Lys Asn Thr Pro Val Pro Ala
```

```
                    565                 570                 575

Asn Pro Pro Glu Val Phe Thr Pro Ala Lys Phe Ala Ser Phe Ile Thr
                580                 585                 590

Gln Tyr Ser Thr Gly Gln Val Ser Val Glu Ile Glu Trp Glu Leu Gln
                595                 600                 605

Lys Glu Asn Ser Lys Arg Trp Asn Pro Glu Ile Gln Tyr Thr Ser Asn
610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 77
<211> LENGTH: 644
<212> TYPE: PRT
<213> ORGANISM: Unknown
<220> FEATURE:
<223> OTHER INFORMATION: capsid protein of AAV serotype, clone 223-7

<400> SEQUENCE: 77

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
                20                  25                  30

Ser Phe Gly Gly Asn Leu Gly Arg Ala Val Phe Gln Ala Lys Lys Arg
            35                  40                  45

Val Leu Glu Pro Leu Gly Leu Val Glu Thr Pro Ala Lys Thr Ala Pro
        50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Pro Glu Tyr Gln Leu Pro
            260                 265                 270

Tyr Val Leu Gly Ser Ala His Gln Gly Cys Leu Pro Pro Phe Pro Ala
        275                 280                 285
```

```
Asp Val Phe Met Ile Pro Gln Tyr Gly Tyr Leu Thr Leu Asn Asn Gly
    290                 295                 300
Ser Gln Ser Val Gly Arg Ser Ser Phe Tyr Cys Leu Glu Tyr Phe Pro
305                 310                 315                 320
Ser Gln Met Leu Arg Thr Gly Asn Asn Phe Thr Phe Ser Tyr Thr Phe
            325                 330                 335
Glu Asp Val Pro Phe His Ser Ser Tyr Ala His Ser Gln Ser Leu Asp
                340                 345                 350
Arg Leu Met Asn Pro Leu Ile Asp Gln Tyr Leu Tyr Tyr Leu Ala Arg
            355                 360                 365
Thr Gln Ser Asn Ala Gly Gly Thr Ala Gly Asn Arg Glu Leu Gln Phe
        370                 375                 380
Tyr Gln Gly Gly Pro Thr Thr Met Ala Glu Gln Ala Lys Asn Trp Leu
385                 390                 395                 400
Pro Gly Pro Cys Phe Arg Gln Gln Arg Val Ser Lys Thr Leu Asp Gln
                405                 410                 415
Asn Asn Asn Ser Asn Phe Ala Trp Thr Gly Ala Thr Lys Tyr His Leu
            420                 425                 430
Asn Gly Arg Asn Ser Leu Val Asn Pro Gly Val Ala Met Ala Thr His
        435                 440                 445
Lys Asp Asp Glu Glu Arg Phe Phe Pro Ser Ser Gly Val Leu Ile Phe
450                 455                 460
Gly Lys Thr Gly Ala Ala Asn Lys Thr Thr Leu Glu Asn Val Leu Met
465                 470                 475                 480
Thr Asn Glu Glu Glu Ile Arg Pro Thr Asn Pro Val Ala Thr Glu Glu
                485                 490                 495
Tyr Gly Ile Val Ser Ser Asn Leu Gln Ala Ala Ser Thr Ala Ala Gln
                500                 505                 510
Thr Gln Val Val Asn Asn Gln Gly Ala Leu Pro Gly Met Val Trp Gln
        515                 520                 525
Asn Arg Asp Val Tyr Leu Gln Gly Pro Ile Trp Ala Lys Ile Pro His
530                 535                 540
Thr Asp Gly Asn Phe His Pro Ser Pro Leu Met Gly Gly Phe Gly Leu
545                 550                 555                 560
Lys His Pro Pro Pro Gln Ile Leu Ile Lys Asn Thr Pro Val Pro Ala
                565                 570                 575
Asn Pro Pro Glu Val Phe Thr Pro Ala Lys Ile Ala Ser Phe Ile Thr
            580                 585                 590
Gln Tyr Ser Thr Gly Gln Val Ser Val Glu Ile Glu Trp Glu Leu Gln
        595                 600                 605
Lys Glu Asn Ser Lys Arg Trp Asn Pro Glu Ile Gln Tyr Thr Ser Asn
610                 615                 620
Phe Asp Lys Gln Thr Gly Val Asp Phe Ala Val Asp Ser Gln Gly Val
625                 630                 635                 640
Tyr Ser Glu Pro

<210> SEQ ID NO 78
<211> LENGTH: 644
<212> TYPE: PRT
<213> ORGANISM: Unknown
<220> FEATURE:
<223> OTHER INFORMATION: capsid protein of AAV serotype, clone 223-6

<400> SEQUENCE: 78
```

```
Lys Ala Tyr Asp Gln Gln Leu Lys Ala Gly Asp Asn Pro Tyr Leu Arg
1               5                   10                  15
Tyr Asn His Ala Asp Ala Glu Phe Gln Glu Arg Leu Gln Glu Asp Thr
            20                  25                  30
Ser Phe Gly Gly Asn Leu Gly Arg Ala Val Phe Gln Ala Lys Lys Arg
        35                  40                  45
Val Leu Glu Pro Leu Gly Leu Val Glu Thr Pro Ala Lys Thr Ala Pro
50                  55                  60
Gly Lys Lys Arg Pro Val Asp Ser Pro Asp Ser Thr Ser Gly Ile Gly
65                  70                  75                  80
Lys Lys Gly Gln Gln Pro Ala Lys Lys Arg Leu Asn Phe Gly Gln Thr
                85                  90                  95
Gly Asp Ser Glu Ser Val Pro Asp Pro Gln Pro Ile Gly Glu Pro Pro
            100                 105                 110
Ala Gly Pro Ser Gly Leu Gly Ser Gly Thr Met Ala Ala Gly Gly Gly
        115                 120                 125
Ala Pro Met Ala Asp Asn Ser Glu Gly Ala Asp Gly Val Gly Asn Ala
    130                 135                 140
Ser Gly Asn Trp His Cys Asp Ser Thr Trp Leu Gly Asp Arg Val Ile
145                 150                 155                 160
Thr Thr Ser Thr Arg Thr Trp Ala Leu Pro Thr Tyr Asn Asn His Leu
                165                 170                 175
Tyr Lys Gln Ile Ser Ser Gln Ser Ala Gly Ser Thr Asn Asp Asn Val
            180                 185                 190
Tyr Phe Gly Tyr Ser Thr Pro Trp Gly Tyr Phe Asp Phe Asn Arg Phe
        195                 200                 205
His Cys His Phe Ser Pro Arg Asp Trp Gln Arg Leu Ile Asn Asn Asn
    210                 215                 220
Trp Gly Phe Arg Pro Lys Lys Leu Asn Phe Lys Leu Phe Asn Ile Gln
225                 230                 235                 240
Val Lys Glu Val Thr Thr Asn Asp Gly Val Thr Thr Ile Ala Asn Asn
                245                 250                 255
Leu Thr Ser Thr Val Gln Val Phe Ser Asp Ser Glu Tyr Gln Leu Pro
            260                 265                 270
Tyr Val Leu Gly Ser Ala His Gln Gly Cys Leu Pro Pro Phe Pro Ala
        275                 280                 285
Asp Val Phe Met Ile Pro Gln Tyr Gly Tyr Leu Thr Leu Asn Asn Gly
    290                 295                 300
Ser Gln Ser Val Gly Arg Ser Ser Phe Tyr Cys Leu Glu Tyr Phe Pro
305                 310                 315                 320
Ser Gln Met Leu Arg Thr Gly Asn Asn Phe Thr Phe Ser Tyr Thr Phe
                325                 330                 335
Glu Asp Val Pro Phe His Ser Ser Tyr Ala His Ser Gln Ser Leu Asp
            340                 345                 350
Arg Leu Met Asn Pro Leu Ile Asp Gln Tyr Leu Tyr Tyr Leu Ala Arg
        355                 360                 365
Thr Gln Ser Asn Ala Gly Gly Thr Ala Gly Asn Arg Glu Leu Gln Phe
    370                 375                 380
Tyr Gln Gly Gly Pro Thr Thr Met Ala Glu Gln Ala Lys Asn Trp Leu
385                 390                 395                 400
Pro Gly Pro Cys Phe Arg Gln Gln Arg Val Ser Lys Thr Leu Asp Gln
                405                 410                 415
Asn Asn Asn Ser Asn Phe Ala Trp Thr Gly Ala Thr Lys Tyr His Leu
```

```
                    420                 425                 430
Asn Gly Arg Asn Ser Leu Val Asn Pro Gly Val Ala Met Ala Thr His
            435                 440                 445
Lys Asp Asp Glu Glu Arg Phe Phe Pro Ser Ser Gly Val Leu Ile Phe
450                 455                 460
Gly Lys Thr Gly Ala Ala Asn Lys Thr Thr Leu Glu Asn Val Leu Met
465                 470                 475                 480
Thr Asn Glu Glu Glu Ile Arg Pro Thr Asn Pro Val Ala Thr Glu Glu
                485                 490                 495
Tyr Gly Ile Val Ser Ser Asn Leu Gln Ala Ala Ser Thr Ala Ala Gln
            500                 505                 510
Thr Gln Val Val Asn Asn Gln Gly Ala Leu Pro Gly Met Val Trp Gln
            515                 520                 525
Asn Arg Asp Val Tyr Leu Gln Gly Pro Ile Trp Ala Lys Ile Pro His
            530                 535                 540
Thr Asp Gly Asn Phe His Pro Ser Pro Leu Met Gly Gly Phe Gly Leu
545                 550                 555                 560
Lys His Pro Pro Pro Gln Ile Leu Ile Lys Asn Thr Pro Val Pro Ala
                565                 570                 575
Asn Pro Pro Glu Val Phe Thr Pro Ala Lys Leu Ala Ser Phe Ile Thr
                580                 585                 590
Gln Tyr Ser Thr Gly Gln Val Ser Val Glu Ile Glu Trp Glu Leu Gln
            595                 600                 605
Lys Glu Asn Ser Lys Arg Trp Asn Pro Glu Ile Gln Tyr Thr Ser Asn
            610                 615                 620
Phe Asp Lys Gln Thr Gly Val Asp Phe Ala Val Asp Ser Gln Gly Val
625                 630                 635                 640
Tyr Ser Glu Pro

<210> SEQ ID NO 79
<211> LENGTH: 738
<212> TYPE: PRT
<213> ORGANISM: Unknown
<220> FEATURE:
<223> OTHER INFORMATION: capsid protein of AAV serotype, clone 44.1

<400> SEQUENCE: 79

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
```

```
Pro Val Glu Pro Ser Pro Gln Arg Ser Pro Asp Ser Thr Gly Ile
145                 150                 155                 160

Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560
```

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 80
<211> LENGTH: 738
<212> TYPE: PRT
<213> ORGANISM: Unknown
<220> FEATURE:
<223> OTHER INFORMATION: capsid protein of AAV serotype, clone 44.5

<400> SEQUENCE: 80

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro

-continued

```
            180                 185                 190
Pro Ala Gly Pro Ser Gly Leu Gly Ser Gly Thr Met Ala Ala Gly Gly
            195                 200                 205
Gly Ala Pro Met Ala Asp Asn Asn Glu Gly Ala Asp Gly Val Gly Ser
            210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
            245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
            275                 280                 285
Arg Phe His Cys His Phe Ser Pro Arg Asp Trp Gln Arg Leu Ile Asn
            290                 295                 300
Asn Asn Trp Gly Phe Arg Pro Lys Arg Pro Asn Phe Lys Leu Phe Asn
305                 310                 315                 320
Ile Gln Val Lys Glu Val Thr Gln Asn Glu Gly Thr Lys Thr Ile Ala
            325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
            370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
            405                 410                 415
Gln Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
            435                 440                 445
Ser Arg Thr Gln Ser Thr Gly Gly Thr Ala Gly Thr Gln Gln Leu Leu
            450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
            485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
            515                 520                 525
His Lys Asp Asp Glu Glu Arg Phe Phe Pro Ser Ser Gly Val Leu Met
            530                 535                 540
Phe Gly Lys Gln Gly Ala Gly Lys Asp Asn Val Asp Tyr Ser Ser Val
545                 550                 555                 560
Met Leu Thr Ser Glu Glu Ile Lys Thr Thr Asn Pro Val Ala Thr
            565                 570                 575
Glu Gln Tyr Gly Val Val Ala Asp Asn Leu Gln Gln Gln Asn Ala Ala
            580                 585                 590
Pro Ile Val Gly Ala Val Asn Ser Gln Gly Ala Leu Pro Gly Met Val
            595                 600                 605
```

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 81
<211> LENGTH: 738
<212> TYPE: PRT
<213> ORGANISM: Unknown
<220> FEATURE:
<223> OTHER INFORMATION: capsid protein of AAV serotype, clone 44.2

<400> SEQUENCE: 81

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

-continued

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Gln Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
            485                 490                 495

Gln Asn Asn Asn Ser Asn Phe Ala Trp Thr Gly Ala Thr Lys Tyr His
        500                 505                 510

Leu Asn Gly Arg Asp Ser Leu Val Asn Pro Gly Val Ala Met Ala Thr
    515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
            565                 570                 575

Glu Gln Tyr Gly Val Val Ala Asp Asn Leu Gln Gln Asn Ala Ala
        580                 585                 590

Pro Ile Val Gly Ala Val Asn Ser Gln Gly Ala Leu Pro Gly Met Val
    595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val 645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 82
<211> LENGTH: 738
<212> TYPE: PRT
<213> ORGANISM: Unknown
<220> FEATURE:
<223> OTHER INFORMATION: capsid protein of AAV serotype, clone 29.3VP1

<400> SEQUENCE: 82

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Thr Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

```
Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala Arg Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Gly Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685
```

```
Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 83
<211> LENGTH: 738
<212> TYPE: PRT
<213> ORGANISM: Unknown
<220> FEATURE:
<223> OTHER INFORMATION: capsid protein of AAV serotype, clone 29.5VP1

<400> SEQUENCE: 83

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Gly Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Ser Leu Asn Phe Lys Leu Phe Asn
```

```
            305                 310                 315                 320

Ile Gln Val Lys Glu Val Thr Gln Asn Glu Gly Thr Lys Thr Ile Ala
                    325                 330                 335

Asn Asn Leu Thr Ser Thr Ile Gln Val Phe Thr Asp Ser Glu Tyr Gln
                    340                 345                 350

Leu Pro Tyr Val Leu Gly Ser Ala His Gln Gly Cys Leu Pro Pro Phe
                    355                 360                 365

Pro Ala Asp Val Phe Met Ile Pro Gln Tyr Gly Tyr Leu Thr Leu Asn
                    370                 375                 380

Asn Gly Ser Gln Ala Val Gly Arg Ser Ser Phe Tyr Cys Leu Glu Tyr
    385                 390                 395                 400

Phe Pro Ser Gln Met Leu Arg Thr Gly Asn Asn Phe Glu Phe Ser Tyr
                    405                 410                 415

Gln Phe Glu Asp Val Pro Phe His Ser Ser Tyr Ala His Ser Gln Ser
                    420                 425                 430

Leu Asp Arg Leu Met Asn Pro Leu Ile Asp Gln Tyr Leu Tyr Tyr Leu
                    435                 440                 445

Ser Arg Thr Gln Ser Thr Gly Gly Thr Ala Gly Thr Gln Gln Leu Leu
                    450                 455                 460

Phe Ser Gln Ala Gly Pro Asn Asn Met Ser Ala Gln Ala Lys Asn Trp
    465                 470                 475                 480

Leu Pro Gly Pro Cys Tyr Arg Gln Gln Arg Val Ser Thr Thr Leu Ser
                    485                 490                 495

Gln Asn Asp Asn Ser Asn Phe Ala Trp Thr Gly Ala Thr Lys Tyr His
                    500                 505                 510

Leu Asn Gly Arg Asp Ser Leu Val Asn Pro Gly Val Ala Met Ala Thr
                    515                 520                 525

His Lys Asp Asp Glu Glu Arg Phe Phe Pro Ser Ser Gly Val Leu Met
                    530                 535                 540

Phe Gly Lys Gln Gly Ala Gly Lys Asp Asn Val Asp Tyr Ser Ser Val
    545                 550                 555                 560

Met Leu Thr Ser Glu Glu Glu Ile Lys Thr Thr Asn Pro Val Ala Thr
                    565                 570                 575

Glu Gln Tyr Gly Val Val Ala Asp Asn Leu Gln Gln Asn Ala Ala
                    580                 585                 590

Pro Ile Val Gly Ala Val Asn Ser Gln Gly Ala Leu Pro Gly Met Val
                    595                 600                 605

Trp Gln Asn Arg Asp Val Tyr Leu Gln Gly Pro Ile Trp Ala Lys Ile
                    610                 615                 620

Pro His Thr Asp Gly Asn Phe His Pro Ser Pro Leu Met Gly Gly Phe
    625                 630                 635                 640

Gly Leu Lys His Pro Pro Gln Ile Leu Ile Lys Asn Thr Pro Val
                    645                 650                 655

Pro Ala Asp Pro Pro Thr Thr Phe Ser Gln Ala Lys Leu Ala Ser Phe
                    660                 665                 670

Ile Thr Gln Tyr Ser Thr Gly Gln Val Ser Val Glu Ile Glu Trp Glu
                    675                 680                 685

Leu Gln Lys Glu Asn Ser Lys Arg Trp Asn Pro Glu Ile Gln Tyr Thr
                    690                 695                 700

Ser Asn Tyr Tyr Lys Ser Thr Asn Val Asp Phe Ala Val Asn Thr Asp
    705                 710                 715                 720

Gly Thr Tyr Ser Glu Pro Arg Pro Ile Gly Thr Arg Tyr Leu Thr Arg
                    725                 730                 735
```

Asn Leu

<210> SEQ ID NO 84
<211> LENGTH: 738
<212> TYPE: PRT
<213> ORGANISM: Unknown
<220> FEATURE:
<223> OTHER INFORMATION: capsid protein of AAV serotype, clone 42.15

<400> SEQUENCE: 84

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

```
Leu Pro Tyr Val Leu Gly Ser Ala His Gln Gly Cys Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Arg Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 85
<211> LENGTH: 738
<212> TYPE: PRT
<213> ORGANISM: Unknown
```

<220> FEATURE:
<223> OTHER INFORMATION: capsid protein of AAV serotype, clone 42.8

<400> SEQUENCE: 85

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu | Ser |
| 1 | | | | 5 | | | | | 10 | | | | | 15 | |
| Glu | Gly | Ile | Arg | Glu | Trp | Trp | Asp | Leu | Lys | Pro | Gly | Ala | Pro | Lys | Pro |
| | | | 20 | | | | | 25 | | | | | 30 | | |
| Lys | Ala | Asn | Gln | Gln | Lys | Gln | Asp | Asp | Gly | Arg | Gly | Leu | Val | Leu | Pro |
| | | | 35 | | | | | 40 | | | | | 45 | | |
| Gly | Tyr | Lys | Tyr | Leu | Gly | Pro | Phe | Asn | Gly | Leu | Asp | Lys | Gly | Glu | Pro |
| | | 50 | | | | | 55 | | | | | 60 | | | |
| Val | Asn | Ala | Ala | Asp | Ala | Ala | Leu | Glu | His | Asp | Lys | Ala | Tyr | Asp |
| 65 | | | | | 70 | | | | | 75 | | | | | 80 |
| Gln | Gln | Leu | Lys | Ala | Gly | Asp | Asn | Pro | Tyr | Leu | Arg | Tyr | Asn | His | Ala |
| | | | | 85 | | | | | 90 | | | | | 95 | |
| Asp | Ala | Glu | Phe | Gln | Glu | Arg | Leu | Gln | Glu | Asp | Thr | Ser | Phe | Gly | Gly |
| | | | 100 | | | | | 105 | | | | | 110 | | |
| Asn | Leu | Gly | Arg | Ala | Val | Phe | Gln | Ala | Lys | Lys | Arg | Val | Leu | Glu | Pro |
| | | | 115 | | | | | 120 | | | | | 125 | | |
| Leu | Gly | Leu | Val | Glu | Glu | Gly | Ala | Lys | Thr | Ala | Pro | Gly | Lys | Lys | Arg |
| 130 | | | | | 135 | | | | | 140 | | | | | |
| Pro | Val | Glu | Pro | Ser | Pro | Gln | Arg | Ser | Pro | Asp | Ser | Ser | Thr | Gly | Ile |
| 145 | | | | | 150 | | | | | 155 | | | | | 160 |
| Gly | Lys | Thr | Gly | Gln | Gln | Pro | Ala | Lys | Lys | Arg | Leu | Asn | Phe | Gly | Gln |
| | | | | 165 | | | | | 170 | | | | | 175 | |
| Thr | Gly | Asp | Ser | Glu | Ser | Val | Pro | Asp | Pro | Gln | Pro | Ile | Gly | Glu | Pro |
| | | | 180 | | | | | 185 | | | | | 190 | | |
| Pro | Ala | Gly | Pro | Ser | Gly | Leu | Gly | Ser | Gly | Thr | Met | Ala | Ala | Gly | Gly |
| | | | 195 | | | | | 200 | | | | | 205 | | |
| Gly | Ala | Pro | Met | Ala | Asp | Asn | Asn | Glu | Gly | Ala | Asp | Gly | Val | Gly | Ser |
| 210 | | | | | 215 | | | | | 220 | | | | | |
| Ser | Ser | Gly | Asn | Trp | His | Cys | Asp | Ser | Thr | Trp | Leu | Gly | Asp | Arg | Val |
| 225 | | | | | 230 | | | | | 235 | | | | | 240 |
| Ile | Thr | Thr | Ser | Thr | Arg | Thr | Trp | Ala | Leu | Pro | Thr | Tyr | Asn | Asn | His |
| | | | | 245 | | | | | 250 | | | | | 255 | |
| Leu | Tyr | Lys | Gln | Ile | Ser | Asn | Gly | Thr | Ser | Gly | Gly | Ser | Thr | Asn | Asp |
| | | | 260 | | | | | 265 | | | | | 270 | | |
| Asn | Thr | Tyr | Phe | Gly | Tyr | Ser | Thr | Pro | Trp | Gly | Tyr | Phe | Asp | Phe | Asn |
| | | | 275 | | | | | 280 | | | | | 285 | | |
| Arg | Phe | His | Cys | His | Phe | Ser | Pro | Arg | Asp | Trp | Gln | Arg | Leu | Ile | Asn |
| | | 290 | | | | | 295 | | | | | 300 | | | |
| Asn | Asn | Trp | Gly | Phe | Arg | Pro | Lys | Arg | Leu | Asn | Phe | Lys | Leu | Phe | Asn |
| 305 | | | | | 310 | | | | | 315 | | | | | 320 |
| Ile | Gln | Val | Lys | Glu | Val | Thr | Gln | Asn | Glu | Gly | Thr | Lys | Thr | Ile | Ala |
| | | | | 325 | | | | | 330 | | | | | 335 | |
| Asn | Asn | Leu | Thr | Ser | Thr | Ile | Gln | Val | Phe | Thr | Asp | Ser | Glu | Tyr | Gln |
| | | | 340 | | | | | 345 | | | | | 350 | | |
| Leu | Pro | Tyr | Val | Leu | Gly | Ser | Ala | His | Gln | Gly | Cys | Leu | Pro | Pro | Phe |
| | | | 355 | | | | | 360 | | | | | 365 | | |
| Pro | Ala | Asp | Val | Phe | Met | Ile | Pro | Gln | Tyr | Gly | Tyr | Leu | Thr | Leu | Asn |
| | | 370 | | | | | 375 | | | | | 380 | | | |
| Asn | Gly | Ser | Gln | Ala | Val | Gly | Arg | Ser | Ser | Phe | Tyr | Cys | Leu | Glu | Tyr |
| 385 | | | | | 390 | | | | | 395 | | | | | 400 |

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 86
<211> LENGTH: 733
<212> TYPE: PRT
<213> ORGANISM: Unknown
<220> FEATURE:
<223> OTHER INFORMATION: capsid protein of AAV serotype, clone 42.13

<400> SEQUENCE: 86

Met Ala Ala Asp Gly Tyr Leu Pro Asp Trp Leu Glu Asp Asn Leu Ser
1               5                   10                  15

```
Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
 50                  55                  60

Val Asn Ala Ala Asp Ala Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
            165                 170                 175

Ser Val Pro Asp Pro Gln Pro Ile Gly Glu Pro Ala Gly Pro Ser
            180                 185                 190

Gly Leu Gly Ser Gly Thr Met Ala Ala Gly Gly Gly Ala Pro Met Ala
            195                 200                 205

Asp Asn Asn Glu Gly Ala Asp Gly Val Gly Ser Ser Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
            245                 250                 255

Ser Asn Gly Thr Ser Gly Gly Ser Thr Asn Asp Asn Thr Tyr Phe Gly
            260                 265                 270

Tyr Ser Thr Pro Trp Gly Tyr Phe Asp Phe Asn Arg Phe His Cys His
            275                 280                 285

Phe Ser Pro Arg Asp Trp Gln Arg Leu Ile Asn Asn Asn Trp Gly Phe
290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
            325                 330                 335

Thr Ile Gln Val Phe Thr Asp Ser Glu Tyr Gln Leu Pro Tyr Val Leu
            340                 345                 350

Gly Ser Ala His Gln Gly Cys Leu Pro Pro Phe Pro Ala Asp Val Phe
            355                 360                 365

Met Ile Pro Gln Tyr Gly Tyr Leu Thr Leu Asn Asn Gly Ser Gln Ala
            370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
            405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
```

435                 440                 445
Thr Gly Gly Thr Ala Gly Thr Gln Gln Leu Leu Phe Ser Gln Ala Gly
            450                 455                 460
Pro Asn Asn Met Ser Ala Gln Ala Lys Asn Trp Leu Pro Gly Pro Cys
465                 470                 475                 480
Tyr Arg Gln Gln Arg Val Ser Thr Thr Val Ser Gln Asn Asn Asn Ser
                485                 490                 495
Asn Phe Ala Trp Thr Gly Ala Thr Lys Tyr His Leu Asn Gly Arg Asp
            500                 505                 510
Ser Leu Val Asn Pro Gly Val Ala Met Ala Thr His Lys Gly Asp Glu
        515                 520                 525
Glu Arg Phe Phe Pro Ser Ser Gly Val Leu Met Phe Gly Lys Gln Gly
        530                 535                 540
Ala Gly Lys Asp Asn Val Asp Tyr Ser Ser Val Met Leu Thr Ser Glu
545                 550                 555                 560
Glu Glu Ile Lys Thr Thr Asn Pro Val Ala Thr Glu Gln Tyr Gly Val
                565                 570                 575
Val Ala Asp Asn Leu Gln Gln Gln Asn Ala Ala Pro Ile Val Gly Ala
            580                 585                 590
Val Asn Ser Gln Gly Ala Leu Pro Gly Met Val Trp Gln Asn Arg Asp
        595                 600                 605
Val Tyr Leu Gln Gly Pro Ile Trp Ala Lys Ile Pro His Thr Asp Gly
    610                 615                 620
Asn Phe His Pro Ser Pro Leu Met Gly Gly Phe Gly Leu Lys His Pro
625                 630                 635                 640
Pro Pro Gln Ile Leu Ile Lys Asn Thr Pro Val Pro Ala Asp Pro Pro
                645                 650                 655
Thr Thr Phe Ser Gln Ala Lys Leu Ala Ser Phe Ile Thr Gln Tyr Ser
            660                 665                 670
Thr Gly Gln Val Ser Val Glu Ile Glu Trp Glu Leu Gln Lys Glu Asn
        675                 680                 685
Ser Lys Arg Trp Asn Pro Glu Ile Gln Tyr Thr Ser Asn Tyr Tyr Lys
        690                 695                 700
Ser Thr Asn Val Asp Phe Ala Val Asn Thr Glu Gly Thr Tyr Ser Glu
705                 710                 715                 720
Pro Arg Pro Ile Gly Thr Arg Tyr Leu Thr Arg Ser Leu
                725                 730

<210> SEQ ID NO 87
<211> LENGTH: 733
<212> TYPE: PRT
<213> ORGANISM: Unknown
<220> FEATURE:
<223> OTHER INFORMATION: capsid protein of AAV serotype, clone 42.3A

<400> SEQUENCE: 87

Met Ala Ala Asp Gly His Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp

```
                65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Gly Ala Lys Thr Ala Pro Gly Lys Lys Arg
            130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
                180                 185                 190

Gly Leu Gly Ser Gly Thr Met Ala Ala Gly Gly Ala Pro Met Ala
            195                 200                 205

Asp Asn Asn Glu Gly Ala Asp Gly Val Gly Ser Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
                260                 265                 270

Tyr Ser Thr Pro Trp Gly Tyr Phe Asp Phe Asn Arg Phe His Cys His
            275                 280                 285

Phe Ser Pro Arg Asp Trp Gln Arg Leu Ile Asn Asn Ser Trp Gly Phe
            290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
                340                 345                 350

Gly Ser Ala His Gln Gly Cys Leu Pro Pro Phe Pro Ala Asp Val Phe
            355                 360                 365

Met Ile Pro Gln Tyr Gly Tyr Leu Thr Leu Asn Asn Gly Ser Gln Ala
            370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
                420                 425                 430

Asn Pro Leu Ile Asp Gln Tyr Leu Tyr Tyr Leu Ser Arg Thr Gln Ser
                435                 440                 445

Thr Gly Gly Thr Ala Gly Thr Gln Gln Leu Leu Phe Ser Gln Ala Gly
            450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Leu Ser Gln Asn Asn Asn Ser
                485                 490                 495
```

```
Asn Phe Ala Trp Thr Gly Ala Thr Lys Tyr His Leu Asn Gly Arg Asp
            500                 505                 510

Ser Leu Val Asn Pro Gly Val Ala Met Ala Thr His Lys Asp Asp Glu
            515                 520                 525

Glu Arg Phe Phe Pro Ser Ser Gly Val Leu Met Phe Gly Lys Gln Gly
            530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575

Val Ala Asp Asn Leu Gln Gln Gln Asn Ala Ala Pro Ile Val Gly Ala
            580                 585                 590

Val Asn Ser Gln Gly Ala Leu Pro Gly Met Val Trp Gln Asn Arg Asp
            595                 600                 605

Val Tyr Leu Gln Gly Pro Ile Trp Ala Lys Ile Pro His Thr Asp Gly
            610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
            645                 650                 655

Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Tyr Lys
            690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
                725                 730

<210> SEQ ID NO 88
<211> LENGTH: 731
<212> TYPE: PRT
<213> ORGANISM: Unknown
<220> FEATURE:
<223> OTHER INFORMATION: capsid protein of AAV serotype, clone 42.4

<400> SEQUENCE: 88

Met Ala Ala Asp Gly Tyr Leu Pro Asp Trp Leu Glu Asp Asn Leu Ser
1                   5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125
```

```
Leu Gly Leu Val Glu Glu Gly Ala Lys Thr Ala Pro Gly Lys Lys Arg
    130                 135                 140
Pro Ile Glu Ser Pro Asp Ser Ser Thr Gly Ile Gly Lys Lys Gly Gln
145                 150                 155                 160
Gln Pro Ala Lys Lys Leu Asn Phe Gly Gln Thr Gly Asp Ser Glu
                165                 170                 175
Ser Val Pro Asp Pro Gln Pro Ile Gly Glu Pro Ala Gly Pro Ser
            180                 185                 190
Gly Leu Gly Ser Gly Thr Met Ala Ala Gly Gly Ala Pro Met Ala
        195                 200                 205
Asp Asn Asn Glu Gly Ala Asp Gly Val Gly Asn Ala Ser Gly Asn Trp
    210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
            260                 265                 270
Thr Pro Trp Gly Tyr Phe Asp Phe Asn Arg Phe His Cys His Phe Ser
        275                 280                 285
Ser Arg Asp Trp Gln Arg Leu Ile Asn Asn Trp Gly Phe Arg Pro
    290                 295                 300
Lys Arg Leu Asn Phe Lys Leu Phe Asn Ile Gln Val Lys Glu Val Thr
305                 310                 315                 320
Gln Asn Glu Gly Thr Lys Thr Ile Ala Asn Asn Leu Thr Ser Thr Ile
                325                 330                 335
Gln Val Phe Thr Asp Ser Glu Tyr Arg Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ala Val Gly
    370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Gln Phe Glu Asp Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ser Arg Thr Gln Ser Thr Gly
        435                 440                 445
Gly Thr Ala Gly Thr Gln Gln Leu Leu Phe Ser Gln Ala Gly Pro Asn
    450                 455                 460
Asn Met Ser Ala Gln Ala Lys Asn Trp Leu Pro Gly Pro Cys Tyr Arg
465                 470                 475                 480
Gln Gln Arg Val Ser Thr Thr Leu Ser Gln Asn Asn Asn Ser Asn Phe
                485                 490                 495
Ala Trp Thr Gly Ala Thr Lys Tyr His Leu Asn Gly Arg Asp Ser Leu
            500                 505                 510
Val Asn Pro Gly Val Ala Met Ala Thr His Lys Asp Asp Glu Glu Arg
        515                 520                 525
Phe Phe Pro Ser Ser Gly Val Leu Met Phe Gly Lys Gln Gly Ala Gly
530                 535                 540
```

```
Lys Asp Asn Val Asp Tyr Ser Ser Val Met Leu Thr Ser Glu Glu Glu
545                 550                 555                 560

Ile Lys Thr Thr Asn Pro Val Ala Thr Glu Gln Tyr Gly Val Val Ala
                565                 570                 575

Asp Asn Leu Gln Gln Gln Asn Ala Ala Pro Ile Val Gly Ala Val Asn
            580                 585                 590

Ser Gln Gly Ala Leu Pro Gly Met Val Trp Gln Asn Arg Asp Val Tyr
        595                 600                 605

Leu Gln Gly Pro Ile Trp Ala Lys Ile Pro His Thr Asp Gly Asn Phe
    610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asp Pro Pro Thr Thr
                645                 650                 655

Phe Ser Gln Ala Lys Pro Ala Ser Phe Ile Thr Gln Tyr Ser Thr Gly
            660                 665                 670

Gln Val Ser Val Glu Ile Glu Trp Glu Leu Gln Lys Glu Asn Ser Lys
        675                 680                 685

Arg Trp Asn Pro Glu Ile Gln Tyr Thr Ser Asn Tyr Tyr Lys Ser Thr
    690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
                725                 730

<210> SEQ ID NO 89
<211> LENGTH: 731
<212> TYPE: PRT
<213> ORGANISM: Unknown
<220> FEATURE:
<223> OTHER INFORMATION: capsid protein of AAV serotype, clone 42.5A

<400> SEQUENCE: 89

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Arg Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175
```

```
Ser Val Pro Asp Pro Gln Pro Leu Gly Glu Pro Ala Ala Pro Ser
            180                 185                 190
Gly Leu Gly Ser Gly Thr Met Ala Ala Gly Gly Ala Pro Met Ala
        195                 200                 205
Asp Asn Asn Glu Gly Ala Asp Gly Val Gly Asn Ala Ser Gly Asn Trp
    210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
            260                 265                 270
Thr Pro Trp Gly Tyr Phe Asp Phe Asn Arg Phe His Cys His Phe Ser
        275                 280                 285
Pro Arg Asp Trp Gln Arg Leu Ile Asn Asn Asn Arg Gly Phe Arg Pro
    290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ser Val Gly
    370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Gln Phe Glu Asp Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ser Arg Thr Gln Ser Thr Gly
        435                 440                 445
Gly Thr Ala Gly Thr Gln Gln Leu Leu Phe Ser Gln Ala Gly Pro Asn
    450                 455                 460
Asn Met Ser Ala Gln Ala Lys Asn Trp Leu Pro Gly Pro Cys Tyr Arg
465                 470                 475                 480
Gln Gln Arg Val Ser Thr Thr Leu Ser Gln Asn Asn Asn Ser Asn Phe
                485                 490                 495
Ala Trp Thr Gly Ala Thr Lys Tyr His Leu Asn Gly Arg Asp Ser Leu
            500                 505                 510
Val Asn Pro Gly Val Ala Met Ala Thr His Lys Asp Asp Glu Glu Arg
        515                 520                 525
Phe Phe Pro Ser Ser Gly Val Leu Met Phe Gly Lys Gln Gly Ala Gly
    530                 535                 540
Lys Asp Asn Val Asp Tyr Ser Ser Val Met Leu Thr Ser Glu Glu Glu
545                 550                 555                 560
Ile Lys Thr Thr Asn Pro Val Ala Thr Glu Gln Tyr Gly Val Val Ala
                565                 570                 575
Asp Asn Leu Gln Gln Gln Asn Ala Ala Pro Ile Val Gly Ala Val Asn
            580                 585                 590
Ser Gln Gly Ala Leu Pro Gly Met Ala Trp Gln Asn Arg Asp Val Tyr
```

```
                595                 600                 605
Leu Gln Gly Pro Ile Trp Ala Lys Ile Pro His Thr Asp Gly Asn Phe
    610                 615                 620

His Pro Ser Pro Leu Met Gly Gly Phe Gly Leu Lys His Pro Pro
625                 630                 635                 640

Gln Ile Leu Ile Lys Asn Thr Pro Val Pro Ala Asp Pro Pro Thr Thr
                645                 650                 655

Phe Ser Gln Ala Lys Leu Ala Ser Phe Ile Thr Gln Tyr Ser Thr Gly
            660                 665                 670

Gln Val Ser Val Glu Ile Glu Trp Glu Leu Gln Lys Glu Asn Ser Lys
        675                 680                 685

Arg Trp Asn Pro Glu Ile Gln Tyr Thr Ser Asn Tyr Tyr Lys Ser Thr
    690                 695                 700

Asn Val Asp Phe Ala Val Asn Thr Glu Gly Thr Tyr Ser Glu Pro Arg
705                 710                 715                 720

Pro Ile Gly Thr Arg Tyr Leu Thr Arg Asn Leu
                725                 730

<210> SEQ ID NO 90
<211> LENGTH: 733
<212> TYPE: PRT
<213> ORGANISM: Unknown
<220> FEATURE:
<223> OTHER INFORMATION: capsid protein of AAV serotype, clone 42.1B

<400> SEQUENCE: 90

Met Ala Ala Asp Gly Tyr Leu Pro Asp Trp Leu Glu Asp Asn Leu Ser
1               5                   10                  15

Glu Gly Ile Arg Glu Trp Trp Asp Leu Arg Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Arg Leu Asn Phe Gly Gln Thr Gly Asp Ser Glu
            165                 170                 175

Ser Val Pro Asp Pro Gln Pro Ile Gly Glu Pro Ala Gly Pro Ser
        180                 185                 190

Gly Leu Gly Ser Gly Thr Met Ala Gly Gly Gly Ala Pro Met Ala
    195                 200                 205

Asp Asn Asn Glu Gly Ala Asp Gly Val Gly Ser Ser Ser Gly Asn Trp
210                 215                 220

His Cys Asp Ser Thr Trp Leu Gly Asp Arg Val Ile Thr Thr Ser Thr
```

-continued

```
            225                 230                 235                 240
Arg Thr Trp Ala Leu Pro Thr Tyr Asn Asn His Leu Tyr Lys Gln Ile
                245                 250                 255
Ser Asn Gly Thr Ser Gly Ser Thr Asn Asp Asn Thr Tyr Phe Gly
            260                 265                 270
Tyr Ser Thr Pro Trp Gly Tyr Phe Asp Phe Asn Arg Phe His Cys His
                275                 280                 285
Phe Ser Pro Arg Asp Trp Gln Arg Leu Ile Asn Asn Trp Gly Phe
    290                 295                 300
Arg Pro Lys Arg Leu Asn Phe Lys Leu Phe Asn Ile Gln Val Lys Glu
305                 310                 315                 320
Val Thr Gln Asn Glu Gly Thr Lys Thr Ile Ala Asn Asn Leu Thr Ser
                325                 330                 335
Thr Ile Gln Val Phe Thr Asp Ser Glu Tyr Gln Leu Pro Tyr Val Leu
                340                 345                 350
Gly Ser Ala His Gln Gly Cys Leu Pro Pro Phe Pro Ala Asp Val Phe
            355                 360                 365
Met Ile Pro Gln Tyr Gly Tyr Leu Thr Leu Asn Asn Gly Ser Gln Ala
    370                 375                 380
Val Gly Arg Ser Ser Phe Tyr Cys Leu Glu Tyr Phe Pro Ser Gln Met
385                 390                 395                 400
Leu Arg Thr Gly Asn Asn Phe Glu Phe Ser Tyr Gln Phe Glu Asp Val
                405                 410                 415
Pro Phe His Ser Ser Tyr Ala His Ser Gln Ser Leu Asp Arg Leu Met
            420                 425                 430
Asn Pro Leu Ile Asp Gln Tyr Leu Tyr Tyr Leu Ser Arg Thr Gln Ser
        435                 440                 445
Thr Gly Gly Thr Ala Gly Thr Gln Gln Leu Leu Phe Ser Gln Ala Gly
    450                 455                 460
Pro Asn Asn Met Ser Ala Gln Ala Lys Asn Trp Leu Pro Gly Pro Cys
465                 470                 475                 480
Tyr Arg Gln Gln Arg Val Ser Thr Thr Val Ser Gln Asn Asn Asn Ser
                485                 490                 495
Asn Phe Ala Trp Thr Gly Ala Thr Lys Tyr His Leu Asn Gly Arg Asp
            500                 505                 510
Ser Leu Val Asn Pro Gly Val Ala Met Ala Thr His Lys Gly Asp Glu
        515                 520                 525
Glu Arg Phe Phe Pro Ser Ser Gly Val Leu Met Phe Gly Lys Gln Gly
    530                 535                 540
Ala Gly Lys Asp Asn Val Asp Tyr Ser Ser Val Met Leu Thr Ser Glu
545                 550                 555                 560
Glu Glu Ile Lys Thr Thr Asn Pro Val Ala Thr Glu Gln Tyr Gly Val
                565                 570                 575
Val Ala Asp Asn Leu Gln Gln Gln Asn Ala Ala Pro Ile Val Gly Ala
            580                 585                 590
Val Asn Ser Gln Gly Ala Leu Pro Gly Met Val Trp Gln Asn Arg Asp
        595                 600                 605
Val Tyr Leu Gln Gly Pro Ile Trp Ala Lys Ile Pro His Thr Asp Gly
    610                 615                 620
Asn Phe His Pro Ser Pro Leu Met Gly Gly Phe Gly Leu Lys His Pro
625                 630                 635                 640
Pro Pro Gln Ile Leu Ile Lys Asn Thr Pro Val Pro Ala Asp Pro Pro
                645                 650                 655
```

```
Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Tyr Lys
690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
                725                 730

<210> SEQ ID NO 91
<211> LENGTH: 738
<212> TYPE: PRT
<213> ORGANISM: Unknown
<220> FEATURE:
<223> OTHER INFORMATION: capsid protein of AAV serotype, clone 42.5B

<400> SEQUENCE: 91

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285
```

-continued

Arg Phe His Cys His Phe Ser Pro Arg Asp Trp Gln Arg Leu Ile Asn
            290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
                580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

```
Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 92
<211> LENGTH: 738
<212> TYPE: PRT
<213> ORGANISM: Unknown
<220> FEATURE:
<223> OTHER INFORMATION: capsid protein of AAV serotype, clone 43.1

<400> SEQUENCE: 92

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
```

-continued

```
                325                 330                 335
Asn Asn Leu Thr Ser Thr Ile Gln Val Phe Thr Asp Ser Glu Tyr Gln
                340                 345                 350
Leu Pro Tyr Val Pro Gly Ser Ala His Gln Gly Cys Leu Pro Pro Phe
                355                 360                 365
Pro Ala Asp Val Phe Met Ile Pro Gln Tyr Gly Tyr Leu Thr Leu Asn
                370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Thr Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Ser Thr Gly Gly Thr Gln Gly Thr Gln Gln Leu Leu
                450                 455                 460
Phe Ser Gln Ala Gly Pro Ala Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
                515                 520                 525
His Lys Asp Asp Glu Glu Arg Phe Phe Pro Ser Ser Gly Val Leu Met
                530                 535                 540
Phe Gly Lys Gln Gly Ala Gly Lys Asp Asn Val Asp Tyr Ser Ser Val
545                 550                 555                 560
Met Leu Thr Ser Glu Glu Glu Ile Lys Thr Thr Asn Pro Val Ala Thr
                565                 570                 575
Glu Gln Tyr Gly Val Val Ala Asp Asn Leu Gln Gln Thr Asn Gly Ala
                580                 585                 590
Pro Ile Val Gly Thr Val Asn Ser Gln Gly Ala Leu Pro Gly Met Val
                595                 600                 605
Trp Gln Asn Arg Asp Val Tyr Leu Gln Gly Pro Ile Trp Ala Lys Ile
                610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Val Lys Asn Thr Pro Val
                645                 650                 655
Pro Ala Asp Pro Pro Thr Thr Phe Ser Gln Ala Lys Leu Ala Ser Phe
                660                 665                 670
Ile Thr Gln Tyr Ser Thr Gly Gln Val Ser Val Glu Ile Glu Trp Glu
                675                 680                 685
Leu Gln Lys Glu Asn Ser Lys Arg Trp Asn Pro Glu Ile Gln Tyr Thr
                690                 695                 700
Ser Asn Tyr Tyr Lys Ser Thr Asn Val Asp Phe Ala Val Asn Thr Glu
705                 710                 715                 720
Gly Thr Tyr Ser Glu Pro Arg Pro Ile Gly Thr Arg Tyr Leu Thr Arg
                725                 730                 735
Asn Leu
```

<210> SEQ ID NO 93
<211> LENGTH: 738
<212> TYPE: PRT
<213> ORGANISM: Unknown
<220> FEATURE:
<223> OTHER INFORMATION: capsid protein of AAV serotype, clone 43.12

<400> SEQUENCE: 93

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365
```

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
            580                 585                 590

Pro Ile Val Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 94
<211> LENGTH: 738
<212> TYPE: PRT
<213> ORGANISM: Unknown
<220> FEATURE:
<223> OTHER INFORMATION: capsid protein of AAV serotype, clone 43.5

<400> SEQUENCE: 94

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415
```

```
Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
            580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 95
<211> LENGTH: 738
<212> TYPE: PRT
<213> ORGANISM: Unknown
<220> FEATURE:
<223> OTHER INFORMATION: capsid protein of AAV serotype, clone AAV8

<400> SEQUENCE: 95

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30
```

```
Lys Ala Asn Gln Gln Lys Gln Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Gln Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
```

```
              450                 455                 460
Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 96
<211> LENGTH: 736
<212> TYPE: PRT
<213> ORGANISM: Unknown
<220> FEATURE:
<223> OTHER INFORMATION: capsid protein of AAV serotype, clone 43.21

<400> SEQUENCE: 96

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Arg Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Ser
                485                 490                 495
```

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Leu
625                 630                 635                 640

Lys His Pro Pro Gln Ile Leu Ile Lys Asn Thr Pro Val Pro Ala
            645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 97
<211> LENGTH: 736
<212> TYPE: PRT
<213> ORGANISM: Unknown
<220> FEATURE:
<223> OTHER INFORMATION: capsid protein of AAV serotype, clone 43.25

<400> SEQUENCE: 97

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile

```
                545                 550                 555                 560
            Thr Asp Glu Glu Glu Ile Lys Ala Thr Asn Pro Val Ala Thr Glu Glu
                            565                 570                 575

Tyr Gly Ala Val Ala Ile Asn Asn Gln Ala Ala Asn Thr Gln Ala Gln
                            580                 585                 590

Thr Gly Leu Val His Asn Gln Gly Val Ile Pro Gly Met Val Trp Gln
                            595                 600                 605

Asn Arg Asp Val Tyr Leu Gln Gly Pro Ile Trp Ala Lys Ile Pro His
                            610                 615                 620

Thr Asp Gly Asn Phe His Pro Ser Pro Leu Met Gly Gly Phe Gly Leu
            625                 630                 635                 640

Lys His Pro Pro Pro Gln Ile Leu Ile Lys Asn Thr Pro Val Pro Ala
                            645                 650                 655

Asp Pro Pro Leu Thr Phe Asn Gln Ala Lys Leu Asn Ser Phe Ile Thr
                            660                 665                 670

Gln Tyr Ser Thr Gly Gln Val Ser Val Glu Ile Glu Trp Glu Leu Gln
                            675                 680                 685

Lys Glu Asn Ser Lys Arg Trp Asn Pro Glu Ile Gln Tyr Thr Ser Asn
                            690                 695                 700

Tyr Tyr Lys Ser Thr Asn Val Asp Phe Ala Val Asn Thr Glu Gly Val
            705                 710                 715                 720

Tyr Ser Glu Pro Arg Pro Ile Gly Thr Arg Tyr Leu Thr Arg Asn Leu
                            725                 730                 735

<210> SEQ ID NO 98
<211> LENGTH: 736
<212> TYPE: PRT
<213> ORGANISM: Unknown
<220> FEATURE:
<223> OTHER INFORMATION: capsid protein of AAV serotype, clone 43.23

<400> SEQUENCE: 98

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
```

-continued

```
                180                 185                 190
Ala Ala Pro Ser Gly Leu Gly Pro Asn Thr Met Ala Ser Gly Gly Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Leu Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Val Pro Gln Tyr Gly Tyr Leu Thr Leu Asn Asn
            370                 375                 380

Gly Ser Gln Ala Leu Gly Arg Ser Ser Phe Tyr Cys Leu Glu Tyr Phe
385                 390                 395                 400

Pro Ser Gln Met Pro Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
            450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
            515                 520                 525

Asp Asp Asp Asp Arg Phe Phe Pro Ser Ser Gly Val Leu Ile Phe Gly
            530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
            595                 600                 605
```

```
Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 99
<211> LENGTH: 736
<212> TYPE: PRT
<213> ORGANISM: Unknown
<220> FEATURE:
<223> OTHER INFORMATION: capsid protein of AAV serotype, clone 43.20

<400> SEQUENCE: 99

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Leu Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240
```

-continued

```
Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Thr Val Pro Gln Tyr Gly Tyr Leu Thr Leu Asn Asn
                370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Val
                435                 440                 445

Arg Thr Gln Thr Thr Gly Thr Gly Gly Thr Gln Thr Leu Ala Phe Ser
                450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Asn Gln Asn
                485                 490                 495

Asn Asn Ser Asn Phe Ala Trp Thr Gly Ala Ala Lys Phe Lys Leu Asn
                500                 505                 510

Gly Arg Asp Ser Leu Met Asn Pro Gly Val Ala Met Ala Ser His Lys
                515                 520                 525

Asp Asp Asp Asp Arg Phe Phe Pro Ser Ser Gly Val Leu Ile Phe Gly
                530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
                580                 585                 590

Thr Gly Leu Val His Asn Gln Gly Val Ile Pro Gly Met Val Trp Gln
                595                 600                 605

Asn Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655
```

```
Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 100
<211> LENGTH: 736
<212> TYPE: PRT
<213> ORGANISM: Unknown
<220> FEATURE:
<223> OTHER INFORMATION: capsid protein of AAV serotype, clone AAV9

<400> SEQUENCE: 100

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Glu Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Gly Thr Lys Thr Ile Ala Asn
                    325                 330                 335
Asn Leu Thr Ser Thr Val Gln Val Phe Thr Asp Ser Glu Tyr Gln Leu
                340                 345                 350
Pro Tyr Val Leu Gly Ser Ala His Gln Gly Cys Leu Pro Pro Phe Pro
            355                 360                 365
Ala Asp Val Phe Met Val Pro Gln Tyr Gly Tyr Leu Thr Leu Asn Asn
370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Val
        435                 440                 445
Arg Thr Gln Thr Thr Gly Thr Gly Gly Thr Gln Thr Leu Ala Phe Ser
    450                 455                 460
Gln Ala Gly Pro Ser Ser Met Ala Asn Gln Ala Arg Asn Trp Val Pro
465                 470                 475                 480
Gly Pro Cys Tyr Arg Gln Gln Arg Val Ser Thr Thr Thr Asn Gln Asn
                485                 490                 495
Asn Asn Ser Asn Phe Ala Trp Thr Gly Ala Ala Lys Phe Lys Leu Asn
            500                 505                 510
Gly Arg Asp Ser Leu Met Asn Pro Gly Val Ala Met Ala Ser His Lys
        515                 520                 525
Asp Asp Glu Asp Arg Phe Phe Pro Ser Ser Gly Val Leu Ile Phe Gly
    530                 535                 540
Lys Gln Gly Ala Gly Asn Asp Gly Val Asp Tyr Ser Gln Val Leu Ile
545                 550                 555                 560
Thr Asp Glu Glu Glu Ile Lys Ala Thr Asn Pro Val Ala Thr Glu Glu
                565                 570                 575
Tyr Gly Ala Val Ala Ile Asn Asn Gln Ala Ala Asn Thr Gln Ala Gln
            580                 585                 590
Thr Gly Leu Val His Asn Gln Gly Val Ile Pro Gly Met Val Trp Gln
        595                 600                 605
Asn Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Leu
625                 630                 635                 640
Lys His Pro Pro Pro Gln Ile Leu Ile Lys Asn Thr Pro Val Pro Ala
                645                 650                 655
Asp Pro Pro Leu Thr Phe Asn Gln Ala Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Tyr Lys Ser Thr Asn Val Asp Phe Ala Val Asn Thr Glu Gly Val
```

```
                  705                 710                 715                 720
Tyr Ser Glu Pro Arg Pro Ile Gly Thr Arg Tyr Leu Thr Arg Asn Leu
                          725                 730                 735

<210> SEQ ID NO 101
<211> LENGTH: 728
<212> TYPE: PRT
<213> ORGANISM: Unknown
<220> FEATURE:
<223> OTHER INFORMATION: capsid protein of AAV serotype, clone 24.1

<400> SEQUENCE: 101

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Arg Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Val Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Ser Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
```

```
                340                 345                 350
Ala His Gln Gly Cys Leu Pro Pro Phe Pro Ala Asp Val Phe Met Ile
                355                 360                 365

Pro Gln Tyr Gly Tyr Leu Thr Leu Asn Asn Gly Ser Gln Ser Val Gly
370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Val His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
            450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Cys Leu Gln Gly
            595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Glu Val Phe Thr Pro
                645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 102
<211> LENGTH: 728
<212> TYPE: PRT
<213> ORGANISM: Unknown
```

<220> FEATURE:
<223> OTHER INFORMATION: capsid protein of AAV serotype, clone 42.2REAL

<400> SEQUENCE: 102

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
370                 375                 380

Arg Ser Ser Phe Tyr Cys Leu Glu Tyr Phe Pro Ser Gln Met Leu Arg
385                 390                 395                 400
```

```
Thr Gly Asn Asn Phe Glu Phe Ser Tyr Thr Phe Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
Gly Ser Thr Arg Glu Leu Gln Phe His Gln Ala Gly Pro Asn Thr Met
    450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Ser Asn Phe Ala Trp
                485                 490                 495
Thr Gly Ala Thr Lys Tyr His Leu Asn Gly Arg Asn Ser Leu Thr Asn
                500                 505                 510
Pro Gly Val Ala Met Ala Thr Asn Lys Asp Asp Glu Asp Gln Phe Phe
            515                 520                 525
Pro Ile Asn Gly Val Leu Val Phe Gly Glu Thr Gly Ala Ala Asn Lys
        530                 535                 540
Thr Thr Leu Glu Asn Val Leu Met Thr Ser Glu Glu Ile Lys Thr
545                 550                 555                 560
Thr Asn Pro Val Ala Thr Glu Glu Tyr Gly Val Val Ser Ser Asn Leu
                565                 570                 575
Gln Ser Ser Thr Ala Gly Pro Gln Thr Gln Thr Val Asn Ser Gln Gly
            580                 585                 590
Ala Leu Pro Gly Met Val Trp Gln Asn Arg Asp Val Tyr Leu Gln Gly
        595                 600                 605
Pro Ile Trp Ala Lys Ile Pro His Thr Asp Gly Asn Phe His Pro Ser
    610                 615                 620
Pro Leu Met Gly Gly Phe Gly Leu Lys His Pro Pro Gln Ile Leu
625                 630                 635                 640
Ile Lys Asn Thr Pro Val Pro Ala Asn Pro Pro Glu Val Phe Thr Pro
                645                 650                 655
Ala Lys Phe Ala Ser Phe Ile Thr Gln Tyr Ser Thr Gly Gln Val Ser
            660                 665                 670
Val Glu Ile Glu Trp Glu Leu Gln Lys Glu Asn Ser Lys Arg Trp Asn
        675                 680                 685
Pro Glu Ile Gln Tyr Thr Ser Asn Tyr Ala Lys Ser Asn Asn Val Glu
    690                 695                 700
Phe Ala Val Asn Asn Glu Gly Val Tyr Thr Glu Pro Arg Pro Ile Gly
705                 710                 715                 720
Thr Arg Tyr Leu Thr Arg Asn Leu
                725

<210> SEQ ID NO 103
<211> LENGTH: 728
<212> TYPE: PRT
<213> ORGANISM: Unknown
<220> FEATURE:
<223> OTHER INFORMATION: capsid protein of AAV serotype, clone 7.2VP1

<400> SEQUENCE: 103

Met Ala Ala Asp Gly Tyr Leu Pro Asp Trp Leu Glu Gly Asn Leu Ser
1               5                   10                  15
Glu Gly Ile Arg Glu Trp Trp Asp Leu Lys Pro Gly Ala Pro Lys Pro
            20                  25                  30
```

Lys Ala Asn Gln Gln Lys Gln Asp Asp Gly Arg Gly Leu Val Leu Pro
                35                  40                  45

Gly Tyr Arg Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65              70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Ile Glu Ser Pro Asp Ser Ser Thr Gly Ile Gly Lys Asn Gly Gln
145                 150                 155                 160

Pro Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
                180                 185                 190

Gly Leu Gly Ser Gly Thr Met Ala Ala Gly Gly Ala Pro Met Ala
                195                 200                 205

Asp Asn Asn Glu Gly Ala Asp Gly Val Gly Asn Ala Ser Gly Asn Trp
                210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
                260                 265                 270

Thr Pro Trp Gly Tyr Phe Asp Phe Asn Arg Phe His Cys His Phe Ser
                275                 280                 285

Pro Arg Asp Trp Gln Arg Leu Ile Asn Asn Asn Trp Gly Phe Arg Pro
                290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
                355                 360                 365

Pro Gln Tyr Gly Tyr Leu Thr Leu Asn Asn Gly Ser Gln Ser Val Gly
                370                 375                 380

Arg Ser Ser Phe Tyr Cys Leu Glu Tyr Phe Pro Ser Gln Met Leu Arg
385                 390                 395                 400

Thr Gly Asp Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
                435                 440                 445

Gly Ser Thr Arg Glu Leu Gln Phe His Gln Ala Gly Pro Asn Thr Met
            450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 104
<211> LENGTH: 728
<212> TYPE: PRT
<213> ORGANISM: Unknown
<220> FEATURE:
<223> OTHER INFORMATION: capsid protein of AAV serotype, clone 27.3VP1

<400> SEQUENCE: 104

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

```
Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
           100                 105                 110

Asn Leu Gly Arg Ala Val Phe Gln Ala Lys Lys Arg Val Leu Glu Pro
           115                 120                 125

Leu Gly Leu Val Glu Glu Gly Ala Lys Thr Ala Ser Gly Lys Lys Arg
           130                 135                 140

Pro Ile Glu Ser Pro Asp Ser Ser Thr Gly Ile Gly Lys Lys Gly Gln
145                 150                 155                 160

Gln Pro Ala Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
           180                 185                 190

Gly Leu Gly Ser Gly Thr Met Ala Ala Gly Gly Ala Pro Met Ala
           195                 200                 205

Asp Asn Asn Glu Gly Ala Asp Gly Val Gly Asn Ala Ser Gly Asn Trp
           210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
               245                 250                 255

Ser Ser Gln Ser Gly Ala Thr Asn Asp Asn His Phe Phe Gly Tyr Ser
               260                 265                 270

Thr Pro Trp Gly Tyr Phe Asp Phe Asn Arg Phe His Cys His Phe Ser
           275                 280                 285

Pro Arg Asp Trp Gln Arg Leu Ile Asn Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
               325                 330                 335

Gln Val Phe Ser Asp Ser Glu Tyr Gln Leu Pro Tyr Val Leu Gly Ser
               340                 345                 350

Ala His Gln Gly Cys Leu Pro Pro Phe Pro Ala Asp Val Phe Met Ile
       355                 360                 365

Pro Gln Tyr Gly Tyr Leu Thr Leu Asn Asn Gly Ser Gln Ser Val Gly
       370                 375                 380

Arg Ser Ser Phe Cys Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
           420                 425                 430

Leu Ile Asp Gln Tyr Leu Tyr Tyr Leu Ala Arg Thr Gln Ser Thr Thr
           435                 440                 445

Gly Ser Thr Arg Glu Leu Gln Phe His Gln Ala Gly Pro Asn Thr Val
       450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
               485                 490                 495

Thr Gly Ala Thr Lys Tyr His Leu Asn Gly Arg Asn Ser Leu Thr Asn
```

```
                    500                 505                 510
Pro Gly Val Ala Met Ala Thr Asn Lys Asp Asp Glu Asp Gln Phe Leu
                515                 520                 525

Pro Ile Asn Gly Val Leu Val Phe Gly Lys Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Arg Thr Gln Thr Val Asn Ser Gln Gly
            580                 585                 590

Ala Leu Pro Gly Met Val Trp Gln Asn Arg Asp Val Tyr Leu Gln Gly
                595                 600                 605

Pro Ile Trp Ala Glu Ile Pro His Thr Asp Gly Asn Phe His Pro Ser
            610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 105
<211> LENGTH: 728
<212> TYPE: PRT
<213> ORGANISM: Unknown
<220> FEATURE:
<223> OTHER INFORMATION: capsid protein of AAV serotype, clone 16.3VP1

<400> SEQUENCE: 105

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
```

```
           130                 135                 140
Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
            180                 185                 190

Gly Leu Gly Ser Gly Thr Met Ala Ala Gly Gly Ala Pro Met Ala
                195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Met Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Gly Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Ile Lys Thr
545                 550                 555                 560
```

```
Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Gly Val Phe Thr Pro
                645                 650                 655

Ala Leu Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 106
<211> LENGTH: 728
<212> TYPE: PRT
<213> ORGANISM: Unknown
<220> FEATURE:
<223> OTHER INFORMATION: capsid protein of AAV serotype, clone 42.10

<400> SEQUENCE: 106

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Arg Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
            180                 185                 190
```

-continued

Gly Leu Gly Ser Gly Thr Met Ala Ala Gly Gly Ala Pro Met Ala
            195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn His Leu Tyr Lys Gln Ile
            245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ser Val Gly
            370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Met
            450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
            485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
            515                 520                 525

Pro Ile Asn Gly Val Leu Val Phe Gly Lys Thr Gly Ala Ala Asn Lys
            530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
            595                 600                 605

```
Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
                675                 680                 685

Pro Glu Ile Gln Tyr Thr Ser Asn Tyr Ala Lys Ser Asn Asn Val Glu
690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 107
<211> LENGTH: 728
<212> TYPE: PRT
<213> ORGANISM: Unknown
<220> FEATURE:
<223> OTHER INFORMATION: capsid protein of AAV serotype, clone 42.3B

<400> SEQUENCE: 107

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
                180                 185                 190

Gly Leu Gly Ser Gly Thr Met Ala Ala Gly Gly Ala Pro Met Ala
            195                 200                 205

Asp Asn Asn Glu Gly Ala Asp Gly Val Gly Asn Ala Ser Gly Asn Trp
                210                 215                 220

His Cys Asp Ser Thr Trp Leu Gly Asp Arg Val Ile Thr Thr Ser Thr
225                 230                 235                 240
```

-continued

```
Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Trp Gly Phe Arg Pro
    290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Thr Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Ile Lys Thr
545                 550                 555                 560

Thr Asn Pro Val Ala Thr Glu Gln Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Glu Val Phe Thr Pro
                645                 650                 655

Ala Lys Phe Ala Ser Phe Ile Thr Gln Tyr Ser Thr Gly Gln Val Ser
```

```
            660                 665                 670
Val Glu Ile Glu Trp Glu Leu Gln Lys Glu Asn Ser Lys Arg Trp Asn
        675                 680                 685

Pro Glu Ile Gln Tyr Thr Ser Asn Tyr Ala Lys Ser Asn Asn Val Glu
    690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 108
<211> LENGTH: 728
<212> TYPE: PRT
<213> ORGANISM: Unknown
<220> FEATURE:
<223> OTHER INFORMATION: capsid protein of AAV serotype, clone 42.11

<400> SEQUENCE: 108

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
```

```
            290             295             300
Arg Lys Leu Arg Phe Lys Leu Phe Asn Ile Gln Val Lys Glu Val Thr
305             310             315             320

Thr Asn Asp Gly Val Thr Thr Ile Ala Asn Asn Leu Thr Ser Thr Ile
                325             330             335

Gln Val Phe Ser Asp Ser Glu Tyr Gln Leu Pro Tyr Val Leu Gly Ser
            340             345             350

Ala His Gln Gly Cys Leu Pro Pro Phe Pro Ala Asp Val Phe Met Ile
            355             360             365

Pro Gln Tyr Gly Tyr Leu Thr Leu Asn Asn Gly Ser Gln Ser Val Gly
        370             375             380

Arg Ser Ser Phe Tyr Cys Leu Glu Tyr Phe Pro Ser Gln Met Leu Arg
385             390             395             400

Thr Gly Asn Asn Phe Glu Phe Ser Tyr Thr Phe Glu Glu Val Pro Phe
                405             410             415

His Ser Ser Tyr Ala His Ser Gln Ser Leu Asp Arg Leu Met Asn Pro
            420             425             430

Leu Ile Asp Gln Tyr Leu Tyr Tyr Leu Ala Arg Thr Gln Ser Thr Thr
        435             440             445

Gly Ser Thr Arg Glu Leu Gln Phe His Gln Ala Gly Pro Asn Thr Met
    450             455             460

Ala Glu Gln Ser Lys Asn Trp Leu Pro Gly Pro Cys Tyr Arg Arg Gln
465             470             475             480

Arg Leu Ser Lys Asp Ile Asp Ser Asn Asn Ser Asn Phe Ala Trp
            485             490             495

Thr Gly Ala Thr Lys Tyr His Leu Asn Gly Arg Asn Ser Leu Thr Asn
            500             505             510

Pro Gly Val Ala Met Ala Thr Asn Lys Asp Asp Glu Asp Gln Phe Phe
            515             520             525

Pro Ile Asn Gly Val Leu Val Phe Gly Lys Thr Gly Ala Ala Asn Lys
        530             535             540

Thr Thr Leu Glu Asn Val Leu Met Thr Ser Glu Glu Ile Lys Thr
545             550             555             560

Thr Asn Pro Val Ala Thr Glu Glu Tyr Gly Val Val Ser Ser Asn Leu
                565             570             575

Gln Ser Ser Thr Ala Gly Pro Thr Gln Thr Val Asn Ser Gln Gly
            580             585             590

Ala Leu Pro Gly Met Val Trp Gln Asn Arg Asp Val Tyr Leu Gln Gly
        595             600             605

Pro Ile Trp Ala Lys Ile Pro His Thr Asp Gly Asn Phe His Pro Ser
610             615             620

Pro Leu Met Gly Gly Phe Gly Leu Lys His Pro Pro Gln Ile Leu
625             630             635             640

Ile Lys Asn Thr Pro Val Pro Ala Asn Pro Glu Val Phe Thr Pro
                645             650             655

Ala Lys Phe Ala Ser Phe Ile Thr Gln Tyr Ser Thr Gly Gln Val Ser
            660             665             670

Val Glu Ile Glu Trp Glu Leu Gln Lys Glu Asn Ser Lys Arg Trp Asn
            675             680             685

Pro Glu Ile Gln Tyr Thr Ser Asn Tyr Ala Lys Ser Asn Asn Val Glu
        690             695             700

Phe Ala Val Asn Asn Glu Gly Val Tyr Thr Glu Pro Arg Pro Ile Gly
705             710             715             720
```

Thr Arg Tyr Leu Thr Arg Asn Leu
                725

<210> SEQ ID NO 109
<211> LENGTH: 729
<212> TYPE: PRT
<213> ORGANISM: Unknown
<220> FEATURE:
<223> OTHER INFORMATION: capsid protein of AAV serotype, clone F1VP1

<400> SEQUENCE: 109

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Ser Val Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Asn Trp Gly Phe Arg
    290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
                325                 330                 335

Val Gln Val Phe Ser Asp Ser Glu Tyr Gln Leu Pro Tyr Val Leu Gly
            340                 345                 350

Ser Ala His Gln Gly Cys Leu Pro Phe Pro Ala Asp Val Phe Met
        355                 360                 365

Ile Pro Gln Tyr Gly Tyr Leu Thr Leu Asn Asn Gly Ser Gln Ser Val
370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
                420                 425                 430

Pro Leu Ile Asp Gln Tyr Leu Tyr Tyr Leu Ala Arg Thr Gln Ser Thr
            435                 440                 445

Thr Gly Ser Thr Arg Glu Leu Gln Phe His Gln Ala Gly Pro Asn Thr
        450                 455                 460

Met Ala Glu Gln Ser Lys Asn Trp Leu Pro Gly Pro Cys Tyr Arg Gln
465                 470                 475                 480

Gln Gly Leu Ser Lys Asn Leu Asp Phe Asn Asn Ser Asn Phe Ala
                485                 490                 495

Trp Thr Ala Ala Thr Lys Tyr His Leu Asn Gly Arg Asn Ser Leu Thr
                500                 505                 510

Asn Pro Gly Ile Pro Met Ala Thr Asn Lys Asp Asp Glu Asp Gln Phe
            515                 520                 525

Phe Pro Ile Asn Gly Val Leu Val Phe Gly Lys Thr Gly Ala Ala Asn
        530                 535                 540

Lys Thr Thr Leu Glu Asn Val Leu Met Thr Ser Glu Glu Glu Ile Lys
545                 550                 555                 560

Thr Thr Asn Pro Val Ala Thr Glu Glu Tyr Gly Val Val Ser Ser Asn
                565                 570                 575

Leu Gln Pro Ser Thr Ala Gly Pro Gln Ser Gln Thr Ile Asn Ser Gln
                580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
        610                 615                 620

Ser Pro Leu Met Gly Gly Phe Gly Leu Lys His Pro Pro Pro Gln Ile
625                 630                 635                 640

Leu Ile Lys Asn Thr Pro Val Pro Ala Asn Pro Pro Glu Val Phe Thr
                645                 650                 655

Pro Ala Lys Phe Ala Ser Phe Ile Thr Gln Tyr Ser Thr Gly Gln Val
                660                 665                 670

Ser Val Glu Ile Glu Trp Glu Leu Gln Lys Glu Asn Ser Lys Arg Trp
            675                 680                 685

Asn Pro Glu Ile Gln Tyr Thr Ser Asn Tyr Ala Lys Ser Asn Asn Val
        690                 695                 700

Glu Phe Ala Val Asn Pro Asp Gly Val Tyr Thr Glu Pro Arg Pro Ile
705                 710                 715                 720

Gly Thr Arg Tyr Leu Pro Arg Asn Leu
                725

<210> SEQ ID NO 110
<211> LENGTH: 729
<212> TYPE: PRT
<213> ORGANISM: Unknown
<220> FEATURE:

<223> OTHER INFORMATION: capsid protein of AAV serotype, clone F5VP1[@0003]

<400> SEQUENCE: 110

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Ile Asp Ser Pro Asp Ser Ser Thr Gly Ile Gly Lys Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Leu Gly Glu Pro Pro Ala Ala Pro Ser
            180                 185                 190
Ser Val Gly Ser Gly Thr Met Ala Ala Gly Gly Gly Ala Pro Thr Ala
        195                 200                 205
Asp Asn Asn Glu Gly Ala Asp Gly Val Gly Asn Ala Ser Gly Asn Trp
    210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Ser Ser Ser Gly Ala Thr Asn Asp Asn His Tyr Phe Gly Tyr
            260                 265                 270
Ser Thr Pro Trp Gly Tyr Phe Asp Phe Asn Arg Phe His Cys His Phe
        275                 280                 285
Ser Pro Arg Asp Trp Gln Arg Leu Ile Asn Asn Asn Trp Gly Phe Arg
    290                 295                 300
Pro Lys Lys Leu Arg Phe Lys Leu Phe Asn Ile Gln Val Lys Glu Val
305                 310                 315                 320
Thr Thr Asn Asp Gly Val Thr Thr Ile Ala Asn Asn Leu Thr Ser Thr
                325                 330                 335
Val Gln Val Phe Ser Asp Ser Glu Tyr Gln Leu Pro Tyr Val Leu Gly
            340                 345                 350
Ser Ala His Gln Gly Cys Leu Pro Pro Phe Pro Ala Asp Val Phe Met
        355                 360                 365
Ile Pro Gln Tyr Gly Tyr Leu Thr Leu Asn Asn Gly Ser Gln Ser Val
    370                 375                 380
Gly Arg Ser Ser Phe Tyr Cys Leu Glu Tyr Phe Pro Ser Gln Met Leu
385                 390                 395                 400
```

-continued

```
Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
            420                 425                 430

Pro Leu Ile Asp Gln Tyr Leu Tyr Leu Ala Arg Thr Gln Ser Thr
        435                 440                 445

Thr Gly Ser Thr Arg Glu Leu Gln Phe His Gln Ala Gly Pro Asn Thr
    450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
            485                 490                 495

Trp Thr Ala Ala Thr Lys Tyr His Leu Asn Gly Arg Asn Ser Leu Thr
                500                 505                 510

Asn Pro Gly Ile Pro Met Ala Thr Asn Lys Asp Asp Glu Asp Gln Phe
            515                 520                 525

Phe Pro Ile Asn Gly Val Leu Val Phe Gly Lys Thr Gly Ala Ala Asn
        530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
            565                 570                 575

Leu Gln Ser Ser Thr Ala Gly Pro Gln Ser Gln Thr Ile Asn Ser Gln
                580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
        610                 615                 620

Ser Pro Leu Met Gly Gly Phe Gly Leu Glu His Pro Pro Gln Ile
625                 630                 635                 640

Leu Ile Lys Asn Thr Pro Val Pro Ala Asn Pro Pro Glu Val Phe Thr
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
        675                 680                 685

Asn Pro Glu Ile Gln Tyr Thr Ser Asn Tyr Ala Lys Ser Asn Asn Val
    690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
                725
```

<210> SEQ ID NO 111
<211> LENGTH: 729
<212> TYPE: PRT
<213> ORGANISM: Unknown
<220> FEATURE:
<223> OTHER INFORMATION: capsid protein of AAV serotype, clone F3VP1

<400> SEQUENCE: 111

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

```
Lys Ala Asn Gln Gln Lys Gln Asp Gly Arg Gly Leu Val Leu Pro
             35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
             85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
130                 135                 140
Pro Ile Gly Ser Pro Asp Ser Ser Thr Gly Ile Gly Lys Lys Gly Gln
145                 150                 155                 160
Gln Pro Ala Lys Lys Leu Asn Phe Gly Gln Thr Gly Asp Ser Glu
            165                 170                 175
Ser Val Pro Asp Pro Gln Pro Leu Gly Glu Pro Pro Ala Ala Pro Ser
            180                 185                 190
Ser Val Gly Ser Gly Thr Met Ala Ala Gly Gly Ala Pro Met Ala
            195                 200                 205
Asp Asn Asn Glu Gly Ala Asp Gly Val Gly Asn Ala Ser Gly Asn Trp
            210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Ser Ser Ser Gly Ala Thr Asn Asp Asn His Tyr Phe Gly Tyr
            260                 265                 270
Ser Thr Pro Trp Gly Tyr Phe Asp Phe Asn Arg Phe His Cys His Phe
            275                 280                 285
Ser Pro Arg Asp Trp Gln Arg Leu Ile Asn Asn Trp Gly Phe Arg
            290                 295                 300
Pro Lys Lys Leu Arg Phe Lys Leu Leu Asn Ile Gln Val Lys Glu Val
305                 310                 315                 320
Thr Thr Asn Asp Gly Val Thr Thr Ile Ala Asn Asn Leu Thr Ser Thr
                325                 330                 335
Val Gln Val Phe Ser Asp Ser Glu Tyr Gln Leu Pro Tyr Val Leu Gly
            340                 345                 350
Ser Ala His Gln Gly Cys Leu Pro Pro Phe Pro Ala Asp Val Phe Met
            355                 360                 365
Ile Pro Gln Tyr Gly Tyr Leu Thr Leu Asp Asn Gly Ser Gln Ser Val
370                 375                 380
Gly Arg Ser Ser Phe Tyr Cys Leu Glu Tyr Phe Pro Ser Gln Met Leu
385                 390                 395                 400
Arg Thr Gly Asn Asn Phe Glu Phe Ser Tyr Ser Phe Glu Asp Val Pro
                405                 410                 415
Phe His Ser Ser Tyr Ala His Ser Gln Ser Leu Asp Arg Leu Met Asn
            420                 425                 430
Pro Leu Ile Asp Gln Tyr Leu Tyr Tyr Leu Ala Arg Thr Gln Ser Thr
            435                 440                 445
Thr Gly Ser Thr Arg Glu Leu Gln Phe His Gln Ala Gly Pro Asn Thr
```

```
                450             455             460
    Met Ala Glu Gln Ser Lys Asn Trp Leu Pro Gly Pro Cys Tyr Arg Gln
    465                 470             475                 480

Gln Arg Leu Ser Lys Asn Leu Asp Phe Asn Asn Ser Asn Phe Ala
                    485             490             495

Trp Thr Ala Ala Thr Lys Tyr His Leu Asn Gly Arg Asn Ser Leu Thr
                    500             505             510

Asn Pro Gly Ile Pro Met Ala Thr Asn Lys Asp Asp Glu Asp Gln Phe
                515             520             525

Phe Pro Ile Asn Gly Val Leu Val Phe Gly Lys Thr Gly Ala Ala Asn
                530             535             540

Lys Thr Thr Leu Glu Asn Val Leu Met Thr Ser Glu Glu Ile Lys
    545             550             555             560

Thr Thr Asn Pro Val Ala Thr Glu Glu Tyr Gly Val Val Ser Ser Asn
                    565             570             575

Leu Gln Ser Ser Thr Ala Gly Pro Gln Ser Gln Thr Ile Asn Ser Gln
                    580             585             590

Gly Ala Leu Pro Gly Met Val Trp Gln Asn Arg Asp Val Tyr Leu Gln
                    595             600             605

Gly Pro Ile Trp Ala Lys Ile Pro His Thr Asp Gly Asn Phe His Pro
                610             615             620

Ser Pro Leu Met Gly Gly Phe Gly Leu Lys His Pro Pro Pro Gln Ile
    625             630             635             640

Leu Ile Lys Asn Thr Pro Val Pro Ala Asn Pro Pro Glu Val Phe Thr
                    645             650             655

Pro Ala Lys Phe Ala Ser Phe Ile Thr Gln Tyr Ser Thr Gly Gln Val
                660             665             670

Ser Val Glu Ile Glu Trp Glu Leu Gln Lys Glu Asn Ser Lys Arg Trp
                675             680             685

Asn Pro Glu Ile Gln Tyr Thr Ser Asn Tyr Ala Lys Ser Asn Asn Val
                690             695             700

Glu Phe Ala Val Asn Pro Asp Gly Val Tyr Thr Glu Pro Arg Pro Ile
    705             710             715             720

Gly Thr Arg Tyr Leu Thr Arg Asn Leu
                    725

<210> SEQ ID NO 112
<211> LENGTH: 735
<212> TYPE: PRT
<213> ORGANISM: Unknown
<220> FEATURE:
<223> OTHER INFORMATION: capsid protein of AAV serotype, clone 42.6B

<400> SEQUENCE: 112

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
```

```
                85                  90                  95
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
            130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Arg Lys Leu Arg Phe Lys Leu Phe Asn
305                 310                 315                 320

Ile Gln Val Lys Glu Val Thr Thr Asp Asp Gly Val Thr Thr Ile Ala
                325                 330                 335

Asn Asn Leu Thr Ser Thr Ile Gln Val Phe Ser Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Glu Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ala Arg Thr Gln Ser Thr Thr Gly Ser Thr Arg Glu Leu Gln Phe His
            450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
                485                 490                 495

Asn Asn Ser Asn Phe Ala Trp Thr Gly Ala Thr Lys Tyr His Leu Asn
            500                 505                 510
```

```
Gly Arg Asn Ser Leu Thr Asn Pro Gly Val Ala Met Ala Thr Asn Lys
            515                 520                 525

Asp Asp Glu Asp Gln Phe Phe Pro Ile Asn Gly Val Leu Val Phe Gly
    530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Tyr
                565                 570                 575

Gly Val Val Ser Ser Asn Leu Gln Ser Ser Thr Ala Gly Pro Gln Thr
            580                 585                 590

Gln Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Asp Gly Phe Gly Leu Lys
625                 630                 635                 640

His Pro Pro Pro Gln Ile Leu Ile Lys Asn Thr Pro Val Pro Ala Asn
                645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Ala Lys Ser Asn Asn Val Glu Phe Ala Val Asn Asn Glu Gly Val Tyr
705                 710                 715                 720

Thr Glu Pro Arg Pro Ile Gly Thr Arg Tyr Leu Thr Arg Asn Leu
                725                 730                 735

<210> SEQ ID NO 113
<211> LENGTH: 685
<212> TYPE: PRT
<213> ORGANISM: Unknown
<220> FEATURE:
<223> OTHER INFORMATION: capsid protein of AAV serotype, clone 42.12

<400> SEQUENCE: 113

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140
```

```
Pro Val Glu Pro Ser Pro Gln Arg Ser Pro Asp Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Thr Asn Pro Leu Ile Asp Gln Tyr Leu Tyr Tyr Leu
        435                 440                 445

Ala Arg Thr Gln Ser Thr Thr Gly Ser Thr Arg Gly Leu Gln Phe His
    450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
                485                 490                 495

Asn Asn Ser Asn Phe Ala Trp Thr Gly Ala Thr Lys Tyr His Leu Asn
            500                 505                 510

Gly Arg Asn Ser Leu Thr Asn Pro Gly Val Ala Met Ala Thr Asn Lys
        515                 520                 525

Asp Asp Glu Asp Gln Phe Phe Pro Ile Asn Gly Val Leu Phe Gly
    530                 535                 540

Lys Thr Gly Ala Ala Asn Lys Thr Thr Leu Glu Asn Val Leu Met Thr
545                 550                 555                 560
```

```
Ser Glu Glu Glu Ile Lys Thr Thr Asn Pro Val Ala Thr Glu Glu Tyr
                565                 570                 575

Gly Val Val Ser Ser Asn Leu Gln Ser Ser Thr Ala Gly Pro Gln Thr
            580                 585                 590

Gln Thr Val Asn Ser Gln Gly Ala Leu Pro Gly Met Val Trp Gln Asn
        595                 600                 605

Arg Asp Val Tyr Leu Gln Gly Pro Ile Trp Ala Lys Ile Pro His Thr
    610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Tyr Thr Ser Asn Tyr Tyr Lys
                645                 650                 655

Ser Thr Asn Val Asp Phe Ala Val Asn Thr Glu Gly Thr Tyr Ser Glu
            660                 665                 670

Pro Arg Pro Ile Gly Thr Arg Tyr Leu Thr Arg Asn Leu
        675                 680                 685

<210> SEQ ID NO 114
<211> LENGTH: 724
<212> TYPE: PRT
<213> ORGANISM: Unknown
<220> FEATURE:
<223> OTHER INFORMATION: capsid protein of AAV serotype, clone AAV5CAP

<400> SEQUENCE: 114

Met Ser Phe Val Asp His Pro Pro Asp Trp Leu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
    115                 120                 125

Gly Leu Val Glu Glu Gly Ala Lys Thr Ala Pro Thr Gly Lys Arg Ile
130                 135                 140

Asp Asp His Phe Pro Lys Arg Lys Lys Ala Arg Thr Glu Glu Asp Ser
                145                 150                 155                 160

Lys Pro Ser Thr Ser Ser Asp Ala Glu Ala Gly Pro Ser Gly Ser Gln
            165                 170                 175

Gln Leu Gln Ile Pro Ala Gln Pro Ala Ser Ser Leu Gly Ala Asp Thr
    180                 185                 190

Met Ser Ala Gly Gly Gly Gly Pro Leu Gly Asp Asn Asn Gln Gly Ala
195                 200                 205

Asp Gly Val Gly Asn Ala Ser Gly Asp Trp His Cys Asp Ser Thr Trp
            210                 215                 220

Met Gly Asp Arg Val Val Thr Lys Ser Thr Arg Thr Trp Val Leu Pro
225                 230                 235                 240
```

-continued

```
Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
```

```
              660                 665                 670
Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
        690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 115
<211> LENGTH: 9
<212> TYPE: DNA
<213> ORGANISM: Artificial Sequence
<220> FEATURE:
<223> OTHER INFORMATION: DraIII restriction enzyme site

<400> SEQUENCE: 115 caccacgtc                                                            9

<210> SEQ ID NO 116
<211> LENGTH: 28
<212> TYPE: DNA
<213> ORGANISM: Unknown
<220> FEATURE:
<223> OTHER INFORMATION: AV2cas

<400> SEQUENCE: 116
cgcagagacc aaagttcaac tgaaacga                                      28

<210> SEQ ID NO 117
<211> LENGTH: 255
<212> TYPE: DNA
<213> ORGANISM: Unknown
<220> FEATURE:
<223> OTHER INFORMATION: adeno-associated virus serotype 10

<400> SEQUENCE: 117
ggtaattcct ccggaaattg gcattgcgat tccacatggc tgggcgacag agtcatcacc    60
accagcaccc gaacctgggt cctgcccacc tacaacaacc acatctacaa gcaaatctcc   120
agcgagacag agccaccaa cgacaaccac tacttcggct acagcacccc ctgggggtat    180
tttgacttta acagattcca ctgccacttt tcaccacgtg actggcagcg actcatcaac   240
aacaactggg gattc                                                   255

<210> SEQ ID NO 118
<211> LENGTH: 258
<212> TYPE: DNA
<213> ORGANISM: Unknown
<220> FEATURE:
<223> OTHER INFORMATION: adeno-associated virus serotype 11

<400> SEQUENCE: 118
ggtaattcct ccggaaattg gcattgcgat tccacatggc tgggcgacag agtcatcacc    60
accagcaccc gaacctgggc cctgccaacc tacaacaacc acctctacaa acaaatctcc   120
agcgcttcaa cggggccag caacgacaac cactactttg ctacagcac ccctggggg     180 tattttgact ttaacagatt ccactgccac ttctcaccac gtgactggca gcgactcatc   240
aacaacaact ggggattc                                                258

<210> SEQ ID NO 119
```

```
<211> LENGTH: 255
<212> TYPE: DNA
<213> ORGANISM: Unknown
<220> FEATURE:
<223> OTHER INFORMATION: adeno-associated virus serotype 12

<400> SEQUENCE: 119
ggtaattcct ccggaaattg gcattgcgat tccacatggc tgggcgaccg agtcattacc      60
accagcaccc ggacttgggc cctgcccacc tacaacaacc acctctacaa gcaaatctcc     120
agccaatcgg gtgccaccaa cgacaaccac tacttcggct acagcacccc ttgggggtat     180
tttgatttca acagattcca ctgccatttc tcaccacgtg actggcagcg actcatcaac     240
aacaactggg gattc                                                     255

<210> SEQ ID NO 120
<211> LENGTH: 2205
<212> TYPE: DNA
<213> ORGANISM: Unknown
<220> FEATURE:
<223> OTHER INFORMATION: adeno-associated virus serotype, clone A3.1vp1

<400> SEQUENCE: 120
atggctgccg atggttatct tccagattgg ctcgaggaca ctctctctga aggaatcaga      60
cagtggtgga agctcaaacc tggcccacca ccgccgaaac ctaaccaaca acaccgggac     120
gacagtaggg gtcttgtgct tcctgggtac aagtacctcg gacccttcaa cggactcgac     180
aaaggagagc cggtcaacga ggcagacgcc gcggccctcg agcacgacaa agcctacgac     240
caccagctca gcaagggga caacccgtac ctcaaataca accacgcgga cgctgaattt     300
caggagcgtc ttcaagaaga tacgtctttc ggggcaacc tcgggcgagc agtcttccag     360
gccaaaaaga gggtactcga gcctcttggt ctggttgagg aagctgttaa gacggctcct     420
ggaaaaaaga gacctataga gcagtctcct gcagaaccgg actcttcctc gggcatcggc     480
aaatcaggcc agcagcccgc taagaaaaga ctcaattttg gtcagactgg cgacacagag     540
tcagtcccag accctcaacc aatcggagaa ccccccgcag cccctctgg tgtgggatct     600
aatacaatgg cttcaggcgg tgggcacca atggcagaca taacgaagg cgccgacgga     660
gtgggtaatt cctcgggaaa ttggcattgc gattccacat ggatgggcga cagagttatc     720
accaccagca aagaacctg ggccctcccc acctacaata tcacctcta caagcaaatc     780
tccagcgaat cgggagccac caacgacaac cactacttcg gctacagcac ccctgggggg     840
tattttgact ttaacagatt ccactgtcac ttctcaccac gtgactggca gcgactcatc     900
aacaacaact ggggatttag acccaagaaa ctcaatttca gctcttcaa catccaagtc     960
aaggaggtca cgcagaatga tggaaccacg accatcgcca taaccttac agcacggtg    1020
caggtcttca cagactctga gtaccagctg ccctacgtcc tcggttcggc tcaccaggc    1080
tgccttccgc cgttcccagc agacgtcttc atgattcctc agtacggcta cttgactctg    1140
aacaatggca gccaagcggt aggacgttct tcattctact gtctagagta tttcccctct    1200
cagatgctga ggacgggaaa caacttcacc ttcagctaca cttttgaaga cgtgcctttc    1260
cacagcagct acgcgcacag ccagagtctg gatcggctga tgaatcctct cattgaccag    1320
tacctgtatt acctgagcaa aactcagggt acaagtggaa caacgcagca atcgagactg    1380
cagttcagcc aagctgggcc tagctccatg gctcagcagg ccaaaaactg gctaccggga    1440
cccagctacc gacagcagcg aatgtctaag acggctaatg acaacaacaa cagtgaattt    1500
gcttggactg cagccaccaa atattacctg aatggaagaa attctctggt caatcccggg    1560
```

```
cccccaatgg ccagtcacaa ggacgatgag gaaaagtatt tccccatgca cggaaatctc    1620
atctttggaa aacaaggcac aggaactacc aatgtggaca ttgaatcagt gcttattaca    1680
gacgaagaag aaatcagaac aactaatcct gtggctacag aacaatacgg acaggttgcc    1740
accaaccatc agagtcagaa caccacagct tcctatggaa gtgtggacag ccagggaatc    1800
ttacctggaa tggtgtggca ggaccgcgat gtctatcttc aaggtcccat ttgggccaaa    1860
actcctcaca cggacggaca ctttcatcct tctccgctca tgggaggctt tggactgaaa    1920
caccctcctc cccagatcct gatcaaaaac acacctgtgc cagcgaatcc cgcgaccact    1980
ttcactcctg gaaagtttgc ttcgttcatt acccagtatt ccaccggaca ggtcagcgtg    2040
gaaatagagt gggagctgca gaaagaaaac agcaaacgct ggaacccaga aattcagtac    2100
acctccaact acaacaagtc ggtgaatgtg gagtttaccg tggacgcaaa cggtgtttat    2160
tctgaacccc gccctattgg cactcgttac cttacccgga acttg                   2205
```